US009907850B2

(12) United States Patent
Schneewind et al.

(10) Patent No.: US 9,907,850 B2
(45) Date of Patent: *Mar. 6, 2018

(54) COMPOSITIONS AND METHODS RELATED TO PROTEIN A (SPA) ANTIBODIES AS AN ENHANCER OF IMMUNE RESPONSE

(71) Applicant: The University of Chicago, Chicago, IL (US)

(72) Inventors: Olaf Schneewind, Chicago, IL (US); Alice Cheng, Boston, MA (US); Dominique M. Missiakas, Chicago, IL (US); Hwan Keun Kim, Naperville, IL (US)

(73) Assignee: The University of Chicago, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/968,023

(22) Filed: Dec. 14, 2015

(65) Prior Publication Data
US 2016/0175441 A1    Jun. 23, 2016

Related U.S. Application Data

(63) Continuation of application No. 14/335,411, filed on Jul. 18, 2014, now Pat. No. 9,212,219, which is a continuation of application No. 13/639,465, filed as application No. PCT/US2011/031213 on Apr. 5, 2011, now Pat. No. 8,808,699, and a continuation-in-part of application No. 13/260,878, filed as application No. PCT/US2010/029959 on Apr. 5, 2010, now Pat. No. 9,567,379.

(60) Provisional application No. 61/321,050, filed on Apr. 5, 2010, provisional application No. 61/287,996, filed on Dec. 18, 2009, provisional application No. 61/237,956, filed on Aug. 28, 2009, provisional application No. 61/166,432, filed on Apr. 3, 2009.

(51) Int. Cl.
| A61K 39/40 | (2006.01) |
| C07K 16/12 | (2006.01) |
| A61K 39/085 | (2006.01) |
| A61K 39/39 | (2006.01) |
| A61K 39/00 | (2006.01) |

(52) U.S. Cl.
CPC ............ *A61K 39/40* (2013.01); *A61K 39/085* (2013.01); *A61K 39/39* (2013.01); *C07K 16/1271* (2013.01); *A61K 2039/505* (2013.01); *A61K 2039/55516* (2013.01); *A61K 2039/57* (2013.01); *C07K 2317/76* (2013.01)

(58) Field of Classification Search
CPC .. C07K 14/31; C07K 16/1271; C07K 14/315; C07K 1/22; C07K 2319/00; C07K 2319/21; C07K 2316/96; C07K 2317/76; A61K 39/085; A61K 2039/505; A61K 2039/53; A61K 2039/55505

See application file for complete search history.

(56) References Cited

U.S. PATENT DOCUMENTS

| 3,791,932 A | 2/1974 | Schuurs et al. ............... 435/7.8 |
| 3,959,064 A | 5/1976 | Touchette ..................... 156/417 |
| 4,174,384 A | 11/1979 | Ullman et al. ............... 436/537 |
| 4,338,298 A | 7/1982 | Myers ........................ 424/242.1 |
| 4,356,170 A | 10/1982 | Jennings et al. ........... 424/194.1 |
| 4,367,110 A | 1/1983 | Yoshikawa ................... 156/219 |
| 4,372,945 A | 2/1983 | Likhite ........................ 530/405 |
| 4,452,901 A | 6/1984 | Gordon et al. ............. 435/7.92 |
| 4,474,757 A | 10/1984 | Arnon et al. ............... 424/186.1 |
| 4,554,101 A | 11/1985 | Hopp ............................ 530/324 |
| 4,578,770 A | 3/1986 | Mitani ....................... 250/559.2 |
| 4,596,792 A | 6/1986 | Vyas .......................... 424/185.1 |
| 4,599,231 A | 7/1986 | Milich et al. .............. 424/189.1 |
| 4,601,903 A | 7/1986 | Frasch ....................... 424/250.1 |
| 4,608,251 A | 8/1986 | Mia ............................ 424/185.1 |
| 4,683,195 A | 7/1987 | Mullis et al. ................ 435/6.11 |
| 4,683,202 A | 7/1987 | Mullis .......................... 435/91.2 |
| 4,684,611 A | 8/1987 | Schilperoort ................. 435/468 |
| 4,690,915 A | 9/1987 | Rosenberg .................. 424/85.2 |
| 4,699,230 A | 10/1987 | Solleder et al. .............. 180/360 |
| 4,748,018 A | 5/1988 | Stolle et al. ................ 424/157.1 |
| 4,800,159 A | 1/1989 | Mullis et al. ................ 435/91.2 |
| 4,879,236 A | 11/1989 | Smith et al. ............... 435/320.1 |
| 4,952,500 A | 8/1990 | Finnerty et al. ............. 435/69.1 |
| 5,084,269 A | 1/1992 | Kullenberg ................ 424/256.1 |
| 5,199,942 A | 4/1993 | Gillis ........................... 604/4.01 |
| 5,221,605 A | 6/1993 | Bard et al. ........................ 435/4 |

(Continued)

FOREIGN PATENT DOCUMENTS

| EP | 0497524 | 8/1992 |
| EP | 0497525 | 8/1992 |

(Continued)

OTHER PUBLICATIONS

Abdallah, et al., Mol Microbiol. 62: 667-9, 2006.
Abdallah, et al., Nat Rev Microbiol. 5:883-91, 2007.
Albus, et al., Infect Immun. 59:1008-14, 1991.
An, J Viol. 71(3):2292-302, 1997.
Andersen, et al., J Immunol. 154: 3359-72, 1995.
Angel, et al., Cell. 49:729, 1987.
Angel, et al., Mol Cell Biol. 7:2256, 1987.
Archer, Clin Infect Dis. 26:1179-81, 1998.
Atchison and Perry, Cell. 46:253, 1986.
Atchison and Perry, Cell. 48:121, 1987.

(Continued)

*Primary Examiner* — Padmavathi Baskar
(74) *Attorney, Agent, or Firm* — Norton Rose Fulbright US LLP

(57) ABSTRACT

The present invention concerns methods and compositions for treating or preventing a bacterial infection, particularly infection by a *Staphylococcus* bacterium. The invention provides methods and compositions for stimulating an immune response against the bacteria. In certain embodiments, the methods and compositions involve a non-toxigenic Protein A (SpA) variant or an antibody directed thereto.

9 Claims, 1 Drawing Sheet

(56) References Cited

U.S. PATENT DOCUMENTS

| | | | |
|---|---|---|---|
| 5,238,808 A | 8/1993 | Bard et al. | 435/4 |
| 5,302,523 A | 4/1994 | Coffee et al. | 435/470 |
| 5,310,687 A | 5/1994 | Bard et al. | 436/518 |
| 5,322,783 A | 6/1994 | Tomes et al. | 800/293 |
| 5,384,253 A | 1/1995 | Krzyzek et al. | 800/292 |
| 5,464,765 A | 11/1995 | Coffee et al. | 435/470 |
| 5,512,282 A | 4/1996 | Krivan et al. | 424/169.1 |
| 5,538,877 A | 7/1996 | Lundquist et al. | 800/265 |
| 5,538,880 A | 7/1996 | Lundquist et al. | 800/265 |
| 5,548,066 A | 8/1996 | Leneau et al. | 530/390.5 |
| 5,550,318 A | 8/1996 | Adams et al. | 800/300.1 |
| 5,563,055 A | 10/1996 | Townsend et al. | 800/294 |
| 5,580,859 A | 12/1996 | Feigner et al. | 514/44 R |
| 5,589,466 A | 12/1996 | Feigner et al. | 514/44 R |
| 5,591,616 A | 1/1997 | Hiei et al. | 435/469 |
| 5,610,042 A | 3/1997 | Chang et al. | 800/288 |
| 5,620,896 A | 4/1997 | Herrmann et al. | 435/320.1 |
| 5,648,240 A | 7/1997 | Hook et al. | 435/69.3 |
| 5,656,610 A | 8/1997 | Shuler et al. | 514/44 R |
| 5,702,932 A | 12/1997 | Hoy et al. | 800/25 |
| 5,736,524 A | 4/1998 | Content et al. | 514/44 R |
| 5,780,448 A | 7/1998 | Davis | 514/44 R |
| 5,789,215 A | 8/1998 | Berus et al. | 800/25 |
| 5,801,234 A | 9/1998 | Hodgson et al. | 536/23.8 |
| 5,840,846 A | 11/1998 | Hook et al. | 530/350 |
| 5,843,650 A | 12/1998 | Segev | 435/6.1 |
| 5,846,709 A | 12/1998 | Segev | 435/6.1 |
| 5,846,783 A | 12/1998 | Wu et al. | 435/91.2 |
| 5,849,497 A | 12/1998 | Steinman | 435/6.11 |
| 5,849,546 A | 12/1998 | Sousa et al. | 435/91.5 |
| 5,849,547 A | 12/1998 | Cleuziat et al. | 435/91.21 |
| 5,858,652 A | 1/1999 | Laffler et al. | 435/5 |
| 5,866,366 A | 2/1999 | Kallender | 435/69.1 |
| 5,871,986 A | 2/1999 | Boyce | 435/183 |
| 5,916,776 A | 6/1999 | Kumar | 435/91.1 |
| 5,922,574 A | 7/1999 | Minter | 435/91.1 |
| 5,925,565 A | 7/1999 | Berlioz et al. | 435/325 |
| 5,928,905 A | 7/1999 | Stemmer et al. | 435/91.1 |
| 5,928,906 A | 7/1999 | Koster et al. | 435/91.2 |
| 5,932,451 A | 8/1999 | Wang | 435/91.21 |
| 5,935,819 A | 8/1999 | Eichner et al. | 435/69.4 |
| 5,935,825 A | 8/1999 | Nishimura et al. | 435/91.2 |
| 5,939,291 A | 8/1999 | Loewy et al. | 435/91.2 |
| 5,942,391 A | 8/1999 | Zhang et al. | 435/6.12 |
| 5,945,100 A | 8/1999 | Fick | 424/93.21 |
| 5,958,895 A | 9/1999 | Pachuk et al. | 514/44 R |
| 5,981,274 A | 11/1999 | Tyrrell et al. | 435/320.1 |
| 5,994,624 A | 11/1999 | Trolinder et al. | 800/278 |
| 6,008,341 A | 12/1999 | Foster et al. | 536/23.7 |
| 6,288,214 B1 | 9/2001 | Hook et al. | 530/387.1 |
| 6,294,177 B1 | 9/2001 | Fattom | 424/243.1 |
| 6,651,655 B1 | 11/2003 | Licalsi et al. | 138/203.15 |
| 6,656,462 B2 | 12/2003 | Dondero et al. | 424/85.2 |
| 6,733,754 B2 | 5/2004 | Roberts et al. | 424/184.1 |
| 6,756,361 B1 | 6/2004 | Fattom et al. | 514/54 |
| 6,770,278 B1 | 8/2004 | Skelly | 424/130.1 |
| 6,793,923 B2 | 9/2004 | Brown et al. | 424/184.1 |
| 6,814,971 B2 | 11/2004 | Roberts et al. | 424/240.1 |
| 6,936,258 B1 | 8/2005 | Pavliak et al. | 424/243.1 |
| 8,808,699 B2 | 8/2014 | Schneewind et al. | 424/139.1 |
| 9,212,219 B2* | 12/2015 | Schneewind | A61K 39/085 |
| 9,567,379 B2* | 2/2017 | Schneewind | C07K 14/31 |
| 2002/0169288 A1 | 11/2002 | Hook et al. | 530/350 |
| 2003/0153022 A1 | 8/2003 | Patti et al. | 424/165.1 |
| 2006/0263792 A1 | 11/2006 | Mohamed et al. | 424/133.1 |
| 2007/0003514 A1 | 1/2007 | Penichet | 514/12 |

FOREIGN PATENT DOCUMENTS

| | | |
|---|---|---|
| EP | 0786519 | 7/1997 |
| JP | 2005520853 | 7/2005 |
| JP | 2008518947 | 6/2008 |
| WO | WO/89/009284 | 5/1989 |
| WO | WO/94/09699 | 5/1994 |
| WO | WO/95/06128 | 3/1995 |
| WO | WO/95/08348 | 3/1995 |
| WO | WO/98/57994 | 12/1998 |
| WO | WO/00/02523 | 1/2000 |
| WO | WO/00/12132 | 3/2000 |
| WO | WO/00/12589 | 3/2000 |
| WO | WO/00/15238 | 3/2000 |
| WO | WO/01/60852 | 8/2001 |
| WO | WO/01/98499 | 12/2001 |
| WO | WO/02/059148 | 8/2002 |
| WO | WO/02/094868 | 11/2002 |
| WO | WO/03/53462 | 7/2003 |
| WO | WO 03080106 | 10/2003 |
| WO | WO/04/43407 | 5/2004 |
| WO | WO/06/032472 | 3/2006 |
| WO | WO/06/032475 | 3/2006 |
| WO | WO/06/032500 | 3/2006 |
| WO | WO 2006050291 | 5/2006 |
| WO | WO/07/113222 | 10/2007 |
| WO | WO/07/113223 | 10/2007 |

OTHER PUBLICATIONS

Ausubel, et al., In: Current Protocols in Molecular Biology. John, Wiley & Sons, Inc. New York, 1996.
Baba, et al., J Bacteriol. 190:300-10, 2007.
Bae and Schneewind, Plasmid. 55:58-63, 2006.
Bae, et al., Proc Natl Acad Sci USA. 101:12312-7, 2004.
Banerji, et al., Cell. 27:299-308, 1981.
Banerji, et al., Cell. 33:729-40, 1983.
Barany and Merrifield, In: The Peptides. Gross & Meienhofer (Eds.), Academic Press, NY, 1-284, 1979.
Behring, EA. Uber das Zustandekommen der Diphtherie—Immunitat bei Thieren. Deutsche Medzinische Wochenschrift, 16:1145-8, 1995.
Bekeredjian-Ding, et al., J Immunol. 178:2803-12, 2007.
Bellus, J Macromol Sci Pure Appl Chem. A31(1): 1355-1376, 1994.
Berkhout, et al., Cell. 59: 273-282, 1989.
Birch-Hirschfeld, L. Uber die Agglutination von Staphylokokken durch Bestandteile des Saugertierblutplasmas. Klinische Woschenschrift. 13:331.
Bjerketorp, et al., FEMS Microbiol Lett. 234:309-314, 2004.
Blanar, et al., EMBO J. 8: 1139, 1989.
Bodine and Ley, EMBO J. 6:2997, 1987.
Borrebaeck, In: Antibody Engineering—A Practical Guide, W.H. Freeman and Co., 1992.
Boshart, et al., Cell. 41:521, 1985.
Bosze, et al., EMBO J. 5(7): 1615-1623, 1986.
Boucher and Corey. Clin Infect Dis. 46: S334-S349, 2008.
Braddock, et al., Cell. 58: 269, 1989.
Brown, et al., Biochemistry. 37: 4397-4406, 1998.
Bubeck, Wardenburg and Schneewind. J Exp Med. 205: 287-294, 2008.
Bubeck-Wardenburg et al., Infect.Immun. 74:1040-1044, 2007.
Bubeck-Wardenburg et al., Proc Natl Acad Sci USA. 103:13831-13836, 2006.
Bulla and Siddiqui, J. Virol., 62:1437, 1986.
Burke et al., J.Inf Dis., 170:1110-1119,1994.
Burlak et al. ,Cell Microbiol., 9:1172-1190, 2007.
Burts and Missiakas, Mol. Microbiol., 69:736-46, 2008.
Burts et al., PNAS USA, 102:1169-1174, 2005.
Campbell and Villarreal, Mol. Cell. Biol., 8:1993, 1988.
Campere and Tilghman, Genes and Dev., 3:537, 1989.
Campo et al., Nature, 303:77, 1983.
Carbonelli et al., FEMS Microbiol. Lett., 177(1):75-82, 1999.
Cedergren et al., Protein Eng., 6:441-448, 1993.
Celander and Haseltine, J. Virology, 61:269, 1987.
Celander et al., J. Virology, 62:1314, 1988.
Cespedes et al., J. Infect. Dis., 191(3):444-52, 2005.
Champion et al., Science, 313:1632-1636,2006.
Chandler et al., Cell, 33:489, 1983.
Chandler et al., PNAS USA, 94(8):3596-601, 1997.
Chang et al., Lancet., 362(9381):362-369, 2003.
Chang et al., Mol. Cell. Biol., 9:2153, 1989.
Chatterjee et al., PNAS USA, 86:9114, 1989.

(56) References Cited

OTHER PUBLICATIONS

Chen and Okayama, Mol. Cell Biol., 7(8):2745-2752, 1987.
Cheng et al., FASEB J., 23:1-12,2009.
Choi et al., Cell, 53:519, 1988.
Cocea, Biotechniques, 23(5):814-816, 1997.
Cohen et al., J. Cell. Physiol., 5:75, 1987.
Cosgrove et al., Infect. Control Hasp. Epidemiol. 26:166-174,2005.
Costa et al., Mol. Cell. Biol., 8:81, 1988.
Cripe et al., Embo J., 6:3745, 1987.
Culotta and Hamer, Mol. Cell. Biol., 9:1376, 1989.
Dalbey and Wickner, J. Biol. Chem., 260:15925-15931, 1985.
Dandolo et al., J. Virology, 47:55-64, 1983.
De Villiers et al., Nature, 312( 5991 ):242-246, 1984.
DeBord et al., Infect. Immun., 74:4910-4914,2006.
DeDent et al., EMBO J. 27:2656-2668, 2008.
DeDent et al., J. Bacteriol. 189:44 73-4484, 2007.
Deisenhofer et al., Hoppe-Seyh Zeitsch. Physiol. Chem. 359:975-985, 1978.
Deisenhofer, Biochemistry 20:2361-23 70, 1981.
Deschamps et al., Science, 230: 11 7 4-11 77, 1985.
Devereux et al., Nucl. Acid Res., 12:387-395, 1984.
Diep et al., J. Infect. Dis., 193:1495-1503, 2006a.
Diep et al., Lancet., 367:731-739, 2006b.
Dinges et al., Clin. Microbiol. Rev., 13:16-34, 2000.
Duthie and Lorenz, J. Gen. Microbiol., 6:95-107, 1952.
Edbrooke et al., Mol. Cell. Biol., 9:1908, 1989.
Edlund et al., Science, 230:912-916, 1985.
Ekstedt and Yotis, Ann. N.Y Acad. Sci., 80:496-500, 1960.
Emori and Gaynes, Clin. Microbiol. Rev., 6:428-442, 1993.
Epitope Mapping Protocols In: Methods in Molecular Biology, vol. 66, Morris (Ed.), 1996.
Extended European Search Report in European Application No. 11766582.8 dated Dec. 12, 2013.
Fechheimer, et al., PNAS USA. 84:8463-8467, 1987.
Feng and Holland, Nature, 334:6178, 1988.
Field and Smith, J. Comp. Pathol., 55:63, 1945.
Firak and Subramanian, Mol. Cell. Biol., 6:3667, 1986.
Foecking and Hofstetter, Gene, 45(1):101-105, 1986.
Fortune et al., PNAS USA. 102:10676-10681,2005.
Foster, Nat. Rev. Microbiol., 3:948-958, 2005.
Fournier et al., Infect. Immun 45:87-93, 1984.
Fraley et al., PNAS USA. 76:3348-3352, 1979.
Friedrich et al., Nature, 425:535-539, 2003.
Fujita et al., Cell, 49:357, 1987.
Garcia-Lara & Foster, Curr Opin Pharmacol. 9:552-7, 2009.
Ghosh, et al., Biochem Biophys Res Comm. 256:142-6, 1999.
Gilles et al., Cell, 33:717, 1983.
Gloss et al., EMBO J., 6:3735, 1987.
Godbout et al., Mol. Cell. Biol., 8:1169, 1988.
Gomez et al., EMBO J. 26:701-709,2007.
Gomez et al., J. Biol. Chem. 281:20190-20196,2006.
Gomez et al., Nature Med. 10:842-8, 2004.
Goodbourn and Maniatis, PNAS USA. 85:1447, 1988.
Goodbourn et al., Cell, 45:601, 1986.
Goodyear and Silverman, J. Exp. Med., 197:1125-1139, 2003.
Goodyear and Silverman, PNAS USA, 101:11392-11397, 2004.
Gopal, Mol. Cell Biol., 5:1188-1190, 1985.
Gouda et al., Biochemistry, 31(40):9665-72, 1992.
Gouda et al., Biochemistry, 37:129-36, 1998.
Graham and VanDer Eb, Virology, 52:456-467, 1973.
Graille et al., PNAS USA. 97:5399-5404, 2000.
Greene et al., Immunology Today, 10:272, 1989.
Grosschedl and Baltimore, Cell, 41:885, 1985.
Guinn et al., Mol. Microbiol., 51:359-370, 2004.
Gusset al., Eur. J. Biochem. 138:413-420, 1984.
Harland and Weintraub, J. Cell Biol., 101(3):1094-1099, 1985.
Harlow et al., Antibodies: A Laboratory Manual, Cold Spring Harbor Laboratory, Cold Spring Harbor, N.Y., Chapter 8, 1988.
Hartleib et al., Blood. 96:2149-2156, 2000.
Harvey et al., PNAS USA, 83:1084-1088, 1986.
Haslinger and Karin, PNAS USA, 82:8572, 1985.
Hauber and Cullen, J. Virology, 62:673, 1988.
Hen et al., Nature, 321:249, 1986.
Hensel et al., Lymphokine Res., 8:347, 1989.
Herr and Clarke, Cell, 45:461, 1986.
Hirochika et al., J. Virol., 61:2599, 1987.
Hirsch et al., Mol. Cell. Biol., 10:1959, 1990.
Holbrooketal., Virology, 157:211,1987.
Horlick and Benfield, Mol. Cell. Biol., 9:2396, 1989.
Hsu et al., PNAS USA, 100:12420-12425, 2003.
Huang et al., Cell, 27:245, 1981.
Hug et al., Mol. Cell. Biol., 8:3065, 1988.
Huston et al., In: Methods in Enzymology, Langone (Ed.), Academic Press, NY, 203:46-88, 1991.
Hwang et al., Mol. Cell. Biol., 10:585, 1990.
Imagawa et al., Cell, 51 :251, 1987.
Imbra and Karin, Nature, 323:555, 1986.
Imler et al., Mol. Cell. Biol., 7:2558, 1987.
Imperiale and Nevins, Mol. Cell. Biol., 4:875, 1984.
Innis et al., PNAS USA, 85(24):9436-9440, 1988.
Inouye and Inouye, Nucleic Acids Res., 13: 3101-3109, 1985.
Internation Preliminary Report on Patentability in PCT/US2011/031213 dated Oct. 18, 2012.
International Preliminary Report on Patentability in International Application No. PCT/US2011/031213 dated Oct. 9, 2012.
Jakobovits et al., Mol. Cell. Biol., 8:2555, 1988.
Jameel and Siddiqui, Mol. Cell. Biol., 6:710, 1986.
Jansson et al., FEMS Immunol. Med. Microbiol. 20:69-78 1998.
Jaynes et al., Mol. Cell. Biol., 8:62, 1988.
Jensen, Acta Path. Microbial. Scandin 44:421-428, 1958.
Johnson et al., Methods in Enzymol., 203:88-99, 1991.
Johnson et al., Mol. Cell. Biol., 9:3393, 1989.
Jones, Carb. Research, 340:1097-1106, 2005.
Jonsson et al., Oral Dis., 8(3):130-140, 2002.
Joyce et al., Carbohydrate Research 338:903-922 (2003.
Kadesch and Berg, Mol. Cell. Biol., 6:2593, 1986.
Kaeppler et al., Plant Cell Rep., 8:415-418, 1990.
Kaneda et al., Science, 243:375-378, 1989.
Karin et al., Mol. Cell. Biol., 7:606, 1987.
Katinka et al., Cell, 20:393, 1980.
Kato et al, J Biol. Chem., 266:3361-3364, 1991.
Kawamoto et al., Mol. Cell. Biol., 8:267, 1988.
Kennedy et al., PNAS USA 105:1327-1332,2008.
Kiledjian et al., Mol. Cell. Biol., 8:145, 1988.
Kim, et al., JEM. 207(9):1863-70, 2010.
Kinoshita, M., N. Kobayashi, S. Nagashima, M. Ishino, S. Otokozawa, K. Mise, A. Sumi, H. Tsutsumi, N. Uehara, N. Watanabe, and M. Endo. 2008. Diversity of staphylocoagulase and identification of novel variants of staphylocoagulase gene in *Staphylococcus aureus*. Microbiol. Imrnunol.s 52:334-348.
Klarnut et al., Mol. Cell. Biol., 10:193, 1990.
Klevens et al., Clin. Infect. Dis., 2008; 47:927-30, 2008.
Klevens et al., JAMA, 298:1763-1771, 2007.
Koch et al., Mol. Cell. Biol., 9:303, 1989.
Kohler and Milstein, Nature 256:495-497 (1975.
Kriegler and Bot chan, In: Eukaryotic Viral Vectors, Gluzman (Ed.), Cold Spring Harbor: Cold Spring Harbor Laboratory, NY, 1982.
Kriegler and Botchan, Mol. Cell. Biol., 3:325, 1983.
Kriegler et al., Cell, 38:483, 1984a.
Kriegler et al., Cell, 53:45, 1988.
Kriegler et al., In: Cancer Cells 2/Oncogenes and Viral Genes, Van de Woude et al. eds, Cold Spring Harbor, Cold Spring Harbor Laboratory, 1984b.
Kroh et al., PNAS USA, 106:7786-7791,2009.
Kuhl et al., Cell, 50:1057, 1987.
Kuklin et al., Infect. Immunol., 74:2215-23, 2006.
Kunz et al., Nucl. Acids Res., 17:1121, 1989.
Kuroda et al., Lancet., 357:1225-1240, 2001.
Kyte and Doolittle, J Mol. Biol., 157(1):105-132, 1982.
Lagergard et al., Eur. J. Clin. Microbiol. Infect. Dis., 11 :341-5, 1992.
Lam et al., J Bacteriol., 86:87-91, 1963.
Larsen et al., PNAS USA., 83:8283, 1986, 1963.

(56) References Cited

OTHER PUBLICATIONS

Laspia et al., Cell, 59:283, 1989.
Latimer et al., Mol. Cell. Biol., 10:760, 1990.
Lee et al., Nature, 294:228, 1981.
Lee et al., Nucleic Acids Res., 12:4191-206, 1984.
Lee, Trends Microbiol. 4( 4 ): 162-166, 1996.
Levenson et al., Hum. Gene Ther., 9(8):1233-1236, 1998.
Levinson et al., Nature, 295:79, 1982.
Lin et al., Mol. Cell. Biol., 10:850, 1990.
Lowy, New Engl. J Med., 339:520-532, 1998.
Luriaetal.,EMBO J., 6:3307,1987.
Lusky and Botchan, PNAS USA, 83:3609, 1986.
Lusky et al., Mol. Cell. Biol., 3:1108, 1983.
Macejak and Samow, Nature, 353:90-94, 1991.
MacGum et al., Mol. Microbiol., 57:1653-1663, 2005.
Maira-Litran et al., Infect. Immunol., 70:4433-4440, 2002.
Maira-Litran et al., Vaccine, 22:872-879, 2004.
Majors and Varmus, PNAS USA, 80:5866, 1983.
Markwardt, Untersuchungen uber Hirudin. Naturwissenschaften, 41:537-538, 1955.
Mazmanian et al., Mol. Microbiol. 40: 1049-1 057, 2001.
Mazmanian et al., Mol. Microbiol., 40(5):1049-1057, 2001.
Mazmanian et al., PNAS USA, 97:5510-5515, 2000.
Mazmanian et al., Science, 285(5428):760-3, 1999.
McLaughlin et al., PLoS Pathog., 3:e105, 2007.
McNeall et al., Gene, 76:81, 1989.
Menzies & Kernodle, Infect Immun 64(5):1839-41, 1996.
Mernaugh et al., In: Molecular Methods in Plant Pathology, Singh et al. (Eds.), CRC Press Inc., Boca Raton, FL, 359-365, 1995.
Merrifield, Science, 232(4748):341-347, 1986.
Miksicek et al., Cell, 46:203, 1986.
Mordacq and Linzer, Genes and Dev., 3:760, 1989.
Moreau et al., Carbohydrate Res., 201:285-297, 1990.
Moreau et al., Nucl. Acids Res., 9:6047, 1981.
Moreillon et al., Infect. Immun., 63:4738-4743, 1995.
Mosmann and Coffman, Ann. Rev. Immunol., 7:145-173, 1989.
Muesing et al., Cell, 48:691, 1987.
Musher et al., Medicine (Baltimore), 73:186-208, 1994.
Navarre and Schneewind, J. Biol. Chem., 274:15847-15856, 1999.
Needleman & Wunsch, J. Mol. Biol., 48:443, 1970.
Ng et al., Nuc. Acids Res., 17:601, 1989.
Nicolau and Sene, Biochem. Biophys. Acta, 721:185-190, 1982.
Nicolau et at., Methods Enzymol., 149:157-176, 1987.
Novick, Mol. Microbiol., 48:1429-1449, 2003.
O'Brien et al., Mol. Microbiol. 44:1033-1044, 2002.
Omirulleh et al., Plant Mol. Biol., 21(3):415-28, 1993.
Ondek et al., EMBO J., 6:1017, 1987.
Ornitz et al., Mol. Cell. Biol., 7:3466, 1987.
O'Seaghdha et al., FEBS J. 273:4831-4841, 2006.
Pallen, Trends Microbiol., 10:209-212, 2002.
Palmiter et al., Nature, 300:611, 1982.
Palmqvist et al., Microbes. Infect., 7:1501-11, 2005.
Panizzi et al., J. Biol. Chem., 281:1179-1187, 2006.
Pankey et al., "Evaluation of Protein A and a Commercial Bacterin as Vaccines Against *Staphylococcus aureus* Mastitis by Experimental Challenge", J. Dairy Sci. 68:726-731, 1985.
Pearson & Lipman, PNAS USA, 85:2444, 1988.
Pech et al., Mol. Cell. Biol., 9:396, 1989.
Pelletier and Sonenberg, Nature, 334(6180):320-325, 1988.
Perez-Stable and Constantini, Mol. Cell. Biol., 10:1116, 1990.
Phonirndaeng et al., Mol. Microbiol., 4:393-404, 1990.
Picard and Schaffner, Nature, 307:83, 1984.
Pinkert et al., Genes and Dev., 1:268, 1987.
Ponta et al., PNAS USA, 82:1020, 1985.
Porton et al., Mol. Cell. Biol., 10:1076, 1990.
Potrykus et al., Mol. Gen. Genet., 199(2): 169-177, 1985.
Pugsley, Microbiol. Rev., 57:50-108, 1993.
Pyrn et al., Mol. Microbiol., 46;709-717, 2002.
Pyrn et al., Nat. Med., 9:533-539,2003.
Queen and Baltimore, Cell, 35:741, 1983.
Quinn et al., Mol. Cell. Biol., 9:4713, 1989.
Redondo et al., Science, 247:1225, 1990.
Reisman and Rotter, Mol. Cell. Biol., 9:3571, 1989.
Remington's Pharmaceutical Sciences, 18th Ed. Mack Printing Company, 1289-1329, 1990.
Resendez Jr. et al., Mol. Cell. Biol., 8:4579, 1988.
Ripe et al., Mol. Cell. Biol., 9:2224, 1989.
Rippe, et al., Mol. Cell Biol., 10:689-695, 1990.
Rittling et al., Nuc. Acids Res., 17:1619, 1989.
Roben et al., J Immunol. 154:6437-6445, 1995.
Rosen et al., Cell, 41:813, 1988.
Sakai et al., Genes and Dev., 2:1144, 1988.
Salid-Salim et al., Infect. Control Hosp. Epidemiol. 24:451-455, 2003.
Sam brook et al., In: Molecular cloning, Cold Spring Harbor Laboratory Press, Cold Spring Harbor, NY, 2001.
Schaffuer et al., J Mol. Biol., 201 :81, 1988.
Schneewind et al., Cell. 70:267-281, 1992.
Schneewind et al., EMBO, 12:4803-4811, 1993.
Schneewind et al., Science, 268:103-6, 1995.
Searle et al., Mol. Cell. Biol., 5:1480, 1985.
Sharp and Marciniak, Cell, 59:229, 1989.
Shaul and Ben-Levy, EMBO J, 6:1913, 1987.
Shaw et al., Microbiology, 150:217-228, 2004.
Sheagren, N Engl. J Med. 310:1368-1373, 1984.
Sherman et al., Mol. Cell. Biol., 9:50, 1989.
Shopsin et al., J Clin. Microbiol., 37:3556-63, 1999.
Sibbald et al., Microbial. Mol Biol. Rev., 70:755-788,2006.
Silverman and Goodyear. Nat. Rev. Immunol., 6:465-75, 2006.
Sjodahl, Eur. J Biochem. 73:343-351, 1977.
Sjoquist et al., Eur. J Biochem. 30:190-194, 1972.
Sleigh and Lockett, J EMBO, 4:3831, 1985.
Smith & Waterman, Adv. Appl. Math., 2:482, 1981.
Smith et al., Brit. J Exp. Pathol., 28:57, 1947.
Sorensen et al.,Infect.Immun., 63:1710-1717,1995.
Spalholz et al., Cell, 42:183, 1985.
Spandau and Lee, J Virology, 62:427, 1988.
Spandidos and Wilkie, EMBO J., 2:1193, 1983.
Srivastava, et al., Mycopathologia. 138:21-8, 1997.
Stanley et al., PNAS USA, 100:13001-13006, 2003.
Stephens and Hentschel, Biochem J, 248:1, 1987.
Stewart and Young, In: Solid Phase Peptide Synthesis, 2d. ed., Pierce Chemical Co., 1984.
Stranger-Jones et al., PNAS USA, 103:16942-16947,2006.
Stuart et al., Nature, 317:828, 1985.
Studier et al., Methods Enzymol. 185:60-89 1990.
Sullivan and Peterlin, Mol. Cell. Biol., 7:3315, 1987.
Swartzendruber and Lehman, .J Cell. Physiology, 85: 1 79, 197 5.
Takebe et al., Mol. Cell. Biol., 8:466, 1988.
Tam et al., J Am. Chem Soc., 105:6442, 1983.
Tavemier et al.,Nature, 301:634,1983.
Taylor and Kingston, Mol. Cell. Biol., 10:165, 1990a.
Taylor and Kingston, Mol. Cell. Biol., 10:176, 1990b.
Taylor et al., J Biol. Chem., 264:15160, 1989.
Thiesen et al., J Virology, 62:614, 1988.
Thomson et al., J Immunol., 157(2):822-826, 1996.
Tigges et al., J Immunol., 156(10):3901-3910, 1996.
Ton-That et al., PNAS USA, 96(22):12424-9, 1999.
Treisman, Cell, 42:889, 1985.
Tronche et al., Mol. Biol. Med., 7:173, 1990.
Trudel and Constantini, Genes and Dev., 6:954, 1987.
Tyndell et al., Nuc. Acids. Res., 9:6231, 1981.
Uhlen et al. J Biol Chem. 259:1695-1702 and 13628 (Corr.) 1984.
van den Ent and Lowe, FEES Lett., 579:3837-3841, 2005.
van Wely et al., FEMS Microbiol. Rev., 25:437-454, 2001.
Vannice and Levinson, J Virology, 62:1305, 1988.
Vasseur et al., PNAS USA, 77:1068, 1980.
Vaughan, et al., Nat. Biotech. 16; 535-539, 1998.
Wang and Calame, Cell, 47:241, 1986.
Wardenburg & Schneewind, JEM. 205(2): 287-294, 2008.
Weber et al., Cell, 36:983, 1984.
Weinberger et al., Mol. Cell. Biol., 8:988, 1984.
Weiss et al, J. Antimicrob. Chemother., 53(3):480-6, 2004.

(56) References Cited

OTHER PUBLICATIONS

Winoto and Baltimore, Cell, 59:649, 1989.
Wong et al., Gene, 10:87-94, 1980.
Xu et al, Mol. Microbiol., 66(3):787-800, 2007.
Xu et al., J. Infect. Dis., 189:2323-2333, 2004.
Yutzey et al. Mol. Cell. Biol., 9:1397, 1989.

* cited by examiner

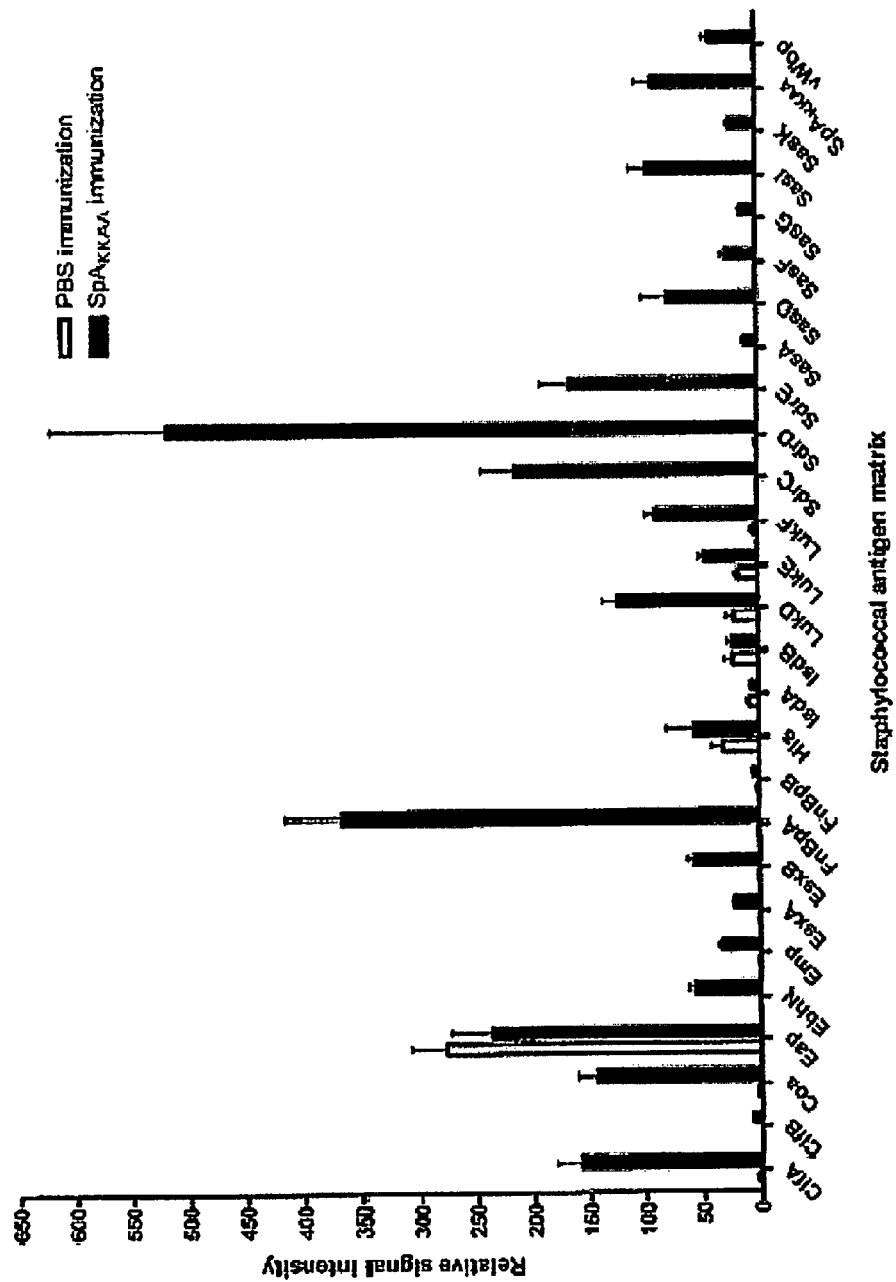

COMPOSITIONS AND METHODS RELATED TO PROTEIN A (SPA) ANTIBODIES AS AN ENHANCER OF IMMUNE RESPONSE

This application is a continuation of U.S. patent application Ser. No. 14/335,411 filed Jul. 18, 2014 (now issued as U.S. Pat. No. 9,212,219), which is a continuation of U.S. patent application Ser. No. 13/639,465 filed Jan. 18, 2013 (now issued as U.S. Pat. No. 8,808,699), which is a national stage application under 35 U.S.C. 371 of International Application No. PCT/US2011/031213 filed Apr. 5, 2011, which claims priority to U.S. Provisional Patent Application Ser. No. 61/321,050 filed Apr. 5, 2010. U.S. patent application Ser. No. 14/335,411 is also a continuation-in-part of U.S. patent application Ser. No. 13/260,878 (now issued as U.S. Pat. No. 9,567,379), which is a national stage application under 35 U.S.C. 371 of International Application No. PCT/US2010/029959 filed Apr. 5, 2010, which claims priority to U.S. Provisional Patent Application Ser. No. 61/287,996 filed Dec. 8, 2009, U.S. Provisional Patent Application Ser. No. 61/237,956 filed Aug. 28, 2009, and U.S. Provisional Patent Application Ser. No. 61/166,432 filed Apr. 3, 2009. The entire contents of each of the above-referenced disclosures are specifically incorporated herein by reference without disclaimer.

This invention was made with government support under AI057153, AI75258, AI052474, and GM007281 awarded by the National Institutes of Health. The United States government has certain rights in the invention.

BACKGROUND OF THE INVENTION

I. Field of the Invention

The present invention relates generally to the fields of immunology, microbiology, and pathology. More particularly, it concerns methods and compositions for enhancing an immune response against a bacterial antigen.

II. Background

The number of both community acquired and hospital acquired infections have increased over recent years with the increased use of intravascular devices. Hospital acquired (nosocomial) infections are a major cause of morbidity and mortality, more particularly in the United States, where it affects more than 2 million patients annually. The most frequent infections are urinary tract infections (33% of the infections), followed by pneumonia (15.5%), surgical site infections (14.8%) and primary bloodstream infections (13%) (Emorl and Gaynes, 1993).

The major nosocomial pathogens include *Staphylococcus aureus*, coagulase-negative Staphylococci (mostly *Staphylococcus epidermidis*), enterococcus spp., *Escherichia coli* and *Pseudomonas aeruginosa*. Although these pathogens cause approximately the same number of infections, the severity of the disorders they can produce combined with the frequency of antibiotic resistant isolates balance this ranking towards *S. aureus* and *S. epidermidis* as being the most significant nosocomial pathogens.

Staphylococci can cause a wide variety of diseases in humans and other animals through either toxin production or invasion. Staphylococcal toxins are also a common cause of food poisoning, as the bacteria can grow in improperly-stored food.

*Staphylococcus epidermidis* is a normal skin commensal, which is also an important opportunistic pathogen responsible for infections of impaired medical devices and infections at sites of surgery. Medical devices infected by *S. epidermidis* include cardiac pacemakers, cerebrospinal fluid shunts, continuous ambulatory peritoneal dialysis catheters, orthopedic devices and prosthetic heart valves.

*Staphylococcus aureus* is the most common cause of nosocomial infections with a significant morbidity and mortality. It is the cause of some cases of osteomyelitis, endocarditis, septic arthritis, pneumonia, abscesses, and toxic shock syndrome. *S. aureus* can survive on dry surfaces, increasing the chance of transmission. Any *S. aureus* infection can cause the staphylococcal scalded skin syndrome, a cutaneous reaction to exotoxin absorbed into the bloodstream. It can also cause a type of septicemia called pyaemia that can be life-threatening Problematically, Methicillin-resistant *Staphylococcus aureus* (MRSA) has become a major cause of hospital-acquired infections.

*S. aureus* and *S. epidermidis* infections are typically treated with antibiotics, with penicillin being the drug of choice, whereas vancomycin is used for methicillin resistant isolates. The percentage of staphylococcal strains exhibiting wide-spectrum resistance to antibiotics has become increasingly prevalent, posing a threat for effective antimicrobial therapy. In addition, the recent emergence of vancomycin resistant *S. aureus* strain has aroused fear that MRSA strains are emerging and spreading for which no effective therapy is available.

An alternative to antibiotic treatment for staphylococcal infections is under investigation that uses antibodies directed against staphylococcal antigens. This therapy involves administration of polyclonal antisera (WO00/15238, WO00/12132) or treatment with monoclonal antibodies against lipoteichoic acid (WO98/57994).

An alternative approach would be the use of active vaccination to generate an immune response against staphylococci. The *S. aureus* genome has been sequenced and many of the coding sequences have been identified (WO02/094868, EP0786519), which can lead to the identification of potential antigens. The same is true for *S. epidermidis* (WO01/34809). As a refinement of this approach, others have identified proteins that are recognized by hyperimmune sera from patients who have suffered staphylococcal infection (WO01/98499, WO02/059148).

*S. aureus* secretes a plethora of virulence factors into the extracellular milieu (Archer, 1998; Dinges et al., 2000; Foster, 2005; Shaw et al., 2004; Sibbald et al., 2006). Like most secreted proteins, these virulence factors are translocated by the Sec machinery across the plasma membrane. Proteins secreted by the Sec machinery bear an N-terminal leader peptide that is removed by leader peptidase once the pre-protein is engaged in the Sec translocon (Dalbey and Wickner, 1985; van Wely et al., 2001). Recent genome analysis suggests that Actinobacteria and members of the Firmicutes encode an additional secretion system that recognizes a subset of proteins in a Sec-independent manner (Pallen, 2002). ESAT-6 (early secreted antigen target 6 kDa) and CFP-10 (culture filtrate antigen 10 kDa) of *Mycobacterium tuberculosis* represent the first substrates of this novel secretion system termed ESX-1 or Snm in *M. tuberculosis* (Andersen et al., 1995; Hsu et al., 2003; Pym et al., 2003; Stanley et al., 2003). In *S. aureus*, two ESAT-6 like factors designated EsxA and EsxB are secreted by the Ess pathway (ESAT-6 secretion system) (Burts et al., 2005).

The first generation of vaccines targeted against *S. aureus* or against the exoproteins it produces have met with limited success (Lee, 1996). There remains a need to develop effective vaccines against staphylococcal infections. Additional compositions for treating staphylococcal infections are also needed.

SUMMARY OF THE INVENTION

Protein A (SpA) (SEQ ID NO:33), a cell wall anchored surface protein of *Staphylococcus aureus*, provides for bacterial evasion from innate and adaptive immune responses. Protein A binds immunoglobulins at their Fc portion, interacts with the VH3 domain of B cell receptors inappropriately stimulating B cell proliferation and apoptosis, binds to von Willebrand factor A1 domains to activate intracellular clotting, and also binds to the TNF Receptor-1 to contribute to the pathogenesis of staphylococcal pneumonia. Due to the fact that Protein A captures immunoglobulin and displays toxic attributes, the possibility that this surface molecule may function as a vaccine in humans has not been rigorously pursued. Here the inventors demonstrate that antibodies specific for Protein A stimulate or enhance an immune response to other bacterial antigens.

Embodiments include the use of antibodies that specifically bind Protein A and peptides that elicit such antibodies in methods and compositions for the treatment, attenuation, or prevention of bacterial and/or staphylococcal infection and/or pathological conditions resulting from such an infection. Furthermore, the present invention provides methods and compositions that can be used to treat (e.g., limiting staphylococcal abscess formation and/or persistence in a subject), attenuate, or prevent bacterial infection or pathological conditions resulting from such infection.

In certain aspects, methods for stimulating or enhancing an immune response involve administering to the subject an effective amount of an isolated protein A (SpA) specific antibody and a bacterial antigen. The bacterial antigen or immunogenic fragment can be administered before, after, and/or concurrently with the protein A specific antibody. The bacterial antigen or immunogenic fragment and the Protein A specific antibody can be administered in the same or a separate composition.

In a further aspect, the methods include stimulating or enhancing an immune response involving administering an SpA polypeptide variant prior to or after the administration of one or more bacterial antigens. The SpA polypeptide variant can be administered 12, 24, 48, 72 hours, or 1, 2, 3, 4, 5, 6, 7, 8, 9, 10 days before or after administration of one or more bacterial antigen. In certain aspects, a subject administered a SpA polypeptide variant can be evaluated for production of SpA specific antibodies prior to administration of one or more bacterial antigens or bacteria. In certain embodiments a SpA polypeptide variant can be administered 1, 2, 3, 4, 5, 6, 7, 8, 9, 10 or more times prior to or after administration of one or more bacterial antigen or bacteria. In certain embodiments the SpA variant is a full length SpA variant comprising a variant A, B, C, D, and/or E domain. In certain aspects, the SpA variant comprises or consists of the amino acid sequence that is 80, 90, 95, 98, 99, or 100% identical to the amino acid sequence of SEQ ID NO:34. In other embodiments the SpA variant comprises a segment of SpA. The SpA segment can comprise at least or at most 1, 2, 3, 4, 5 or more IgG binding domains. The IgG domains can be at least or at most 1, 2, 3, 4, 5 or more variant A, B, C, D, or E domains. In certain aspects the SpA variant comprises at least or at most 1, 2, 3, 4, 5, or more variant A domains. In a further aspect the SpA variant comprises at least or at most 1, 2, 3, 4, 5, or more variant B domains. In still a further aspect the SpA variant comprises at least or at most 1, 2, 3, 4, 5, or more variant C domains. In yet a further aspect the SpA variant comprises at least or at most 1, 2, 3, 4, 5, or more variant D domains. In certain aspects the SpA variant comprises at least or at most 1, 2, 3, 4, 5, or more variant E domains. In a further aspect the SpA variant comprises a combination of A, B, C, D, and E domains in various combinations and permutations. The combinations can include all or part of a SpA signal peptide segment, a SpA region X segment, and/or a SpA sorting signal segment. In other aspects the SpA variant does not include a SpA signal peptide segment, a SpA region X segment, and/or a SpA sorting signal segment. In certain aspects a variant A domain comprises a substitution at position(s) 7, 8, 34, and/or 35 of SEQ ID NO:4. In another aspect a variant B domain comprises a substitution at position(s) 7, 8, 34, and/or 35 of SEQ ID NO:6. In still anther aspect a variant C domain comprises a substitution at position(s) 7, 8, 34, and/or 35 of SEQ ID NO:5. In certain aspects a variant D domain comprises a substitution at position(s) 9, 10, 36, and/or 37 of SEQ ID NO:2. In a further aspect a variant E domain comprises a substitution at position(s) 6, 7, 33, and/or 34 of SEQ ID NO:3. In certain aspects, an SpA domain D variant or its equivalent can comprise a mutation at position 9 and 36; 9 and 37; 9 and 10; 36 and 37; 10 and 36; 10 and 37; 9, 36, and 37; 10, 36, and 37, 9, 10 and 36; or 9, 10 and 37 of SEQ ID NO:2. In a further aspect, analogous mutations can be included in one or more of domains A, B, C, or E. In further aspects, the amino acid glutamine (Q) at position 9 of SEQ ID NO:2 (or its analogous amino acid in other SpA domains) can be replaced with an alanine (A), an asparagine (N), an aspartic acid (D), a cysteine (C), a glutamic acid (E), a phenylalanine (F), a glycine (G), a histidine (H), an isoleucine (I), a lysine (K), a leucine (L), a methionine (M), a proline (P), a serine (S), a threonine (T), a valine (V), a tryptophane (W), or a tyrosine (Y). In some aspects the glutamine at position 9 can be substituted with an arginine (R). In a further aspect, the glutamine at position 9 of SEQ ID NO:2, or its equivalent, can be substituted with a lysine or a glycine. Any 1, 2, 3, 4, 5, 6, 7, 8, 9, 10, or more of the substitutions can be explicitly excluded. In another aspect, the amino acid glutamine (Q) at position 10 of SEQ ID NO:2 (or its analogous amino acid in other SpA domains) can be replaced with an alanine (A), an asparagine (N), an aspartic acid (D), a cysteine (C), a glutamic acid (E), a phenylalanine (F), a glycine (G), a histidine (H), an isoleucine (I), a lysine (K), a leucine (L), a methionine (M), a proline (P), a serine (S), a threonine (T), a valine (V), a tryptophane (W), or a tyrosine (Y). In some aspects the glutamine at position 10 can be substituted with an arginine (R). In a further aspect, the glutamine at position 10 of SEQ ID NO:2, or its equivalent, can be substituted with a lysine or a glycine. Any 1, 2, 3, 4, 5, 6, 7, 8, 9, 10, or more of the substitutions can be explicitly excluded. In certain aspects, the aspartic acid (D) at position 36 of SEQ ID NO:2 (or its analogous amino acid in other SpA domains) can be replaced with an alanine (A), an asparagine (N), an arginine (R), a cysteine (C), a phenylalanine (F), a glycine (G), a histidine (H), an isoleucine (I), a lysine (K), a leucine (L), a methionine (M), a proline (P), a glutamine (Q), a serine (S), a threonine (T), a valine (V), a tryptophane (W), or a tyrosine (Y). In some aspects the aspartic acid at position 36 can be substituted with a glutamic acid (E). In certain aspects, an aspartic acid at position 36 of SEQ ID NO:2, or its equivalent, can be substituted with an alanine or a serine. Any 1, 2, 3, 4, 5, 6, 7, 8, 9, 10, or more of the substitutions can be explicitly excluded. In another aspect, the aspartic acid (D) at position 37 of SEQ ID NO:2 (or its analogous amino acid in other SpA domains) can be replaced with an alanine (A), an asparagine (N), an arginine (R), a cysteine (C), a phenylalanine (F), a glycine (G), a histidine (H), an isoleucine (I), a lysine (K), a leucine (L), a methionine (M), a proline (P), a glutamine (Q), a serine (S), a threonine (T), a valine (V), a tryptophane (W), or a tyrosine (Y). In some aspects the aspartic acid at position 37 can be substituted with a glutamic acid (E). In certain aspects, an aspartic acid at position 37 of SEQ ID NO:2, or its equivalent, can be substituted with an alanine or a serine. Any 1, 2, 3, 4, 5, 6, 7, 8, 9, 10, or more of the substitutions can be explicitly excluded. In a particular embodiment the amino at position 9 of SEQ ID NO:2 (or an analogous amino acid in another SpA domain) is replaced by an alanine (A), a glycine (G), an isoleucine (I), a leucine (L), a proline (P), a serine (S), or a valine (V). In certain aspects the amino acid at position 9 of SEQ ID NO:2 is replaced by a glycine. In a further aspect the amino acid at position 9 of SEQ ID NO:2 is replaced by a lysine. In a particular embodiment the amino at position 10 of SEQ ID NO:2 (or an analogous amino acid in another SpA domain) is replaced by an alanine (A), a glycine (G), an isoleucine (1), a leucine (L), a proline (P), a serine (S), or a valine (V). In certain aspects the amino acid at position 10 of SEQ ID NO:2 is replaced by a glycine. In a further aspect the amino acid at position 10 of SEQ ID NO:2 is replaced by a lysine. In a particular embodiment the amino at position 36 of SEQ ID NO:2 (or an analogous amino acid in another SpA domain) is replaced by an alanine (A), a glycine (G), an isoleucine (I), a leucine (L), a proline (P), a serine (S), or a valine (V). In certain aspects the amino acid at position 36 of SEQ ID NO:2 is replaced by a serine. In a further aspect the amino acid at position 36 of SEQ ID NO:2 is replaced by an alanine. In a particular embodiment the amino at position 37 of SEQ ID NO:2 (or an analogous amino acid in another SpA domain) is replaced by an alanine (A), a glycine (G), an isoleucine (1), a leucine (L), a proline (P), a serine (S), or a valine (V). In certain aspects the amino acid at position 37 of SEQ ID NO:2 is replaced by a serine. In a further aspect the amino acid at position 37 of SEQ ID NO:2 is replaced by an alanine. In certain aspects the SpA variant includes a substitution of (a) one or more amino acid substitution in an IgG Fc binding sub-domain of SpA domain A, B, C, D, and/or E that disrupts or decreases binding to IgG Fc, and (b) one or more amino acid substitution in a $V_H3$ binding sub-domain of SpA domain A, B, C, D, and/or E that disrupts or decreases binding to $V_H3$. In still further aspects the amino acid sequence of a SpA variant comprises an amino acid sequence that is at least 50%, 60%, 70%, 80%, 90%, 95%, or 100% identical, including all values and ranges there between, to the amino acid sequence of SEQ ID NOs:2-6. In a further aspect the SpA variant includes (a) one or more amino acid substitution in an IgG Fc binding sub-domain of SpA domain D, or at a corresponding amino acid position in other IgG domains, that disrupts or decreases binding to IgG Fc, and (b) one or more amino acid substitution in a $V_H3$ binding sub-domain of SpA domain D, or at a corresponding amino acid position in other IgG domains, that disrupts or decreases binding to $V_H3$. In certain aspects amino acid residue F5, Q9, Q10, S11, F13, Y14, L17, N28, I31, and/or K35 (SEQ ID NO:2, QQNNFNKDQQSAFYEILNMPNLNEAQRNGFIQS-LKDDPSQSTNVLGEAKKLNES) of the IgG Fc binding sub-domain of domain D are modified or substituted. In certain aspects amino acid residue Q26, G29, F30, S33, D36, D37, Q40, N43, and/or E47 (SEQ ID NO:2) of the $V_H3$ binding sub-domain of domain D are modified or substituted such that binding to Fc or $V_H3$ is attenuated. In further aspects corresponding modifications or substitutions can be engineered in corresponding positions of the domain A, B, C, and/or E. Corresponding positions are defined by alignment of the domain D amino acid sequence with one or more of the amino acid sequences from other IgG binding domains of SpA. In certain aspects the amino acid substitution can be any of the other 20 amino acids. In a further aspect conservative amino acid substitutions can be specifically excluded from possible amino acid substitutions. In other aspects only non-conservative substitutions are included. In any event, any substitution or combination of substitutions that reduces the binding of the domain such that SpA toxicity is significantly reduced is contemplated. The significance of the reduction in binding refers to a variant that produces minimal to no toxicity when introduced into a subject and can be assessed using in vitro methods described herein. In certain embodiments, a variant SpA comprises at least or at most 1, 2, 3, 4, 5, 6, 7, 8, 9, 10, or more variant SpA domain D peptides. In certain aspects 1, 2, 3, 4, 5, 6, 7, 8, 9, 10, 11, 12, 13, 14, 15, 16, 17, 18, or 19 or more amino acid residues of the variant SpA are substituted or modified—including but not limited to amino acids F5, Q9, Q10, S11, F13, Y14, L17, N28, I31, and/or K35 (SEQ ID NO:2) of the IgG Fc binding sub-domain of domain D and amino acid residue Q26, G29, F30, S33, D36, D37, Q40, N43, and/or E47 (SEQ ID NO:2) of the $V_H3$ binding sub-domain of domain D. In one aspect of the invention glutamine residues at position 9 and/or 10 of SEQ ID NO:2 (or corresponding positions in other domains) are mutated. In another aspect, aspartic acid residues 36 and/or 37 of SEQ ID NO:2 (or corresponding positions in other domains) are mutated. In a further aspect, glutamine 9 and 10, and aspartic acid residues 36 and 37 are mutated. Purified non-toxigenic SpA or SpA-D mutants/variants described herein are no longer able to significantly bind (i.e., demonstrate attenuated or disrupted binding affinity) Fcγ or F(ab)₂ $V_H3$ and also do not stimulate B cell apoptosis. These non-toxigenic Protein A variants can be used to enhance or stimulate an immune response against a bacterial antigen, thereby raising humoral immune responses that confer protective immunity against S. aureus challenge. Compared to wild-type full-length Protein A or the wild-type SpA-domain D, immunization with SpA-D variants resulted in an increase in Protein A specific antibody. Using a mouse model of staphylococcal challenge and abscess formation, it was observed that immunization with the non-toxigenic Protein A variants generated significant protection from staphylococcal infection and abscess formation. As virtually all S. aureus strains express Protein A, immunization of humans with the non-toxigenic Protein A variants can neutralize this virulence factor and thereby establish protective immunity. In certain aspects the protective immunity protects or ameliorates infection by drug resistant strains of Staphylococcus, such as USA300 and other MRSA strains. In certain embodiments 1, 2, 3, 4, 5, 6, 7, 8, 9 10 or more SpA variants can be specifically excluded from the claimed invention.

Bacterial antigens include, but are not limited to (i) a secreted virulence factor, and/or a cell surface protein or peptide, or (ii) a recombinant nucleic acid molecule encoding a secreted virulence factor, and/or a cell surface protein or peptide. The bacterial antigen can include one or more of at least or at most 1, 2, 3, 4, 5, 6, 7, 8, 9, 10, 11, 12, 13, 14, 15, 16, 17, 18, or 19 additional staphylococcal antigen or immunogenic fragment thereof, including, but not limited to FnBpA, FnBpB, LukD (GI:2765304), LukE (GI:2765303), LukF (GI:12231006), SasA, SasD, SasG, SasI, SasK, SpA (and variants thereof), Eap, Ebh, Emp, EsaB, EsaC, EsxA, EsxB, SdrC, SdrD, SdrE, IsdA, IsdB, ClfA, ClfB, Coa, Hla (e.g., H35 mutants), IsdC, SasF, vWbp, vWh, 52 kDa vitronectin binding protein (WO 01/60852), Aaa (GenBank CAC80837), Aap (GenBank accession AJ249487), Ant (GenBank accession NP_372518), autolysin glucosaminidase, autolysin amidase, Cna, collagen binding protein (U.S. Pat. No. 6,288,214), EFB (FIB), Elastin binding protein (EbpS), EPB, FbpA, fibrinogen binding protein (U.S. Pat. No. 6,008,341), Fibronectin binding protein (U.S. Pat. No. 5,840,846), FnbA, FnbB, GehD (US 2002/0169288), HarA, HBP, Immunodominant ABC transporter, IsaA/PisA, laminin receptor, Lipase GehD, MAP, Mg2+ transporter, MHC II analogue (U.S. Pat. No. 5,648,240), MRPII, Npase, RNA III activating protein (RAP), SasA, SasB, SasC, SasD, SasK, SBI, SdrF (WO 00/12689), SdrG/Fig (WO 00/12689), SdrH (WO 00/12689), SEA exotoxins (WO 00/02523), SEB exotoxins (WO 00/02523), SitC and Ni ABC transporter, SitC/MntC/saliva binding protein (U.S. Pat. No. 5,801,234), SsaA, SSP-1, SSP-2, and/or Vitronectin binding protein (see PCT publications WO2007/113222, WO2007/113223, WO2006/032472, WO2006/032475, WO2006/032500, each of which is incorporated herein by reference in their entirety). In certain aspects, the bacterial antigen is a staphylococcal antigen. The staphylococcal antigen can be selected from the group consisting of: FnBpA, FnBpB, LukD, LukE, LukF, SasA, SasD, SasG, SasI, SasK, SpA (and variants thereof), Eap, Ebh, Emp, EsaB, EsaC, EsxA, EsxB, SdrC, SdrD, SdrE, IsdA, IsdB, ClfA, ClfB, Coa, Hla (e.g., H35 mutants), IsdC, SasF, vWbp, vWh and immunogenic fragments thereof. In certain aspects the bacterial antigens include one or more of sta001, sta002, sta003, sta004, sta005, sta006, sta007, sta008, sta009, sta010, sta011, sta012, sta013, sta014, sta015, sta016, sta017, sta018, sta019, sta020, sta021, sta022, sta023, sta024, sta025, sta026, sta027, sta028, sta029, sta030, sta031, sta032, sta033, sta034, sta035, sta036, sta037, sta038, sta039, sta040, sta041, sta042, sta043, sta044, sta045, sta046, sta047, sta048, sta049, sta050, sta051, sta052, sta053, sta054, sta055, sta056, sta057, sta058, sta059, sta060, sta061, sta062, sta063, sta064, sta065, sta066, sta067, sta068, sta069, sta070, sta071, sta072, sta073, sta074, sta075, sta076, sta077, sta078, sta079, sta080, sta081, sta082, sta083, sta084, sta085, sta086, sta087, sta088, sta089, sta090, sta091, sta092, sta093, sta094, sta095, sta096, sta097, sta098, sta099, sta100, sta101, sta102, sta103, sta104, sta105, sta106, sta107, sta108, sta109, sta110, sta111, sta112, sta113, sta114, sta115, sta116, sta117, sta118, sta119, sta120, or EsxAB hybrid (SEQ ID NO:155) polypeptide or immunogenic fragment thereof (see PCT publication WO/2010/119343, which is incorporated herein by reference in its entirety).

In certain embodiments, the claimed invention specifically excludes 1, 2, 3, 4, 5, 6, 7, 8, 9, 10 or more of FnBpA, FnBpB, LukD (GI:2765304), LukE (GI:2765303), LukF (GI:12231006), SasA, SasD, SasG, SasI, SasK, SpA (and variants thereof), Eap, Ebh, Emp, EsaB, EsaC, EsxA, EsxB, SdrC, SdrD, SdrE, IsdA, IsdB, ClfA, ClfB, Coa, Hla (e.g., H35 mutants), IsdC, SasF, vWbp, vWh, 52 kDa vitronectin binding protein (WO 01/60852), Aaa (GenBank CAC80837), Aap (GenBank accession AJ249487), Ant (GenBank accession NP_372518), autolysin glucosaminidase, autolysin amidase, Cna, collagen binding protein (U.S. Pat. No. 6,288,214), EFB (FIB), Elastin binding protein (EbpS), EPB, FbpA, fibrinogen binding protein (U.S. Pat. No. 6,008,341), Fibronectin binding protein (U.S. Pat. No. 5,840,846), FnbA, FnbB, GehD (US 2002/0169288), HarA, HBP, Immunodominant ABC transporter, IsaA/PisA, laminin receptor, Lipase GehD, MAP, Mg2+ transporter, MHC II analogue (U.S. Pat. No. 5,648,240), MRPII, Npase, RNA III activating protein (RAP), SasA, SasB, SasC, SasD, SasK, SBI, SdrF (WO 00/12689), SdrG/Fig (WO 00/12689), SdrH (WO 00/12689), SEA exotoxins (WO 00/02523), SEB exotoxins (WO 00/02523), SitC and Ni ABC transporter, SitC/MntC/saliva binding protein (U.S. Pat. No. 5,801,234), SsaA, SSP-1, SSP-2, and/or Vitronectin binding protein (see PCT publications WO2007/113222, WO2007/113223, WO2006/032472, WO2006/032475, WO2006/032500, each of which is incorporated herein by reference in their entirety). In certain aspects, the bacterial antigen is a staphylococcal antigen. The staphylococcal antigen can be selected from the group consisting of: FnBpA, FnBpB, LukD, LukE, LukF, SasA, SasD, SasG, SasI, SasK, SpA (and variants thereof), Eap, Ebh, Emp, EsaB, EsaC, EsxA, EsxB, SdrC, SdrD, SdrE, IsdA, IsdB, ClfA, ClfB, Coa, Hla (e.g., H35 mutants), IsdC, SasF, vWbp, vWh and immunogenic fragments thereof. In certain aspects the bacterial antigens include one or more of sta001, sta002, sta003, sta004, sta005, sta006, sta007, sta008, sta009, sta010, sta011, sta012, sta013, sta014, sta015, sta016, sta017, sta018, sta019, sta020, sta021, sta022, sta023, sta024, sta025, sta026, sta027, sta028, sta029, sta030, sta031, sta032, sta033, sta034, sta035, sta036, sta037, sta038, sta039, sta040, sta041, sta042, sta043, sta044, sta045, sta046, sta047, sta048, sta049, sta050, sta051, sta052, sta053, sta054, sta055, sta056, sta057, sta058, sta059, sta060, sta061, sta062, sta063, sta064, sta065, sta066, sta067, sta068, sta069, sta070, sta071, sta072, sta073, sta074, sta075, sta076, sta077, sta078, sta079, sta080, sta081, sta082, sta083, sta084, sta085, sta086, sta087, sta088, sta089, sta090, sta091, sta092, sta093, sta094, sta095, sta096, sta097, sta098, sta099, sta100, sta101, sta102, sta103, sta104, sta105, sta106, sta107, sta108, sta109, sta110, sta111, sta112, sta113, sta114, sta115, sta116, sta117, sta118, sta119, sta120, or EsxAB hybrid polypeptide or immunogenic fragment thereof Certain embodiments are directed to an immunogenic composition comprising an isolated Protein A (SpA) specific antibody and a bacterial antigen, wherein the Protein A specific antibody enhances an immune response to the bacterial antigen. In certain aspects, the antibody is a polyclonal antibody, a monoclonal antibody, or an antibody fragment. In still further aspects, the bacterial antigen is comprised in or on a bacteria. The bacteria can be an attenuated bacteria, in particular an attenuated staphylococcal bacteria.

In certain embodiments a subject is administered an SpA polypeptide variant (before or after administering one or more bacterial antigens) or administered a protein A specific antibody in combination with one or more bacterial antigens selected from: FnBpA antigen or immunogenic fragment thereof, FnBpB antigen or immunogenic fragment thereof, LukD antigen or immunogenic fragment thereof, LukE antigen or immunogenic fragment thereof, LukF antigen or immunogenic fragment thereof, SasA antigen or immunogenic fragment thereof, SasD antigen or immunogenic fragment thereof, SasG antigen or immunogenic fragment thereof, SasI antigen or immunogenic fragment thereof, SasK antigen or immunogenic fragment thereof, SpA (and variants thereof) antigen or immunogenic fragment thereof, Eap antigen or immunogenic fragment thereof, Ebh antigen or immunogenic fragment thereof, Emp antigen or immunogenic fragment thereof, EsaB antigen or immunogenic fragment thereof, EsaC antigen or immunogenic fragment thereof, EsxA antigen or immunogenic fragment thereof, EsxB antigen or immunogenic fragment thereof, SdrC antigen or immunogenic fragment thereof, SdrD antigen or immunogenic fragment thereof, SdrE antigen or immunogenic fragment thereof, IsdA antigen or immunogenic fragment thereof, IsdB antigen or immunogenic fragment thereof, ClfA antigen or immunogenic fragment thereof, ClfB antigen or immunogenic fragment thereof, Coa antigen or immunogenic fragment thereof, Hla (e.g., H35 mutants) antigen or immunogenic fragment thereof, IsdC antigen or immunogenic fragment thereof, SasF antigen or immunogenic fragment thereof, vWbp antigen or immunogenic fragment thereof, vWh antigen or immunogenic fragment thereof, sta001 antigen or immunogenic fragment thereof, sta002 antigen or immunogenic fragment thereof, sta003 antigen or immunogenic fragment thereof, sta004 antigen or immunogenic fragment thereof, sta005 antigen or immunogenic fragment thereof, sta006 antigen or immunogenic fragment thereof, sta007 antigen or immunogenic fragment thereof, sta008 antigen or immunogenic fragment thereof, sta009 antigen or immunogenic fragment thereof, sta010 antigen or immunogenic fragment thereof, sta011 antigen or immunogenic fragment thereof, sta012 antigen or immunogenic fragment thereof, sta013 antigen or immunogenic fragment thereof, sta014 antigen or immunogenic fragment thereof, sta015 antigen or immunogenic fragment thereof, sta016 antigen or immunogenic fragment thereof, sta017 antigen or immunogenic fragment thereof, sta018 antigen or immunogenic fragment thereof, sta019 antigen or immunogenic fragment thereof, sta020 antigen or immunogenic fragment thereof, sta021 antigen or immunogenic fragment thereof, sta022 antigen or immunogenic fragment thereof, sta023 antigen or immunogenic fragment thereof, sta024 antigen or immunogenic fragment thereof, sta025 antigen or immunogenic fragment thereof, sta026 antigen or immunogenic fragment thereof, sta027 antigen or immunogenic fragment thereof, sta028 antigen or immunogenic fragment thereof, sta029 antigen or immunogenic fragment thereof, sta030 antigen or immunogenic fragment thereof, sta031 antigen or immunogenic fragment thereof, sta032 antigen or immunogenic fragment thereof, sta033 antigen or immunogenic fragment thereof, sta034 antigen or immunogenic fragment thereof, sta035 antigen or immunogenic fragment thereof, sta036 antigen or immunogenic fragment thereof, sta037 antigen or immunogenic fragment thereof, sta038 antigen or immunogenic fragment thereof, sta039 antigen or immunogenic fragment thereof, sta040 antigen or immunogenic fragment thereof, sta041 antigen or immunogenic fragment thereof, sta042 antigen or immunogenic fragment thereof, sta043 antigen or immunogenic fragment thereof, sta044 antigen or immunogenic fragment thereof, sta045 antigen or immunogenic fragment thereof, sta046 antigen or immunogenic fragment thereof, sta047 antigen or immunogenic fragment thereof, sta048 antigen or immunogenic fragment thereof, sta049 antigen or immunogenic fragment thereof, sta050 antigen or immunogenic fragment thereof, sta051 antigen or immunogenic fragment thereof, sta052 antigen or immunogenic fragment thereof, sta053 antigen or immunogenic fragment thereof, sta054 antigen or immunogenic fragment thereof, sta055 antigen or immunogenic fragment thereof, sta056 antigen or immunogenic fragment thereof, sta057 antigen or immunogenic fragment thereof, sta058 antigen or immunogenic fragment thereof, sta059 antigen or immunogenic fragment thereof, sta060 antigen or immunogenic fragment thereof, sta061 antigen or immunogenic fragment thereof, sta062 antigen or immunogenic fragment thereof, sta063 antigen or immunogenic fragment thereof, sta064 antigen or immunogenic fragment thereof, sta065 antigen or immunogenic fragment thereof, sta066 antigen or immunogenic fragment thereof, sta067 antigen or immunogenic fragment thereof, sta068 antigen or immunogenic fragment thereof, sta069 antigen or immunogenic fragment thereof, sta070 antigen or immunogenic fragment thereof, sta071 antigen or immunogenic fragment thereof, sta072 antigen or immunogenic fragment thereof, sta073 antigen or immunogenic fragment thereof, sta074 antigen or immunogenic fragment thereof, sta075 antigen or immunogenic fragment thereof, sta076 antigen or immunogenic fragment thereof, sta077 antigen or immunogenic fragment thereof, sta078 antigen or immunogenic fragment thereof, sta079 antigen or immunogenic fragment thereof, sta080 antigen or immunogenic fragment thereof, sta081 antigen or immunogenic fragment thereof, sta082 antigen or immunogenic fragment thereof, sta083 antigen or immunogenic fragment thereof, sta084 antigen or immunogenic fragment thereof, sta085 antigen or immunogenic fragment thereof, sta086 antigen or immunogenic fragment thereof, sta087 antigen or immunogenic fragment thereof, sta088 antigen or immunogenic fragment thereof, sta089 antigen or immunogenic fragment thereof, sta090 antigen or immunogenic fragment thereof, sta091 antigen or immunogenic fragment thereof, sta092 antigen or immunogenic fragment thereof, sta093 antigen or immunogenic fragment thereof, sta094 antigen or immunogenic fragment thereof, sta095 antigen or immunogenic fragment thereof, sta096 antigen or immunogenic fragment thereof, sta097 antigen or immunogenic fragment thereof, sta098 antigen or immunogenic fragment thereof, sta099 antigen or immunogenic fragment thereof, sta100 antigen or immunogenic fragment thereof, sta101 antigen or immunogenic fragment thereof, sta102 antigen or immunogenic fragment thereof, sta103 antigen or immunogenic fragment thereof, sta104 antigen or immunogenic fragment thereof, sta105 antigen or immunogenic fragment thereof, sta106 antigen or immunogenic fragment thereof, sta107 antigen or immunogenic fragment thereof, sta108 antigen or immunogenic fragment thereof, sta109 antigen or immunogenic fragment thereof, sta110 antigen or immunogenic fragment thereof, sta111 antigen or immunogenic fragment thereof, sta112 antigen or immunogenic fragment thereof, sta113 antigen or immunogenic fragment thereof, sta114 antigen or immunogenic fragment thereof, sta115 antigen or immunogenic fragment thereof, sta116 antigen or immunogenic fragment thereof, sta117 antigen or immunogenic fragment thereof, sta118 antigen or immunogenic fragment thereof, sta119 antigen or immunogenic fragment thereof, sta120 antigen or immunogenic fragment thereof, or EsxAB hybrid polypeptide or immunogenic fragment thereof.

In other aspects, a subject is administered an SpA polypeptide variant (before or after one or more bacterial antigens) or administered a protein A antibody (before, concurrently or after one or more bacterial antigens) in combination with FnBpA and 1, 2, 3, 4, 5, 6, 7, 8, 9, 10, 11, 12, 13, 14, 15, 16, 17, 18, 19, 20, or more bacterial antigens selected from FnBpB, LukD, LukE, LukF, SasA, SasD, SasG, SasI, SasK, SpA (and variants thereof), Eap, Ebh, Emp, EsaB, EsaC, EsxA, EsxB, SdrC, SdrD, SdrE, IsdA, IsdB, ClfA, ClfB, Coa, Hla (e.g., H35 mutants), IsdC, SasF, vWbp, vWh, sta001, sta002, sta003, sta004, sta005, sta006, sta007, sta008, sta009, sta010, sta011, sta012, sta013, sta014, sta015, sta016, sta017, sta018, sta019, sta020, sta021, sta022, sta023, sta024, sta025, sta026, sta027, sta028, sta029, sta030, sta031, sta032, sta033, sta034, sta035, sta036, sta037, sta038, sta039, sta040, sta041, sta042, sta043, sta044, sta045, sta046, sta047, sta048, sta049, sta050, sta051, sta052, sta053, sta054, sta055, sta056, sta057, sta058, sta059, sta060, sta061, sta062, sta063, sta064, sta065, sta066, sta067, sta068, sta069, sta070, sta071, sta072, sta073, sta074, sta075, sta076, sta077, sta078, sta079, sta080, sta081, sta082, sta083, sta084, sta085, sta086, sta087, sta088, sta089, sta090, sta091, sta092, sta093, sta094, sta095, sta096, sta097, sta098, sta099, sta100, sta101, sta102, sta103, sta104, sta105, sta106, sta107, sta108, sta109, sta110, sta111, sta112, sta113, sta114, sta115, sta116, sta117, sta118, sta119, sta120, or EsxAB hybrid polypeptide or immunogenic fragment thereof.

In other aspects, a subject is administered an SpA polypeptide variant (before or after one or more bacterial antigens) or administered a protein A antibody (before, concurrently or after one or more bacterial antigens) in combination with FnBpB and 1, 2, 3, 4, 5, 6, 7, 8, 9, 10, 11, 12, 13, 14, 15, 16, 17, 18, 19, 20, or more bacterial antigens selected from FnBpA, LukD, LukE, LukF, SasA, SasD, SasG, SasI, SasK, SpA (and variants thereof), Eap, Ebh, Emp, EsaB, EsaC, EsxA, EsxB, SdrC, SdrD, SdrE, IsdA, IsdB, ClfA, ClfB, Coa, Hla (e.g., H35 mutants), IsdC, SasF, vWbp, vWh, sta001, sta002, sta003, sta004, sta005, sta006, sta007, sta008, sta009, sta010, sta011, sta012, sta013, sta014, sta015, sta016, sta017, sta018, sta019, sta020, sta021, sta022, sta023, sta024, sta025, sta026, sta027, sta028, sta029, sta030, sta031, sta032, sta033, sta034, sta035, sta036, sta037, sta038, sta039, sta040, sta041, sta042, sta043, sta044, sta045, sta046, sta047, sta048, sta049, sta050, sta051, sta052, sta053, sta054, sta055, sta056, sta057, sta058, sta059, sta060, sta061, sta062, sta063, sta064, sta065, sta066, sta067, sta068, sta069, sta070, sta071, sta072, sta073, sta074, sta075, sta076, sta077, sta078, sta079, sta080, sta081, sta082, sta083, sta084, sta085, sta086, sta087, sta088, sta089, sta090, sta091, sta092, sta093, sta094, sta095, sta096, sta097, sta098, sta099, sta100, sta101, sta102, sta103, sta104, sta105, sta106, sta107, sta108, sta109, sta110, sta111, sta112, sta113, sta114, sta115, sta116, sta117, sta118, sta119, sta120, or EsxAB hybrid polypeptide or immunogenic fragment thereof.

In other aspects, a subject is administered an SpA polypeptide variant (before or after one or more bacterial antigens) or administered a protein A antibody (before, concurrently or after one or more bacterial antigens) in combination with LukD and 1, 2, 3, 4, 5, 6, 7, 8, 9, 10, 11, 12, 13, 14, 15, 16, 17, 18, 19, 20, or more bacterial antigens selected from FnBpA, FnBpB, LukE, LukF, SasA, SasD, SasG, SasI, SasK, SpA (and variants thereof), Eap, Ebh, Emp, EsaB, EsaC, EsxA, EsxB, SdrC, SdrD, SdrE, IsdA, IsdB, ClfA, ClfB, Coa, Hla (e.g., H35 mutants), IsdC, SasF, vWbp, vWh, sta001, sta002, sta003, sta004, sta005, sta006, sta007, sta008, sta009, sta010, sta011, sta012, sta013, sta014, sta015, sta016, sta017, sta018, sta019, sta020, sta021, sta022, sta023, sta024, sta025, sta026, sta027, sta028, sta029, sta030, sta031, sta032, sta033, sta034, sta035, sta036, sta037, sta038, sta039, sta040, sta041, sta042, sta043, sta044, sta045, sta046, sta047, sta048, sta049, sta050, sta051, sta052, sta053, sta054, sta055, sta056, sta057, sta058, sta059, sta060, sta061, sta062, sta063, sta064, sta065, sta066, sta067, sta068, sta069, sta070, sta071, sta072, sta073, sta074, sta075, sta076, sta077, sta078, sta079, sta080, sta081, sta082, sta083, sta084, sta085, sta086, sta087, sta088, sta089, sta090, sta091, sta092, sta093, sta094, sta095, sta096, sta097, sta098, sta099, sta100, sta101, sta102, sta103, sta104, sta105, sta106, sta107, sta108, sta109, sta110, sta111, sta112, sta113, sta114, sta115, sta116, sta117, sta118, sta119, sta120, or EsxAB hybrid polypeptide or immunogenic fragment thereof.

In other aspects, a subject is administered an SpA polypeptide variant (before or after one or more bacterial antigens) or administered a protein A antibody (before, concurrently or after one or more bacterial antigens) in combination with LukE and 1, 2, 3, 4, 5, 6, 7, 8, 9, 10, 11, 12, 13, 14, 15, 16, 17, 18, 19, 20, or more bacterial antigens selected from FnBpA, FnBpB, LukD, LukF, SasA, SasD, SasG, SasI, SasK, SpA (and variants thereof), Eap, Ebh, Emp, EsaB, EsaC, EsxA, EsxB, SdrC, SdrD, SdrE, IsdA, IsdB, ClfA, ClfB, Coa, Hla (e.g., H35 mutants), IsdC, SasF, vWbp, vWh, sta001, sta002, sta003, sta004, sta005, sta006, sta007, sta008, sta009, sta010, sta011, sta012, sta013, sta014, sta015, sta016, sta017, sta018, sta019, sta020, sta021, sta022, sta023, sta024, sta025, sta026, sta027, sta028, sta029, sta030, sta031, sta032, sta033, sta034, sta035, sta036, sta037, sta038, sta039, sta040, sta041, sta042, sta043, sta044, sta045, sta046, sta047, sta048, sta049, sta050, sta051, sta052, sta053, sta054, sta055, sta056, sta057, sta058, sta059, sta060, sta061, sta062, sta063, sta064, sta065, sta066, sta067, sta068, sta069, sta070, sta071, sta072, sta073, sta074, sta075, sta076, sta077, sta078, sta079, sta080, sta081, sta082, sta083, sta084, sta085, sta086, sta087, sta088, sta089, sta090, sta091, sta092, sta093, sta094, sta095, sta096, sta097, sta098, sta099, sta100, sta101, sta102, sta103, sta104, sta105, sta106, sta107, sta108, sta109, sta110, sta111, sta112, sta113, sta114, sta115, sta116, sta117, sta118, sta119, sta120, or EsxAB hybrid polypeptide or immunogenic fragment thereof.

In other aspects, a subject is administered an SpA polypeptide variant (before or after one or more bacterial antigens) or administered a protein A antibody (before, concurrently or after one or more bacterial antigens) in combination with LukF and 1, 2, 3, 4, 5, 6, 7, 8, 9, 10, 11, 12, 13, 14, 15, 16, 17, 18, 19, 20, or more bacterial antigens selected from FnBpA, FnBpB, LukD, LukE, SasA, SasD, SasG, SasI, SasK, SpA (and variants thereof), Eap, Ebh, Emp, EsaB, EsaC, EsxA, EsxB, SdrC, SdrD, SdrE, IsdA, IsdB, ClfA, ClfB, Coa, Hla (e.g., H35 mutants), IsdC, SasF, vWbp, vWh, sta001, sta002, sta003, sta004, sta005, sta006, sta007, sta008, sta009, sta010, sta011, sta012, sta013, sta014, sta015, sta016, sta017, sta018, sta019, sta020, sta021, sta022, sta023, sta024, sta025, sta026, sta027, sta028, sta029, sta030, sta031, sta032, sta033, sta034, sta035, sta036, sta037, sta038, sta039, sta040, sta041, sta042, sta043, sta044, sta045, sta046, sta047, sta048, sta049, sta050, sta051, sta052, sta053, sta054, sta055, sta056, sta057, sta058, sta059, sta060, sta061, sta062, sta063, sta064, sta065, sta066, sta067, sta068, sta069, sta070, sta071, sta072, sta073, sta074, sta075, sta076, sta077, sta078, sta079, sta080, sta081, sta082, sta083, sta084, sta085, sta086, sta087, sta088, sta089, sta090, sta091, sta092, sta093, sta094, sta095, sta096, sta097, sta098, sta099, sta100, sta101, sta102, sta103, sta104, sta105, sta106, sta107, sta108, sta109, sta110, sta111, sta112, sta113, sta114, sta115, sta116, sta117, sta118, sta119, sta120, or EsxAB hybrid polypeptide or immunogenic fragment thereof.

In other aspects, a subject is administered an SpA polypeptide variant (before or after one or more bacterial antigens) or administered a protein A antibody (before, concurrently or after one or more bacterial antigens) in combination with SasA and 1, 2, 3, 4, 5, 6, 7, 8, 9, 10, 11, 12, 13, 14, 15, 16, 17, 18, 19, 20, or more bacterial antigens selected from FnBpA, FnBpB, LukD, LukE, LukF, SasD, SasG, SasI, SasK, SpA (and variants thereof), Eap, Ebh, Emp, EsaB, EsaC, EsxA, EsxB, SdrC, SdrD, SdrE, IsdA, IsdB, ClfA, ClfB, Coa, Hla (e.g., H35 mutants), IsdC, SasF, vWbp, vWh, sta001, sta002, sta003, sta004, sta005, sta006, sta007, sta008, sta009, sta010, sta011, sta012, sta013, sta014, sta015, sta016, sta017, sta018, sta019, sta020, sta021, sta022, sta023, sta024, sta025, sta026, sta027, sta028, sta029, sta030, sta031, sta032, sta033, sta034, sta035, sta036, sta037, sta038, sta039, sta040, sta041, sta042, sta043, sta044, sta045, sta046, sta047, sta048, sta049, sta050, sta051, sta052, sta053, sta054, sta055, sta056, sta057, sta058, sta059, sta060, sta061, sta062, sta063, sta064, sta065, sta066, sta067, sta068, sta069, sta070, sta071, sta072, sta073, sta074, sta075, sta076, sta077, sta078, sta079, sta080, sta081, sta082, sta083, sta084, sta085, sta086, sta087, sta088, sta089, sta090, sta091, sta092, sta093, sta094, sta095, sta096, sta097, sta098, sta099, sta100, sta101, sta102, sta103, sta104, sta105, sta106, sta107, sta108, sta109, sta111, sta111, sta112, sta113, sta114, sta115, sta116, sta117, sta118, sta119, sta120, or EsxAB hybrid polypeptide or immunogenic fragment thereof.

In other aspects, a subject is administered an SpA polypeptide variant (before or after one or more bacterial antigens) or administered a protein A antibody (before, concurrently or after one or more bacterial antigens) in combination with SasD and 1, 2, 3, 4, 5, 6, 7, 8, 9, 10, 11, 12, 13, 14, 15, 16, 17, 18, 19, 20, or more bacterial antigens selected from FnBpA, FnBpB, LukD, LukE, LukF, SasA, SasG, SasI, SasK, SpA (and variants thereof), Eap, Ebh, Emp, EsaB, EsaC, EsxA, EsxB, SdrC, SdrD, SdrE, IsdA, IsdB, ClfA, ClfB, Coa, Hla (e.g., H35 mutants), IsdC, SasF, vWbp, vWh, sta001, sta002, sta003, sta004, sta005, sta006, sta007, sta008, sta009, sta010, sta011, sta012, sta013, sta014, sta015, sta016, sta017, sta018, sta019, sta020, sta021, sta022, sta023, sta024, sta025, sta026, sta027, sta028, sta029, sta030, sta031, sta032, sta033, sta034, sta035, sta036, sta037, sta038, sta039, sta040, sta041, sta042, sta043, sta044, sta045, sta046, sta047, sta048, sta049, sta050, sta051, sta052, sta053, sta054, sta055, sta056, sta057, sta058, sta059, sta060, sta061, sta062, sta063, sta064, sta065, sta066, sta067, sta068, sta069, sta070, sta071, sta072, sta073, sta074, sta075, sta076, sta077, sta078, sta079, sta080, sta081, sta082, sta083, sta084, sta085, sta086, sta087, sta088, sta089, sta090, sta091, sta092, sta093, sta094, sta095, sta096, sta097, sta098, sta099, sta100, sta101, sta102, sta103, sta104, sta105, sta106, sta107, sta108, sta109, sta110, sta111, sta112, sta113, sta114, sta115, sta116, sta117, sta118, sta119, sta120, or EsxAB hybrid polypeptide or immunogenic fragment thereof.

In other aspects, a subject is administered an SpA polypeptide variant (before or after one or more bacterial antigens) or administered a protein A antibody (before, concurrently or after one or more bacterial antigens) in combination with SasG and 1, 2, 3, 4, 5, 6, 7, 8, 9, 10, 11, 12, 13, 14, 15, 16, 17, 18, 19, 20, or more bacterial antigens selected from FnBpA, FnBpB, LukD, LukE, LukF, SasA, SasD, SasI, SasK, SpA (and variants thereof), Eap, Ebh, Emp, EsaB, EsaC, EsxA, EsxB, SdrC, SdrD, SdrE, IsdA, IsdB, ClfA, ClfB, Coa, Hla (e.g., H35 mutants), IsdC, SasF, vWbp, vWh, sta001, sta002, sta003, sta004, sta005, sta006, sta007, sta008, sta009, sta010, sta011, sta012, sta013, sta014, sta015, sta016, sta017, sta018, sta019, sta020, sta021, sta022, sta023, sta024, sta025, sta026, sta027, sta028, sta029, sta030, sta031, sta032, sta033, sta034, sta035, sta036, sta037, sta038, sta039, sta040, sta041, sta042, sta043, sta044, sta045, sta046, sta047, sta048, sta049, sta050, sta051, sta052, sta053, sta054, sta055, sta056, sta057, sta058, sta059, sta060, sta061, sta062, sta063, sta064, sta065, sta066, sta067, sta068, sta069, sta070, sta071, sta072, sta073, sta074, sta075, sta076, sta077, sta078, sta079, sta080, sta081, sta082, sta083, sta084, sta085, sta086, sta087, sta088, sta089, sta090, sta091, sta092, sta093, sta094, sta095, sta096, sta097, sta098, sta099, sta100, sta101, sta102, sta103, sta104, sta105, sta106, sta107, sta108, sta109, sta110, sta111, sta112, sta113, sta114, sta115, sta116, sta117, sta118, sta119, sta120, or EsxAB hybrid polypeptide or immunogenic fragment thereof.

In other aspects, a subject is administered an SpA polypeptide variant (before or after one or more bacterial antigens) or administered a protein A antibody (before, concurrently or after one or more bacterial antigens) in combination with SasI and 1, 2, 3, 4, 5, 6, 7, 8, 9, 10, 11, 12, 13, 14, 15, 16, 17, 18, 19, 20, or more bacterial antigens selected from FnBpA, FnBpB, LukD, LukE, LukF, SasA, SasD, SasG, SasK, SpA (and variants thereof), Eap, Ebh, Emp, EsaB, EsaC, EsxA, EsxB, SdrC, SdrD, SdrE, IsdA, IsdB, ClfA, ClfB, Coa, Hla (e.g., H35 mutants), IsdC, SasF, vWbp, vWh, sta001, sta002, sta003, sta004, sta005, sta006, sta007, sta008, sta009, sta010, sta011, sta012, sta013, sta014, sta015, sta016, sta017, sta018, sta019, sta020, sta021, sta022, sta023, sta024, sta025, sta026, sta027, sta028, sta029, sta030, sta031, sta032, sta033, sta034, sta035, sta036, sta037, sta038, sta039, sta040, sta041, sta042, sta043, sta044, sta045, sta046, sta047, sta048, sta049, sta050, sta051, sta052, sta053, sta054, sta055, sta056, sta057, sta058, sta059, sta060, sta061, sta062, sta063, sta064, sta065, sta066, sta067, sta068, sta069, sta070, sta071, sta072, sta073, sta074, sta075, sta076, sta077, sta078, sta079, sta080, sta081, sta082, sta083, sta084, sta085, sta086, sta087, sta088, sta089, sta090, sta091, sta092, sta093, sta094, sta095, sta096, sta097, sta098, sta099, sta100, sta101, sta102, sta103, sta104, sta105, sta106, sta107, sta108, sta109, sta110, sta111, sta112, sta113, sta114, sta115, sta116, sta117, sta118, sta119, sta120, or EsxAB hybrid polypeptide or immunogenic fragment thereof.

In other aspects, a subject is administered an SpA polypeptide variant (before or after one or more bacterial antigens) or administered a protein A antibody (before, concurrently or after one or more bacterial antigens) in combination with SasK and 1, 2, 3, 4, 5, 6, 7, 8, 9, 10, 11, 12, 13, 14, 15, 16, 17, 18, 19, 20, or more bacterial antigens selected from FnBpA, FnBpB, LukD, LukE, LukF, SasA, SasD, SasG, SasI, SpA (and variants thereof), Eap, Ebh, Emp, EsaB, EsaC, EsxA, EsxB, SdrC, SdrD, SdrE, IsdA, IsdB, ClfA, ClfB, Coa, Hla (e.g., H35 mutants), IsdC, SasF, vWbp, vWh, sta001, sta002, sta003, sta004, sta005, sta006, sta007, sta008, sta009, sta010, sta011, sta012, sta013, sta014, sta015, sta016, sta017, sta018, sta019, sta020, sta021, sta022, sta023, sta024, sta025, sta026, sta027, sta028, sta029, sta030, sta031, sta032, sta033, sta034, sta035, sta036, sta037, sta038, sta039, sta040, sta041, sta042, sta043, sta044, sta045, sta046, sta047, sta048, sta049, sta050, sta051, sta052, sta053, sta054, sta055, sta056, sta057, sta058, sta059, sta060, sta061, sta062, sta063, sta064, sta065, sta066, sta067, sta068, sta069, sta070, sta071, sta072, sta073, sta074, sta075, sta076, sta077, sta078, sta079, sta080, sta081, sta082, sta083, sta084, sta085, sta086, sta087, sta088, sta089, sta090, sta091, sta092, sta093, sta094, sta095, sta096, sta097, sta098, sta099, sta100, sta101, sta102, sta103, sta104, sta105, sta106, sta107, sta108, sta109, sta110, sta111, sta112, sta113, sta114, sta115, sta116, sta117, sta118, sta119, sta120, or EsxAB hybrid polypeptide or immunogenic fragment thereof.

In other aspects, a subject is administered an SpA polypeptide variant (before or after one or more bacterial antigens) or administered a protein A antibody (before, concurrently or after one or more bacterial antigens) in combination with SpA (and variants thereof) and 1, 2, 3, 4, 5, 6, 7, 8, 9, 10, 11, 12, 13, 14, 15, 16, 17, 18, 19, 20, or more bacterial antigens selected from FnBpA, FnBpB, LukD, LukE, LukF, SasA, SasD, SasG, SasI, SasK, Eap, Ebh, Emp, EsaB, EsaC, EsxA, EsxB, SdrC, SdrD, SdrE, IsdA, IsdB, ClfA, ClfB, Coa, Hla (e.g., H35 mutants), IsdC, SasF, vWbp, vWh, sta001, sta002, sta003, sta004, sta005, sta006, sta007, sta008, sta009, sta010, sta011, sta012, sta013, sta014, sta015, sta016, sta017, sta018, sta019, sta020, sta021, sta022, sta023, sta024, sta025, sta026, sta027, sta028, sta029, sta030, sta031, sta032, sta033, sta034, sta035, sta036, sta037, sta038, sta039, sta040, sta041, sta042, sta043, sta044, sta045, sta046, sta047, sta048, sta049, sta050, sta051, sta052, sta053, sta054, sta055, sta056, sta057, sta058, sta059, sta060, sta061, sta062, sta063, sta064, sta065, sta066, sta067, sta068, sta069, sta070, sta071, sta072, sta073, sta074, sta075, sta076, sta077, sta078, sta079, sta080, sta081, sta082, sta083, sta084, sta085, sta086, sta087, sta088, sta089, sta090, sta091, sta092, sta093, sta094, sta095, sta096, sta097, sta098, sta099, sta100, sta101, sta102, sta103, sta104, sta105, sta106, sta107, sta108, sta109, sta110, sta111, sta112, sta113, sta114, sta115, sta116, sta117, sta118, sta119, sta120, or EsxAB hybrid polypeptide or immunogenic fragment thereof.

In other aspects, a subject is administered an SpA polypeptide variant (before or after one or more bacterial antigens) or administered a protein A antibody (before, concurrently or after one or more bacterial antigens) in combination with Eap and 1, 2, 3, 4, 5, 6, 7, 8, 9, 10, 11, 12, 13, 14, 15, 16, 17, 18, 19, 20, or more bacterial antigens selected from FnBpA, FnBpB, LukD, LukE, LukF, SasA, SasD, SasG, SasI, SasK, SpA (and variants thereof), Ebh, Emp, EsaB, EsaC, EsxA, EsxB, SdrC, SdrD, SdrE, IsdA, IsdB, ClfA, ClfB, Coa, Hla (e.g., H35 mutants), IsdC, SasF, vWbp, vWh, sta001, sta002, sta003, sta004, sta005, sta006, sta007, sta008, sta009, sta010, sta011, sta012, sta013, sta014, sta015, sta016, sta017, sta018, sta019, sta020, sta021, sta022, sta023, sta024, sta025, sta026, sta027, sta028, sta029, sta030, sta031, sta032, sta033, sta034, sta035, sta036, sta037, sta038, sta039, sta040, sta041, sta042, sta043, sta044, sta045, sta046, sta047, sta048, sta049, sta050, sta051, sta052, sta053, sta054, sta055, sta056, sta057, sta058, sta059, sta060, sta061, sta062, sta063, sta064, sta065, sta066, sta067, sta068, sta069, sta070, sta071, sta072, sta073, sta074, sta075, sta076, sta077, sta078, sta079, sta080, sta081, sta082, sta083, sta084, sta085, sta086, sta087, sta088, sta089, sta090, sta091, sta092, sta093, sta094, sta095, sta096, sta097, sta098, sta099, sta100, sta101, sta102, sta103, sta104, sta105, sta106, sta107, sta108, sta109, sta110, sta111, sta112, sta113, sta114, sta115, sta116, sta117, sta118, sta119, sta120, or EsxAB hybrid polypeptide or immunogenic fragment thereof.

In other aspects, a subject is administered an SpA polypeptide variant (before or after one or more bacterial antigens) or administered a protein A antibody (before, concurrently or after one or more bacterial antigens) in combination with Ebh and 1, 2, 3, 4, 5, 6, 7, 8, 9, 10, 11, 12, 13, 14, 15, 16, 17, 18, 19, 20, or more bacterial antigens selected from FnBpA, FnBpB, LukD, LukE, LukF, SasA, SasD, SasG, SasI, SasK, SpA (and variants thereof), Eap, Emp, EsaB, EsaC, EsxA, EsxB, SdrC, SdrD, SdrE, IsdA, IsdB, ClfA, ClfB, Coa, Hla (e.g., H35 mutants), IsdC, SasF, vWbp, vWh, sta001, sta002, sta003, sta004, sta005, sta006, sta007, sta008, sta009, sta010, sta011, sta012, sta013, sta014, sta015, sta016, sta017, sta018, sta019, sta020, sta021, sta022, sta023, sta024, sta025, sta026, sta027, sta028, sta029, sta030, sta031, sta032, sta033, sta034, sta035, sta036, sta037, sta038, sta039, sta040, sta041, sta042, sta043, sta044, sta045, sta046, sta047, sta048, sta049, sta050, sta051, sta052, sta053, sta054, sta055, sta056, sta057, sta058, sta059, sta060, sta061, sta062, sta063, sta064, sta065, sta066, sta067, sta068, sta069, sta070, sta071, sta072, sta073, sta074, sta075, sta076, sta077, sta078, sta079, sta080, sta081, sta082, sta083, sta084, sta085, sta086, sta087, sta088, sta089, sta090, sta091, sta092, sta093, sta094, sta095, sta096, sta097, sta098, sta099, sta100, sta101, sta102, sta103, sta104, sta105, sta106, sta107, sta108, sta109, sta110, sta111, sta112, sta113, sta114, sta115, sta116, sta117, sta118, sta119, sta120, or EsxAB hybrid polypeptide or immunogenic fragment thereof.

In other aspects, a subject is administered an SpA polypeptide variant (before or after one or more bacterial antigens) or administered a protein A antibody (before, concurrently or after one or more bacterial antigens) in combination with Emp and 1, 2, 3, 4, 5, 6, 7, 8, 9, 10, 11, 12, 13, 14, 15, 16, 17, 18, 19, 20, or more bacterial antigens selected from FnBpA, FnBpB, LukD, LukE, LukF, SasA, SasD, SasG, SasI, SasK, SpA (and variants thereof), Eap, Ebh, EsaB, EsaC, EsxA, EsxB, SdrC, SdrD, SdrE, IsdA, IsdB, ClfA, ClfB, Coa, Hla (e.g., H35 mutants), IsdC, SasF, vWbp, vWh, sta001, sta002, sta003, sta004, sta005, sta006, sta007, sta008, sta009, sta010, sta011, sta012, sta013, sta014, sta015, sta016, sta017, sta018, sta019, sta020, sta021, sta022, sta023, sta024, sta025, sta026, sta027, sta028, sta029, sta030, sta031, sta032, sta033, sta034, sta035, sta036, sta037, sta038, sta039, sta040, sta041, sta042, sta043, sta044, sta045, sta046, sta047, sta048, sta049, sta050, sta051, sta052, sta053, sta054, sta055, sta056, sta057, sta058, sta059, sta060, sta061, sta062, sta063, sta064, sta065, sta066, sta067, sta068, sta069, sta070, sta071, sta072, sta073, sta074, sta075, sta076, sta077, sta078, sta079, sta080, sta081, sta082, sta083, sta084, sta085, sta086, sta087, sta088, sta089, sta090, sta091, sta092, sta093, sta094, sta095, sta096, sta097, sta098, sta099, sta100, sta101, sta102, sta103, sta104, sta105, sta106, sta107, sta108, sta109, sta110, sta111, sta112, sta113, sta114, sta115, sta116, sta117, sta118, sta119, sta120, or EsxAB hybrid polypeptide or immunogenic fragment thereof.

In other aspects, a subject is administered an SpA polypeptide variant (before or after one or more bacterial antigens) or administered a protein A antibody (before, concurrently or after one or more bacterial antigens) in combination with EsaB and 1, 2, 3, 4, 5, 6, 7, 8, 9, 10, 11, 12, 13, 14, 15, 16, 17, 18, 19, 20, or more bacterial antigens selected from FnBpA, FnBpB, LukD, LukE, LukF, SasA, SasD, SasG, SasI, SasK, SpA (and variants thereof), Eap, Ebh, Emp, EsaC, EsxA, EsxB, SdrC, SdrD, SdrE, IsdA, IsdB, ClfA, ClfB, Coa, Hla (e.g., H35 mutants), IsdC, SasF, vWbp, vWh, sta001, sta002, sta003, sta004, sta005, sta006, sta007, sta008, sta009, sta010, sta011, sta012, sta013, sta014, sta015, sta016, sta017, sta018, sta019, sta020, sta021, sta022, sta023, sta024, sta025, sta026, sta027, sta028, sta029, sta030, sta031, sta032, sta033, sta034, sta035, sta036, sta037, sta038, sta039, sta040, sta041, sta042, sta043, sta044, sta045, sta046, sta047, sta048, sta049, sta050, sta051, sta052, sta053, sta054, sta055, sta056, sta057, sta058, sta059, sta060, sta061, sta062, sta063, sta064, sta065, sta066, sta067, sta068, sta069, sta070, sta071, sta072, sta073, sta074, sta075, sta076, sta077, sta078, sta079, sta080, sta081, sta082, sta083, sta084, sta085, sta086, sta087, sta088, sta089, sta090, sta091, sta092, sta093, sta094, sta095, sta096, sta097, sta098, sta099, sta100, sta101, sta102, sta103, sta104, sta105, sta106, sta107, sta108, sta109, sta110, sta111, sta112, sta113, sta114, sta115, sta116, sta117, sta118, sta119, sta120, or EsxAB hybrid polypeptide or immunogenic fragment thereof.

In other aspects, a subject is administered an SpA polypeptide variant (before or after one or more bacterial antigens) or administered a protein A antibody (before, concurrently or after one or more bacterial antigens) in combination with EsaC and 1, 2, 3, 4, 5, 6, 7, 8, 9, 10, 11, 12, 13, 14, 15, 16, 17, 18, 19, 20, or more bacterial antigens selected from FnBpA, FnBpB, LukD, LukE, LukF, SasA, SasD, SasG, SasI, SasK, SpA (and variants thereof), Eap, Ebh, Emp, EsaB, EsxA, EsxB, SdrC, SdrD, SdrE, IsdA, IsdB, ClfA, ClfB, Coa, Hla (e.g., H35 mutants), IsdC, SasF, vWbp, vWh, sta001, sta002, sta003, sta004, sta005, sta006, sta007, sta008, sta009, sta010, sta011, sta012, sta013, sta014, sta015, sta016, sta017, sta018, sta019, sta020, sta021, sta022, sta023, sta024, sta025, sta026, sta027, sta028, sta029, sta030, sta031, sta032, sta033, sta034, sta035, sta036, sta037, sta038, sta039, sta040, sta041, sta042, sta043, sta044, sta045, sta046, sta047, sta048, sta049, sta050, sta051, sta052, sta053, sta054, sta055, sta056, sta057, sta058, sta059, sta060, sta061, sta062, sta063, sta064, sta065, sta066, sta067, sta068, sta069, sta070, sta071, sta072, sta073, sta074, sta075, sta076, sta077, sta078, sta079, sta080, sta081, sta082, sta083, sta084, sta085, sta086, sta087, sta088, sta089, sta090, sta091, sta092, sta093, sta094, sta095, sta096, sta097, sta098, sta099, sta100, sta101, sta102, sta103, sta104, sta105, sta106, sta107, sta108, sta109, sta110, sta111, sta112, sta113, sta114, sta115, sta116, sta117, sta118, sta119, sta120, or EsxAB hybrid polypeptide or immunogenic fragment thereof.

In other aspects, a subject is administered an SpA polypeptide variant (before or after one or more bacterial antigens) or administered a protein A antibody (before, concurrently or after one or more bacterial antigens) in combination with EsxA and 1, 2, 3, 4, 5, 6, 7, 8, 9, 10, 11, 12, 13, 14, 15, 16, 17, 18, 19, 20, or more bacterial antigens selected from FnBpA, FnBpB, LukD, LukE, LukF, SasA, SasD, SasG, SasI, SasK, SpA (and variants thereof), Eap, Ebh, Emp, EsaB, EsaC, EsxB, SdrC, SdrD, SdrE, IsdA, IsdB, ClfA, ClfB, Coa, Hla (e.g., H35 mutants), IsdC, SasF, vWbp, vWh, sta001, sta002, sta003, sta004, sta005, sta006, sta007, sta008, sta009, sta010, sta011, sta012, sta013, sta014, sta015, sta016, sta017, sta018, sta019, sta020, sta021, sta022, sta023, sta024, sta025, sta026, sta027, sta028, sta029, sta030, sta031, sta032, sta033, sta034, sta035, sta036, sta037, sta038, sta039, sta040, sta041, sta042, sta043, sta044, sta045, sta046, sta047, sta048, sta049, sta050, sta051, sta052, sta053, sta054, sta055, sta056, sta057, sta058, sta059, sta060, sta061, sta062, sta063, sta064, sta065, sta066, sta067, sta068, sta069, sta070, sta071, sta072, sta073, sta074, sta075, sta076, sta077, sta078, sta079, sta080, sta081, sta082, sta083, sta084, sta085, sta086, sta087, sta088, sta089, sta090, sta091, sta092, sta093, sta094, sta095, sta096, sta097, sta098, sta099, sta100, sta101, sta102, sta103, sta104, sta105, sta106, sta107, sta108, sta109, sta110, sta111, sta112, sta113, sta114, sta115, sta116, sta117, sta118, sta119, sta120, or EsxAB hybrid polypeptide or immunogenic fragment thereof.

In other aspects, a subject is administered an SpA polypeptide variant (before or after one or more bacterial antigens) or administered a protein A antibody (before, concurrently or after one or more bacterial antigens) in combination with EsxB and 1, 2, 3, 4, 5, 6, 7, 8, 9, 10, 11, 12, 13, 14, 15, 16, 17, 18, 19, 20, or more bacterial antigens selected from FnBpA, FnBpB, LukD, LukE, LukF, SasA, SasD, SasG, SasI, SasK, SpA (and variants thereof), Eap, Ebh, Emp, EsaB, EsaC, EsxA, SdrC, SdrD, SdrE, IsdA, IsdB, ClfA, ClfB, Coa, Hla (e.g., H35 mutants), IsdC, SasF, vWbp, vWh, sta001, sta002, sta003, sta004, sta005, sta006, sta007, sta008, sta009, sta010, sta011, sta012, sta013, sta014, sta015, sta016, sta017, sta018, sta019, sta020, sta021, sta022, sta023, sta024, sta025, sta026, sta027, sta028, sta029, sta030, sta031, sta032, sta033, sta034, sta035, sta036, sta037, sta038, sta039, sta040, sta041, sta042, sta043, sta044, sta045, sta046, sta047, sta048, sta049, sta050, sta051, sta052, sta053, sta054, sta055, sta056, sta057, sta058, sta059, sta060, sta061, sta062, sta063, sta064, sta065, sta066, sta067, sta068, sta069, sta070, sta071, sta072, sta073, sta074, sta075, sta076, sta077, sta078, sta079, sta080, sta081, sta082, sta083, sta084, sta085, sta086, sta087, sta088, sta089, sta090, sta091, sta092, sta093, sta094, sta095, sta096, sta097, sta098, sta099, sta100, sta101, sta102, sta103, sta104, sta105, sta106, sta107, sta108, sta109, sta110, sta111, sta112, sta113, sta114, sta115, sta116, sta117, sta118, sta119, sta120, or EsxAB hybrid polypeptide or immunogenic fragment thereof.

In other aspects, a subject is administered an SpA polypeptide variant (before or after one or more bacterial antigens) or administered a protein A antibody (before, concurrently or after one or more bacterial antigens) in combination with SdrC and 1, 2, 3, 4, 5, 6, 7, 8, 9, 10, 11, 12, 13, 14, 15, 16, 17, 18, 19, 20, or more bacterial antigens selected from FnBpA, FnBpB, LukD, LukE, LukF, SasA, SasD, SasG, SasI, SasK, SpA (and variants thereof), Eap, Ebh, Emp, EsaB, EsaC, EsxA, EsxB, SdrD, SdrE, IsdA, IsdB, ClfA, ClfB, Coa, Hla (e.g., H35 mutants), IsdC, SasF, vWbp, vWh, sta001, sta002, sta003, sta004, sta005, sta006, sta007, sta008, sta009, sta010, sta011, sta012, sta013, sta014, sta015, sta016, sta017, sta018, sta019, sta020, sta021, sta022, sta023, sta024, sta025, sta026, sta027, sta028, sta029, sta030, sta031, sta032, sta033, sta034, sta035, sta036, sta037, sta038, sta039, sta040, sta041, sta042, sta043, sta044, sta045, sta046, sta047, sta048, sta049, sta050, sta051, sta052, sta053, sta054, sta055, sta056, sta057, sta058, sta059, sta060, sta061, sta062, sta063, sta064, sta065, sta066, sta067, sta068, sta069, sta070, sta071, sta072, sta073, sta074, sta075, sta076, sta077, sta078, sta079, sta080, sta081, sta082, sta083, sta084, sta085, sta086, sta087, sta088, sta089, sta090, sta091, sta092, sta093, sta094, sta095, sta096, sta097, sta098, sta099, sta100, sta101, sta102, sta103, sta104, sta105, sta106, sta107, sta108, sta109, sta110, sta111, sta112, sta113, sta114, sta115, sta116, sta117, sta118, sta119, sta120, or EsxAB hybrid polypeptide or immunogenic fragment thereof.

In other aspects, a subject is administered an SpA polypeptide variant (before or after one or more bacterial antigens) or administered a protein A antibody (before, concurrently or after one or more bacterial antigens) in combination with SdrD and 1, 2, 3, 4, 5, 6, 7, 8, 9, 10, 11, 12, 13, 14, 15, 16, 17, 18, 19, 20, or more bacterial antigens selected from FnBpA, FnBpB, LukD, LukE, LukF, SasA, SasD, SasG, SasI, SasK, SpA (and variants thereof), Eap, Ebh, Emp, EsaB, EsaC, EsxA, EsxB, SdrC, SdrE, IsdA, IsdB, ClfA, ClfB, Coa, Hla (e.g., H35 mutants), IsdC, SasF, vWbp, vWh, sta001, sta002, sta003, sta004, sta005, sta006, sta007, sta008, sta009, sta010, sta011, sta012, sta013, sta014, sta015, sta016, sta017, sta018, sta019, sta020, sta021, sta022, sta023, sta024, sta025, sta026, sta027, sta028, sta029, sta030, sta031, sta032, sta033, sta034, sta035, sta036, sta037, sta038, sta039, sta040, sta041, sta042, sta043, sta044, sta045, sta046, sta047, sta048, sta049, sta050, sta051, sta052, sta053, sta054, sta055, sta056, sta057, sta058, sta059, sta060, sta061, sta062, sta063, sta064, sta065, sta066, sta067, sta068, sta069, sta070, sta071, sta072, sta073, sta074, sta075, sta076, sta077, sta078, sta079, sta080, sta081, sta082, sta083, sta084, sta085, sta086, sta087, sta088, sta089, sta090, sta091, sta092, sta093, sta094, sta095, sta096, sta097, sta098, sta099, sta100, sta101, sta102, sta103, sta104, sta105, sta106, sta107, sta108, sta109, sta110, sta111, sta112, sta113, sta114, sta115, sta116, sta117, sta118, sta119, sta120, or EsxAB hybrid polypeptide or immunogenic fragment thereof.

In other aspects, a subject is administered an SpA polypeptide variant (before or after one or more bacterial antigens) or administered a protein A antibody (before, concurrently or after one or more bacterial antigens) in combination with SdrE and 1, 2, 3, 4, 5, 6, 7, 8, 9, 10, 11, 12, 13, 14, 15, 16, 17, 18, 19, 20, or more bacterial antigens selected from FnBpA, FnBpB, LukD, LukE, LukF, SasA, SasD, SasG, SasI, SasK, SpA (and variants thereof), Eap, Ebh, Emp, EsaB, EsaC, EsxA, EsxB, SdrC, SdrD, IsdA, IsdB, ClfA, ClfB, Coa, Hla (e.g., H35 mutants), IsdC, SasF, vWbp, vWh, sta001, sta002, sta003, sta004, sta005, sta006, sta007, sta008, sta009, sta010, sta011, sta012, sta013, sta014, sta015, sta016, sta017, sta018, sta019, sta020, sta021, sta022, sta023, sta024, sta025, sta026, sta027, sta028, sta029, sta030, sta031, sta032, sta033, sta034, sta035, sta036, sta037, sta038, sta039, sta040, sta041, sta042, sta043, sta044, sta045, sta046, sta047, sta048, sta049, sta050, sta051, sta052, sta053, sta054, sta055, sta056, sta057, sta058, sta059, sta060, sta061, sta062, sta063, sta064, sta065, sta066, sta067, sta068, sta069, sta070, sta071, sta072, sta073, sta074, sta075, sta076, sta077, sta078, sta079, sta080, sta081, sta082, sta083, sta084, sta085, sta086, sta087, sta088, sta089, sta090, sta091, sta092, sta093, sta094, sta095, sta096, sta097, sta098, sta099, sta100, sta101, sta102, sta103, sta104, sta105, sta106, sta107, sta108, sta109, sta110, sta111, sta112, sta113, sta114, sta115, sta116, sta117, sta118, sta119, sta120, or EsxAB hybrid polypeptide or immunogenic fragment thereof.

In other aspects, a subject is administered an SpA polypeptide variant (before or after one or more bacterial antigens) or administered a protein A antibody (before, concurrently or after one or more bacterial antigens) in combination with IsdA and 1, 2, 3, 4, 5, 6, 7, 8, 9, 10, 11, 12, 13, 14, 15, 16, 17, 18, 19, 20, or more bacterial antigens selected from FnBpA, FnBpB, LukD, LukE, LukF, SasA, SasD, SasG, SasI, SasK, SpA (and variants thereof), Eap, Ebh, Emp, EsaB, EsaC, EsxA, EsxB, SdrC, SdrD, SdrE, IsdB, ClfA, ClfB, Coa, Hla (e.g., H35 mutants), IsdC, SasF, vWbp, vWh, sta001, sta002, sta003, sta004, sta005, sta006, sta007, sta008, sta009, sta010, sta011, sta012, sta013, sta014, sta015, sta016, sta017, sta018, sta019, sta020, sta021, sta022, sta023, sta024, sta025, sta026, sta027, sta028, sta029, sta030, sta031, sta032, sta033, sta034, sta035, sta036, sta037, sta038, sta039, sta040, sta041, sta042, sta043, sta044, sta045, sta046, sta047, sta048, sta049, sta050, sta051, sta052, sta053, sta054, sta055, sta056, sta057, sta058, sta059, sta060, sta061, sta062, sta063, sta064, sta065, sta066, sta067, sta068, sta069, sta070, sta071, sta072, sta073, sta074, sta075, sta076, sta077, sta078, sta079, sta080, sta081, sta082, sta083, sta084, sta085, sta086, sta087, sta088, sta089, sta090, sta091, sta092, sta093, sta094, sta095, sta096, sta097, sta098, sta099, sta100, sta101, sta102, sta103, sta104, sta105, sta106, sta107, sta108, sta109, sta110, sta111, sta112, sta113, sta114, sta115, sta116, sta117, sta118, sta119, sta120, or EsxAB hybrid polypeptide or immunogenic fragment thereof.

In other aspects, a subject is administered an SpA polypeptide variant (before or after one or more bacterial antigens) or administered a protein A antibody (before, concurrently or after one or more bacterial antigens) in combination with IsdB and 1, 2, 3, 4, 5, 6, 7, 8, 9, 10, 11, 12, 13, 14, 15, 16, 17, 18, 19, 20, or more bacterial antigens selected from FnBpA, FnBpB, LukD, LukE, LukF, SasA, SasD, SasG, SasI, SasK, SpA (and variants thereof), Eap, Ebh, Emp, EsaB, EsaC, EsxA, EsxB, SdrC, SdrD, SdrE, IsdA, ClfA, ClfB, Coa, Hla (e.g., H35 mutants), IsdC, SasF, vWbp, vWh, sta001, sta002, sta003, sta004, sta005, sta006, sta007, sta008, sta009, sta010, sta011, sta012, sta013, sta014, sta015, sta016, sta017, sta018, sta019, sta020, sta021, sta022, sta023, sta024, sta025, sta026, sta027, sta028, sta029, sta030, sta031, sta032, sta033, sta034, sta035, sta036, sta037, sta038, sta039, sta040, sta041, sta042, sta043, sta044, sta045, sta046, sta047, sta048, sta049, sta050, sta051, sta052, sta053, sta054, sta055, sta056, sta057, sta058, sta059, sta060, sta061, sta062, sta063, sta064, sta065, sta066, sta067, sta068, sta069, sta070, sta071, sta072, sta073, sta074, sta075, sta076, sta077, sta078, sta079, sta080, sta081, sta082, sta083, sta084, sta085, sta086, sta087, sta088, sta089, sta090, sta091, sta092, sta093, sta094, sta095, sta096, sta097, sta098, sta099, sta100, sta101, sta102, sta103, sta104, sta105, sta106, sta107, sta108, sta109, sta111, sta111, sta112, sta113, sta114, sta115, sta116, sta117, sta118, sta119, sta120, or EsxAB hybrid polypeptide or immunogenic fragment thereof.

In other aspects, a subject is administered an SpA polypeptide variant (before or after one or more bacterial antigens) or administered a protein A antibody (before, concurrently or after one or more bacterial antigens) in combination with ClfA and 1, 2, 3, 4, 5, 6, 7, 8, 9, 10, 11, 12, 13, 14, 15, 16, 17, 18, 19, 20, or more bacterial antigens selected from FnBpA, FnBpB, LukD, LukE, LukF, SasA, SasD, SasG, SasI, SasK, SpA (and variants thereof), Eap, Ebh, Emp, EsaB, EsaC, EsxA, EsxB, SdrC, SdrD, SdrE, IsdA, IsdB, ClfB, Coa, Hla (e.g., H35 mutants), IsdC, SasF, vWbp, vWh, sta001, sta002, sta003, sta004, sta005, sta006, sta007, sta008, sta009, sta010, sta011, sta012, sta013, sta014, sta015, sta016, sta017, sta018, sta019, sta020, sta021, sta022, sta023, sta024, sta025, sta026, sta027, sta028, sta029, sta030, sta031, sta032, sta033, sta034, sta035, sta036, sta037, sta038, sta039, sta040, sta041, sta042, sta043, sta044, sta045, sta046, sta047, sta048, sta049, sta050, sta051, sta052, sta053, sta054, sta055, sta056, sta057, sta058, sta059, sta060, sta061, sta062, sta063, sta064, sta065, sta066, sta067, sta068, sta069, sta070, sta071, sta072, sta073, sta074, sta075, sta076, sta077, sta078, sta079, sta080, sta081, sta082, sta083, sta084, sta085, sta086, sta087, sta088, sta089, sta090, sta091, sta092, sta093, sta094, sta095, sta096, sta097, sta098, sta099, sta100, sta101, sta102, sta103, sta104, sta105, sta106, sta107, sta108, sta109, sta110, sta111, sta112, sta113, sta114, sta115, sta116, sta117, sta118, sta119, sta120, or EsxAB hybrid polypeptide or immunogenic fragment thereof.

In other aspects, a subject is administered an SpA polypeptide variant (before or after one or more bacterial antigens) or administered a protein A antibody (before, concurrently or after one or more bacterial antigens) in combination with ClfB and 1, 2, 3, 4, 5, 6, 7, 8, 9, 10, 11, 12, 13, 14, 15, 16, 17, 18, 19, 20, or more bacterial antigens selected from FnBpA, FnBpB, LukD, LukE, LukF, SasA, SasD, SasG, SasI, SasK, SpA (and variants thereof), Eap, Ebh, Emp, EsaB, EsaC, EsxA, EsxB, SdrC, SdrD, SdrE, IsdA, IsdB, ClfA, Coa, Hla (e.g., H35 mutants), IsdC, SasF, vWbp, vWh, sta001, sta002, sta003, sta004, sta005, sta006, sta007, sta008, sta009, sta010, sta011, sta012, sta013, sta014, sta015, sta016, sta017, sta018, sta019, sta020, sta021, sta022, sta023, sta024, sta025, sta026, sta027, sta028, sta029, sta030, sta031, sta032, sta033, sta034, sta035, sta036, sta037, sta038, sta039, sta040, sta041, sta042, sta043, sta044, sta045, sta046, sta047, sta048, sta049, sta050, sta051, sta052, sta053, sta054, sta055, sta056, sta057, sta058, sta059, sta060, sta061, sta062, sta063, sta064, sta065, sta066, sta067, sta068, sta069, sta070, sta071, sta072, sta073, sta074, sta075, sta076, sta077, sta078, sta079, sta080, sta081, sta082, sta083, sta084, sta085, sta086, sta087, sta088, sta089, sta090, sta091, sta092, sta093, sta094, sta095, sta096, sta097, sta098, sta099, sta100, sta101, sta102, sta103, sta104, sta105, sta106, sta107, sta108, sta109, sta110, sta111, sta112, sta113, sta114, sta115, sta116, sta117, sta118, sta119, sta120, or EsxAB hybrid polypeptide or immunogenic fragment thereof.

In other aspects, a subject is administered an SpA polypeptide variant (before or after one or more bacterial antigens) or administered a protein A antibody (before, concurrently or after one or more bacterial antigens) in combination with Coa and 1, 2, 3, 4, 5, 6, 7, 8, 9, 10, 11, 12, 13, 14, 15, 16, 17, 18, 19, 20, or more bacterial antigens selected from FnBpA, FnBpB, LukD, LukE, LukF, SasA, SasD, SasG, SasI, SasK, SpA (and variants thereof), Eap, Ebh, Emp, EsaB, EsaC, EsxA, EsxB, SdrC, SdrD, SdrE, IsdA, IsdB, ClfA, ClfB, Hla (e.g., H35 mutants), IsdC, SasF, vWbp, vWh, sta001, sta002, sta003, sta004, sta005, sta006, sta007, sta008, sta009, sta010, sta011, sta012, sta013, sta014, sta015, sta016, sta017, sta018, sta019, sta020, sta021, sta022, sta023, sta024, sta025, sta026, sta027, sta028, sta029, sta030, sta031, sta032, sta033, sta034, sta035, sta036, sta037, sta038, sta039, sta040, sta041, sta042, sta043, sta044, sta045, sta046, sta047, sta048, sta049, sta050, sta051, sta052, sta053, sta054, sta055, sta056, sta057, sta058, sta059, sta060, sta061, sta062, sta063, sta064, sta065, sta066, sta067, sta068, sta069, sta070, sta071, sta072, sta073, sta074, sta075, sta076, sta077, sta078, sta079, sta080, sta081, sta082, sta083, sta084, sta085, sta086, sta087, sta088, sta089, sta090, sta091, sta092, sta093, sta094, sta095, sta096, sta097, sta098, sta099, sta100, sta101, sta102, sta103, sta104, sta105, sta106, sta107, sta108, sta109, sta110, sta111, sta112, sta113, sta114, sta115, sta116, sta117, sta118, sta119, sta120, or EsxAB hybrid polypeptide or immunogenic fragment thereof.

In other aspects, a subject is administered an SpA polypeptide variant (before or after one or more bacterial antigens) or administered a protein A antibody (before, concurrently or after one or more bacterial antigens) in combination with Hla (e.g., H35 mutants) and 1, 2, 3, 4, 5, 6, 7, 8, 9, 10, 11, 12, 13, 14, 15, 16, 17, 18, 19, 20, or more bacterial antigens selected from FnBpA, FnBpB, LukD, LukE, LukF, SasA, SasD, SasG, SasI, SasK, SpA (and variants thereof), Eap, Ebh, Emp, EsaB, EsaC, EsxA, EsxB, SdrC, SdrD, SdrE, IsdA, IsdB, ClfA, ClfB, Coa, IsdC, SasF, vWbp, vWh, sta001, sta002, sta003, sta004, sta005, sta006, sta007, sta008, sta009, sta010, sta011, sta012, sta013, sta014, sta015, sta016, sta017, sta018, sta019, sta020, sta021, sta022, sta023, sta024, sta025, sta026, sta027, sta028, sta029, sta030, sta031, sta032, sta033, sta034, sta035, sta036, sta037, sta038, sta039, sta040, sta041, sta042, sta043, sta044, sta045, sta046, sta047, sta048, sta049, sta050, sta051, sta052, sta053, sta054, sta055, sta056, sta057, sta058, sta059, sta060, sta061, sta062, sta063, sta064, sta065, sta066, sta067, sta068, sta069, sta070, sta071, sta072, sta073, sta074, sta075, sta076, sta077, sta078, sta079, sta080, sta081, sta082, sta083, sta084, sta085, sta086, sta087, sta088, sta089, sta090, sta091, sta092, sta093, sta094, sta095, sta096, sta097, sta098, sta099, sta100, sta101, sta102, sta103, sta104, sta105, sta106, sta107, sta108, sta109, sta110, sta111, sta112, sta113, sta114, sta115, sta116, sta117, sta118, sta119, sta120, or EsxAB hybrid polypeptide or immunogenic fragment thereof.

In other aspects, a subject is administered an SpA polypeptide variant (before or after one or more bacterial antigens) or administered a protein A antibody (before, concurrently or after one or more bacterial antigens) in combination with IsdC and 1, 2, 3, 4, 5, 6, 7, 8, 9, 10, 11, 12, 13, 14, 15, 16, 17, 18, 19, 20, or more bacterial antigens selected from FnBpA, FnBpB, LukD, LukE, LukF, SasA, SasD, SasG, SasI, SasK, SpA (and variants thereof), Eap, Ebh, Emp, EsaB, EsaC, EsxA, EsxB, SdrC, SdrD, SdrE, IsdA, IsdB, ClfA, ClfB, Coa, Hla (e.g., H35 mutants), SasF, vWbp, vWh, sta001, sta002, sta003, sta004, sta005, sta006, sta007, sta008, sta009, sta010, sta011, sta012, sta013, sta014, sta015, sta016, sta017, sta018, sta019, sta020, sta021, sta022, sta023, sta024, sta025, sta026, sta027, sta028, sta029, sta030, sta031, sta032, sta033, sta034, sta035, sta036, sta037, sta038, sta039, sta040, sta041, sta042, sta043, sta044, sta045, sta046, sta047, sta048, sta049, sta050, sta051, sta052, sta053, sta054, sta055, sta056, sta057, sta058, sta059, sta060, sta061, sta062, sta063, sta064, sta065, sta066, sta067, sta068, sta069, sta070, sta071, sta072, sta073, sta074, sta075, sta076, sta077, sta078, sta079, sta080, sta081, sta082, sta083, sta084, sta085, sta086, sta087, sta088, sta089, sta090, sta091, sta092, sta093, sta094, sta095, sta096, sta097, sta098, sta099, sta100, sta101, sta102, sta103, sta104, sta105, sta106, sta107, sta108, sta109, sta110, sta111, sta112, sta113, sta114, sta115, sta116, sta117, sta118, sta119, sta120, or EsxAB hybrid polypeptide or immunogenic fragment thereof.

In other aspects, a subject is administered an SpA polypeptide variant (before or after one or more bacterial antigens) or administered a protein A antibody (before, concurrently or after one or more bacterial antigens) in combination with SasF and 1, 2, 3, 4, 5, 6, 7, 8, 9, 10, 11, 12, 13, 14, 15, 16, 17, 18, 19, 20, or more bacterial antigens selected from FnBpA, FnBpB, LukD, LukE, LukF, SasA, SasD, SasG, SasI, SasK, SpA (and variants thereof), Eap, Ebh, Emp, EsaB, EsaC, EsxA, EsxB, SdrC, SdrD, SdrE, IsdA, IsdB, ClfA, ClfB, Coa, Hla (e.g., H35 mutants), IsdC, SasF, vWbp, vWh, sta001, sta002, sta003, sta004, sta005, sta006, sta007, sta008, sta009, sta010, sta011, sta012, sta013, sta014, sta015, sta016, sta017, sta018, sta019, sta020, sta021, sta022, sta023, sta024, sta025, sta026, sta027, sta028, sta029, sta030, sta031, sta032, sta033, sta034, sta035, sta036, sta037, sta038, sta039, sta040, sta041, sta042, sta043, sta044, sta045, sta046, sta047, sta048, sta049, sta050, sta051, sta052, sta053, sta054, sta055, sta056, sta057, sta058, sta059, sta060, sta061, sta062, sta063, sta064, sta065, sta066, sta067, sta068, sta069, sta070, sta071, sta072, sta073, sta074, sta075, sta076, sta077, sta078, sta079, sta080, sta081, sta082, sta083, sta084, sta085, sta086, sta087, sta088, sta089, sta090, sta091, sta092, sta093, sta094, sta095, sta096, sta097, sta098, sta099, sta100, sta101, sta102, sta103, sta104, sta105, sta106, sta107, sta108, sta109, sta110, sta111, sta112, sta113, sta114, sta115, sta116, sta117, sta118, sta119, sta120, or EsxAB hybrid polypeptide or immunogenic fragment thereof.

In other aspects, a subject is administered an SpA polypeptide variant (before or after one or more bacterial antigens) or administered a protein A antibody (before, concurrently or after one or more bacterial antigens) in combination with vWbp and 1, 2, 3, 4, 5, 6, 7, 8, 9, 10, 11, 12, 13, 14, 15, 16, 17, 18, 19, 20, or more bacterial antigens selected from FnBpA, FnBpB, LukD, LukE, LukF, SasA, SasD, SasG, SasI, SasK, SpA (and variants thereof), Eap, Ebh, Emp, EsaB, EsaC, EsxA, EsxB, SdrC, SdrD, SdrE, IsdA, IsdB, ClfA, ClfB, Coa, Hla (e.g., H35 mutants), IsdC, SasF, vWh, sta001, sta002, sta003, sta004, sta005, sta006, sta007, sta008, sta009, sta010, sta011, sta012, sta013, sta014, sta015, sta016, sta017, sta018, sta019, sta020, sta021, sta022, sta023, sta024, sta025, sta026, sta027, sta028, sta029, sta030, sta031, sta032, sta033, sta034, sta035, sta036, sta037, sta038, sta039, sta040, sta041, sta042, sta043, sta044, sta045, sta046, sta047, sta048, sta049, sta050, sta051, sta052, sta053, sta054, sta055, sta056, sta057, sta058, sta059, sta060, sta061, sta062, sta063, sta064, sta065, sta066, sta067, sta068, sta069, sta070, sta071, sta072, sta073, sta074, sta075, sta076, sta077, sta078, sta079, sta080, sta081, sta082, sta083, sta084, sta085, sta086, sta087, sta088, sta089, sta090, sta091, sta092, sta093, sta094, sta095, sta096, sta097, sta098, sta099, sta100, sta101, sta102, sta103, sta104, sta105, sta106, sta107, sta108, sta109, sta110, sta111, sta112, sta113, sta114, sta115, sta116, sta117, sta118, sta119, sta120, or EsxAB hybrid polypeptide or immunogenic fragment thereof.

In other aspects, a subject is administered an SpA polypeptide variant (before or after one or more bacterial antigens) or administered a protein A antibody (before, concurrently or after one or more bacterial antigens) in combination with vWh and 1, 2, 3, 4, 5, 6, 7, 8, 9, 10, 11, 12, 13, 14, 15, 16, 17, 18, 19, 20, or more bacterial antigens selected from FnBpA, FnBpB, LukD, LukE, LukF, SasA, SasD, SasG, SasI, SasK, SpA (and variants thereof), Eap, Ebh, Emp, EsaB, EsaC, EsxA, EsxB, SdrC, SdrD, SdrE, IsdA, IsdB, ClfA, ClfB, Coa, Hla (e.g., H35 mutants), IsdC, SasF, vWbp, sta001, sta002, sta003, sta004, sta005, sta006, sta007, sta008, sta009, sta010, sta011, sta012, sta013, sta014, sta015, sta016, sta017, sta018, sta019, sta020, sta021, sta022, sta023, sta024, sta025, sta026, sta027, sta028, sta029, sta030, sta031, sta032, sta033, sta034, sta035, sta036, sta037, sta038, sta039, sta040, sta041, sta042, sta043, sta044, sta045, sta046, sta047, sta048, sta049, sta050, sta051, sta052, sta053, sta054, sta055, sta056, sta057, sta058, sta059, sta060, sta061, sta062, sta063, sta064, sta065, sta066, sta067, sta068, sta069, sta070, sta071, sta072, sta073, sta074, sta075, sta076, sta077, sta078, sta079, sta080, sta081, sta082, sta083, sta084, sta085, sta086, sta087, sta088, sta089, sta090, sta091, sta092, sta093, sta094, sta095, sta096, sta097, sta098, sta099, sta100, sta101, sta102, sta103, sta104, sta105, sta106, sta107, sta108, sta109, sta110, sta111, sta112, sta113, sta114, sta115, sta116, sta117, sta118, sta119, sta120, or EsxAB hybrid polypeptide or immunogenic fragment thereof.

Certain embodiment are directed to the above listed antibody and bacterial antigen combinations comprised in a vaccine composition having a pharmaceutically acceptable excipient.

Further embodiments include methods of making a vaccine comprising the steps of mixing antibody and antigens to make the compositions described herein.

Still further embodiments include methods of preventing or treating staphylococcal infection comprising the step of administering the vaccine as described herein to a patient in need thereof.

Certain embodiments are directed to use of the compositions described herein in the treatment or prevention of bacterial or staphylococcal infection. Certain embodiments are directed to use of the compositions described herein in the treatment or prevention of pathological conditions resulting from bacterial or staphylococcal infection.

A further embodiment includes methods for treating a bacterial infection in a subject comprising providing to a subject having, suspected of having or at risk of developing a bacterial infection effective amounts of an isolated Protein A (SpA) specific antibody and one or more bacterial antigens. In certain aspects, the one or more bacterial antigens are comprised in or on a bacteria, or are isolated recombinant polypeptides or peptides. In a further aspect the bacteria comprising the antigens is an attenuated bacteria, in a particular aspect the attenuated bacteria is a staphylococcal bacteria. In certain aspects the subject is diagnosed with a staphylococcal infection. In various aspects described above, the bacterial antigen is a staphylococcal antigen. The staphylococcal antigen can be selected from the group consisting of: FnBpA, FnBpB, LukD, LukE, LukF, SasA, SasD, SasG, SasI, SasK, SpA (and variants thereof), Eap, Ebh, Emp, EsaB, EsaC, EsxA, EsxB, SdrC, SdrD, SdrE, IsdA, IsdB, ClfA, ClfB, Coa, Hla (e.g., H35 mutants), IsdC, SasF, vWbp, vWh and immunogenic fragments thereof.

The methods further include steps wherein two or more bacterial antigens are provided to the subject. In certain aspects the Protein A (SpA) specific antibody is provided before, after, and/or concurrently with the bacterial antigen. In certain aspects, the Protein A (SpA) specific antibody and the one or more bacterial antigens are provided in the same composition. In a further aspect, the subject is a mammal, particularly human.

Embodiments include methods for enhancing an immune response against a bacterium in a subject. In certain aspects the methods include providing to the subject effective amounts of an isolated Protein A (SpA) specific antibody and one or more antigens from the bacterium. In a further aspect the methods include pre-immunization with an SpA polypeptide variant followed by administration of one or more antigens from the bacterium. Still further aspects include administration of an SpA polypeptide variant after administration of one or more antigens from the bacterium. In certain aspects, one or more bacterial antigens are comprised in or on or produced by a bacteria, or are isolated recombinant polypeptides or peptides. In a further aspect the bacteria comprising the antigens is an attenuated bacteria, in a particular aspect the attenuated bacteria is a staphylococcal bacteria. In certain aspects the subject is diagnosed with a staphylococcal infection. In various aspects described above, the bacterial antigen is a staphylococcal antigen. The staphylococcal antigen can be selected from the group consisting of: FnBpA, FnBpB, LukD, LukE, LukF, SasA, SasD, SasG, SasI, SasK, SpA (and variants thereof), Eap, Ebh, Emp, EsaB, EsaC, EsxA, EsxB, SdrC, SdrD, SdrE, IsdA, IsdB, ClfA, ClfB, Coa, Hla (e.g., H35 mutants), IsdC, SasF, vWbp, vWh and immunogenic fragments thereof. In certain aspects the *staphylococcus* bacterium is a *S. aureus* bacterium. In a further aspect, the *staphylococcus* bacterium is resistant to one or more treatments, such as methicillin resistant. In certain aspects the composition is administered more than one time to the subject.

In certain aspects, a bacterium delivering a composition of the invention will be limited or attenuated with respect to prolonged or persistent growth or abscess formation. In yet a further aspect, bacterial antigens can be overexpressed in an attenuated bacterium to further enhance or supplement an immune response or vaccine formulation.

The term "FnBpA protein" refers to a protein that includes isolated wild-type FnBpA polypeptides from *staphylococcus* bacteria and segments thereof, as well as variants that stimulate an immune response against *staphylococcus* bacteria FnBpA proteins.

The term "FnBpB protein" refers to a protein that includes isolated wild-type FnBpB polypeptides from *staphylococcus* bacteria and segments thereof, as well as variants that stimulate an immune response against *staphylococcus* bacteria FnBpB proteins.

The term "LukD protein" refers to a protein that includes isolated wild-type LukD polypeptides from *staphylococcus* bacteria and segments thereof, as well as variants that stimulate an immune response against *staphylococcus* bacteria LukD proteins.

The term "LukE protein" refers to a protein that includes isolated wild-type LukE polypeptides from *staphylococcus* bacteria and segments thereof, as well as variants that stimulate an immune response against *staphylococcus* bacteria LukE proteins.

The term "LukF protein" refers to a protein that includes isolated wild-type LukF polypeptides from *staphylococcus* bacteria and segments thereof, as well as variants that stimulate an immune response against *staphylococcus* bacteria LukF proteins.

The term "SasA protein" refers to a protein that includes isolated wild-type SasA polypeptides from *staphylococcus* bacteria and segments thereof, as well as variants that stimulate an immune response against *staphylococcus* bacteria SasA proteins.

The term "SasD protein" refers to a protein that includes isolated wild-type SasD polypeptides from *staphylococcus* bacteria and segments thereof, as well as variants that stimulate an immune response against *staphylococcus* bacteria SasD proteins.

The term "SasG protein" refers to a protein that includes isolated wild-type SasG polypeptides from *staphylococcus* bacteria and segments thereof, as well as variants that stimulate an immune response against *staphylococcus* bacteria SasG proteins.

The term "SasI protein" refers to a protein that includes isolated wild-type SasI polypeptides from *staphylococcus* bacteria and segments thereof, as well as variants that stimulate an immune response against *staphylococcus* bacteria SasI proteins.

The term "SasK protein" refers to a protein that includes isolated wild-type SasK polypeptides from *staphylococcus* bacteria and segments thereof, as well as variants that stimulate an immune response against *staphylococcus* bacteria SasK proteins.

The term "EsxA protein" refers to a protein that includes isolated wild-type EsxA polypeptides from *staphylococcus* bacteria and segments thereof, as well as variants that stimulate an immune response against *staphylococcus* bacteria EsxA proteins.

The term "EsxB protein" refers to a protein that includes isolated wild-type EsxB polypeptides from *staphylococcus* bacteria and segments thereof, as well as variants that stimulate an immune response against *staphylococcus* bacteria EsxB proteins.

The term "SdrD protein" refers to a protein that includes isolated wild-type SdrD polypeptides from *staphylococcus* bacteria and segments thereof, as well as variants that stimulate an immune response against *staphylococcus* bacteria SdrD proteins.

The term "SdrE protein" refers to a protein that includes isolated wild-type SdrE polypeptides from *staphylococcus* bacteria and segments thereof, as well as variants that stimulate an immune response against *staphylococcus* bacteria SdrE proteins.

The term "IsdA protein" refers to a protein that includes isolated wild-type IsdA polypeptides from *staphylococcus* bacteria and segments thereof, as well as variants that stimulate an immune response against *staphylococcus* bacteria IsdA proteins.

The term "IsdB protein" refers to a protein that includes isolated wild-type IsdB polypeptides from *staphylococcus* bacteria and segments thereof, as well as variants that stimulate an immune response against *staphylococcus* bacteria IsdB proteins.

The term "Eap protein" refers to a protein that includes isolated wild-type Eap polypeptides from *staphylococcus* bacteria and segments thereof, as well as variants that stimulate an immune response against *staphylococcus* bacteria Eap proteins.

The term "Ebh protein" refers to a protein that includes isolated wild-type Ebh polypeptides from *staphylococcus* bacteria and segments thereof, as well as variants that stimulate an immune response against *staphylococcus* bacteria Ebh proteins.

The term "Emp protein" refers to a protein that includes isolated wild-type Emp polypeptides from *staphylococcus* bacteria and segments thereof, as well as variants that stimulate an immune response against *staphylococcus* bacteria Emp proteins.

The term "EsaB protein" refers to a protein that includes isolated wild-type EsaB polypeptides from *staphylococcus* bacteria and segments thereof, as well as variants that stimulate an immune response against *staphylococcus* bacteria EsaB proteins.

The term "EsaC protein" refers to a protein that includes isolated wild-type EsaC polypeptides from *staphylococcus* bacteria and segments thereof, as well as variants that stimulate an immune response against *staphylococcus* bacteria EsaC proteins.

The term "SdrC protein" refers to a protein that includes isolated wild-type SdrC polypeptides from *staphylococcus* bacteria and segments thereof, as well as variants that stimulate an immune response against *staphylococcus* bacteria SdrC proteins.

The term "ClfA protein" refers to a protein that includes isolated wild-type ClfA polypeptides from *staphylococcus* bacteria and segments thereof, as well as variants that stimulate an immune response against *staphylococcus* bacteria ClfA proteins.

The term "ClfB protein" refers to a protein that includes isolated wild-type ClfB polypeptides from *staphylococcus* bacteria and segments thereof, as well as variants that stimulate an immune response against *staphylococcus* bacteria ClfB proteins.

The term "Coa protein" refers to a protein that includes isolated wild-type Coa polypeptides from *staphylococcus* bacteria and segments thereof, as well as variants that stimulate an immune response against *staphylococcus* bacteria Coa proteins.

The term "Hla protein" refers to a protein that includes isolated wild-type Hla polypeptides from *staphylococcus* bacteria and segments thereof, as well as variants that stimulate an immune response against *staphylococcus* bacteria Hla proteins.

The term "IsdC protein" refers to a protein that includes isolated wild-type IsdC polypeptides from *staphylococcus* bacteria and segments thereof, as well as variants that stimulate an immune response against *staphylococcus* bacteria IsdC proteins.

The term "SasF protein" refers to a protein that includes isolated wild-type SasF polypeptides from *staphylococcus* bacteria and segments thereof, as well as variants that stimulate an immune response against *staphylococcus* bacteria SasF proteins.

The term "vWbp protein" refers to a protein that includes isolated wild-type vWbp (von Willebrand factor binding protein) polypeptides from *staphylococcus* bacteria and segments thereof, as well as variants that stimulate an immune response against *staphylococcus* bacteria vWbp proteins.

The term "vWh protein" refers to a protein that includes isolated wild-type vWh (von Willebrand factor binding protein homolog) polypeptides from *staphylococcus* bacteria and segments thereof, as well as variants that stimulate an immune response against *staphylococcus* bacteria vWh proteins.

An immune response refers to a humoral response, a cellular response, or both a humoral and cellular response in an organism. An immune response can be measured by assays that include, but are not limited to, assays measuring the presence or amount of antibodies that specifically recognize a protein or cell surface protein, assays measuring T-cell activation or proliferation, and/or assays that measure modulation in terms of activity or expression of one or more cytokines.

In still further embodiments of the invention a composition may include a polypeptide, peptide, or protein that is or is at least 70%, 75%, 80%, 85%, 90%, 95%, 96%, 97%, 98%, or 99% identical or similar to a FnBpA protein. In certain aspects the FnBpA protein will have all or part of the amino acid sequence of accession number A32192/GI: 97812.

In still further embodiments of the invention a composition may include a polypeptide, peptide, or protein that is or is at least 70%, 75%, 80%, 85%, 90%, 95%, 96%, 97%, 98%, or 99% identical or similar to an FnBpB protein. In certain aspects the FnBpB protein will have all or part of the amino acid sequence of accession number A32192/GI: 97812.

In still further embodiments of the invention a composition may include a polypeptide, peptide, or protein that is or is at least 70%, 75%, 80%, 85%, 90%, 95%, 96%, 97%, 98%, or 99% identical or similar to an LukD protein. In certain aspects the LukD protein will have all or part of the amino acid sequence of accession number CAA73668/GI: 2765304.

In still further embodiments of the invention a composition may include a polypeptide, peptide, or protein that is or is at least 70%, 75%, 80%, 85%, 90%, 95%, 96%, 97%, 98%, or 99% identical or similar to an LukE protein. In certain aspects the LukE protein will have all or part of the amino acid sequence of accession number CAA73667.1/GI: 2765303.

In still further embodiments of the invention a composition may include a polypeptide, peptide, or protein that is or is at least 70%, 75%, 80%, 85%, 90%, 95%, 96%, 97%, 98%, or 99% identical or similar to an LukF protein. In certain aspects the LukF protein will have all or part of the amino acid sequence of accession number AAC60446.1/GI: 410007.

In still further embodiments of the invention a composition may include a polypeptide, peptide, or protein that is or is at least 70%, 75%, 80%, 85%, 90%, 95%, 96%, 97%, 98%, or 99% identical or similar to an SasA protein. In certain aspects the SasA protein will have all or part of the amino acid sequence of accession number Q06904.2/GI: 93141309.

In still further embodiments of the invention a composition may include a polypeptide, peptide, or protein that is or is at least 70%, 75%, 80%, 85%, 90%, 95%, 96%, 97%, 98%, or 99% identical or similar to an SasD protein. In certain aspects the SasD protein will have all or part of the amino acid sequence of accession number AAR15215.1/GI: 38259745.

In still further embodiments of the invention a composition may include a polypeptide, peptide, or protein that is or is at least 70%, 75%, 80%, 85%, 90%, 95%, 96%, 97%, 98%, or 99% identical or similar to an SasG protein. In certain aspects the SasG protein will have all or part of the amino acid sequence of accession number Q2G2B2.1/GI: 122540575.

In still further embodiments of the invention a composition may include a polypeptide, peptide, or protein that is or is at least 70%, 75%, 80%, 85%, 90%, 95%, 96%, 97%, 98%, or 99% identical or similar to an SasI protein. In certain aspects the SasI protein will have all or part of the amino acid sequence of accession number AAR15295.1/GI: 38259905.

In still further embodiments of the invention a composition may include a polypeptide, peptide, or protein that is or is at least 70%, 75%, 80%, 85%, 90%, 95%, 96%, 97%, 98%, or 99% identical or similar to an SasK protein. In certain aspects the SasK protein will have all or part of the amino acid sequence of accession number ZP_06340589.1/GI:283767674.

In still further embodiments of the invention a composition may include a polypeptide, peptide, or protein that is or is at least 70%, 75%, 80%, 85%, 90%, 95%, 96%, 97%, 98%, or 99% identical or similar to an EsxA protein. In certain aspects the EsxA protein will have all or part of the amino acid sequence of SEQ ID NO:11.

In still further embodiments of the invention a composition may include a polypeptide, peptide, or protein that is or is at least 70%, 75%, 80%, 85%, 90%, 95%, 96%, 97%, 98%, or 99% identical or similar to an EsxB protein. In certain aspects the EsxB protein will have all or part of the amino acid sequence of SEQ ID NO:12.

In yet still further embodiments of the invention a composition may include a polypeptide, peptide, or protein that is or is at least 70%, 75%, 80%, 85%, 90%, 95%, 96%, 97%, 98%, or 99% identical or similar to an SdrD protein. In certain aspects the SdrD protein will have all or part of the amino acid sequence of SEQ ID NO:13.

In further embodiments of the invention a composition may include a polypeptide, peptide, or protein that is or is at least 70%, 75%, 80%, 85%, 90%, 95%, 96%, 97%, 98%, or 99% identical or similar to an SdrE protein. In certain aspects the SdrE protein will have all or part of the amino acid sequence of SEQ ID NO:14.

In still further embodiments of the invention a composition may include a polypeptide, peptide, or protein that is or is at least 70%, 75%, 80%, 85%, 90%, 95%, 96%, 97%, 98%, or 99% identical or similar to an IsdA protein. In certain aspects the IsdA protein will have all or part of the amino acid sequence of SEQ ID NO:15.

In yet still further embodiments of the invention a composition may include a polypeptide, peptide, or protein that is or is at least 70%, 75%, 80%, 85%, 90%, 95%, 96%, 97%, 98%, or 99% identical or similar to an IsdB protein. In certain aspects the IsdB protein will have all or part of the amino acid sequence of SEQ ID NO:16.

Embodiments of the invention include compositions that include a polypeptide, peptide, or protein that is or is at least 70%, 75%, 80%, 85%, 90%, 95%, 96%, 97%, 98%, or 99% identical or similar to a EsaB protein. In certain aspects the EsaB protein will have all or part of the amino acid sequence of SEQ ID NO:17.

In a further embodiments of the invention a composition may include a polypeptide, peptide, or protein that is or is at least 70%, 75%, 80%, 85%, 90%, 95%, 96%, 97%, 98%, or 99% identical or similar to a ClfB protein. In certain aspects the ClfB protein will have all or part of the amino acid sequence of SEQ ID NO:18.

In still further embodiments of the invention a composition may include a polypeptide, peptide, or protein that is or is at least 70%, 75%, 80%, 85%, 90%, 95%, 96%, 97%, 98%, or 99% identical or similar to an IsdC protein. In certain aspects the IsdC protein will have all or part of the amino acid sequence of SEQ ID NO:19.

In yet further embodiments of the invention a composition may include a polypeptide, peptide, or protein that is or is at least 70%, 75%, 80%, 85%, 90%, 95%, 96%, 97%, 98%, or 99% identical or similar to a SasF protein. In certain aspects the SasF protein will have all or part of the amino acid sequence of SEQ ID NO:20.

In yet still further embodiments of the invention a composition may include a polypeptide, peptide, or protein that is or is at least 70%, 75%, 80%, 85%, 90%, 95%, 96%, 97%, 98%, or 99% identical or similar to a SdrC protein. In certain aspects the SdrC protein will have all or part of the amino acid sequence of SEQ ID NO:21.

In yet still further embodiments of the invention a composition may include a polypeptide, peptide, or protein that is or is at least 70%, 75%, 80%, 85%, 90%, 95%, 96%, 97%, 98%, or 99% identical or similar to a ClfA protein. In certain aspects the ClfA protein will have all or part of the amino acid sequence of SEQ ID NO:22.

In yet still further embodiments of the invention a composition may include a polypeptide, peptide, or protein that is or is at least 70%, 75%, 80%, 85%, 90%, 95%, 96%, 97%, 98%, or 99% identical or similar to an Eap protein. In certain aspects the Eap protein will have all or part of the amino acid sequence of SEQ ID NO:23.

In yet still further embodiments of the invention a composition may include a polypeptide, peptide, or protein that is or is at least 70%, 75%, 80%, 85%, 90%, 95%, 96%, 97%, 98%, or 99% identical or similar to an Ebh protein. In certain aspects the Ebh protein will have all or part of the amino acid sequence of SEQ ID NO:24.

In yet still further embodiments of the invention a composition may include a polypeptide, peptide, or protein that is or is at least 70%, 75%, 80%, 85%, 90%, 95%, 96%, 97%, 98%, or 99% identical or similar to an Emp protein. In certain aspects the Emp protein will have all or part of the amino acid sequence of SEQ ID NO:25.

In yet still further embodiments of the invention a composition may include a polypeptide, peptide, or protein that is or is at least 70%, 75%, 80%, 85%, 90%, 95%, 96%, 97%, 98%, or 99% identical or similar to an EsaC protein. In certain aspects the EsaC protein will have all or part of the amino acid sequence of SEQ ID NO:26. Sequence of EsaC polypeptides can be found in the protein databases and include, but are not limited to accession numbers ZP_02760162 (GI:168727885), NP_645081.1 (GI: 21281993), and NP_370813.1 (GI:15923279), each of which is incorporated herein by reference as of the priority date of this application.

In yet still further embodiments of the invention a composition may include a polypeptide, peptide, or protein that is or is at least 70%, 75%, 80%, 85%, 90%, 95%, 96%, 97%, 98%, or 99% identical or similar to a Coa protein. In certain aspects the Coa protein will have all or part of the amino acid sequence of SEQ ID NO:27.

In yet still further embodiments of the invention a composition may include a polypeptide, peptide, or protein that is or is at least 70%, 75%, 80%, 85%, 90%, 95%, 96%, 97%, 98%, or 99% identical or similar to a Hla protein. In certain aspects the Hla protein will have all or part of the amino acid sequence of SEQ ID NO:28.

In yet still further embodiments of the invention a composition may include a polypeptide, peptide, or protein that is or is at least 70%, 75%, 80%, 85%, 90%, 95%, 96%, 97%, 98%, or 99% identical or similar to a vWa protein. In certain aspects the vWa protein will have all or part of the amino acid sequence of SEQ ID NO:29.

In yet still further embodiments of the invention a composition may include a polypeptide, peptide, or protein that is or is at least 70%, 75%, 80%, 85%, 90%, 95%, 96%, 97%, 98%, or 99% identical or similar to a vWbp protein. In certain aspects the vWbp protein will have all or part of the amino acid sequence of SEQ ID NO:32.

In certain aspects, a polypeptide or segment/fragment can have a sequence that is at least 85%, at least 90%, at least 95%, at least 98%, or at least 99% or more identical to the amino acid sequence of the reference polypeptide. The term "similarity" refers to a polypeptide that has a sequence that has a certain percentage of amino acids that are either identical with the reference polypeptide or constitute conservative substitutions with the reference polypeptides.

The 'sta001' antigen is annotated as '5'-nucleotidase family protein'. In the NCTC 8325 strain sta001 is SAOUHSC_00025 and has amino acid sequence SEQ ID NO:35 (GI:88193846). In the Newman strain it is nwmn_0022 (GI:151220234). It has also been referred to as AdsA and SasH and SA0024.

Useful sta001 antigens can elicit an antibody (e.g. when administered to a human) that recognizes SEQ ID NO:35 and/or may comprise an amino acid sequence: (a) having 50%, 60%, 65%, 70%, 75%, 80%, 85%, 90%, 91%, 92%, 93%, 94%, 95%, 96%, 97%, 98%, 99%, 99.5% or more identity to SEQ ID NO: 35; and/or (b) comprising a fragment of at least 'n' consecutive amino acids of SEQ ID NO: 35, wherein 'n' is 7 or more (e.g. 8, 10, 12, 14, 16, 18, 20, 25, 30, 35, 40, 50, 60, 70, 80, 90, 100, 150, 200, 250 or more). These sta001 proteins include variants of SEQ ID NO: 35. Preferred fragments of (b) comprise an epitope from SEQ ID NO: 35. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 35 while retaining at least one epitope of SEQ ID NO: 35. The final 34 C-terminal amino acids of SEQ ID NO: 35 can usefully be omitted. The first 38 N-terminal amino acids of SEQ ID NO: 35 can usefully be omitted. Other fragments omit one or more protein domains.

The sta002 antigen is annotated as 'lipoprotein'. In the NCTC•8325 strain sta002 is SAOUHSC 00356 and has amino acid sequence SEQ ID NO:36 (GI:88194155). In the Newman strain it is nwmn_0364 (GI:151220576).

Useful sta002 antigens can elicit an antibody (e.g. when administered to a human) that recognizes SEQ ID NO:36 and/or may comprise an amino acid sequence: (a) having 50%, 60%, 65%, 70%, 75%, 80%, 85%, 90%, 91%, 92%, 93%, 94%, 95%, 96%, 97%, 98%, 99%, 99.5% or more identity to SEQ ID NO:36; and/or (b) comprising a fragment of at least 'n' consecutive amino acids of SEQ ID NO:36, wherein 'n' is 7 or more (e.g. 8, 10, 12, 14, 16, 18, 20, 25, 30, 35, 40, 50, 60, 70, 80, 90, 100, 150 or more). These sta002 proteins include variants of SEQ ID NO:36. Preferred 5 fragments of (b) comprise an epitope from SEQ ID NO:36. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:36 while retaining at least one epitope of SEQ ID NO:36. The first 18 N-terminal amino acids of SEQ ID NO:36 can usefully be omitted. Other fragments omit one or more protein domains. sta002$_{19-187}$ and sta002$_{19-124}$ are two useful fragments of SEQ ID NO:36 which reduce the antigen's similarity with human proteins.

The 'sta003' antigen is annotated as 'surface protein'. In the NCTC 8325 strain sta003 is SAOUHSC_00400 and has amino acid sequence SEQ ID NO:37 (GI:88194195). In the Newman strain it is nwmn_0401 (GI:151220613).

Useful sta003 antigens can elicit an antibody (e.g. when administered to a human) that recognizes SEQ ID NO:37 and/or may comprise an amino acid sequence: (a) having 50%, 60%, 65%, 70%, 75%, 80%, 85%, 90%, 91%, 92%, 93%, 94%, 95%, 96%, 97%, 98%, 99%, 99.5% or more identity to SEQ ID NO:37; and/or (b) comprising a fragment of at least 'n' consecutive amino acids of SEQ ID NO:37, wherein 'n' is 7 or more (e.g. 8, 10, 12, 14, 16, 18, 20, 25, 30, 35, 40, 50, 60, 70, 80, 90, 100, 150, 200, 250 or more). These sta003 proteins include variants of SEQ ID NO:37. Preferred fragments of (b) comprise an epitope from SEQ ID NO:37. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:37 while retaining at least one epitope of SEQ ID NO:37. The first 32 N-terminal amino acids of SEQ ID NO:37 can usefully be omitted. Other fragments omit one or more protein domains.

The 'sta004' antigen is annotated as 'Siderophore binding protein FatB'. In the NCTC 8325 strain sta004 is SAOUHSC_00749 and has amino acid sequence SEQ ID NO:38 (GI:88194514). In the Newman strain it is nwmn_0705 (GI:151220917).

Useful sta004 antigens can elicit an antibody (e.g. when administered to a human) that recognizes SEQ ID NO:38 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:38; and/or (b) comprising a fragment of at least 'n' consecutive amino acids of SEQ ID NO:38, wherein 'n' is 7 or more (e.g. 8, 10, 12, 14, 16, 18, 20, 25, 30, 35, 40, 50, 60, 70, 80, 90, 100, 150, 200, 250 or more). These sta004 proteins include variants of SEQ ID NO:38. Preferred fragments of (b) comprise an epitope from SEQ ID NO:38. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:38 while retaining at least one epitope of SEQ ID NO:38. The first 18 N-terminal amino acids of SEQ ID NO:38 can usefully be omitted. Other fragments omit one or more protein domains.

The 'sta005' antigen is annotated as 'superantigen-like protein'. In the NCTC 8325 strain sta005 is 10 SAOUHSC_01127 and has amino acid sequence SEQ ID NO:39 (GI:88194870). In the Newman strain it is nwmn_1077 (GI:151221289).

Useful sta005 antigens can elicit an antibody (e.g. when administered to a human) that recognizes SEQ ID NO:39 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:39; and/or (b) comprising a fragment of at least 'n' consecutive amino acids of SEQ ID NO:39, wherein 'n' is 7 or more (e.g. 8, 10, 12, 14, 16, 18, 20, 25, 30, 35, 40, 50, 60, 70, 80, 90, 100, 150, 200 or more). These sta005 proteins include variants of SEQ ID NO:39. Preferred fragments of (b) comprise an epitope from SEQ ID NO:39. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:39 while retaining at least one epitope of SEQ ID NO:39. The first 18 N-terminal amino acids of SEQ ID NO:39 can usefully be omitted. Other fragments omit one or more protein domains.

The 'sta006' antigen is annotated as 'ferrichrome-binding protein', and has also been referred to as 25 'FhuD2' in the literature. In the NCTC 8325 strain sta006 is SAOUHSC_02554 and has amino acid sequence SEQ ID NO:40 (GI:88196199). In the Newman strain it is nwmn 2185 (GI:151222397).

Useful sta006 antigens can elicit an antibody (e.g. when administered to a human) that recognizes SEQ ID NO:40 and/or may comprise an amino acid sequence: (a) having 50% or more identity (e.g. 30, 60%, 65%, 70%, 75%, 80%, 85%, 90%, 91%, 92%, 93%, 94%, 95%, 96%, 97%, 98%, 99%, 99.5% or more) to SEQ ID NO:40; and/or (b) comprising a fragment of at least 'n' consecutive amino acids of SEQ ID NO:40, wherein 'n' is 7 or more (e.g. 8, 10, 12, 14, 16, 18, 20, 25, 30, 35, 40, 50, 60, 70, 80, 90, 100, 150, 200, 250 or more). These sta006 proteins include variants of SEQ ID NO:40. Preferred fragments of (b) comprise an epitope from SEQ ID NO:40. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:40 while retaining at least one epitope of SEQ ID NO:40. The first 17 N-terminal amino acids of SEQ ID NO:40 can usefully be omitted.

Other fragments omit one or more protein domains. A sta006 antigen may be lipidated e.g. with an acylated N-terminus cysteine. One useful sta006 sequence has a Met-Ala-Ser- sequence at the N-terminus.

The 'sta007' antigen is annotated as 'secretory antigen precursor'. In the NCTC 8325 strain sta007 is SAOUHSC_02571 and has amino acid sequence SEQ ID NO:41 (GI:88196215). In the Newman strain it is nwmn_2199 (GI:151222411). Proteomic analysis has revealed that this protein is secreted or surface-exposed.

Useful sta007 antigens can elicit an antibody (e.g. when administered to a human) that recognizes SEQ ID NO:41 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:41; and/or (b) comprising a fragment of at least 'n' consecutive amino acids of SEQ ID NO:41, wherein 'n' is 7 or more (e.g. 8, 10, 12, 14, 16, 18, 20, 25, 30, 35, 40, 50, 60, 70, 80, 90, 100, 150, 200, 250 or more). These sta007 proteins include variants of SEQ ID NO:41. Preferred fragments of (b) comprise an epitope from SEQ ID NO:41. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:41 while retaining at least one epitope of SEQ ID NO:41. The first 27 N-terminal amino acids of SEQ ID NO:41 can usefully be omitted. Other fragments omit one or more protein domains.

The 'sta008' antigen is annotated as 'lipoprotein'. In the NCTC 8325 strain sta008 is SAOUHSC_02650 and has amino acid sequence SEQ ID NO:42 (GI:88196290). In the Newman strain it is nwmn_2270 (GI:151222482).

Useful sta008 antigens can elicit an antibody (e.g. when administered to a human) that recognizes SEQ ID NO:42 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:42; and/or (b) comprising a fragment of at least 'n' consecutive amino acids of SEQ ID NO:42, wherein 'n' is 7 or more (e.g. 8, 10, 12, 14, 16, 18, 20, 25, 30, 35, 40, 50, 60, 70, 80, 90, 100, 150, 200 or more). These sta008 proteins include variants of SEQ ID NO:42. Preferred fragments of (b) comprise an epitope from SEQ ID NO:42. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:42 while retaining at least one epitope of SEQ ID NO:42. The first 17 N-terminal amino acids of SEQ ID NO:42 can usefully be omitted. Other fragments omit one or more protein domains.

The 'sta009' antigen is annotated as 'immunoglobulin G-binding protein Sbi'. In the NCTC 8325 strain sta009 is SAOUHSC_02706 and has amino acid sequence SEQ ID NO:43 (GI:88196346). In the Newman strain it is nwmn_2317 (GI:151222529).

Useful sta009 antigens can elicit an antibody (e.g. when administered to a human) that recognizes SEQ ID NO:43 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:43; and/or (b) comprising a fragment of at least 'n' consecutive amino acids of SEQ ID NO:43, wherein 'n' is 7 or more (e.g. 8, 10, 12, 14, 16, 18, 20, 25, 30, 35, 40, 50, 60, 70, 80, 90, 100, 150, 200, 250 or more). These sta009 proteins include variants of SEQ ID NO:43. Preferred fragments of (b) comprise an epitope from SEQ ID NO:43. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:43 while retaining at least one epitope of SEQ ID NO:43. The first 29 N-terminal amino acids of SEQ ID NO:43 can usefully be omitted. Other fragments omit one or more protein domains.

The 'sta010' antigen is annotated as 'immunodominant antigen A'. In the NCTC 8325 strain sta010 is SAOUHSC_02887 and has amino acid sequence SEQ ID NO:44 (GI:88196515). In the Newman strain it is nwmn_2469 (GI:151222681). Proteomic analysis has revealed that this protein is secreted or surface-exposed.

Useful sta010 antigens can elicit an antibody (e.g. when administered to a human) that recognizes SEQ ID NO:44 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:44; and/or (b) comprising a fragment of at least 'n' consecutive amino acids of SEQ ID NO:44, wherein 'n' is 7 or more (e.g. 8, 10, 12, 14, 16, 18, 20, 25, 30, 35, 40, 50, 60, 70, 80, 90, 100, 150, 200 or more). These sta010 proteins include variants of SEQ ID NO:44. Preferred fragments of (b) comprise an epitope from SEQ ID NO:44. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:44 while retaining at least one epitope of SEQ ID NO:44. The first 29 N-terminal amino acids of SEQ ID NO:44 can usefully be omitted. Other fragments omit one or more protein domains.

The 'sta011' antigen is annotated as 'lipoprotein'. In the NCTC 8325 strain sta011 is SAOUHSC_00052 and has amino acid sequence SEQ ID NO:45 (GI:88193872).

Useful sta011 antigens can elicit an antibody (e.g. when administered to a human) that recognizes SEQ ID NO:45 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:45; and/or (b) comprising a fragment of at least 'n' consecutive amino acids of SEQ ID NO:45, wherein 'n' is 7 or more (e.g. 8, 10, 12, 14, 16, 18, 20, 25, 30, 35, 40, 50, 60, 70, 80, 90, 100, 150, 200, 250 or more). These sta011 proteins include variants of SEQ ID NO:45. Preferred fragments of (b) comprise an epitope from SEQ ID NO:45. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:45 while retaining at least one epitope of SEQ ID NO:45. The first 23 N-terminal amino acids of SEQ ID NO:45 can usefully be omitted. Other fragments omit one or more protein domains. A sta011 antigen may be lipidated e.g. with an acylated N-terminus cysteine.

The 'sta012' antigen is annotated as 'protein with leader'. In the NCTC 8325 strain sta012 is SAOUHSC_00106 and has amino acid sequence SEQ ID NO:46 (GI:88193919).

Useful sta012 antigens can elicit an antibody (e.g. when administered to a human) that recognizes SEQ ID NO:46 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:46; and/or (b) comprising a fragment of at least 'n' consecutive amino acids of SEQ ID NO:46, wherein 'n' is 7 or more (e.g. 8, 10, 12, 14, 16, 18, 20, 25, 30, 35, 40, 50, 60, 70, 80, 90, 100, 150, 200, 250 or more). These sta012 proteins include variants of SEQ ID NO:46. Preferred fragments of (b) comprise an epitope from SEQ ID NO:46. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:46 while retaining at least one epitope of SEQ ID NO:46. The first 21 N-terminal amino acids of SEQ ID NO:46 can usefully be omitted. Other fragments omit one or more protein domains.

The 'sta013' antigen is annotated as 'poly-gamma-glutamate capsule biosynthesis protein'. In the NCTC 8325 strain staOB is SAOUHSC_00107 and has amino acid sequence SEQ ID NO:47 (GI:88193920).

Useful sta013 antigens can elicit an antibody (e.g. when administered to a human) that recognizes SEQ ID NO:47 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:47; and/or (b) comprising a fragment of at least 'n' consecutive amino acids of SEQ ID NO:47, wherein 'n' is 7 or more (e.g. 8, 10, 12, 14, 16, 18, 20, 25, 30, 35, 40, 50, 60, 70, 80, 90, 100, 150, 200, 250 or more). These sta013 proteins include variants of SEQ ID NO:47. Preferred fragments of (b) comprise an epitope from SEQ ID NO:47. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:47 while retaining at least one epitope of SEQ ID NO:47. Other fragments omit one or more protein domains.

The 'sta014' antigen is annotated as 'lipoprotein'. In the NCTC 8325 strain sta014 is SAOUHSC_00137 and has amino acid sequence SEQ ID NO:48 (GI:88193950).

Useful sta014 antigens can elicit an antibody (e.g. when administered to a human) that recognizes SEQ ID NO:48 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:48; and/or (b) comprising a fragment of at least 'n' consecutive amino acids of SEQ ID NO:48, wherein 'n' is 7 or more (e.g. 8, 10, 12, 14, 16, 18, 20, 25, 30, 35, 40, 50, 60, 70, 80, 90, 100, 150, 200, 250 or more). These sta014 proteins include variants of SEQ ID NO:48. Preferred fragments of (b) comprise an epitope from SEQ ID NO:48. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:48 while retaining at least one epitope of SEQ ID NO:48. The first 17 N-terminal amino acids of SEQ ID NO:48 can usefully be omitted. Other fragments omit one or more protein domains.

The 'sta015' antigen is annotated as 'extracellular solute-binding protein; ROD containing lipoprotein'. In the NCTC 8325 strain sta015 is SAOUHSC_00170 and has amino acid sequence SEQ ID NO:49 (GI:88193980).

Useful sta015 antigens can elicit an antibody (e.g. when administered to a human) that recognizes SEQ ID NO:49 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:49; and/or (b) comprising a fragment of at least 'n' consecutive amino acids of SEQ ID NO:49, wherein 'n' is 7 or more (e.g. 8, 10, 12, 14, 16, 18, 20, 25, 30, 35, 40, 50, 60, 70, 80, 90, 100, 150, 200, 250 or more). These sta015 proteins include variants of SEQ ID NO:49. Preferred fragments of (b) comprise an epitope from SEQ ID NO:49. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:49 while retaining at least one epitope of SEQ ID NO:49. The first 18 N-terminal amino acids of SEQ ID NO:49 can usefully be omitted. Other fragments omit one or more protein domains.

The 'sta016' antigen is annotated as 'gamma-glutamyl-transpeptidase'. In the NCTC 8325 strain sta016 is SAOUHSC_00171 and has amino acid sequence SEQ ID NO:50 (GI:88193981).

Useful sta016 antigens can elicit an antibody (e.g. when administered to a human) that recognizes SEQ ID NO:50 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:50; and/or (b) comprising a fragment of at least 'n' consecutive amino acids of SEQ ID NO:50, wherein 'n' is 7 or more (e.g. 8, 10, 12, 14, 16, 18, 20, 25, 30, 35, 40, 50, 60, 70, 80, 90, 100, 150, 200, 250 or more). These sta016 proteins include variants of SEQ ID NO:50. Preferred fragments of (b) comprise an epitope from SEQ ID NO:50. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:50 while retaining at least one epitope of SEQ ID NO:50. Other fragments omit one or more protein domains.

The 'sta017' antigen is annotated as 'lipoprotein'. In the NCTC 8325 strain sta017 is SAOUHSC_00186 and has amino acid sequence SEQ ID NO:51 (GI:88193996).

Useful sta017 antigens can elicit an antibody (e.g. when administered to a human) that recognizes SEQ ID NO:51 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:51; and/or (b) comprising a fragment of at least 'n' consecutive amino acids of SEQ ID NO:51, wherein In' is 7 or more (e.g. 8, 10, 12, 14, 16, 18, 20, 25, 30, 35, 40, 50, 60, 70, 80, 90, 100, 150, 200, 250 or more). These sta017 proteins include variants of SEQ ID NO:51. Preferred fragments of (b) comprise an epitope from SEQ ID NO:51. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:51 while retaining at least one epitope of SEQ ID NO:51. The first 17 N-terminal amino acids of SEQ ID NO:51 can usefully be omitted. Other fragments omit one or more protein domains.

The 'sta018' antigen is annotated as 'extracellular solute-binding protein'. In the NCTC 8325 strain sta018 is SAOUHSC_00201 and has amino acid sequence SEQ ID NO:52 (GI:88194011).

Useful sta018 antigens can elicit an antibody (e.g. when administered to a human) that recognizes SEQ ID NO:52 and/or may comprise an amino acid sequence: (a) having 50%, 60%, 65%, 70%, 75%, 80%, 85%, 90%, 91%, 92%, 93%, 94%, 95%, 96%, 97%, 98%, 99%, 99.5% or more identity to SEQ ID NO:52; and/or (b) comprising a fragment of at least 'n' consecutive amino acids of SEQ ID NO:52, wherein 'n' is 7 or more (e.g. 8, 10, 12, 14, 16, 18, 20, 25, 30, 35, 40, 50, 60, 70, 80, 90, 100, 150, 200, 250 or more). These sta018 proteins include variants of SEQ ID NO:52. Preferred fragments of (b) comprise an epitope from SEQ ID NO:52. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:52 while retaining at least one epitope of SEQ ID NO:52. Other fragments omit one or more protein domains.

The 'sta019' antigen is annotated as 'peptidoglycan hydrolase'. In the NCTC 8325 strain sta019 is SAOUHSC_00248 and has amino acid sequence SEQ ID NO:53 (GI:88194055). In the Newman strain it is nwmn_0210 (GI:151220422).

Useful sta019 antigens can elicit an antibody (e.g. when administered to a human) that recognizes SEQ ID NO:53 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:53; and/or (b) comprising a fragment of at least 'n' consecutive amino acids of SEQ ID NO:53, wherein 'n' is 7 or more (e.g. 8, 10, 12, 14, 16, 18, 20, 25, 30, 35, 40, 50, 60, 70, 80, 90, 100, 150, 200, 250 or more). These sta019 proteins include variants of SEQ ID NO:53. Preferred fragments of (b) comprise an epitope from SEQ ID NO:53. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:53 while retaining at least one epitope of SEQ ID NO:53. The first 25 N-terminal amino acids of SEQ ID NO:53 can usefully be omitted. Other fragments omit one or more protein domains.

Sta019 does not adsorb well to aluminium hydroxide adjuvants, so Sta019 present in a composition may be unadsorbed or may be adsorbed to an alternative adjuvant e.g. to an aluminium phosphate.

The 'sta020' antigen is annotated as 'exported protein'. In the NCTC 8325 strain sta020 is SAOUHSC_00253 and has amino acid sequence SEQ ID NO:54 (GI:88 194059).

Useful sta020 antigens can elicit an antibody (e.g. when administered to a human) that recognizes SEQ ID NO:54 and/or may comprise an amino acid sequence: (a) having 50%, 60%, 65%, 70%, 75%, 80%, 85%, 90%, 91%, 92%, 93%, 94%, 95%, 96%, 97%, 98%, 99%, 99.5% or more identity to SEQ ID NO:54; and/or (b) comprising a fragment of at least 'n' consecutive amino acids of SEQ ID NO:54, wherein 'n' is 7 or more (e.g. 8, 10, 12, 14, 16, 18, 20, 25, 30, 35, 40, 50, 60, 70, 80, 90, 100, 150, 200, 250 or more). These sta020 proteins include variants of SEQ ID NO:54. Preferred fragments of (b) comprise an epitope from SEQ ID NO:54. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:54 while retaining at least one epitope of SEQ ID NO:54. The first 30 N-terminal amino acids of SEQ ID NO:54 can usefully be omitted. Other fragments omit one or more protein domains.

The 'sta021' antigen is annotated as 'secretory antigen SsaA-like protein'. In the NCTC 8325 strain sta021 is SAOUHSC_00256 and has amino acid sequence SEQ ID NO:55 (GI:88194062).

Useful sta021 antigens can elicit an antibody (e.g. when administered to a human) that recognizes SEQ ID NO:55 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:55; and/or (b) comprising a fragment of at least 'n' consecutive amino acids of SEQ ID NO:55, wherein 'n' is 7 or more (e.g. 8, 10, 12, 14, 16, 18, 20, 25, 30, 35, 40, 50, 60, 70, 80, 90, 100, 150, 200, 250 or more). These sta021 proteins include variants of SEQ ID NO:55. Preferred fragments of (b) comprise an epitope from SEQ ID NO:55. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:55 while retaining at least one epitope of SEQ ID NO:55. The first 24 N-terminal amino acids of SEQ ID NO:55 can usefully be omitted. Other fragments omit one or more protein domains.

The 'sta022' antigen is annotated as 'lipoprotein'. In the NCTC 8325 strain sta022 is SAOUHSC_00279 and has amino acid sequence SEQ ID NO:56 (GI:88194083).

Useful sta022 antigens can elicit an antibody (e.g. when administered to a human) that recognizes SEQ ID NO:56 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:56; and/or (b) comprising a fragment of at least 'n' consecutive amino acids of SEQ ID NO:56, wherein 'n' is 7 or more (e.g. 8, 10, 12, 14, 16, 18, 20, 25, 30, 35, 40, 50, 60, 70, 80, 90, 100 or more). These sta022 proteins include variants of SEQ ID NO:56. Preferred fragments of (b) comprise an epitope from SEQ ID NO:56. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:56 while retaining at least one epitope of SEQ ID NO:56. The first 17 N-terminal amino acids of SEQ ID NO:56 can usefully be omitted. Other fragments omit one or more protein domains.

The 'sta023' antigen is annotated as '5'-nucleotidase; lipoprotein e(P4) family'. In the NCTC 8325 strain sta023 is SAOUHSC_00284 and has amino acid sequence SEQ ID NO:57 (GI:88194087).

Useful sta023 antigens can elicit an antibody (e.g. when administered to a human) that recognizes SEQ ID NO:57 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:57; and/or (b) comprising a fragment of at least 'n' consecutive amino acids of SEQ ID NO:57, wherein 'n' is 7 or more (e.g. 8, 10, 12, 14, 16, 18, 20, 25, 30, 35, 40, 50, 60, 70, 80, 90, 100, 150, 200, 250 or more). These sta023 proteins include variants of SEQ ID NO:57. Preferred fragments of (b) comprise an epitope from SEQ ID NO:57. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:57 while retaining at least one epitope of SEQ ID NO:57. The first 31 N-terminal amino acids of SEQ ID NO:57 can usefully be omitted. Other fragments omit one or more protein domains.

The 'sta024' antigen is annotated as 'lipase precursor'. In the NCTC 8325 strain sta024 is SAOUHSC_00300 and has amino acid sequence SEQ ID NO:58 (GI:88194101).

Useful sta024 antigens can elicit an antibody (e.g. when administered to a human) that recognizes SEQ ID NO:58 and/or may comprise an amino acid sequence: (a) having 50%, 60%, 65%, 70%, 75%, 80%, 85%, 90%, 91%, 92%, 93%, 94%, 95%, 96%, 97%, 98%, 99%, 99.5% or more identity to SEQ ID NO:58; and/or (b) comprising a fragment of at least 'n' consecutive amino acids of SEQ ID NO:58, wherein 'n' is 7 or more (e.g. 8, 10, 12, 14, 16, 18, 20, 25, 30, 35, 40, 50, 60, 70, 80, 90, 100, 150, 200, 250 or more). These sta024 proteins include variants of SEQ ID NO:58. Preferred fragments of (b) comprise an epitope from SEQ ID NO:58. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:58 while retaining at least one epitope of SEQ ID NO:58. The first 37 N-terminal amino acids of SEQ ID NO:58 can usefully be omitted. Other fragments omit one or more protein domains.

The 'sta025' antigen is annotated as 'lipoprotein'. In the NCTC 8325 strain sta025 is SAOUHSC_00362 and has amino acid sequence SEQ ID NO:59 (GI:88194160).

Useful sta025 antigens can elicit an antibody (e.g. when administered to a human) that recognizes SEQ ID NO:59 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:59; and/or (b) comprising a fragment of at least In' consecutive amino acids of SEQ ID NO:59, wherein 'n' is 7 or more (e.g. 8, 10, 12, 14, 16, 18, 20, 25, 30, 35, 40, 50, 60, 70, 80, 90, 100, 150, 200 or more). These sta025 proteins include variants of SEQ ID NO:59. Preferred fragments of (b) comprise an epitope from SEQ ID NO:59. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:59 while retaining at least one epitope of SEQ ID NO:59. The first 19 N-terminal amino acids of SEQ ID NO:59 can usefully be omitted. Other fragments omit one or more protein domains.

The 'sta026' antigen is annotated as 'lipoprotein'. In the NCTC 8325 strain sta026 is SAOUHSC_00404 and has amino acid sequence SEQ ID NO:60 (GI:88194198).

Useful sta026 antigens can elicit an antibody (e.g. when administered to a human) that recognizes SEQ ID NO:60 and/or may comprise an amino acid sequence: (a) having 50%, 60%, 65%, 70%, 75%, 80%, 85%, 90%, 91%, 92%, 93%, 94%, 95%, 96%, 97%, 98%, 99%, 99.5% or more identity to SEQ ID NO:60; and/or (b) comprising a fragment of at least 'n' consecutive amino acids of SEQ ID NO:60, wherein In' is 7 or more (e.g. 8, 10, 12, 14, 16, 18, 20, 25, 30, 35, 40, 50, 60, 70, 80, 90, 100, 150, 200, 250 or more). These sta026 proteins include variants of SEQ ID NO:60. Preferred fragments of (b) comprise an epitope from SEQ ID NO:60. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:60 while retaining at least one epitope of SEQ ID NO:60. The first 22 N-terminal amino acids of SEQ ID NO:60 can usefully be omitted. Other fragments omit one or more protein domains.

The 'sta027' antigen is annotated as 'probable lipase'. In the NCTC 8325 strain sta027 is SAOUHSC_00661 and has amino acid sequence SEQ ID NO:61 (GI:88194426).

Useful sta027 antigens can elicit an antibody (e.g. when administered to a human) that recognizes SEQ ID NO:61 and/or may comprise an amino acid sequence: (a) having 50%, 60%, 65%, 70%, 75%, 80%, 85%, 90%, 91%, 92%, 93%, 94%, 95%, 96%, 97%, 98%, 99%, 99.5% or more identity to SEQ ID NO:61; and/or (b) comprising a fragment of at least 'n' consecutive amino acids of SEQ ID NO:61, wherein 'n' is 7 or more (e.g. 8, 10, 12, 14, 16, 18, 20, 25, 30, 35, 40, 50, 60, 70, 80, 90, 100, 150, 200, 250 or more). These sta027 proteins include variants of SEQ ID NO:61. Preferred fragments of (b) comprise an epitope from SEQ ID NO:61. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:61 while retaining at least one epitope of SEQ ID NO:61. The first 23 N-terminal amino acids of SEQ ID NO:61 can usefully be omitted. Other fragments omit one or more protein domains.

The 'sta028' antigen is annotated as 'secretory antigen SsaA-like protein'. In the NCTC 8325 strain sta028 is SAOUHSC_00671 and has amino acid sequence SEQ ID NO:62 (GI:88194436). In the Newman strain it is nwmn_0634 (GI:151220846).

Useful sta028 antigens can elicit an antibody (e.g. when administered to a human) that recognizes SEQ ID NO:62 and/or may comprise an amino acid sequence: (a) having 50%, 60%, 65%, 70%, 75%, 80%, 85%, 90%, 91%, 92%, 93%, 94%, 95%, 96%, 97%, 98%, 99%, 99.5% or more identity to SEQ ID NO:62; and/or (b) comprising a fragment of at least 'n' consecutive amino acids of SEQ ID NO:62, wherein 'n' is 7 or more (e.g. 8, 10, 12, 14, 16, 18, 20, 25, 30, 35, 40, 50, 60, 70, 80, 90, 100, 150, 200, 250 or more). These sta028 proteins include variants of SEQ ID NO:62. Preferred fragments of (b) comprise an epitope from SEQ ID NO:62. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:62 while retaining at least one epitope of SEQ ID NO:62. The first 25 N-terminal amino acids of SEQ ID NO:62 can usefully be omitted. Other fragments omit one or more protein domains.

The 'sta029' antigen is annotated as 'ferrichrome binding protein'. In the NCTC 8325 strain sta029 is SAOUHSC_00754 and has amino acid sequence SEQ ID NO:63 (GI:88194518).

Useful sta029 antigens can elicit an antibody (e.g. when administered to a human) that recognizes SEQ ID NO:63 and/or may comprise an amino acid sequence: (a) having 50%, 60%, 65%, 70%, 75%, 80%, 85%, 90%, 91%, 92%, 93%, 94%, 95%, 96%, 97%, 98%, 99%, 99.5% or more identity to SEQ ID NO:63; and/or (b) comprising a fragment of at least 'n' consecutive amino acids of SEQ ID NO:63, wherein 'n' is 7 or more (e.g. 8, 10, 12, 14, 16, 18, 20, 25, 30, 35, 40, 50, 60, 70, 80, 90, 100, 150, 200, 250 or more). These sta029 proteins include variants of SEQ ID NO:63. Preferred fragments of (b) comprise an epitope from SEQ ID NO:63. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:63 while retaining at least one epitope of SEQ ID NO:63. The final 25 C-terminal amino acids of SEQ ID NO:63 can usefully be omitted. The first 19 N-terminal amino acids of SEQ ID NO:63 can usefully be omitted. Other fragments omit one or more protein domains.

The 'sta030' antigen is annotated as 'lipoprotein'. In the NCTC 8325 strain sta030 is SAOUHSC_00808 and has amino acid sequence SEQ ID NO:64 (GI:88194568).

Useful sta030 antigens can elicit an antibody (e.g. when administered to a human) that recognizes SEQ ID NO:64 and/or may comprise an amino acid sequence: (a) having 50%, 60%, 65%, 70%, 75%, 80%, 85%, 90%, 91%, 92%, 93%, 94%, 95%, 96%, 97%, 98%, 99%, 99.5% or more identity to SEQ ID NO:64; and/or (b) comprising a fragment of at least 'n' consecutive amino acids of SEQ ID NO:64, wherein 'n' is 7 or more (e.g. 8, 10, 12, 14, 16, 18, 20, 25, 30, 35, 40, 50, 60, 70, 80, 90, 100, 150, 200 or more). These sta030 proteins include variants of SEQ ID NO:64. Preferred fragments of (b) comprise an epitope from SEQ ID NO:64. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:64 while retaining at least one epitope of SEQ ID NO:64. The first 17 N-terminal amino acids of SEQ ID NO:64 can usefully be omitted. Other fragments omit one or more protein domains.

The 'sta031' antigen is annotated as '5-nucleotidase family protein'. In the NCTC 8325 strain sta031 is SAOUHSC_00860 and has amino acid sequence SEQ ID NO:65 (GI:88194617).

Useful sta031 antigens can elicit an antibody (e.g. when administered to a human) that recognizes SEQ ID NO:65 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:65; and/or (b) comprising a fragment of at least 'n' consecutive amino acids of SEQ ID NO:65, wherein 'n' is 7 or more (e.g. 8, 10, 12, 14, 16, 18, 20, 25, 30, 35, 40, 50, 60, 70, 80, 90, 100, 150, 200, 250 or more). These sta031 proteins include variants of SEQ ID NO:65. Preferred fragments of (b) comprise an epitope from SEQ ID NO:65. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:65 while retaining at least one epitope of SEQ ID NO:65. Other fragments omit one or more protein domains.

The 'sta032' antigen is annotated as 'serine protease HtrA'. In the NCTC 8325 strain sta032 is SAOUHSC 00958 and has amino acid sequence SEQ ID NO:66 (GI: 88194715).

Useful sta032 antigens can elicit an antibody (e.g. when administered to a human) that recognizes SEQ ID NO:66 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:66; and/or (b) comprising a fragment of at least 'n' consecutive amino acids of SEQ ID NO:66, wherein 'n' is 7 or more (e.g. 8, 10, 12, 14, 16, 18, 20, 25, 30, 35, 40, 50, 60, 70, 80, 90, 100, 150, 200, 250 or more). These sta032 proteins include variants of SEQ ID NO:66. Preferred fragments of (b) comprise an epitope from SEQ ID NO:66. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:66 while retaining at least one epitope of SEQ ID NO:66. Other fragments omit one or more protein domains.

The 'sta033' antigen is annotated as 'cysteine protease precursor'. In the NCTC 8325 strain sta033 is SAOUHSC_00987 and has amino acid sequence SEQ ID NO:67 (GI:88194744).

Useful sta033 antigens can elicit an antibody (e.g. when administered to a human) that recognizes SEQ ID NO:67 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:67; and/or (b) comprising a fragment of at least 'n' consecutive amino acids of SEQ ID NO:67, wherein 'n' is 7 or more (e.g. 8, 10, 12, 14, 16, 18, 20, 25, 30, 35, 40, 50, 60, 70, 80, 90, 100, 150, 200, 250 or more). These sta033 proteins include variants of SEQ ID NO:67. Preferred fragments of (b) comprise an epitope from SEQ ID NO:67. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:67 while retaining at least one epitope of SEQ ID NO:67. The first 29 N-terminal amino acids of SEQ ID NO:67 can usefully be omitted. Other fragments omit one or more protein domains.

The 'sta034' antigen is annotated as 'glutamyl endopeptidase precursor'. In the NCTC 8325 strain sta034 is SAOUHSC_00988 and has amino acid sequence SEQ ID NO:68 (GI:88194745).

Useful sta034 antigens can elicit an antibody (e.g. when administered to a human) that recognizes SEQ ID NO:68 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:68; and/or (b) comprising a fragment of at least 'n' consecutive amino acids of SEQ ID NO:68, wherein 'n' is 7 or more (e.g. 8, 10, 12, 14, 16, 18, 20, 25, 30, 35, 40, 50, 60, 70, 80, 90, 100, 150, 200, 250 or more). These sta034 proteins include variants of SEQ ID NO:68. Preferred fragments of (b) comprise an epitope from SEQ ID NO:68. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:68 while retaining at least one epitope of SEQ ID NO:68. The first 29 N-terminal amino acids of SEQ ID NO:68 can usefully be omitted. Other fragments omit one or more protein domains.

The 'sta035' antigen is annotated as 'fmt protein'. In the NCTC 8325 strain sta035 is SAOUHSC_00998 and has amino acid sequence SEQ ID NO:69 (GI:88194754).

Useful sta035 antigens can elicit an antibody (e.g. when administered to a human) that recognizes SEQ ID NO:69 and/or may comprise an amino acid sequence: (a) having 50%, 60%, 65%, 70%, 75%, 80%, 85%, 90%, 91%, 92%, 93%, 94%, 95%, 96%, 97%, 98%, 99%, 99.5% or more identity to SEQ ID NO:69; and/or (b) comprising a fragment of at least 'n' consecutive amino acids of SEQ ID NO:69, wherein 'n' is 7 or more (e.g. 8, 10, 12, 14, 16, 18, 20, 25, 30, 35, 40, 50, 60, 70, 80, 90, 100, 150, 200, 250 or more). These sta035 proteins include variants of SEQ ID NO:69. Preferred fragments of (b) comprise an epitope from SEQ ID NO:69. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:69 while retaining at least one epitope of SEQ ID NO:69. The first 25 N-terminal amino acids of SEQ ID NO:69 can usefully be omitted. Other fragments omit one or more protein domains.

The 'sta036' antigen is annotated as 'iron-regulated protein with leader'. In the NCTC 8325 strain sta036 is SAOUHSC_01084 and has amino acid sequence SEQ ID NO:70 (GI:88194831).

Useful sta036 antigens can elicit an antibody (e.g. when administered to a human) that recognizes SEQ ID NO:70 and/or may comprise an amino acid sequence: (a) having 50%, 60%, 65%, 70%, 75%, 80%, 85%, 90%, 91%, 92%, 93%, 94%, 95%, 96%, 97%, 98%, 99%, 99.5% or more identity to SEQ ID NO:70; and/or (b) comprising a fragment of at least 'n' consecutive amino acids of SEQ ID NO:70, wherein 'n' is 7 or more (e.g. 8, 10, 12, 14, 16, 18, 20, 25, 30, 35, 40, 50, 60, 70, 80, 90, 100, 150, 200, 250 or more). These sta036 proteins include variants of SEQ ID NO:70. Preferred fragments of (b) comprise an epitope from SEQ ID NO:70. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:70 while retaining at least one epitope of SEQ ID NO:70. The first 27 C-terminal amino acids of SEQ ID NO:70 can usefully be omitted. The first 32 N-terminal amino acids of SEQ ID NO:70 can usefully be omitted. Other fragments omit one or more protein domains.

The 'sta037' antigen is annotated as 'iron ABC transporter; iron-binding protein IsdE'. In the NCTC 8325 strain sta037 is SAOUHSC 01085 and has amino acid sequence SEQ ID NO:71 (GI:88194832).

Useful sta037 antigens can elicit an antibody (e.g. when administered to a human) that recognizes SEQ ID NO:71 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:71; and/or (b) comprising a fragment of at least 'n' consecutive amino acids of SEQ ID NO:71, wherein 'n' is 7 or more (e.g. 8, 10, 12, 14, 16, 18, 20, 25, 30, 35, 40, 50, 60, 70, 80, 90, 100, 150, 200, 250 or more). These sta037 proteins include variants of SEQ ID NO:71. Preferred fragments of (b) comprise an epitope from SEQ ID NO:71. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:71 while retaining at least one epitope of SEQ ID NO:71. The first 9 N-terminal amino acids of SEQ ID NO:71 can usefully be omitted. Other fragments omit one or more protein domains.

The 'sta038' antigen is annotated as 'NPQTN specific sortase B'. In the NCTC 8325 strain sta038 is SAOUHSC_01088 and has amino acid sequence SEQ ID NO:72 (GI:88194835).

Useful sta038 antigens can elicit an antibody (e.g. when administered to a human) that recognizes SEQ ID NO:72 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:72; and/or (b) comprising a fragment of at least 'n' consecutive amino acids of SEQ ID NO:72, wherein '11' is 7 or more (e.g. 8, 10, 12, 14, 16, 18, 20, 25, 30, 35, 40, 50, 60, 70, 80, 90, 100, 150, 200 or more). These sta038 proteins include variants of SEQ ID NO:72. Preferred fragments of (b) comprise an epitope from SEQ ID NO:72. Other preferred fragments lack one or more amino acids)(e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:72 while retaining at least one epitope of SEQ ID NO:72. The first 21 N-terminal amino acids of SEQ ID NO:72 can usefully be omitted. Other fragments omit one or more protein domains.

The 'sta039' antigen is annotated as 'superantigen-like protein'. In the NCTC 8325 strain sta039 is SAOUHSC_01124 and has amino acid sequence SEQ ID NO:73 (GI:88194868).

Useful sta039 antigens can elicit an antibody (e.g. when administered to a human) that recognizes SEQ ID NO:73 and/or may comprise an amino acid sequence: (a) having 50%, 60%, 65%, 70%, 75%, 80%, 85%, 90%, 91%, 92%, 93%, 94%, 95%, 96%, 97%, 98%, 99%, 99.5% or more identity to SEQ ID NO:73; and/or (b) comprising a fragment of at least 'n' consecutive amino acids of SEQ ID NO:73, wherein 'n' is 7 or more (e.g. 8, 10, 12, 14, 16, 18, 20, 25, 30, 35, 40, 50, 60, 70, 80, 90, 100, 150, 200 or more). These sta039 proteins include variants of SEQ ID NO:73. Preferred fragments of (b) comprise an epitope from SEQ ID NO:73. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:73 while retaining at least one epitope of SEQ ID NO:73. The first 22 N-terminal amino acids of SEQ ID NO:73 can usefully be omitted. Other fragments omit one or more protein domains.

The 'sta040' antigen is annotated as 'superantigen-like protein'. In the NCTC 8325 strain sta040 is SAOUHSC_011125 and has amino acid sequence SEQ ID NO:74 (GI:88194869). In the Newman strain it is nwmn_1076 (GI:151221288).

Useful sta040 antigens can elicit an antibody (e.g. when administered to a human) that recognizes SEQ ID NO:74 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:74; and/or (b) comprising a fragment of at least 'n' consecutive amino acids of SEQ ID NO:74, wherein 'n' is 7 or more (e.g. 8, 10, 12, 14, 16, 18, 20, 25, 30, 35, 40, 50, 60, 70, 80, 90, 100, 150, 200 or more). These sta040 proteins include variants of SEQ ID NO:74. Preferred fragments of (b) comprise an epitope from SEQ ID NO:74. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:74 while retaining at least one epitope of SEQ ID NO:74. The first 21 N-terminal amino acids of SEQ ID NO:74 can usefully be omitted. Other fragments omit one or more protein domains.

The 'sta041' antigen is annotated as 'fibronectin-binding protein A-related'. In the NCTC 8325 strain sta041 is SAOUHSC_01175 and has amino acid sequence SEQ ID NO:75 (GI:88194914).

Useful sta041 antigens can elicit an antibody (e.g. when administered to a human) that recognizes SEQ ID NO:75 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:75; and/or (b) comprising a fragment of at least 'n' consecutive amino acids of SEQ ID NO:75, wherein 'n' is 7 or more (e.g. 8, 10, 12, 14, 16, 18, 20, 25, 30, 35, 40, 50, 60, 70, 80, 90, 100, 150, 200, 250 or more). These sta041 proteins include variants of SEQ ID NO:75. Preferred fragments of (b) comprise an epitope from SEQ ID NO:75. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:75 while retaining at least one epitope of SEQ ID NO:75. Other fragments omit one or more protein domains.

The 'sta042, antigen is annotated as 'lipoprotein'. In the NCTC 8325 strain sta042 is SAOUHSC_01180 and has amino acid sequence SEQ ID NO:76 (GI:88194919).

Useful sta042 antigens can elicit an antibody (e.g. when administered to a human) that recognizes SEQ ID NO:76 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:76; and/or (b) comprising a fragment of at least 'n' consecutive amino acids of SEQ ID NO:76, wherein 'n' is 7 or more (e.g. 8, 10, 12, 14, 16, 18, 20, 25, 30, 35, 40, 50, 60, 70, 80, 90, 100, 150, 200, 250 or more). These sta042 proteins include variants of SEQ ID NO:76. Preferred fragments of (b) comprise an epitope from SEQ ID NO:76. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:76 while retaining at least one epitope of SEQ ID NO:76. The first 18 N-terminal amino acids of SEQ ID NO:76 can usefully be omitted. Other fragments omit one or more protein domains.

The 'sta043', antigen is annotated as 'cell wall hydrolase'. In the NCTC 8325 strain sta043 is SAOUHSC_01219 and has amino acid sequence SEQ ID NO:77 (GI:88194955).

Useful sta043 antigens can elicit an antibody (e.g. when administered to a human) that recognizes SEQ ID NO:77 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:77; and/or (b) comprising a fragment of at least 'n' consecutive amino acids of SEQ ID NO:77, wherein 'n' is 7 or more (e.g. 8, 10, 12, 14, 16, 18, 20, 25, 30, 35, 40, 50, 60, 70, 80, 90, 100, 150, 200, 250 or more). These sta043 proteins include variants of SEQ ID NO:77. Preferred fragments of (b) comprise an epitope from SEQ ID NO:77. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:77 while retaining at least one epitope of SEQ ID NO:77. The first 38 N-terminal amino acids of SEQ ID NO:77 can usefully be omitted. Other fragments omit one or more protein domains.

The 'sta044' antigen is annotated as 'lipoprotein'. In the NCTC 8325 strain sta044 is SAOUHSC_01508 and has amino acid sequence SEQ ID NO:78 (GI:88195223).

Useful sta044 antigens can elicit an antibody (e.g. when administered to a human) that recognizes SEQ ID NO:78 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:78; and/or (b) comprising a fragment of at least 'n' consecutive amino acids of SEQ ID NO:78, wherein 'n' is 7 or more (e.g. 8, 10, 12, 14, 16, 18, 20, 25, 30, 35, 40, 50, 60, 70, 80, 90, 100, 150, 200, 250 or more). These sta044 proteins include variants of SEQ ID NO:78. Preferred fragments of (b) comprise an epitope from SEQ ID NO:78. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:78 while retaining at least one epitope of SEQ ID NO:78. The first 17 N-terminal amino acids of SEQ ID NO:78 can usefully be omitted. Other fragments omit one or more protein domains.

The 'sta045' antigen is annotated as 'lipoprotein'. In the NCTC 8325 strain sta045 is SAOUHSC_01627 and has amino acid sequence SEQ ID NO:79 (GI:88195337).

Useful sta045 antigens can elicit an antibody (e.g. when administered to a human) that recognizes SEQ ID NO:79 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:79; and/or (b) comprising a fragment of at least 'n' consecutive amino acids of SEQ ID NO:79, wherein 'n' is 7 or more (e.g. 8, 10, 12, 14, 16, 18, 20, 25, 30, 35, 40, 50, 60, 70, 80, 90, 100, 150 or more). These sta045 proteins include variants of SEQ ID NO:79. Preferred fragments of (b) comprise an epitope from SEQ ID NO:79. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:79 while retaining at least one epitope of SEQ ID NO:79. The first 16 N-terminal amino acids of SEQ ID NO:79 can usefully be omitted. Other fragments omit one or more protein domains.

The 'sta046' antigen is annotated as 'Excalibur protein'. In the NCTC 8325 strain sta046 is SAOUHSC_01918 and has amino acid sequence SEQ ID NO:80 (GI:88195613).

Useful sta046 antigens can elicit an antibody (e.g. when administered to a human) that recognizes SEQ ID NO:80 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:80; and/or (b) comprising a fragment of at least 'n' consecutive amino acids of SEQ ID NO:80, wherein 'n' is 7 or more (e.g. 8, 10, 12, 14, 16, 18, 20, 25, 30, 35, 40, 50, 60, 70, 80, 90, 100, 150, 200 or more). These sta046 proteins include variants of SEQ ID NO:80. Preferred fragments of (b) comprise an epitope from SEQ ID NO:80. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:80 while retaining at least one epitope of SEQ ID NO:80. The first 53 N-terminal amino acids of SEQ ID NO:80 can usefully be omitted. Other fragments omit one or more protein domains.

The 'sta047' antigen is annotated as 'lipoprotein'. In the NCTC 8325 strain sta047 is SAOUHSC_01920 and has amino acid sequence SEQ ID NO:81 (GI:88195615).

Useful sta047 antigens can elicit an antibody (e.g. when administered to a human) that recognizes SEQ ID NO:81 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:81; and/or (b) comprising a fragment of at least 'n' consecutive amino acids of SEQ ID NO:81, wherein 'n' is 7 or more (e.g. 8, 10, 12, 14, 16, 18, 20, 25, 30, 35, 40, 50, 60, 70, 80, 90, 100, 150, 200 or more). These sta047 proteins include variants of SEQ ID NO:81. Preferred fragments of (b) comprise an epitope from SEQ ID NO:81. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:81 while retaining at least one epitope of SEQ ID NO:81. The first 18 N-terminal amino acids of SEQ ID NO:81 can usefully be omitted. Other fragments omit one or more protein domains.

The 'sta048' antigen is annotated as 'intracellular serine protease'. In the NCTC 8325 strain sta048 is SAOUHSC_01949 and has amino acid sequence SEQ ID NO:82 (GI:88195642).

Useful sta048 antigens can elicit an antibody (e.g. when administered to a human) that recognizes SEQ ID NO:82 and/or may comprise an amino acid sequence: (a) having 50%, 60%, 65%, 70%, 75%, 80%, 85%, 90%, 91%, 92%, 93%, 94%, 95%, 96%, 97%, 98%, 99%, 99.5% or more identity to SEQ ID NO:82; and/or (b) comprising a fragment of at least 'n' consecutive amino acids of SEQ ID NO:82, wherein 'n' is 7 or more (e.g. 8, 10, 12, 14, 16, 18, 20, 25, 30, 35, 40, 50, 60, 70, 80, 90, 100, 150, 200, 250 or more). These sta048 proteins include variants of SEQ ID NO:82. Preferred fragments of (b) comprise an epitope from SEQ ID NO:82. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:82 while retaining at least one epitope of SEQ ID NO:82. The first 27 N-terminal amino acids of SEQ ID NO:82 can usefully be omitted. Other fragments omit one or more protein domains.

The 'sta049' antigen is annotated as 'protein export protein PrsA'. In the NCTC 8325 strain sta049 is SAOUHSC_01972 and has amino acid sequence SEQ ID NO:83 (GI:88195663). In the Newman strain it is nwmn_I733 (GI:151221945).

Useful sta049 antigens can elicit an antibody (e.g. when administered to a human) that recognizes SEQ ID NO:83 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:83; and/or (b) comprising a fragment of at least 'n' consecutive amino acids of SEQ ID NO:83, wherein 'n' is 7 or more (e.g. 8, 10, 12, 14, 16, 18, 20, 25, 30, 35, 40, 50, 60, 70, 80, 90, 100, 150, 200, 250 or more). These sta049 proteins include variants of SEQ ID NO:83. Preferred fragments of (b) comprise an epitope from SEQ ID NO:83. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:83 while retaining at least one epitope of SEQ ID NO:83. The first 25 N-terminal amino acids of SEQ ID NO:83 can usefully be omitted. Other fragments omit one or more protein domains.

The 'sta050' antigen is annotated as 'staphopain thiol proteinase'. In the NCTC 8325 strain sta050 is SAOUHSC_02127 and has amino acid sequence SEQ ID NO:84 (GI:88195808).

Useful sta050 antigens can elicit an antibody (e.g. when administered to a human) that recognizes SEQ ID NO:84 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:84; and/or (b) comprising a fragment of at least 'n' consecutive amino acids of SEQ ID NO:84, wherein 'n' is 7 or more (e.g. 8, 10, 12, 14, 16, 18, 20, 25, 30, 35, 40, 50, 60, 70, 80, 90, 100, 150, 200, 250 or more). These sta050 proteins include variants of SEQ ID NO:84. Preferred fragments of (b) comprise an epitope from SEQ ID NO:84. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:84 while retaining at least one epitope of SEQ ID NO:84. The first 25 N-terminal amino acids of SEQ ID NO:84 can usefully be omitted. Other fragments omit one or more protein domains.

The 'sta051' antigen is annotated as 'protein with leader'. In the NCTC 8325 strain sta051 is SAOUHSC_02147 and has amino acid sequence SEQ ID NO:85 (GI:88195827).

Useful sta051 antigens can elicit an antibody (e.g. when administered to a human) that recognizes SEQ ID NO:85 and/or may comprise an amino acid sequence: (a) having 50%, 60%, 65%, 70%, 75%, 80%, 85%, 90%, 91%, 92%, 93%, 94%, 95%, 96%, 97%, 98%, 99%, 99.5% or more identity to SEQ ID NO:85; and/or (b) comprising a fragment of at least 'n' consecutive amino acids of SEQ ID NO:85, wherein 'n' is 7 or more (e.g. 8, 10, 12, 14, 16, 18, 20, 25, 30, 35, 40, 50, 60, 70, 80, 90, 100, 150, 200, 250 or more). These sta051 proteins include variants of SEQ ID NO:85. Preferred fragments of (b) comprise an epitope from SEQ ID NO:85. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:85 while retaining at least one epitope of SEQ ID NO:85. The first 24 N-terminal amino acids of SEQ ID NO:85 can usefully be omitted. Other fragments omit one or more protein domains.

The 'sta052' antigen is annotated as 'ferric hydroxamate receptor I'. In the NCTC 8325 strain sta052 is SAOUHSC_02246 and has amino acid sequence SEQ ID NO:86 (GI:88195918).

Useful sta052 antigens can elicit an antibody (e.g. when administered to a human) that recognizes SEQ ID NO:86 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:86; and/or (b) comprising a fragment of at least 'n' consecutive amino acids of SEQ ID NO:86, wherein In' is 7 or more (e.g. 8, 10, 12, 14, 16, 18, 20, 25, 30, 35, 40, 50, 60, 70, 80, 90, 100, 150, 200, 250 or more). These sta052 proteins include variants of SEQ ID NO:86. Preferred fragments of (b) comprise an epitope from SEQ ID NO:86. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:86 while retaining at least one epitope of SEQ ID NO:86. The first 17 N-terminal amino acids of SEQ ID NO:86 can usefully be omitted. Other fragments omit one or more protein domains.

The 'sta053' antigen is annotated as 'srdH family protein'. In the NCTC 8325 strain sta053 is SAOUHSC_02257 and has amino acid sequence SEQ ID NO:87 (GI:88195928).

Useful sta053 antigens can elicit an antibody (e.g. when administered to a human) that recognizes SEQ ID NO:87 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:87; and/or (b) comprising a fragment of at least 'n' consecutive amino acids of SEQ ID NO:87, wherein 'n' is 7 or more (e.g. 8, 10, 12, 14, 16, 18, 20, 25, 30, 35, 40, 50, 60, 70, 80, 90, 100, 150, 200, 250 or more). These sta053 proteins include variants of SEQ ID NO:87. Preferred fragments of (b) comprise an epitope from SEQ ID NO:87. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:87 while retaining at least one epitope of SEQ ID NO:87. The first 26 N-terminal amino acids of SEQ ID NO:87 can usefully be omitted. Other fragments omit one or more protein domains.

The 'sta054' antigen is annotated as 'Probable transglycosylase isaA precursor'. In the NCTC 8325 strain sta054 is SAOUHSC_02333 and has amino acid sequence SEQ ID NO:88 (GI:88195999).

Useful sta054 antigens can elicit an antibody (e.g. when administered to a human) that recognizes SEQ ID NO:88 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:88; and/or (b) comprising a fragment of at least 'n' consecutive amino acids of SEQ ID NO:88, wherein 'n' is 7 or more (e.g. 8, 10, 12, 14, 16, 18, 20, 25, 30, 35, 40, 50, 60, 70, 80, 90, 100, 150, 200 or more). These sta054 proteins include variants of SEQ ID NO:88. Preferred fragments of (b) comprise an epitope from SEQ ID NO:88. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:88 while retaining at least one epitope of SEQ ID NO:88. The first 27 N-terminal amino acids of SEQ ID NO:88 can usefully be omitted. Other fragments omit one or more protein domains.

The 'sta055' antigen is annotated as 'surface hydrolase'. In the NCTC 8325 strain sta055 is SAOUHSC_02448 and has amino acid sequence SEQ ID NO:89 (GI:88196100).

Useful sta055 antigens can elicit an antibody (e.g. when administered to a human) that recognizes SEQ ID NO:89 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:89; and/or (b) comprising a fragment of at least 'n' consecutive amino acids of SEQ ID NO:89, wherein 'n' is 7 or more (e.g. 8, 10, 12, 14, 16, 18, 20, 25, 30, 35, 40, 50, 60, 70, 80, 90, 100, 150, 200, 250 or more). These sta055 proteins include variants of SEQ ID NO:89. Preferred fragments of (b) comprise an epitope from SEQ ID NO:89. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:89 while retaining at least one epitope of SEQ ID NO:89. The first 31 N-terminal amino acids of SEQ ID NO:89 can usefully be omitted. Other fragments omit one or more protein domains.

The 'sta056' antigen is annotated as 'hyaluronate lyase'. In the NCTC 8325 strain sta056 is SAOUHSC_02463 and has amino acid sequence SEQ ID NO:90 (GI:88196115).

Useful sta056 antigens can elicit an antibody (e.g. when administered to a human) that recognizes SEQ ID NO:90 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:90; and/or (b) comprising a fragment of at least 'n' consecutive amino acids of SEQ ID NO:90, wherein 'n' is 7 or more (e.g. 8, 10, 12, 14, 16, 18, 20, 25, 30, 35, 40, 50, 60, 70, 80, 90, 100, 150, 200, 250 or more). These sta056 proteins include variants of SEQ ID NO:90. Preferred fragments of (b) comprise an epitope from SEQ ID NO:90. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:90 while retaining at least one epitope of SEQ ID NO:90. The first 24 N-terminal amino acids of SEQ ID NO:90 can usefully be omitted. Other fragments omit one or more protein domains.

The 'sta057' antigen is annotated as 'secretory antigen precursor SsaA'. In the NCTC 8325 strain sta057 is SAOUHSC_02576 and has amino acid sequence SEQ ID NO:91 (GI:88 196220). In the Newman strain it is nwmn_2203 (GI:I51222415).

Useful sta057 antigens can elicit an antibody (e.g. when administered to a human) that recognizes SEQ ID NO:91 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:91; and/or (b) comprising a fragment of at least 'n' consecutive amino acids of SEQ ID NO:91, wherein 'n' is 7 or more (e.g. 8, 10, 12, 14, 16, 18, 20, 25, 30, 35, 40, 50, 60, 70, 80, 90, 100, 150 or more). These sta057 proteins include variants of SEQ ID NO:91. Preferred fragments of (b) comprise an epitope from SEQ ID NO:91. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:91 while retaining at least one epitope of SEQ ID NO:91. The first 27 N-terminal amino acids of SEQ ID NO:91 can usefully be omitted. Other fragments omit one or more protein domains.

The 'sta058' antigen is annotated as 'Zn-binding lipoprotein adcA-like'. In the NCTC 8325 strain sta058 is SAOUHSC_02690 and has amino acid sequence SEQ ID NO:92 (GI:88196330).

Useful sta058 antigens can elicit an antibody (e.g. when administered to a human) that recognizes SEQ ID NO:92 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:92; and/or (b) comprising a fragment of at least 'n' consecutive amino acids of SEQ ID NO:92, wherein 'n' is 7 or more (e.g. 8, 10, 12, 14, 16, 18, 20, 25, 30, 35, 40, 50, 60, 70, 80, 90, 100, 150, 200, 250 or more). These sta058 proteins include variants of SEQ ID NO:92. Preferred fragments of (b) comprise an epitope from SEQ ID NO:92. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:92 while retaining at least one epitope of SEQ ID NO:92. The first 20 N-terminal amino acids of SEQ ID NO:92 can usefully be omitted. Other fragments omit one or more protein domains.

The 'sta059' antigen is annotated as 'gamma-hemolysin h-gamma-ii subunit'. In the NCTC 8325 strain sta059 is SAOUHSC_02708 and has amino acid sequence SEQ ID NO:93 (GI:88196348).

Useful sta059 antigens can elicit an antibody (e.g. when administered to a human) that recognizes SEQ ID NO:93 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ In NO:93; and/or (b) comprising a fragment of at least 'n' consecutive amino acids of SEQ In NO:93, wherein 'n' is 7 or more (e.g. 8, 10, 12, 14, 16, 18, 20, 25, 30, 35, 40, 50, 60, 70, 80, 90, 100, 150, 200, 250 or more). These sta059 proteins include variants of SEQ ID NO:93. Preferred fragments of (b) comprise an epitope from SEQ ID NO:93. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ In NO:93 while retaining at least one epitope of SEQ ID NO:93. The first 20 N-terminal amino acids of SEQ In NO:93 can usefully be omitted. Other fragments omit one or more protein domains.

The 'sta060' antigen is annotated as 'peptide ABC transporter; peptide-binding protein'. In the NCTC 8325 strain sta060 IS SAOUHSC 02767 and has amino acid sequence SEQ ID NO:94 (GI:88196403).

Useful sta060 antigens can elicit an antibody (e.g. when administered to a human) that recognizes SEQ ID NO:94 and/or may comprise an amino acid sequence: (a) having 50%, 60%, 65%, 70%, 75%, 80%, 85%, 90%, 91%, 92%, 93%, 94%, 95%, 96%, 97%, 98%, 99%, 99.5% or more identity to SEQ In NO:94; and/or (b) comprising a fragment of at least 'n' consecutive amino acids of SEQ In NO:94, wherein 'n' is 7 or more (e.g. 8, 10, 12, 14, 16, 18, 20, 25, 30, 35, 40, 50, 60, 70, 80, 90, 100, 150, 200, 250 or more). These sta060 proteins include variants of SEQ ID NO:94. Preferred fragments of (b) comprise an epitope from SEQ In NO:94. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:94 while retaining at least one epitope of SEQ In NO:94. The first 20 N-terminal amino acids of SEQ In NO:94 can usefully be omitted. Other fragments omit one or more protein domains.

The 'sta061' antigen is annotated as 'protein with leader'. In the NCTC 8325 strain sta061 is SAOUHSC_02783 and has amino acid sequence SEQ ID NO:95 (GI:88196419).

Useful sta061 antigens can elicit an antibody (e.g. when administered to a human) that recognizes SEQ In NO:95 and/or may comprise an amino acid sequence: (a) having 50%, 60%, 65%, 70%, 75%, 80%, 85%, 90%, 91%, 92%, 93%, 94%, 95%, 96%, 97%, 98%, 99%, 99.5% or more identity to SEQ ID NO:95; and/or (b) comprising a fragment of at least 'n' consecutive amino acids of SEQ ID NO:95, wherein 'n' is 7 or more (e.g. 8, 10, 12, 14, 16, 18, 20, 25, 30, 35, 40, 50, 60, 70, 80, 90, 100, 150, 200, 250 or more). These sta061 proteins include variants of SEQ ID NO:95. Preferred fragments of (b) comprise an epitope from SEQ ID NO:95. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:95 while retaining at least one epitope of SEQ ID NO:95. The first 21 N-terminal amino acids of SEQ ID NO:95 can usefully be omitted. Other fragments omit one or more protein domains.

The 'sta062' antigen is annotated as 'protein with leader'. In the NCTC 8325 strain sta062 is SAOUHSC_02788 and has amino acid sequence SEQ ID NO:96 (GI:88 196424).

Useful sta062 antigens can elicit an antibody (e.g. when administered to a human) that recognizes SEQ ID NO:96 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:96; and/or (b) comprising a fragment of at least 'n' consecutive amino acids of SEQ ID NO:96, wherein 'n' is 7 or more (e.g. 8, 10, 12, 14, 16, 18, 20, 25, 30, 35, 40, 50, 60, 70, 80, 90, 100, 150, 200, 250 or more). These sta062 proteins include variants of SEQ ID NO:96. Preferred fragments of (b) comprise an epitope from SEQ ID NO:96. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:96 while retaining at least one epitope of SEQ ID NO:96. The first 22 N-terminal amino acids of SEQ ID NO:96 can usefully be omitted. Other fragments omit one or more protein domains.

The 'sta063, antigen is annotated as 'aurcolysin'. In the NCTC 8325 strain sta063 is SAOUHSC_02971 and has amino acid sequence SEQ ID NO:97 (GI:88196592).

Useful sta063 antigens can elicit an antibody (e.g. when administered to a human) that recognizes SEQ ID NO:97 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:97; and/or (b) comprising a fragment of at least 'n' consecutive amino acids of SEQ ID NO:97, wherein 'n' is 7 or more (e.g. 8, 10, 12, 14, 16, 18, 20, 25, 30, 35, 40, 50, 60, 70, 80, 90, 100, 150, 200, 250 or more). These sta063 proteins include variants of SEQ ID NO:97. Preferred fragments of (b) comprise an epitope from SEQ ID NO:97. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:97 while retaining at least one epitope of SEQ ID NO:97. The first 16 N-terminal amino acids of SEQ ID NO:97 can usefully be omitted. Other fragments omit one or more protein domains.

The 'sta064' antigen is annotated as 'lipase'. In the NCTC 8325 strain sta064 is SAOUHSC_03006 and has amino acid sequence SEQ ID NO:98 (GI:88 196625). In the Newman strain it is nwmn 2569 (GI:151222781).

Useful sta064 antigens can elicit an antibody (e.g. when administered to a human) that recognizes SEQ ID NO:98 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:98; and/or (b) comprising a fragment of at least In' consecutive amino acids of SEQ ID NO:98, wherein 'n' is 7 or more (e.g. 8, 10, 12, 14, 16, 18, 20, 25, 30, 35, 40, 50, 60, 70, 80, 90, 100, 150, 200, 250 or more). These sta064 proteins include variants of SEQ ID NO:98. Preferred fragments of (b) comprise an epitope from SEQ ID NO:98. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:98 while retaining at least one epitope of SEQ ID NO:98. The first 34 N-terminal amino acids of SEQ ID NO:98 can usefully be omitted. Other fragments omit one or more protein domains.

The 'sta065' antigen is annotated as '1-phosphatidylinositol phosphodiesterase precursor'. In the NCTC 8325 strain sta065 is SAOUHSC 00051 and has amino acid sequence SEQ ID NO:99 (GI:88193871).

Useful sta065 antigens can elicit an antibody (e.g. when administered to a human) that recognizes SEQ ID NO:99 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:99; and/or (b) comprising a fragment of at least 'n' consecutive amino acids of SEQ ID NO:99, wherein In' is 7 or more (e.g. 8, 10, 12, 14, 16, 18, 20, 25, 30, 35, 40, 50, 60, 70, 80, 90, 100, 150, 200, 250 or more). These sta065 proteins include variants of SEQ ID NO:99. Preferred fragments of (b) comprise an epitope from SEQ ID NO:99. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:99 while retaining at least one epitope of SEQ ID NO:99. The first 26 N-terminal amino acids of SEQ ID NO:99 can usefully be omitted. Other fragments omit one or more protein domains.

The 'sta066' antigen is annotated as 'protein'. In the NCTC 8325 strain sta066 is SAOUHSC_00172 and has amino acid sequence SEQ ID NO:100 (GI:88193982).

Useful sta066 antigens can elicit an antibody (e.g. when administered to a human) that recognizes SEQ ID NO:100 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:100; and/or (b) comprising a fragment of at least 'n' consecutive amino acids of SEQ ID NO:100, wherein 'n' is 7 or more (e.g. 8, 10, 12, 14, 16, 18, 20, 25, 30, 35, 40, 50, 60, 70, 80, 90, 100, 150, 200, 250 or more). These sta066 proteins include variants of SEQ ID NO:100. Preferred fragments of (b) comprise an epitope from SEQ ID NO:100. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:100 while retaining at least one epitope of SEQ ID NO:100. The first 21 N-terminal amino acids of SEQ ID NO:100 can usefully be omitted. Other fragments omit one or more protein domains.

The 'sta067' antigen is annotated as 'bacterial extracellular solute-binding protein'. In the NCTC 8325 strain sta067 is SAOUHSC_00176 and has amino acid sequence SEQ ID NO:101 (GI:88 193986).

Useful sta067 antigens can elicit an antibody (e.g. when administered to a human) that recognizes SEQ ID NO:101 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:101; and/or (b) comprising a fragment of at least 'n' consecutive amino acids of SEQ ID NO:101, wherein 'n' is 7 or more (e.g. 8, 10, 12, 14, 16, 18, 20, 25, 30, 35, 40, 50, 60, 70, 80, 90, 100, 150, 200, 250 or more). These sta067 proteins include variants of SEQ ID NO:101. Preferred fragments of (b) comprise an epitope from SEQ ID NO:101. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:101 while retaining at least one epitope of SEQ ID NO:101. The first 20 N-terminal amino acids of SEQ ID NO:101 can usefully be omitted. Other fragments omit one or more protein domains.

The 'sta068' antigen is annotated as 'iron permease FTRI'. In the NCTC 8325 strain sta068 is SAOUHSC_00327 and has amino acid sequence SEQ ID NO:102 (GI:88194127).

Useful sta068 antigens can elicit an antibody (e.g. when administered to a human) that recognizes SEQ ID NO:102 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:102; and/or (b) comprising a fragment of at least 'n' consecutive amino acids of SEQ ID NO:102, wherein 'n' is 7 or more (e.g. 8, 10, 12, 14, 16, 18, 20, 25, 30, 35, 40, 50, 60, 70, 80, 90, 100, 150, 200, 250 or more). These sta068 proteins include variants of SEQ ID NO:102. Preferred fragments of (b) comprise an epitope from SEQ ID NO:102. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:102 while retaining at least one epitope of SEQ ID NO:102. The final 20 C-terminal amino acids of SEQ ID NO:102 can usefully be omitted. The first 14 N-terminal amino acids of SEQ ID NO:102 can usefully be omitted. Other fragments omit one or more protein domains.

The 'sta069' antigen is annotated as 'autolysin precursor'. In the NCTC 8325 strain sta069 is SAOUHSC_00427 and has amino acid sequence SEQ ID NO:103 (GI:88194219).

Useful sta069 antigens can elicit an antibody (e.g. when administered to a human) that recognizes SEQ ID NO:103 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:103; and/or (b) comprising a fragment of at least 'n' consecutive amino acids of SEQ ID NO:103, wherein 'n' is 7 or more (e.g. 8, 10, 12, 14, 16, 18, 20, 25, 30, 35, 40, 50, 60, 70, 80, 90, 100, 150, 200, 250 or more). These sta069 proteins include variants of SEQ ID NO:103. Preferred fragments of (b) comprise an epitope from SEQ ID NO:103. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:103 while retaining at least one epitope of SEQ ID NO:103. The first 25 N-terminal amino acids of SEQ ID NO:103 can usefully be omitted. Other fragments omit one or more protein domains.

The 'sta070' antigen is annotated as 'immunogenic secreted precursor-like protein (truncated)'. In the NCTC 8325 strain sta070 is SAOUHSC_00773 and has amino acid sequence SEQ ID NO:104 (GI:88194535).

Useful sta070 antigens can elicit an antibody (e.g. when administered to a human) that recognizes SEQ ID NO:104 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:104; and/or (b) comprising a fragment of at least 'n' consecutive amino acids of SEQ ID NO:104, wherein 'n' is 7 or more (e.g. 8, 10, 12, 14, 16, 18, 20, 25, 30, 35, 40, 50, 60, 70, 80, 90, 100, 150, 200, 250 or more). These sta070 proteins include variants of SEQ ID NO:104. Preferred fragments of (b) comprise an epitope from SEQ ID NO:104. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:104 while retaining at least one epitope of SEQ ID NO:104. The first 24 N-terminal amino acids of SEQ ID NO:104 can usefully be omitted. Other fragments omit one or more protein domains.

The 'sta071' antigen is annotated as 'hemolysin'. In the NCTC 8325 strain sta071 is SAOUHSC_00854 and has amino acid sequence SEQ ID NO:105 (GI:88194612).

Useful sta071 antigens can elicit an antibody (e.g. when administered to a human) that recognizes SEQ ID NO:105 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:105; and/or (b) comprising a fragment of at least 'n' consecutive amino acids of SEQ ID NO:105, wherein 'n' is 7 or more (e.g. 8, 10, 12, 14, 16, 18, 20, 25, 30, 35, 40, 50, 60, 70, 80, 90, 100, 150, 200, 250 or more). These sta071 proteins include variants of SEQ ID NO:105. Preferred fragments of (b) comprise an epitope from SEQ ID NO:105. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:105 while retaining at least one epitope of SEQ ID NO:105. The first 24 N-terminal amino acids of SEQ ID NO:105 can usefully be omitted. Other fragments omit one or more protein domains.

The 'sta072' antigen is annotated as 'extramembranal protein'. In the NCTC 8325 strain sta072 is SAOUHSC_00872 and has amino acid sequence SEQ ID NO:106 (GI:88194629).

Useful sta072 antigens can elicit an antibody (e.g. when administered to a human) that recognizes SEQ ID NO:106 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:106; and/or (b) comprising a fragment of at least 'n' consecutive amino acids of SEQ ID NO:106, wherein 'n' is 7 or more (e.g. 8, 10, 12, 14, 16, 18, 20, 25, 30, 35, 40, 50, 60, 70, 80, 90, 100, 150, 200, 250 or more). These sta072 proteins include variants of SEQ ID NO:106. Preferred fragments of (b) comprise an epitope from SEQ ID NO:106. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:106 while retaining at least one epitope of SEQ ID NO:106. The first 24 N-terminal amino acids of SEQ ID NO:106 can usefully be omitted. Other fragments omit one or more protein domains.

The 'sta073' antigen is annotated as 'bifunctional autolysin precursor'. In the NCTC 8325 strain sta073 is SAOUHSC_00994 and has amino acid sequence SEQ ID NO:107 (GI:88194750). In the Newman strain it is nwmn_0922 (GI:151221134). Proteomic analysis has revealed that this protein is secreted or surface-exposed.

Useful sta073 antigens can elicit an antibody (e.g. when administered to a human) that recognizes SEQ ID NO:107 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:107; and/or (b) comprising a fragment of at least 'n' consecutive amino acids of SEQ ID NO:107, wherein 'n' is 7 or more (e.g. 8, 10, 12, 14, 16, 18, 20, 25, 30, 35, 40, 50, 60, 70, 80, 90, 100, 150, 200, 250 or more). These sta073 proteins include variants of SEQ ID NO:107. Preferred fragments of (b) comprise an epitope from SEQ ID NO:107. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:107 while retaining at least one epitope of SEQ ID NO:107. The first 24 N-terminal amino acids of SEQ ID NO:107 can usefully be omitted. Other fragments omit one or more protein domains.

A Sta073 antigen can usefully be included in a composition in combination with a Sta112. Sta073 does not adsorb well to aluminium hydroxide adjuvants, so Sta073 present in a composition may be unadsorbed or may be adsorbed to an alternative adjuvant e.g. to an aluminium phosphate.

The 'sta074' antigen is annotated as 'factor essential for methicillin resistance'. In the NCTC 8325 strain sta074 is SAOUHSC_01220 and has amino acid sequence SEQ ID NO:108 (GI:88194956).

Useful sta074 antigens can elicit an antibody (e.g. when administered to a human) that recognizes SEQ ID NO:108 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:108; and/or (b) comprising a fragment of at least 'n' consecutive amino acids of SEQ ID NO:108, wherein 'n' is 7 or more (e.g. 8, 10, 12, 14, 16, 18, 20, 25, 30, 35, 40, 50, 60, 70, 80, 90, 100, 150, 200, 250 or more). These sta074 proteins include variants of SEQ ID NO:108. Preferred fragments of (b) comprise an epitope from SEQ ID NO:108. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:108 while retaining at least one epitope of SEQ ID NO:108. Other fragments omit one or more protein domains.

The 'sta075' antigen is annotated as 'insulysin; peptidase family M16'. In the NCTC 8325 strain sta075 is SAOUHSC_01256 and has amino acid sequence SEQ ID NO:109 (GI:88194989).

Useful sta075 antigens can elicit an antibody (e.g. when administered to a human) that recognizes SEQ ID NO:109 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:109; and/or (b) comprising a fragment of at least 'n' consecutive amino acids of SEQ ID NO:109, wherein 'n' is 7 or more (e.g. 8, 10, 12, 14, 16, 18, 20, 25, 30, 35, 40, 50, 60, 70, 80, 90, 100, 150, 200, 250 or more). These sta075 proteins include variants of SEQ ID 10 NO:109. Preferred fragments of (b) comprise an epitope from SEQ ID NO:109. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:109 while retaining at least one epitope of SEQ ID NO:109. Other fragments omit one or more protein domains.

The 'sta076' antigen is annotated as 'hydrolase'. In the NCTC 8325 strain sta076 is SAOUHSC_01263 and has amino acid sequence SEQ ID NO:110 (GI:88194996).

Useful sta076 antigens can elicit an antibody (e.g. when administered to a human) that recognizes SEQ ID NO:110 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:110; and/or (b) comprising a fragment of at least 'n' consecutive amino acids of SEQ ID NO:110, wherein 'n' is 7 or more (e.g. 8, 10, 12, 14, 16, 18, 20, 25, 30, 35, 40, 50, 60, 70, 80, 90, 100, 150, 200, 250 or more). These sta076 proteins include variants of SEQ ID NO:110. Preferred fragments of (b) comprise an epitope from SEQ ID NO:110. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:110 while retaining at least one epitope of SEQ ID NO:110. The first 24 N-terminal amino acids of SEQ ID NO:110 can usefully be omitted. Other fragments omit one or more protein domains.

The 'sta077' antigen is annotated as 'protein'. In the NCTC 8325 strain sta077 is SAOUHSC_01317 and has amino acid sequence SEQ ID NO:111 (GI:88195047). Protcomic analysis has revealed that this protein is secreted or surface-exposed.

Useful sta077 antigens can elicit an antibody (e.g. when administered to a human) that recognizes SEQ ID NO:111 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:111; and/or (b) comprising a fragment of at least 'n' consecutive amino acids of SEQ ID NO:111, wherein 'n' is 7 or more (e.g. 8, 10, 12, 14, 16, 18, 20, 25, 30, 35, 40, 50, 60, 70, 80, 90, 100, 150, 200, 250 or more). These sta077 proteins include variants of SEQ ID NO:111. Preferred fragments of (b) comprise an epitope from SEQ ID NO:111. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:111 while retaining at least one epitope of SEQ ID NO:111. The first 20 N-terminal amino acids of SEQ ID NO:111 can usefully be omitted. Other fragments omit one or more protein domains.

The 'sta078' antigen is annotated as 'FtsK/SpoIIIE family protein'. In the NCTC 8325 strain sta078 is SAOUHSC_01857 and has amino acid sequence SEQ ID NO:112 (GI:88195555).

Useful sta078 antigens can elicit an antibody (e.g. when administered to a human) that recognizes SEQ ID NO:112 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:112; and/or (b) comprising a fragment of at least 'n' consecutive amino acids of SEQ ID NO:112, wherein 'n' is 7 or more (e.g. 8, 10, 12, 14, 16, 18, 20, 25, 30, 35, 40, 50, 60, 70, 80, 90, 100, 150, 200, 250 or more). These sta078 proteins include variants of SEQ ID NO:112. Preferred fragments of (b) comprise an epitope from SEQ ID NO:112. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:112 while retaining at least one epitope of SEQ ID NO:112. Other fragments omit one or more protein domains.

The 'sta079' antigen is annotated as 'serine protease SpIF'. In the NCTC 8325 strain sta079 is SAOUHSC_01935 and has amino acid sequence SEQ ID NO:113 (GI:88195630).

Useful sta079 antigens can elicit an antibody (e.g. when administered to a human) that recognizes SEQ ID NO:113 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 30 99.5% or more) to SEQ ID NO:113; and/or (b) comprising a fragment of at least 'n' consecutive amino acids of SEQ ID NO:113, wherein 'n' is 7 or more (e.g. 8, 10, 12, 14, 16, 18, 20, 25, 30, 35, 40, 50, 60, 70, 80, 90, 100, 150, 200 or more). These sta079 proteins include variants of SEQ ID NO:113. Preferred fragments of (b) comprise an epitope from SEQ ID NO:113. Other preferred fragments lack one or more amino acids (e.g. 1, 2, 3, 4, 5, 6, 7, 8, 9, 10, 15, 20, 25 or more) from the 35 C-terminus and/or one or more amino acids (e.g. 1, 2, 3, 4, 5, 6, 7, 8, 9, 10, 15, 20, 25 or more) from the N-terminus of SEQ ID NO:113 while retaining at least one epitope of SEQ ID NO:113. The first 36 N-terminal amino acids of SEQ ID NO:113 can usefully be omitted. Other fragments omit one or more protein domains.

The 'sta080' antigen is annotated as 'serine protease SpIE'. In the NCTC 8325 strain sta080 is SAOUHSC_01936 and has amino acid sequence SEQ ID NO:114 (GI:88195631).

Useful sta080 antigens can elicit an antibody (e.g. when administered to a human) that recognizes SEQ ID NO:114 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:114; and/or (b) comprising a fragment of at least 'n' consecutive amino acids of SEQ ID NO:114, wherein 'n' is 7 or more (e.g. 8, 10, 12, 14, 16, 18, 20, 25, 30, 35, 40, 50, 60, 70, 80, 90, 100, 150, 200 or more). These sta080 proteins include variants of SEQ ID NO:114. Preferred fragments of (b) comprise an epitope from SEQ ID NO:114. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:114 while retaining at least one epitope of SEQ ID NO:114. The first 36 N-terminal amino acids of SEQ ID NO:114 can usefully be omitted. Other fragments omit one or more protein domains.

The 'sta081' antigen is annotated as 'serine protease SpID (EC:3.4.21.19)'. In the NCTC 8325 strain sta081 is SAOUHSC_01938 and has amino acid sequence SEQ ID NO:154 (GI:88195633).

Useful sta081 antigens can elicit an antibody (e.g. when administered to a human) that recognizes SEQ ID NO:154 and/or may comprise an amino acid sequence: (a) having 50%, 60%, 65%, 70%, 75%, 80%, 85%, 90%, 91%, 92%, 93%, 94%, 95%, 96%, 97%, 98%, 99%, 99.5% or more identity to SEQ ID NO:154; and/or (b) comprising a fragment of at least 'n' consecutive amino acids of SEQ ID NO:154, wherein 'n' is 7 or more (e.g. 8, 10, 12, 14, 16, 18, 20, 25, 30, 35, 40, 50, 60, 70, 80, 90, 100, 150, 200 or more). These sta081 proteins include variants of SEQ ID NO:154. Preferred fragments of (b) comprise an epitope from SEQ ID NO:154. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from 30 the N-terminus of SEQ ID NO:154 while retaining at least one epitope of SEQ ID NO:154. The first 36 N-terminal amino acids of SEQ ID NO:154 can usefully be omitted. Other fragments omit one or more protein domains.

The 'sta082' antigen is annotated as 'serine protease SpIC'. In the NCTC 8325 strain sta082 is SAOUHSC_01939 and has amino acid sequence SEQ ID NO:115 (GI:88195634).

Useful sta082 antigens can elicit an antibody (e.g. when administered to a human) that recognizes SEQ ID NO:115 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:115; and/or (b) comprising a fragment of at least 'n' consecutive amino acids of SEQ ID NO:115, wherein 'n' is 7 or more (e.g. 8, 10, 12, 14, 16, 18, 20, 25, 30, 35, 40, 50, 60, 70, 80, 90, 100, 150, 200 or more). These sta082 proteins include variants of SEQ ID NO:115. Preferred fragments of (b) comprise an epitope from SEQ ID NO:115. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:115 while retaining at least one epitope of SEQ ID NO:115. The first 36 N-terminal amino acids of SEQ ID NO:115 can usefully be omitted. Other fragments omit one or more protein domains.

The 'sta083' antigen is annotated as 'serine protease SplB'. In the NCTC 8325 strain sta083 is SAOUHSC_01941 and has amino acid sequence SEQ ID NO:116 (GI:88195635).

Useful sta083 antigens can elicit an antibody (e.g. when administered to a human) that recognizes SEQ ID NO:116 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:116; and/or (b) comprising a fragment of at least 'n' consecutive amino acids of SEQ ID NO:116, wherein 'n' is 7 or more (e.g. 8, 10, 12, 14, 16, 18, 20, 25, 30, 35, 40, 50, 60, 70, 80, 90, 100, 150, 200 or more). These sta083 proteins include variants of SEQ ID NO:116. Preferred fragments of (b) comprise an epitope from SEQ ID NO:116. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:116 while retaining at least one epitope of SEQ ID NO:116. The first 36 N-terminal amino acids of SEQ ID NO:116 can usefully be omitted. Other fragments omit one or more protein domains.

The 'sta084' antigen is annotated as 'serine protease SplA'. In the NCTC 8325 strain sta084 is SAOUHSC_01942 and has amino acid sequence SEQ ID NO:117 (GI:88195636).

Useful sta084 antigens can elicit an antibody (e.g. when administered to a human) that recognizes SEQ ID NO:117 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:117; and/or (b) comprising a fragment of at least 'n' consecutive amino acids of SEQ ID NO:117, wherein 'n' is 7 or more (e.g. 8, 10, 12, 14, 16, 18, 20, 25, 30, 35, 40, 50, 60, 70, 80, 90, 100, 150, 200 or more). These sta084 proteins include variants of SEQ ID NO:117. Preferred fragments of (b) comprise an epitope from SEQ ID NO:117. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:117 while retaining at least one epitope of SEQ ID NO:117. The first N-terminal amino acids of SEQ ID NO:117 can usefully be omitted. Other fragments omit one or more protein domains.

The 'sta085' antigen is annotated as 'staphylokinase precursor'. In the NCTC 8325 strain sta085 is SAOUHSC_02171 and has amino acid sequence SEQ ID NO:118 (GI:88195848).

Useful sta085 antigens can elicit an antibody (e.g. when administered to a human) that recognizes SEQ ID NO:118 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:118; and/or (b) comprising a fragment of at least 'n' consecutive amino acids of SEQ ID NO:118, wherein 'n' is 7 or more (e.g. 8, 10, 12, 14, 16, 18, 20, 25, 30, 35, 40, 50, 60, 70, 80, 90, 100, 150 or more). These sta085 proteins include variants of SEQ ID NO:118. Preferred fragments of (b) comprise an epitope from SEQ ID NO:118. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:118 while retaining at least one epitope of SEQ ID NO:118. The first 27 N-terminal amino acids of SEQ ID NO:118 can usefully be omitted. Other fragments omit one or 20 more protein domains.

The 'sta086' antigen is annotated as 'OxaA-like protein'. In the NCTC 8325 strain sta086 is SAOUHSC_02327 and has amino acid sequence SEQ ID NO:119 (GI:88195993).

Useful sta086 antigens can elicit an antibody (e.g. when administered to a human) that recognizes SEQ ID NO:119 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:119; and/or (b) comprising a fragment of at least 'n' consecutive amino acids of SEQ ID NO:119, wherein 'n' is 7 or more (e.g. 8, 10, 12, 14, 16, 18, 20, 25, 30, 35, 40, 50, 60, 70, 80, 90, 100, 150, 200, 250 or more). These sta086 proteins include variants of SEQ ID NO:119. Preferred fragments of (b) comprise an epitope from SEQ ID NO:119. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:119 while retaining at least one epitope of SEQ ID NO:119. The first 19 N-terminal amino acids of SEQ ID NO:119 can usefully be omitted. Other fragments omit one or more protein domains.

The 'sta087' antigen is annotated as 'teicoplanin resistance protein TcaA'. In the NCTC 8325 strain sta087 is SAOUHSC_02635 and has amino acid sequence SEQ ID NO:120 (GI:88196276).

Useful sta087 antigens can elicit an antibody (e.g. when administered to a human) that recognizes SEQ ID NO:120 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:120; and/or (b) comprising a fragment of at least 'n' consecutive amino acids of SEQ ID NO:120, wherein 'n' is 7 or more (e.g. 8, 10, 12, 14, 16, 18, 20, 25, 30, 35, 40, 50, 60, 70, 80, 90, 100, 150, 200, 250 or more). These sta087 proteins include variants of SEQ ID NO:120. Preferred fragments of (b) comprise an epitope from SEQ ID NO:120. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:120 while retaining at least one epitope of SEQ ID NO:120. Other fragments omit one or more protein domains.

The 'sta088' antigen is annotated as 'esterase'. In the NCTC 8325 strain sta088 is SAOUHSC_02844 and has amino acid sequence SEQ ID NO:121 (GI:88196477).

Useful sta088 antigens can elicit an antibody (e.g. when administered to a human) that recognizes SEQ ID NO:121 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:121; and/or (b) comprising a fragment of at least 'n' consecutive amino acids of SEQ ID NO:121, wherein 'n' is 7 or more (e.g. 8, 10, 12, 14, 16, 18, 20, 25, 30, 35, 40, 50, 60, 70, 80, 90, 100, 150, 200, 250 or more). These sta088 proteins include variants of SEQ ID NO:121. Preferred fragments of (b) comprise an epitope from SEQ ID NO:121. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:121 while retaining at least one epitope of SEQ ID NO:121. The first 18 N-terminal amino acids of SEQ ID NO:121 can usefully be omitted. Other fragments omit one or more protein domains.

The 'sta089' antigen is annotated as 'LysM domain protein'. In the NCTC 8325 strain sta089 is SAOUHSC_02855 and has amino acid sequence SEQ ID NO:122 (GI: 88196486).

Useful sta089 antigens can elicit an antibody (e.g. when administered to a human) that recognizes SEQ ID NO:122 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:122; and/or (b) comprising a fragment of at least 'n' consecutive amino acids of SEQ ID NO:122, wherein 'n' is 7 or more (e.g. 8, 10, 12, 14, 16, 18, 20, 25, 30, 35, 40, 50, 60, 70, 80, 90, 100 or more). These sta089 proteins include variants of SEQ ID NO:122. Preferred fragments of (b) comprise an epitope from SEQ ID NO:122. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:122 while retaining at least one epitope of SEQ ID NO:122. The first 20 N-terminal amino acids of SEQ ID NO:122 can usefully be omitted. Other fragments omit one or more protein domains.

The 'sta090' antigen is annotated as 'LysM domain protein'. In the NCTC 8325 strain sta090 is SAOUHSC_02883 and has amino acid sequence SEQ ID NO:123 (GI: 88196512).

Useful sta090 antigens can elicit an antibody (e.g. when administered to a human) that recognizes SEQ ID NO:123 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:123; and/or (b) comprising a fragment of at least 'n' consecutive amino acids of SEQ ID NO:123, wherein 'n' is 7 or more (e.g. 8, 10, 12, 14, 16, 18, 20, 25, 30, 35, 40, 50, 60, 70, 80, 90, 100, 150, 200, 250 or more). These sta090 proteins include variants of SEQ ID NO:123. Preferred fragments of (b) comprise an epitope from SEQ ID NO:123. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:123 while retaining at least one epitope of SEQ ID NO:123. The first 26 N-terminal amino acids of SEQ ID NO:123 can usefully be omitted. Other fragments omit one or more protein domains.

The 'sta091' antigen is annotated as 'lipoprotein'. In the NCTC 8325 strain sta091 is SAOUHSC_00685 and has amino acid sequence SEQ ID NO:124 (GI:88194450).

Useful sta091 antigens can elicit an antibody (e.g. when administered to a human) that recognizes SEQ ID NO:124 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:124; and/or (b) comprising a fragment of at least 'n' consecutive amino acids of SEQ ID NO:124, wherein 'n' is 7 or more (e.g. 8, 10, 12, 14, 16, 18, 20, 25, 30, 35, 40, 50, 60, 70, 80, 90, 100 or more). These sta091 proteins include variants of SEQ ID NO:124. Preferred fragments of (b) comprise an epitope from SEQ ID NO:124. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:124 while retaining at least one epitope of SEQ ID NO:124. The first 15 N-terminal amino acids of SEQ ID NO:124 can usefully be omitted. Other fragments omit one or more protein domains.

The 'sta092' antigen is annotated as 'M23/M37 peptidase domain protein'. In the NCTC 8325 strain sta092 is SAOUHSC_00174 and has amino acid sequence SEQ ID NO:125 (GI:88193984).

Useful sta092 antigens can elicit an antibody (e.g. when administered to a human) that recognizes SEQ ID NO:125 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:125; and/or (b) comprising a fragment of at least 'n' consecutive amino acids of SEQ ID NO:125, wherein 'n' is 7 or more (e.g. 8, 10, 12, 14, 16, 18, 20, 25, 30, 35, 40, 50, 60, 70, 80, 90, 100, 150 or more). These sta092 proteins include variants of SEQ ID NO:125. Preferred fragments of (b) comprise an epitope from SEQ ID NO:125. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:125 while retaining at least one epitope of SEQ ID NO:125. The first 25 N-terminal amino acids of SEQ ID NO:125 can usefully be omitted. Other fragments omit one or more protein domains.

The 'sta093, antigen is annotated as 'protein'. In the NCTC 8325 strain sta093 is SAOUHSC_01854 and has amino acid sequence SEQ ID NO:126 (GI:88195552).

Useful sta093 antigens can elicit an antibody (e.g. when administered to a human) that recognizes SEQ ID NO:126 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:126; and/or (b) comprising a fragment of at least 'n' consecutive amino acids of SEQ ID NO:126, wherein 'n' is 7 or more (e.g. 8, 10, 12, 14, 16, 18, 20, 25, 30, 35, 40, 50, 60, 70, 80, 90, 100, 150, 200, 250 or more). These sta093 proteins include variants of SEQ ID NO:126. Preferred fragments of (b) comprise an epitope from SEQ ID NO:126. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:126 while retaining at least one epitope of SEQ ID NO:126. Other fragments omit one or more protein domains.

The 'sta094' antigen is annotated as 'protein'. In the NCTC 8325 strain sta094 is SAOUHSC_01512 and has amino acid sequence SEQ ID NO:127 (GI:88195226).

Useful sta094 antigens can elicit an antibody (e.g. when administered to a human) that recognizes SEQ ID NO:127 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:127; and/or (b) comprising a fragment of at least 'n' consecutive amino acids of SEQ ID NO:127, wherein 'n' is 7 or more (e.g. 8, 10, 12, 14, 16, 18, 20, 25, 30, 35, 40, 50, 60, 70, 80, 90, 100, 150, 200, 250 or more). These sta094 proteins include variants of SEQ ID NO:127. Preferred fragments of (b) comprise an epitope from SEQ ID NO:127. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:127 while retaining at least one epitope of SEQ ID NO:127. The first 17 N-terminal amino acids of SEQ ID NO:127 can usefully be omitted. Other fragments omit one or more protein domains.

The 'sta095' antigen is annotated as 'superantigen-like protein'. In the NCTC 8325 strain sta095 is SAOUHSC_00383 and has amino acid sequence SEQ ID NO:128 (GI:88194180). In the Newman strain it is nwmn_0388 (GI:151220600).

Useful sta095 antigens can elicit an antibody (e.g. when administered to a human) that recognizes SEQ ID NO:128 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:128; and/or (b) comprising a fragment of at least 'n' consecutive amino acids of SEQ ID NO:128, wherein 'n' is 7 or more (e.g. 8, 10, 12, 14, 16, 18, 20, 25, 30, 35, 20 40, 50, 60, 70, 80, 90, 100, 150, 200 or more). These sta095 proteins include variants of SEQ ID NO:128. Preferred fragments of (b) comprise an epitope from SEQ ID NO:128. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:128 while retaining at least one epitope of SEQ ID NO:128. The first 32 N-terminal amino acids of SEQ ID NO:128 can usefully be omitted. Other fragments omit one or more protein domains.

The 'sta096' antigen is annotated as 'superantigen-like protein'. In the NCTC 8325 strain sta096 is SAOUHSC_00384 and has amino acid sequence SEQ ID NO:129 (GI:88194181). Useful sta096 antigens can elicit an antibody (e.g. when administered to a human) that recognizes SEQ ID NO:129 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:129; and/or (b) comprising a fragment of at least 'n' consecutive amino acids of SEQ ID NO:129, wherein 'n' is 7 or more (e.g. 8, 10, 12, 14, 16, 18, 20, 25, 30, 35, 35 40, 50, 60, 70, 80, 90, 100, 150, 200 or more). These sta096 proteins include variants of SEQ ID NO:129. Preferred fragments of (b) comprise an epitope from SEQ ID NO:129. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:129 while retaining at least one epitope of SEQ ID NO:129. The first 30 N-terminal amino acids of SEQ ID NO:129 can usefully be omitted. Other fragments omit one or more protein domains.

The 'sta097' antigen is annotated as 'superantigen-like protein'. In the NCTC 8325 strain sta097 is SAOUHSC_00386 and has amino acid sequence SEQ ID NO:130 (GI:88194182).

Useful sta097 antigens can elicit an antibody (e.g. when administered to a human) that recognizes SEQ ID NO:130 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:130; and/or (b) comprising a fragment of at least 'n' consecutive amino acids of SEQ ID NO:130, wherein 'n' is 7 or more (e.g. 8, 10, 12, 14, 16, 18, 20, 25, 30, 35, 40, 50, 60, 70, 80, 90, 100, 150, 200, 250 or more). These sta097 proteins include variants of SEQ ID NO:130. Preferred fragments of (b) comprise an epitope from SEQ ID NO:130. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:130 while retaining at least one epitope of SEQ ID NO:130. The first 30 N-terminal amino acids of SEQ ID NO:130 can usefully be omitted. Other fragments omit one or more protein domains.

The 'sta098' antigen is annotated as 'superantigen-like protein'. In the NCTC 8325 strain sta098 is SAOUHSC_00389 and has amino acid sequence SEQ ID NO:131 (GI:88194184). In the Newman strain it is nwmn_0391 (GI:151220603).

Useful sta098 antigens can elicit an antibody (e.g. when administered to a human) that recognizes SEQ ID NO:131 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:131; and/or (b) comprising a fragment of at least 'n' consecutive amino acids of SEQ ID NO:131, wherein 'n' is 7 or more (e.g. 8, 10, 12, 14, 16, 18, 20, 25, 30, 35, 40, 50, 60, 70, 80, 90, 100, 150, 200, 250 or more). These sta098 proteins include variants of SEQ ID NO:131. Preferred fragments of (b) comprise an epitope from SEQ ID NO:131. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:131 while retaining at least one epitope of SEQ ID NO:131. The first 30 N-terminal amino acids of SEQ ID NO:131 can usefully be omitted. Other fragments omit one or more protein domains.

The 'sta099' antigen is annotated as 'superantigen-like protein 5'. In the NCTC 8325 strain sta099 is SAOUHSC_00390 and has amino acid sequence SEQ ID NO:132 (GI:88194185).

Useful sta099 antigens can elicit an antibody (e.g. when administered to a human) that recognizes SEQ ID NO:132 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:132; and/or (b)

comprising a fragment of at least 'n' consecutive amino acids of SEQ ID NO:132, wherein 'n' is 7 or more (e.g. 8, 10, 12, 14, 16, 18, 20, 25, 30, 35, 40, 50, 60, 70, 80, 90, 100, 150, 200 or more). These sta099 proteins include variants of SEQ ID NO:132. Preferred fragments of (b) comprise an epitope from SEQ ID NO:132. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:132 while retaining at least one epitope of SEQ ID NO:132. The first 30 N-terminal amino acids of SEQ ID NO:132 can usefully be omitted. Other fragments omit one or more protein domains.

The 'sta100' antigen is annotated as 'superantigen-like protein'. In the NCTC 8325 strain sta100 is SAOUHSC_00391 and has amino acid sequence SEQ ID NO:133 (GI:88194186).

Useful sta100 antigens can elicit an antibody (e.g. when administered to a human) that recognizes SEQ ID NO:133 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:133; and/or (b) comprising a fragment of at least 'n' consecutive amino acids of SEQ ID NO:133, wherein 'n' is 7 or more (e.g. 8, 10, 12, 14, 16, 18, 20, 25, 30, 35, 40, 50, 60, 70, 80, 90, 100, 150, 200 or more). These sta100 proteins include variants of SEQ ID NO:133. Preferred fragments of (b) comprise an epitope from SEQ ID NO:133. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:133 while retaining at least one epitope of SEQ ID NO:133. The first 30 N-terminal amino acids of SEQ ID NO:133 can usefully be omitted. Other fragments omit one or more protein domains.

The 'sta101' antigen is annotated as 'superantigen-like protein 7'. In the NCTC 8325 strain sta101 is SAOUHSC_00392 and has amino acid sequence SEQ ID NO:134 (GI:88194187). In the Newman strain it is nwmn_0394 (GI:151220606).

Useful sta101 antigens can elicit an antibody (e.g. when administered to a human) that recognizes SEQ ID NO:134 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:134; and/or (b) comprising a fragment of at least 'n' consecutive amino acids of SEQ ID NO:134, wherein 'n' is 7 or more (e.g. 8, 10, 12, 14, 16, 18, 20, 25, 30, 35, 40, 50, 60, 70, 80, 90, 100, 150, 200 or more). These sta101 proteins include variants of SEQ ID NO:134. Preferred fragments of (b) comprise an epitope from SEQ ID NO:134. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:134 while retaining at least one epitope of SEQ ID NO:134. The first 30 N-terminal amino acids of SEQ ID NO:134 can usefully be omitted. Other fragments omit one or more protein domains.

The 'sta102' antigen is annotated as 'superantigen-like protein'. In the NCTC 8325 strain sta102 is SAOUHSC_00393 and has amino acid sequence SEQ ID NO:135 (GI:88194188).

Useful sta102 antigens can elicit an antibody (e.g. when administered to a human) that recognizes SEQ ID NO:135 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:135; and/or (b) comprising a fragment of at least 'n' consecutive amino acids of SEQ ID NO:135, wherein 'n' is 7 or more (e.g. 8, 10, 12, 14, 16, 18, 20, 25, 30, 35, 40, 50, 60, 70, 80, 90, 100, 150, 200 or more). These sta102 proteins include variants of SEQ ID NO:135. Preferred fragments of (b) comprise an epitope from SEQ ID NO:135. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:135 while retaining at least one epitope of SEQ ID NO:135. The first 17 N-terminal amino acids of SEQ ID NO:135 can usefully be omitted. Other fragments omit one or more protein domains.

The 'sta103' antigen is annotated as 'superantigen-like protein'. In the NCTC 8325 strain sta103 is SAOUHSC_00394 and has amino acid sequence SEQ ID NO:136 (GI:88194189).

Useful sta103 antigens can elicit an antibody (e.g. when administered to a human) that recognizes SEQ ID NO:136 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:136; and/or (b) comprising a fragment of at least 'n' consecutive amino acids of SEQ ID NO:136, wherein 'n' is 7 or more (e.g. 8, 10, 12, 14, 16, 18, 20, 25, 30, 35, 40, 50, 60, 70, 80, 90, 100, 150, 200 or more). These sta103 proteins include variants of SEQ ID NO:136. Preferred fragments of (b) comprise an epitope from SEQ ID NO:136. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:136 while retaining at least one epitope of SEQ ID NO:136. The first 23 N-terminal amino acids of SEQ ID NO:136 can usefully be omitted. Other fragments omit one or more protein domains.

The 'sta104' antigen is annotated as 'superantigen-like protein'. In the NCTC 8325 strain sta104 is SAOUHSC_00395 and has amino acid sequence SEQ ID NO:137 (GI:88194190).

Useful sta104 antigens can elicit an antibody (e.g. when administered to a human) that recognizes SEQ ID NO:137 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:137; and/or (b) comprising a fragment of at least 'n' consecutive amino acids of SEQ ID NO:137, wherein 'n' is 7 or more (e.g. 8, 10, 12, 14, 16, 18, 20, 25, 30, 35, 40, 50, 60, 70, 80, 90, 100, 150, 200 or more). These sta104 proteins include variants of SEQ ID NO:137. Preferred fragments of (b) comprise an epitope from SEQ ID NO:137. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:137 while retaining at least one epitope of SEQ ID NO:137. Other fragments omit one or more protein domains.

The 'sta105' antigen is annotated as 'superantigen-like protein'. In the NCTC 8325 strain sta105 is SAOUHSC_00399 and has amino acid sequence SEQ ID NO:138 (GI:88194194). In the Newman strain it is nwmn_0400 (GI:151220612).

Useful sta105 antigens can elicit an antibody (e.g. when administered to a human) that recognizes SEQ ID NO:138 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:138; and/or (b) comprising a fragment of at least 'n' consecutive amino acids of SEQ ID NO:138, wherein 'n' is 7 or more (e.g. 8, 10, 12, 14, 16, 18, 20, 25, 30, 35, 40, 50, 60, 70, 80, 90, 100, 150, 200 or more). These sta105 proteins include variants of SEQ ID NO:138. Preferred fragments of (b) comprise an epitope from SEQ ID NO:138. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:138 while retaining at least one epitope of SEQ ID NO:138. The first 30 N-terminal amino acids of SEQ ID NO:138 can usefully be omitted. Other fragments omit one or more protein domains.

The 'sta106' antigen is annotated as 'hypothetical protein'. In the NCTC 8325 strain sta106 is SAOUHSC_01115 and has amino acid sequence SEQ ID NO:139 (GI: 88194861).

Useful sta106 antigens can elicit an antibody (e.g. when administered to a human) that recognizes SEQ ID NO:139 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:139; and/or (b) comprising a fragment of at least 'n' consecutive amino acids of SEQ ID NO:139, wherein 'n' is 7 or more (e.g. 8, 10, 12, 14, 16, 18, 20, 25, 30, 35, 40, 50, 60, 70, 80, 90, 100 or more). These sta106 proteins include variants of SEQ ID NO:139. Preferred fragments of (b) comprise an epitope from SEQ ID NO:139. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:139 while retaining at least one epitope of SEQ ID NO:139. The first 16 N-terminal amino acids of SEQ ID NO:139 can usefully be omitted. Other fragments omit one or more protein domains.

The 'sta107' antigen is annotated as 'hypothetical protein'. In the NCTC 8325 strain sta107 is SAOUHSC_00354 and has amino acid sequence SEQ ID NO:140 (GI: 88194153).

Useful sta107 antigens can elicit an antibody (e.g. when administered to a human) that recognizes SEQ ID NO:140 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:140; and/or (b) comprising a fragment of at least 'n' consecutive amino acids of SEQ ID NO:140, wherein 'n' is 7 or more (e.g. 8, 10, 12, 14, 16, 18, 20, 25, 30, 35, 40, 50, 60, 70, 80, 90, 100, 150, 200 or more). These sta107 proteins include variants of SEQ ID NO:140. Preferred fragments of (b) comprise an epitope from SEQ ID NO:140. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:140 while retaining at least one epitope of SEQ ID NO:140. The first 35 N-terminal amino acids of SEQ ID NO:140 can usefully be omitted. Other fragments omit one or more protein domains.

The 'sta108' antigen is annotated as 'hypothetical protein'. In the NCTC 8325 strain sta108 is SAOUHSC_00717 and has amino acid sequence SEQ ID NO:141 (GI: 88194482).

Useful sta108 antigens can elicit an antibody (e.g. when administered to a human) that recognizes SEQ ID NO:141 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:141; and/or (b) comprising a fragment of at least 'n' consecutive amino acids of SEQ ID NO:141, wherein 'n' is 7 or more (e.g. 8, 10, 12, 14, 16, 18, 20, 25, 30, 35, 40, 50, 60, 70, 80, 90, 100 or more). These sta108 proteins include variants of SEQ ID NO:141. Preferred fragments of (b) comprise an epitope from SEQ ID NO:141. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:141 while retaining at least one epitope of SEQ ID NO:141. The first 20 N-terminal amino acids of SEQ ID NO:141 can usefully be omitted. Other fragments omit one or more protein domains.

The 'sta109' antigen is annotated as 'N-acetylmuramoyl-L-alanine amidase'. In the NCTC 8325 strain sta109 is SAOUHSC_02979 and has amino acid sequence SEQ ID NO:142 (GI:88196599).

Useful sta109 antigens can elicit an antibody (e.g. when administered to a human) that recognizes SEQ ID NO:142 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:142; and/or (b) comprising a fragment of at least 'n' consecutive amino acids of SEQ ID NO:142, wherein 'n' is 7 or more (e.g. 8, 10, 12, 14, 16, 18, 20, 25, 30, 35, 40, 50, 60, 70, 80, 90, 100, 150, 200, 250 or more). These sta109 proteins include variants of SEQ ID NO:142. Preferred fragments of (b) comprise an epitope from SEQ ID NO:142. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:142 while retaining at least one epitope of SEQ ID NO:142. The first 27 N-terminal amino acids of SEQ ID NO:142 can usefully be omitted. Other fragments omit one or more protein domains.

The 'sta110' antigen is annotated as 'hypothetical protein'. In the NCTC 8325 strain sta110 is SAOUHSC_01039 and has amino acid sequence SEQ ID NO:143 (GI: 88194791).

Useful sta110 antigens can elicit an antibody (e.g. when administered to a human) that recognizes SEQ ID NO:143 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:143; and/or (b) comprising a fragment of at least 'n' consecutive amino acids of SEQ ID NO:143, wherein 'n' is 7 or more (e.g. 8, 10, 12, 14, 16, 18, 20, 25, 30, 35, 40, 50, 60, 70, 80, 90, 100, 150, 200 or more). These sta110 proteins include variants of SEQ ID NO:143. Preferred fragments of (b) comprise an epitope from SEQ ID NO:143. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:143 while retaining at least one epitope of SEQ ID NO:143. The first 19 N-terminal amino acids of SEQ ID NO:143 can usefully be omitted. Other fragments omit one or more protein domains.

The 'sta111' antigen is annotated as 'hypothetical protein'. In the NCTC 8325 strain sta111 is SAOUHSC_01005 and has amino acid sequence SEQ ID NO:144 (GI: 88194760).

Useful sta111 antigens can elicit an antibody (e.g. when administered to a human) that recognizes SEQ ID NO:144 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:144; and/or (b) comprising a fragment of at least 'n' consecutive amino acids of SEQ ID NO:144, wherein 'n' is 7 or more (e.g. 8, 10, 12, 14, 16, 18, 20, 25, 30, 35, 40, 50, 60, 70, 80, 90, 100 or more). These sta111 proteins include variants of SEQ ID NO:144. Preferred fragments of (b) comprise an epitope from SEQ ID NO:144. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:144 while retaining at least one epitope of SEQ ID NO:144. The first 20 N-terminal amino acids of SEQ ID NO:144 can usefully be omitted. Other fragments omit one or more protein domains.

The 'sta112' antigen is annotated as a putative 'ABC transporter, substrate-binding protein'. In the NCTC 8325 strain sta112 is SAOUHSC_00634 and has amino acid sequence SEQ ID NO:145 (GI:88194402).

Useful sta112 antigens can elicit an antibody (e.g. when administered to a human) that recognizes SEQ ID NO:145 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:145; and/or (b) comprising a fragment of at least 'n' consecutive amino acids of SEQ ID NO:145, wherein 'n' is 7 or more (e.g. 8, 10, 12, 14, 16, 18, 20, 25, 30, 35, 40, 50, 60, 70, 80, 90, 100, 150, 200, 250 or more). These sta112 proteins include variants of SEQ ID NO:145. Preferred fragments of (b) comprise an epitope from SEQ ID NO:145. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:145 while retaining at least one epitope of SEQ ID NO:145. The first 17 N-terminal amino acids of SEQ ID NO:145 can usefully be omitted. Other fragments omit one or more protein domains.

The 'sta113' antigen is annotated as 'hypothetical protein'. In the NCTC 8325 strain sta113 is SAOUHSC_00728 and has amino acid sequence SEQ ID NO:146 (GI: 88194493).

Useful sta113 antigens can elicit an antibody (e.g. when administered to a human) that recognizes SEQ ID NO:146 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:146; and/or (b) comprising a fragment of at least 'n' consecutive amino acids of SEQ ID NO:146, wherein 'n' is 7 or more (e.g. 8, 10, 12, 14, 16, 18, 20, 25, 30, 35, 40, 50, 60, 70, 80, 90, 100, 150, 200, 250 or more). These sta113 proteins include variants of SEQ ID NO:146. Preferred fragments of (b) comprise an epitope from SEQ ID NO:146. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from 10 the N-terminus of SEQ ID NO:146 while retaining at least one epitope of SEQ ID NO:146. The first 173 N-terminal amino acids of SEQ ID NO:146 can usefully be omitted. Other fragments omit one or more protein domains.

The 'sta114' antigen is annotated as 'hypothetical protein'. In the NCTC 8325 strain sta114 is SAOUHSC_00810 and has amino acid sequence SEQ ID NO:147 (GI: 88194570).

Useful sta114 antigens can elicit an antibody (e.g. when administered to a human) that recognizes SEQ ID NO:147 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:147; and/or (b) comprising a fragment of at least 'n' consecutive amino acids of SEQ ID NO:147, wherein 'n' is 7 or more (e.g. 8, 10, 12, 14, 16, 18, 20, 25, 30, 35, 40, 50, 60, 70, 80, 90, 100, 150 or more). These sta114 proteins include variants of SEQ ID NO:147. Preferred fragments of (b) comprise an epitope from SEQ ID NO:147. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:147 while retaining at least one epitope of SEQ ID NO:147. Other fragments omit one or more protein domains.

The 'sta115' antigen is annotated as 'hypothetical protein'. In the NCTC 8325 strain sta115 is SAOUHSC_00817 and has amino acid sequence SEQ ID NO:148 (GI: 88194576).

Useful sta115 antigens can elicit an antibody (e.g. when administered to a human) that recognizes SEQ ID NO:148 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:148; and/or (b) comprising a fragment of at least 'n' consecutive amino acids of SEQ ID NO:148, wherein 'n' is 7 or more (e.g. 8, 10, 12, 14, 16, 18, 20, 25, 30, 35, 35 40, 50, 60, 70, 80, 90, 100, 150 or more). These sta115 proteins include variants of SEQ ID NO:148. Preferred fragments of (b) comprise an epitope from SEQ ID NO:148. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:148 while retaining at least one epitope of SEQ ID NO:148. The first 18 N-terminal amino acids of SEQ ID NO:148 can usefully be omitted. Other fragments omit one or more protein domains.

The 'sta116' antigen is annotated as 'formyl peptide receptor-like 1 inhibitory protein'. In the NCTC 8325 strain sta116 IS SAOUHSC 01112 and has amino acid sequence SEQ ID NO:149 (GI:88194858).

Useful sta116 antigens can elicit an antibody (e.g. when administered to a human) that recognizes SEQ ID NO:149 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:149; and/or (b) comprising a fragment of at least 'n' consecutive amino acids of SEQ ID NO:149, wherein 'n' is 7 or more (e.g. 8, 10, 12, 14, 16, 18, 20, 25, 30, 35, 40, 50, 60, 70, 80, 90, 100 or more). These sta116 proteins include variants of SEQ ID NO:149. Preferred fragments of (b) comprise an epitope from SEQ ID NO:149. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:149 while retaining at least one epitope of SEQ ID NO:149. The first 20 N-terminal amino acids of SEQ ID NO:149 can usefully be omitted. Other fragments omit one or more protein domains.

The 'sta117' antigen is annotated as 'truncated beta-hemolysin'. In the NCTC 8325 strain sta117 is SAOUHSC_02240 and has amino acid sequence SEQ ID NO:150 (GI:88195913).

Useful sta117 antigens can elicit an antibody (e.g. when administered to a human) that recognizes SEQ ID NO:150 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:150; and/or (b) comprising a fragment of at least 'n' consecutive amino acids of SEQ ID NO:150, wherein 'n' is 7 or more (e.g. 8, 10, 12, 14, 16, 18, 20, 25, 30, 35, 40, 50, 60, 70, 80, 90, 100, 150, 200, 250 or more). These sta117 proteins include variants of SEQ ID NO:150. Preferred fragments of (b) comprise an epitope from SEQ ID NO:150. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:150 while retaining at least one epitope of SEQ ID NO:150. Other fragments omit one or more protein domains.

The 'sta118' antigen is annotated as 'cell division protein FtsZ'. In the NCTC 8325 strain sta118 is SAOUHSC_01150 and has amino acid sequence SEQ ID NO:151 (GI:88194892).

Useful sta118 antigens can elicit an antibody (e.g. when administered to a human) that recognizes SEQ ID NO:151 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:151; and/or (b) comprising a fragment of at least 'n' consecutive amino acids of SEQ ID NO:151, wherein 'n' is 7 or more (e.g. 8, 10, 12, 14, 16, 18, 20, 25, 30, 35, 40, 50, 60, 70, 80, 90, 100, 150, 200, 250 or more). These sta118 proteins include variants of SEQ ID NO:151. Preferred fragments of (b) comprise an epitope from SEQ ID NO:151. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:151 while retaining at least one epitope of SEQ ID NO:151. Other fragments omit one or more protein domains.

The 'sta119' antigen is annotated as 'thioredoxin'. In the NCTC 8325 strain sta119 is SAOUHSC_01100 and has amino acid sequence SEQ ID NO:152 (GI:88194846).

Useful sta119 antigens can elicit an antibody (e.g. when administered to a human) that recognizes SEQ ID NO:152 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO:152; and/or (b) comprising a fragment of at least 'n' consecutive amino acids of SEQ ID NO:152, wherein 'n' is 7 or more (e.g. 8, 10, 12, 14, 16, 18, 20, 25, 30, 35, 40, 50, 60, 70, 80, 90, 100 or more). These sta119 proteins include variants of SEQ ID NO:152. Preferred fragments of (b) comprise an epitope from SEQ ID NO:152. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:152 while retaining at least one epitope of SEQ ID NO:152. Other fragments omit one or more protein domains.

The 'sta120' antigen is annotated as 'alkyl hydroperoxide reductase subunit c'. In the NCTC 8325 strain sta120 is SAOUHSC_00365 and has amino acid sequence SEQ ID NO:153 (GI:88194163).

Useful sta120 antigens can elicit an antibody (e.g. when administered to a human) that recognizes SEQ ID NO:153 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 35 99.5% or more) to SEQ ID NO:153; and/or (b) comprising a fragment of at least 'n' consecutive amino acids of SEQ ID NO:153, wherein 'n' is 7 or more (e.g. 8, 10, 12, 14, 16, 18, 20, 25, 30, 35, 40, 50, 60, 70, 80, 90, 100, 150 or more). These sta120 proteins include variants of SEQ ID NO:153. Preferred fragments of (b) comprise an epitope from SEQ ID NO:153. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO:153 while retaining at least one epitope of SEQ ID NO:153. Other fragments omit one or more protein domains.

The polypeptides described herein may include 1, 2, 3, 4, 5, 6, 7, 8, 9, 10, 11, 12, 13, 14, 15, or more variant amino acids within at least, or at most 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more contiguous amino acids, or any range derivable therein, of SEQ ID NO:2-30, or SEQ ID NO:32-155.

A polypeptide segment or immunogenic fragment as described herein may include 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more contiguous amino acids, or any range derivable therein, of SEQ ID NO:2-30, or SEQ ID NO:33-155.

The immunogenic compositions of the invention may further comprise capsular polysaccharides including one or more of PIA (also known as PNAG) and/or *S. aureus* Type V and/or type VIII capsular polysaccharide and/or *S. epidermidis* Type I, and/or Type II and/or Type III capsular polysaccharide.

The compositions may be formulated in a pharmaceutically acceptable composition. In certain aspects of the invention the *staphylococcus* bacterium is an *S. aureus* bacterium.

In further aspects, a composition may be administered more than one time to the subject, and may be administered 1, 2, 3, 4, 5, 6, 7, 8, 9, 10, 15, 20 or more times. The administration of the compositions include, but is not limited to oral, parenteral, subcutaneous, intramuscular, intravenous, or various combinations thereof, including inhalation or aspiration.

In still further embodiments, a composition comprises a recombinant nucleic acid molecule encoding a polypeptide described herein or segments/fragments thereof. Typically a recombinant nucleic acid molecule encoding a polypeptide described herein contains a heterologous promoter. In certain aspects, a recombinant nucleic acid molecule of the invention is a vector, in still other aspects the vector is a plasmid. In certain embodiments the vector is a viral vector. In certain aspects a composition includes a recombinant, non-*staphylococcus* bacterium containing or expressing a polypeptide described herein. In particular aspects the recombinant non-*staphylococcus* bacteria is *Salmonella* or another gram-positive bacteria. A composition is typically administered to mammals, such as human subjects, but administration to other animals that are capable of eliciting an immune response is contemplated. In further aspects the *staphylococcus* bacterium containing or expressing the polypeptide is *Staphylococcus aureus*. In further embodiments the immune response is a protective immune response.

In further embodiments a composition comprises a recombinant nucleic acid molecule encoding all or part of one or more of a SpA, SpA polypeptide variant, Eap, Ebh, Emp, EsaB, EsaC, EsxA, EsxB, SdrC, SdrD, SdrE, IsdA, IsdB, ClfA, ClfB, Coa, Hla, IsdC, SasF, SpA, vWbp, or vWh protein or peptide or variant thereof. Additional staphylococcal antigens that can be used in combination with the polypeptides described herein include, but are not limited to 52 kDa vitronectin binding protein (WO 01/60852), Aaa, Aap, Ant, autolysin glucosaminidase, autolysin amidase, Cna, collagen binding protein (U.S. Pat. No. 6,288,214), EFB (FIB), Elastin binding protein (EbpS), EPB, FbpA, fibrinogen binding protein (U.S. Pat. No. 6,008,341), Fibronectin binding protein (U.S. Pat. No. 5,840,846), FnbA, FnbB, GehD (US 2002/0169288), HarA, HBP, Immunodominant ABC transporter, IsaA/PisA, laminin receptor, Lipase GehD, MAP, Mg2+ transporter, MHC II analogue (U.S. Pat. No. 5,648,240), MRPII, Npase, RNA III activating protein (RAP), SasA, SasB, SasC, SasD, SasK, SBI, SdrF (WO 00/12689), SdrG/Fig (WO 00/12689), SdrH (WO 00/12689), SEA exotoxins (WO 00/02523), SEB exotoxins (WO 00/02523), SitC and Ni ABC transporter, SitC/MntC/saliva binding protein (U.S. Pat. No. 5,801,234), SsaA, SSP-1, SSP-2, and/or Vitronectin binding protein. In particular aspects, a bacteria is a recombinant non-*staphylococcus* bacteria, such as a *Salmonella* or other gram-positive bacteria. Certain embodiments include compositions comprising recombinant nucleic acid molecules encoding all or part of one or more of, sta001, sta002, sta003, sta004, sta005, sta006, sta007, sta008, sta009, sta010, sta011, sta012, sta013, sta014, sta015, sta016, sta017, sta018, sta019, sta020, sta021, sta022, sta023, sta024, sta025, sta026, sta027, sta028, sta029, sta030, sta031, sta032, sta033, sta034, sta035, sta036, sta037, sta038, sta039, sta040, sta041, sta042, sta043, sta044, sta045, sta046, sta047, sta048, sta049, sta050, sta051, sta052, sta053, sta054, sta055, sta056, sta057, sta058, sta059, sta060, sta061, sta062, sta063, sta064, sta065, sta066, sta067, sta068, sta069, sta070, sta071, sta072, sta073, sta074, sta075, sta076, sta077, sta078, sta079, sta080, sta081, sta082, sta083, sta084, sta085, sta086, sta087, sta088, sta089, sta090, sta091, sta092, sta093, sta094, sta095, sta096, sta097, sta098, sta099, sta100, sta101, sta102, sta103, sta104, sta105, sta106, sta107, sta108, sta109, sta110, sta111, sta112, sta113, sta114, sta115, sta116, sta117, sta118, sta119, sta120, or EsxAB hybrid polypeptide or immunogenic fragment thereof.

Compositions of the invention are typically administered to human subjects, but administration to other animals that are capable of eliciting an immune response to a bacterium, e.g., a *staphylococcus* bacterium, is contemplated, particularly cattle, horses, goats, sheep and other domestic animals, i.e., mammals.

In certain aspects the *staphylococcus* bacterium is a *Staphylococcus aureus*. In further embodiments the immune response is a protective immune response. In still further aspects, the methods and compositions of the invention can be used to prevent, ameliorate, reduce, or treat infection of tissues or glands, e.g., mammary glands, particularly mastitis and other infections. Other methods include, but are not limited to prophylactically reducing bacterial burden in a subject not exhibiting signs of infection, particularly those subjects suspected of or at risk of being colonized by a target bacteria, e.g., patients that are or will be at risk or susceptible to infection during a hospital stay, treatment, and/or recovery.

Any embodiment discussed with respect to one aspect of the invention applies to other aspects of the invention as well. In particular, any embodiment discussed in the context of a SpA variant polypeptide, peptide, nucleic acid, or antibody may specifically exclude one or more of Eap, Ebh, Emp, EsaC, EsxA, EsxB, SdrC, SdrD, SdrE, IsdA, IsdB, ClfA, ClfB, Coa, Hla, IsdC, SasF, vWbp, vWh, 52 kDa vitronectin binding protein (WO 01/60852), Aaa, Aap, Ant, autolysin glucosaminidase, autolysin amidase, Cna, collagen binding protein (U.S. Pat. No. 6,288,214), EFB (FIB), Elastin binding protein (EbpS), EPB, FbpA, fibrinogen binding protein (U.S. Pat. No. 6,008,341), Fibronectin binding protein (U.S. Pat. No. 5,840,846), FnbA, FnbB, GehD (US 2002/0169288), HarA, HBP, Immunodominant ABC transporter, IsaA/PisA, laminin receptor, Lipase GchD, MAP, Mg2+ transporter, MHC II analogue (U.S. Pat. No. 5,648,240), MRPII, Npase, RNA III activating protein (RAP), SasA, SasB, SasC, SasD, SasK, SBI, SdrF (WO 00/12689), SdrG/Fig (WO 00/12689), SdrH (WO 00/12689), SEA exotoxins (WO 00/02523), SEB exotoxins (WO 00/02523), SitC and Ni ABC transporter, SitC/MntC/saliva binding protein (U.S. Pat. No. 5,801,234), SsaA, SSP-1, SSP-2, and/or Vitronectin binding protein (or nucleic acids), sta001, sta002, sta003, sta004, sta005, sta006, sta007, sta008, sta009, sta010, sta011, sta012, sta013, sta014, sta015, sta016, sta017, sta018, sta019, sta020, sta021, sta022, sta023, sta024, sta025, sta026, sta027, sta028, sta029, sta030, sta031, sta032, sta033, sta034, sta035, sta036, sta037, sta038, sta039, sta040, sta041, sta042, sta043, sta044, sta045, sta046, sta047, sta048, sta049, sta050, sta051, sta052, sta053, sta054, sta055, sta056, sta057, sta058, sta059, sta060, sta061, sta062, sta063, sta064, sta065, sta066, sta067, sta068, sta069, sta070, sta071, sta072, sta073, sta074, sta075, sta076, sta077, sta078, sta079, sta080, sta081, sta082, sta083, sta084, sta085, sta086, sta087, sta088, sta089, sta090, sta091, sta092, sta093, sta094, sta095, sta096, sta097, sta098, sta099, sta100, sta101, sta102, sta103, sta104, sta105, sta106, sta107, sta108, sta109, sta110, sta111, sta112, sta113, sta114, sta115, sta116, sta117, sta118, sta119, sta120, or EsxAB hybrid polypeptide or immunogenic fragment thereof and vice versa.

Embodiments of the invention include compositions that contain or do not contain a bacterium. A composition may or may not include an attenuated or viable or intact staphylococcal bacterium. In certain aspects, the composition comprises a bacterium that is not a staphylococcal bacterium or does not contain staphylococcal bacteria. In certain embodiments a bacterial composition comprises an isolated or recombinantly expressed staphylococcal Protein A variant or a nucleotide encoding the same. The composition may be or include a recombinantly engineered *staphylococcus* bacterium that has been altered in a way that comprises specifically altering the bacterium with respect to a secreted virulence factor or cell surface protein. For example, the bacteria may be recombinantly modified to express more of the virulence factor or cell surface protein than it would express if unmodified.

The term "isolated" can refer to a nucleic acid or polypeptide that is substantially free of cellular material, bacterial material, viral material, or culture medium (when produced by recombinant DNA techniques) of their source of origin, or chemical precursors or other chemicals (when chemically synthesized). Moreover, an isolated compound refers to one that can be administered to a subject as an isolated compound; in other words, the compound may not simply be considered "isolated" if it is adhered to a column or embedded in an agarose gel. Moreover, an "isolated nucleic acid fragment" or "isolated peptide" is a nucleic acid or protein fragment that is not naturally occurring as a fragment and/or is not typically in the functional state.

Moieties of the invention, such as polypeptides, peptides, antigens, or immunogens, may be conjugated or linked covalently or noncovalently to other moieties such as adjuvants, proteins, peptides, supports, fluorescence moieties, or labels. The term "conjugate" or "immunoconjugate" is broadly used to define the operative association of one moiety with another agent and is not intended to refer solely to any type of operative association, and is particularly not limited to chemical "conjugation." Recombinant fusion proteins are particularly contemplated. Compositions of the invention may further comprise an adjuvant or a pharmaceutically acceptable excipient. An adjuvant may be covalently or non-covalently coupled to a polypeptide or peptide of the invention. In certain aspects, the adjuvant is chemically conjugated to a protein, polypeptide, or peptide.

The term "providing" is used according to its ordinary meaning to indicate "to supply or furnish for use." In some embodiments, the protein is provided directly by administering the protein, while in other embodiments, the protein is effectively provided by administering a nucleic acid that encodes the protein. In certain aspects the invention contemplates compositions comprising various combinations of nucleic acid, antigens, peptides, and/or epitopes.

The subject will have (e.g., are diagnosed with a staphylococcal infection), will be suspected of having, or will be determined to be at risk of developing a staphylococcal infection. Compositions of the present invention include immunogenic compositions wherein the antigen(s) or epitope(s) are contained in an amount effective to achieve the intended purpose. More specifically, an effective amount means an amount of active ingredients necessary to stimulate or elicit an immune response, or provide resistance to, amelioration of, or mitigation of infection. In more specific aspects, an effective amount prevents, alleviates or ameliorates symptoms of disease or infection, or prolongs the survival of the subject being treated. Determination of the effective amount is well within the capability of those skilled in the art, especially in light of the detailed disclosure provided herein. For any preparation used in the methods of the invention, an effective amount or dose can be estimated initially from in vitro studies, cell culture, and/or animal model assays. For example, a dose can be formulated in animal models to achieve a desired immune response or circulating antibody concentration or titer. Such information can be used to more accurately determine useful doses in humans.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

So that the matter in which the above-recited features, advantages and objects of the invention as well as others which will become clear are attained and can be understood in detail, more particular descriptions and certain embodiments of the invention briefly summarized above are illustrated in the appended drawings. These drawings form a part of the specification. It is to be noted, however, that the appended drawings illustrate certain embodiments of the invention and therefore are not to be considered limiting in their scope.

FIG. 1 Immunization with SpA$_{KKAA}$ modifies host immune responses to staphylococcal infection. Cohorts of BALB/c mice (n=15) were immunized with SpA$_{KKAA}$ or with PBS/adjuvant control (mock) and then challenged by intravenous inoculation with 5×10$^6$ CFU *S. aureus* USA300 LAC. Thirty days after infection, animals were bled and serum samples were analyzed for antibody responses to staphylococcal antigens. Twenty-seven recombinant, six-histidyl tagged staphylococcal proteins (ClfA, ClfB, Coa, Eap, Ebh, Emp, EsxA, EsxB, FnbpA, FnbpB, Hla, IsdA, IsdB, LukD, LukE, LukF, SdrC, SdrD, SdrE, SasA, SasD, SasF, SasG, SasI, SasK, SpA$_{KKAA}$ and vWbp) were purified by Ni-NTA affinity chromatography and immobilized on nitrocellulose membrane at 2 µg. Signal intensities in sera from mice were quantified and normalized by infrared imaging. Data are the means, and error bars represent SEM (±).

DETAILED DESCRIPTION

*Staphylococcus aureus* is a commensal of the human skin and nares, and the leading cause of bloodstream, skin and soft tissue infections (Klevens et al., 2007). Recent dramatic increases in the mortality of staphylococcal diseases are attributed to the spread of methicillin-resistant *S. aureus* (MRSA) strains often not susceptible to antibiotics (Kennedy et al., 2008). In a large retrospective study, the incidence of MRSA infections was 4.6% of all hospital admissions in the United States (Klevens et al., 2007). The annual health care costs for 94,300 MRSA infected individuals in the United States exceed $2.4 billion (Klevens et al., 2007). The current MRSA epidemic has precipitated a public health crisis that needs to be addressed by development of a preventive vaccine (Boucher and Corey, 2008). To date, an FDA licensed vaccine that prevents *S. aureus* diseases is not available.

The inventors describe here the use of Protein A, a cell wall anchored surface protein of staphylococci, for the generation of variants that can serve as subunit vaccines. The pathogenesis of staphylococcal infections is initiated as bacteria invade the skin or blood stream via trauma, surgical wounds, or medical devices (Lowy, 1998). Although the invading pathogen may be phagocytosed and killed, staphylococci can also escape innate immune defenses and seed infections in organ tissues, inducing inflammatory responses that attract macrophages, neutrophils, and other phagocytes (Lowy, 1998). The responsive invasion of immune cells to the site of infection is accompanied by liquefaction necrosis as the host seeks to prevent staphylococcal spread and allow for removal of necrotic tissue debris (Lam et al., 1963). Such lesions can be observed by microscopy as hypercellular areas containing necrotic tissue, leukocytes, and a central nidus of bacteria (Lam et al., 1963). Unless staphylococcal abscesses are surgically drained and treated with antibiotics, disseminated infection and septicemia produce a lethal outcome (Sheagren, 1984).

I. STAPHYLOCOCCAL ANTIGENS

A. Staphylcoccal Protein A (SpA)

All *Staphylococcus aureus* strains express the structural gene for Protein A (spa) (Jensen, 1958; Said-Salim et al., 2003), a well characterized virulence factor whose cell wall anchored surface protein product (SpA) encompasses five highly homologous immunoglobulin binding domains designated E, D, A, B, and C (Sjodahl, 1977). These domains display ~80% identity at the amino acid level, are 56 to 61 residues in length, and are organized as tandem repeats (Uhlen et al., 1984). SpA is synthesized as a precursor protein with an N-terminal YSIRK/GS signal peptide and a C-terminal LPXTG motif sorting signal (DeDent et al., 2008; Schneewind et al., 1992). Cell wall anchored Protein A is displayed in great abundance on the staphylococcal surface (DeDent et al., 2007; Sjoquist et al., 1972). Each of its immunoglobulin binding domains is composed of antiparallel α-helices that assemble into a three helix bundle and bind the Fc domain of immunoglobulin G (IgG) (Deisenhofer, 1981; Deisenhofer et al., 1978), the VH3 heavy chain (Fab) of IgM (i.e., the B cell receptor) (Graille et al., 2000), the von Willebrand factor at its A1 domain [vWF AI is a ligand for platelets] (O'Seaghdha et al., 2006) and the tumor necrosis factor α (TNF-α) receptor I (TNFRI) (Gomez et al., 2006), which is displayed on surfaces of airway epithelia (Gomez et al., 2004; Gomez et al., 2007).

SpA impedes neutrophil phagocytosis of staphylococci through its attribute of binding the Fc component of IgG (Jensen, 1958; Uhlen et al., 1984). Moreover, SpA is able to activate intravascular clotting via its binding to von Willebrand factor AI domains (Hartleib et al., 2000). Plasma proteins such as fibrinogen and fibronectin act as bridges between staphylococci (ClfA and ClfB) and the platelet integrin GPIIb/IIIa (O'Brien et al., 2002), an activity that is supplemented through Protein A association with vWF AI, which allows staphylococci to capture platelets via the GPIb-α platelet receptor (Foster, 2005; O'Seaghdha et al., 2006). SpA also binds TNFRI and this interaction contributes to the pathogenesis of staphylococcal pneumonia (Gomez et al., 2004). SpA activates proinflammatory signaling through TNFR1 mediated activation of TRAF2, the p38/c-Jun kinase, mitogen activate protein kinase (MAPK) and the Rel-transcription factor NF-KB. SpA binding further induces TNFR1 shedding, an activity that appears to require the TNF-converting enzyme (TACE) (Gomez et al., 2007). All of the aforementioned SpA activities are mediated through its five IgG binding domains and can be perturbed by the same amino acid substitutions, initially defined by their requirement for the interaction between Protein A and human IgG1 (Cedergren et al., 1993.

SpA also functions as a B cell superantigen by capturing the Fab region of VH3 bearing IgM, the B cell receptor (Gomez et al., 2007; Goodyear et al., 2003; Goodyear and Silverman, 2004; Roben et al., 1995). Following intravenous challenge, staphylococcal Protein A (SpA) mutations show a reduction in staphylococcal load in organ tissues and dramatically diminished ability to form abscesses (described herein). During infection with wildtype *S. aureus*, abscesses are formed within forty-eight hours and are detectable by light microscopy of hematoxylin-eosin stained, thin-sectioned kidney tissue, initially marked by an influx of polymorphonuclear leukocytes (PMNs). On day 5 of infection, abscesses increase in size and enclosed a central population of staphylococci, surrounded by a layer of eosinophilic, amorphous material and a large cuff of PMNs. Histopathology revealed massive necrosis of PMNs in proximity to the staphylococcal nidus at the center of abscess lesions as well as a mantle of healthy phagocytes. The inventors also observed a rim of necrotic PMNs at the periphery of abscess lesions, bordering the eosinophilic pseudocapsule that separated healthy renal tissue from the infectious lesion. Staphylococcal variants lacking Protein A are unable to establish the histopathology features of abscesses and are cleared during infection.

In previous studies, Cedergren et al. (1993) engineered five individual substitutions in the Fc frgament binding sub-domain of the B domain of SpA, L17D, N28A, I31A and K35A. These authors created these proteins to test data gathered from a three dimensional structure of a complex between one domain of SpA and $Fc_1$. Cedergren et al. determined the effects of these mutations on stability and binding, but did not contemplate use of such substitutions for the production of a vaccine antigen.

Brown et al. (1998) describe studies designed to engineer new proteins based on SpA that allow the use of more favorable elution conditions when used as affinity ligands. The mutations studied included single mutations of Q13A, Q14H, N15A, N15H, F17H, Y18F, L21H, N32H, or K39H. Brown et al. report that Q13A, N15A, N15H, and N32H substitutions made little difference to the dissociation constant values and that the Y18F substitution resulted in a 2 fold decrease in binding affinity as compared to wild type SpA. Brown et al. also report that L21H and F17H substitutions decrease the binding affinity by five-fold and a hundred-fold respectively. The authors also studied analogous substitutions in two tandem domains. Thus, the Brown et al. studies were directed to generating a SpA with a more favorable elution profile, hence the use of His substitutions to provide a pH sensitive alteration in the binding affinity. Brown et al. is silent on the use of SpA as a vaccine antigen.

Graille et al. (2000) describe a crystal structure of domain D of SpA and the Fab fragment of a human IgM antibody. Graille et al. define by analysis of a crystal structure the D domain amino acid residues that interact with the Fab fragment as residues Q26, G29, F30, Q32, S33, D36, D37, Q40, N43, E47, or L51, as well as the amino acid residues that form the interface between the domain D sub-domains. Graille et al. define the molecular interactions of these two proteins, but is silent in regard to any use of substitutions in the interacting residues in producing a vaccine antigen.

O'Scaghdha et al. (2006) describe studies directed at elucidating which sub-domain of domain D binds vWF. The authors generated single mutations in either the Fc or VH3 binding sub-domains, i.e., amino acid residues F5A, Q9A, Q10A, F13A, Y14A, L17A, N28A, I31A, K35A, G29A, F30A, S33A, D36A, D37A, Q40A, E47A, or Q32A. The authors discovered that vWF binds the same sub-domain that binds Fc. O'Seaghda et al. define the sub-domain of domain D responsible for binding vWF, but is silent in regard to any use of substitutions in the interacting residues in producing a vaccine antigen.

Gomez et al. (2006) describe the identification of residues responsible for activation of the TNFR1 by using single mutations of F5A, F13A, Y14A, L17A, N21A, I31A, Q32A, and K35A. Gomez et al. is silent in regard to any use of substitutions in the interacting residues in producing a vaccine antigen.

Recombinant affinity tagged Protein A, a polypeptide encompassing the five IgG domains (EDCAB) (Sjodahl, 1977) but lacking the C-terminal Region X (Guss et al., 1984), was purified from recombinant E. coli and used as a vaccine antigen (Stranger-Jones et al., 2006). Because of the attributes of SpA in binding the Fc portion of IgG, a specific humoral immune response to Protein A could not be measured (Stranger-Jones et al., 2006). The inventors have overcome this obstacle through the generation of SpA-DQ9, 10K; D36,37A. BALB/c mice immunized with recombinant Protein A (SpA) displayed significant protection against intravenous challenge with S. aureus strains: a 2.951 log reduction in staphylococcal load as compared to the wild-type (P>0.005; Student's t-test) (Stranger-Jones et al., 2006). SpA specific antibodies may cause phagocytic clearance prior to abscess formation and/or impact the formation of the aforementioned eosinophilic barrier in abscesses that separate staphylococcal communities from immune cells since these do not form during infection with Protein A mutant strains. Each of the five SpA domains (i.e., domains formed from three helix bundles designated E, D, A, B, and C) exerts similar binding properties (Jansson et al., 1998). The solution and crystal structure of the domain D has been solved both with and without the Fc and VH3 (Fab) ligands, which bind Protein A in a non-competitive manner at distinct sites (Graille et al., 2000). Mutations in residues known to be involved in IgG binding (FS, Q9, Q10, S11, F13, Y14, L17, N28, I31 and K35) are also required for vWF A1 and TNFR1 binding (Cedergren et al., 1993; Gomez et al., 2006; O'Seaghdha et al., 2006), whereas residues important for the VH3 interaction (Q26, G29, F30, S33, D36, D37, Q40, N43, E47) appear to have no impact on the other binding activities (Graille et al., 2000; Jansson et al., 1998). SpA specifically targets a subset of B cells that express VH3 family related IgM on their surface, i.e., VH3 type B cell receptors (Roben et al., 1995). Upon interaction with SpA, these B cells proliferate and commit to apoptosis, leading to preferential and prolonged deletion of innate-like B lymphocytes (i.e., marginal zone B cells and follicular B2 cells) (Goodyear et al., 2003; Goodyear et al., 2004).

Molecular Basis of Protein a Surface Display and Function.

Protein A is synthesized as a precursor in the bacterial cytoplasm and secreted via its YSIRK signal peptide at the cross wall, i.e. the cell division septum of staphylococci (FIG. 1) (DeDent et al., 2007; DeDent et al., 2008). Following cleavage of the C-terminal LPXTG sorting signal, Protein A is anchored to bacterial peptidoglycan cross-bridges by sortase A (Mazmanian et al., 1999; Schneewind et al., 1995; Mazmanian et al., 2000). Protein A is the most abundant surface protein of staphylococci; the molecule is expressed by virtually all S. aureus strains (Cespedes et al., 2005; Kennedy et al., 2008; Said-Salim et al., 2003). Staphylococci turn over 15-20% of their cell wall per division cycle (Navarre and Schneewind, 1999). Murine hydrolases cleave the glycan strands and wall peptides of peptidoglycan, thereby releasing Protein A with its attached C-terminal cell wall disaccharide tetrapeptide into the extracellular medium (Ton-That et al., 1999). Thus, by physiological design, Protein A is both anchored to the cell wall and displayed on the bacterial surface but also released into surrounding tissues during host infection (Marraffini et al., 2006).

Protein A captures immunoglobulins on the bacterial surface and this biochemical activity enables staphylococcal escape from host innate and acquired immune responses (Jensen, 1958; Goodyear et al., 2004). Interestingly, region X of Protein A (Guss et al., 1984), a repeat domain that tethers the IgG binding domains to the LPXTG sorting signal/cell wall anchor, is perhaps the most variable portion of the staphylococcal genome (Said-Salim, 2003; Schneewind et al., 1992). Each of the five immunoglobulin binding domains of Protein A (SpA), formed from three helix bundles and designated E, D, A, B, and C, exerts similar structural and functional properties (Sjodahl, 1977; Jansson et al., 1998). The solution and crystal structure of the domain D has been solved both with and without the Fc and $V_H 3$ (Fab) ligands, which bind Protein A in a non-competitive manner at distinct sites (Graille 2000).

In the crystal structure complex, the Fab interacts with helix II and helix III of domain D via a surface composed of four VH region β-strands (Graille 2000). The major axis of helix II of domain D is approximately 50° to the orientation of the strands, and the interhelical portion of domain D is most proximal to the C0 strand. The site of interaction on Fab is remote from the Ig light chain and the heavy chain constant region. The interaction involves the following domain D residues: Asp-36 of helix II, Asp-37 and Gln-40 in the loop between helix II and helix III and several other residues (Graille 2000). Both interacting surfaces are composed predominantly of polar side chains, with three negatively charged residues on domain D and two positively charged residues on the 2A2 Fab buried by the interaction, providing an overall electrostatic attraction between the two molecules. Of the five polar interactions identified between Fab and domain D, three are between side chains. A salt bridge is formed between Arg-H19 and Asp-36 and two hydrogen bonds are made between Tyr-H59 and Asp-37 and between Asn-H82a and Ser-33. Because of the conservation of Asp-36 and Asp-37 in all five IgG binding domains of Protein A, the inventors mutated these residues.

The SpA-D sites responsible for Fab binding are structurally separate from the domain surface that mediates Fcγ binding. The interaction of Fcγ with domain D primarily involves residues in helix I with lesser involvement of helix II (Gouda et al., 1992; Deisenhofer, 1981). With the exception of the Gln-32, a minor contact in both complexes, none of the residues that mediate the Fcγ interaction are involved in Fab binding. To examine the spatial relationship between these different Ig-binding sites, the SpA domains in these complexes have been superimposed to construct a model of a complex between Fab, the SpA-domain D, and the Fcγ molecule. In this ternary model, Fab and Fcγ form a sandwich about opposite faces of the helix II without evidence of steric hindrance of either interaction. These findings illustrate how, despite its small size (i.e., 56-61 aa), an SpA domain can simultaneously display both activities, explaining experimental evidence that the interactions of Fab with an individual domain are noncompetitive. Residues for the interaction between SpA-D and Fcγ are Gln-9 and Gln-10.

In contrast, occupancy of the Fc portion of IgG on the domain D blocks its interaction with vWF A1 and probably also TNFR1 (O'Seaghdha et al., 2006). Mutations in residues essential for IgG Fc binding (F5, Q9, Q10, S11, F13, Y14, L17, N28, I131 and K35) are also required for vWF A1 and TNFR1 binding (O'Seaghdha et al., 2006; Cedergren et al., 1993; Gomez et al., 2006), whereas residues critical for the VH3 interaction (Q26, G29, F30, S33, D36, D37, Q40, N43, E47) have no impact on the binding activities of IgG Fc, vWF A1 or TNFR1 (Jansson et al., 1998; Graille et al., 2000). The Protein A immunoglobulin Fab binding activity targets a subset of B cells that express $V_H3$ family related IgM on their surface, i.e., these molecules function as VH3type B cell receptors (Roben et al., 1995). Upon interaction with SpA, these B cells rapidly proliferate and then commit to apoptosis, leading to preferential and prolonged deletion of innate-like B lymphocytes (i.e., marginal zone B cells and follicular B2 cells) (Goodyear and Silverman, 2004; Goodyear and Silverman, 2003). More than 40% of circulating B cells are targeted by the Protein A interaction and the $V_H3$ family represents the largest family of human B cell receptors to impart protective humoral responses against pathogens (Goodyear and Silverman, 2004; Goodyear and Silverman, 2003). Thus, Protein A functions analogously to staphylococcal superantigens (Roben et al., 1995), albeit that the latter class of molecules, for example SEB, TSST-1, TSST-2, form complexes with the T cell receptor to inappropriately stimulate host immune responses and thereby precipitating characteristic disease features of staphylococcal infections (Roben et al., 1995; Tiedemann et al., 1995). Together these findings document the contributions of Protein A in establishing staphylococcal infections and in modulating host immune responses.

In sum, Protein A domains can viewed as displaying two different interfaces for binding with host molecules and any development of Protein A based vaccines must consider the generation of variants that do not perturb host cell signaling, platelet aggregation, sequestration of immunoglobulins or the induction of B cell proliferation and apoptosis. Such Protein A variants should also be useful in analyzing vaccines for the ability of raising antibodies that block the aforementioned SpA activities and occupy the five repeat domains at their dual binding interfaces. This goal is articulated and pursued here for the first time and methods are described in detail for the generation of Protein A variants that can be used as a safe vaccine for humans. To perturb IgG Fcγ, vWF A1 and TNFR1 binding, glutamine (Q) 9 and 10 [numbering derived from the SpA domain D as described in Uhlen et al., 1984] were mutated, and generated lysine substitutions for both glutamines with the expectation that these abolish the ligand attributes at the first binding interface. To perturb IgM Fab VH3 binding, aspartate (D) 36 and 37 were mutated, each of which is required for the association with the B cell receptor. D36 and D37 were both substituted with alanine Q9,10K and D36,37A mutations are here combined in the recombinant molecule SpA-DQ9,10K; D36,37A and tested for the binding attributes of Protein A. Further, SpA-D and SpA-DQ9,10K; D36,37A are subjected to immunization studies in mice and rabbits and analyzed for [1] the production of specific antibodies (SpA-D Ab); [2] the ability of SpA-D Ab to block the association between Protein A and its four different ligands; and, [3] the attributes of SpA-D Ab to generate protective immunity against staphylococcal infections.

In certain embodiments the SpA variant is a full length SpA variant comprising a variant A, B, C, D, and E domain. In certain aspects, the SpA variant comprises or consists of the amino acid sequence that is 80, 90, 95, 98, 99, or 100% identical to the amino acid sequence of SEQ ID NO:34 In other embodiments the SpA variant comprises a segment of SpA. The SpA segment can comprise at least or at most 1, 2, 3, 4, 5 or more IgG binding domains. The IgG domains can be at least or at most 1, 2, 3, 4, 5 or more variant A, B, C, D, or E domains. In certain aspects the SpA variant comprises at least or at most 1, 2, 3, 4, 5, or more variant A domains. In a further aspect the SpA variant comprises at least or at most 1, 2, 3, 4, 5, or more variant B domains. In still a further aspect the SpA variant comprises at least or at most 1, 2, 3, 4, 5, or more variant C domains. In yet a further aspect the SpA variant comprises at least or at most 1, 2, 3, 4, 5, or more variant D domains. In certain aspects the SpA variant comprises at least or at most 1, 2, 3, 4, 5, or more variant E domains. In a further aspect the SpA variant comprises a combination of A, B, C, D, and E domains in various combinations and permutations. The combinations can include all or part of a SpA signal peptide segment, a SpA region X segment, and/or a SpA sorting signal segment. In other aspects the SpA variant does not include a SpA signal peptide segment, a SpA region X segment, and/or a SpA sorting signal segment. In certain aspects a variant A domain comprises a substitution at position(s) 7, 8, 34, and/or 35 of SEQ ID NO:4. In another aspect a variant B domain comprises a substitution at position(s) 7, 8, 34, and/or 35 of SEQ ID NO:6. In still anther aspect a variant C domain comprises a substitution at position(s) 7, 8, 34, and/or 35 of SEQ ID NO:5. In certain aspects a variant D domain comprises a substitution at position(s) 9, 10, 37, and/or 38 of SEQ ID NO:2. In a further aspect a variant E domain comprises a substitution at position(s) 6, 7, 33, and/or 34 of SEQ ID NO:3.

In certain aspects the SpA variant includes a substitution of (a) one or more amino acid substitution in an IgG Fc binding sub-domain of SpA domain A, B, C, D, and/or E that disrupts or decreases binding to IgG Fc, and (b) one or more amino acid substitution in a $V_H3$ binding sub-domain of SpA domain A, B, C, D, and/or E that disrupts or decreases binding to $V_H3$. In still further aspects the amino acid sequence of a SpA variant comprises an amino acid sequence that is at least 50%, 60%, 70%, 80%, 90%, 95%, or 100% identical, including all values and ranges there between, to the amino acid sequence of SEQ ID NOs:2-6.

In a further aspect the SpA variant includes (a) one or more amino acid substitution in an IgG Fc binding sub-domain of SpA domain D, or at a corresponding amino acid position in other IgG domains, that disrupts or decreases binding to IgG Fc, and (b) one or more amino acid substitution in a $V_H3$ binding sub-domain of SpA domain D, or at a corresponding amino acid position in other IgG domains, that disrupts or decreases binding to $V_H3$. In certain aspects amino acid residue F5, Q9, Q10, S11, F13, Y14, L17, N28, I31, and/or K35 (SEQ ID NO:2, QQNNFNKDQQSA-FYEILNMPNLNEAQRNGFIQSLKDDPSQSTNV-LGEAKKLNES) of the IgG Fc binding sub-domain of domain D are modified or substituted. In certain aspects amino acid residue Q26, G29, F30, S33, D36, D37, Q40, N43, and/or E47 (SEQ ID NO:2) of the $V_H3$ binding sub-domain of domain D are modified or substituted such that binding to Fc or $V_H3$ is attenuated. In further aspects corresponding modifications or substitutions can be engineered in corresponding positions of the domain A, B, C, and/or E. Corresponding positions are defined by alignment of the domain D amino acid sequence with one or more of the amino acid sequences from other IgG binding domains of SpA. In certain aspects the amino acid substitution can be any of the other 20 amino acids. In a further aspect conservative amino acid substitutions can be specifically excluded from possible amino acid substitutions. In other aspects only non-conservative substitutions are included. In any event, any substitution or combination of substitutions that reduces the binding of the domain such that SpA toxicity is significantly reduced is contemplated. The significance of the reduction in binding refers to a variant that produces minimal to no toxicity when introduced into a subject and can be assessed using in vitro methods described herein.

In certain embodiments, a variant SpA comprises at least or at most 1, 2, 3, 4, 5, 6, 7, 8, 9, 10, or more variant SpA domain D peptides. In certain aspects 1, 2, 3, 4, 5, 6, 7, 8, 9, 10, 11, 12, 13, 14, 15, 16, 17, 18, or 19 or more amino acid residues of the variant SpA are substituted or modified—including but not limited to amino acids F5, Q9, Q10, S11, F13, Y14, L17, N28, I31, and/or K35 (SEQ ID NO:2) of the IgG Fc binding sub-domain of domain D and amino acid residue Q26, G29, F30, S33, D36, D37, Q40, N43, and/or E47 (SEQ ID NO:2) of the $V_H3$ binding sub-domain of domain D. In one aspect of the invention glutamine residues at position 9 and/or 10 of SEQ ID NO:2 (or corresponding positions in other domains) are mutated. In another aspect, aspartic acid residues 36 and/or 37 of SEQ ID NO:2 (or corresponding positions in other domains) are mutated. In a further aspect, glutamine 9 and 10, and aspartic acid residues 36 and 37 are mutated. Purified non-toxigenic SpA or SpA-D mutants/variants described herein are no longer able to significantly bind (i.e., demonstrate attenuated or disrupted binding affinity) Fcγ or F(ab)$_2$ $V_H3$ and also do not stimulate B cell apoptosis. These non-toxigenic Protein A variants can be used as subunit vaccines and raise humoral immune responses and confer protective immunity against *S. aureus* challenge. Compared to wild-type full-length Protein A or the wild-type SpA-domain D, immunization with SpA-D variants resulted in an increase in Protein A specific antibody. Using a mouse model of staphylococcal challenge and abscess formation, it was observed that immunization with the non-toxigenic Protein A variants generated significant protection from staphylococcal infection and abscess formation. As virtually all *S. aureus* strains express Protein A, immunization of humans with the non-toxigenic Protein A variants can neutralize this virulence factor and thereby establish protective immunity. In certain aspects the protective immunity protects or ameliorates infection by drug resistant strains of *Staphylococcus*, such as USA300 and other MRSA strains.

In still further aspects, the bacterial antigen is multimerized, e.g., dimerized or a linear fusion of two or more polypeptides or peptide segments. In certain aspects of the invention, a composition comprises multimers or concatamers of 1, 2, 3, 4, 5, 6, 7, 8, 9, 10, 11, 12, 13, 14, 15, 16, 17, 18, 19, 20 or more isolated cell surface proteins or segments thereof. Concatamers are linear polypeptides having one or more repeating peptide units. Bacterial antigens or fragments can be consecutive or separated by a spacer or other peptide sequences, e.g., one or more additional bacterial peptide. In a further aspect, the other polypeptides or peptides contained in the multimer or concatamer can include, but are not limited to 1, 2, 3, 4, 5, 6, 7, 8, 9, 10, 11, 12, 13, 14, 15, 16, 17, 18, 19 of FnBpA, FnBpB, LukD, LukE, LukF, SasA, SasD, SasG, SasI, SasK, SpA (and variants thereof), Eap, Ebh, Emp, EsaB, EsaC, EsxA, EsxB, SdrC, SdrD, SdrE, IsdA, IsdB, ClfA, ClfB, Coa, Hla (e.g., H35 mutants), IsdC, SasF, vWbp, or vWh or immunogenic fragments thereof. Additional staphylococcal antigens that can be used including, but are not limited to 52 kDa vitronectin binding protein (WO 01/60852), Aaa, Aap, Ant, autolysin glucosaminidase, autolysin amidase, Cna, collagen binding protein (U.S. Pat. No. 6,288,214), EFB (FIB), Elastin binding protein (EbpS), EPB, FbpA, fibrinogen binding protein (U.S. Pat. No. 6,008,341), Fibronectin binding protein (U.S. Pat. No. 5,840,846), FnbA, FnbB, GchD (US 2002/0169288), HarA, HBP, Immunodominant ABC transporter, IsaA/PisA, laminin receptor, Lipase GehD, MAP, Mg2+ transporter, MHC II analogue (U.S. Pat. No. 5,648,240), MRPII, Npase, RNA III activating protein (RAP), SasA, SasB, SasC, SasD, SasK, SBI, SdrF (WO 00/12689), SdrG/Fig (WO 00/12689), SdrH (WO 00/12689), SEA exotoxins (WO 00/02523), SEB exotoxins (WO 00/02523), SitC and Ni ABC transporter, SitC/MntC/saliva binding protein (U.S. Pat. No. 5,801,234), SsaA, SSP-1, SSP-2, and/or Vitronectin binding protein.

Yet still further embodiments include vaccines comprising a pharmaceutically acceptable composition having a combination or permutation of protein(s) or peptide(s) described herein, wherein the composition is capable of stimulating and/or enhancing an immune response against a *staphylococcus* bacterium. The vaccine may comprise an isolated protein(s) or peptide(s) described. In certain aspects of the invention the bacterial antigen, or any other combination or permutation of protein(s) or peptide(s) described are multimerized, e.g., dimerized or concatamerized. In a further aspect, the vaccine composition is contaminated by less than about 10, 9, 8, 7, 6, 5, 4, 3, 2, 1, 0.5, 0.25, 0.05% (or any range derivable therein) of other Staphylococcal proteins. A composition may further comprise an isolated protein A specific antibody or fragment thereof.

B. Staphylococcal Coagulases

Coagulases are enzymes produced by *Staphylococcus* bacteria that convert fibrinogen to fibrin. Coa and vW$_h$ activate prothrombin without proteolysis (Friedrich et al., 2003). The coagulase•prothrombin complex recognizes fibrinogen as a specific substrate, converting it directly into fibrin. The crystal structure of the active complex revealed binding of the D1 and D2 domains to prothrombin and insertion of its Ile1-Val$^2$ N-terminus into the Ile$^{16}$ pocket, inducing a functional active site in the zymogen through conformational change (Friedrich et al., 2003). Exosite I of α-thrombin, the fibrinogen recognition site, and proexosite I on prothrombin are blocked by the D2 of Coa (Friedrich et al., 2003). Nevertheless, association of the tetrameric (Coa•prothrombin)$_2$ complex binds fibrinogen at a new site with high affinity (Panizzi et al., 2006). This model explains the coagulant properties and efficient fibrinogen conversion by coagulase (Panizzi et al., 2006).

Fibrinogen is a large glycoprotein (Mr ~340,000), formed by three pairs of Aα-, Bβ-, and γ-chains covalently linked to form a "dimer of trimers," where A and B designate the fibrinopeptides released by thrombin cleavage (Panizzi et al., 2006). The elongated molecule folds into three separate domains, a central fragment E that contains the N-termini of all six chains and two flanking fragments D formed mainly by the C-termini of the Bβ- and γ-chains. These globular domains are connected by long triple-helical structures. Coagulase-prothrombin complexes, which convert human fibrinogen to the self-polymerizing fibrin, are not targeted by circulating thrombin inhibitors (Panizzi et al., 2006). Thus, staphylococcal coagulases bypass the physiological blood coagulation pathway.

All *S. aureus* strains secrete coagulase and vWbp (Bjerketorp et al., 2004; Field and Smith, 1945). Although early work reported important contributions of coagulase to the pathogenesis of staphylococcal infections (Ekstedt and Yotis, 1960; Smith et al., 1947), more recent investigations with molecular genetics tools challenged this view by observing no virulence phenotypes with endocarditis, skin abscess and mastitis models in mice (Moreillon et al., 1995; Phonimdaeng et al., 1990). Generating isogenic variants of *S. aureus* Newman, a fully virulent clinical isolate (Duthie et al., 1952), it is described herein that coa mutants indeed display virulence defects in a lethal bacteremia and renal abscess model in mice. In the inventors experience, *S. aureus* 8325-4 is not fully virulent and it is presumed that mutational lesions in this strain may not be able to reveal virulence defects in vivo. Moreover, antibodies raised against Coa or vWbp perturb the pathogenesis of *S. aureus* Newman infections to a degree mirroring the impact of gene deletions. Coa and vWbp contribute to staphylococcal abscess formation and lethal bacteremia and may also function as protective antigens in subunit vaccines.

Biochemical studies document the biological value of antibodies against Coa and vWbp. By binding to antigen and blocking its association with clotting factors, the antibodies prevent the formation of Coa•prothrombinand vWbp•prothrombin complexes. Passive transfer studies revealed protection of experimental animals against staphylococcal abscess formation and lethal challenge by Coa and vWbp antibodies. Thus, Coa and vWbp neutralizing antibodies generate immune protection against staphylococcal disease.

Earlier studies revealed a requirement of coagulase for resisting phagocytosis in blood (Smith et al., 1947) and the inventors observed a similar phenotype for Δcoa mutants in lepirudin-treated mouse blood (see Example 3 below). As vWbp displays higher affinity for human prothrombin than the mouse counterpart, it is suspected the same may be true for ΔvWbp variants in human blood. Further, expression of Coa and vWbp in abscess lesions as well as their striking distribution in the eosinophilic pseudocapsule surrounding (staphylococcal abscess communities (SACs) or the peripheral fibrin wall, suggest that secreted coagulases contribute to the establishment of these lesions. This hypothesis was tested and, indeed, Δcoa mutants were defective in the establishment of abscesses. A corresponding test, blocking Coa function with specific antibodies, produced the same effect. Consequently, it is proposed that the clotting of fibrin is a critical event in the establishment of staphylococcal abscesses that can be targeted for the development of protective vaccines. Due to their overlapping function on human prothrombin, both Coa and vWbp are considered excellent candidates for vaccine development.

C. Other Staphylococcal Antigens

Research over the past several decades identified *S. aureus* exotoxins, surface proteins and regulatory molecules as important virulence factors (Foster, 2005; Mazmanian et al., 2001; Novick, 2003). Much progress has been achieved regarding the regulation of these genes. For example, staphylococci perform a bacterial census via the secretion of auto-inducing peptides that bind to a cognate receptor at threshold concentration, thereby activating phospho-relay reactions and transcriptional activation of many of the exotoxin genes (Novick, 2003). The pathogenesis of staphylococcal infections relies on these virulence factors (secreted exotoxins, exopolysaccharides, and surface adhesins). The development of staphylococcal vaccines is hindered by the multifaceted nature of staphylococcal invasion mechanisms. It is well established that live attenuated microorganisms are highly effective vaccines; immune responses elicited by such vaccines are often of greater magnitude and of longer duration than those produced by non-replicating immunogens. One explanation for this may be that live attenuated strains establish limited infections in the host and mimic the early stages of natural infection. Embodiments of the invention are directed to compositions and methods including variant SpA polypeptides and peptides, as well as other immunogenic extracellular proteins, polypeptides, and peptides (including both secreted and cell surface proteins or peptides) of gram positive bacteria for the use in mitigating or immunizing against infection. In particular embodiments the bacteria is a *staphylococcus* bacteria. Extracellular proteins, polypeptides, or peptides include, but are not limited to secreted and cell surface proteins of the targeted bacteria.

The human pathogen *S. aureus* secretes EsxA and EsxB, two ESAT-6 like proteins, across the bacterial envelope (Burts et al., 2005, which is incorporated herein by reference). Staphylococcal esxA and esxB are clustered with six other genes in the order of transcription: esxA esaA essA esaB essB essC esaC esxB. The acronyms esa, ess, and esx stand for ESAT-6 secretion accessory, system, and extracellular, respectively, depending whether the encoded proteins play an accessory (esa) or direct (ess) role for secretion, or are secreted (esx) in the extracellular milieu. The entire cluster of eight genes is herein referred to as the Ess cluster. EsxA, esxB, essA, essB, and essC are all required for synthesis or secretion of EsxA and EsxB. Mutants that fail to produce EsxA, EsxB, and EssC display defects in the pathogenesis of S. aureus murine abscesses, suggesting that this specialized secretion system may be a general strategy of human bacterial pathogenesis. Secretion of non-WXG100 substrates by the ESX-1 pathway has been reported for several antigens including EspA, EspB, Rv3483c, and Rv3615c (Fortune et al., 2005; MacGurn et al., 2005; McLaughlin et al., 2007; Xu et al., 2007). The alternate ESX-5 pathway has also been shown to secrete both WXG100 and non-WXG100 proteins in pathogenic mycobacteria (Abdallah et al., 2007; Abdallah et al., 2006).

The Staphylococcus aureus Ess pathway can be viewed as a secretion module equipped with specialized transport components (Ess), accessory factors (Esa) and cognate secretion substrates (Esx). EssA, EssB and EssC are required for EsxA and EsxB secretion. Because EssA, EssB and EssC are predicted to be transmembrane proteins, it is contemplated that these proteins form a secretion apparatus. Some of the proteins in the ess gene cluster may actively transport secreted substrates (acting as motor) while others may regulate transport (regulator). Regulation may be achieved, but need not be limited to, transcriptional or post-translational mechanisms for secreted polypeptides, sorting of specific substrates to defined locations (e.g., extracellular medium or host cells), or timing of secretion events during infection. At this point, it is unclear whether all secreted Esx proteins function as toxins or contribute indirectly to pathogenesis.

Staphylococci rely on surface protein mediated-adhesion to host cells or invasion of tissues as a strategy for escape from immune defenses. Furthermore, S. aureus utilize surface proteins to sequester iron from the host during infection. The majority of surface proteins involved in staphylococcal pathogenesis carry C-terminal sorting signals, i.e., they are covalently linked to the cell wall envelope by sortase. Further, staphylococcal strains lacking the genes required for surface protein anchoring, i.e., sortase A and B, display a dramatic defect in the virulence in several different mouse models of disease. Thus, surface protein antigens represent a validated vaccine target as the corresponding genes are essential for the development of staphylococcal disease and can be exploited in various embodiments of the invention. The sortase enzyme superfamily are Gram-positive transpeptidases responsible for anchoring surface protein virulence factors to the peptidoglycan cell wall layer. Two sortase isoforms have been identified in Staphylococcus aureus, SrtA and SrtB. These enzymes have been shown to recognize a LPXTG motif in substrate proteins. The SrtB isoform appears to be important in heme iron acquisition and iron homeostasis, whereas the SrtA isoform plays a critical role in the pathogenesis of Gram-positive bacteria by modulating the ability of the bacterium to adhere to host tissue via the covalent anchoring of adhesins and other proteins to the cell wall peptidoglycan. In certain embodiments the SpA variants described herein can be used in combination with other staphylococcal proteins such as Coa, Eap, Ebh, Emp, EsaC, EsaB, EsxA, EsxB, Hla, SdrC, SdrD, SdrE, IsdA, IsdB, ClfA, ClfB, IsdC, SasF, vWbp, and/or vWh proteins.

Certain aspects of the invention include methods and compositions concerning proteinaceous compositions including polypeptides, peptides, or nucleic acid encoding SpA variant(s) and other staphylococcal antigens such as other proteins transported by the Ess pathway, or sortase substrates. These proteins may be modified by deletion, insertion, and/or substitution.

The Esx polypeptides include the amino acid sequence of Esx proteins from bacteria in the Staphylococcus genus. The Esx sequence may be from a particular staphylococcus species, such as Staphylococcus aureus, and may be from a particular strain, such as Newman. In certain embodiments, the EsxA sequence is SAV0282 from strain Mu50 (which is the same amino acid sequence for Newman) and can be accessed using Genbank Accession Number Q99WU4 (gi|68565539), which is hereby incorporated by reference. In other embodiments, the EsxB sequence is SAV0290 from strain Mu50 (which is the same amino acid sequence for Newman) and can be accessed using Genbank Accession Number Q99WT7 (gi|68565532), which is hereby incorporated by reference. In further embodiments, other polypeptides transported by the Ess pathway may be used, the sequences of which may be identified by one of skill in the art using databases and internet accessible resources.

The sortase substrate polypeptides include, but are not limited to the amino acid sequence of SdrC, SdrD, SdrE, IsdA, IsdB, ClfA, ClfB, IsdC or SasF proteins from bacteria in the Staphylococcus genus. The sortase substrate polypeptide sequence may be from a particular staphylococcus species, such as Staphylococcus aureus, and may be from a particular strain, such as Newman. In certain embodiments, the SdrD sequence is from strain N315 and can be accessed using Genbank Accession Number NP_373773.1 (gi|15926240), which is incorporated by reference. In other embodiments, the SdrE sequence is from strain N315 and can be accessed using Genbank Accession Number NP_373774.1 (gi|15926241), which is incorporated by reference. In other embodiments, the IsdA sequence is SAV1130 from strain Mu50 (which is the same amino acid sequence for Newman) and can be accessed using Genbank Accession Number NP_371654.1 (gi|15924120), which is incorporated by reference. In other embodiments, the IsdB sequence is SAV1129 from strain Mu50 (which is the same amino acid sequence for Newman) and can be accessed using Genbank Accession Number NP_371653.1 (gi|15924119), which is incorporated by reference. In further embodiments, other polypeptides transported by the Ess pathway or processed by sortase may be used, the sequences of which may be identified by one of skill in the art using databases and internet accessible resources.

Examples of various proteins that can be used in the context of the present invention can be identified by analysis of database submissions of bacterial genomes, including but not limited to accession numbers NC_002951 (GI:57650036 and GenBank CP000046), NC_002758 (GI:57634611 and GenBank BA000017), NC_002745 (GI:29165615 and GenBank BA000018), NC_003923 (GI:21281729 and GenBank BA000033), NC_002952 (GI:49482253 and GenBank BX571856), NC_002953 (GI:49484912 and GenBank BX571857), NC_007793 (GI:87125858 and GenBank CP000255), NC_007795 (GI:87201381 and GenBank CP000253) each of which are incorporated by reference.

As used herein, a "protein" or "polypeptide" refers to a molecule comprising at least ten amino acid residues. In some embodiments, a wild-type version of a protein or polypeptide are employed, however, in many embodiments of the invention, a modified protein or polypeptide is employed to generate an immune response. The terms described above may be used interchangeably. A "modified protein" or "modified polypeptide" or a "variant" refers to a protein or polypeptide whose chemical structure, particularly its amino acid sequence, is altered with respect to the wild-type protein or polypeptide. In some embodiments, a modified/variant protein or polypeptide has at least one modified activity or function (recognizing that proteins or polypeptides may have multiple activities or functions). It is specifically contemplated that a modified/variant protein or polypeptide may be altered with respect to one activity or function yet retain a wild-type activity or function in other respects, such as immunogenicity.

In certain embodiments the size of a protein or polypeptide (wild-type or modified) may comprise, but is not limited to, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1100, 1200, 1300, 1400, 1500, 1750, 2000, 2250, 2500 amino molecules or greater, and any range derivable therein, or derivative of a corresponding amino sequence described or referenced herein. It is contemplated that polypeptides may be mutated by truncation, rendering them shorter than their corresponding wild-type form, but also they might be altered by fusing or conjugating a heterologous protein sequence with a particular function (e.g., for targeting or localization, for enhanced immunogenicity, for purification purposes, etc.).

As used herein, an "amino molecule" refers to any amino acid, amino acid derivative, or amino acid mimic known in the art. In certain embodiments, the residues of the proteinaceous molecule are sequential, without any non-amino molecule interrupting the sequence of amino molecule residues. In other embodiments, the sequence may comprise one or more non-amino molecule moieties. In particular embodiments, the sequence of residues of the proteinaceous molecule may be interrupted by one or more non-amino molecule moieties.

Accordingly, the term "proteinaceous composition" encompasses amino molecule sequences comprising at least one of the 20 common amino acids in naturally synthesized proteins, or at least one modified or unusual amino acid.

Proteinaceous compositions may be made by any technique known to those of skill in the art, including (i) the expression of proteins, polypeptides, or peptides through standard molecular biological techniques, (ii) the isolation of proteinaceous compounds from natural sources, or (iii) the chemical synthesis of proteinaceous materials. The nucleotide as well as the protein, polypeptide, and peptide sequences for various genes have been previously disclosed, and may be found in the recognized computerized databases. One such database is the National Center for Biotechnology Information's Genbank and GenPept databases (on the World Wide Web at ncbi.nlm.nih.gov/). The coding regions for these genes may be amplified and/or expressed using the techniques disclosed herein or as would be known to those of ordinary skill in the art.

Amino acid sequence variants of SpA, coagulases and other polypeptides of the invention can be substitutional, insertional, or deletion variants. A variation in a polypeptide of the invention may affect 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more non-contiguous or contiguous amino acids of the polypeptide, as compared to wild-type. A variant can comprise an amino acid sequence that is at least 50%, 60%, 70%, 80%, or 90%, including all values and ranges there between, identical to any sequence provided or referenced herein, e.g., SEQ ID NO:2-8 or SEQ ID NO:11-30, A variant can include 2, 3, 4, 5, 6, 7, 8, 9, 10, 11, 12, 13, 14, 15, 16, 17, 18, 19, 20, or more substitute amino acids. A polypeptide processed or secreted by the Ess pathway or other surface proteins (see Table 1) or sortase substrates from any *staphylococcus* species and strain are contemplated for use in compositions and methods described herein.

Deletion variants typically lack one or more residues of the native or wild-type protein. Individual residues can be deleted or a number of contiguous amino acids can be deleted. A stop codon may be introduced (by substitution or insertion) into an encoding nucleic acid sequence to generate a truncated protein. Insertional mutants typically involve the addition of material at a non-terminal point in the polypeptide. This may include the insertion of one or more residues. Terminal additions, called fusion proteins, may also be generated. These fusion proteins include multimers or concatamers of one or more peptide or polypeptide described or referenced herein.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

TABLE 1

Exemplary surface proteins of *S. aureus* strains.

| SAV # | SA# | Surface | MW2 | Mu50 | N315 | Newman | MRSA252* | MSSA476* |
|---|---|---|---|---|---|---|---|---|
| SAV0111 | SA0107 | Spa | 492 | 450 | 450 | 520 | 516 | 492 |
| SAV2503 | SA2291 | FnBPA | 1015 | 1038 | 1038 | 741 | — | 1015 |
| SAV2502 | SA2290 | FnBPB | 943 | 961 | 961 | 677 | 965 | 957 |
| SAV0811 | SA0742 | ClfA | 946 | 935 | 989 | 933 | 1029 | 928 |
| SAV2630 | SA2423 | ClfB | 907 | 877 | 877 | 913 | 873 | 905 |

TABLE 1-continued

Exemplary surface proteins of S. aureus strains.

| SAV # | SA# | Surface | MW2 | Mu50 | N315 | Newman | MRSA252* | MSSA476* |
|---|---|---|---|---|---|---|---|---|
| Np | Np | Cna | 1183 | — | — | — | 1183 | 1183 |
| SAV0561 | SA0519 | SdrC | 955 | 953 | 953 | 947 | 906 | 957 |
| SAV0562 | SA0520 | SdrD | 1347 | 1385 | 1385 | 1315 | — | 1365 |
| SAV0563 | SA0521 | SdrE | 1141 | 1141 | 1141 | 1166 | 1137 | 1141 |
| Np | Np | Pls | — | — | — | — | — | — |
| SAV2654 | SA2447 | SasA | 2275 | 2271 | 2271 | 2271 | 1351 | 2275 |
| SAV2160 | SA1964 | SasB | 686 | 2481 | 2481 | 2481 | 2222 | 685 |
|  | SA1577 | SasC | 2186 | 213 | 2186 | 2186 | 2189 | 2186 |
| SAV0134 | SA0129 | SasD | 241 | 241 | 241 | 241 | 221 | 241 |
| SAV1130 | SA0977 | SasE/IsdA | 350 | 350 | 350 | 350 | 354 | 350 |
| SAV2646 | SA2439 | SasF | 635 | 635 | 635 | 635 | 627 | 635 |
| SAV2496 |  | SasG | 1371 | 525 | 927 | — | — | 1371 |
| SAV0023 | SA0022 | SasH | 772 | — | 772 | 772 | 786 | 786 |
| SAV1731 | SA1552 | SasI | 895 | 891 | 891 | 891 | 534 | 895 |
| SAV1129 | SA0976 | SasJ/IsdB | 645 | 645 | 645 | 645 | 652 | 645 |
|  | SA2381 | SasK | 198 | 211 | 211 | — | — | 197 |
|  | Np | SasL | — | 232 | — | — | — | — |
| SAV1131 | SA0978 | IsdC | 227 | 227 | 227 | 227 | 227 | 227 |

Proteins of the invention may be recombinant, or synthesized in vitro. Alternatively, a non-recombinant or recombinant protein may be isolated from bacteria. It is also contemplated that a bacteria containing such a variant may be implemented in compositions and methods of the invention. Consequently, a protein need not be isolated.

The term "functionally equivalent codon" is used herein to refer to codons that encode the same amino acid, such as the six codons for arginine or serine, and also refers to codons that encode biologically equivalent amino acids (see Table 2, below).

TABLE 2

Codon Table

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It also will be understood that amino acid and nucleic acid sequences may include additional residues, such as additional N- or C-terminal amino acids, or 5' or 3' sequences, respectively, and yet still be essentially as set forth in one of the sequences disclosed herein, so long as the sequence meets the criteria set forth above, including the maintenance of biological protein activity (e.g., immunogenicity) where protein expression is concerned. The addition of terminal sequences particularly applies to nucleic acid sequences that may, for example, include various non-coding sequences flanking either of the 5' or 3' portions of the coding region.

The following is a discussion based upon changing of the amino acids of a protein to create a variant polypeptide or peptide. For example, certain amino acids may be substituted for other amino acids in a protein structure with or without appreciable loss of interactive binding capacity with structures such as, for example, antigen-binding regions of antibodies or binding sites on substrate molecules. Since it is the interactive capacity and nature of a protein that defines that protein's functional activity, certain amino acid substitutions can be made in a protein sequence, and in its underlying DNA coding sequence, and nevertheless produce a protein with a desirable property. It is thus contemplated by the inventors that various changes may be made in the DNA sequences of genes.

It is contemplated that in compositions of the invention, there is between about 0.001 mg and about 10 mg of total polypeptide, peptide, and/or protein per ml. The concentration of protein in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mg/ml or more (or any range derivable therein). Of this, about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% may be an SpA variant or a coagulase, and may be used in combination with other peptides or polypeptides, such as other bacterial peptides and/or antigens.

The present invention contemplates the administration of variant SpA polypeptides or peptides to effect a preventative therapy or therapeutic effect against the development of a disease or condition associated with infection by a staphylococcus pathogen.

In certain aspects, combinations of staphylococcal antigens are used in the production of an immunogenic composition that is effective at treating or preventing staphylococcal infection. Staphylococcal infections progress through several different stages. For example, the staphylococcal life cycle involves commensal colonization, initiation of infection by accessing adjoining tissues or the bloodstream, and/or anaerobic multiplication in the blood. The interplay between *S. aureus* virulence determinants and the host defense mechanisms can induce complications such as endocarditis, metastatic abscess formation, and sepsis syndrome. Different molecules on the surface of the bacterium are involved in different steps of the infection cycle. Combinations of certain antigens can elicit an immune response which protects against multiple stages of staphylococcal infection. The effectiveness of the immune response can be measured either in animal model assays and/or using an opsonophagocytic assay.

D. Polypeptides and Polypeptide Production

The present invention describes polypeptides, peptides, and proteins and immunogenic fragments thereof for use in various embodiments of the present invention. For example, specific polypeptides are assayed for or used to elicit an immune response. In specific embodiments, all or part of the proteins of the invention can also be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference.

Alternatively, recombinant DNA technology may be employed wherein a nucleotide sequence which encodes a peptide of the invention is inserted into an expression vector, transformed or transfected into an appropriate host cell and cultivated under conditions suitable for expression.

One embodiment of the invention includes the use of gene transfer to cells, including microorganisms, for the production and/or presentation of polypeptides or peptides. The gene for the polypeptide or peptide of interest may be transferred into appropriate host cells followed by culture of cells under the appropriate conditions. The generation of recombinant expression vectors, and the elements included therein, are well known in the art and briefly discussed herein. Alternatively, the protein to be produced may be an endogenous protein normally synthesized by the cell that is isolated and purified.

Another embodiment of the present invention uses autologous B lymphocyte cell lines, which are transfected with a viral vector that expresses an immunogen product, and more specifically, a protein having immunogenic activity. Other examples of mammalian host cell lines include, but are not limited to Vero and HeLa cells, other B- and T-cell lines, such as CEM, 721.221, H9, Jurkat, Raji, as well as cell lines of Chinese hamster ovary, W138, BHK, COS-7, 293, HcpG2, 3T3, RIN and MDCK cells. In addition, a host cell strain may be chosen that modulates the expression of the inserted sequences, or that modifies and processes the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the foreign protein expressed.

A number of selection systems may be used including, but not limited to HSV thymidine kinase, hypoxanthine-guanine phosphoribosyltransferase, and adenine phosphoribosyltransferase genes, in tk-, hgprt- or aprt-cells, respectively. Also, anti-metabolite resistance can be used as the basis of selection: for dhfr, which confers resistance to trimethoprim and methotrexate; gpt, which confers resistance to mycophenolic acid; neo, which confers resistance to the aminoglycoside G418; and hygro, which confers resistance to hygromycin.

Animal cells can be propagated in vitro in two modes: as non-anchorage-dependent cells growing in suspension throughout the bulk of the culture or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. However, suspension cultured cells have limitations, such as tumorigenic potential and lower protein production than adherent cells.

Where a protein is specifically mentioned herein, it is preferably a reference to a native or recombinant protein or optionally a protein in which any signal sequence has been removed. The protein may be isolated directly from the staphylococcal strain or produced by recombinant DNA techniques. Immunogenic fragments of the protein may be incorporated into the immunogenic composition of the invention. These are fragments comprising at least 10 amino acids, 20 amino acids, 30 amino acids, 40 amino acids, 50 amino acids, or 100 amino acids, including all values and ranges there between, taken contiguously from the amino acid sequence of the protein. In addition, such immunogenic fragments are immunologically reactive with antibodies generated against the Staphylococcal proteins or with antibodies generated by infection of a mammalian host with Staphylococci. Immunogenic fragments also include fragments that when administered at an effective dose, (either alone or as a hapten bound to a carrier), elicit a protective or therapeutic immune response against Staphylococcal infection, in certain aspects it is protective against *S. aureus* and/or *S. epidermidis* infection. Such an immunogenic fragment may include, for example, the protein lacking an N-terminal leader sequence, and/or a transmembrane domain and/or a C-terminal anchor domain. In a preferred aspect the immunogenic fragment according to the invention comprises substantially all of the extracellular domain of a protein which has at least 80% identity, at least 85% identity, at least 90% identity, at least 95% identity, or at least 97-99% identity, including all values and ranges there between, to a sequence selected segment of a polypeptide described or referenced herein.

Also included in immunogenic compositions of the invention are fusion proteins composed of one or more Staphylococcal proteins, or immunogenic fragments of staphylococcal proteins. Such fusion proteins may be made recombinantly and may comprise one portion of at least 1, 2, 3, 4, 5, or 6 staphylococcal proteins or segments. Alternatively, a fusion protein may comprise multiple portions of at least 1, 2, 3, 4 or 5 staphylococcal proteins. These may combine different Staphylococcal proteins and/or multiples of the same protein or proten fragment, or immunogenic fragments in the same protein (forming a multimer or a concatamer). Alternatively, the invention also includes individual fusion proteins of Staphylococcal proteins or immunogenic fragments thereof, as a fusion protein with heterologous sequences such as a provider of T-cell epitopes or purification tags, for example: β-galactosidase, glutathione-S-transferase, green fluorescent proteins (GFP), epitope tags such as FLAG, myc tag, poly histidine, or viral surface proteins such as influenza virus haemagglutinin, or bacterial proteins such as tetanus toxoid, diphtheria toxoid, or CRM197.

II. NUCLEIC ACIDS

In certain embodiments, the present invention concerns recombinant polynucleotides encoding the proteins, polypeptides, peptides of the invention. The nucleic acid sequences for SpA, coagulases and other bacterial proteins are included, all of which are incorporated by reference, and can be used to prepare peptides or polypeptides.

As used in this application, the term "polynucleotide" refers to a nucleic acid molecule that either is recombinant or has been isolated free of total genomic nucleic acid. Included within the term "polynucleotide" are oligonucleotides (nucleic acids of 100 residues or less in length), recombinant vectors, including, for example, plasmids, cosmids, phage, viruses, and the like. Polynucleotides include, in certain aspects, regulatory sequences, isolated substantially away from their naturally occurring genes or protein encoding sequences. Polynucleotides may be single-stranded (coding or antisense) or double-stranded, and may be RNA, DNA (genomic, cDNA or synthetic), analogs thereof, or a combination thereof. Additional coding or non-coding sequences may, but need not, be present within a polynucleotide.

In this respect, the term "gene," "polynucleotide," or "nucleic acid" is used to refer to a nucleic acid that encodes a protein, polypeptide, or peptide (including any sequences required for proper transcription, post-translational modification, or localization). As will be understood by those in the art, this term encompasses genomic sequences, expression cassettes, cDNA sequences, and smaller engineered nucleic acid segments that express, or may be adapted to express, proteins, polypeptides, domains, peptides, fusion proteins, and mutants. A nucleic acid encoding all or part of a polypeptide may contain a contiguous nucleic acid sequence of: 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1095, 1100, 1500, 2000, 2500, 3000, 3500, 4000, 4500, 5000, 5500, 6000, 6500, 7000, 7500, 8000, 9000, 10000, or more nucleotides, nucleosides, or base pairs, including all values and ranges therebetween, of a polynucleotide encoding one or more amino acid sequence described or referenced herein. It also is contemplated that a particular polypeptide may be encoded by nucleic acids containing variations having slightly different nucleic acid sequences but, nonetheless, encode the same or substantially similar protein (see Table 2 above).

In particular embodiments, the invention concerns isolated nucleic acid segments and recombinant vectors incorporating nucleic acid sequences that encode a variant SpA or coagulase. The term "recombinant" may be used in conjunction with a polynucleotide or polypeptide and generally refers to a polypeptide or polynucleotide produced and/or manipulated in vitro or that is a replication product of such a molecule.

In other embodiments, the invention concerns isolated nucleic acid segments and recombinant vectors incorporating nucleic acid sequences that encode a variant SpA or coagulase polypeptide or peptide to generate an immune response in a subject. In various embodiments the nucleic acids of the invention may be used in genetic vaccines.

The nucleic acid segments used in the present invention can be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant nucleic acid protocol. In some cases, a nucleic acid sequence may encode a polypeptide sequence with additional heterologous coding sequences, for example to allow for purification of the polypeptide, transport, secretion, post-translational modification, or for therapeutic benefits such as targeting or efficacy. As discussed above, a tag or other heterologous polypeptide may be added to the modified polypeptide-encoding sequence, wherein "heterologous" refers to a polypeptide that is not the same as the modified polypeptide.

In certain other embodiments, the invention concerns isolated nucleic acid segments and recombinant vectors that include within their sequence a contiguous nucleic acid sequence from SEQ ID NO:1 (SpA domain D) or SEQ ID NO:3 (SpA) or any other nucleic acid sequences encoding coagulases or other secreted virulence factors and/or surface proteins including proteins transported by the Ess pathway, processed by sortase, or proteins incorporated herein by reference.

In certain embodiments, the present invention provides polynucleotide variants having substantial identity to the sequences disclosed herein; those comprising at least 70%, 75%, 80%, 85%, 90%, 95%, 96%, 97%, 98%, or 99% or higher sequence identity, including all values and ranges there between, compared to a polynucleotide sequence of this invention using the methods described herein (e.g., BLAST analysis using standard parameters).

The invention also contemplates the use of polynucleotides which are complementary to all the above described polynucleotides.

A. Vectors

Polypeptides of the invention may be encoded by a nucleic acid molecule comprised in a vector. The term "vector" is used to refer to a carrier nucleic acid molecule into which a heterologous nucleic acid sequence can be inserted for introduction into a cell where it can be replicated and expressed. A nucleic acid sequence can be "heterologous," which means that it is in a context foreign to the cell in which the vector is being introduced or to the nucleic acid in which is incorporated, which includes a sequence homologous to a sequence in the cell or nucleic acid but in a position within the host cell or nucleic acid where it is ordinarily not found. Vectors include DNAs, RNAs, plasmids, cosmids, viruses (bacteriophage, animal viruses, and plant viruses), and artificial chromosomes (e.g., YACs). One of skill in the art would be well equipped to construct a vector through standard recombinant techniques (for example Sambrook et al., 2001; Ausubel et al., 1996, both incorporated herein by reference). In addition to encoding a variant SpA polypeptide the vector can encode other polypeptide sequences such as a one or more other bacterial peptide, a tag, or an immunogenicity enhancing peptide. Useful vectors encoding such fusion proteins include pIN vectors (Inouye et al., 1985), vectors encoding a stretch of histidines, and pGEX vectors, for use in generating glutathione S-transferase (GST) soluble fusion proteins for later purification and separation or cleavage.

The term "expression vector" refers to a vector containing a nucleic acid sequence coding for at least part of a gene product capable of being transcribed. In some cases, RNA molecules are then translated into a protein, polypeptide, or peptide. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described herein.

1. Promoters and Enhancers

A "promoter" is a control sequence. The promoter is typically a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and expression of that sequence. A promoter may or may not be used in conjunction with an "enhancer," which refers to a cis-acting regulatory sequence involved in the transcriptional activation of a nucleic acid sequence.

Naturally, it may be important to employ a promoter and/or enhancer that effectively directs the expression of the DNA segment in the cell type or organism chosen for expression. Those of skill in the art of molecular biology generally know the use of promoters, enhancers, and cell type combinations for protein expression (see Sambrook et al., 2001, incorporated herein by reference). The promoters employed may be constitutive, tissue-specific, or inducible and in certain embodiments may direct high level expression of the introduced DNA segment under specified conditions, such as large-scale production of recombinant proteins or peptides.

Various elements/promoters may be employed in the context of the present invention to regulate the expression of a gene. Examples of such inducible elements, which are regions of a nucleic acid sequence that can be activated in response to a specific stimulus, include but are not limited to Immunoglobulin Heavy Chain (Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990), Immunoglobulin Light Chain (Queen et al., 1983; Picard et al., 1984), T Cell Receptor (Luria et al., 1987; Winoto et al., 1989; Redondo et al.; 1990), HLA DQ α and/or DQ β (Sullivan et al., 1987), β Interferon (Goodbourn et al., 1986; Fujita et al., 1987; Goodbourn et al., 1988), Interleukin-2 (Greene et al., 1989), Interleukin-2 Receptor (Greene et al., 1989; Lin et al., 1990), MHC Class II 5 (Koch et al., 1989), MHC Class II HLA-DRα (Sherman et al., 1989), β-Actin (Kawamoto et al., 1988; Ng et al.; 1989), Muscle Creatine Kinase (MCK) (Jaynes et al., 1988; Horlick et al., 1989; Johnson et al., 1989), Prealbumin (Transthyretin) (Costa et al., 1988), Elastase I (Ornitz et al., 1987), Metallothionein (MTII) (Karin et al., 1987; Culotta et al., 1989), Collagenase (Pinkert et al., 1987; Angel et al., 1987), Albumin (Pinkert et al., 1987; Tronche et al., 1989, 1990), α-Fetoprotein (Godbout et al., 1988; Campere et al., 1989), γ-Globin (Bodine et al., 1987; Perez-Stable et al., 1990), β-Globin (Trudel et al., 1987), c-fos (Cohen et al., 1987), c-Ha-Ras (Triesman, 1986; Deschamps et al., 1985), Insulin (Edlund et al., 1985), Neural Cell Adhesion Molecule (NCAM) (Hirsh et al., 1990), α1-Antitrypain (Latimer et al., 1990), H2B (TH2B) Histone (Hwang et al., 1990), Mouse and/or Type I Collagen (Ripe et al., 1989), Glucose-Regulated Proteins (GRP94 and GRP78) (Chang et al., 1989), Rat Growth Hormone (Larsen et al., 1986), Human Serum Amyloid A (SAA) (Edbrooke et al., 1989), Troponin I (TN I) (Yutzey et al., 1989), Platelet-Derived Growth Factor (PDGF) (Pech et al., 1989), Duchenne Muscular Dystrophy (Klamut et al., 1990), SV40 (Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988), Polyoma (Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell et al., 1988), Retroviruses (Kriegler et al., 1982, 1983; Levinson et al., 1982; Kriegler et al., 1983, 1984a, b, 1988; Bosze et al., 1986; Miksieck et al., 1986; Celander et al., 1987; Thiesen et al., 1988; Celander et al., 1988; Choi et al., 1988; Reisman et al., 1989), Papilloma Virus (Campo et al., 1983; Lusky et al., 1983; Spandidos and Wilkie, 1983; Spalholz et al., 1985; Lusky et al., 1986; Cripe et al., 1987; Gloss et al., 1987; Hirochika et al., 1987; Stephens et al., 1987), Hepatitis B Virus (Bulla et al., 1986; Jameel et al., 1986; Shaul et al., 1987; Spandau et al., 1988; Vannice et al., 1988), Human Immunodeficiency Virus (Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989), Cytomegalovirus (CMV) IE (Weber et al., 1984; Boshart et al., 1985; Foecking et al., 1986), Gibbon Ape Leukemia Virus (Holbrook et al., 1987; Quinn et al., 1989).

Inducible elements include, but are not limited to MT II-Phorbol Ester (TFA)/Heavy metals (Palmiter et al., 1982; Haslinger et al., 1985; Searle et al., 1985; Stuart et al., 1985; Imagawa et al., 1987, Karin et al., 1987; Angel et al., 1987b; McNeall et al., 1989); MMTV (mouse mammary tumor virus)—Glucocorticoids (Huang et al., 1981; Lee et al., 1981; Majors et al., 1983; Chandler et al., 1983; Lee et al., 1984; Ponta et al., 1985; Sakai et al., 1988); β-Interferon-poly(rI)x/poly(rc) (Tavernier et al., 1983); Adenovirus 5 E2-E1A (Imperiale et al., 1984); Collagenase-Phorbol Ester (TPA) (Angel et al., 1987a); Stromelysin-Phorbol Ester (TPA) (Angel et al., 1987b); SV40-Phorbol Ester (TPA) (Angel et al., 1987b); Murine MX Gene-Interferon, Newcastle Disease Virus (Hug et al., 1988); GRP78 Gene-A23187 (Resendez et al., 1988); α-2-Macroglobulin-IL-6 (Kunz et al., 1989); Vimentin-Serum (Rittling et al., 1989); MHC Class I Gene H-2-κb-Interferon (Blanar et al., 1989); HSP70-E1A/SV40 Large T Antigen (Taylor et al., 1989, 1990a, 1990b); Proliferin-Phorbol Ester/TPA (Mordacq et al., 1989); Tumor Necrosis Factor-PMA (Hensel et al., 1989); and Thyroid Stimulating Hormone α Gene-Thyroid Hormone (Chatterjee et al., 1989).

The particular promoter that is employed to control the expression of peptide or protein encoding polynucleotide of the invention is not believed to be critical, so long as it is capable of expressing the polynucleotide in a targeted cell, preferably a bacterial cell. Where a human cell is targeted, it is preferable to position the polynucleotide coding region adjacent to and under the control of a promoter that is capable of being expressed in a human cell. Generally speaking, such a promoter might include either a bacterial, human or viral promoter.

In embodiments in which a vector is administered to a subject for expression of the protein, it is contemplated that a desirable promoter for use with the vector is one that is not down-regulated by cytokines or one that is strong enough that even if down-regulated, it produces an effective amount of a variant SpA for eliciting an immune response. Non-limiting examples of these are CMV IE and RSV LTR. Tissue specific promoters can be used, particularly if expression is in cells in which expression of an antigen is desirable, such as dendritic cells or macrophages. The mammalian MHC I and MHC II promoters are examples of such tissue-specific promoters.

2. Initiation Signals and Internal Ribosome Binding Sites (IRES)

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988; Macejak and Sarnow, 1991). IRES elements can be linked to heterologous open reading frames. Multiple open reading frames can be transcribed together, each separated by an IRES, creating polycistronic messages. Multiple genes can be efficiently expressed using a single promoter/enhancer to transcribe a single message (see U.S. Pat. Nos. 5,925,565 and 5,935,819, herein incorporated by reference).

3. Selectable and Screenable Markers

In certain embodiments of the invention, cells containing a nucleic acid construct of the present invention may be identified in vitro or in vivo by encoding a screenable or selectable marker in the expression vector. When transcribed and translated, a marker confers an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

B. Host Cells

As used herein, the terms “cell,” “cell line,” and “cell culture” may be used interchangeably. All of these terms also include their progeny, which is any and all subsequent generations. It is understood that all progeny may not be identical due to deliberate or inadvertent mutations. In the context of expressing a heterologous nucleic acid sequence, “host cell” refers to a prokaryotic or eukaryotic cell, and it includes any transformable organism that is capable of replicating a vector or expressing a heterologous gene encoded by a vector. A host cell can, and has been, used as a recipient for vectors or viruses. A host cell may be “transfected” or “transformed,” which refers to a process by which exogenous nucleic acid, such as a recombinant protein-encoding sequence, is transferred or introduced into the host cell. A transformed cell includes the primary subject cell and its progeny.

Host cells may be derived from prokaryotes or eukaryotes, including bacteria, yeast cells, insect cells, and mammalian cells for replication of the vector or expression of part or all of the nucleic acid sequence(s). Numerous cell lines and cultures are available for use as a host cell, and they can be obtained through the American Type Culture Collection (ATCC), which is an organization that serves as an archive for living cultures and genetic materials (www.atcc.org).

C. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

In addition to the disclosed expression systems of the invention, other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

III. POLYSACCHARIDES

The immunogenic compositions of the invention may further comprise capsular polysaccharides including one or more of PIA (also known as PNAG) and/or *S. aureus* Type V and/or type VIII capsular polysaccharide and/or *S. epidermidis* Type I, and/or Type II and/or Type III capsular polysaccharide.

A. PIA (PNAG)

It is now clear that the various forms of staphylococcal surface polysaccharides identified as PS/A, PIA and SAA are the same chemical entity—PNAG (Maira-Litran et al., 2004). Therefore the term PIA or PNAG encompasses all these polysaccharides or oligosaccharides derived from them.

PIA is a polysaccharide intercellular adhesin and is composed of a polymer of β-(1→6)-linked glucosamine substituted with N-acetyl and O-succinyl constituents. This polysaccharide is present in both *S. aureus* and *S. epidermidis* and can be isolated from either source (Joyce et al., 2003; Maira-Litran et al., 2002). For example, PNAG may be isolated from *S. aureus* strain MN8m (WO04/43407). PIA isolated from *S. epidermidis* is a integral constituent of biofilm. It is responsible for mediating cell-cell adhesion and probably also functions to shield the growing colony from the host's immune response. The polysaccharide previously known as poly-N-succinyl-β-(1→6)-glucosamine (PNSG) was recently shown not to have the expected structure since the identification of N-succinylation was incorrect (Maira-Litran et al., 2002). Therefore the polysaccharide formally known as PNSG and now found to be PNAG is also encompassed by the term PIA.

PIA (or PNAG) may be of different sizes varying from over 400 kDa to between 75 and 400 kDa to between 10 and 75 kDa to oligosaccharides composed of up to 30 repeat units (of β-(1→6)-linked glucosamine substituted with N-acetyl and O-succinyl constituents). Any size of PIA polysaccharide or oligosaccharide may be use in an immunogenic composition of the invention, in one aspect the polysaccharide is over 40 kDa. Sizing may be achieved by any method known in the art, for instance by microfluidization, ultrasonic irradiation or by chemical cleavage (WO 03/53462, EP497524, EP497525). In certain aspects PIA (PNAG) is at least or at most 40-400 kDa, 40-300 kDa, 50-350 kDa, 60-300 kDa, 50-250 kDa and 60-200 kDa.

PIA (PNAG) can have different degree of acetylation due to substitution on the amino groups by acetate. PIA produced in vitro is almost fully substituted on amino groups (95-100%). Alternatively, a deacetylated PIA (PNAG) can be used having less than 60%, 50%, 40%, 30%, 20%, 10% acetylation. Use of a deacetylated PTA (PNAG) is preferred since non-acetylated epitopes of PNAG are efficient at mediating opsonic killing of Gram positive bacteria, preferably *S. aureus* and/or *S. epidermidis*. In certain aspects, the PIA (PNAG) has a size between 40 kDa and 300 kDa and is deacetylated so that less than 60%, 50%, 40%, 30% or 20% of amino groups are acetylated.

The term deacetylated PNAG (dPNAG) refers to a PNAG polysaccharide or oligosaccharide in which less than 60%, 50%, 40%, 30%, 20% or 10% of the amino a groups are acetylated. In certain aspects, PNAG is deaceylated to form dPNAG by chemically treating the native polysaccharide. For example, the native PNAG is treated with a basic solution such that the pH rises to above 10. For instance the PNAG is treated with 0.1-5 M, 0.2-4 M, 0.3-3 M, 0.5-2 M, 0.75-1.5 M or 1 M NaOH, KOH or NH₄OH. Treatment is for at least 10 to 30 minutes, or 1, 2, 3, 4, 5, 10, 15 or 20 hours at a temperature of 20-100, 25-80, 30-60 or 30-50 or 35-45° C. dPNAG may be prepared as described in WO 04/43405.

The polysaccharide(s) can be conjugated or unconjugated to a carrier protein.

B. Type 5 and Type 8 Polysaccharides from *S. aureus*

Most strains of *S. aureus* that cause infection in man contain either Type 5 or Type 8 polysaccharides. Approximately 60% of human strains are Type 8 and approximately 30% are Type 5. The structures of Type 5 and Type 8 capsular polysaccharide antigens are described in Moreau et al., (1990) and Fournier et al., (1984). Both have FucNAcp in their repeat unit as well as ManNAcA which can be used to introduce a sulfhydryl group. The structures are:

Type 5
→4)-β-D-ManNAcA(3OAc)-(1→4)-α-L-FucNAc (1→3)-β-D-FucNAc-(1→

Type 8
→3)-β-D-ManNAcA(4OAc)-(1→3)-α-L-FucNAc (1→3)-β-D-FucNAc-(1→Recently (Jones, 2005) NMR spectroscopy revised the structures to:

Type 5
→4)-β-D-ManNAcA-(1→4)-α-L-FucNAc(3 OAc)-(1→3)-β-D-FucNAc-(1→

Type 8
→3)-β-D-ManNAcA(4OAc)-(1→3)-α-L-FucNAc (1→3)-α-D-FucNAc(1→

Polysaccharides may be extracted from the appropriate strain of *S. aureus* using method well known to of skill in the art, See U.S. Pat. No. 6,294,177. For example, ATCC 12902 is a Type 5 *S. aureus* strain and ATCC 12605 is a Type 8 *S. aureus* strain.

Polysaccharides are of native size or alternatively may be sized, for instance by microfluidisation, ultrasonic irradiation, or by chemical treatment. The invention also covers oligosaccharides derived from the type 5 and 8 polysaccharides from *S. aureus*. The type 5 and 8 polysaccharides included in the immunogenic composition of the invention are preferably conjugated to a carrier protein as described below or are alternatively unconjugated. The immunogenic compositions of the invention alternatively contains either type 5 or type 8 polysaccharide.

C. *S. aureus* 336 Antigen

In an embodiment, the immunogenic composition of the invention comprises the *S. aureus* 336 antigen described in U.S. Pat. No. 6,294,177. The 336 antigen comprises β-linked hexosamine, contains no O-acetyl groups, and specifically binds to antibodies to *S. aureus* Type 336 deposited under ATCC 55804. In an embodiment, the 336 antigen is a polysaccharide which is of native size or alternatively may be sized, for instance by microfluidisation, ultrasonic irradiation, or by chemical treatment. The invention also covers oligosaccharides derived from the 336 antigen. The 336 antigen can be unconjugated or conjugated to a carrier protein.

D. Type I, II and III Polysaccharides from *S. epidermidis*

Amongst the problems associated with the use of polysaccharides in vaccination, is the fact that polysaccharides per se are poor immunogens. It is preferred that the polysaccharides utilized in the invention are linked to a protein carrier which provide bystander T-cell help to improve immunogenicity. Examples of such carriers which may be conjugated to polysaccharide immunogens include the Diphtheria and Tetanus toxoids (DT, DT CRM197 and TT respectively), Keyhole Limpet Haemocyanin (KLH), and the purified protein derivative of Tuberculin (PPD), *Pseudomonas aeruginosa* exoprotein A (rEPA), protein D from *Haemophilus influenzae*, pneumolysin or fragments of any of the above. Fragments suitable for use include fragments encompassing T-helper epitopes. In particular the protein D fragment from *H. influenza* will preferably contain the N-terminal ⅓ of the protein. Protein D is an IgD-binding protein from *Haemophilus influenzae* (EP 0 594 610 B1) and is a potential immunogen. In addition, staphylococcal proteins may be used as a carrier protein in the polysaccharide conjugates of the invention.

A carrier protein that would be particularly advantageous to use in the context of a staphylococcal vaccine is staphylococcal alpha toxoid. The native form may be conjugated to a polysaccharide since the process of conjugation reduces toxicity. Preferably genetically detoxified alpha toxins such as the His35Leu or His35Arg variants are used as carriers since residual toxicity is lower. Alternatively the alpha toxin is chemically detoxified by treatment with a cross-linking reagent, formaldehyde or glutaraldehyde. A genetically detoxified alpha toxin is optionally chemically detoxified, preferably by treatment with a cross-linking reagent, formaldehyde or glutaraldehyde to further reduce toxicity.

The polysaccharides may be linked to the carrier protein(s) by any known method (for example those methods described in U.S. Pat. Nos. 4,372,945, 4,474,757, and 4,356,170). Preferably, CDAP conjugation chemistry is carried out (see WO95/08348). In CDAP, the cyanylating reagent 1-cyano-dimethylaminopyridinium tetrafluoroborate (CDAP) is preferably used for the synthesis of polysaccharide-protein conjugates. The cyanylation reaction can be performed under relatively mild conditions, which avoids hydrolysis of the alkaline sensitive polysaccharides. This synthesis allows direct coupling to a carrier protein.

Conjugation preferably involves producing a direct linkage between the carrier protein and polysaccharide. Optionally a spacer (such as adipic dihydride (ADH)) may be introduced between the carrier protein and the polysaccharide.

IV. IMMUNE RESPONSE AND ASSAYS

As discussed above, the invention concerns evoking or inducing an immune response in a subject against a variant SpA or coagulase peptide. In one embodiment, the immune response can protect against or treat a subject having, suspected of having, or at risk of developing an infection or related disease, particularly those related to staphylococci. One use of the immunogenic compositions of the invention is to prevent nosocomial infections by inoculating a subject prior to undergoing procedures in a hospital or other environment having an increased risk of infection.

A. Immunoassays

The present invention includes the implementation of serological assays to evaluate whether and to what extent an immune response is induced or evoked by compositions of the invention. There are many types of immunoassays that can be implemented. Immunoassays encompassed by the present invention include, but are not limited to, those described in U.S. Pat. No. 4,367,110 (double monoclonal antibody sandwich assay) and U.S. Pat. No. 4,452,901 (western blot). Other assays include immunoprecipitation of labeled ligands and immunocytochemistry, both in vitro and in vivo.

Immunoassays generally are binding assays. Certain preferred immunoassays are the various types of enzyme linked immunosorbent assays (ELISAs) and radioimmunoassays (RIA) known in the art. Immunohistochemical detection using tissue sections is also particularly useful. In one example, antibodies or antigens are immobilized on a selected surface, such as a well in a polystyrene microtiter plate, dipstick, or column support. Then, a test composition suspected of containing the desired antigen or antibody, such as a clinical sample, is added to the wells. After binding and washing to remove non specifically bound immune complexes, the bound antigen or antibody may be detected. Detection is generally achieved by the addition of another antibody, specific for the desired antigen or antibody, that is linked to a detectable label. This type of ELISA is known as a "sandwich ELISA." Detection also may be achieved by the addition of a second antibody specific for the desired antigen, followed by the addition of a third antibody that has binding affinity for the second antibody, with the third antibody being linked to a detectable label.

Competition ELISAs are also possible implementations in which test samples compete for binding with known amounts of labeled antigens or antibodies. The amount of reactive species in the unknown sample is determined by mixing the sample with the known labeled species before or during incubation with coated wells. The presence of reactive species in the sample acts to reduce the amount of labeled species available for binding to the well and thus reduces the ultimate signal. Irrespective of the format employed, ELISAs have certain features in common, such as coating, incubating or binding, washing to remove non specifically bound species, and detecting the bound immune complexes.

Antigen or antibodies may also be linked to a solid support, such as in the form of plate, beads, dipstick, membrane, or column matrix, and the sample to be analyzed is applied to the immobilized antigen or antibody. In coating a plate with either antigen or antibody, one will generally incubate the wells of the plate with a solution of the antigen or antibody, either overnight or for a specified period. The wells of the plate will then be washed to remove incompletely-adsorbed material. Any remaining available surfaces of the wells are then "coated" with a nonspecific protein that is antigenically neutral with regard to the test antisera. These include bovine serum albumin (BSA), casein, and solutions of milk powder. The coating allows for blocking of nonspecific adsorption sites on the immobilizing surface and thus reduces the background caused by nonspecific binding of antisera onto the surface.

B. Diagnosis of Bacterial Infection

In addition to the use of proteins, polypeptides, and/or peptides, as well as antibodies binding these polypeptides, proteins, and/or peptides, to treat or prevent infection as described above, the present invention contemplates the use of these polypeptides, proteins, peptides, and/or antibodies in a variety of ways, including the detection of the presence of Staphylococci to diagnose an infection, whether in a patient or on medical equipment which may also become infected. In accordance with the invention, a preferred method of detecting the presence of infections involves the steps of obtaining a sample suspected of being infected by one or more staphylococcal bacteria species or strains, such as a sample taken from an individual, for example, from one's blood, saliva, tissues, bone, muscle, cartilage, or skin. Following isolation of the sample, diagnostic assays utilizing the polypeptides, proteins, peptides, and/or antibodies of the present invention may be carried out to detect the presence of staphylococci, and such assay techniques for determining such presence in a sample are well known to those skilled in the art and include methods such as radioimmunoassay, western blot analysis and ELISA assays. In general, in accordance with the invention, a method of diagnosing an infection is contemplated wherein a sample suspected of being infected with staphylococci has added to it the polypeptide, protein, peptide, antibody, or monoclonal antibody in accordance with the present invention, and staphylococci are indicated by antibody binding to the polypeptides, proteins, and/or peptides, or polypeptides, proteins, and/or peptides binding to the antibodies in the sample.

Accordingly, antibodies in accordance with the invention may be used for the prevention of infection from staphylococcal bacteria (i.e., passive immunization), for the treatment of an ongoing infection, or for use as research tools. The term "antibodies" as used herein includes monoclonal, polyclonal, chimeric, single chain, bispecific, simianized, and humanized or primatized antibodies as well as Fab fragments, such as those fragments which maintain the binding specificity of the antibodies, including the products of an Fab immunoglobulin expression library. Accordingly, the invention contemplates the use of single chains such as the variable heavy and light chains of the antibodies. Generation of any of these types of antibodies or antibody fragments is well known to those skilled in the art. Specific examples of the generation of an antibody to a bacterial protein can be found in U.S. Patent Application Pub. No. 20030153022, which is incorporated herein by reference in its entirety.

Any of the above described polypeptides, proteins, peptides, and/or antibodies may be labeled directly with a detectable label for identification and quantification of staphylococcal bacteria. Labels for use in immunoassays are generally known to those skilled in the art and include enzymes, radioisotopes, and fluorescent, luminescent and chromogenic substances, including colored particles such as colloidal gold or latex beads. Suitable immunoassays include enzyme-linked immunosorbent assays (ELISA).

C. Protective Immunity

In some embodiments of the invention, proteinaceous compositions confer protective immunity to a subject. Protective immunity refers to a body's ability to mount a specific immune response that protects the subject from developing a particular disease or condition that involves the agent against which there is an immune response. An immunogenically effective amount is capable of conferring protective immunity to the subject.

As used herein in the specification and in the claims section that follows, the term polypeptide or peptide refer to a stretch of amino acids covalently linked there amongst via peptide bonds. Different polypeptides have different functionalities according to the present invention. While according to one aspect, a polypeptide is derived from an immunogen designed to induce an active immune response in a recipient, according to another aspect of the invention, a polypeptide is derived from an antibody which results following the elicitation of an active immune response in, for example, an animal, and which can serve to induce a passive immune response in the recipient. In both cases, however, the polypeptide is encoded by a polynucleotide according to any possible codon usage.

As used herein the phrase "immune response" or its equivalent "immunological response" refers to the development of a humoral (antibody mediated), cellular (mediated by antigen-specific T cells or their secretion products) or both humoral and cellular response directed against a protein, peptide, carbohydrate, or polypeptide of the invention in a recipient patient. Such a response can be an active response induced by administration of immunogen or a passive response induced by administration of antibody, antibody containing material, or primed T-cells. A cellular immune response is elicited by the presentation of polypeptide epitopes in association with Class I or Class II MHC molecules, to activate antigen-specific CD4 (+) T helper cells and/or CD8 (+) cytotoxic T cells. The response may also involve activation of monocytes, macrophages, NK cells, basophils, dendritic cells, astrocytes, microglia cells, eosinophils or other components of innate immunity. As used herein "active immunity" refers to any immunity conferred upon a subject by administration of an antigen.

As used herein "passive immunity" refers to any immunity conferred upon a subject without administration of an antigen to the subject. "Passive immunity" therefore includes, but is not limited to, administration of activated immune effectors including cellular mediators or protein mediators (e.g., monoclonal and/or polyclonal antibodies) of an immune response. A monoclonal or polyclonal antibody composition may be used in passive immunization for the prevention or treatment of infection by organisms that carry the antigen recognized by the antibody. An antibody composition may include antibodies that bind to a variety of antigens that may in turn be associated with various organisms. The antibody component can be a polyclonal antiserum. In certain aspects the antibody or antibodies are affinity purified from an animal or second subject that has been challenged with an antigen(s). Alternatively, an antibody mixture may be used, which is a mixture of monoclonal and/or polyclonal antibodies to antigens present in the same, related, or different microbes or organisms, such as gram-positive bacteria, gram-negative bacteria, including but not limited to *staphylococcus* bacteria.

Passive immunity may be imparted to a patient or subject by administering to the patient immunoglobulins (Ig) and/or other immune factors obtained from a donor or other non-patient source having a known immunoreactivity. In other aspects, an antigenic composition of the present invention can be administered to a subject who then acts as a source or donor for globulin, produced in response to challenge with the antigenic composition ("hyperimmune globulin"), that contains antibodies directed against *Staphylococcus* or other organism. A subject thus treated would donate plasma from which hyperimmune globulin would then be obtained, via conventional plasma-fractionation methodology, and administered to another subject in order to impart resistance against or to treat *staphylococcus* infection. Hyperimmune globulins according to the invention are particularly useful for immune-compromised individuals, for individuals undergoing invasive procedures or where time does not permit the individual to produce their own antibodies in response to vaccination. See U.S. Pat. Nos. 6,936,258, 6,770,278, 6,756,361, 5,548,066, 5,512,282, 4,338,298, and 4,748,018, each of which is incorporated herein by reference in its entirety, for exemplary methods and compositions related to passive immunity.

For purposes of this specification and the accompanying claims the terms "epitope" and "antigenic determinant" are used interchangeably to refer to a site on an antigen to which B and/or T cells respond or recognize. B-cell epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols (1996). Antibodies that recognize the same epitope can be identified in a simple immunoassay showing the ability of one antibody to block the binding of another antibody to a target antigen. T-cells recognize continuous epitopes of about nine amino acids for CD8 cells or about 13-15 amino acids for CD4 cells. T cells that recognize the epitope can be identified by in vitro assays that measure antigen-dependent proliferation, as determined by $^3$H-thymidine incorporation by primed T cells in response to an epitope (Burke et al., 1994), by antigen-dependent killing (cytotoxic T lymphocyte assay, Tigges et al., 1996) or by cytokine secretion.

The presence of a cell-mediated immunological response can be determined by proliferation assays (CD4 (+) T cells) or CTL (cytotoxic T lymphocyte) assays. The relative contributions of humoral and cellular responses to the protective or therapeutic effect of an immunogen can be distinguished by separately isolating IgG and T-cells from an immunized syngeneic animal and measuring protective or therapeutic effect in a second subject.

As used herein and in the claims, the terms "antibody" or "immunoglobulin" are used interchangeably and refer to any of several classes of structurally related proteins that function as part of the immune response of an animal or recipient, which proteins include IgG, IgD, IgE, IgA, IgM and related proteins.

Under normal physiological conditions antibodies are found in plasma and other body fluids and in the membrane of certain cells and are produced by lymphocytes of the type denoted B cells or their functional equivalent. Antibodies of the IgG class are made up of four polypeptide chains linked together by disulfide bonds. The four chains of intact IgG molecules are two identical heavy chains referred to as H-chains and two identical light chains referred to as L-chains.

In order to produce polyclonal antibodies, a host, such as a rabbit or goat, is immunized with the antigen or antigen fragment, generally with an adjuvant and, if necessary, coupled to a carrier. Antibodies to the antigen are subsequently collected from the sera of the host. The polyclonal antibody can be affinity purified against the antigen rendering it monospecific.

Monoclonal antibodies can be produced by hyperimmunization of an appropriate donor with the antigen or ex-vivo by use of primary cultures of splenic cells or cell lines derived from spleen (Anavi, 1998; Huston et al., 1991; Johnson et al., 1991; Mernaugh et al., 1995).

As used herein and in the claims, the phrase "an immunological portion of an antibody" includes a Fab fragment of an antibody, a Fv fragment of an antibody, a heavy chain of an antibody, a light chain of an antibody, a heterodimer consisting of a heavy chain and a light chain of an antibody, a variable fragment of a light chain of an antibody, a variable fragment of a heavy chain of an antibody, and a single chain variant of an antibody, which is also known as scFv. In addition, the term includes chimeric immunoglobulins which are the expression products of fused genes derived from different species, one of the species can be a human, in which case a chimeric immunoglobulin is said to be humanized. Typically, an immunological portion of an antibody competes with the intact antibody from which it was derived for specific binding to an antigen.

Optionally, an antibody or preferably an immunological portion of an antibody, can be chemically conjugated to, or expressed as, a fusion protein with other proteins. For purposes of this specification and the accompanying claims, all such fused proteins are included in the definition of antibodies or an immunological portion of an antibody.

As used herein the terms "immunogenic agent" or "immunogen" or "antigen" are used interchangeably to describe a molecule capable of inducing an immunological response against itself on administration to a recipient, either alone, in conjunction with an adjuvant, or presented on a display vehicle.

D. Treatment Methods

A method of the present invention includes treatment for a disease or condition caused by a *staphylococcus* pathogen. An immunogenic polypeptide of the invention can be given to induce an immune response in a person infected with *staphylococcus* or suspected of having been exposed to *staphylococcus*. Methods may be employed with respect to individuals who have tested positive for exposure to *staphylococcus* or who are deemed to be at risk for infection based on possible exposure.

In particular, the invention encompasses a method of treatment for staphylococcal infection, particularly hospital acquired nosocomial infections. The immunogenic compositions and vaccines of the invention are particularly advantageous to use in cases of elective surgery. Such patients will know the date of surgery in advance and could be inoculated in advance. The immunogenic compositions and vaccines of the invention are also advantageous to use to inoculate health care workers.

In some embodiments, the treatment is administered in the presence of adjuvants or carriers or other staphylococcal antigens. Furthermore, in some examples, treatment comprises administration of other agents commonly used against bacterial infection, such as one or more antibiotics.

The use of peptides for vaccination can require, but not necessarily, conjugation of the peptide to an immunogenic carrier protein, such as hepatitis B surface antigen, keyhole limpet hemocyanin, or bovine serum albumin. Methods for performing this conjugation are well known in the art.

V. VACCINE AND OTHER PHARMACEUTICAL COMPOSITIONS AND ADMINISTRATION

A. Vaccines

The present invention includes methods for preventing or ameliorating staphylococcal infections, particularly hospital acquired nosocomial infections. As such, the invention contemplates vaccines for use in both active and passive immunization embodiments. Immunogenic compositions, proposed to be suitable for use as a vaccine, may be prepared from immunogenic SpA polypeptide(s), such as a SpA domain D variant, or immunogenic coagulases. In other embodiments SpA or coagulases can be used in combination with other secreted virulence proteins, surface proteins or immunogenic fragments thereof. In certain aspects, antigenic material is extensively dialyzed to remove undesired small molecular weight molecules and/or lyophilized for more ready formulation into a desired vehicle.

Other options for a protein/peptide-based vaccine involve introducing nucleic acids encoding the antigen(s) as DNA vaccines. In this regard, recent reports described construction of recombinant vaccinia viruses expressing either 10 contiguous minimal CTL epitopes (Thomson, 1996) or a combination of B cell, cytotoxic T-lymphocyte (CTL), and T-helper (Th) epitopes from several microbes (An, 1997), and successful use of such constructs to immunize mice for priming protective immune responses. Thus, there is ample evidence in the literature for successful utilization of peptides, peptide-pulsed antigen presenting cells (APCs), and peptide-encoding constructs for efficient in vivo priming of protective immune responses. The use of nucleic acid sequences as vaccines is exemplified in U.S. Pat. Nos. 5,958,895 and 5,620,896.

The preparation of vaccines that contain polypeptide or peptide sequence(s) as active ingredients is generally well understood in the art, as exemplified by U.S. Pat. Nos. 4,608,251; 4,601,903; 4,599,231; 4,599,230; 4,596,792; and 4,578,770, all of which are incorporated herein by reference. Typically, such vaccines are prepared as injectables either as liquid solutions or suspensions: solid forms suitable for solution in or suspension in liquid prior to injection may also be prepared. The preparation may also be emulsified. The active immunogenic ingredient is often mixed with excipients that are pharmaceutically acceptable and compatible with the active ingredient. Suitable excipients are, for example, water, saline, dextrose, glycerol, ethanol, or the like and combinations thereof. In addition, if desired, the vaccine may contain amounts of auxiliary substances such as wetting or emulsifying agents, pH buffering agents, or adjuvants that enhance the effectiveness of the vaccines. In specific embodiments, vaccines are formulated with a combination of substances, as described in U.S. Pat. Nos. 6,793,923 and 6,733,754, which are incorporated herein by reference.

Vaccines may be conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides: such suppositories may be formed from mixtures containing the active ingredient in the range of about 0.5% to about 10%, preferably about 1% to about 2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain about 10% to about 95% of active ingredient, preferably about 25% to about 70%.

The polypeptides and polypeptide-encoding DNA constructs may be formulated into a vaccine as neutral or salt forms. Pharmaceutically-acceptable salts include the acid addition salts (formed with the free amino groups of the peptide) and those that are formed with inorganic acids such as, for example, hydrochloric or phosphoric acids, or such organic acids as acetic, oxalic, tartaric, mandelic, and the like.

Typically, vaccines are administered in a manner compatible with the dosage formulation, and in such amount as will be therapeutically effective and immunogenic. The quantity to be administered depends on the subject to be treated, including the capacity of the individual's immune system to synthesize antibodies and the degree of protection desired. Precise amounts of active ingredient required to be administered depend on the judgment of the practitioner. However, suitable dosage ranges are of the order of several hundred micrograms of active ingredient per vaccination. Suitable regimes for initial administration and booster shots are also variable, but are typified by an initial administration followed by subsequent inoculations or other administrations.

The manner of application may be varied widely. Any of the conventional methods for administration of a vaccine are applicable. These are believed to include oral application within a solid physiologically acceptable base or in a physiologically acceptable dispersion, parenterally, by injection and the like. The dosage of the vaccine will depend on the route of administration and will vary according to the size and health of the subject.

In certain instances, it will be desirable to have multiple administrations of the vaccine, e.g., 2, 3, 4, 5, 6 or more administrations. The vaccinations can be at 1, 2, 3, 4, 5, 6, 7, 8, to 5, 6, 7, 8, 9, 10, 11, 12 twelve week intervals, including all ranges there between. Periodic boosters at intervals of 1-5 years will be desirable to maintain protective levels of the antibodies. The course of the immunization may be followed by assays for antibodies against the antigens, as described in U.S. Pat. Nos. 3,791,932; 4,174,384 and 3,949,064.

1. Carriers

A given composition may vary in its immunogenicity. It is often necessary therefore to boost the host immune system, as may be achieved by coupling a peptide or polypeptide to a carrier. Exemplary and preferred carriers are keyhole limpet hemocyanin (KLH) and bovine serum albumin (BSA). Other albumins such as ovalbumin, mouse serum albumin, or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde, and bis-biazotized benzidine.

2. Adjuvants

The immunogenicity of polypeptide or peptide compositions can be enhanced by the use of non-specific stimulators of the immune response, known as adjuvants. Suitable adjuvants include all acceptable immunostimulatory compounds, such as cytokines, toxins, or synthetic compositions. A number of adjuvants can be used to enhance an antibody response against a variant SpA polypeptide or coagulase, or any other bacterial protein or combination contemplated herein. Adjuvants can (1) trap the antigen in the body to cause a slow release; (2) attract cells involved in the immune response to the site of administration; (3) induce proliferation or activation of immune system cells; or (4) improve the spread of the antigen throughout the subject's body.

Adjuvants include, but are not limited to, oil-in-water emulsions, water-in-oil emulsions, mineral salts, polynucleotides, and natural substances. Specific adjuvants that may be used include IL-1, IL-2, IL-4, IL-7, IL-12, γ-interferon, GMCSP, BCG, aluminum salts, such as aluminum hydroxide or other aluminum compound, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM), and cell wall skeleton (CWS) in a 2% squalene/Tween 80 emulsion. MHC antigens may even be used. Others adjuvants or methods are exemplified in U.S. Pat. Nos. 6,814,971, 5,084,269, 6,656,462, each of which is incorporated herein by reference).

Various methods of achieving adjuvant affect for the vaccine includes use of agents such as aluminum hydroxide or phosphate (alum), commonly used as about 0.05 to about 0.1% solution in phosphate buffered saline, admixture with synthetic polymers of sugars (Carbopol®) used as an about 0.25% solution, aggregation of the protein in the vaccine by heat treatment with temperatures ranging between about 70° to about 101° C. for a 30-second to 2-minute period, respectively. Aggregation by reactivating with pepsin-treated (Fab) antibodies to albumin; mixture with bacterial cells (e.g., C. parvum), endotoxins or lipopolysaccharide components of Gram-negative bacteria; emulsion in physiologically acceptable oil vehicles (e.g., mannide monooleate (Aracel A)); or emulsion with a 20% solution of a perfluorocarbon (Fluosol-DA®) used as a block substitute may also be employed to produce an adjuvant effect.

Examples of and often preferred adjuvants include complete Freund's adjuvant (a non-specific stimulator of the immune response containing killed Mycobacterium tuberculosis), incomplete Freund's adjuvants, and aluminum hydroxide.

In some aspects, it is preferred that the adjuvant be selected to be a preferential inducer of either a Th1 or a Th2 type of response. High levels of Th1-type cytokines tend to favor the induction of cell mediated immune responses to a given antigen, while high levels of Th2-type cytokines tend to favor the induction of humoral immune responses to the antigen.

The distinction of Th1 and Th2-type immune response is not absolute. In reality an individual will support an immune response which is described as being predominantly Th1 or predominantly Th2. However, it is often convenient to consider the families of cytokines in terms of that described in murine CD4+ T cell clones by Mosmann and Coffman (Mosmann, and Coffman, 1989). Traditionally, Th1-type responses are associated with the production of the INF-γ and IL-2 cytokines by T-lymphocytes. Other cytokines often directly associated with the induction of Th1-type immune responses are not produced by T-cells, such as IL-12. In contrast, Th2-type responses are associated with the secretion of IL-4, IL-5, IL-6, IL-10.

In addition to adjuvants, it may be desirable to co-administer biologic response modifiers (BRM) to enhance immune responses. BRMs have been shown to upregulate T cell immunity or downregulate suppresser cell activity. Such BRMs include, but are not limited to, Cimetidinc (CIM; 1200 mg/d) (Smith/Kline, PA); or low-dose Cyclophosphamide (CYP; 300 mg/m$^2$) (Johnson/Mead, NJ) and cytokines such as γ-interferon, IL-2, or IL-12 or genes encoding proteins involved in immune helper functions, such as B-7.

B. Lipid Components and Moieties

In certain embodiments, the present invention concerns compositions comprising one or more lipids associated with a nucleic acid or a polypeptide/peptide. A lipid is a substance that is insoluble in water and extractable with an organic solvent. Compounds other than those specifically described herein are understood by one of skill in the art as lipids, and are encompassed by the compositions and methods of the present invention. A lipid component and a non-lipid may be attached to one another, either covalently or non-covalently.

A lipid may be a naturally occurring lipid or a synthetic lipid. However, a lipid is usually a biological substance. Biological lipids are well known in the art, and include for example, neutral fats, phospholipids, phosphoglycerides, steroids, terpenes, lysolipids, glycosphingolipids, glucolipids, sulphatides, lipids with ether and ester-linked fatty acids and polymerizable lipids, and combinations thereof.

A nucleic acid molecule or a polypeptide/peptide, associated with a lipid may be dispersed in a solution containing a lipid, dissolved with a lipid, emulsified with a lipid, mixed with a lipid, combined with a lipid, covalently bonded to a lipid, contained as a suspension in a lipid or otherwise associated with a lipid. A lipid or lipid-poxvirus-associated composition of the present invention is not limited to any particular structure. For example, they may also simply be interspersed in a solution, possibly forming aggregates which are not uniform in either size or shape. In another example, they may be present in a bilayer structure, as micelles, or with a "collapsed" structure. In another non-limiting example, a lipofectamine(Gibco BRL)-poxvirus or Superfect (Qiagen)-poxvirus complex is also contemplated.

In certain embodiments, a composition may comprise about 1%, about 2%, about 3%, about 4% about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or any range therebetween, of a particular lipid, lipid type, or non-lipid component such as an adjuvant, antigen, peptide, polypeptide, sugar, nucleic acid or other material disclosed herein or as would be known to one of skill in the art. In a non-limiting example, a composition may comprise about 10% to about 20% neutral lipids, and about 33% to about 34% of a cerebroside, and about 1% cholesterol. In another non-limiting example, a liposome may comprise about 4% to about 12% terpenes, wherein about 1% of the micelle is specifically lycopene, leaving about 3% to about 11% of the liposome as comprising other terpenes; and about 10% to about 35% phosphatidyl choline, and about 1% of a non-lipid component. Thus, it is contemplated that compositions of the present invention may comprise any of the lipids, lipid types or other components in any combination or percentage range.

C. Combination Therapy

The compositions and related methods of the present invention, particularly administration of a secreted virulence factor or surface protein, including a variant SpA polypeptide or peptide, and/or other bacterial peptides or proteins to a patient/subject, may also be used in combination with the administration of traditional therapies. These include, but are not limited to, the administration of antibiotics such as streptomycin, ciprofloxacin, doxycycline, gentamycin, chloramphenicol, trimethoprim, sulfamethoxazole, ampicillin, tetracycline or various combinations of antibiotics.

In one aspect, it is contemplated that a polypeptide vaccine and/or therapy is used in conjunction with antibacterial treatment. Alternatively, the therapy may precede or follow the other agent treatment by intervals ranging from minutes to weeks. In embodiments where the other agents and/or a proteins or polynucleotides are administered separately, one would generally ensure that a significant period of time did not expire between the time of each delivery, such that the agent and antigenic composition would still be able to exert an advantageously combined effect on the subject. In such instances, it is contemplated that one may administer both modalities within about 12-24 h of each other or within about 6-12 h of each other. In some situations, it may be desirable to extend the time period for administration significantly, where several days (2, 3, 4, 5, 6 or 7) to several weeks (1, 2, 3, 4, 5, 6, 7 or 8) lapse between the respective administrations.

Various combinations may be employed, for example antibiotic therapy is "A" and the immunogenic molecule given as part of an immune therapy regime, such as an antigen, is "B":

A/B/A B/A/B B/B/A A/A/B A/B/B B/A/A A/B/B/B B/A/B/B

B/B/B/A B/B/A/B A/A/B/B A/B/A/B A/B/B/A B/B/A/A

B/A/B/A B/A/A/B A/A/A/B B/A/A/A A/B/A/A A/A/B/A

Administration of the immunogenic compositions of the present invention to a patient/subject will follow general protocols for the administration of such compounds, taking into account the toxicity, if any, of the SpA composition, or other compositions described herein. It is expected that the treatment cycles would be repeated as necessary. It also is contemplated that various standard therapies, such as hydration, may be applied in combination with the described therapy.

D. General Pharmaceutical Compositions

In some embodiments, pharmaceutical compositions are administered to a subject. Different aspects of the present invention involve administering an effective amount of a composition to a subject. In some embodiments of the present invention, staphylococcal antigens, members of the Ess pathway, including polypeptides or peptides of the Esa or Esx class, and/or members of sortase substrates may be administered to the patient to protect against infection by one or more *staphylococcus* pathogens. Alternatively, an expression vector encoding one or more such polypeptides or peptides may be given to a patient as a preventative treatment. Additionally, such compounds can be administered in combination with an antibiotic or an antibacterial. Such compositions will generally be dissolved or dispersed in a pharmaceutically acceptable carrier or aqueous medium.

In addition to the compounds formulated for parenteral administration, such as those for intravenous or intramuscular injection, other pharmaceutically acceptable forms include, e.g., tablets or other solids for oral administration; time release capsules; and any other form currently used, including creams, lotions, mouthwashes, inhalants and the like.

The active compounds of the present invention can be formulated for parenteral administration, e.g., formulated for injection via the intravenous, intramuscular, subcutaneous, or even intraperitoneal routes. The preparation of an aqueous composition that contains a compound or compounds that increase the expression of an MHC class I molecule will be known to those of skill in the art in light of the present disclosure. Typically, such compositions can be prepared as injectables, either as liquid solutions or suspensions; solid forms suitable for use to prepare solutions or suspensions upon the addition of a liquid prior to injection can also be prepared; and, the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The proteinaceous compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Administration of the compositions according to the present invention will typically be via any common route. This includes, but is not limited to oral, nasal, or buccal administration. Alternatively, administration may be by orthotopic, intradermal, subcutaneous, intramuscular, intraperitoneal, intranasal, or intravenous injection. In certain embodiments, a vaccine composition may be inhaled (e.g., U.S. Pat. No. 6,651,655, which is specifically incorporated by reference). Such compositions would normally be administered as pharmaceutically acceptable compositions that include physiologically acceptable carriers, buffers or other excipients. As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. The term "pharmaceutically acceptable carrier," means a pharmaceutically acceptable material, composition or vehicle, such as a liquid or solid filler, diluent, excipient, solvent or encapsulating material, involved in carrying or transporting a chemical agent.

For parenteral administration in an aqueous solution, for example, the solution should be suitably buffered, if necessary, and the liquid diluent first rendered isotonic with sufficient saline or glucose. These particular aqueous solutions are especially suitable for intravenous, intramuscular, subcutaneous, and intraperitoneal administration. In this connection, sterile aqueous media which can be employed will be known to those of skill in the art in light of the present disclosure. For example, one dosage could be dissolved in isotonic NaCl solution and either added to hypodermoclysis fluid or injected at the proposed site of infusion, (see for example, Remington's Pharmaceutical Sciences, 1990). Some variation in dosage will necessarily occur depending on the condition of the subject. The person responsible for administration will, in any event, determine the appropriate dose for the individual subject.

An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the protection desired. It is contemplated that in compositions of the invention, there is between about 0.001 mg and about 10 mg of total antigen, antibody, polypeptide, peptide, and/or protein per ml. The concentration of protein in a composition can be about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mg/ml or more (or any range derivable therein). Of this, about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% may be an SpA variant or an antibody that specifically binds SpA. In certain embodiments a dose of about, at least about or at most about 0.001, 0.010, 0.050, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mg/kg or more, including all values and ranges there between are administered to a subject.

Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition.

Upon formulation, solutions will be administered in a manner compatible with the dosage formulation and in such amount as is therapeutically or prophylactically effective. The formulations are easily administered in a variety of dosage forms, such as the type of injectable solutions described above.

E. In Vitro, Ex Vivo, or In Vivo Administration

As used herein, the term in vitro administration refers to manipulations performed on cells removed from or outside of a subject, including, but not limited to cells in culture. The term ex vivo administration refers to cells which have been manipulated in vitro, and are subsequently administered to a subject. The term in vivo administration includes all manipulations performed within a subject.

In certain aspects of the present invention, the compositions may be administered either in vitro, ex vivo, or in vivo. In certain in vitro embodiments, autologous B-lymphocyte cell lines are incubated with a virus vector of the instant invention for 24 to 48 hours or with a variant SpA and/or cogaulase and/or any other composition described herein for two hours. The transduced cells can then be used for in vitro analysis, or alternatively for ex vivo administration. U.S. Pat. Nos. 4,690,915 and 5,199,942, both incorporated herein by reference, disclose methods for ex vivo manipulation of blood mononuclear cells and bone marrow cells for use in therapeutic applications.

F. Antibodies and Passive Immunization

Another aspect of the invention is a method of preparing an immunoglobulin for use in prevention or treatment of staphylococcal infection comprising the steps of immunizing a recipient or donor with the vaccine of the invention and isolating immunoglobulin from the recipient or donor. An immunoglobulin prepared by this method is a further aspect of the invention. A pharmaceutical composition comprising the immunoglobulin of the invention and a pharmaceutically acceptable carrier is a further aspect of the invention which could be used in the manufacture of a medicament for the treatment or prevention of staphylococcal disease. A method for treatment or prevention of staphylococcal infection comprising a step of administering to a patient an effective amount of the pharmaceutical preparation of the invention is a further aspect of the invention.

Inocula for polyclonal antibody production are typically prepared by dispersing the antigenic composition in a physiologically tolerable diluent such as saline or other adjuvants suitable for human use to form an aqueous composition. An immunostimulatory amount of inoculum is administered to a mammal and the inoculated mammal is then maintained for a time sufficient for the antigenic composition to induce protective antibodies.

The antibodies can be isolated to the extent desired by well known techniques such as affinity chromatography (Harlow and Lane, 1988). Antibodies can include antiserum preparations from a variety of commonly used animals, e.g. goats, primates, donkeys, swine, horses, guinea pigs, rats or man.

An immunoglobulin produced in accordance with the present invention can include whole antibodies, antibody fragments or subfragments. Antibodies can be whole immunoglobulins of any class (e.g., IgG, IgM, IgA, IgD or IgE), chimeric antibodies or hybrid antibodies with dual specificity to two or more antigens of the invention. They may also be fragments (e.g., F(ab')2, Fab', Fab, Fv and the like) including hybrid fragments. An immunoglobulin also includes natural, synthetic, or genetically engineered proteins that act like an antibody by binding to specific antigens to form a complex.

A vaccine of the present invention can be administered to a recipient who then acts as a source of immunoglobulin, produced in response to challenge from the specific vaccine. A subject thus treated would donate plasma from which hyperimmune globulin would be obtained via conventional plasma fractionation methodology. The hyperimmune globulin would be administered to another subject in order to impart resistance against or treat staphylococcal infection. Hyperimmune globulins of the invention are particularly useful for treatment or prevention of staphylococcal disease in infants, immune compromised individuals, or where treatment is required and there is no time for the individual to produce antibodies in response to vaccination.

An additional aspect of the invention is a pharmaceutical composition comprising two of more monoclonal antibodies (or fragments thereof; preferably human or humanised) reactive against at least two constituents of the immunogenic composition of the invention, which could be used to treat or prevent infection by Gram positive bacteria, preferably staphylococci, more preferably *S. aureus* or *S. epidermidis*. Such pharmaceutical compositions comprise monoclonal antibodies that can be whole immunoglobulins of any class, chimeric antibodies, or hybrid antibodies with specificity to two or more antigens of the invention. They may also be fragments (e.g., F(ab')2, Fab', Fab, Fv and the like) including hybrid fragments.

Methods of making monoclonal antibodies are well known in the art and can include the fusion of splenocytes with myeloma cells (Kohler and Milstein, 1975; Harlow and Lane, 1988). Alternatively, monoclonal Fv fragments can be obtained by screening a suitable phage display library (Vaughan et al., 1998). Monoclonal antibodies may be humanized or part humanized by known methods.

VI. EXAMPLES

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Immunization with $SpA_{KKAA}$ Modifies Host Immune Responses to Staphylococcal Infection The model of immune evasion during *S. aureus* infections includes the initial activation of B cells via IgM receptor crosslinking by cell wall anchored or secreted protein A—up to 20% of peptidoglycan with attached surface protein is released during each bacterial division event (Ton-That et al., 1999). In the absence of specific antigen stimuli, activated B cells undergo apoptotic collapse, thereby diminishing host antibody production against antigens that are presented during staphylococcal infection. If so, neutralizing SpA-specific antibodies may enable animals to develop humoral immune responses against many different staphylococcal antigens. This possibility was investigated by immunizing BALB/c mice with $SpA_{KKAA}$ or an adjuvant (aluminum hydroxide) control followed by intravenous challenge with a sublethal dose of MRSA strain USA300. Serum samples were withdrawn thirty days after MRSA challenge and then analyzed by immunoblotting with 27 staphylococcal antigens immobilized on a membrane filter (FIG. 1). Naïve mice, which had not been infected with the MRSA strain USA300 LAC, did not harbor antibodies against ClfA, ClfB, Coa, Eap, Ebh, Emp, EsxA, EsxB, FnbpA, FnbpB, Hla, IsdA, IsdB, LukD, LukE, LukF, SdrC, SdrD, SdrE, SasA, SasD, SasF, SasG, SasI, SasK, $SpA_{KKAA}$ or vWbp (data not shown). Mock immunized mice that had been subjected to USA300 infection developed high-titer antibodies against the Eap protein as well as low-titer antibodies against IsdA, IsdB, Hla, LukD, LukE and LukF (FIG. 1). Animals that been immunized and that elaborated $SpA_{KKAA}$-specific antibodies [IgG titer 2,907 (±357); P<0.001 $SpA_{KKAA}$ vs. mock] mounted humoral immune responses against every one of the 27 antigens in response to a challenge with the MRSA strain USA300 (FIG. 1). With the exception of Eap, IsdA and IsdB antibodies, the serum of $SpA_{KKAA}$-immunized animals harbored higher antibody titers against each staphylococcal antigen when compared to mice that had been naïve at the time of challenge (FIG. 1).

REFERENCES

The following references, to the extent that they provide exemplary procedural or other details supplementary to those set forth herein, are specifically incorporated herein by reference.

U.S. Pat. No. 3,791,932
U.S. Pat. No. 3,949,064
U.S. Pat. No. 4,174,384
U.S. Pat. No. 4,338,298
U.S. Pat. No. 4,356,170
U.S. Pat. No. 4,367,110
U.S. Pat. No. 4,372,945
U.S. Pat. No. 4,452,901
U.S. Pat. No. 4,474,757
U.S. Pat. No. 4,554,101
U.S. Pat. No. 4,578,770
U.S. Pat. No. 4,596,792
U.S. Pat. No. 4,599,230
U.S. Pat. No. 4,599,231
U.S. Pat. No. 4,601,903
U.S. Pat. No. 4,608,251
U.S. Pat. No. 4,683,195
U.S. Pat. No. 4,683,202
U.S. Pat. No. 4,684,611
U.S. Pat. No. 4,690,915
U.S. Pat. No. 4,690,915
U.S. Pat. No. 4,748,018
U.S. Pat. No. 4,800,159
U.S. Pat. No. 4,879,236
U.S. Pat. No. 4,952,500
U.S. Pat. No. 5,084,269
U.S. Pat. No. 5,199,942
U.S. Pat. No. 5,221,605
U.S. Pat. No. 5,238,808
U.S. Pat. No. 5,302,523
U.S. Pat. No. 5,310,687
U.S. Pat. No. 5,322,783
U.S. Pat. No. 5,384,253
U.S. Pat. No. 5,464,765
U.S. Pat. No. 5,512,282
U.S. Pat. No. 5,512,282
U.S. Pat. No. 5,538,877
U.S. Pat. No. 5,538,880
U.S. Pat. No. 5,548,066
U.S. Pat. No. 5,550,318
U.S. Pat. No. 5,563,055
U.S. Pat. No. 5,580,859
U.S. Pat. No. 5,589,466
U.S. Pat. No. 5,591,616
U.S. Pat. No. 5,610,042
U.S. Pat. No. 5,620,896
U.S. Pat. No. 5,648,240
U.S. Pat. No. 5,656,610
U.S. Pat. No. 5,702,932
U.S. Pat. No. 5,736,524
U.S. Pat. No. 5,780,448
U.S. Pat. No. 5,789,215
U.S. Pat. No. 5,801,234
U.S. Pat. No. 5,840,846
U.S. Pat. No. 5,843,650
U.S. Pat. No. 5,846,709
U.S. Pat. No. 5,846,783
U.S. Pat. No. 5,849,497
U.S. Pat. No. 5,849,546
U.S. Pat. No. 5,849,547
U.S. Pat. No. 5,858,652
U.S. Pat. No. 5,866,366
U.S. Pat. No. 5,871,986
U.S. Pat. No. 5,916,776
U.S. Pat. No. 5,922,574
U.S. Pat. No. 5,925,565
U.S. Pat. No. 5,925,565
U.S. Pat. No. 5,928,905
U.S. Pat. No. 5,928,906
U.S. Pat. No. 5,932,451
U.S. Pat. No. 5,935,819
U.S. Pat. No. 5,935,825
U.S. Pat. No. 5,939,291
U.S. Pat. No. 5,942,391
U.S. Pat. No. 5,945,100
U.S. Pat. No. 5,958,895

U.S. Pat. No. 5,981,274
U.S. Pat. No. 5,994,624
U.S. Pat. No. 6,008,341
U.S. Pat. No. 6,288,214
U.S. Pat. No. 6,294,177
U.S. Pat. No. 6,651,655
U.S. Pat. No. 6,656,462
U.S. Pat. No. 6,733,754
U.S. Pat. No. 6,756,361
U.S. Pat. No. 6,770,278
U.S. Pat. No. 6,793,923
U.S. Pat. No. 6,814,971
U.S. Pat. No. 6,936,258
U.S. Patent Appln. 2002/0169288
U.S. Patent Appln. 2003/0153022
Abdallah et al., *Mol. Microbiol.*, 62, 667-679, 2006.
Abdallah et al., *Nat. Rev. Microbiol.*, 5, 883-891, 2007.
Albus et al., *Infect. Immun.*, 59:1008-1014, 1991.
An, *J. Virol.*, 71(3):2292-302, 1997.
Anavi, Sc. thesis from the department of Molecular Microbiology and Biotechnology of the Tel-Aviv University, Israel, 1998.
Andersen et al., *J. Immunol.*, 154, 3359-3372, 1995.
Angel et al., *Cell*, 49:729, 1987b.
Angel et al., *Mol. Cell. Biol.*, 7:2256, 1987a.
Archer, *Clin. Infect. Dis.*, 26, 1179-1181, 1998.
Atchison and Perry, *Cell*, 46:253, 1986.
Atchison and Perry, *Cell*, 48:121, 1987.
Ausubel et al., In: *Current Protocols in Molecular Biology*, John, Wiley & Sons, Inc, New York, 1996.
Baba et al., *J. Bacteriol.* 190:300-310, 2007.
Bae and Schneewind, *Plasmid*, 55:58-63, 2006.
Bae et al., *Proc. Natl. Acad. Sci. USA*, 101, 12312-12317, 2004.
Banerji et al., *Cell*, 27(2 Pt 1):299-308, 1981.
Banerji et al., *Cell*, 33(3):729-740, 1983.
Barany and Merrifield, In: *The Peptides*, Gross and Meienhofer (Eds.), Academic Press, NY, 1-284, 1979.
Behring E A. Über das Zustandekommen der Diphtherie—Immunität bei Thieren. Deutsche Medzinische Wochenschrift, 16:1145-8, 1890.
Bellus, *J. Macromol. Sci. Pure Appl. Chem.*, A31(1): 1355-1376, 1994.
Berkhout et al., *Cell*, 59:273-282, 1989.
Birch-Hirschfeld, L. 1934. Über die Agglutination von Staphylokokken durch Bestandteile des Säugetierblutplasmas. Klinische Woschenschrift 13:331.
Bjerketorp et al., *FEMS Microbiol. Lett.*, 234:309-314, 2004.
Blanar et al., *EMBO J.*, 8:1139, 1989.
Bodine and Ley, *EMBO J.*, 6:2997, 1987.
Borrebaeck, In: *Antibody Engineering*—A Practical Guide, W. H. Freeman and Co., 1992.
Boshart et al., *Cell*, 41:521, 1985.
Bosze et al., *EMBO J.*, 5(7):1615-1623, 1986.
Boucher and Corey. *Clin. Infect. Dis.* 46:S334-S349, 2008.
Braddock et al., *Cell*, 58:269, 1989.
Brown et al., *Biochemistry*, 37:4397-4406, 1998.
Bubeck Wardenburg and Schneewind. *J. Exp. Med.* 205: 287-294, 2008.
Bubeck-Wardenburg et al., *Infect. Immun.* 74:1040-1044, 2007.
Bubeck-Wardenburg et al., *Proc. Natl. Acad. Sci. USA*, 103:13831-13836, 2006.
Bulla and Siddiqui, *J. Virol.*, 62:1437, 1986.
Burke et al., *J. Inf. Dis.*, 170:1110-1119, 1994.
Burlak et al., *Cell Microbiol.*, 9:1172-1190, 2007.
Burts and Missiakas, *Mol. Microbiol.*, 69:736-46, 2008.
Burts et al., *Proc. Natl. Acad. Sci. USA*, 102:1169-1174, 2005.
Campbell and Villarreal, *Mol. Cell. Biol.*, 8:1993, 1988.
Campere and Tilghman, *Genes and Dev.*, 3:537, 1989.
Campo et al., *Nature*, 303:77, 1983.
Carbonelli et al., *FEMS Microbiol. Lett.*, 177(1):75-82, 1999.
Cedergren et al., *Protein Eng.*, 6:441-448, 1993.
Celander and Haseltine, *J. Virology*, 61:269, 1987.
Celander et al., *J. Virology*, 62:1314, 1988.
Cespedes et al., *J. Infect. Dis.*, 191(3):444-52, 2005.
Champion et al., *Science*, 313:1632-1636, 2006.
Chandler et al., *Cell*, 33:489, 1983.
Chandler et al., *Proc. Natl. Acad. Sci. USA*, 94(8):3596-601, 1997.
Chang et al., *Lancet.*, 362(9381):362-369, 2003.
Chang et al., *Mol. Cell. Biol.*, 9:2153, 1989.
Chatterjee et al., *Proc. Natl. Acad. Sci. USA*, 86:9114, 1989.
Chen and Okayama, *Mol. Cell Biol.*, 7(8):2745-2752, 1987.
Cheng et al., *FASEB J.*, 23:1-12, 2009.
Choi et al., *Cell*, 53:519, 1988.
Cocea, *Biotechniques*, 23(5):814-816, 1997.
Cohen et al., *J. Cell. Physiol.*, 5:75, 1987.
Cosgrove et al., *Infect. Control Hosp. Epidemiol.* 26:166-174, 2005.
Costa et al., *Mol. Cell. Biol.*, 8:81, 1988.
Cripe et al., *EMBO J.*, 6:3745, 1987.
Culotta and Hamer, *Mol. Cell. Biol.*, 9:1376, 1989.
Dalbey and Wickner, *J. Biol. Chem.*, 260:15925-15931, 1985.
Dandolo et al., *J. Virology*, 47:55-64, 1983.
De Villiers et al., *Nature*, 312(5991):242-246, 1984.
DeBord et al., *Infect. Immun.*, 74:4910-4914, 2006.
DeDent et al., *EMBO J.* 27:2656-2668, 2008.
DeDent et al., *J. Bacteriol.* 189:4473-4484, 2007.
Deisenhofer et al., *Hoppe-Seyh Zeitsch. Physiol. Chem.* 359:975-985, 1978.
Deisenhofer, *Biochemistry* 20:2361-2370, 1981.
Deschamps et al., *Science*, 230:1174-1177, 1985.
Devereux et al., *Nucl. Acid Res.*, 12:387-395, 1984.
Diep et al., *J. Infect. Dis.*, 193:1495-1503, 2006a.
Diep et al., *Lancet.*, 367:731-739, 2006b.
Dinges et al., *Clin. Microbiol. Rev.*, 13:16-34, 2000.
Duthie and Lorenz, *J. Gen. Microbiol.*, 6:95-107, 1952.
Edbrooke et al., *Mol. Cell. Biol.*, 9:1908, 1989.
Edlund et al., *Science*, 230:912-916, 1985.
Ekstedt and Yotis, *Ann. N.Y. Acad. Sci.*, 80:496-500, 1960.
Emorl and Gaynes, *Clin. Microbiol. Rev.*, 6:428-442, 1993.
EP 0786519
EP 497524
EP 497525
Epitope Mapping Protocols In: *Methods in Molecular Biology*, Vol. 66, Morris (Ed.), 1996.
Fechheimer, et al., *Proc Natl. Acad. Sci. USA*, 84:8463-8467, 1987.
Feng and Holland, *Nature*, 334:6178, 1988.
Field and Smith, *J. Comp. Pathol.*, 55:63, 1945.
Firak and Subramanian, *Mol. Cell. Biol.*, 6:3667, 1986.
Foecking and Hofstetter, *Gene*, 45(1):101-105, 1986.
Fortune et al., *Proc Natl. Acad. Sci. USA*, 102:10676-10681, 2005.
Foster, *Nat. Rev. Microbiol.*, 3:948-958, 2005.
Fournier et al., *Infect. Immun.*, 45:87-93, 1984.
Fraley et al., *Proc. Natl. Acad. Sci. USA*, 76:3348-3352, 1979.
Friedrich et al., *Nature*, 425:535-539, 2003.

Fujita et al., *Cell*, 49:357, 1987.
GB Appln. 2 202 328
Gilles et al., *Cell*, 33:717, 1983.
Gloss et al., *EMBO J.*, 6:3735, 1987.
Godbout et al., *Mol. Cell. Biol.*, 8:1169, 1988.
Gomez et al., *EMBO J.* 26:701-709, 2007.
Gomez et al., *J. Biol. Chem.* 281:20190-20196, 2006.
Gomez et al., *Nature Med.* 10:842-8, 2004.
Goodbourn and Maniatis, *Proc. Natl. Acad. Sci. USA*, 85:1447, 1988.
Goodbourn et al., *Cell*, 45:601, 1986.
Goodyear and Silverman, *J. Exp. Med.*, 197:1125-1139, 2003.
Goodyear and Silverman, *Proc. Nat. Acad. Sci. USA*, 101: 11392-11397, 2004.
Gopal, *Mol. Cell Biol.*, 5:1188-1190, 1985.
Gouda et al., *Biochemistry*, 31(40):9665-72, 1992.
Gouda et al., *Biochemistry*, 37:129-36, 1998.
Graham and Van Der Eb, *Virology*, 52:456-467, 1973.
Graille et al., *Proc. Nat. Acad. Sci. USA* 97:5399-5404, 2000.
Greene et al., *Immunology Today*, 10:272, 1989
Grosschedl and Baltimore, *Cell*, 41:885, 1985.
Guinn et al., *Mol. Microbiol.*, 51:359-370, 2004.
Guss et al., *Eur. J. Biochem.* 138:413-420, 1984.
Harland and Weintraub, *J. Cell Biol.*, 101(3):1094-1099, 1985.
Harlow et al., *Antibodies: A Laboratory Manual*, Cold Spring Harbor Laboratory, Cold Spring Harbor, N.Y., Chapter 8, 1988.
Hartleib et al., *Blood* 96:2149-2156, 2000.
Harvey et al., *Proc. Natl. Acad. Sci. USA*, 83:1084-1088, 1986.
Haslinger and Karin, *Proc. Natl. Acad. Sci. USA*, 82:8572, 1985.
Hauber and Cullen, *J. Virology*, 62:673, 1988.
Hen et al., *Nature*, 321:249, 1986.
Hensel et al., *Lymphokine Res.*, 8:347, 1989.
Herr and Clarke, *Cell*, 45:461, 1986.
Hirochika et al., *J. Virol.*, 61:2599, 1987.
Hirsch et al., *Mol. Cell. Biol.*, 10:1959, 1990.
Holbrook et al., *Virology*, 157:211, 1987.
Horlick and Benfield, *Mol. Cell. Biol.*, 9:2396, 1989.
Hsu et al., *Proc. Natl. Acad. Sci. USA*, 100:12420-12425, 2003.
Huang et al., *Cell*, 27:245, 1981.
Hug et al., *Mol. Cell. Biol.*, 8:3065, 1988.
Huston et al., In: *Methods in Enzymology*, Langone (Ed.), Academic Press, NY, 203:46-88, 1991.
Hwang et al., *Mol. Cell. Biol.*, 10:585, 1990.
Imagawa et al., *Cell*, 51:251, 1987.
Imbra and Karin, *Nature*, 323:555, 1986.
Imler et al., *Mol. Cell. Biol.*, 7:2558, 1987.
Imperiale and Nevins, *Mol. Cell. Biol.*, 4:875, 1984.
Innis et al., *Proc Natl Acad Sci USA*, 85(24):9436-9440, 1988.
Inouye and Inouye, *Nucleic Acids Res.*, 13: 3101-3109, 1985.
Jakobovits et al., *Mol. Cell. Biol.*, 8:2555, 1988.
Jameel and Siddiqui, *Mol. Cell. Biol.*, 6:710, 1986.
Jansson et al., *FEMS Immunol. Med. Microbiol.* 20:69-78 1998.
Jaynes et al., *Mol. Cell. Biol.*, 8:62, 1988.
Jensen, *Acta Path. Microbiol. Scandin.* 44:421-428, 1958.
Johnson et al., *Methods in Enzymol.*, 203:88-99, 1991.
Johnson et al., *Mol. Cell. Biol.*, 9:3393, 1989.
Jones, *Carb. Research*, 340:1097-1106, 2005.
Jonsson et al., *Oral Dis.*, 8(3):130-140, 2002.
Joyce et al., *Carbohydrate Research* 338:903-922 (2003
Kadesch and Berg, *Mol. Cell. Biol.*, 6:2593, 1986.
Kaeppler et al., *Plant Cell Rep.*, 8:415-418, 1990.
Kaneda et al., *Science*, 243:375-378, 1989.
Karin et al., *Mol. Cell. Biol.*, 7:606, 1987.
Katinka et al., *Cell*, 20:393, 1980.
Kato et al, *J. Biol. Chem.*, 266:3361-3364, 1991.
Kawamoto et al., *Mol. Cell. Biol.*, 8:267, 1988.
Kennedy et al., *Proc. Natl. Acad. Sci. USA* 105:1327-1332, 2008.
Kiledjian et al., *Mol. Cell. Biol.*, 8:145, 1988.
Kinoshita, M., N. Kobayashi, S. Nagashima, M. Ishino, S. Otokozawa, K. Mise, A. Sumi, H. Tsutsumi, N. Uehara, N. Watanabe, and M. Endo. 2008. Diversity of staphylocoagulase and identification of novel variants of staphylocoagulase gene in Staphylococcus aureus. Microbiol. Immunol.s 52:334-348.
Klamut et al., *Mol. Cell. Biol.*, 10:193, 1990.
Klevens et al., *Clin. Infect. Dis.*, 2008; 47:927-30, 2008.
Klevens et al., *JAMA*, 298:1763-1771, 2007.
Koch et al., *Mol. Cell. Biol.*, 9:303, 1989.
Kohler and Milstein, *Nature* 256:495-497 (1975
Kriegler and Botchan, In: *Eukaryotic Viral Vectors*, Gluzman (Ed.), Cold Spring Harbor: Cold Spring Harbor Laboratory, N Y, 1982.
Kriegler and Botchan, *Mol. Cell. Biol.*, 3:325, 1983.
Kriegler et al., *Cell*, 38:483, 1984a.
Kriegler et al., *Cell*, 53:45, 1988.
Kriegler et al., In: *Cancer Cells 2/Oncogenes and Viral Genes*, Van de Woude et al. eds, Cold Spring Harbor, Cold Spring Harbor Laboratory, 1984b.
Kroh et al., *Proc. Natl. Acad. Sci. USA*, 106:7786-7791, 2009.
Kuhl et al., *Cell*, 50:1057, 1987.
Kuklin et al., *Infect. Immun.*, 74:2215-23, 2006.
Kunz et al., *Nucl. Acids Res.*, 17:1121, 1989.
Kuroda et al., *Lancet.*, 357:1225-1240, 2001.
Kyte and Doolittle, *J. Mol. Biol.*, 157(1):105-132, 1982.
Lagergard et al., *Eur. J. Clin. Microbiol. Infect. Dis.*, 11:341-5, 1992.
Lam et al., *J. Bacteriol.*, 86:87-91, 1963.
Larsen et al., *Proc Natl. Acad. Sci. USA.*, 83:8283, 1986, 1963.
Laspia et al., *Cell*, 59:283, 1989.
Latimer et al., *Mol. Cell. Biol.*, 10:760, 1990.
Lee et al., *Nature*, 294:228, 1981.
Lee et al., *Nucleic Acids Res.*, 12:4191-206, 1984.
Lee, *Trends Microbiol.* 4(4):162-166, 1996.
Levenson et al., *Hum. Gene Ther.*, 9(8):1233-1236, 1998.
Levinson et al., *Nature*, 295:79, 1982.
Lin et al., *Mol. Cell. Biol.*, 10:850, 1990.
Lowy, *New Engl. J. Med.*, 339:520-532, 1998.
Luria et al., *EMBO J.*, 6:3307, 1987.
Lusky and Botchan, *Proc. Natl. Acad. Sci. USA*, 83:3609, 1986.
Lusky et al., *Mol. Cell. Biol.*, 3:1108, 1983.
Macejak and Sarnow, *Nature*, 353:90-94, 1991.
MacGurn et al., *Mol. Microbiol.*, 57:1653-1663, 2005.
Maira-Litran et al., *Infect. Immun.*, 70:4433-4440, 2002.
Maira-Litran et al., *Vaccine*, 22:872-879, 2004.
Majors and Varmus, *Proc. Natl. Acad. Sci. USA*, 80:5866, 1983.
Markwardt, Untersuchungen über Hirudin. Naturwissenschaften, 41:537-538, 1955.
Mazmanian et al., *Mol. Microbiol.* 40, 1049-1057, 2001.
Mazmanian et al., *Mol. Microbiol.*, 40(5):1049-1057, 2001.

Mazmanian et al., *Proc. Natl. Acad. Sci. USA,* 97:5510-5515, 2000.
Mazmanian et al., *Science,* 285(5428):760-3, 1999.
McLaughlin et al., *PLoS Pathog.,* 3:e105, 2007.
McNeall et al., *Gene,* 76:81, 1989.
Mernaugh et al., In: *Molecular Methods in Plant Pathology,* Singh et al. (Eds.), CRC Press Inc., Boca Raton, Fla., 359-365, 1995.
Merrifield, *Science,* 232(4748):341-347, 1986.
Miksicek et al., *Cell,* 46:203, 1986.
Mordacq and Linzer, *Genes and Dev.,* 3:760, 1989.
Moreau et al., *Carbohydrate Res.,* 201:285-297, 1990.
Moreau et al., *Nucl. Acids Res.,* 9:6047, 1981.
Moreillon et al., *Infect. Immun.,* 63:4738-4743, 1995.
Moreillon et al., *Infect. Immun.,* 63:4738-4743, 1995.
Mosmann and Coffman, *Ann. Rev. Immunol.,* 7:145-173, 1989.
Muesing et al., *Cell,* 48:691, 1987.
Musher et al., *Medicine (Baltimore),* 73:186-208, 1994.
Navarre and Schneewind, *J. Biol. Chem.,* 274:15847-15856, 1999.
Needleman & Wunsch, *J. Mol. Biol.,* 48:443, 1970.
Ng et al., *Nuc. Acids Res.,* 17:601, 1989.
Nicolau and Sene, *Biochim. Biophys. Acta,* 721:185-190, 1982.
Nicolau et al., *Methods Enzymol.,* 149:157-176, 1987.
Novick, *Mol. Microbiol.,* 48:1429-1449, 2003.
O'Brien et al., *Mol. Microbiol.* 44:1033-1044, 2002.
O'Seaghdha et al., *FEBS J.* 273:4831-4841, 2006.
Omirulleh et al., *Plant Mol. Biol.,* 21(3):415-28, 1993.
Ondek et al., *EMBO J.,* 6:1017, 1987.
Ornitz et al., *Mol. Cell. Biol.,* 7:3466, 1987.
Pallen, *Trends Microbiol.,* 10:209-212, 2002.
Palmiter et al., *Nature,* 300:611, 1982.
Palmqvist et al., *Microbes. Infect.,* 7:1501-11, 2005.
Panizzi et al., *J. Biol. Chem.,* 281:1179-1187, 2006.
PCT Appln. PCT/US89/01025
PCT Appln. WO 00/02523
PCT Appln. WO 00/12132
PCT Appln. WO 00/12689
PCT Appln. WO 00/15238
PCT Appln. WO 01/34809
PCT Appln. WO 01/60852
PCT Appln. WO 01/98499
PCT Appln. WO 02/059148
PCT Appln. WO 02/094868
PCT Appln. WO 03/53462
PCT Appln. WO 04/43407
PCT Appln. WO 06/032472
PCT Appln. WO 06/032475
PCT Appln. WO 06/032500
PCT Appln. WO 07/113222
PCT Appln. WO 07/113223
PCT Appln. WO 94/09699
PCT Appln. WO 95/06128
PCT Appln. WO 95/08348
PCT Appln. WO 98/57994
Pearson & Lipman, *Proc. Natl. Acad. Sci. USA,* 85:2444, 1988.
Pech et al., *Mol. Cell. Biol.,* 9:396, 1989.
Pelletier and Sonenberg, *Nature,* 334(6180):320-325, 1988.
Perez-Stable and Constantini, *Mol. Cell. Biol.,* 10:1116, 1990.
Phonimdaeng et al., *Mol. Microbiol.,* 4:393-404, 1990.
Picard and Schaffner, *Nature,* 307:83, 1984.
Pinkert et al., *Genes and Dev.,* 1:268, 1987.
Ponta et al., *Proc. Natl. Acad. Sci. USA,* 82:1020, 1985.
Porton et al., *Mol. Cell. Biol.,* 10:1076, 1990.
Potrykus et al., *Mol. Gen. Genet.,* 199(2):169-177, 1985.
Pugsley, *Microbiol. Rev.,* 57:50-108, 1993.
Pym et al., *Mol. Microbiol.,* 46; 709-717, 2002.
Pym et al., *Nat. Med.,* 9:533-539, 2003.
Queen and Baltimore, *Cell,* 35:741, 1983.
Quinn et al., *Mol. Cell. Biol.,* 9:4713, 1989.
Redondo et al., *Science,* 247:1225, 1990.
Reisman and Rotter, *Mol. Cell. Biol.,* 9:3571, 1989.
Remington's Pharmaceutical Sciences, 18th Ed. Mack Printing Company, 1289-1329, 1990.
Resendez Jr. et al., *Mol. Cell. Biol.,* 8:4579, 1988.
Ripe et al., *Mol. Cell. Biol.,* 9:2224, 1989.
Rippe, et al., *Mol. Cell Biol.,* 10:689-695, 1990.
Rittling et al., *Nuc. Acids Res.,* 17:1619, 1989.
Roben et al., *J. Immunol.* 154:6437-6445, 1995.
Rosen et al., *Cell,* 41:813, 1988.
Sakai et al., *Genes and Dev.,* 2:1144, 1988.
Salid-Salim et al., *Infect. Control Hosp. Epidemiol.* 24:451-455, 2003.
Sambrook et al., In: *Molecular cloning,* Cold Spring Harbor Laboratory Press, Cold Spring Harbor, N Y, 2001.
Schaffner et al., *J. Mol. Biol.,* 201:81, 1988.
Schneewind et al., *Cell* 70:267-281, 1992.
Schneewind et al., *EMBO,* 12:4803-4811, 1993.
Schneewind et al., *Science,* 268:103-6, 1995.
Searle et al., *Mol. Cell. Biol.,* 5:1480, 1985.
Sharp and Marciniak, *Cell,* 59:229, 1989.
Shaul and Ben-Levy, *EMBO J.,* 6:1913, 1987.
Shaw et al., *Microbiology,* 150:217-228, 2004.
Sheagren, *N. Engl. J. Med.* 310:1368-1373, 1984.
Sherman et al., *Mol. Cell. Biol.,* 9:50, 1989.
Shopsin et al., *J. Clin. Microbiol.,* 37:3556-63, 1999.
Sibbald et al., *Microbiol. Mol Biol. Rev.,* 70:755-788, 2006.
Silverman and Goodyear. *Nat. Rev. Immunol.,* 6:465-75, 2006.
Sjodahl, *Eur. J. Biochem.* 73:343-351, 1977.
Sjoquist et al., *Eur. J. Biochem.* 30:190-194, 1972.
Sleigh and Lockett, *J. EMBO,* 4:3831, 1985.
Smith & Waterman, *Adv. Appl. Math.,* 2:482, 1981.
Smith et al., *Brit. J. Exp. Pathol.,* 28:57, 1947.
Sorensen et al., *Infect. Immun.,* 63:1710-1717, 1995.
Spalholz et al., *Cell,* 42:183, 1985.
Spandau and Lee, *J. Virology,* 62:427, 1988.
Spandidos and Wilkie, *EMBO J.,* 2:1193, 1983.
Stanley et al., *Proc. Natl. Acad. Sci. USA,* 100:13001-13006, 2003.
Stephens and Hentschel, *Biochem. J.,* 248:1, 1987.
Stewart and Young, In: *Solid Phase Peptide Synthesis,* 2d. ed., Pierce Chemical Co., 1984.
Stranger-Jones et al., *Proc. Nat. Acad. Sci. USA,* 103:16942-16947, 2006.
Stuart et al., *Nature,* 317:828, 1985.
Studier et al., *Methods Enzymol.* 185:60-89 1990.
Sullivan and Peterlin, *Mol. Cell. Biol.,* 7:3315, 1987.
Swartzendruber and Lehman, *J. Cell. Physiology,* 85:179, 1975.
Takebe et al., *Mol. Cell. Biol.,* 8:466, 1988.
Tam et al., *J. Am. Chem. Soc.,* 105:6442, 1983.
Tavernier et al., *Nature,* 301:634, 1983.
Taylor and Kingston, *Mol. Cell. Biol.,* 10:165, 1990a.
Taylor and Kingston, *Mol. Cell. Biol.,* 10:176, 1990b.
Taylor et al., *J. Biol. Chem.,* 264:15160, 1989.
Thiesen et al., *J. Virology,* 62:614, 1988.
Thomson et al., *J. Immunol.,* 157(2):822-826, 1996.
Tigges et al., *J. Immunol.,* 156(10):3901-3910, 1996.
Tigges et al., *J. Immunol.,* 156(10):3901-3910, 1996.

Ton-That et al., *Proc. Natl. Acad. Sci. USA*, 96(22):12424-9, 1999.
Treisman, *Cell*, 42:889, 1985.
Tronche et al., *Mol. Biol. Med.*, 7:173, 1990.
Trudel and Constantini, *Genes and Dev.*, 6:954, 1987.
Tyndell et al., *Nuc. Acids. Res.*, 9:6231, 1981.
Uhlen et al., *J. Biol. Chem.* 259:1695-1702 and 13628 (Corr.) 1984.
van den Ent and Lowe, *FEBS Lett.*, 579:3837-3841, 2005.
van Wely et al., *FEMS Microbiol. Rev.*, 25:437-454, 2001.
Vannice and Levinson, *J. Virology*, 62:1305, 1988.
Vasseur et al., *Proc Natl. Acad. Sci. USA*, 77:1068, 1980.
Vaughan, et al., *Nat. Biotech.* 16; 535-539, 1998.
Wang and Calame, *Cell*, 47:241, 1986.
Weber et al., *Cell*, 36:983, 1984.
Weinberger et al. *Mol. Cell. Biol.*, 8:988, 1984.
Weiss et al., *J. Antimicrob. Chemother.*, 53(3):480-6, 2004.
Winoto and Baltimore, *Cell*, 59:649, 1989.
Wong et al., *Gene*, 10:87-94, 1980.
Xu et al., *J. Infect. Dis.*, 189:2323-2333, 2004.
Xu et al., *Mol. Microbiol.*, 66(3):787-800, 2007.
Yutzey et al. *Mol. Cell. Biol.*, 9:1397, 1989.

What is claimed is:

1. A method for enhancing a subject's ability to mount an immune response to a *Staphylococcus aureus* antigen comprising providing to the subject a composition comprising an isolated antibody that specifically binds to a nontoxigenic *Staphylococcus aureus* protein (SpA) variant, the SpA variant having (a) amino acid substitutions in an IgG Fc binding subdomain of each of SpA domains A, B, C, D, and E that disrupt or decrease binding to IgG Fc, wherein the amino acid substitutions are in SpA domain A at position 7 and 8 of SEQ ID NO:4, in SpA domain B at position 7 and 8 of SEQ ID NO:6, in SpA domain C at position 7 and 8 of SEQ ID NO:5, in SpA domain D at position 9 and 10 of SEQ ID NO:2; and in SpA domain E at position 6 and 7 of SEQ ID NO:3; and (b) amino acid substitutions in a $V_H3$ binding sub-domain of each of SpA domains A, B, C, D, and E that disrupt or decrease binding to VH3, wherein the amino acid substitutions are in SpA domain A at position 34 and 35 of SEQ ID NO:4, in SpA domain B at position 34 and 35 of SEQ ID NO:6, in SpA domain C at position 34 and 35 of SEQ ID NO:5, in SpA domain D at position 36 and 37 of SEQ ID NO:2; in SpA domain E at position 33 and 34 of SEQ ID NO:3 wherein the antibody enhances the subject's ability to mount an immune response to a *Staphylococcus aureus* antigen selected from the group consisting of FnBpA, FnBpB, LukD, LukE, LukF, SasA, SasD, SasG, SasI, SasK, Ebh, Emp, EsaB, EsaC, EsxA, EsxB, SdrC, SdrD, SdrE, ClfA, ClfB, Coa, Hla, IsdC, SasF, vWbp, and vWh.

2. The method of claim 1, wherein the *Staphylococcus aureus* antigen is present in or on a *Staphylococcus aureus* bacterium.

3. The method of claim 1, further comprising providing to the subject a *Staphylococcus aureus* antigen.

4. The method of claim 3, wherein the *Staphylococcus aureus* antigen is present in or on a *Staphylococcus aureus* bacterium.

5. The method of claim 3, wherein the *Staphylococcus aureus* antigen is selected from the group consisting of FnBpA, FnBpB, LukD, LukE, LukF, SasA, SasD, SasG, SasI, SasK, Eap, Ebh, Emp, EsaB, EsaC, EsxA, EsxB, SdrC, SdrD, SdrE, IsdA, IsdB, ClfA, ClfB, Coa, Hla, IsdC, SasF, vWbp, and vWh.

6. The method of claim 1, wherein the antibody is a polyclonal antibody, a monoclonal antibody, or an antibody fragment.

7. The method of claim 1, wherein the antibody was generated using the nontoxigenic SpA variant as an antigen.

8. The method of claim 1, wherein the subject is at risk of developing a *Staphylococcus aureus* infection.

9. The method of claim 1, wherein the subject has a *Staphylococcus aureus* infection.

* * * * *

UNITED STATES PATENT AND TRADEMARK OFFICE
CERTIFICATE OF CORRECTION

PATENT NO. : 9,907,850 B2
APPLICATION NO. : 14/968023
DATED : March 6, 2018
INVENTOR(S) : Olaf Schneewind et al.

It is certified that error appears in the above-identified patent and that said Letters Patent is hereby corrected as shown below:

In the Specification

On Column 1, Line 26, the paragraph should read as follows:
-- This invention was made with government support under grant numbers AI057153, AI075258, AI052474, AI092711, and GM007281 awarded by the National Institutes of Health. The government has certain rights in the invention. --

Signed and Sealed this
Thirtieth Day of August, 2022

Katherine Kelly Vidal
*Director of the United States Patent and Trademark Office*

SEQUENCE LISTING

```
<160> NUMBER OF SEQ ID NOS: 155

<210> SEQ ID NO 1
<211> LENGTH: 150
<212> TYPE: DNA
<213> ORGANISM: Staphylococcus sp

<400> SEQUENCE: 1
ttcaacaaag atcaacaaag cgccttctat gaaatcttga acatgcctaa cttaaacgaa      60
gcgcaacgta acggcttcat tcaaagtctt aaagacgacc caagccaaag cactaatgtt     120
ttaggtgaag ctaaaaaatt aaacgaatct                                      150

<210> SEQ ID NO 2
<211> LENGTH: 54
<212> TYPE: PRT
<213> ORGANISM: Staphylococcus sp

<400> SEQUENCE: 2

Gln Gln Asn Asn Phe Asn Lys Asp Gln Gln Ser Ala Phe Tyr Glu Ile
1               5                   10                  15

Leu Asn Met Pro Asn Leu Asn Glu Ala Gln Arg Asn Gly Phe Ile Gln
                20                  25                  30

Ser Leu Lys Asp Asp Pro Ser Gln Ser Thr Asn Val Leu Gly Glu Ala
            35                  40                  45

Lys Lys Leu Asn Glu Ser
    50

<210> SEQ ID NO 3
<211> LENGTH: 51
<212> TYPE: PRT
<213> ORGANISM: Staphylococcus sp

<400> SEQUENCE: 3

Gln His Asp Glu Ala Gln Gln Asn Ala Phe Tyr Gln Val Leu Asn Met
1               5                   10                  15

Pro Asn Leu Asn Ala Asp Gln Arg Asn Gly Phe Ile Gln Ser Leu Lys
                20                  25                  30

Asp Asp Pro Ser Gln Ser Ala Asn Val Leu Gly Glu Ala Gln Lys Leu
            35                  40                  45

Asn Asp Ser
    50

<210> SEQ ID NO 4
<211> LENGTH: 52
<212> TYPE: PRT
<213> ORGANISM: Staphylococcus sp

<400> SEQUENCE: 4
```

```
Asn Asn Phe Asn Lys Glu Gln Gln Asn Ala Phe Tyr Glu Ile Leu Asn
1               5                   10                  15

Met Pro Asn Leu Asn Glu Glu Arg Asn Gly Phe Ile Gln Ser Leu
            20                  25                  30

Lys Asp Asp Pro Ser Gln Ser Ala Asn Leu Leu Ser Glu Ala Lys Lys
            35                  40                  45

Leu Asn Glu Ser
    50

<210> SEQ ID NO 5
<211> LENGTH: 52
<212> TYPE: PRT
<213> ORGANISM: Staphylococcus sp

<400> SEQUENCE: 5

Asn Lys Phe Asn Lys Glu Gln Gln Asn Ala Phe Tyr Glu Ile Leu His
1               5                   10                  15

Leu Pro Asn Leu Thr Glu Glu Gln Arg Asn Gly Phe Ile Gln Ser Leu
            20                  25                  30

Lys Asp Asp Pro Ser Val Ser Lys Glu Ile Leu Ala Glu Ala Lys Lys
            35                  40                  45

Leu Asn Asp Ala
    50

<210> SEQ ID NO 6
<211> LENGTH: 52
<212> TYPE: PRT
<213> ORGANISM: Staphylococcus sp

<400> SEQUENCE: 6

Asn Lys Phe Asn Lys Glu Gln Gln Asn Ala Phe Tyr Glu Ile Leu His
1               5                   10                  15

Leu Pro Asn Leu Asn Glu Glu Gln Arg Asn Gly Phe Ile Gln Ser Leu
            20                  25                  30

Lys Asp Asp Pro Ser Gln Ser Ala Asn Leu Leu Ala Glu Ala Lys Lys
            35                  40                  45

Leu Asn Asp Ala
    50

<210> SEQ ID NO 7
<211> LENGTH: 52
<212> TYPE: PRT
<213> ORGANISM: Staphylococcus sp
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (34)..(35)
<223> OTHER INFORMATION: Xaa can be any naturally occurring amino acid

<400> SEQUENCE: 7

Asn Asn Phe Asn Lys Asp Xaa Xaa Ser Ala Phe Tyr Glu Ile Leu Asn
1               5                   10                  15

Met Pro Asn Leu Asn Glu Ala Gln Arg Asn Gly Phe Ile Gln Ser Leu
            20                  25                  30

Lys Xaa Xaa Pro Ser Gln Ser Thr Asn Val Leu Gly Glu Ala Lys Lys
            35                  40                  45

Leu Asn Glu Ser
    50
```

```
<210> SEQ ID NO 8
<211> LENGTH: 52
<212> TYPE: PRT
<213> ORGANISM: Staphylococcus sp
<220> FEATURE:
<221> NAME/KEY: misc_feature
<222> LOCATION: (7)..(8)
<223> OTHER INFORMATION: Xaa can be any naturally occurring amino acid

<400> SEQUENCE: 8

Asn Asn Phe Asn Lys Asp Xaa Xaa Ser Ala Phe Tyr Glu Ile Leu Asn
1               5                   10                  15

Met Pro Asn Leu Asn Glu Ala Gln Arg Asn Gly Phe Ile Gln Ser Leu
            20                  25                  30

Lys Tyr Tyr Pro Ser Gln Ser Thr Asn Val Leu Gly Glu Ala Lys Lys
        35                  40                  45

Leu Asn Glu Ser
        50

<210> SEQ ID NO 9
<211> LENGTH: 450
<212> TYPE: PRT
<213> ORGANISM: Staphylococcus sp

<400> SEQUENCE: 9

Met Lys Lys Lys Asn Ile Tyr Ser Ile Arg Lys Leu Gly Val Gly Ile
1               5                   10                  15

Ala Ser Val Thr Leu Gly Thr Leu Leu Ile Ser Gly Gly Val Thr Pro
            20                  25                  30

Ala Ala Asn Ala Ala Gln His Asp Glu Ala Gln Gln Asn Ala Phe Tyr
        35                  40                  45

Gln Val Leu Asn Met Pro Asn Leu Asn Ala Asp Gln Arg Asn Gly Phe
    50                  55                  60

Ile Gln Ser Leu Lys Asp Asp Pro Ser Gln Ser Ala Asn Val Leu Gly
65                  70                  75                  80

Glu Ala Gln Lys Leu Asn Asp Ser Gln Ala Pro Lys Ala Asp Ala Gln
                85                  90                  95

Gln Asn Asn Phe Asn Lys Asp Gln Gln Ser Ala Phe Tyr Glu Ile Leu
            100                 105                 110

Asn Met Pro Asn Leu Asn Glu Ala Gln Arg Asn Gly Phe Ile Gln Ser
        115                 120                 125

Leu Lys Asp Asp Pro Ser Gln Ser Thr Asn Val Leu Gly Glu Ala Lys
    130                 135                 140

Lys Leu Asn Glu Ser Gln Ala Pro Lys Ala Asp Asn Asn Phe Asn Lys
145                 150                 155                 160

Glu Gln Gln Asn Ala Phe Tyr Glu Ile Leu Asn Met Pro Asn Leu Asn
                165                 170                 175

Glu Glu Gln Arg Asn Gly Phe Ile Gln Ser Leu Lys Asp Asp Pro Ser
            180                 185                 190

Gln Ser Ala Asn Leu Leu Ser Glu Ala Lys Lys Leu Asn Glu Ser Gln
        195                 200                 205

Ala Pro Lys Ala Asp Asn Lys Phe Asn Lys Glu Gln Gln Asn Ala Phe
    210                 215                 220

Tyr Glu Ile Leu His Leu Pro Asn Leu Asn Glu Glu Gln Arg Asn Gly
225                 230                 235                 240

Phe Ile Gln Ser Leu Lys Asp Asp Pro Ser Val Ser Lys Glu Ile Leu
```

-continued

```
                245                 250                 255
Ala Glu Ala Lys Lys Leu Asn Asp Ala Gln Ala Pro Lys Glu Glu Asp
            260                 265                 270

Asn Lys Lys Pro Gly Lys Glu Asp Gly Asn Lys Pro Gly Lys Glu Asp
        275                 280                 285

Gly Asn Lys Pro Gly Lys Glu Asp Asn Lys Lys Pro Gly Lys Glu Asp
    290                 295                 300

Gly Asn Lys Pro Gly Lys Glu Asp Asn Lys Pro Gly Lys Glu Asp
305                 310                 315                 320

Gly Asn Lys Pro Gly Lys Glu Asp Asn Lys Pro Gly Lys Glu Asp
            325                 330                 335

Gly Asn Lys Pro Gly Lys Glu Asp Gly Asn Lys Pro Gly Lys Glu Asp
        340                 345                 350

Gly Asn Gly Val His Val Val Lys Pro Gly Asp Thr Val Asn Asp Ile
    355                 360                 365

Ala Lys Ala Asn Gly Thr Thr Ala Asp Lys Ile Ala Ala Asp Asn Lys
    370                 375                 380

Leu Ala Asp Lys Asn Met Ile Lys Pro Gly Gln Glu Leu Val Val Asp
385                 390                 395                 400

Lys Lys Gln Pro Ala Asn His Ala Asp Ala Asn Lys Ala Gln Ala Leu
                405                 410                 415

Pro Glu Thr Gly Glu Glu Asn Pro Phe Ile Gly Thr Thr Val Phe Gly
            420                 425                 430

Gly Leu Ser Leu Ala Leu Gly Ala Ala Leu Leu Ala Gly Arg Arg Arg
        435                 440                 445

Glu Leu
    450

<210> SEQ ID NO 10
<211> LENGTH: 450
<212> TYPE: PRT
<213> ORGANISM: Staphylococcus sp

<400> SEQUENCE: 10

Met Lys Lys Asn Ile Tyr Ser Ile Arg Lys Leu Gly Val Gly Ile
1               5                   10                  15

Ala Ser Val Thr Leu Gly Thr Leu Leu Ile Ser Gly Gly Val Thr Pro
            20                  25                  30

Ala Ala Asn Ala Ala Gln His Asp Glu Ala Gln Gln Asn Ala Phe Tyr
        35                  40                  45

Gln Val Leu Asn Met Pro Asn Leu Asn Ala Asp Gln Arg Asn Gly Phe
    50                  55                  60

Ile Gln Ser Leu Lys Asp Asp Pro Ser Gln Ser Ala Asn Val Leu Gly
65                  70                  75                  80

Glu Ala Gln Lys Leu Asn Asp Ser Gln Ala Pro Lys Ala Asp Ala Gln
                85                  90                  95

Gln Asn Asn Phe Asn Lys Asp Gln Gln Ser Ala Phe Tyr Glu Ile Leu
            100                 105                 110

Asn Met Pro Asn Leu Asn Glu Ala Gln Arg Asn Gly Phe Ile Gln Ser
        115                 120                 125

Leu Lys Asp Asp Pro Ser Gln Ser Thr Asn Val Leu Gly Glu Ala Lys
    130                 135                 140

Lys Leu Asn Glu Ser Gln Ala Pro Lys Ala Asp Asn Asn Phe Asn Lys
145                 150                 155                 160
```

```
Glu Gln Gln Asn Ala Phe Tyr Glu Ile Leu Asn Met Pro Asn Leu Asn
                165                 170                 175

Glu Glu Gln Arg Asn Gly Phe Ile Gln Ser Leu Lys Asp Asp Pro Ser
            180                 185                 190

Gln Ser Ala Asn Leu Leu Ser Glu Ala Lys Lys Leu Asn Glu Ser Gln
        195                 200                 205

Ala Pro Lys Ala Asp Asn Lys Phe Asn Lys Glu Gln Gln Asn Ala Phe
    210                 215                 220

Tyr Glu Ile Leu His Leu Pro Asn Leu Asn Glu Gln Arg Asn Gly
225                 230                 235                 240

Phe Ile Gln Ser Leu Lys Asp Asp Pro Ser Val Ser Lys Glu Ile Leu
                245                 250                 255

Ala Glu Ala Lys Lys Leu Asn Asp Ala Gln Ala Pro Lys Glu Glu Asp
            260                 265                 270

Asn Lys Lys Pro Gly Lys Glu Asp Gly Asn Lys Pro Gly Lys Glu Asp
        275                 280                 285

Gly Asn Lys Pro Gly Lys Glu Asp Asn Lys Pro Gly Lys Glu Asp
    290                 295                 300

Gly Asn Lys Pro Gly Lys Glu Asp Asn Asn Lys Pro Gly Lys Glu Asp
305                 310                 315                 320

Gly Asn Lys Pro Gly Lys Glu Asp Asn Asn Lys Pro Gly Lys Glu Asp
                325                 330                 335

Gly Asn Lys Pro Gly Lys Glu Asp Gly Asn Lys Pro Gly Lys Glu Asp
            340                 345                 350

Gly Asn Gly Val His Val Val Lys Pro Gly Asp Thr Val Asn Asp Ile
        355                 360                 365

Ala Lys Ala Asn Gly Thr Thr Ala Asp Lys Ile Ala Ala Asp Asn Lys
    370                 375                 380

Leu Ala Asp Lys Asn Met Ile Lys Pro Gly Gln Glu Leu Val Val Asp
385                 390                 395                 400

Lys Lys Gln Pro Ala Asn His Ala Asp Ala Asn Lys Ala Gln Ala Leu
                405                 410                 415

Pro Glu Thr Gly Glu Glu Asn Pro Phe Ile Gly Thr Thr Val Phe Gly
            420                 425                 430

Gly Leu Ser Leu Ala Leu Gly Ala Ala Leu Leu Ala Gly Arg Arg Arg
        435                 440                 445

Glu Leu
    450

<210> SEQ ID NO 11
<211> LENGTH: 97
<212> TYPE: PRT
<213> ORGANISM: Staphylococcus sp

<400> SEQUENCE: 11

Met Ala Met Ile Lys Met Ser Pro Glu Glu Ile Arg Ala Lys Ser Gln
1               5                   10                  15

Ser Tyr Gly Gln Gly Ser Asp Gln Ile Arg Gln Ile Leu Ser Asp Leu
            20                  25                  30

Thr Arg Ala Gln Gly Glu Ile Ala Ala Asn Trp Glu Gly Gln Ala Phe
        35                  40                  45

Ser Arg Phe Glu Glu Gln Phe Gln Leu Ser Pro Lys Val Glu Lys
    50                  55                  60

Phe Ala Gln Leu Leu Glu Glu Ile Lys Gln Gln Leu Asn Ser Thr Ala
65                  70                  75                  80
```

```
Asp Ala Val Gln Glu Gln Asp Gln Gln Leu Ser Asn Asn Phe Gly Leu
                85                  90                  95

Gln

<210> SEQ ID NO 12
<211> LENGTH: 102
<212> TYPE: PRT
<213> ORGANISM: Staphylococcus sp

<400> SEQUENCE: 12

Met Gly Gly Tyr Lys Gly Ile Lys Ala Asp Gly Gly Lys Val Asn Gln
1               5                   10                  15

Ala Lys Gln Leu Ala Ala Lys Ile Ala Lys Asp Ile Glu Ala Cys Gln
            20                  25                  30

Lys Gln Thr Gln Gln Leu Ala Glu Tyr Ile Glu Gly Ser Asp Trp Glu
        35                  40                  45

Gly Gln Phe Ala Asn Lys Val Lys Asp Val Leu Leu Ile Met Ala Lys
    50                  55                  60

Phe Gln Glu Glu Leu Val Gln Pro Met Ala Asp His Gln Lys Ala Ile
65                  70                  75                  80

Asp Asn Leu Ser Gln Asn Leu Ala Lys Tyr Asp Thr Leu Ser Ile Lys
                85                  90                  95

Gln Gly Leu Asp Arg Val
            100

<210> SEQ ID NO 13
<211> LENGTH: 1385
<212> TYPE: PRT
<213> ORGANISM: Staphylococcus sp

<400> SEQUENCE: 13

Met Leu Asn Arg Glu Asn Lys Thr Ala Ile Thr Arg Lys Gly Met Val
1               5                   10                  15

Ser Asn Arg Leu Asn Lys Phe Ser Ile Arg Lys Tyr Thr Val Gly Thr
            20                  25                  30

Ala Ser Ile Leu Val Gly Thr Thr Leu Ile Phe Gly Leu Gly Asn Gln
        35                  40                  45

Glu Ala Lys Ala Ala Glu Ser Thr Asn Lys Glu Leu Asn Glu Ala Thr
    50                  55                  60

Thr Ser Ala Ser Asp Asn Gln Ser Ser Asp Lys Val Asp Met Gln Gln
65                  70                  75                  80

Leu Asn Gln Glu Asp Asn Thr Lys Asn Asp Asn Gln Lys Glu Met Val
                85                  90                  95

Ser Ser Gln Gly Asn Glu Thr Thr Ser Asn Gly Asn Lys Ser Ile Glu
                100                 105                 110

Lys Glu Ser Val Gln Ser Thr Thr Gly Asn Lys Val Glu Val Ser Thr
            115                 120                 125

Ala Lys Ser Asp Glu Gln Ala Ser Pro Lys Ser Thr Asn Glu Asp Leu
        130                 135                 140

Asn Thr Lys Gln Thr Ile Ser Asn Gln Glu Gly Leu Gln Pro Asp Leu
145                 150                 155                 160

Leu Glu Asn Lys Ser Val Val Asn Val Gln Pro Thr Asn Glu Glu Asn
                165                 170                 175

Lys Lys Val Asp Ala Lys Thr Glu Ser Thr Thr Leu Asn Val Lys Ser
                180                 185                 190
```

```
Asp Ala Ile Lys Ser Asn Ala Glu Thr Leu Val Asp Asn Asn Ser Asn
            195                 200                 205

Ser Asn Asn Glu Asn Asn Ala Asp Ile Ile Leu Pro Lys Ser Thr Ala
    210                 215                 220

Pro Lys Ser Leu Asn Thr Arg Met Arg Met Ala Ala Ile Gln Pro Asn
225                 230                 235                 240

Ser Thr Asp Ser Lys Asn Val Asn Asp Leu Ile Thr Ser Asn Thr Thr
                245                 250                 255

Leu Thr Val Val Asp Ala Asp Asn Ser Lys Thr Ile Val Pro Ala Gln
            260                 265                 270

Asp Tyr Leu Ser Leu Lys Ser Gln Ile Thr Val Asp Asp Lys Val Lys
        275                 280                 285

Ser Gly Asp Tyr Phe Thr Ile Lys Tyr Ser Asp Thr Val Gln Val Tyr
    290                 295                 300

Gly Leu Asn Pro Glu Asp Ile Lys Asn Ile Gly Asp Ile Lys Asp Pro
305                 310                 315                 320

Asn Asn Gly Glu Thr Ile Ala Thr Ala Lys His Asp Thr Ala Asn Asn
                325                 330                 335

Leu Ile Thr Tyr Thr Phe Thr Asp Tyr Val Asp Arg Phe Asn Ser Val
            340                 345                 350

Lys Met Gly Ile Asn Tyr Ser Ile Tyr Met Asp Ala Asp Thr Ile Pro
        355                 360                 365

Val Asp Lys Lys Asp Val Pro Phe Ser Val Thr Ile Gly Asn Gln Ile
    370                 375                 380

Thr Thr Thr Thr Ala Asp Ile Thr Tyr Pro Ala Tyr Lys Glu Ala Asp
385                 390                 395                 400

Asn Asn Ser Ile Gly Ser Ala Phe Thr Glu Thr Val Ser His Val Gly
                405                 410                 415

Asn Val Glu Asp Pro Gly Tyr Tyr Asn Gln Val Val Tyr Val Asn Pro
            420                 425                 430

Met Asp Lys Asp Leu Lys Gly Ala Lys Leu Lys Val Glu Ala Tyr His
        435                 440                 445

Pro Lys Tyr Pro Thr Asn Ile Gly Gln Ile Asn Gln Asn Val Thr Asn
450                 455                 460

Ile Lys Ile Tyr Arg Val Pro Glu Gly Tyr Thr Leu Asn Lys Gly Tyr
465                 470                 475                 480

Asp Val Asn Thr Asn Asp Leu Val Asp Val Thr Asp Glu Phe Lys Asn
                485                 490                 495

Lys Met Thr Tyr Gly Ser Asn Gln Ser Val Asn Leu Asp Phe Gly Asp
            500                 505                 510

Ile Thr Ser Ala Tyr Val Val Met Val Asn Thr Lys Phe Gln Tyr Thr
        515                 520                 525

Asn Ser Glu Ser Pro Thr Leu Val Gln Met Ala Thr Leu Ser Ser Thr
    530                 535                 540

Gly Asn Lys Ser Val Ser Thr Gly Asn Ala Leu Gly Phe Thr Asn Asn
545                 550                 555                 560

Gln Ser Gly Gly Ala Gly Gln Glu Val Tyr Lys Ile Gly Asn Tyr Val
                565                 570                 575

Trp Glu Asp Thr Asn Lys Asn Gly Val Gln Glu Leu Gly Glu Lys Gly
            580                 585                 590

Val Gly Asn Val Thr Val Thr Val Phe Asp Asn Asn Thr Asn Thr Lys
        595                 600                 605

Val Gly Glu Ala Val Thr Lys Glu Asp Gly Ser Tyr Leu Ile Pro Asn
```

-continued

```
            610                 615                 620
Leu Pro Asn Gly Asp Tyr Arg Val Glu Phe Ser Asn Leu Pro Lys Gly
625                 630                 635                 640

Tyr Glu Val Thr Pro Ser Lys Gln Gly Asn Asn Glu Glu Leu Asp Ser
                    645                 650                 655

Asn Gly Leu Ser Ser Val Ile Thr Val Asn Gly Lys Asp Asn Leu Ser
                660                 665                 670

Ala Asp Leu Gly Ile Tyr Lys Pro Lys Tyr Asn Leu Gly Asp Tyr Val
            675                 680                 685

Trp Glu Asp Thr Asn Lys Asn Gly Ile Gln Asp Gln Asp Glu Lys Gly
        690                 695                 700

Ile Ser Gly Val Thr Val Thr Leu Lys Asp Glu Asn Gly Asn Val Leu
705                 710                 715                 720

Lys Thr Val Thr Thr Asp Ala Asp Gly Lys Tyr Lys Phe Thr Asp Leu
                    725                 730                 735

Asp Asn Gly Asn Tyr Lys Val Glu Phe Thr Thr Pro Glu Gly Tyr Thr
                740                 745                 750

Pro Thr Thr Val Thr Ser Gly Ser Asp Ile Glu Lys Asp Ser Asn Gly
            755                 760                 765

Leu Thr Thr Gly Val Ile Asn Gly Ala Asp Asn Met Thr Leu Asp
        770                 775                 780

Ser Gly Phe Tyr Lys Thr Pro Lys Tyr Asn Leu Gly Asn Tyr Val Trp
785                 790                 795                 800

Glu Asp Thr Asn Lys Asp Gly Lys Gln Asp Ser Thr Glu Lys Gly Ile
                    805                 810                 815

Ser Gly Val Thr Val Thr Leu Lys Asn Glu Asn Gly Glu Val Leu Gln
                820                 825                 830

Thr Thr Lys Thr Asp Lys Asp Gly Lys Tyr Gln Phe Thr Gly Leu Glu
            835                 840                 845

Asn Gly Thr Tyr Lys Val Glu Phe Glu Thr Pro Ser Gly Tyr Thr Pro
        850                 855                 860

Thr Gln Val Gly Ser Gly Thr Asp Glu Gly Ile Asp Ser Asn Gly Thr
865                 870                 875                 880

Ser Thr Thr Gly Val Ile Lys Asp Lys Asp Asn Asp Thr Ile Asp Ser
                    885                 890                 895

Gly Phe Tyr Lys Pro Thr Tyr Asn Leu Gly Asp Tyr Val Trp Glu Asp
                900                 905                 910

Thr Asn Lys Asn Gly Val Gln Asp Lys Asp Glu Lys Gly Ile Ser Gly
            915                 920                 925

Val Thr Val Thr Leu Lys Asp Glu Asn Asp Lys Val Leu Lys Thr Val
930                 935                 940

Thr Thr Asp Glu Asn Gly Lys Tyr Gln Phe Thr Asp Leu Asn Asn Gly
945                 950                 955                 960

Thr Tyr Lys Val Glu Phe Glu Thr Pro Ser Gly Tyr Thr Pro Thr Ser
                    965                 970                 975

Val Thr Ser Gly Asn Asp Thr Glu Lys Asp Ser Asn Gly Leu Thr Thr
                980                 985                 990

Thr Gly Val Ile Lys Asp Ala Asp Asn Met Thr Leu Asp Ser Gly Phe
            995                 1000                1005

Tyr Lys Thr Pro Lys Tyr Ser Leu Gly Asp Tyr Val Trp Tyr Asp
        1010                1015                1020

Ser Asn Lys Asp Gly Lys Gln Asp Ser Thr Glu Lys Gly Ile Lys
    1025                1030                1035
```

```
Asp Val Lys Val Ile Leu Leu Asn Glu Lys Gly Glu Val Ile Gly
    1040                1045                1050

Thr Thr Lys Thr Asp Glu Asn Gly Lys Tyr Arg Phe Asp Asn Leu
    1055                1060                1065

Asp Ser Gly Lys Tyr Lys Val Ile Phe Glu Lys Pro Thr Gly Leu
    1070                1075                1080

Thr Gln Thr Gly Thr Asn Thr Thr Glu Asp Asp Lys Asp Ala Asp
    1085                1090                1095

Gly Gly Glu Val Asp Val Thr Ile Thr Asp His Asp Asp Phe Thr
    1100                1105                1110

Leu Asp Asn Gly Tyr Tyr Glu Glu Thr Ser Asp Ser Asp Ser
    1115                1120                1125

Asp Ser Asp Ser Asp Ser Asp Ser Asp Ser Asp Ser Asp Ser Asp
    1130                1135                1140

Ser Asp Ser Asp Ser Asp Ser Asp Ser Asp Ser Asp Ser Asp Ser
    1145                1150                1155

Asp Ser Asp Ser Asp Ser Asp Ser Asp Ser Asp Ser Asp Ser Asp
    1160                1165                1170

Ser Asp Ser Asp Ser Asp Ser Asp Ser Asp Ser Asp Ser Asp Ser
    1175                1180                1185

Asp Ser Asp Ser Asp Ser Asp Ser Asp Ser Asp Ser Asp Ser Asp
    1190                1195                1200

Ser Asp Ser Asp Ser Asp Ser Asp Ser Asp Ser Asp Ser Asp Ser
    1205                1210                1215

Asp Ser Asp Ser Asp Ser Asp Ser Asp Ser Asp Ser Asp Ser Asp
    1220                1225                1230

Ser Asp Ser Asp Ser Asp Ser Asp Ser Asp Ser Asp Ser Asp Ser
    1235                1240                1245

Asp Ser Asp Ser Asp Ser Asp Ser Asp Ser Asp Ser Asp Ser Asp
    1250                1255                1260

Ser Asp Ser Asp Ser Asp Ser Asp Ser Asp Ser Asp Ser Asp Ser
    1265                1270                1275

Asp Ser Asp Ser Asp Ser Asp Ser Asp Ser Asp Ser Asp Ser Asp
    1280                1285                1290

Ser Asp Ser Asp Ser Asp Ser Asp Ser Asp Ser Asp Ser Asp Ser
    1295                1300                1305

Asp Ser Asp Ser Asp Ser Asp Ser Asp Ser Asp Ser Asp Ser Asp
    1310                1315                1320

Ser Asp Ala Gly Lys His Thr Pro Val Lys Pro Met Ser Thr Thr
    1325                1330                1335

Lys Asp His His Asn Lys Ala Lys Ala Leu Pro Glu Thr Gly Asn
    1340                1345                1350

Glu Asn Ser Gly Ser Asn Asn Ala Thr Leu Phe Gly Gly Leu Phe
    1355                1360                1365

Ala Ala Leu Gly Ser Leu Leu Leu Phe Gly Arg Arg Lys Lys Gln
    1370                1375                1380

Asn Lys
    1385

<210> SEQ ID NO 14
<211> LENGTH: 1141
<212> TYPE: PRT
<213> ORGANISM: Staphylococcus sp
```

```
<400> SEQUENCE: 14

Met Ile Asn Arg Asp Asn Lys Lys Ala Ile Thr Lys Lys Gly Met Ile
1               5                   10                  15

Ser Asn Arg Leu Asn Lys Phe Ser Ile Arg Lys Tyr Thr Val Gly Thr
            20                  25                  30

Ala Ser Ile Leu Val Gly Thr Thr Leu Ile Phe Gly Leu Gly Asn Gln
        35                  40                  45

Glu Ala Lys Ala Ala Glu Asn Thr Ser Thr Glu Asn Ala Lys Gln Asp
    50                  55                  60

Asp Ala Thr Thr Ser Asp Asn Lys Glu Val Val Ser Glu Thr Glu Asn
65                  70                  75                  80

Asn Ser Thr Thr Glu Asn Asp Ser Thr Asn Pro Ile Lys Lys Glu Thr
                85                  90                  95

Asn Thr Asp Ser Gln Pro Glu Ala Lys Glu Ser Thr Thr Ser Ser
            100                 105                 110

Thr Gln Gln Gln Gln Asn Asn Val Thr Ala Thr Thr Glu Thr Lys Pro
            115                 120                 125

Gln Asn Ile Glu Lys Glu Asn Val Lys Pro Ser Thr Asp Lys Thr Ala
            130                 135                 140

Thr Glu Asp Thr Ser Val Ile Leu Glu Glu Lys Lys Ala Pro Asn Tyr
145                 150                 155                 160

Thr Asn Asn Asp Val Thr Thr Lys Pro Ser Thr Ser Glu Ile Gln Thr
                165                 170                 175

Lys Pro Thr Thr Pro Gln Glu Ser Thr Asn Ile Glu Asn Ser Gln Pro
            180                 185                 190

Gln Pro Thr Pro Ser Lys Val Asp Asn Gln Val Thr Asp Ala Thr Asn
            195                 200                 205

Pro Lys Glu Pro Val Asn Val Ser Lys Glu Glu Leu Lys Asn Asn Pro
210                 215                 220

Glu Lys Leu Lys Glu Leu Val Arg Asn Asp Asn Thr Asp Arg Ser
225                 230                 235                 240

Thr Lys Pro Val Ala Thr Ala Pro Thr Ser Val Ala Pro Lys Arg Leu
            245                 250                 255

Asn Ala Lys Met Arg Phe Ala Val Ala Gln Pro Ala Ala Val Ala Ser
            260                 265                 270

Asn Asn Val Asn Asp Leu Ile Thr Val Thr Lys Gln Thr Ile Lys Val
            275                 280                 285

Gly Asp Gly Lys Asp Asn Val Ala Ala Ala His Asp Gly Lys Asp Ile
            290                 295                 300

Glu Tyr Asp Thr Glu Phe Thr Ile Asp Asn Lys Val Lys Lys Gly Asp
305                 310                 315                 320

Thr Met Thr Ile Asn Tyr Asp Lys Asn Val Ile Pro Ser Asp Leu Thr
                325                 330                 335

Asp Lys Asn Asp Pro Ile Asp Ile Thr Asp Pro Ser Gly Glu Val Ile
            340                 345                 350

Ala Lys Gly Thr Phe Asp Lys Ala Thr Lys Gln Ile Thr Tyr Thr Phe
            355                 360                 365

Thr Asp Tyr Val Asp Lys Tyr Glu Asp Ile Lys Ala Arg Leu Thr Leu
370                 375                 380

Tyr Ser Tyr Ile Asp Lys Gln Ala Val Pro Asn Glu Thr Ser Leu Asn
385                 390                 395                 400

Leu Thr Phe Ala Thr Ala Gly Lys Glu Thr Ser Gln Asn Val Ser Val
            405                 410                 415
```

-continued

```
Asp Tyr Gln Asp Pro Met Val His Gly Asp Ser Asn Ile Gln Ser Ile
            420                 425                 430

Phe Thr Lys Leu Asp Glu Asn Lys Gln Thr Ile Glu Gln Gln Ile Tyr
        435                 440                 445

Val Asn Pro Leu Lys Lys Thr Ala Thr Asn Thr Lys Val Asp Ile Ala
    450                 455                 460

Gly Ser Gln Val Asp Asp Tyr Gly Asn Ile Lys Leu Gly Asn Gly Ser
465                 470                 475                 480

Thr Ile Ile Asp Gln Asn Thr Glu Ile Lys Val Tyr Lys Val Asn Pro
                485                 490                 495

Asn Gln Gln Leu Pro Gln Ser Asn Arg Ile Tyr Asp Phe Ser Gln Tyr
            500                 505                 510

Glu Asp Val Thr Ser Gln Phe Asp Asn Lys Ser Phe Ser Asn Asn
        515                 520                 525

Val Ala Thr Leu Asp Phe Gly Asp Ile Asn Ser Ala Tyr Ile Ile Lys
    530                 535                 540

Val Val Ser Lys Tyr Thr Pro Thr Ser Asp Gly Glu Leu Asp Ile Ala
545                 550                 555                 560

Gln Gly Thr Ser Met Arg Thr Thr Asp Lys Tyr Gly Tyr Tyr Asn Tyr
                565                 570                 575

Ala Gly Tyr Ser Asn Phe Ile Val Thr Ser Asn Asp Thr Gly Gly Gly
            580                 585                 590

Asp Gly Thr Val Lys Pro Glu Glu Lys Leu Tyr Lys Ile Gly Asp Tyr
        595                 600                 605

Val Trp Glu Asp Val Asp Lys Asp Gly Val Gln Gly Thr Asp Ser Lys
    610                 615                 620

Glu Lys Pro Met Ala Asn Val Leu Val Thr Leu Thr Tyr Pro Asp Gly
625                 630                 635                 640

Thr Thr Lys Ser Val Arg Thr Asp Ala Asn Gly His Tyr Glu Phe Gly
                645                 650                 655

Gly Leu Lys Asp Gly Glu Thr Tyr Thr Val Lys Phe Glu Thr Pro Ala
            660                 665                 670

Gly Tyr Leu Pro Thr Lys Val Asn Gly Thr Thr Asp Gly Glu Lys Asp
        675                 680                 685

Ser Asn Gly Ser Ser Ile Thr Val Lys Ile Asn Gly Lys Asp Asp Met
    690                 695                 700

Ser Leu Asp Thr Gly Phe Tyr Lys Glu Pro Lys Tyr Asn Leu Gly Asp
705                 710                 715                 720

Tyr Val Trp Glu Asp Thr Asn Lys Asp Gly Ile Gln Asp Ala Asn Glu
                725                 730                 735

Pro Gly Ile Lys Asp Val Lys Val Thr Leu Lys Asp Ser Thr Gly Lys
            740                 745                 750

Val Ile Gly Thr Thr Thr Thr Asp Ala Ser Gly Lys Tyr Lys Phe Thr
        755                 760                 765

Asp Leu Asp Asn Gly Asn Tyr Thr Val Glu Phe Glu Thr Pro Ala Gly
    770                 775                 780

Tyr Thr Pro Thr Val Lys Asn Thr Thr Ala Glu Asp Lys Asp Ser Asn
785                 790                 795                 800

Gly Leu Thr Thr Thr Gly Val Ile Lys Asp Ala Asp Asn Met Thr Leu
                805                 810                 815

Asp Ser Gly Phe Tyr Lys Thr Pro Lys Tyr Ser Leu Gly Asp Tyr Val
            820                 825                 830
```

-continued

Trp Tyr Asp Ser Asn Lys Asp Gly Lys Gln Asp Ser Thr Glu Lys Gly
            835                 840                 845

Ile Lys Asp Val Lys Val Thr Leu Leu Asn Glu Lys Gly Glu Val Ile
850                 855                 860

Gly Thr Thr Lys Thr Asp Glu Asn Gly Lys Tyr Arg Phe Asp Asn Leu
865                 870                 875                 880

Asp Ser Gly Lys Tyr Lys Val Ile Phe Glu Lys Pro Ala Gly Leu Thr
            885                 890                 895

Gln Thr Val Thr Asn Thr Thr Glu Asp Lys Asp Ala Asp Gly Gly
            900                 905                 910

Glu Val Asp Val Thr Ile Thr Asp His Asp Asp Phe Thr Leu Asp Asn
            915                 920                 925

Gly Tyr Phe Glu Glu Asp Thr Ser Asp Ser Asp Ser Asp Ser Asp Ser
930                 935                 940

Asp Ser Asp Ser Asp Ser Asp Ser Asp Ser Asp Ser Asp Ser Asp Ser
945                 950                 955                 960

Asp Ser Asp Ser Asp Ser Asp Ser Asp Ser Asp Ser Asp Ser Asp Ser
            965                 970                 975

Asp Ser Asp Ser Asp Ser Asp Ser Asp Ser Asp Ser Asp Ser Asp Ser
            980                 985                 990

Asp Ser Asp Ser Asp Ser Asp Ser Asp Ser Asp Ser Asp Ser Asp Ser
            995                 1000                1005

Asp Ser Asp Ser Asp Ser Asp Ser Asp Ser Asp Ser Asp Ser Asp
            1010                1015                1020

Ser Asp Ser Asp Ser Asp Ser Asp Ser Asp Ser Asp Ser Asp Ser
            1025                1030                1035

Asp Ser Asp Ser Asp Ser Asp Ser Asp Ser Asp Ser Asp Ser Asp
            1040                1045                1050

Ser Asp Ser Asp Ser Asp Ser Asp Ser Asp Ser Asp Ser Asp Ser
            1055                1060                1065

Asp Ser Asp Ser Asp Ser Asp Ser Asp Ser Asp Ser Asp Ala Gly
            1070                1075                1080

Lys His Thr Pro Val Lys Pro Met Ser Thr Thr Lys Asp His His
            1085                1090                1095

Asn Lys Ala Lys Ala Leu Pro Glu Thr Gly Ser Glu Asn Asn Gly
            1100                1105                1110

Ser Asn Asn Ala Thr Leu Phe Gly Gly Leu Phe Ala Ala Leu Gly
            1115                1120                1125

Ser Leu Leu Leu Phe Gly Arg Arg Lys Lys Gln Asn Lys
            1130                1135                1140

<210> SEQ ID NO 15
<211> LENGTH: 350
<212> TYPE: PRT
<213> ORGANISM: Staphylococcus sp

<400> SEQUENCE: 15

Met Thr Lys His Tyr Leu Asn Ser Lys Tyr Gln Ser Glu Gln Arg Ser
1               5                   10                  15

Ser Ala Met Lys Lys Ile Thr Met Gly Thr Ala Ser Ile Ile Leu Gly
            20                  25                  30

Ser Leu Val Tyr Ile Gly Ala Asp Ser Gln Gln Val Asn Ala Ala Thr
        35                  40                  45

Glu Ala Thr Asn Ala Thr Asn Asn Gln Ser Thr Gln Val Ser Gln Ala
    50                  55                  60

```
Thr Ser Gln Pro Ile Asn Phe Gln Val Gln Lys Asp Gly Ser Ser Glu
65                  70                  75                  80

Lys Ser His Met Asp Asp Tyr Met Gln His Pro Gly Lys Val Ile Lys
                85                  90                  95

Gln Asn Asn Lys Tyr Tyr Phe Gln Thr Val Leu Asn Asn Ala Ser Phe
            100                 105                 110

Trp Lys Glu Tyr Lys Phe Tyr Asn Ala Asn Asn Gln Glu Leu Ala Thr
        115                 120                 125

Thr Val Val Asn Asp Asn Lys Lys Ala Asp Thr Arg Thr Ile Asn Val
130                 135                 140

Ala Val Glu Pro Gly Tyr Lys Ser Leu Thr Thr Lys Val His Ile Val
145                 150                 155                 160

Val Pro Gln Ile Asn Tyr Asn His Arg Tyr Thr Thr His Leu Glu Phe
                165                 170                 175

Glu Lys Ala Ile Pro Thr Leu Ala Asp Ala Ala Lys Pro Asn Asn Val
            180                 185                 190

Lys Pro Val Gln Pro Lys Pro Ala Gln Pro Lys Thr Pro Thr Glu Gln
        195                 200                 205

Thr Lys Pro Val Gln Pro Lys Val Glu Lys Val Lys Pro Thr Val Thr
210                 215                 220

Thr Thr Ser Lys Val Glu Asp Asn His Ser Thr Lys Val Val Ser Thr
225                 230                 235                 240

Asp Thr Thr Lys Asp Gln Thr Lys Thr Gln Thr Ala His Thr Val Lys
                245                 250                 255

Thr Ala Gln Thr Ala Gln Glu Gln Asn Lys Val Gln Thr Pro Val Lys
            260                 265                 270

Asp Val Ala Thr Ala Lys Ser Glu Ser Asn Asn Gln Ala Val Ser Asp
        275                 280                 285

Asn Lys Ser Gln Gln Thr Asn Lys Val Thr Lys His Asn Glu Thr Pro
290                 295                 300

Lys Gln Ala Ser Lys Ala Lys Glu Leu Pro Lys Thr Gly Leu Thr Ser
305                 310                 315                 320

Val Asp Asn Phe Ile Ser Thr Val Ala Phe Ala Thr Leu Ala Leu Leu
                325                 330                 335

Gly Ser Leu Ser Leu Leu Leu Phe Lys Arg Lys Glu Ser Lys
            340                 345                 350

<210> SEQ ID NO 16
<211> LENGTH: 645
<212> TYPE: PRT
<213> ORGANISM: Staphylococcus sp

<400> SEQUENCE: 16

Met Asn Lys Gln Gln Lys Glu Phe Lys Ser Phe Tyr Ser Ile Arg Lys
1               5                   10                  15

Ser Ser Leu Gly Val Ala Ser Val Ala Ile Ser Thr Leu Leu Leu Leu
            20                  25                  30

Met Ser Asn Gly Glu Ala Gln Ala Ala Ala Glu Glu Thr Gly Gly Thr
        35                  40                  45

Asn Thr Glu Ala Gln Pro Lys Thr Glu Ala Val Ala Ser Pro Thr Thr
    50                  55                  60

Thr Ser Glu Lys Ala Pro Glu Thr Lys Pro Val Ala Asn Ala Val Ser
65                  70                  75                  80

Val Ser Asn Lys Glu Val Glu Ala Pro Thr Ser Glu Thr Lys Glu Ala
```

```
                    85                  90                  95
Lys Glu Val Lys Glu Val Lys Ala Pro Lys Glu Thr Lys Ala Val Lys
                100                 105                 110

Pro Ala Ala Lys Ala Thr Asn Asn Thr Tyr Pro Ile Leu Asn Gln Glu
                115                 120                 125

Leu Arg Glu Ala Ile Lys Asn Pro Ala Ile Lys Asp Lys Asp His Ser
    130                 135                 140

Ala Pro Asn Ser Arg Pro Ile Asp Phe Glu Met Lys Lys Glu Asn Gly
145                 150                 155                 160

Glu Gln Gln Phe Tyr His Tyr Ala Ser Ser Val Lys Pro Ala Arg Val
                165                 170                 175

Ile Phe Thr Asp Ser Lys Pro Glu Ile Glu Leu Gly Leu Gln Ser Gly
                180                 185                 190

Gln Phe Trp Arg Lys Phe Glu Val Tyr Glu Gly Asp Lys Lys Leu Pro
                195                 200                 205

Ile Lys Leu Val Ser Tyr Asp Thr Val Lys Asp Tyr Ala Tyr Ile Arg
    210                 215                 220

Phe Ser Val Ser Asn Gly Thr Lys Ala Val Lys Ile Val Ser Ser Thr
225                 230                 235                 240

His Phe Asn Asn Lys Glu Lys Tyr Asp Tyr Thr Leu Met Glu Phe
                245                 250                 255

Ala Gln Pro Ile Tyr Asn Ser Ala Asp Lys Phe Lys Thr Glu Glu Asp
                260                 265                 270

Tyr Lys Ala Glu Lys Leu Leu Ala Pro Tyr Lys Lys Ala Lys Thr Leu
                275                 280                 285

Glu Arg Gln Val Tyr Glu Leu Asn Lys Ile Gln Asp Lys Leu Pro Glu
                290                 295                 300

Lys Leu Lys Ala Glu Tyr Lys Lys Lys Leu Glu Asp Thr Lys Lys Ala
305                 310                 315                 320

Leu Asp Glu Gln Val Lys Ser Ala Ile Thr Glu Phe Gln Asn Val Gln
                325                 330                 335

Pro Thr Asn Glu Lys Met Thr Asp Leu Gln Asp Thr Lys Tyr Val Val
                340                 345                 350

Tyr Glu Ser Val Glu Asn Asn Glu Ser Met Met Asp Thr Phe Val Lys
                355                 360                 365

His Pro Ile Lys Thr Gly Met Leu Asn Gly Lys Lys Tyr Met Val Met
                370                 375                 380

Glu Thr Thr Asn Asp Asp Tyr Trp Lys Asp Phe Met Val Glu Gly Gln
385                 390                 395                 400

Arg Val Arg Thr Ile Ser Lys Asp Ala Lys Asn Asn Thr Arg Thr Ile
                405                 410                 415

Ile Phe Pro Tyr Val Glu Gly Lys Thr Leu Tyr Asp Ala Ile Val Lys
                420                 425                 430

Val His Val Lys Thr Ile Asp Tyr Asp Gly Gln Tyr His Val Arg Ile
                435                 440                 445

Val Asp Lys Glu Ala Phe Thr Lys Ala Asn Thr Asp Lys Ser Asn Lys
                450                 455                 460

Lys Glu Gln Gln Asp Asn Ser Ala Lys Lys Glu Ala Thr Pro Ala Thr
465                 470                 475                 480

Pro Ser Lys Pro Thr Pro Ser Pro Val Glu Lys Glu Ser Gln Lys Gln
                485                 490                 495

Asp Ser Gln Lys Asp Asp Asn Lys Gln Leu Pro Ser Val Glu Lys Glu
                500                 505                 510
```

```
Asn Asp Ala Ser Ser Glu Ser Gly Lys Asp Lys Thr Pro Ala Thr Lys
            515                 520                 525

Pro Thr Lys Gly Glu Val Glu Ser Ser Ser Thr Thr Pro Thr Lys Val
        530                 535                 540

Val Ser Thr Thr Gln Asn Val Ala Lys Pro Thr Thr Ala Ser Ser Lys
545                 550                 555                 560

Thr Thr Lys Asp Val Val Gln Thr Ser Ala Gly Ser Ser Glu Ala Lys
                565                 570                 575

Asp Ser Ala Pro Leu Gln Lys Ala Asn Ile Lys Asn Thr Asn Asp Gly
            580                 585                 590

His Thr Gln Ser Gln Asn Asn Lys Asn Thr Gln Glu Asn Lys Ala Lys
        595                 600                 605

Ser Leu Pro Gln Thr Gly Glu Glu Ser Asn Lys Asp Met Thr Leu Pro
            610                 615                 620

Leu Met Ala Leu Leu Ala Leu Ser Ser Ile Val Ala Phe Val Leu Pro
625                 630                 635                 640

Arg Lys Arg Lys Asn
                645

<210> SEQ ID NO 17
<211> LENGTH: 80
<212> TYPE: PRT
<213> ORGANISM: Staphylococcus sp

<400> SEQUENCE: 17

Met Asn Gln His Val Lys Val Thr Phe Asp Phe Thr Asn Tyr Asn Tyr
1               5                   10                  15

Gly Thr Tyr Asp Leu Ala Val Pro Ala Tyr Leu Pro Ile Lys Asn Leu
            20                  25                  30

Ile Ala Leu Val Leu Asp Ser Leu Asp Ile Ser Ile Phe Asp Val Asn
        35                  40                  45

Thr Gln Ile Lys Val Met Thr Lys Gly Gln Leu Leu Val Glu Asn Asp
    50                  55                  60

Arg Leu Ile Asp Tyr Gln Ile Ala Asp Gly Asp Ile Leu Lys Leu Leu
65                  70                  75                  80

<210> SEQ ID NO 18
<211> LENGTH: 877
<212> TYPE: PRT
<213> ORGANISM: Staphylococcus sp

<400> SEQUENCE: 18

Met Lys Lys Arg Ile Asp Tyr Leu Ser Asn Lys Gln Asn Lys Tyr Ser
1               5                   10                  15

Ile Arg Arg Phe Thr Val Gly Thr Thr Ser Val Ile Val Gly Ala Thr
            20                  25                  30

Ile Leu Phe Gly Ile Gly Asn His Gln Ala Gln Ala Ser Glu Gln Ser
        35                  40                  45

Asn Asp Thr Thr Gln Ser Ser Lys Asn Asn Ala Ser Ala Asp Ser Glu
    50                  55                  60

Lys Asn Asn Met Ile Glu Thr Pro Gln Leu Asn Thr Thr Ala Asn Asp
65                  70                  75                  80

Thr Ser Asp Ile Ser Ala Asn Thr Asn Ser Ala Asn Val Asp Ser Thr
                85                  90                  95

Thr Lys Pro Met Ser Thr Gln Thr Ser Asn Thr Thr Thr Thr Glu Pro
            100                 105                 110
```

```
Ala Ser Thr Asn Glu Thr Pro Gln Pro Thr Ala Ile Lys Asn Gln Ala
            115                 120                 125
Thr Ala Ala Lys Met Gln Asp Gln Thr Val Pro Gln Glu Ala Asn Ser
        130                 135                 140
Gln Val Asp Asn Lys Thr Thr Asn Asp Ala Asn Ser Ile Ala Thr Asn
145                 150                 155                 160
Ser Glu Leu Lys Asn Ser Gln Thr Leu Asp Leu Pro Gln Ser Ser Pro
                165                 170                 175
Gln Thr Ile Ser Asn Ala Gln Gly Thr Ser Lys Pro Ser Val Arg Thr
            180                 185                 190
Arg Ala Val Arg Ser Leu Ala Val Ala Glu Pro Val Val Asn Ala Ala
        195                 200                 205
Asp Ala Lys Gly Thr Asn Val Asn Asp Lys Val Thr Ala Ser Asn Phe
    210                 215                 220
Lys Leu Glu Lys Thr Thr Phe Asp Pro Asn Gln Ser Gly Asn Thr Phe
225                 230                 235                 240
Met Ala Ala Asn Phe Thr Val Thr Asp Lys Val Lys Ser Gly Asp Tyr
                245                 250                 255
Phe Thr Ala Lys Leu Pro Asp Ser Leu Thr Gly Asn Gly Asp Val Asp
            260                 265                 270
Tyr Ser Asn Ser Asn Asn Thr Met Pro Ile Ala Asp Ile Lys Ser Thr
        275                 280                 285
Asn Gly Asp Val Val Ala Lys Ala Thr Tyr Asp Ile Leu Thr Lys Thr
    290                 295                 300
Tyr Thr Phe Val Phe Thr Asp Tyr Val Asn Asn Lys Glu Asn Ile Asn
305                 310                 315                 320
Gly Gln Phe Ser Leu Pro Leu Phe Thr Asp Arg Ala Lys Ala Pro Lys
                325                 330                 335
Ser Gly Thr Tyr Asp Ala Asn Ile Asn Ile Ala Asp Glu Met Phe Asn
            340                 345                 350
Asn Lys Ile Thr Tyr Asn Tyr Ser Ser Pro Ile Ala Gly Ile Asp Lys
        355                 360                 365
Pro Asn Gly Ala Asn Ile Ser Ser Gln Ile Ile Gly Val Asp Thr Ala
    370                 375                 380
Ser Gly Gln Asn Thr Tyr Lys Gln Thr Val Phe Val Asn Pro Lys Gln
385                 390                 395                 400
Arg Val Leu Gly Asn Thr Trp Val Tyr Ile Lys Gly Tyr Gln Asp Lys
                405                 410                 415
Ile Glu Glu Ser Ser Gly Lys Val Ser Ala Thr Asp Thr Lys Leu Arg
            420                 425                 430
Ile Phe Glu Val Asn Asp Thr Ser Lys Leu Ser Asp Ser Tyr Tyr Ala
        435                 440                 445
Asp Pro Asn Asp Ser Asn Leu Lys Glu Val Thr Asp Gln Phe Lys Asn
    450                 455                 460
Arg Ile Tyr Tyr Glu His Pro Asn Val Ala Ser Ile Lys Phe Gly Asp
465                 470                 475                 480
Ile Thr Lys Thr Tyr Val Val Leu Val Glu Gly His Tyr Asp Asn Thr
                485                 490                 495
Gly Lys Asn Leu Lys Thr Gln Val Ile Gln Glu Asn Val Asp Pro Val
            500                 505                 510
Thr Asn Arg Asp Tyr Ser Ile Phe Gly Trp Asn Asn Glu Asn Val Val
        515                 520                 525
```

```
Arg Tyr Gly Gly Gly Ser Ala Asp Gly Asp Ser Ala Val Asn Pro Lys
        530                 535                 540

Asp Pro Thr Pro Gly Pro Pro Val Asp Pro Glu Pro Ser Pro Asp Pro
545                 550                 555                 560

Glu Pro Glu Pro Thr Pro Asp Pro Glu Pro Ser Pro Asp Pro Glu Pro
                565                 570                 575

Glu Pro Ser Pro Asp Pro Asp Pro Asp Ser Asp Ser Asp Ser Asp Ser
                580                 585                 590

Gly Ser Asp Ser Asp Ser Gly Ser Asp Ser Asp Ser Glu Ser Asp Ser
        595                 600                 605

Asp Ser Asp Ser Asp Ser Asp Ser Asp Ser Asp Ser Asp Ser Glu Ser
        610                 615                 620

Asp Ser Asp Ser Glu Ser Asp Ser Asp Ser Asp Ser Asp Ser Asp Ser
625                 630                 635                 640

Asp Ser Asp Ser Asp Ser Glu Ser Asp Ser Asp Ser Asp Ser Asp Ser
                645                 650                 655

Asp Ser Asp Ser Asp Ser Asp Ser Glu Ser Asp Ser Asp Ser Glu Ser
        660                 665                 670

Asp Ser Glu Ser Asp Ser Asp Ser Asp Ser Asp Ser Asp Ser Asp Ser
        675                 680                 685

Asp Ser Asp Ser Asp Ser Asp Ser Asp Ser Asp Ser Asp Ser Asp Ser
690                 695                 700

Asp Ser Asp Ser Asp Ser Asp Ser Glu Ser Asp Ser Asp Ser Asp Ser
705                 710                 715                 720

Asp Ser Asp Ser Asp Ser Asp Ser Asp Ser Asp Ser Asp Ser Asp Ser
                725                 730                 735

Asp Ser Asp Ser Asp Ser Asp Ser Asp Ser Asp Ser Asp Ser Asp Ser
                740                 745                 750

Asp Ser Asp Ser Asp Ser Asp Ser Asp Ser Asp Ser Asp Ser Asp Ser
        755                 760                 765

Asp Ser Asp Ser Asp Ser Asp Ser Asp Ser Asp Ser Asp Ser Asp Ser
        770                 775                 780

Asp Ser Asp Ser Asp Ser Asp Ser Asp Ser Asp Ser Asp Ser Asp Ser
785                 790                 795                 800

Asp Ser Asp Ser Arg Val Thr Pro Pro Asn Asn Glu Gln Lys Ala Pro
                805                 810                 815

Ser Asn Pro Lys Gly Glu Val Asn His Ser Asn Lys Val Ser Lys Gln
                820                 825                 830

His Lys Thr Asp Ala Leu Pro Glu Thr Gly Asp Lys Ser Glu Asn Thr
                835                 840                 845

Asn Ala Thr Leu Phe Gly Ala Met Met Ala Leu Leu Gly Ser Leu Leu
850                 855                 860

Leu Phe Arg Lys Arg Lys Gln Asp His Lys Glu Lys Ala
865                 870                 875

<210> SEQ ID NO 19
<211> LENGTH: 227
<212> TYPE: PRT
<213> ORGANISM: Staphylococcus sp

<400> SEQUENCE: 19

Met Lys Asn Ile Leu Lys Val Phe Asn Thr Thr Ile Leu Ala Leu Ile
1               5                   10                  15

Ile Ile Ile Ala Thr Phe Ser Asn Ser Ala Asn Ala Ala Asp Ser Gly
            20                  25                  30
```

```
Thr Leu Asn Tyr Glu Val Tyr Lys Tyr Asn Thr Asn Asp Thr Ser Ile
         35                   40                  45

Ala Asn Asp Tyr Phe Asn Lys Pro Ala Lys Tyr Ile Lys Lys Asn Gly
 50                  55                  60

Lys Leu Tyr Val Gln Ile Thr Val Asn His Ser His Trp Ile Thr Gly
 65                  70                  75                  80

Met Ser Ile Glu Gly His Lys Glu Asn Ile Ile Ser Lys Asn Thr Ala
                 85                  90                  95

Lys Asp Glu Arg Thr Ser Glu Phe Glu Val Ser Lys Leu Asn Gly Lys
                100                 105                 110

Ile Asp Gly Lys Ile Asp Val Tyr Ile Asp Lys Val Asn Gly Lys
                115                 120                 125

Pro Phe Lys Tyr Asp His His Tyr Asn Ile Thr Tyr Lys Phe Asn Gly
    130                 135                 140

Pro Thr Asp Val Ala Gly Ala Asn Ala Pro Gly Lys Asp Asp Lys Asn
145                 150                 155                 160

Ser Ala Ser Gly Ser Asp Lys Gly Ser Asp Gly Thr Thr Thr Gly Gln
                165                 170                 175

Ser Glu Ser Asn Ser Ser Asn Lys Asp Lys Val Glu Asn Pro Gln Thr
                180                 185                 190

Asn Ala Gly Thr Pro Ala Tyr Ile Tyr Ala Ile Pro Val Ala Ser Leu
                195                 200                 205

Ala Leu Leu Ile Ala Ile Thr Leu Phe Val Arg Lys Ser Lys Gly
    210                 215                 220

Asn Val Glu
225

<210> SEQ ID NO 20
<211> LENGTH: 635
<212> TYPE: PRT
<213> ORGANISM: Staphylococcus sp

<400> SEQUENCE: 20

Met Ala Lys Tyr Arg Gly Lys Pro Phe Gln Leu Tyr Val Lys Leu Ser
 1               5                  10                  15

Cys Ser Thr Met Met Ala Ser Ser Ile Ile Leu Thr Asn Ile Leu Pro
                 20                  25                  30

Tyr Asp Ala Gln Ala Ala Ser Glu Lys Asp Thr Glu Ile Ser Lys Glu
             35                  40                  45

Ile Leu Ser Lys Gln Asp Leu Leu Asp Lys Val Asp Lys Ala Ile Arg
 50                  55                  60

Gln Ile Glu Gln Leu Lys Gln Leu Ser Ala Ser Ser Lys Ala His Tyr
 65                  70                  75                  80

Lys Ala Gln Leu Asn Glu Ala Lys Thr Ala Ser Gln Ile Asp Glu Ile
                 85                  90                  95

Ile Lys Arg Ala Asn Glu Leu Asp Ser Lys Glu Asn Lys Ser Ser His
                100                 105                 110

Thr Glu Met Asn Gly Gln Ser Asp Ile Asp Ser Lys Leu Asp Gln Leu
             115                 120                 125

Leu Lys Asp Leu Asn Glu Val Ser Asn Val Asp Arg Gly Gln Gln
             130                 135                 140

Ser Gly Glu Asp Asp Leu Asn Ala Met Lys Asn Asp Met Ser Gln Thr
145                 150                 155                 160

Ala Thr Thr Lys Tyr Gly Glu Lys Asp Asp Lys Asn Asp Glu Ala Met
```

```
                165                 170                 175
Val Asn Lys Ala Leu Glu Asp Leu Asp His Leu Asn Gln Gln Ile His
                    180                 185                 190
Lys Ser Lys Asp Ala Leu Lys Asp Ala Ser Lys Asp Pro Ala Val Ser
                195                 200                 205
Thr Thr Asp Ser Asn His Glu Val Ala Lys Thr Pro Asn Asn Asp Gly
                    210                 215                 220
Ser Gly His Val Val Leu Asn Lys Phe Leu Ser Asn Glu Glu Asn Gln
225                 230                 235                 240
Ser His Ser Asn Gln Leu Thr Asp Lys Leu Gln Gly Ser Asp Lys Ile
                    245                 250                 255
Asn His Ala Met Ile Glu Lys Leu Ala Lys Ser Asn Ala Ser Thr Gln
                260                 265                 270
His Tyr Thr Tyr His Lys Leu Asn Thr Leu Gln Ser Leu Asp Gln Arg
                    275                 280                 285
Ile Ala Asn Thr Gln Leu Pro Lys Asn Gln Lys Ser Asp Leu Met Ser
                290                 295                 300
Glu Val Asn Lys Thr Lys Glu Arg Ile Lys Ser Gln Arg Asn Ile Ile
305                 310                 315                 320
Leu Glu Glu Leu Ala Arg Thr Asp Lys Lys Tyr Ala Thr Gln Ser
                    325                 330                 335
Ile Leu Glu Ser Ile Phe Asn Lys Asp Glu Ala Asp Lys Ile Leu Lys
                340                 345                 350
Asp Ile Arg Val Asp Gly Lys Thr Gln Gln Ile Ala Asp Gln Ile
                    355                 360                 365
Thr Arg His Ile Asp Gln Leu Ser Leu Thr Thr Ser Asp Asp Leu Leu
                370                 375                 380
Thr Ser Leu Ile Asp Gln Ser Gln Asp Lys Ser Leu Leu Ile Ser Gln
385                 390                 395                 400
Ile Leu Gln Thr Lys Leu Gly Lys Ala Glu Ala Asp Lys Leu Ala Lys
                    405                 410                 415
Asp Trp Thr Asn Lys Gly Leu Ser Asn Arg Gln Ile Val Asp Gln Leu
                420                 425                 430
Lys Lys His Phe Ala Ser Thr Gly Asp Thr Ser Ser Asp Asp Ile Leu
                    435                 440                 445
Lys Ala Ile Leu Asn Asn Ala Lys Asp Lys Gln Ala Ile Glu Thr
                450                 455                 460
Ile Leu Ala Thr Arg Ile Glu Arg Gln Lys Ala Lys Leu Leu Ala Asp
465                 470                 475                 480
Leu Ile Thr Lys Ile Glu Thr Asp Gln Asn Lys Ile Phe Asn Leu Val
                    485                 490                 495
Lys Ser Ala Leu Asn Gly Lys Ala Asp Asp Leu Leu Asn Leu Gln Lys
                500                 505                 510
Arg Leu Asn Gln Thr Lys Lys Asp Ile Asp Tyr Ile Leu Ser Pro Ile
                    515                 520                 525
Val Asn Arg Pro Ser Leu Leu Asp Arg Leu Asn Lys Asn Gly Lys Thr
                530                 535                 540
Thr Asp Leu Asn Lys Leu Ala Asn Leu Met Asn Gln Gly Ser Asn Leu
545                 550                 555                 560
Leu Asp Ser Ile Pro Asp Ile Pro Thr Pro Lys Pro Glu Lys Thr Leu
                    565                 570                 575
Thr Leu Gly Lys Gly Asn Gly Leu Leu Ser Gly Leu Leu Asn Ala Asp
                580                 585                 590
```

```
Gly Asn Val Ser Leu Pro Lys Ala Gly Glu Thr Ile Lys Glu His Trp
            595                 600                 605

Leu Pro Ile Ser Val Ile Val Gly Ala Met Gly Val Leu Met Ile Trp
610                 615                 620

Leu Ser Arg Arg Asn Lys Leu Lys Asn Lys Ala
625                 630                 635

<210> SEQ ID NO 21
<211> LENGTH: 953
<212> TYPE: PRT
<213> ORGANISM: Staphylococcus sp

<400> SEQUENCE: 21

Met Asn Asn Lys Lys Thr Ala Thr Asn Arg Lys Gly Met Ile Pro Asn
1               5                   10                  15

Arg Leu Asn Lys Phe Ser Ile Arg Lys Tyr Ser Val Gly Thr Ala Ser
            20                  25                  30

Ile Leu Val Gly Thr Thr Leu Ile Phe Gly Leu Ser Gly His Glu Ala
        35                  40                  45

Lys Ala Ala Glu His Thr Asn Gly Glu Leu Asn Gln Ser Lys Asn Glu
50                  55                  60

Thr Thr Ala Pro Ser Glu Asn Lys Thr Thr Glu Lys Val Asp Ser Arg
65                  70                  75                  80

Gln Leu Lys Asp Asn Thr Gln Thr Ala Thr Ala Asp Gln Pro Lys Val
                85                  90                  95

Thr Met Ser Asp Ser Ala Thr Val Lys Glu Thr Ser Ser Asn Met Gln
            100                 105                 110

Ser Pro Gln Asn Ala Thr Ala Ser Gln Ser Thr Thr Gln Thr Ser Asn
        115                 120                 125

Val Thr Thr Asn Asp Lys Ser Ser Thr Thr Tyr Ser Asn Glu Thr Asp
130                 135                 140

Lys Ser Asn Leu Thr Gln Ala Lys Asn Val Ser Thr Thr Pro Lys Thr
145                 150                 155                 160

Thr Thr Ile Lys Gln Arg Ala Leu Asn Arg Met Ala Val Asn Thr Val
                165                 170                 175

Ala Ala Pro Gln Gln Gly Thr Asn Val Asn Asp Lys Val His Phe Thr
            180                 185                 190

Asn Ile Asp Ile Ala Ile Asp Lys Gly His Val Asn Lys Thr Thr Gly
        195                 200                 205

Asn Thr Glu Phe Trp Ala Thr Ser Ser Asp Val Leu Lys Leu Lys Ala
    210                 215                 220

Asn Tyr Thr Ile Asp Asp Ser Val Lys Glu Gly Asp Thr Phe Thr Phe
225                 230                 235                 240

Lys Tyr Gly Gln Tyr Phe Arg Pro Gly Ser Val Arg Leu Pro Ser Gln
                245                 250                 255

Thr Gln Asn Leu Tyr Asn Ala Gln Gly Asn Ile Ile Ala Lys Gly Ile
            260                 265                 270

Tyr Asp Ser Lys Thr Asn Thr Thr Thr Tyr Thr Phe Thr Asn Tyr Val
        275                 280                 285

Asp Gln Tyr Thr Asn Val Ser Gly Ser Phe Glu Gln Val Ala Phe Ala
    290                 295                 300

Lys Arg Glu Asn Ala Thr Thr Asp Lys Thr Ala Tyr Lys Met Glu Val
305                 310                 315                 320

Thr Leu Gly Asn Asp Thr Tyr Ser Lys Asp Val Ile Val Asp Tyr Gly
```

-continued

```
                325                 330                 335
Asn Gln Lys Gly Gln Gln Leu Ile Ser Ser Thr Asn Tyr Ile Asn Asn
                340                 345                 350
Glu Asp Leu Ser Arg Asn Met Thr Val Tyr Val Asn Gln Pro Lys Lys
                355                 360                 365
Thr Tyr Thr Lys Glu Thr Phe Val Thr Asn Leu Thr Gly Tyr Lys Phe
                370                 375                 380
Asn Pro Asp Ala Lys Asn Phe Lys Ile Tyr Glu Val Thr Asp Gln Asn
385                 390                 395                 400
Gln Phe Val Asp Ser Phe Thr Pro Asp Thr Ser Lys Leu Lys Asp Val
                405                 410                 415
Thr Gly Gln Phe Asp Val Ile Tyr Ser Asn Asp Asn Lys Thr Ala Thr
                420                 425                 430
Val Asp Leu Leu Asn Gly Gln Ser Ser Asp Lys Gln Tyr Ile Ile
                435                 440                 445
Gln Gln Val Ala Tyr Pro Asp Asn Ser Ser Thr Asp Asn Gly Lys Ile
                450                 455                 460
Asp Tyr Thr Leu Glu Thr Gln Asn Gly Lys Ser Ser Trp Ser Asn Ser
465                 470                 475                 480
Tyr Ser Asn Val Asn Gly Ser Ser Thr Ala Asn Gly Asp Gln Lys Lys
                485                 490                 495
Tyr Asn Leu Gly Asp Tyr Val Trp Glu Asp Thr Asn Lys Asp Gly Lys
                500                 505                 510
Gln Asp Ala Asn Glu Lys Gly Ile Lys Gly Val Tyr Val Ile Leu Lys
                515                 520                 525
Asp Ser Asn Gly Lys Glu Leu Asp Arg Thr Thr Asp Glu Asn Gly
                530                 535                 540
Lys Tyr Gln Phe Thr Gly Leu Ser Asn Gly Thr Tyr Ser Val Glu Phe
545                 550                 555                 560
Ser Thr Pro Ala Gly Tyr Thr Pro Thr Ala Asn Ala Gly Thr Asp
                565                 570                 575
Asp Ala Val Asp Ser Asp Gly Leu Thr Thr Thr Gly Val Ile Lys Asp
                580                 585                 590
Ala Asp Asn Met Thr Leu Asp Ser Gly Phe Tyr Lys Thr Pro Lys Tyr
                595                 600                 605
Ser Leu Gly Asp Tyr Val Trp Tyr Asp Ser Asn Lys Asp Gly Lys Gln
                610                 615                 620
Asp Ser Thr Glu Lys Gly Ile Lys Gly Val Lys Val Thr Leu Gln Asn
625                 630                 635                 640
Glu Lys Gly Glu Val Ile Gly Thr Thr Glu Thr Asp Glu Asn Gly Lys
                645                 650                 655
Tyr Arg Phe Asp Asn Leu Asp Ser Gly Lys Tyr Lys Val Ile Phe Glu
                660                 665                 670
Lys Pro Ala Gly Leu Thr Gln Thr Gly Thr Asn Thr Thr Glu Asp Asp
                675                 680                 685
Lys Asp Ala Asp Gly Gly Glu Val Asp Val Thr Ile Thr Asp His Asp
                690                 695                 700
Asp Phe Thr Leu Asp Asn Gly Tyr Tyr Glu Glu Glu Thr Ser Asp Ser
705                 710                 715                 720
Asp Ser Asp Ser Asp Ser Asp Ser Asp Ser Asp Ser Asp Ser Asp Ser
                725                 730                 735
Asp Ser Asp Ser Asp Ser Asp Ser Asp Ser Asp Ser Asp Ser Asp Ser
                740                 745                 750
```

```
Asp Ser Asp Ser Asp Ser Asp Ser Asp Ser Asp Ser Asp Ser
        755                 760                 765

Asp Ser Asp Ser Glu Ser Asp Ser Asp Ser Asp Ser Asp Ser
    770                 775                 780

Asp Ser Asp Ser Asp Ser Asp Ser Asp Ser Asp Ser Asp Ser
785                 790                 795                 800

Asp Ser Asp Ser Asp Ser Asp Ser Asp Ser Asp Ser Asp Ser
        805                 810                 815

Asp Ser Asp Ser Asp Ser Asp Asn Asp Ser Asp Ser Asp Ser
        820                 825                 830

Asp Ser Asp Ser Asp Ser Asp Ser Asp Ser Asp Ser Asp Ser
        835                 840                 845

Asp Ser Asp Ser Asp Ser Asp Ser Asp Ser Asp Ser Asp Ser
850                 855                 860

Asp Ser Asp Ser Asp Ser Asp Ser Asp Ser Asp Ser Asp Ser
865                 870                 875                 880

Asp Ser Asp Ser Asp Ser Asp Ser Asp Ser Asp Ala Gly Lys
        885                 890                 895

His Thr Pro Thr Lys Pro Met Ser Thr Val Lys Asp Gln His Lys Thr
                900                 905                 910

Ala Lys Ala Leu Pro Glu Thr Gly Ser Glu Asn Asn Asn Ser Asn Asn
        915                 920                 925

Gly Thr Leu Phe Gly Gly Leu Phe Ala Ala Leu Gly Ser Leu Leu Leu
    930                 935                 940

Phe Gly Arg Arg Lys Lys Gln Asn Lys
945                 950

<210> SEQ ID NO 22
<211> LENGTH: 989
<212> TYPE: PRT
<213> ORGANISM: Staphylococcus sp

<400> SEQUENCE: 22

Met Asn Met Lys Lys Lys Glu Lys His Ala Ile Arg Lys Lys Ser Ile
1               5                   10                  15

Gly Val Ala Ser Val Leu Val Gly Thr Leu Ile Gly Phe Gly Leu Leu
            20                  25                  30

Ser Ser Lys Glu Ala Asp Ala Ser Glu Asn Ser Val Thr Gln Ser Asp
        35                  40                  45

Ser Ala Ser Asn Glu Ser Lys Ser Asn Asp Ser Ser Val Ser Ala
    50                  55                  60

Ala Pro Lys Thr Asp Asp Thr Asn Val Ser Asp Thr Lys Thr Ser Ser
65                  70                  75                  80

Asn Thr Asn Asn Gly Glu Thr Ser Val Ala Gln Asn Pro Ala Gln Gln
                85                  90                  95

Glu Thr Thr Gln Ser Ser Thr Asn Ala Thr Thr Glu Glu Thr Pro
            100                 105                 110

Val Thr Gly Glu Ala Thr Thr Thr Thr Asn Gln Ala Asn Thr Pro
        115                 120                 125

Ala Thr Thr Gln Ser Ser Asn Thr Asn Ala Glu Glu Leu Val Asn Gln
    130                 135                 140

Thr Ser Asn Glu Thr Thr Ser Asn Asp Thr Asn Thr Val Ser Ser Val
145                 150                 155                 160

Asn Ser Pro Gln Asn Ser Thr Asn Ala Glu Asn Val Ser Thr Thr Gln
```

-continued

```
                165                 170                 175
Asp Thr Ser Thr Glu Ala Thr Pro Ser Asn Asn Glu Ser Ala Pro Gln
                180                 185                 190

Asn Thr Asp Ala Ser Asn Lys Asp Val Val Ser Gln Ala Val Asn Pro
                195                 200                 205

Ser Thr Pro Arg Met Arg Ala Phe Ser Leu Ala Ala Val Ala Ala Asp
210                 215                 220

Ala Pro Ala Ala Gly Thr Asp Ile Thr Asn Gln Leu Thr Asp Val Lys
225                 230                 235                 240

Val Thr Ile Asp Ser Gly Thr Thr Val Tyr Pro His Gln Ala Gly Tyr
                245                 250                 255

Val Lys Leu Asn Tyr Gly Phe Ser Val Pro Asn Ser Ala Val Lys Gly
                260                 265                 270

Asp Thr Phe Lys Ile Thr Val Pro Lys Glu Leu Asn Leu Asn Gly Val
                275                 280                 285

Thr Ser Thr Ala Lys Val Pro Pro Ile Met Ala Gly Asp Gln Val Leu
                290                 295                 300

Ala Asn Gly Val Ile Asp Ser Asp Gly Asn Val Ile Tyr Thr Phe Thr
305                 310                 315                 320

Asp Tyr Val Asp Asn Lys Glu Asn Val Thr Ala Asn Ile Thr Met Pro
                325                 330                 335

Ala Tyr Ile Asp Pro Glu Asn Val Thr Lys Thr Gly Asn Val Thr Leu
                340                 345                 350

Thr Thr Gly Ile Gly Thr Asn Thr Ala Ser Lys Thr Val Leu Ile Asp
                355                 360                 365

Tyr Glu Lys Tyr Gly Gln Phe His Asn Leu Ser Ile Lys Gly Thr Ile
                370                 375                 380

Asp Gln Ile Asp Lys Thr Asn Asn Thr Tyr Arg Gln Thr Ile Tyr Val
385                 390                 395                 400

Asn Pro Ser Gly Asp Asn Val Val Leu Pro Ala Leu Thr Gly Asn Leu
                405                 410                 415

Ile Pro Asn Thr Lys Ser Asn Ala Leu Ile Asp Ala Lys Asn Thr Asp
                420                 425                 430

Ile Lys Val Tyr Arg Val Asp Asn Ala Asn Asp Leu Ser Glu Ser Tyr
                435                 440                 445

Tyr Val Asn Pro Ser Asp Phe Glu Asp Val Thr Asn Gln Val Arg Ile
                450                 455                 460

Ser Phe Pro Asn Ala Asn Gln Tyr Lys Val Glu Phe Pro Thr Asp Asp
465                 470                 475                 480

Asp Gln Ile Thr Thr Pro Tyr Ile Val Val Asn Gly His Ile Asp
                485                 490                 495

Pro Ala Ser Thr Gly Asp Leu Ala Leu Arg Ser Thr Phe Tyr Gly Tyr
                500                 505                 510

Asp Ser Asn Phe Ile Trp Arg Ser Met Ser Trp Asp Asn Glu Val Ala
                515                 520                 525

Phe Asn Asn Gly Ser Gly Ser Gly Asp Gly Ile Asp Lys Pro Val Val
530                 535                 540

Pro Glu Gln Pro Asp Glu Pro Gly Glu Ile Glu Pro Ile Pro Glu Asp
545                 550                 555                 560

Ser Asp Ser Asp Pro Gly Ser Asp Ser Gly Ser Asp Ser Asn Ser Asp
                565                 570                 575

Ser Gly Ser Asp Ser Gly Ser Asp Ser Thr Ser Asp Ser Gly Ser Asp
                580                 585                 590
```

Ser Ala Ser Asp Ser Asp Ser Ala Ser Asp Ser Asp Ser Ala Ser Asp
        595                 600                 605

Ser Asp Ser Ala Ser Asp Ser Asp Ser Ala Ser Asp Ser Asp Ser Ala
    610                 615                 620

Ser Asp Ser Asp Ser Ala Ser Asp Ser Asp Ser Ala Ser Asp Ser Asp
625                 630                 635                 640

Ser Ala Ser Asp Ser Asp Ser Ala Ser Asp Ser Asp Ser Ala Ser Asp
            645                 650                 655

Ser Asp Ser Ala Ser Asp Ser Asp Ser Ala Ser Asp Ser Asp Ser Asp
        660                 665                 670

Ser Asp Ser Asp Ser Asp Ser Asp Ser Asp Ser Asp Ser Asp Ser Asp
    675                 680                 685

Ser Asp Ser Asp Ser Asp Ser Asp Ser Asp Ser Asp Ser Asp Ser Asp
690                 695                 700

Ser Asp Ser Asp Ser Asp Ser Asp Ser Asp Ser Asp Ser Asp Ser Asp
705                 710                 715                 720

Ser Asp Ser Asp Ser Asp Ser Asp Ser Asp Ser Asp Ser Asp Ser Asp
            725                 730                 735

Ser Asp Ser Asp Ser Asp Ser Asp Ser Asp Ser Asp Ser Asp Ser Asp
        740                 745                 750

Ser Asp Ser Asp Ser Asp Ser Asp Ser Asp Ser Asp Ser Asp Ser Asp
    755                 760                 765

Ser Asp Ser Asp Ser Asp Ser Asp Ser Asp Ser Asp Ser Asp Ser Asp
770                 775                 780

Ser Asp Ser Asp Ser Asp Ser Asp Ser Asp Ser Asp Ser Asp Ser Asp
785                 790                 795                 800

Ser Asp Ser Asp Ser Asp Ser Asp Ser Asp Ser Asp Ser Asp Ser Asp
            805                 810                 815

Ser Asp Ser Asp Ser Ala Ser Asp Ser Asp Ser Asp Ser Asp Ser Glu
        820                 825                 830

Ser Asp Ser Asp Ser Asp Ser Asp Ser Asp Ser Asp Ser Asp Ser Asp
    835                 840                 845

Ser Asp Ser Asp Ser Asp Ser Glu Ser Asp Ser Asp Ser Asp Ser Asp
850                 855                 860

Ser Asp Ser Glu Ser Asp Ser Asp Ser Asp Ser Asp Ser Asp Ser Asp
865                 870                 875                 880

Ser Ala Ser Asp Ser Asp Ser Gly Ser Asp Ser Asp Ser Ser Ser Asp
            885                 890                 895

Ser Asp Ser Asp Ser Thr Ser Asp Thr Gly Ser Asp Asn Ser Asp
        900                 905                 910

Ser Asp Ser Asn Ser Asp Ser Glu Ser Gly Ser Asn Asn Asn Val Val
        915                 920                 925

Pro Pro Asn Ser Pro Lys Asn Gly Thr Asn Ala Ser Asn Lys Asn Glu
    930                 935                 940

Ala Lys Asp Ser Lys Glu Pro Leu Pro Asp Thr Gly Ser Glu Asp Glu
945                 950                 955                 960

Ala Asn Thr Ser Leu Ile Trp Gly Leu Leu Ala Ser Leu Gly Ser Leu
            965                 970                 975

Leu Leu Phe Arg Arg Lys Lys Glu Asn Lys Asp Lys Lys
        980                 985

<210> SEQ ID NO 23
<211> LENGTH: 584

```
<212> TYPE: PRT
<213> ORGANISM: Staphylococcus sp

<400> SEQUENCE: 23

Met Lys Phe Lys Ser Leu Ile Thr Thr Thr Leu Ala Leu Gly Val Leu
1               5                   10                  15

Ala Ser Thr Gly Ala Asn Phe Asn Asn Asn Glu Ala Ser Ala Ala
            20                  25                  30

Lys Pro Leu Asp Lys Ser Ser Ser Leu His His Gly Tyr Ser Lys
            35                  40                  45

Val His Val Pro Tyr Ala Ile Thr Val Asn Gly Thr Ser Gln Asn Ile
    50                  55                  60

Leu Ser Ser Leu Thr Phe Asn Lys Asn Gln Asn Ile Ser Tyr Lys Asp
65                  70                  75                  80

Leu Glu Asp Arg Val Lys Ser Val Leu Lys Ser Asp Arg Gly Ile Ser
                85                  90                  95

Asp Ile Asp Leu Arg Leu Ser Lys Gln Ala Lys Tyr Thr Val Tyr Phe
                100                 105                 110

Lys Asn Gly Thr Lys Lys Val Ile Asp Leu Lys Ala Gly Ile Tyr Thr
            115                 120                 125

Ala Asp Leu Ile Asn Thr Ser Glu Ile Lys Ala Ile Asn Ile Asn Val
            130                 135                 140

Asp Thr Lys Lys Gln Val Glu Asp Lys Lys Asp Lys Ala Asn Tyr
145                 150                 155                 160

Gln Val Pro Tyr Thr Ile Thr Val Asn Gly Thr Ser Gln Asn Ile Leu
                165                 170                 175

Ser Asn Leu Thr Phe Asn Lys Asn Gln Asn Ile Ser Tyr Lys Asp Leu
            180                 185                 190

Glu Asp Lys Val Lys Ser Val Leu Glu Ser Asn Arg Gly Ile Thr Asp
            195                 200                 205

Val Asp Leu Arg Leu Ser Lys Gln Ala Lys Tyr Thr Val Asn Phe Lys
    210                 215                 220

Asn Gly Thr Lys Lys Val Ile Asp Leu Lys Ser Gly Ile Tyr Thr Ala
225                 230                 235                 240

Asn Leu Ile Asn Ser Ser Asp Ile Lys Ser Ile Asn Ile Asn Val Asp
                245                 250                 255

Thr Lys Lys His Ile Glu Asn Lys Ala Lys Arg Asn Tyr Gln Val Pro
            260                 265                 270

Tyr Ser Ile Asn Leu Asn Gly Thr Ser Thr Asn Ile Leu Ser Asn Leu
    275                 280                 285

Ser Phe Ser Asn Lys Pro Trp Thr Asn Tyr Lys Asn Leu Thr Ser Gln
    290                 295                 300

Ile Lys Ser Val Leu His Asp Arg Gly Ile Ser Glu Gln Asp Leu
305                 310                 315                 320

Lys Tyr Ala Lys Lys Ala Tyr Tyr Thr Val Tyr Phe Lys Asn Gly Gly
                325                 330                 335

Lys Arg Ile Leu Gln Leu Asn Ser Lys Asn Tyr Thr Ala Asn Leu Val
            340                 345                 350

His Ala Lys Asp Val Lys Arg Ile Glu Ile Thr Val Lys Thr Gly Thr
            355                 360                 365

Lys Ala Lys Ala Asp Arg Tyr Val Pro Tyr Thr Ile Ala Val Asn Gly
            370                 375                 380

Thr Ser Thr Pro Ile Leu Ser Asp Leu Lys Phe Thr Gly Asp Pro Arg
385                 390                 395                 400
```

Val Gly Tyr Lys Asp Ile Ser Lys Val Lys Ser Val Leu Lys His
            405                 410                 415

Asp Arg Gly Ile Gly Glu Arg Glu Leu Lys Tyr Ala Lys Lys Ala Thr
            420                 425                 430

Tyr Thr Val His Phe Lys Asn Gly Thr Lys Lys Val Ile Asn Ile Asn
            435                 440                 445

Ser Asn Ile Ser Gln Leu Asn Leu Leu Tyr Val Gln Asp Ile Lys Lys
        450                 455                 460

Ile Asp Ile Asp Val Lys Thr Gly Thr Lys Ala Lys Ala Asp Ser Tyr
465                 470                 475                 480

Val Pro Tyr Thr Ile Ala Val Asn Gly Thr Ser Thr Pro Ile Leu Ser
            485                 490                 495

Lys Leu Lys Ile Ser Asn Lys Gln Leu Ile Ser Tyr Lys Tyr Leu Asn
            500                 505                 510

Asp Lys Val Lys Ser Val Leu Lys Ser Glu Arg Gly Ile Ser Asp Leu
            515                 520                 525

Asp Leu Lys Phe Ala Lys Gln Ala Lys Tyr Thr Val Tyr Phe Lys Asn
        530                 535                 540

Gly Lys Lys Gln Val Val Asn Leu Lys Ser Asp Ile Phe Thr Pro Asn
545                 550                 555                 560

Leu Phe Ser Ala Lys Asp Ile Lys Lys Ile Asp Ile Asp Val Lys Gln
                565                 570                 575

Tyr Thr Lys Ser Lys Lys Asn Lys
            580

<210> SEQ ID NO 24
<211> LENGTH: 10419
<212> TYPE: PRT
<213> ORGANISM: Staphylococcus sp

<400> SEQUENCE: 24

Met Asn Tyr Arg Asp Lys Ile Gln Lys Phe Ser Ile Arg Lys Tyr Thr
1               5                   10                  15

Val Gly Thr Phe Ser Thr Val Ile Ala Thr Leu Val Phe Leu Gly Phe
            20                  25                  30

Asn Thr Ser Gln Ala His Ala Ala Glu Thr Asn Gln Pro Ala Ser Val
        35                  40                  45

Val Lys Gln Lys Gln Gln Ser Asn Asn Glu Gln Thr Glu Asn Arg Glu
    50                  55                  60

Ser Gln Val Gln Asn Ser Gln Asn Ser Gln Asn Gly Gln Ser Leu Ser
65                  70                  75                  80

Ala Thr His Glu Asn Glu Gln Pro Asn Ile Ser Gln Ala Asn Leu Val
                85                  90                  95

Asp Gln Lys Val Ala Gln Ser Ser Thr Thr Asn Asp Glu Gln Pro Ala
            100                 105                 110

Ser Gln Asn Val Asn Thr Lys Lys Asp Ser Ala Thr Ala Ala Thr Thr
        115                 120                 125

Gln Pro Asp Lys Glu Gln Ser Lys His Lys Gln Asn Glu Ser Gln Ser
    130                 135                 140

Ala Asn Lys Asn Gly Asn Asp Asn Arg Ala Ala His Val Glu Asn His
145                 150                 155                 160

Glu Ala Asn Val Val Thr Ala Ser Asp Ser Ser Asp Asn Gly Asn Val
                165                 170                 175

Gln His Asp Arg Asn Glu Leu Gln Ala Phe Phe Asp Ala Asn Tyr His

```
            180                 185                 190
Asp Tyr Arg Phe Ile Asp Arg Glu Asn Ala Asp Ser Gly Thr Phe Asn
        195                 200                 205

Tyr Val Lys Gly Ile Phe Asp Lys Ile Asn Thr Leu Leu Gly Ser Asn
        210                 215                 220

Asp Pro Ile Asn Asn Lys Asp Leu Gln Leu Ala Tyr Lys Glu Leu Glu
225                 230                 235                 240

Gln Ala Val Ala Leu Ile Arg Thr Met Pro Gln Arg Gln Gln Thr Ser
                245                 250                 255

Arg Arg Ser Asn Arg Ile Gln Thr Arg Ser Val Glu Ser Arg Ala Ala
                260                 265                 270

Glu Pro Arg Ser Val Ser Asp Tyr Gln Asn Ala Asn Ser Ser Tyr Tyr
                275                 280                 285

Val Glu Asn Ala Asn Asp Gly Ser Gly Tyr Pro Val Gly Thr Tyr Ile
        290                 295                 300

Asn Ala Ser Ser Lys Gly Ala Pro Tyr Asn Leu Pro Thr Thr Pro Trp
305                 310                 315                 320

Asn Thr Leu Lys Ala Ser Asp Ser Lys Glu Ile Ala Leu Met Thr Ala
                325                 330                 335

Lys Gln Thr Gly Asp Gly Tyr Gln Trp Val Ile Lys Phe Asn Lys Gly
                340                 345                 350

His Ala Pro His Gln Asn Met Ile Phe Trp Phe Ala Leu Pro Ala Asp
                355                 360                 365

Gln Val Pro Val Gly Arg Thr Asp Phe Val Thr Val Asn Ser Asp Gly
                370                 375                 380

Thr Asn Val Gln Trp Ser His Gly Ala Gly Ala Gly Ala Asn Lys Pro
385                 390                 395                 400

Leu Gln Gln Met Trp Glu Tyr Gly Val Asn Asp Pro His Arg Ser His
                405                 410                 415

Asp Phe Lys Ile Arg Asn Arg Ser Gly Gln Val Ile Tyr Asp Trp Pro
                420                 425                 430

Thr Val His Ile Tyr Ser Leu Glu Asp Leu Ser Arg Ala Ser Asp Tyr
                435                 440                 445

Phe Ser Glu Ala Gly Ala Thr Pro Ala Thr Lys Ala Phe Gly Arg Gln
450                 455                 460

Asn Phe Glu Tyr Ile Asn Gly Gln Lys Pro Ala Glu Ser Pro Gly Val
465                 470                 475                 480

Pro Lys Val Tyr Thr Phe Ile Gly Gln Gly Asp Ala Ser Tyr Thr Ile
                485                 490                 495

Ser Phe Lys Thr Gln Gly Pro Thr Val Asn Lys Leu Tyr Tyr Ala Ala
                500                 505                 510

Gly Gly Arg Ala Leu Glu Tyr Asn Gln Leu Phe Met Tyr Ser Gln Leu
                515                 520                 525

Tyr Val Glu Ser Thr Gln Asp His Gln Gln Arg Leu Asn Gly Leu Arg
        530                 535                 540

Gln Val Val Asn Arg Thr Tyr Arg Ile Gly Thr Thr Lys Arg Val Glu
545                 550                 555                 560

Val Ser Gln Gly Asn Val Gln Thr Lys Lys Val Leu Glu Ser Thr Asn
                565                 570                 575

Leu Asn Ile Asp Asp Phe Val Asp Pro Leu Ser Tyr Val Lys Thr
                580                 585                 590

Pro Ser Asn Lys Val Leu Gly Phe Tyr Ser Asn Asn Ala Asn Thr Asn
                595                 600                 605
```

```
Ala Phe Arg Pro Gly Gly Ala Gln Gln Leu Asn Glu Tyr Gln Leu Ser
    610                 615                 620

Gln Leu Phe Thr Asp Gln Lys Leu Gln Glu Ala Ala Arg Thr Arg Asn
625                 630                 635                 640

Pro Ile Arg Leu Met Ile Gly Phe Asp Tyr Pro Asp Ala Tyr Gly Asn
                645                 650                 655

Ser Glu Thr Leu Val Pro Val Asn Leu Thr Val Leu Pro Glu Ile Gln
                660                 665                 670

His Asn Ile Lys Phe Phe Lys Asn Asp Asp Thr Gln Asn Ile Ala Glu
                675                 680                 685

Lys Pro Phe Ser Lys Gln Ala Gly His Pro Val Phe Tyr Val Tyr Ala
    690                 695                 700

Gly Asn Gln Gly Asn Ala Ser Val Asn Leu Gly Gly Ser Val Thr Ser
705                 710                 715                 720

Ile Gln Pro Leu Arg Ile Asn Leu Thr Ser Asn Glu Asn Phe Thr Asp
                725                 730                 735

Lys Asp Trp Gln Ile Thr Gly Ile Pro Arg Thr Leu His Ile Glu Asn
                740                 745                 750

Ser Thr Asn Arg Pro Asn Asn Ala Arg Glu Arg Asn Ile Glu Leu Val
    755                 760                 765

Gly Asn Leu Leu Pro Gly Asp Tyr Phe Gly Thr Ile Arg Phe Gly Arg
770                 775                 780

Lys Glu Gln Leu Phe Glu Ile Arg Val Lys Pro His Thr Pro Thr Ile
785                 790                 795                 800

Thr Thr Thr Ala Glu Gln Leu Arg Gly Thr Ala Leu Gln Lys Val Pro
                805                 810                 815

Val Asn Ile Ser Gly Ile Pro Leu Asp Pro Ser Ala Leu Val Tyr Leu
                820                 825                 830

Val Ala Pro Thr Asn Gln Thr Thr Asn Gly Gly Ser Glu Ala Asp Gln
    835                 840                 845

Ile Pro Ser Gly Tyr Thr Ile Leu Ala Thr Gly Thr Pro Asp Gly Val
    850                 855                 860

His Asn Thr Ile Thr Ile Arg Pro Gln Asp Tyr Val Val Phe Ile Pro
865                 870                 875                 880

Pro Val Gly Lys Gln Ile Arg Ala Val Val Tyr Tyr Asn Lys Val Val
                885                 890                 895

Ala Ser Asn Met Ser Asn Ala Val Thr Ile Leu Pro Asp Asp Ile Pro
                900                 905                 910

Pro Thr Ile Asn Asn Pro Val Gly Ile Asn Ala Lys Tyr Tyr Arg Gly
                915                 920                 925

Asp Glu Val Asn Phe Thr Met Gly Val Ser Asp Arg His Ser Gly Ile
    930                 935                 940

Lys Asn Thr Thr Ile Thr Thr Leu Pro Asn Gly Trp Thr Ser Asn Leu
945                 950                 955                 960

Thr Lys Ala Asp Lys Asn Gly Ser Leu Ser Ile Thr Gly Arg Val
                965                 970                 975

Ser Met Asn Gln Ala Phe Asn Ser Asp Ile Thr Phe Lys Val Ser Ala
                980                 985                 990

Thr Asp Asn Val Asn Asn Thr Thr  Asn Asp Ser Gln Ser  Lys His Val
                995                 1000                1005

Ser Ile  His Val Gly Lys Ile  Ser Glu Asp Ala His  Pro Ile Val
    1010                1015                1020
```

-continued

```
Leu Gly Asn Thr Glu Lys Val Val Val Asn Pro Thr Ala Val
    1025                1030                1035

Ser Asn Asp Glu Lys Gln Ser Ile Ile Thr Ala Phe Met Asn Lys
    1040                1045                1050

Asn Gln Asn Ile Arg Gly Tyr Leu Ala Ser Thr Asp Pro Val Thr
    1055                1060                1065

Val Asp Asn Gly Asn Val Thr Leu His Tyr Arg Asp Gly Ser
    1070                1075                1080

Ser Thr Thr Leu Asp Ala Thr Asn Val Met Thr Tyr Glu Pro Val
    1085                1090                1095

Val Lys Pro Glu Tyr Gln Thr Val Asn Ala Ala Lys Thr Ala Thr
    1100                1105                1110

Val Thr Ile Ala Lys Gly Gln Ser Phe Ser Ile Gly Asp Ile Lys
    1115                1120                1125

Gln Tyr Phe Thr Leu Ser Asn Gly Gln Pro Ile Pro Ser Gly Thr
    1130                1135                1140

Phe Thr Asn Ile Thr Ser Asp Arg Thr Ile Pro Thr Ala Gln Glu
    1145                1150                1155

Val Ser Gln Met Asn Ala Gly Thr Gln Leu Tyr His Ile Thr Ala
    1160                1165                1170

Thr Asn Ala Tyr His Lys Asp Ser Glu Asp Phe Tyr Ile Ser Leu
    1175                1180                1185

Lys Ile Ile Asp Val Lys Gln Pro Glu Gly Asp Gln Arg Val Tyr
    1190                1195                1200

Arg Thr Ser Thr Tyr Asp Leu Thr Thr Asp Glu Ile Ser Lys Val
    1205                1210                1215

Lys Gln Ala Phe Ile Asn Ala Asn Arg Asp Val Ile Thr Leu Ala
    1220                1225                1230

Glu Gly Asp Ile Ser Val Thr Asn Thr Pro Asn Gly Ala Asn Val
    1235                1240                1245

Ser Thr Ile Thr Val Asn Ile Asn Lys Gly Arg Leu Thr Lys Ser
    1250                1255                1260

Phe Ala Ser Asn Leu Ala Asn Met Asn Phe Leu Arg Trp Val Asn
    1265                1270                1275

Phe Pro Gln Asp Tyr Thr Val Thr Trp Thr Asn Ala Lys Ile Ala
    1280                1285                1290

Asn Arg Pro Thr Asp Gly Gly Leu Ser Trp Ser Asp Asp His Lys
    1295                1300                1305

Ser Leu Ile Tyr Arg Tyr Asp Ala Thr Leu Gly Thr Gln Ile Thr
    1310                1315                1320

Thr Asn Asp Ile Leu Thr Met Leu Lys Ala Thr Thr Val Pro
    1325                1330                1335

Gly Leu Arg Asn Asn Ile Thr Gly Asn Glu Lys Ser Gln Ala Glu
    1340                1345                1350

Ala Gly Gly Arg Pro Asn Phe Arg Thr Thr Gly Tyr Ser Gln Ser
    1355                1360                1365

Asn Ala Thr Thr Asp Gly Gln Arg Gln Phe Thr Leu Asn Gly Gln
    1370                1375                1380

Val Ile Gln Val Leu Asp Ile Ile Asn Pro Ser Asn Gly Tyr Gly
    1385                1390                1395

Gly Gln Pro Val Thr Asn Ser Asn Thr Arg Ala Asn His Ser Asn
    1400                1405                1410

Ser Thr Val Val Asn Val Asn Glu Pro Ala Ala Asn Gly Ala Gly
```

-continued

```
           1415                1420                1425

Ala Phe Thr Ile Asp His Val Val Lys Ser Asn Ser Thr His Asn
        1430                1435                1440

Ala Ser Asp Ala Val Tyr Lys Ala Gln Leu Tyr Leu Thr Pro Tyr
        1445                1450                1455

Gly Pro Lys Gln Tyr Val Glu His Leu Asn Gln Asn Thr Gly Asn
        1460                1465                1470

Thr Thr Asp Ala Ile Asn Ile Tyr Phe Val Pro Ser Asp Leu Val
        1475                1480                1485

Asn Pro Thr Ile Ser Val Gly Asn Tyr Thr Asn His Gln Val Phe
        1490                1495                1500

Ser Gly Glu Thr Phe Thr Asn Thr Ile Thr Ala Asn Asp Asn Phe
        1505                1510                1515

Gly Val Gln Ser Val Thr Val Pro Asn Thr Ser Gln Ile Thr Gly
        1520                1525                1530

Thr Val Asp Asn Asn His Gln His Val Ser Ala Thr Ala Pro Asn
        1535                1540                1545

Val Thr Ser Ala Thr Asn Lys Thr Ile Asn Leu Leu Ala Thr Asp
        1550                1555                1560

Thr Ser Gly Asn Thr Ala Thr Thr Ser Phe Asn Val Thr Val Lys
        1565                1570                1575

Pro Leu Arg Asp Lys Tyr Arg Val Gly Thr Ser Ser Thr Ala Ala
        1580                1585                1590

Asn Pro Val Arg Ile Ala Asn Ile Ser Asn Asn Ala Thr Val Ser
        1595                1600                1605

Gln Ala Asp Gln Thr Thr Ile Ile Asn Ser Leu Thr Phe Thr Glu
        1610                1615                1620

Thr Val Pro Asn Arg Ser Tyr Ala Arg Ala Ser Ala Asn Glu Ile
        1625                1630                1635

Thr Ser Lys Thr Val Ser Asn Val Ser Arg Thr Gly Asn Asn Ala
        1640                1645                1650

Asn Val Thr Val Thr Val Thr Tyr Gln Asp Gly Thr Thr Ser Thr
        1655                1660                1665

Val Thr Val Pro Val Lys His Val Ile Pro Glu Ile Val Ala His
        1670                1675                1680

Ser His Tyr Thr Val Gln Gly Gln Asp Phe Pro Ala Gly Asn Gly
        1685                1690                1695

Ser Ser Ala Ser Asp Tyr Phe Lys Leu Ser Asn Gly Ser Asp Ile
        1700                1705                1710

Ala Asp Ala Thr Ile Thr Trp Val Ser Gly Gln Ala Pro Asn Lys
        1715                1720                1725

Asp Asn Thr Arg Ile Gly Glu Asp Ile Thr Val Thr Ala His Ile
        1730                1735                1740

Leu Ile Asp Gly Glu Thr Thr Pro Ile Thr Lys Thr Ala Thr Tyr
        1745                1750                1755

Lys Val Val Arg Thr Val Pro Lys His Val Phe Glu Thr Ala Arg
        1760                1765                1770

Gly Val Leu Tyr Pro Gly Val Ser Asp Met Tyr Asp Ala Lys Gln
        1775                1780                1785

Tyr Val Lys Pro Val Asn Asn Ser Trp Ser Thr Asn Ala Gln His
        1790                1795                1800

Met Asn Phe Gln Phe Val Gly Thr Tyr Gly Pro Asn Lys Asp Val
        1805                1810                1815
```

-continued

```
Val Gly Ile Ser Thr Arg Leu Ile Arg Val Thr Tyr Asp Asn Arg
1820                1825                1830

Gln Thr Glu Asp Leu Thr Ile Leu Ser Lys Val Lys Pro Asp Pro
1835                1840                1845

Pro Arg Ile Asp Ala Asn Ser Val Thr Tyr Lys Ala Gly Leu Thr
1850                1855                1860

Asn Gln Glu Ile Lys Val Asn Asn Val Leu Asn Asn Ser Ser Val
1865                1870                1875

Lys Leu Phe Lys Ala Asp Asn Thr Pro Leu Asn Val Thr Asn Ile
1880                1885                1890

Thr His Gly Ser Gly Phe Ser Ser Val Val Thr Val Ser Asp Ala
1895                1900                1905

Leu Pro Asn Gly Gly Ile Lys Ala Lys Ser Ser Ile Ser Met Asn
1910                1915                1920

Asn Val Thr Tyr Thr Thr Gln Asp Glu His Gly Gln Val Val Thr
1925                1930                1935

Val Thr Arg Asn Glu Ser Val Asp Ser Asn Asp Ser Ala Thr Val
1940                1945                1950

Thr Val Thr Pro Gln Leu Gln Ala Thr Thr Glu Gly Ala Val Phe
1955                1960                1965

Ile Lys Gly Gly Asp Gly Phe Asp Phe Gly His Val Glu Arg Phe
1970                1975                1980

Ile Gln Asn Pro Pro His Gly Ala Thr Val Ala Trp His Asp Ser
1985                1990                1995

Pro Asp Thr Trp Lys Asn Thr Val Gly Asn Thr His Lys Thr Ala
2000                2005                2010

Val Val Thr Leu Pro Asn Gly Gln Gly Thr Arg Asn Val Glu Val
2015                2020                2025

Pro Val Lys Val Tyr Pro Val Ala Asn Ala Lys Ala Pro Ser Arg
2030                2035                2040

Asp Val Lys Gly Gln Asn Leu Thr Asn Gly Thr Asp Ala Met Asn
2045                2050                2055

Tyr Ile Thr Phe Asp Pro Asn Thr Asn Thr Asn Gly Ile Thr Ala
2060                2065                2070

Ala Trp Ala Asn Arg Gln Gln Pro Asn Asn Gln Gln Ala Gly Val
2075                2080                2085

Gln His Leu Asn Val Asp Val Thr Tyr Pro Gly Ile Ser Ala Ala
2090                2095                2100

Lys Arg Val Pro Val Thr Val Asn Val Tyr Gln Phe Glu Phe Pro
2105                2110                2115

Gln Thr Thr Tyr Thr Thr Thr Val Gly Gly Thr Leu Ala Ser Gly
2120                2125                2130

Thr Gln Ala Ser Gly Tyr Ala His Met Gln Asn Ala Thr Gly Leu
2135                2140                2145

Pro Thr Asp Gly Phe Thr Tyr Lys Trp Asn Arg Asp Thr Thr Gly
2150                2155                2160

Thr Asn Asp Ala Asn Trp Ser Ala Met Asn Lys Pro Asn Val Ala
2165                2170                2175

Lys Val Val Asn Ala Lys Tyr Asp Val Ile Tyr Asn Gly His Thr
2180                2185                2190

Phe Ala Thr Ser Leu Pro Ala Lys Phe Val Val Lys Asp Val Gln
2195                2200                2205
```

```
Pro Ala Lys Pro Thr Val Thr Glu Thr Ala Ala Gly Ala Ile Thr
    2210            2215                2220
Ile Ala Pro Gly Ala Asn Gln Thr Val Asn Thr His Ala Gly Asn
2225            2230                2235
Val Thr Thr Tyr Ala Asp Lys Leu Val Ile Lys Arg Asn Gly Asn
    2240            2245                2250
Val Val Thr Thr Phe Thr Arg Arg Asn Asn Thr Ser Pro Trp Val
2255            2260                2265
Lys Glu Ala Ser Ala Ala Thr Val Ala Gly Ile Ala Gly Thr Asn
    2270            2275                2280
Asn Gly Ile Thr Val Ala Ala Gly Thr Phe Asn Pro Ala Asp Thr
2285            2290                2295
Ile Gln Val Val Ala Thr Gln Gly Ser Gly Glu Thr Val Ser Asp
    2300            2305                2310
Glu Gln Arg Ser Asp Asp Phe Thr Val Val Ala Pro Gln Pro Asn
2315            2320                2325
Gln Ala Thr Thr Lys Ile Trp Gln Asn Gly His Ile Asp Ile Thr
    2330            2335                2340
Pro Asn Asn Pro Ser Gly His Leu Ile Asn Pro Thr Gln Ala Met
2345            2350                2355
Asp Ile Ala Tyr Thr Glu Lys Val Gly Asn Gly Ala Glu His Ser
    2360            2365                2370
Lys Thr Ile Asn Val Val Arg Gly Gln Asn Asn Gln Trp Thr Ile
2375            2380                2385
Ala Asn Lys Pro Asp Tyr Val Thr Leu Asp Ala Gln Thr Gly Lys
    2390            2395                2400
Val Thr Phe Asn Ala Asn Thr Ile Lys Pro Asn Ser Ser Ile Thr
2405            2410                2415
Ile Thr Pro Lys Ala Gly Thr Gly His Ser Val Ser Ser Asn Pro
    2420            2425                2430
Ser Thr Leu Thr Ala Pro Ala Ala His Thr Val Asn Thr Thr Glu
2435            2440                2445
Ile Val Lys Asp Tyr Gly Ser Asn Val Thr Ala Ala Glu Ile Asn
    2450            2455                2460
Asn Ala Val Gln Val Ala Asn Lys Arg Thr Ala Thr Ile Lys Asn
2465            2470                2475
Gly Thr Ala Met Pro Thr Asn Leu Ala Gly Gly Ser Thr Thr Thr
    2480            2485                2490
Ile Pro Val Thr Val Thr Tyr Asn Asp Gly Ser Thr Glu Glu Val
2495            2500                2505
Gln Glu Ser Ile Phe Thr Lys Ala Asp Lys Arg Glu Leu Ile Thr
    2510            2515                2520
Ala Lys Asn His Leu Asp Asp Pro Val Ser Thr Glu Gly Lys Lys
2525            2530                2535
Pro Gly Thr Ile Thr Gln Tyr Asn Asn Ala Met His Asn Ala Gln
    2540            2545                2550
Gln Gln Ile Asn Thr Ala Lys Thr Glu Ala Gln Gln Val Ile Asn
2555            2560                2565
Asn Glu Arg Ala Thr Pro Gln Gln Val Ser Asp Ala Leu Thr Lys
    2570            2575                2580
Val Arg Ala Ala Gln Thr Lys Ile Asp Gln Ala Lys Ala Leu Leu
2585            2590                2595
Gln Asn Lys Glu Asp Asn Ser Gln Leu Val Thr Ser Lys Asn Asn
```

```
                2600                2605                2610

Leu Gln Ser Ser Val Asn Gln Val Pro Ser Thr Ala Gly Met Thr
    2615                2620                2625

Gln Gln Ser Ile Asp Asn Tyr Asn Ala Lys Lys Arg Glu Ala Glu
    2630                2635                2640

Thr Glu Ile Thr Ala Ala Gln Arg Val Ile Asp Asn Gly Asp Ala
    2645                2650                2655

Thr Ala Gln Gln Ile Ser Asp Glu Lys His Arg Val Asp Asn Ala
    2660                2665                2670

Leu Thr Ala Leu Asn Gln Ala Lys His Asp Leu Thr Ala Asp Thr
    2675                2680                2685

His Ala Leu Glu Gln Ala Val Gln Gln Leu Asn Arg Thr Gly Thr
    2690                2695                2700

Thr Thr Gly Lys Lys Pro Ala Ser Ile Thr Ala Tyr Asn Asn Ser
    2705                2710                2715

Ile Arg Ala Leu Gln Ser Asp Leu Thr Ser Ala Lys Asn Ser Ala
    2720                2725                2730

Asn Ala Ile Ile Gln Lys Pro Ile Arg Thr Val Gln Glu Val Gln
    2735                2740                2745

Ser Ala Leu Thr Asn Val Asn Arg Val Asn Glu Arg Leu Thr Gln
    2750                2755                2760

Ala Ile Asn Gln Leu Val Pro Leu Ala Asp Asn Ser Ala Leu Lys
    2765                2770                2775

Thr Ala Lys Thr Lys Leu Asp Glu Glu Ile Asn Lys Ser Val Thr
    2780                2785                2790

Thr Asp Gly Met Thr Gln Ser Ser Ile Gln Ala Tyr Glu Asn Ala
    2795                2800                2805

Lys Arg Ala Gly Gln Thr Glu Ser Thr Asn Ala Gln Asn Val Ile
    2810                2815                2820

Asn Asn Gly Asp Ala Thr Asp Gln Gln Ile Ala Ala Glu Lys Thr
    2825                2830                2835

Lys Val Glu Glu Lys Tyr Asn Ser Leu Lys Gln Ala Ile Ala Gly
    2840                2845                2850

Leu Thr Pro Asp Leu Ala Pro Leu Gln Thr Ala Lys Thr Gln Leu
    2855                2860                2865

Gln Asn Asp Ile Asp Gln Pro Thr Ser Thr Thr Gly Met Thr Ser
    2870                2875                2880

Ala Ser Ile Ala Ala Phe Asn Glu Lys Leu Ser Ala Ala Arg Thr
    2885                2890                2895

Lys Ile Gln Glu Ile Asp Arg Val Leu Ala Ser His Pro Asp Val
    2900                2905                2910

Ala Thr Ile Arg Gln Asn Val Thr Ala Ala Asn Ala Ala Lys Ser
    2915                2920                2925

Ala Leu Asp Gln Ala Arg Asn Gly Leu Thr Val Asp Lys Ala Pro
    2930                2935                2940

Leu Glu Asn Ala Lys Asn Gln Leu Gln His Ser Ile Asp Thr Gln
    2945                2950                2955

Thr Ser Thr Thr Gly Met Thr Gln Asp Ser Ile Asn Ala Tyr Asn
    2960                2965                2970

Ala Lys Leu Thr Ala Ala Arg Asn Lys Ile Gln Gln Ile Asn Gln
    2975                2980                2985

Val Leu Ala Gly Ser Pro Thr Val Glu Gln Ile Asn Thr Asn Thr
    2990                2995                3000
```

-continued

```
Ser Thr Ala Asn Gln Ala Lys Ser Asp Leu Asp His Ala Arg Gln
3005                3010                3015

Ala Leu Thr Pro Asp Lys Ala Pro Leu Gln Thr Ala Lys Thr Gln
3020                3025                3030

Leu Glu Gln Ser Ile Asn Gln Pro Thr Asp Thr Thr Gly Met Thr
3035                3040                3045

Thr Ala Ser Leu Asn Ala Tyr Asn Gln Lys Leu Gln Ala Ala Arg
3050                3055                3060

Gln Lys Leu Thr Glu Ile Asn Gln Val Leu Asn Gly Asn Pro Thr
3065                3070                3075

Val Gln Asn Ile Asn Asp Lys Val Thr Glu Ala Asn Gln Ala Lys
3080                3085                3090

Asp Gln Leu Asn Thr Ala Arg Gln Gly Leu Thr Leu Asp Arg Gln
3095                3100                3105

Pro Ala Leu Thr Thr Leu His Gly Ala Ser Asn Leu Asn Gln Ala
3110                3115                3120

Gln Gln Asn Asn Phe Thr Gln Gln Ile Asn Ala Ala Gln Asn His
3125                3130                3135

Ala Ala Leu Glu Thr Ile Lys Ser Asn Ile Thr Ala Leu Asn Thr
3140                3145                3150

Ala Met Thr Lys Leu Lys Asp Ser Val Ala Asp Asn Asn Thr Ile
3155                3160                3165

Lys Ser Asp Gln Asn Tyr Thr Asp Ala Thr Pro Ala Asn Lys Gln
3170                3175                3180

Ala Tyr Asp Asn Ala Val Asn Ala Ala Lys Gly Val Ile Gly Glu
3185                3190                3195

Thr Thr Asn Pro Thr Met Asp Val Asn Thr Val Asn Gln Lys Ala
3200                3205                3210

Ala Ser Val Lys Ser Thr Lys Asp Ala Leu Asp Gly Gln Gln Asn
3215                3220                3225

Leu Gln Arg Ala Lys Thr Glu Ala Thr Asn Ala Ile Thr His Ala
3230                3235                3240

Ser Asp Leu Asn Gln Ala Gln Lys Asn Ala Leu Thr Gln Gln Val
3245                3250                3255

Asn Ser Ala Gln Asn Val Gln Ala Val Asn Asp Ile Lys Gln Thr
3260                3265                3270

Thr Gln Ser Leu Asn Thr Ala Met Thr Gly Leu Lys Arg Gly Val
3275                3280                3285

Ala Asn His Asn Gln Val Val Gln Ser Asp Asn Tyr Val Asn Ala
3290                3295                3300

Asp Thr Asn Lys Lys Asn Asp Tyr Asn Asn Ala Tyr Asn His Ala
3305                3310                3315

Asn Asp Ile Ile Asn Gly Asn Ala Gln His Pro Val Ile Thr Pro
3320                3325                3330

Ser Asp Val Asn Asn Ala Leu Ser Asn Val Thr Ser Lys Glu His
3335                3340                3345

Ala Leu Asn Gly Glu Ala Lys Leu Asn Ala Ala Lys Gln Glu Ala
3350                3355                3360

Asn Thr Ala Leu Gly His Leu Asn Asn Leu Asn Asn Ala Gln Arg
3365                3370                3375

Gln Asn Leu Gln Ser Gln Ile Asn Gly Ala His Gln Ile Asp Ala
3380                3385                3390
```

-continued

| | | | | | | | | | | | |
|---|---|---|---|---|---|---|---|---|---|---|---|
|Val|Asn|Thr|Ile|Lys|Gln|Asn|Ala|Thr|Asn|Leu|Asn Ser Ala Met|
| |3395| | | |3400| | | |3405| | |
|Gly|Asn|Leu|Arg|Gln|Ala|Val|Ala|Asp|Lys|Asp|Gln Val Lys Arg|
| |3410| | | |3415| | | |3420| | |
|Thr|Glu|Asp|Tyr|Ala|Asp|Asp|Thr|Ala|Lys|Gln|Asn Ala Tyr|
| |3425| | | |3430| | | |3435| | |
|Asn|Ser|Ala|Val|Ser|Ser|Ala|Glu|Thr|Ile|Ile|Asn Gln Thr Thr|
| |3440| | | |3445| | | |3450| | |
|Asn|Pro|Thr|Met|Ser|Val|Asp|Asp|Val|Asn|Arg|Ala Thr Ser Ala|
| |3455| | | |3460| | | |3465| | |
|Val|Thr|Ser|Asn|Lys|Asn|Ala|Leu|Asn|Gly|Tyr|Glu Lys Leu Ala|
| |3470| | | |3475| | | |3480| | |
|Gln|Ser|Lys|Thr|Asp|Ala|Ala|Arg|Ala|Ile|Asp|Ala Leu Pro His|
| |3485| | | |3490| | | |3495| | |
|Leu|Asn|Asn|Ala|Gln|Lys|Ala|Asp|Val|Lys|Ser|Lys Ile Asn Ala|
| |3500| | | |3505| | | |3510| | |
|Ala|Ser|Asn|Ile|Ala|Gly|Val|Asn|Thr|Val|Lys|Gln Gln Gly Thr|
| |3515| | | |3520| | | |3525| | |
|Asp|Leu|Asn|Thr|Ala|Met|Gly|Asn|Leu|Gln|Gly|Ala Ile Asn Asp|
| |3530| | | |3535| | | |3540| | |
|Glu|Gln|Thr|Thr|Leu|Asn|Ser|Gln|Asn|Tyr|Gln|Asp Ala Thr Pro|
| |3545| | | |3550| | | |3555| | |
|Ser|Lys|Lys|Thr|Ala|Tyr|Thr|Asn|Ala|Val|Gln|Ala Ala Lys Asp|
| |3560| | | |3565| | | |3570| | |
|Ile|Leu|Asn|Lys|Ser|Asn|Gly|Gln|Asn|Lys|Thr|Lys Asp Gln Val|
| |3575| | | |3580| | | |3585| | |
|Thr|Glu|Ala|Met|Asn|Gln|Val|Asn|Ser|Ala|Lys|Asn Asn Leu Asp|
| |3590| | | |3595| | | |3600| | |
|Gly|Thr|Arg|Leu|Leu|Asp|Gln|Ala|Lys|Gln|Thr|Ala Lys Gln Gln|
| |3605| | | |3610| | | |3615| | |
|Leu|Asn|Asn|Met|Thr|His|Leu|Thr|Thr|Ala|Gln|Lys Thr Asn Leu|
| |3620| | | |3625| | | |3630| | |
|Thr|Asn|Gln|Ile|Asn|Ser|Gly|Thr|Thr|Val|Ala|Gly Val Gln Thr|
| |3635| | | |3640| | | |3645| | |
|Val|Gln|Ser|Asn|Ala|Asn|Thr|Leu|Asp|Gln|Ala|Met Asn Thr Leu|
| |3650| | | |3655| | | |3660| | |
|Arg|Gln|Ser|Ile|Ala|Asn|Lys|Asp|Ala|Thr|Lys|Ala Ser Glu Asp|
| |3665| | | |3670| | | |3675| | |
|Tyr|Val|Asp|Ala|Asn|Asn|Asp|Lys|Gln|Thr|Ala|Tyr Asn Asn Ala|
| |3680| | | |3685| | | |3690| | |
|Val|Ala|Ala|Ala|Glu|Thr|Ile|Ile|Asn|Ala|Asn|Ser Asn Pro Glu|
| |3695| | | |3700| | | |3705| | |
|Met|Asn|Pro|Ser|Thr|Ile|Thr|Gln|Lys|Ala|Glu|Gln Val Asn Ser|
| |3710| | | |3715| | | |3720| | |
|Ser|Lys|Thr|Ala|Leu|Asn|Gly|Asp|Glu|Asn|Leu|Ala Ala Ala Lys|
| |3725| | | |3730| | | |3735| | |
|Gln|Asn|Ala|Lys|Thr|Tyr|Leu|Asn|Thr|Leu|Thr|Ser Ile Thr Asp|
| |3740| | | |3745| | | |3750| | |
|Ala|Gln|Lys|Asn|Asn|Leu|Ile|Ser|Gln|Ile|Thr|Ser Ala Thr Arg|
| |3755| | | |3760| | | |3765| | |
|Val|Ser|Gly|Val|Asp|Thr|Val|Lys|Gln|Asn|Ala|Gln His Leu Asp|
| |3770| | | |3775| | | |3780| | |
|Gln|Ala|Met|Ala|Ser|Leu|Gln|Asn|Gly|Ile|Asn|Asn Glu Ser Gln|

-continued

```
                3785                3790                3795
Val Lys Ser Ser Glu Lys Tyr Arg Asp Ala Asp Thr Asn Lys Gln
    3800                3805                3810

Gln Glu Tyr Asp Asn Ala Ile Thr Ala Ala Lys Ala Ile Leu Asn
    3815                3820                3825

Lys Ser Thr Gly Pro Asn Thr Ala Gln Asn Ala Val Glu Ala Ala
    3830                3835                3840

Leu Gln Arg Val Asn Asn Ala Lys Asp Ala Leu Asn Gly Asp Ala
    3845                3850                3855

Lys Leu Ile Ala Ala Gln Asn Ala Ala Lys Gln His Leu Gly Thr
    3860                3865                3870

Leu Thr His Ile Thr Thr Ala Gln Arg Asn Asp Leu Thr Asn Gln
    3875                3880                3885

Ile Ser Gln Ala Thr Asn Leu Ala Gly Val Glu Ser Val Lys Gln
    3890                3895                3900

Asn Ala Asn Ser Leu Asp Gly Ala Met Gly Asn Leu Gln Thr Ala
    3905                3910                3915

Ile Asn Asp Lys Ser Gly Thr Leu Ala Ser Gln Asn Phe Leu Asp
    3920                3925                3930

Ala Asp Glu Gln Lys Arg Asn Ala Tyr Asn Gln Ala Val Ser Ala
    3935                3940                3945

Ala Glu Thr Ile Leu Asn Lys Gln Thr Gly Pro Asn Thr Ala Lys
    3950                3955                3960

Thr Ala Val Glu Gln Ala Leu Asn Asn Val Asn Asn Ala Lys His
    3965                3970                3975

Ala Leu Asn Gly Thr Gln Asn Leu Asn Asn Ala Lys Gln Ala Ala
    3980                3985                3990

Ile Thr Ala Ile Asn Gly Ala Ser Asp Leu Asn Gln Lys Gln Lys
    3995                4000                4005

Asp Ala Leu Lys Ala Gln Ala Asn Gly Ala Gln Arg Val Ser Asn
    4010                4015                4020

Ala Gln Asp Val Gln His Asn Ala Thr Glu Leu Asn Thr Ala Met
    4025                4030                4035

Gly Thr Leu Lys His Ala Ile Ala Asp Lys Thr Asn Thr Leu Ala
    4040                4045                4050

Ser Ser Lys Tyr Val Asn Ala Asp Ser Thr Lys Gln Asn Ala Tyr
    4055                4060                4065

Thr Thr Lys Val Thr Asn Ala Glu His Ile Ile Ser Gly Thr Pro
    4070                4075                4080

Thr Val Val Thr Thr Pro Ser Glu Val Thr Ala Ala Ala Asn Gln
    4085                4090                4095

Val Asn Ser Ala Lys Gln Glu Leu Asn Gly Asp Glu Arg Leu Arg
    4100                4105                4110

Glu Ala Lys Gln Asn Ala Asn Thr Ala Ile Asp Ala Leu Thr Gln
    4115                4120                4125

Leu Asn Thr Pro Gln Lys Ala Lys Leu Lys Glu Gln Val Gly Gln
    4130                4135                4140

Ala Asn Arg Leu Glu Asp Val Gln Thr Val Gln Thr Asn Gly Gln
    4145                4150                4155

Ala Leu Asn Asn Ala Met Lys Gly Leu Arg Asp Ser Ile Ala Asn
    4160                4165                4170

Glu Thr Thr Val Lys Thr Ser Gln Asn Tyr Thr Asp Ala Ser Pro
    4175                4180                4185
```

```
Asn Asn Gln Ser Thr Tyr Asn Ser Ala Val Ser Asn Ala Lys Gly
    4190                4195                4200

Ile Ile Asn Gln Thr Asn Asn Pro Thr Met Asp Thr Ser Ala Ile
    4205                4210                4215

Thr Gln Ala Thr Thr Gln Val Asn Asn Ala Lys Asn Gly Leu Asn
    4220                4225                4230

Gly Ala Glu Asn Leu Arg Asn Ala Gln Asn Thr Ala Lys Gln Asn
    4235                4240                4245

Leu Asn Thr Leu Ser His Leu Thr Asn Asn Gln Lys Ser Ala Ile
    4250                4255                4260

Ser Ser Gln Ile Asp Arg Ala Gly His Val Ser Glu Val Thr Ala
    4265                4270                4275

Thr Lys Asn Ala Ala Thr Glu Leu Asn Thr Gln Met Gly Asn Leu
    4280                4285                4290

Glu Gln Ala Ile His Asp Gln Asn Thr Val Lys Gln Ser Val Lys
    4295                4300                4305

Phe Thr Asp Ala Asp Lys Ala Lys Arg Asp Ala Tyr Thr Asn Ala
    4310                4315                4320

Val Ser Arg Ala Glu Ala Ile Leu Asn Lys Thr Gln Gly Ala Asn
    4325                4330                4335

Thr Ser Lys Gln Asp Val Glu Ala Ala Ile Gln Asn Val Ser Ser
    4340                4345                4350

Ala Lys Asn Ala Leu Asn Gly Asp Gln Asn Val Thr Asn Ala Lys
    4355                4360                4365

Asn Ala Ala Lys Asn Ala Leu Asn Asn Leu Thr Ser Ile Asn Asn
    4370                4375                4380

Ala Gln Lys Arg Asp Leu Thr Thr Lys Ile Asp Gln Ala Thr Thr
    4385                4390                4395

Val Ala Gly Val Glu Ala Val Ser Asn Thr Ser Thr Gln Leu Asn
    4400                4405                4410

Thr Ala Met Ala Asn Leu Gln Asn Gly Ile Asn Asp Lys Thr Asn
    4415                4420                4425

Thr Leu Ala Ser Glu Asn Tyr His Asp Ala Asp Ser Asp Lys Lys
    4430                4435                4440

Thr Ala Tyr Thr Gln Ala Val Thr Asn Ala Glu Asn Ile Leu Asn
    4445                4450                4455

Lys Asn Ser Gly Ser Asn Leu Asp Lys Thr Ala Val Glu Asn Ala
    4460                4465                4470

Leu Ser Gln Val Ala Asn Ala Lys Gly Ala Leu Asn Gly Asn His
    4475                4480                4485

Asn Leu Glu Gln Ala Lys Ser Asn Ala Asn Thr Thr Ile Asn Gly
    4490                4495                4500

Leu Gln His Leu Thr Thr Ala Gln Lys Asp Lys Leu Lys Gln Gln
    4505                4510                4515

Val Gln Gln Ala Gln Asn Val Ala Gly Val Asp Thr Val Lys Ser
    4520                4525                4530

Ser Ala Asn Thr Leu Asn Gly Ala Met Gly Thr Leu Arg Asn Ser
    4535                4540                4545

Ile Gln Asp Asn Thr Ala Thr Lys Asn Gly Gln Asn Tyr Leu Asp
    4550                4555                4560

Ala Thr Glu Arg Asn Lys Thr Asn Tyr Asn Asn Ala Val Asp Ser
    4565                4570                4575
```

```
Ala Asn Gly Val Ile Asn Ala   Thr Ser Asn Pro Asn   Met Asp Ala
    4580                4585                 4590

Asn Ala Ile Asn Gln Ile Ala   Thr Gln Val Thr Ser   Thr Lys Asn
    4595                4600                 4605

Ala Leu Asp Gly Thr His Asn   Leu Thr Gln Ala Lys   Gln Thr Ala
    4610                4615                 4620

Thr Asn Ala Ile Asp Gly Ala   Thr Asn Leu Asn Lys   Ala Gln Lys
    4625                4630                 4635

Asp Ala Leu Lys Ala Gln Val   Thr Ser Ala Gln Arg   Val Ala Asn
    4640                4645                 4650

Val Thr Ser Ile Gln Gln Thr   Ala Asn Glu Leu Asn   Thr Ala Met
    4655                4660                 4665

Gly Gln Leu Gln His Gly Ile   Asp Asp Glu Asn Ala   Thr Lys Gln
    4670                4675                 4680

Thr Gln Lys Tyr Arg Asp Ala   Glu Gln Ser Lys Lys   Thr Ala Tyr
    4685                4690                 4695

Asp Gln Ala Val Ala Ala Ala   Lys Ala Ile Leu Asn   Lys Gln Thr
    4700                4705                 4710

Gly Ser Asn Ser Asp Lys Ala   Ala Val Asp Arg Ala   Leu Gln Gln
    4715                4720                 4725

Val Thr Ser Thr Lys Asp Ala   Leu Asn Gly Asp Ala   Lys Leu Ala
    4730                4735                 4740

Glu Ala Lys Ala Ala Ala Lys   Gln Asn Leu Gly Thr   Leu Asn His
    4745                4750                 4755

Ile Thr Asn Ala Gln Arg Thr   Asp Leu Glu Gly Gln   Ile Asn Gln
    4760                4765                 4770

Ala Thr Thr Val Asp Gly Val   Asn Thr Val Lys Thr   Asn Ala Asn
    4775                4780                 4785

Thr Leu Asp Gly Ala Met Asn   Ser Leu Gln Gly Ser   Ile Asn Asp
    4790                4795                 4800

Lys Asp Ala Thr Leu Arg Asn   Gln Asn Tyr Leu Asp   Ala Asp Glu
    4805                4810                 4815

Ser Lys Arg Asn Ala Tyr Thr   Gln Ala Val Thr Ala   Ala Glu Gly
    4820                4825                 4830

Ile Leu Asn Lys Gln Thr Gly   Gly Asn Thr Ser Lys   Ala Asp Val
    4835                4840                 4845

Asp Asn Ala Leu Asn Ala Val   Thr Arg Ala Lys Ala   Ala Leu Asn
    4850                4855                 4860

Gly Ala Asp Asn Leu Arg Asn   Ala Lys Thr Ser Ala   Thr Asn Thr
    4865                4870                 4875

Ile Asp Gly Leu Pro Asn Leu   Thr Gln Leu Gln Lys   Asp Asn Leu
    4880                4885                 4890

Lys His Gln Val Glu Gln Ala   Gln Asn Val Ala Gly   Val Asn Gly
    4895                4900                 4905

Val Lys Asp Lys Gly Asn Thr   Leu Asn Thr Ala Met   Gly Ala Leu
    4910                4915                 4920

Arg Thr Ser Ile Gln Asn Asp   Asn Thr Thr Lys Thr   Ser Gln Asn
    4925                4930                 4935

Tyr Leu Asp Ala Ser Asp Ser   Asn Lys Asn Asn Tyr   Asn Thr Ala
    4940                4945                 4950

Val Asn Asn Ala Asn Gly Val   Ile Asn Ala Thr Asn   Asn Pro Asn
    4955                4960                 4965

Met Asp Ala Asn Ala Ile Asn   Gly Met Ala Asn Gln   Val Asn Thr
```

-continued

```
            4970                4975                4980
Thr Lys Ala Ala Leu Asn Gly Ala Gln Asn Leu Ala Gln Ala Lys
       4985                4990                4995

Thr Asn Ala Thr Asn Thr Ile Asn Asn Ala His Asp Leu Asn Gln
       5000                5005                5010

Lys Gln Lys Asp Ala Leu Lys Thr Gln Val Asn Asn Ala Gln Arg
       5015                5020                5025

Val Ser Asp Ala Asn Asn Val Gln His Thr Ala Thr Glu Leu Asn
       5030                5035                5040

Ser Ala Met Thr Ala Leu Lys Ala Ala Ile Ala Asp Lys Glu Arg
       5045                5050                5055

Thr Lys Ala Ser Gly Asn Tyr Val Asn Ala Asp Gln Glu Lys Arg
       5060                5065                5070

Gln Ala Tyr Asp Ser Lys Val Thr Asn Ala Glu Asn Ile Ile Ser
       5075                5080                5085

Gly Thr Pro Asn Ala Thr Leu Thr Val Asn Asp Val Asn Ser Ala
       5090                5095                5100

Ala Ser Gln Val Asn Ala Ala Lys Thr Ala Leu Asn Gly Asp Asn
       5105                5110                5115

Asn Leu Arg Val Ala Lys Glu His Ala Asn Asn Thr Ile Asp Gly
       5120                5125                5130

Leu Ala Gln Leu Asn Asn Ala Gln Lys Ala Lys Leu Lys Glu Gln
       5135                5140                5145

Val Gln Ser Ala Thr Thr Leu Asp Gly Val Gln Thr Val Lys Asn
       5150                5155                5160

Ser Ser Gln Thr Leu Asn Thr Ala Met Lys Gly Leu Arg Asp Ser
       5165                5170                5175

Ile Ala Asn Glu Ala Thr Ile Lys Ala Gly Gln Asn Tyr Thr Asp
       5180                5185                5190

Ala Ser Pro Asn Asn Arg Asn Glu Tyr Asp Ser Ala Val Thr Ala
       5195                5200                5205

Ala Lys Ala Ile Ile Asn Gln Thr Ser Asn Pro Thr Met Glu Pro
       5210                5215                5220

Asn Thr Ile Thr Gln Val Thr Ser Gln Val Thr Thr Lys Glu Gln
       5225                5230                5235

Ala Leu Asn Gly Ala Arg Asn Leu Ala Gln Ala Lys Thr Thr Ala
       5240                5245                5250

Lys Asn Asn Leu Asn Asn Leu Thr Ser Ile Asn Asn Ala Gln Lys
       5255                5260                5265

Asp Ala Leu Thr Arg Ser Ile Asp Gly Ala Thr Thr Val Ala Gly
       5270                5275                5280

Val Asn Gln Glu Thr Ala Lys Ala Thr Glu Leu Asn Asn Ala Met
       5285                5290                5295

His Ser Leu Gln Asn Gly Ile Asn Asp Glu Thr Gln Thr Lys Gln
       5300                5305                5310

Thr Gln Lys Tyr Leu Asp Ala Glu Pro Ser Lys Lys Ser Ala Tyr
       5315                5320                5325

Asp Gln Ala Val Asn Ala Ala Lys Ala Ile Leu Thr Lys Ala Ser
       5330                5335                5340

Gly Gln Asn Val Asp Lys Ala Ala Val Glu Gln Ala Leu Gln Asn
       5345                5350                5355

Val Asn Ser Thr Lys Thr Ala Leu Asn Gly Asp Ala Lys Leu Asn
       5360                5365                5370
```

-continued

Glu Ala Lys Ala Ala Ala Lys Gln Thr Leu Gly Thr Leu Thr His
5375 5380 5385

Ile Asn Asn Ala Gln Arg Thr Ala Leu Asp Asn Glu Ile Thr Gln
5390 5395 5400

Ala Thr Asn Val Glu Gly Val Asn Thr Val Lys Ala Lys Ala Gln
5405 5410 5415

Gln Leu Asp Gly Ala Met Gly Gln Leu Glu Thr Ser Ile Arg Asp
5420 5425 5430

Lys Asp Thr Thr Leu Gln Ser Gln Asn Tyr Gln Asp Ala Asp Asp
5435 5440 5445

Ala Lys Arg Thr Ala Tyr Ser Gln Ala Val Asn Ala Ala Ala Thr
5450 5455 5460

Ile Leu Asn Lys Thr Ala Gly Gly Asn Thr Pro Lys Ala Asp Val
5465 5470 5475

Glu Arg Ala Met Gln Ala Val Thr Gln Ala Asn Thr Ala Leu Asn
5480 5485 5490

Gly Ile Gln Asn Leu Asp Arg Ala Lys Gln Ala Ala Asn Thr Ala
5495 5500 5505

Ile Thr Asn Ala Ser Asp Leu Asn Thr Lys Gln Lys Glu Ala Leu
5510 5515 5520

Lys Ala Gln Val Thr Ser Ala Gly Arg Val Ser Ala Ala Asn Gly
5525 5530 5535

Val Glu His Thr Ala Thr Glu Leu Asn Thr Ala Met Thr Ala Leu
5540 5545 5550

Lys Arg Ala Ile Ala Asp Lys Ala Glu Thr Lys Ala Ser Gly Asn
5555 5560 5565

Tyr Val Asn Ala Asp Ala Asn Lys Arg Gln Ala Tyr Asp Glu Lys
5570 5575 5580

Val Thr Ala Ala Glu Asn Ile Val Ser Gly Thr Pro Thr Pro Thr
5585 5590 5595

Leu Thr Pro Ala Asp Val Thr Asn Ala Ala Thr Gln Val Thr Asn
5600 5605 5610

Ala Lys Thr Gln Leu Asn Gly Asn His Asn Leu Glu Val Ala Lys
5615 5620 5625

Gln Asn Ala Asn Thr Ala Ile Asp Gly Leu Thr Ser Leu Asn Gly
5630 5635 5640

Pro Gln Lys Ala Lys Leu Lys Glu Gln Val Gly Gln Ala Thr Thr
5645 5650 5655

Leu Pro Asn Val Gln Thr Val Arg Asp Asn Ala Gln Thr Leu Asn
5660 5665 5670

Thr Ala Met Lys Gly Leu Arg Asp Ser Ile Ala Asn Glu Ala Thr
5675 5680 5685

Ile Lys Ala Gly Gln Asn Tyr Thr Asp Ala Ser Gln Asn Lys Gln
5690 5695 5700

Thr Asp Tyr Asn Ser Ala Val Thr Ala Ala Lys Ala Ile Ile Gly
5705 5710 5715

Gln Thr Thr Ser Pro Ser Met Asn Ala Gln Glu Ile Asn Gln Ala
5720 5725 5730

Lys Asp Gln Val Thr Ala Lys Gln Gln Ala Leu Asn Gly Gln Glu
5735 5740 5745

Asn Leu Arg Thr Ala Gln Thr Asn Ala Lys Gln His Leu Asn Gly
5750 5755 5760

-continued

| | | | | | | | | | | | |
|---|---|---|---|---|---|---|---|---|---|---|---|
| Leu | Ser | Asp | Leu | Thr | Asp | Ala | Gln | Lys | Asp | Ala | Val | Lys | Arg | Gln |
| | 5765 | | | | 5770 | | | | | 5775 | | | | |

Leu Ser Asp Leu Thr Asp Ala Gln Lys Asp Ala Val Lys Arg Gln
    5765                5770            5775

Ile Glu Gly Ala Thr His Val Asn Glu Val Thr Gln Ala Gln Asn
    5780                5785            5790

Asn Ala Asp Ala Leu Asn Thr Ala Met Thr Asn Leu Lys Asn Gly
    5795                5800            5805

Ile Gln Asp Gln Asn Thr Ile Lys Gln Gly Val Asn Phe Thr Asp
    5810                5815            5820

Ala Asp Glu Ala Lys Arg Asn Ala Tyr Thr Asn Ala Val Thr Gln
    5825                5830            5835

Ala Glu Gln Ile Leu Asn Lys Ala Gln Gly Pro Asn Thr Ser Lys
    5840                5845            5850

Asp Gly Val Glu Thr Ala Leu Glu Asn Val Gln Arg Ala Lys Asn
    5855                5860            5865

Glu Leu Asn Gly Asn Gln Asn Val Ala Asn Ala Lys Thr Thr Ala
    5870                5875            5880

Lys Asn Ala Leu Asn Asn Leu Thr Ser Ile Asn Asn Ala Gln Lys
    5885                5890            5895

Glu Ala Leu Lys Ser Gln Ile Glu Gly Ala Thr Thr Val Ala Gly
    5900                5905            5910

Val Asn Gln Val Ser Thr Thr Ala Ser Glu Leu Asn Thr Ala Met
    5915                5920            5925

Ser Asn Leu Gln Asn Gly Ile Asn Asp Glu Ala Ala Thr Lys Ala
    5930                5935            5940

Ala Gln Lys Tyr Thr Asp Ala Asp Arg Glu Lys Gln Thr Ala Tyr
    5945                5950            5955

Asn Asp Ala Val Thr Ala Ala Lys Thr Leu Leu Asp Lys Thr Ala
    5960                5965            5970

Gly Ser Asn Asp Asn Lys Ala Ala Val Glu Gln Ala Leu Gln Arg
    5975                5980            5985

Val Asn Thr Ala Lys Thr Ala Leu Asn Gly Asp Glu Arg Leu Asn
    5990                5995            6000

Glu Ala Lys Asn Thr Ala Lys Gln Gln Val Ala Thr Met Ser His
    6005                6010            6015

Leu Thr Asp Ala Gln Lys Ala Asn Leu Thr Ser Gln Ile Glu Ser
    6020                6025            6030

Gly Thr Thr Val Ala Gly Val Gln Gly Ile Gln Ala Asn Ala Gly
    6035                6040            6045

Thr Leu Asp Gln Ala Met Asn Gln Leu Arg Gln Ser Ile Ala Ser
    6050                6055            6060

Lys Asp Ala Thr Lys Ser Ser Glu Asp Tyr Gln Asp Ala Asn Ala
    6065                6070            6075

Asp Leu Gln Asn Ala Tyr Asn Asp Ala Val Thr Asn Ala Glu Gly
    6080                6085            6090

Ile Ile Ser Ala Thr Asn Asn Pro Glu Met Asn Pro Asp Thr Ile
    6095                6100            6105

Asn Gln Lys Ala Ser Gln Val Asn Ser Ala Lys Ser Ala Leu Asn
    6110                6115            6120

Gly Asp Glu Lys Leu Ala Ala Ala Lys Gln Thr Ala Lys Ser Asp
    6125                6130            6135

Ile Gly Arg Leu Thr Asp Leu Asn Asn Ala Gln Arg Thr Ala Ala
    6140                6145            6150

Asn Ala Glu Val Asp Gln Ala Pro Asn Leu Ala Ala Val Thr Ala

```
                6155                6160                6165

Ala Lys Asn Lys Ala Thr Ser Leu Asn Thr Ala Met Gly Asn Leu
        6170                6175                6180

Lys His Ala Leu Ala Glu Lys Asp Asn Thr Lys Arg Ser Val Asn
        6185                6190                6195

Tyr Thr Asp Ala Asp Gln Pro Lys Gln Gln Ala Tyr Asp Thr Ala
        6200                6205                6210

Val Thr Gln Ala Glu Ala Ile Thr Asn Ala Asn Gly Ser Asn Ala
        6215                6220                6225

Asn Glu Thr Gln Val Gln Ala Ala Leu Asn Gln Leu Asn Gln Ala
        6230                6235                6240

Lys Asn Asp Leu Asn Gly Asp Asn Lys Val Ala Gln Ala Lys Glu
        6245                6250                6255

Ser Ala Lys Arg Ala Leu Ala Ser Tyr Ser Asn Leu Asn Asn Ala
        6260                6265                6270

Gln Ser Thr Ala Ala Ile Ser Gln Ile Asp Asn Ala Thr Thr Val
        6275                6280                6285

Ala Gly Val Thr Ala Ala Gln Asn Thr Ala Asn Glu Leu Asn Thr
        6290                6295                6300

Ala Met Gly Gln Leu Gln Asn Gly Ile Asn Asp Gln Asn Thr Val
        6305                6310                6315

Lys Gln Gln Val Asn Phe Thr Asp Ala Asp Gln Gly Lys Lys Asp
        6320                6325                6330

Ala Tyr Thr Asn Ala Val Thr Asn Ala Gln Gly Ile Leu Asp Lys
        6335                6340                6345

Ala His Gly Gln Asn Met Thr Lys Ala Gln Val Glu Ala Ala Leu
        6350                6355                6360

Asn Gln Val Thr Thr Ala Lys Asn Ala Leu Asn Gly Asp Ala Asn
        6365                6370                6375

Val Arg Gln Ala Lys Ser Asp Ala Lys Ala Asn Leu Gly Thr Leu
        6380                6385                6390

Thr His Leu Asn Asn Ala Gln Lys Gln Asp Leu Thr Ser Gln Ile
        6395                6400                6405

Glu Gly Ala Thr Thr Val Asn Gly Val Asn Gly Val Lys Thr Lys
        6410                6415                6420

Ala Gln Asp Leu Asp Gly Ala Met Gln Arg Leu Gln Ser Ala Ile
        6425                6430                6435

Ala Asn Lys Asp Gln Thr Lys Ala Ser Glu Asn Tyr Ile Asp Ala
        6440                6445                6450

Asp Pro Thr Lys Lys Thr Ala Phe Asp Asn Ala Ile Thr Gln Ala
        6455                6460                6465

Glu Ser Tyr Leu Asn Lys Asp His Gly Ala Asn Lys Asp Lys Gln
        6470                6475                6480

Ala Val Glu Gln Ala Ile Gln Ser Val Thr Ser Thr Glu Asn Ala
        6485                6490                6495

Leu Asn Gly Asp Ala Asn Leu Gln Arg Ala Lys Thr Glu Ala Ile
        6500                6505                6510

Gln Ala Ile Asp Asn Leu Thr His Leu Asn Thr Pro Gln Lys Thr
        6515                6520                6525

Ala Leu Lys Gln Gln Val Asn Ala Ala Gln Arg Val Ser Gly Val
        6530                6535                6540

Thr Asp Leu Lys Asn Ser Ala Thr Ser Leu Asn Asn Ala Met Asp
        6545                6550                6555
```

```
Gln Leu Lys Gln Ala Ile Ala Asp His Asp Thr Ile Val Ala Ser
    6560            6565                6570

Gly Asn Tyr Thr Asn Ala Ser Pro Asp Lys Gln Gly Ala Tyr Thr
    6575            6580                6585

Asp Ala Tyr Asn Ala Ala Lys Asn Ile Val Asn Gly Ser Pro Asn
    6590            6595                6600

Val Ile Thr Asn Ala Ala Asp Val Thr Ala Ala Thr Gln Arg Val
    6605            6610                6615

Asn Asn Ala Glu Thr Gly Leu Asn Gly Asp Thr Asn Leu Ala Thr
    6620            6625                6630

Ala Lys Gln Gln Ala Lys Asp Ala Leu Arg Gln Met Thr His Leu
    6635            6640                6645

Ser Asp Ala Gln Lys Gln Ser Ile Thr Gly Gln Ile Asp Ser Ala
    6650            6655                6660

Thr Gln Val Thr Gly Val Gln Ser Val Lys Asp Asn Ala Thr Asn
    6665            6670                6675

Leu Asp Asn Ala Met Asn Gln Leu Arg Asn Ser Ile Ala Asn Lys
    6680            6685                6690

Asp Asp Val Lys Ala Ser Gln Pro Tyr Val Asp Ala Asp Arg Asp
    6695            6700                6705

Lys Gln Asn Ala Tyr Asn Thr Ala Val Thr Asn Ala Glu Asn Ile
    6710            6715                6720

Ile Asn Ala Thr Ser Gln Pro Thr Leu Asp Pro Ser Ala Val Thr
    6725            6730                6735

Gln Ala Ala Asn Gln Val Ser Thr Asn Lys Thr Ala Leu Asn Gly
    6740            6745                6750

Ala Gln Asn Leu Ala Asn Lys Lys Gln Glu Thr Thr Ala Asn Ile
    6755            6760                6765

Asn Gln Leu Ser His Leu Asn Asn Ala Gln Lys Gln Asp Leu Asn
    6770            6775                6780

Thr Gln Val Thr Asn Ala Pro Asn Ile Ser Thr Val Asn Gln Val
    6785            6790                6795

Lys Thr Lys Ala Glu Gln Leu Asp Gln Ala Met Glu Arg Leu Ile
    6800            6805                6810

Asn Gly Ile Gln Asp Lys Asp Gln Val Lys Gln Ser Val Asn Phe
    6815            6820                6825

Thr Asp Ala Asp Pro Glu Lys Gln Thr Ala Tyr Asn Asn Ala Val
    6830            6835                6840

Thr Ala Ala Glu Asn Ile Ile Asn Gln Ala Asn Gly Thr Asn Ala
    6845            6850                6855

Asn Gln Ser Gln Val Glu Ala Ala Leu Ser Thr Val Thr Thr Thr
    6860            6865                6870

Lys Gln Ala Leu Asn Gly Asp Arg Lys Val Thr Asp Ala Lys Asn
    6875            6880                6885

Asn Ala Asn Gln Thr Leu Ser Thr Leu Asp Asn Leu Asn Asn Ala
    6890            6895                6900

Gln Lys Gly Ala Val Thr Gly Asn Ile Asn Gln Ala His Thr Val
    6905            6910                6915

Ala Glu Val Thr Gln Ala Ile Gln Thr Ala Gln Glu Leu Asn Thr
    6920            6925                6930

Ala Met Gly Asn Leu Lys Asn Ser Leu Asn Asp Lys Asp Thr Thr
    6935            6940                6945
```

```
Leu Gly Ser Gln Asn Phe Ala Asp Ala Asp Pro Glu Lys Lys Asn
    6950                6955                6960
Ala Tyr Asn Glu Ala Val His Asn Ala Glu Asn Ile Leu Asn Lys
    6965                6970                6975
Ser Thr Gly Thr Asn Val Pro Lys Asp Gln Val Glu Ala Ala Met
    6980                6985                6990
Asn Gln Val Asn Ala Thr Lys Ala Ala Leu Asn Gly Thr Gln Asn
    6995                7000                7005
Leu Glu Lys Ala Lys Gln His Ala Asn Thr Ala Ile Asp Gly Leu
    7010                7015                7020
Ser His Leu Thr Asn Ala Gln Lys Glu Ala Leu Lys Gln Leu Val
    7025                7030                7035
Gln Gln Ser Thr Thr Val Ala Glu Ala Gln Gly Asn Glu Gln Lys
    7040                7045                7050
Ala Asn Asn Val Asp Ala Ala Met Asp Lys Leu Arg Gln Ser Ile
    7055                7060                7065
Ala Asp Asn Ala Thr Thr Lys Gln Asn Gln Asn Tyr Thr Asp Ala
    7070                7075                7080
Ser Gln Asn Lys Lys Asp Ala Tyr Asn Asn Ala Val Thr Thr Ala
    7085                7090                7095
Gln Gly Ile Ile Asp Gln Thr Thr Ser Pro Thr Leu Asp Pro Thr
    7100                7105                7110
Val Ile Asn Gln Ala Ala Gly Gln Val Ser Thr Thr Lys Asn Ala
    7115                7120                7125
Leu Asn Gly Asn Glu Asn Leu Glu Ala Ala Lys Gln Gln Ala Ser
    7130                7135                7140
Gln Ser Leu Gly Ser Leu Asp Asn Leu Asn Asn Ala Gln Lys Gln
    7145                7150                7155
Thr Val Thr Asp Gln Ile Asn Gly Ala His Thr Val Asp Glu Ala
    7160                7165                7170
Asn Gln Ile Lys Gln Asn Ala Gln Asn Leu Asn Thr Ala Met Gly
    7175                7180                7185
Asn Leu Lys Gln Ala Ile Ala Asp Lys Asp Ala Thr Lys Ala Thr
    7190                7195                7200
Val Asn Phe Thr Asp Ala Asp Gln Ala Lys Gln Gln Ala Tyr Asn
    7205                7210                7215
Thr Ala Val Thr Asn Ala Glu Asn Ile Ser Lys Ala Asn Gly Asn
    7220                7225                7230
Ala Thr Gln Ala Glu Val Gln Ala Ile Lys Gln Val Asn Ala
    7235                7240                7245
Ala Lys Gln Ala Leu Asn Gly Asn Ala Asn Val Gln His Ala Lys
    7250                7255                7260
Asp Glu Ala Thr Ala Leu Ile Asn Ser Ser Asn Asp Leu Asn Gln
    7265                7270                7275
Ala Gln Lys Asp Ala Leu Lys Gln Gln Val Gln Asn Ala Thr Thr
    7280                7285                7290
Val Ala Gly Val Asn Asn Val Lys Gln Thr Ala Gln Glu Leu Asn
    7295                7300                7305
Asn Ala Met Thr Gln Leu Lys Gln Gly Ile Ala Asp Lys Glu Gln
    7310                7315                7320
Thr Lys Ala Asp Gly Asn Phe Val Asn Ala Asp Pro Asp Lys Gln
    7325                7330                7335
Asn Ala Tyr Asn Gln Ala Val Ala Lys Ala Glu Ala Leu Ile Ser
```

```
                    7340              7345              7350

Ala Thr Pro Asp Val Val Thr Pro Ser Glu Ile Thr Ala Ala
    7355              7360              7365

Leu Asn Lys Val Thr Gln Ala Lys Asn Asp Leu Asn Gly Asn Thr
    7370              7375              7380

Asn Leu Ala Thr Ala Lys Gln Asn Val Gln His Ala Ile Asp Gln
    7385              7390              7395

Leu Pro Asn Leu Asn Gln Ala Gln Arg Asp Glu Tyr Ser Lys Gln
    7400              7405              7410

Ile Thr Gln Ala Thr Leu Val Pro Asn Val Asn Ala Ile Gln Gln
    7415              7420              7425

Ala Ala Thr Thr Leu Asn Asp Ala Met Thr Gln Leu Lys Gln Gly
    7430              7435              7440

Ile Ala Asn Lys Ala Gln Ile Lys Gly Ser Glu Asn Tyr His Asp
    7445              7450              7455

Ala Asp Thr Asp Lys Gln Thr Ala Tyr Asp Asn Ala Val Thr Lys
    7460              7465              7470

Ala Glu Glu Leu Leu Lys Gln Thr Thr Asn Pro Thr Met Asp Pro
    7475              7480              7485

Asn Thr Ile Gln Gln Ala Leu Thr Lys Val Asn Asp Thr Asn Gln
    7490              7495              7500

Ala Leu Asn Gly Asn Gln Lys Leu Ala Asp Ala Lys Gln Asp Ala
    7505              7510              7515

Lys Thr Thr Leu Gly Thr Leu Asp His Leu Asn Asp Ala Gln Lys
    7520              7525              7530

Gln Ala Leu Thr Thr Gln Val Glu Gln Ala Pro Asp Ile Ala Thr
    7535              7540              7545

Val Asn Asn Val Lys Gln Asn Ala Gln Asn Leu Asn Asn Ala Met
    7550              7555              7560

Thr Asn Leu Asn Asn Ala Leu Gln Asp Lys Thr Glu Thr Leu Asn
    7565              7570              7575

Ser Ile Asn Phe Thr Asp Ala Asp Gln Ala Lys Lys Asp Ala Tyr
    7580              7585              7590

Thr Asn Ala Val Ser His Ala Glu Gly Ile Leu Ser Lys Ala Asn
    7595              7600              7605

Gly Ser Asn Ala Ser Gln Thr Glu Val Glu Gln Ala Met Gln Arg
    7610              7615              7620

Val Asn Glu Ala Lys Gln Ala Leu Asn Gly Asn Asp Asn Val Gln
    7625              7630              7635

Arg Ala Lys Asp Ala Ala Lys Gln Val Ile Thr Asn Ala Asn Asp
    7640              7645              7650

Leu Asn Gln Ala Gln Lys Asp Ala Leu Lys Gln Gln Val Asp Ala
    7655              7660              7665

Ala Gln Thr Val Ala Asn Val Asn Thr Ile Lys Gln Thr Ala Gln
    7670              7675              7680

Asp Leu Asn Gln Ala Met Thr Gln Leu Lys Gln Gly Ile Ala Asp
    7685              7690              7695

Lys Asp Gln Thr Lys Ala Asn Gly Asn Phe Val Asn Ala Asp Thr
    7700              7705              7710

Asp Lys Gln Asn Ala Tyr Asn Asn Ala Val Ala His Ala Glu Gln
    7715              7720              7725

Ile Ile Ser Gly Thr Pro Asn Ala Asn Val Asp Pro Gln Gln Val
    7730              7735              7740
```

```
Ala Gln Ala Leu Gln Gln Val Asn Gln Ala Lys Gly Asp Leu Asn
    7745                7750                7755
Gly Asn His Asn Leu Gln Val Ala Lys Asp Asn Ala Asn Thr Ala
    7760                7765                7770
Ile Asp Gln Leu Pro Asn Leu Asn Gln Pro Gln Lys Thr Ala Leu
    7775                7780                7785
Lys Asp Gln Val Ser His Ala Glu Leu Val Thr Gly Val Asn Ala
    7790                7795                7800
Ile Lys Gln Asn Ala Asp Ala Leu Asn Asn Ala Met Gly Thr Leu
    7805                7810                7815
Lys Gln Gln Ile Gln Ala Asn Ser Gln Val Pro Gln Ser Val Asp
    7820                7825                7830
Phe Thr Gln Ala Asp Gln Asp Lys Gln Gln Ala Tyr Asn Asn Ala
    7835                7840                7845
Ala Asn Gln Ala Gln Gln Ile Ala Asn Gly Ile Pro Thr Pro Val
    7850                7855                7860
Leu Thr Pro Asp Thr Val Thr Gln Ala Val Thr Thr Met Asn Gln
    7865                7870                7875
Ala Lys Asp Ala Leu Asn Gly Asp Glu Lys Leu Ala Gln Ala Lys
    7880                7885                7890
Gln Glu Ala Leu Ala Asn Leu Asp Thr Leu Arg Asp Leu Asn Gln
    7895                7900                7905
Pro Gln Arg Asp Ala Leu Arg Asn Gln Ile Asn Gln Ala Gln Ala
    7910                7915                7920
Leu Ala Thr Val Glu Gln Thr Lys Gln Asn Ala Gln Asn Val Asn
    7925                7930                7935
Thr Ala Met Ser Asn Leu Lys Gln Gly Ile Ala Asn Lys Asp Thr
    7940                7945                7950
Val Lys Ala Ser Glu Asn Tyr His Asp Ala Asp Ala Asp Lys Gln
    7955                7960                7965
Thr Ala Tyr Thr Asn Ala Val Ser Gln Ala Glu Gly Ile Ile Asn
    7970                7975                7980
Gln Thr Thr Asn Pro Thr Leu Asn Pro Asp Glu Ile Thr Arg Ala
    7985                7990                7995
Leu Thr Gln Val Thr Asp Ala Lys Asn Gly Leu Asn Gly Glu Ala
    8000                8005                8010
Lys Leu Ala Thr Glu Lys Gln Asn Ala Lys Asp Ala Val Ser Gly
    8015                8020                8025
Met Thr His Leu Asn Asp Ala Gln Lys Gln Ala Leu Lys Gly Gln
    8030                8035                8040
Ile Asp Gln Ser Pro Glu Ile Ala Thr Val Asn Gln Val Lys Gln
    8045                8050                8055
Thr Ala Thr Ser Leu Asp Gln Ala Met Asp Gln Leu Ser Gln Ala
    8060                8065                8070
Ile Asn Asp Lys Ala Gln Thr Leu Ala Asp Gly Asn Tyr Leu Asn
    8075                8080                8085
Ala Asp Pro Asp Lys Gln Asn Ala Tyr Lys Gln Ala Val Ala Lys
    8090                8095                8100
Ala Glu Ala Leu Leu Asn Lys Gln Ser Gly Thr Asn Glu Val Gln
    8105                8110                8115
Ala Gln Val Glu Ser Ile Thr Asn Glu Val Asn Ala Ala Lys Gln
    8120                8125                8130
```

-continued

```
Ala Leu Asn Gly Asn Asp Asn Leu Ala Asn Ala Lys Gln Gln Ala
    8135                8140                8145

Lys Gln Gln Leu Ala Asn Leu Thr His Leu Asn Asp Ala Gln Lys
    8150                8155                8160

Gln Ser Phe Glu Ser Gln Ile Thr Gln Ala Pro Leu Val Thr Asp
    8165                8170                8175

Val Thr Thr Ile Asn Gln Lys Ala Gln Thr Leu Asp His Ala Met
    8180                8185                8190

Glu Leu Leu Arg Asn Ser Val Ala Asp Asn Gln Thr Thr Leu Ala
    8195                8200                8205

Ser Glu Asp Tyr His Asp Ala Thr Ala Gln Arg Gln Asn Asp Tyr
    8210                8215                8220

Asn Gln Ala Val Thr Ala Ala Asn Asn Ile Ile Asn Gln Thr Thr
    8225                8230                8235

Ser Pro Thr Met Asn Pro Asp Asp Val Asn Gly Ala Thr Thr Gln
    8240                8245                8250

Val Asn Asn Thr Lys Val Ala Leu Asp Gly Asp Glu Asn Leu Ala
    8255                8260                8265

Ala Ala Lys Gln Gln Ala Asn Asn Arg Leu Asp Gln Leu Asp His
    8270                8275                8280

Leu Asn Asn Ala Gln Lys Gln Gln Leu Gln Ser Gln Ile Thr Gln
    8285                8290                8295

Ser Ser Asp Ile Ala Ala Val Asn Gly His Lys Gln Thr Ala Glu
    8300                8305                8310

Ser Leu Asn Thr Ala Met Gly Asn Leu Ile Asn Ala Ile Ala Asp
    8315                8320                8325

His Gln Ala Val Glu Gln Arg Gly Asn Phe Ile Asn Ala Asp Thr
    8330                8335                8340

Asp Lys Gln Thr Ala Tyr Asn Thr Ala Val Asn Glu Ala Ala Ala
    8345                8350                8355

Met Ile Asn Lys Gln Thr Gly Gln Asn Ala Asn Gln Thr Glu Val
    8360                8365                8370

Glu Gln Ala Ile Thr Lys Val Gln Thr Thr Leu Gln Ala Leu Asn
    8375                8380                8385

Gly Asp His Asn Leu Gln Val Ala Lys Thr Asn Ala Thr Gln Ala
    8390                8395                8400

Ile Asp Ala Leu Thr Ser Leu Asn Asp Pro Gln Lys Thr Ala Leu
    8405                8410                8415

Lys Asp Gln Val Thr Ala Ala Thr Leu Val Thr Ala Val His Gln
    8420                8425                8430

Ile Glu Gln Asn Ala Asn Thr Leu Asn Gln Ala Met His Gly Leu
    8435                8440                8445

Arg Gln Ser Ile Gln Asp Asn Ala Ala Thr Lys Ala Asn Ser Lys
    8450                8455                8460

Tyr Ile Asn Glu Asp Gln Pro Glu Gln Gln Asn Tyr Asp Gln Ala
    8465                8470                8475

Val Gln Ala Ala Asn Asn Ile Ile Asn Glu Gln Thr Ala Thr Leu
    8480                8485                8490

Asp Asn Asn Ala Ile Asn Gln Ala Ala Thr Thr Val Asn Thr Thr
    8495                8500                8505

Lys Ala Ala Leu His Gly Asp Val Lys Leu Gln Asn Asp Lys Asp
    8510                8515                8520

His Ala Lys Gln Thr Val Ser Gln Leu Ala His Leu Asn Asn Ala
```

```
                8525                8530                8535

Gln Lys His Met Glu Asp Thr Leu Ile Asp Ser Glu Thr Thr Arg
    8540                8545                8550

Thr Ala Val Lys Gln Asp Leu Thr Glu Ala Gln Ala Leu Asp Gln
    8555                8560                8565

Leu Met Asp Ala Leu Gln Gln Ser Ile Ala Asp Lys Asp Ala Thr
    8570                8575                8580

Arg Ala Ser Ser Ala Tyr Val Asn Ala Glu Pro Asn Lys Lys Gln
    8585                8590                8595

Ser Tyr Asp Glu Ala Val Gln Asn Ala Glu Ser Ile Ile Ala Gly
    8600                8605                8610

Leu Asn Asn Pro Thr Ile Asn Lys Gly Asn Val Ser Ser Ala Thr
    8615                8620                8625

Gln Ala Val Ile Ser Ser Lys Asn Ala Leu Asp Gly Val Glu Arg
    8630                8635                8640

Leu Ala Gln Asp Lys Gln Thr Ala Gly Asn Ser Leu Asn His Leu
    8645                8650                8655

Asp Gln Leu Thr Pro Ala Gln Gln Ala Leu Glu Asn Gln Ile
    8660                8665                8670

Asn Asn Ala Thr Thr Arg Gly Glu Val Ala Gln Lys Leu Thr Glu
    8675                8680                8685

Ala Gln Ala Leu Asn Gln Ala Met Glu Ala Leu Arg Asn Ser Ile
    8690                8695                8700

Gln Asp Gln Gln Gln Thr Glu Ala Gly Ser Lys Phe Ile Asn Glu
    8705                8710                8715

Asp Lys Pro Gln Lys Asp Ala Tyr Gln Ala Ala Val Gln Asn Ala
    8720                8725                8730

Lys Asp Leu Ile Asn Gln Thr Asn Asn Pro Thr Leu Asp Lys Ala
    8735                8740                8745

Gln Val Glu Gln Leu Thr Gln Ala Val Asn Gln Ala Lys Asp Asn
    8750                8755                8760

Leu His Gly Asp Gln Lys Leu Ala Asp Asp Lys Gln His Ala Val
    8765                8770                8775

Thr Asp Leu Asn Gln Leu Asn Gly Leu Asn Asn Pro Gln Arg Gln
    8780                8785                8790

Ala Leu Glu Ser Gln Ile Asn Asn Ala Ala Thr Arg Gly Glu Val
    8795                8800                8805

Ala Gln Lys Leu Ala Glu Ala Lys Ala Leu Asp Gln Ala Met Gln
    8810                8815                8820

Ala Leu Arg Asn Ser Ile Gln Asp Gln Gln Thr Glu Ser Gly
    8825                8830                8835

Ser Lys Phe Ile Asn Glu Asp Lys Pro Gln Lys Asp Ala Tyr Gln
    8840                8845                8850

Ala Ala Val Gln Asn Ala Lys Asp Leu Ile Asn Gln Thr Gly Asn
    8855                8860                8865

Pro Thr Leu Asp Lys Ser Gln Val Glu Gln Leu Thr Gln Ala Val
    8870                8875                8880

Thr Thr Ala Lys Asp Asn Leu His Gly Asp Gln Lys Leu Ala Arg
    8885                8890                8895

Asp Gln Gln Gln Ala Val Thr Thr Val Asn Ala Leu Pro Asn Leu
    8900                8905                8910

Asn His Ala Gln Gln Gln Ala Leu Thr Asp Ala Ile Asn Ala Ala
    8915                8920                8925
```

```
Pro Thr Arg Thr Glu Val Ala Gln His Val Gln Thr Ala Thr Glu
    8930            8935                8940

Leu Asp His Ala Met Glu Thr Leu Lys Asn Lys Val Asp Gln Val
    8945            8950                8955

Asn Thr Asp Lys Ala Gln Pro Asn Tyr Thr Glu Ala Ser Thr Asp
    8960            8965                8970

Lys Lys Glu Ala Val Asp Gln Ala Leu Gln Ala Ala Glu Ser Ile
    8975            8980                8985

Thr Asp Pro Thr Asn Gly Ser Asn Ala Asn Lys Asp Ala Val Asp
    8990            8995                9000

Gln Val Leu Thr Lys Leu Gln Glu Lys Glu Asn Glu Leu Asn Gly
    9005            9010                9015

Asn Glu Arg Val Ala Glu Ala Lys Thr Gln Ala Lys Gln Thr Ile
    9020            9025                9030

Asp Gln Leu Thr His Leu Asn Ala Asp Gln Ile Ala Thr Ala Lys
    9035            9040                9045

Gln Asn Ile Asp Gln Ala Thr Lys Leu Gln Pro Ile Ala Glu Leu
    9050            9055                9060

Val Asp Gln Ala Thr Gln Leu Asn Gln Ser Met Asp Gln Leu Gln
    9065            9070                9075

Gln Ala Val Asn Glu His Ala Asn Val Glu Gln Thr Val Asp Tyr
    9080            9085                9090

Thr Gln Ala Asp Ser Asp Lys Gln Asn Ala Tyr Lys Gln Ala Ile
    9095            9100                9105

Ala Asp Ala Glu Asn Val Leu Lys Gln Asn Ala Asn Lys Gln Gln
    9110            9115                9120

Val Asp Gln Ala Leu Gln Asn Ile Leu Asn Ala Lys Gln Ala Leu
    9125            9130                9135

Asn Gly Asp Glu Arg Val Ala Leu Ala Lys Thr Asn Gly Lys His
    9140            9145                9150

Asp Ile Asp Gln Leu Asn Ala Leu Asn Asn Ala Gln Gln Asp Gly
    9155            9160                9165

Phe Lys Gly Arg Ile Asp Gln Ser Asn Asp Leu Asn Gln Ile Gln
    9170            9175                9180

Gln Ile Val Asp Glu Ala Lys Ala Leu Asn Arg Ala Met Asp Gln
    9185            9190                9195

Leu Ser Gln Glu Ile Thr Asp Asn Glu Gly Arg Thr Lys Gly Ser
    9200            9205                9210

Thr Asn Tyr Val Asn Ala Asp Thr Gln Val Lys Gln Val Tyr Asp
    9215            9220                9225

Glu Thr Val Asp Lys Ala Lys Gln Ala Leu Asp Lys Ser Thr Gly
    9230            9235                9240

Gln Asn Leu Thr Ala Lys Gln Val Ile Lys Leu Asn Asp Ala Val
    9245            9250                9255

Thr Ala Ala Lys Lys Ala Leu Asn Gly Glu Glu Arg Leu Asn Asn
    9260            9265                9270

Arg Lys Ala Glu Ala Leu Gln Arg Leu Asp Gln Leu Thr His Leu
    9275            9280                9285

Asn Asn Ala Gln Arg Gln Leu Ala Ile Gln Gln Ile Asn Asn Ala
    9290            9295                9300

Glu Thr Leu Asn Lys Ala Ser Arg Ala Ile Asn Arg Ala Thr Lys
    9305            9310                9315
```

Leu Asp Asn Ala Met Gly Ala Val Gln Gln Tyr Ile Asp Glu Gln
9320            9325                9330

His Leu Gly Val Ile Ser Ser Thr Asn Tyr Ile Asn Ala Asp Asp
9335            9340                9345

Asn Leu Lys Ala Asn Tyr Asp Asn Ala Ile Ala Asn Ala Ala His
9350            9355                9360

Glu Leu Asp Lys Val Gln Gly Asn Ala Ile Ala Lys Ala Glu Ala
9365            9370                9375

Glu Gln Leu Lys Gln Asn Ile Ile Asp Ala Gln Asn Ala Leu Asn
9380            9385                9390

Gly Asp Gln Asn Leu Ala Asn Ala Lys Asp Lys Ala Asn Ala Phe
9395            9400                9405

Val Asn Ser Leu Asn Gly Leu Asn Gln Gln Gln Asp Leu Ala
9410            9415                9420

His Lys Ala Ile Asn Asn Ala Asp Thr Val Ser Asp Val Thr Asp
9425            9430                9435

Ile Val Asn Asn Gln Ile Asp Leu Asn Asp Ala Met Glu Thr Leu
9440            9445                9450

Lys His Leu Val Asp Asn Glu Ile Pro Asn Ala Glu Gln Thr Val
9455            9460                9465

Asn Tyr Gln Asn Ala Asp Asp Asn Ala Lys Thr Asn Phe Asp Asp
9470            9475                9480

Ala Lys Arg Leu Ala Asn Thr Leu Leu Asn Ser Asp Asn Thr Asn
9485            9490                9495

Val Asn Asp Ile Asn Gly Ala Ile Gln Ala Val Asn Asp Ala Ile
9500            9505                9510

His Asn Leu Asn Gly Asp Gln Arg Leu Gln Asp Ala Lys Asp Lys
9515            9520                9525

Ala Ile Gln Ser Ile Asn Gln Ala Leu Ala Asn Lys Leu Lys Glu
9530            9535                9540

Ile Glu Ala Ser Asn Ala Thr Asp Gln Asp Lys Leu Ile Ala Lys
9545            9550                9555

Asn Lys Ala Glu Glu Leu Ala Asn Ser Ile Ile Asn Asn Ile Asn
9560            9565                9570

Lys Ala Thr Ser Asn Gln Ala Val Ser Gln Val Gln Thr Ala Gly
9575            9580                9585

Asn His Ala Ile Glu Gln Val His Ala Asn Glu Ile Pro Lys Ala
9590            9595                9600

Lys Ile Asp Ala Asn Lys Asp Val Asp Lys Gln Val Gln Ala Leu
9605            9610                9615

Ile Asp Glu Ile Asp Arg Asn Pro Asn Leu Thr Asp Lys Glu Lys
9620            9625                9630

Gln Ala Leu Lys Asp Arg Ile Asn Gln Ile Leu Gln Gln Gly His
9635            9640                9645

Asn Gly Ile Asn Asn Ala Met Thr Lys Glu Glu Ile Glu Gln Ala
9650            9655                9660

Lys Ala Gln Leu Ala Gln Ala Leu Gln Asp Ile Lys Asp Leu Val
9665            9670                9675

Lys Ala Lys Glu Asp Ala Lys Gln Asp Val Asp Lys Gln Val Gln
9680            9685                9690

Ala Leu Ile Asp Glu Ile Asp Gln Asn Pro Asn Leu Thr Asp Lys
9695            9700                9705

Glu Lys Gln Ala Leu Lys Tyr Arg Ile Asn Gln Ile Leu Gln Gln

-continued

```
                9710                9715                9720
Gly His  Asn Asp Ile Asn  Asn Ala Leu Thr  Lys Glu Glu Ile Glu
     9725                9730                9735
Gln Ala  Lys Ala Gln Leu  Ala Gln Ala Leu  Gln Asp Ile Lys Asp
     9740                9745                9750
Leu Val  Lys Ala Lys Glu  Asp Ala Lys Asn  Ala Ile Lys Ala Leu
     9755                9760                9765
Ala Asn  Ala Lys Arg Asp  Gln Ile Asn Ser  Asn Pro Asp Leu Thr
     9770                9775                9780
Pro Glu  Gln Lys Ala Lys  Ala Leu Lys Glu  Ile Asp Glu Ala Glu
     9785                9790                9795
Lys Arg  Ala Leu Gln Asn  Val Glu Asn Ala  Gln Thr Ile Asp Gln
     9800                9805                9810
Leu Asn  Arg Gly Leu Asn  Leu Gly Leu Asp  Asp Ile Arg Asn Thr
     9815                9820                9825
His Val  Trp Glu Val Asp  Glu Gln Pro Ala  Val Asn Glu Ile Phe
     9830                9835                9840
Glu Ala  Thr Pro Glu Gln  Ile Leu Val Asn  Gly Glu Leu Ile Val
     9845                9850                9855
His Arg  Asp Asp Ile Ile  Thr Glu Gln Asp  Ile Leu Ala His Ile
     9860                9865                9870
Asn Leu  Ile Asp Gln Leu  Ser Ala Glu Val  Ile Asp Thr Pro Ser
     9875                9880                9885
Thr Ala  Thr Ile Ser Asp  Ser Leu Thr Ala  Lys Val Glu Val Thr
     9890                9895                9900
Leu Leu  Asp Gly Ser Lys  Val Ile Val Asn  Val Pro Val Lys Val
     9905                9910                9915
Val Glu  Lys Glu Leu Ser  Val Val Lys Gln  Gln Ala Ile Glu Ser
     9920                9925                9930
Ile Glu  Asn Ala Ala Gln  Gln Lys Ile Asn  Glu Ile Asn Asn Ser
     9935                9940                9945
Val Thr  Leu Thr Leu Glu  Gln Lys Glu Ala  Ala Ile Ala Glu Val
     9950                9955                9960
Asn Lys  Leu Lys Gln Gln  Ala Ile Asp His  Val Asn Asn Ala Pro
     9965                9970                9975
Asp Val  His Ser Val Glu  Glu Ile Gln Gln  Gln Glu Gln Ala His
     9980                9985                9990
Ile Glu  Gln Phe Asn Pro  Glu Gln Phe Thr  Ile Glu Gln Ala Lys
     9995               10000               10005
Ser Asn  Ala Ile Lys Ser  Ile Glu Asp Ala  Ile Gln His Met Ile
    10010               10015               10020
Asp Glu  Ile Lys Ala Arg  Thr Asp Leu Thr  Asp Lys Glu Lys Gln
    10025               10030               10035
Glu Ala  Ile Ala Lys Leu  Asn Gln Leu Lys  Glu Gln Ala Ile Gln
    10040               10045               10050
Ala Ile  Gln Arg Ala Gln  Ser Ile Asp Glu  Ile Ser Glu Gln Leu
    10055               10060               10065
Glu Gln  Phe Lys Ala Gln  Met Lys Ala Ala  Asn Pro Thr Ala Lys
    10070               10075               10080
Glu Leu  Ala Lys Arg Lys  Gln Glu Ala Ile  Ser Arg Ile Lys Asp
    10085               10090               10095
Phe Ser  Asn Glu Lys Ile  Asn Ser Ile Arg  Asn Ser Glu Ile Gly
    10100               10105               10110
```

Thr Ala Asp Glu Lys Gln Ala Ala Met Asn Gln Ile Asn Glu Ile
    10115           10120               10125

Val Leu Glu Thr Ile Arg Asp Ile Asn Asn Ala His Thr Leu Gln
    10130           10135               10140

Gln Val Glu Ala Ala Leu Asn Asn Gly Ile Ala Arg Ile Ser Ala
    10145           10150               10155

Val Gln Ile Val Thr Ser Asp Arg Ala Lys Gln Ser Ser Ser Thr
    10160           10165               10170

Gly Asn Glu Ser Asn Ser His Leu Thr Ile Gly Tyr Gly Thr Ala
    10175           10180               10185

Asn His Pro Phe Asn Ser Ser Thr Ile Gly His Lys Lys Lys Leu
    10190           10195               10200

Asp Glu Asp Asp Ile Asp Pro Leu His Met Arg His Phe Ser
    10205           10210               10215

Asn Asn Phe Gly Asn Val Ile Lys Asn Ala Ile Gly Val Val Gly
    10220           10225               10230

Ile Ser Gly Leu Leu Ala Ser Phe Trp Phe Ile Ala Lys Arg
    10235           10240               10245

Arg Arg Lys Glu Asp Glu Glu Glu Leu Glu Ile Arg Asp Asn
    10250           10255               10260

Asn Lys Asp Ser Ile Lys Glu Thr Leu Asp Asp Thr Lys His Leu
    10265           10270               10275

Pro Leu Leu Phe Ala Lys Arg Arg Arg Lys Glu Asp Glu Glu Asp
    10280           10285               10290

Val Thr Val Glu Glu Lys Asp Ser Leu Asn Asn Gly Glu Ser Leu
    10295           10300               10305

Asp Lys Val Lys His Thr Pro Phe Phe Leu Pro Lys Arg Arg Arg
    10310           10315               10320

Lys Glu Asp Glu Glu Asp Val Glu Val Thr Asn Glu Asn Thr Asp
    10325           10330               10335

Glu Lys Val Leu Lys Asp Asn Glu His Ser Pro Leu Leu Phe Ala
    10340           10345               10350

Lys Arg Arg Lys Asp Lys Glu Glu Asp Val Glu Thr Thr Thr Ser
    10355           10360               10365

Ile Glu Ser Lys Asp Glu Asp Val Pro Leu Leu Leu Ala Lys Lys
    10370           10375               10380

Lys Asn Gln Lys Asp Asn Gln Ser Lys Asp Lys Lys Ser Ala Ser
    10385           10390               10395

Lys Asn Thr Ser Lys Lys Val Ala Ala Lys Lys Lys Lys Lys Lys
    10400           10405               10410

Ala Lys Lys Asn Lys Lys
    10415

<210> SEQ ID NO 25
<211> LENGTH: 340
<212> TYPE: PRT
<213> ORGANISM: Staphylococcus sp

<400> SEQUENCE: 25

Met Lys Lys Lys Leu Leu Val Leu Thr Met Ser Thr Leu Phe Ala Thr
1               5                   10                  15

Gln Ile Met Asn Ser Asn His Ala Lys Ala Ser Val Thr Glu Ser Val
            20                  25                  30

Asp Lys Lys Phe Val Val Pro Glu Ser Gly Ile Asn Lys Ile Ile Pro

```
            35                  40                  45
Ala Tyr Asp Glu Phe Lys Asn Ser Pro Lys Val Asn Val Ser Asn Leu
 50                  55                  60

Thr Asp Asn Lys Asn Phe Val Ala Ser Glu Asp Lys Leu Asn Lys Ile
 65                  70                  75                  80

Ala Asp Ser Ser Ala Ala Ser Lys Ile Val Asp Lys Asn Phe Val Val
                 85                  90                  95

Pro Glu Ser Lys Leu Gly Asn Ile Val Pro Glu Tyr Lys Glu Ile Asn
                100                 105                 110

Asn Arg Val Asn Val Ala Thr Asn Asn Pro Ala Ser Gln Gln Val Asp
            115                 120                 125

Lys His Phe Val Ala Lys Gly Pro Glu Val Asn Arg Phe Ile Thr Gln
130                 135                 140

Asn Lys Val Asn His His Phe Ile Thr Thr Gln Thr His Tyr Lys Lys
145                 150                 155                 160

Val Ile Thr Ser Tyr Lys Ser Thr His Val His Lys His Val Asn His
                165                 170                 175

Ala Lys Asp Ser Ile Asn Lys His Phe Ile Val Lys Pro Ser Glu Ser
            180                 185                 190

Pro Arg Tyr Thr His Pro Ser Gln Ser Leu Ile Ile Lys His His Phe
        195                 200                 205

Ala Val Pro Gly Tyr His Ala His Lys Phe Val Thr Pro Gly His Ala
    210                 215                 220

Ser Ile Lys Ile Asn His Phe Cys Val Val Pro Gln Ile Asn Ser Phe
225                 230                 235                 240

Lys Val Ile Pro Pro Tyr Gly His Asn Ser His Arg Met His Val Pro
                245                 250                 255

Ser Phe Gln Asn Asn Thr Thr Ala Thr His Gln Asn Ala Lys Val Asn
            260                 265                 270

Lys Ala Tyr Asp Tyr Lys Tyr Phe Tyr Ser Tyr Lys Val Val Lys Gly
        275                 280                 285

Val Lys Lys Tyr Phe Ser Phe Ser Gln Ser Asn Gly Tyr Lys Ile Gly
    290                 295                 300

Lys Pro Ser Leu Asn Ile Lys Asn Val Asn Tyr Gln Tyr Ala Val Pro
305                 310                 315                 320

Ser Tyr Ser Pro Thr His Tyr Val Pro Glu Phe Lys Gly Ser Leu Pro
                325                 330                 335

Ala Pro Arg Val
            340

<210> SEQ ID NO 26
<211> LENGTH: 130
<212> TYPE: PRT
<213> ORGANISM: Staphylococcus sp

<400> SEQUENCE: 26

Met Asn Phe Asn Asp Ile Glu Thr Met Val Lys Ser Lys Phe Lys Asp
 1               5                  10                  15

Ile Lys Lys His Ala Glu Glu Ile Ala His Glu Ile Glu Val Arg Ser
             20                  25                  30

Gly Tyr Leu Arg Lys Ala Glu Gln Tyr Lys Arg Leu Glu Phe Asn Leu
         35                  40                  45

Ser Phe Ala Leu Asp Asp Ile Glu Ser Thr Ala Lys Asp Val Gln Thr
     50                  55                  60
```

```
Ala Lys Ser Ser Ala Asn Lys Asp Ser Val Thr Val Lys Gly Lys Ala
 65                  70                  75                  80

Pro Asn Thr Leu Tyr Ile Glu Lys Arg Asn Leu Met Lys Gln Lys Leu
                 85                  90                  95

Glu Met Leu Gly Glu Asp Ile Asp Lys Asn Lys Glu Ser Leu Gln Lys
            100                 105                 110

Ala Lys Glu Ile Ala Gly Glu Lys Ala Ser Glu Tyr Phe Asn Lys Ala
        115                 120                 125

Met Asn
    130

<210> SEQ ID NO 27
<211> LENGTH: 636
<212> TYPE: PRT
<213> ORGANISM: Staphylococcus sp

<400> SEQUENCE: 27

Met Lys Lys Gln Ile Ile Ser Leu Gly Ala Leu Ala Val Ala Ser Ser
  1               5                  10                  15

Leu Phe Thr Trp Asp Asn Lys Ala Asp Ala Ile Val Thr Lys Asp Tyr
                 20                  25                  30

Ser Gly Lys Ser Gln Val Asn Ala Gly Ser Lys Asn Gly Thr Leu Ile
             35                  40                  45

Asp Ser Arg Tyr Leu Asn Ser Ala Leu Tyr Tyr Leu Glu Asp Tyr Ile
         50                  55                  60

Ile Tyr Ala Ile Gly Leu Thr Asn Lys Tyr Glu Tyr Gly Asp Asn Ile
 65                  70                  75                  80

Tyr Lys Glu Ala Lys Asp Arg Leu Leu Glu Lys Val Leu Arg Glu Asp
                 85                  90                  95

Gln Tyr Leu Leu Glu Arg Lys Lys Ser Gln Tyr Glu Asp Tyr Lys Gln
            100                 105                 110

Trp Tyr Ala Asn Tyr Lys Lys Glu Asn Pro Arg Thr Asp Leu Lys Met
        115                 120                 125

Ala Asn Phe His Lys Tyr Asn Leu Glu Glu Leu Ser Met Lys Glu Tyr
    130                 135                 140

Asn Glu Leu Gln Asp Ala Leu Lys Arg Ala Leu Asp Asp Phe His Arg
145                 150                 155                 160

Glu Val Lys Asp Ile Lys Asp Lys Asn Ser Asp Leu Lys Thr Phe Asn
                165                 170                 175

Ala Ala Glu Glu Asp Lys Ala Thr Lys Glu Val Tyr Asp Leu Val Ser
            180                 185                 190

Glu Ile Asp Thr Leu Val Val Ser Tyr Tyr Gly Asp Lys Asp Tyr Gly
        195                 200                 205

Glu His Ala Lys Glu Leu Arg Ala Lys Leu Asp Leu Ile Leu Gly Asp
    210                 215                 220

Thr Asp Asn Pro His Lys Ile Thr Asn Glu Arg Ile Lys Lys Glu Met
225                 230                 235                 240

Ile Asp Asp Leu Asn Ser Ile Ile Asp Phe Phe Met Glu Thr Lys
                245                 250                 255

Gln Asn Arg Pro Lys Ser Ile Thr Lys Tyr Asn Pro Thr His Asn
            260                 265                 270

Tyr Lys Thr Asn Ser Asp Asn Lys Pro Asn Phe Asp Lys Leu Val Glu
        275                 280                 285

Glu Thr Lys Lys Ala Val Lys Glu Ala Asp Asp Ser Trp Lys Lys Lys
    290                 295                 300
```

```
Thr Val Lys Lys Tyr Gly Glu Thr Glu Thr Lys Ser Pro Val Val Lys
305                 310                 315                 320

Glu Glu Lys Lys Val Glu Pro Gln Ala Pro Lys Val Asp Asn Gln
            325                 330                 335

Gln Glu Val Lys Thr Thr Ala Gly Lys Ala Glu Thr Thr Gln Pro
        340                 345                 350

Val Ala Gln Pro Leu Val Lys Ile Pro Gln Gly Thr Ile Thr Gly Glu
            355                 360                 365

Ile Val Lys Gly Pro Glu Tyr Pro Thr Met Glu Asn Lys Thr Val Gln
370                 375                 380

Gly Glu Ile Val Gln Gly Pro Asp Phe Leu Thr Met Glu Gln Ser Gly
385                 390                 395                 400

Pro Ser Leu Ser Asn Asn Tyr Thr Asn Pro Pro Leu Thr Asn Pro Ile
            405                 410                 415

Leu Glu Gly Leu Glu Gly Ser Ser Ser Lys Leu Glu Ile Lys Pro Gln
            420                 425                 430

Gly Thr Glu Ser Thr Leu Lys Gly Thr Gln Gly Glu Ser Ser Asp Ile
            435                 440                 445

Glu Val Lys Pro Gln Ala Thr Glu Thr Thr Glu Ala Ser Gln Tyr Gly
    450                 455                 460

Pro Arg Pro Gln Phe Asn Lys Thr Pro Lys Tyr Val Lys Tyr Arg Asp
465                 470                 475                 480

Ala Gly Thr Gly Ile Arg Glu Tyr Asn Asp Gly Thr Phe Gly Tyr Glu
                485                 490                 495

Ala Arg Pro Arg Phe Asn Lys Pro Ser Glu Thr Asn Ala Tyr Asn Val
            500                 505                 510

Thr Thr His Ala Asn Gly Gln Val Ser Tyr Gly Ala Arg Pro Thr Tyr
            515                 520                 525

Lys Lys Pro Ser Glu Thr Asn Ala Tyr Asn Val Thr Thr His Ala Asn
    530                 535                 540

Gly Gln Val Ser Tyr Gly Ala Arg Pro Thr Gln Asn Lys Pro Ser Lys
545                 550                 555                 560

Thr Asn Ala Tyr Asn Val Thr Thr His Gly Asn Gly Gln Val Ser Tyr
                565                 570                 575

Gly Ala Arg Pro Thr Gln Asn Lys Pro Ser Lys Thr Asn Ala Tyr Asn
            580                 585                 590

Val Thr Thr His Ala Asn Gly Gln Val Ser Tyr Gly Ala Arg Pro Thr
            595                 600                 605

Tyr Lys Lys Pro Ser Lys Thr Asn Ala Tyr Asn Val Thr Thr His Ala
    610                 615                 620

Asp Gly Thr Ala Thr Tyr Gly Pro Arg Val Thr Lys
625                 630                 635

<210> SEQ ID NO 28
<211> LENGTH: 745
<212> TYPE: PRT
<213> ORGANISM: Staphylococcus sp

<400> SEQUENCE: 28

Ala Glu Gln His Thr Pro Met Lys Ala His Ala Val Thr Thr Ile Asp
1               5                   10                  15

Lys Ala Thr Thr Asp Lys Gln Gln Val Pro Pro Thr Lys Glu Ala Ala
            20                  25                  30

His His Ser Gly Lys Glu Ala Ala Thr Asn Val Ser Ala Ser Ala Gln
```

```
            35                  40                  45
Gly Thr Ala Asp Asp Thr Asn Ser Lys Val Thr Ser Asn Ala Pro Ser
 50                  55                  60

Asn Lys Pro Ser Thr Val Val Ser Thr Lys Val Asn Glu Thr Arg Asp
 65                  70                  75                  80

Val Asp Thr Gln Gln Ala Ser Thr Gln Lys Pro Thr His Thr Ala Thr
                     85                  90                  95

Phe Lys Leu Ser Asn Ala Lys Thr Ala Ser Leu Ser Pro Arg Met Phe
                100                 105                 110

Ala Ala Asn Ala Pro Gln Thr Thr Thr His Lys Ile Leu His Thr Asn
            115                 120                 125

Asp Ile His Gly Arg Leu Ala Glu Glu Lys Gly Arg Val Ile Gly Met
        130                 135                 140

Ala Lys Leu Lys Thr Val Lys Glu Gln Glu Lys Pro Asp Leu Met Leu
145                 150                 155                 160

Asp Ala Gly Asp Ala Phe Gln Gly Leu Pro Leu Ser Asn Gln Ser Lys
                    165                 170                 175

Gly Glu Glu Met Ala Lys Ala Met Asn Ala Val Gly Tyr Asp Ala Met
                180                 185                 190

Ala Val Gly Asn His Glu Phe Asp Phe Gly Tyr Asp Gln Leu Lys Lys
            195                 200                 205

Leu Glu Gly Met Leu Asp Phe Pro Met Leu Ser Thr Asn Val Tyr Lys
        210                 215                 220

Asp Gly Lys Arg Ala Phe Lys Pro Ser Thr Ile Val Thr Lys Asn Gly
225                 230                 235                 240

Ile Arg Tyr Gly Ile Ile Gly Val Thr Thr Pro Glu Thr Lys Thr Lys
                    245                 250                 255

Thr Arg Pro Glu Gly Ile Lys Gly Val Glu Phe Arg Asp Pro Leu Gln
                260                 265                 270

Ser Val Thr Ala Glu Met Met Arg Ile Tyr Lys Asp Val Asp Thr Phe
            275                 280                 285

Val Val Ile Ser His Leu Gly Ile Asp Pro Ser Thr Gln Glu Thr Trp
290                 295                 300

Arg Gly Asp Tyr Leu Val Lys Gln Leu Ser Gln Asn Pro Gln Leu Lys
305                 310                 315                 320

Lys Arg Ile Thr Val Ile Asp Gly His Ser His Thr Val Leu Gln Asn
                325                 330                 335

Gly Gln Ile Tyr Asn Asn Asp Ala Leu Ala Gln Thr Gly Thr Ala Leu
                340                 345                 350

Ala Asn Ile Gly Lys Ile Thr Phe Asn Tyr Arg Asn Gly Glu Val Ser
            355                 360                 365

Asn Ile Lys Pro Ser Leu Ile Asn Val Lys Asp Val Glu Asn Val Thr
        370                 375                 380

Pro Asn Lys Ala Leu Ala Glu Gln Ile Asn Gln Ala Asp Gln Thr Phe
385                 390                 395                 400

Arg Ala Gln Thr Ala Glu Val Ile Ile Pro Asn Asn Thr Ile Asp Phe
                    405                 410                 415

Lys Gly Glu Arg Asp Asp Val Arg Thr Glu Thr Asn Leu Gly Asn
                420                 425                 430

Ala Ile Ala Asp Ala Met Glu Ala Tyr Gly Val Lys Asn Phe Ser Lys
            435                 440                 445

Lys Thr Asp Phe Ala Val Thr Asn Gly Gly Gly Ile Arg Ala Ser Ile
        450                 455                 460
```

```
Ala Lys Gly Lys Val Thr Arg Tyr Asp Leu Ile Ser Val Leu Pro Phe
465                 470                 475                 480

Gly Asn Thr Ile Ala Gln Ile Asp Val Lys Gly Ser Asp Val Trp Thr
                485                 490                 495

Ala Phe Glu His Ser Leu Gly Ala Pro Thr Thr Gln Lys Asp Gly Lys
            500                 505                 510

Thr Val Leu Thr Ala Asn Gly Gly Leu Leu His Ile Ser Asp Ser Ile
            515                 520                 525

Arg Val Tyr Tyr Asp Ile Asn Lys Pro Ser Gly Lys Arg Ile Asn Ala
530                 535                 540

Ile Gln Ile Leu Asn Lys Glu Thr Gly Lys Phe Glu Asn Ile Asp Leu
545                 550                 555                 560

Lys Arg Val Tyr His Val Thr Met Asn Asp Phe Thr Ala Ser Gly Gly
                565                 570                 575

Asp Gly Tyr Ser Met Phe Gly Gly Pro Arg Glu Glu Gly Ile Ser Leu
                580                 585                 590

Asp Gln Val Leu Ala Ser Tyr Leu Lys Thr Ala Asn Leu Ala Lys Tyr
            595                 600                 605

Asp Thr Thr Glu Pro Gln Arg Met Leu Leu Gly Lys Pro Ala Val Ser
            610                 615                 620

Glu Gln Pro Ala Lys Gly Gln Gln Gly Ser Lys Gly Ser Lys Ser Gly
625                 630                 635                 640

Lys Asp Thr Gln Pro Ile Gly Asp Asp Lys Val Met Asp Pro Ala Lys
                645                 650                 655

Lys Pro Ala Pro Gly Lys Val Val Leu Leu Ala His Arg Gly Thr
                660                 665                 670

Val Ser Ser Gly Thr Glu Gly Ser Gly Arg Thr Ile Glu Gly Ala Thr
                675                 680                 685

Val Ser Ser Lys Ser Gly Lys Gln Leu Ala Arg Met Ser Val Pro Lys
                690                 695                 700

Gly Ser Ala His Glu Lys Gln Leu Pro Lys Thr Gly Thr Asn Gln Ser
705                 710                 715                 720

Ser Ser Pro Glu Ala Met Phe Val Leu Leu Ala Gly Ile Gly Leu Ile
                725                 730                 735

Ala Thr Val Arg Arg Arg Lys Ala Ser
                740                 745

<210> SEQ ID NO 29
<211> LENGTH: 628
<212> TYPE: PRT
<213> ORGANISM: Staphylococcus sp

<400> SEQUENCE: 29

Met Ser Asp Arg Phe Ile Lys Phe Asn Asp Glu Gln Leu Asp Ala Lys
1               5                   10                  15

Gln Val Met Met Leu Gln Asp Leu Ala Arg Leu Leu Leu Lys Asn Glu
                20                  25                  30

Gln Thr Gln Val Lys Ile Gln Lys Phe Pro Tyr Tyr Asn Pro Val Gln
            35                  40                  45

Asn Val Leu Ile Thr Ser Trp Phe Trp Ser His Arg Pro Ser His Ile
            50                  55                  60

Glu Met Ala Gly Leu Lys Thr Asp Val Met Leu Ala Ala Tyr Gly Tyr
65                  70                  75                  80

His Met Met Asp Val Gln Ile Val Asn Glu Val Val Gln Asp Lys Thr
```

-continued

```
                    85                  90                  95
Phe Lys His Pro Lys Phe Tyr Gln Gln Leu Phe Lys Leu Leu Glu Asp
                100                 105                 110
Met Arg Val Leu Asn Ser Ile Lys Val Glu Arg Pro Ser Thr Ala Lys
                115                 120                 125
Leu Ile Asp Leu Arg Leu Asp Thr Arg Ile Ser Tyr Thr Glu Ser Gln
130                 135                 140
Ile Lys Val Tyr Arg Thr Lys Thr Gln Tyr Thr Asp Leu Leu Phe Leu
145                 150                 155                 160
Tyr Leu Glu His Ala Phe Leu Ser Gln Asp Phe Phe Asp Ile Pro Ser
                165                 170                 175
Ile His Ser Asp Leu Asp Asp Ile Leu Val Asn Met Phe Leu Tyr Leu
                180                 185                 190
Pro Asn Phe Phe Gln Asn Gln Asn Ser Glu Asp Asn Met Tyr Leu Ala
                195                 200                 205
Gln Arg Ile Met Tyr Gln Val Asp Asp Ile Leu Lys Glu Asp Met Leu
                210                 215                 220
Asn Glu Tyr Tyr Tyr Leu Pro Lys Thr Leu Tyr Asn Thr Leu Ala Ser
225                 230                 235                 240
Pro Glu Phe Asp Asp Leu Lys Arg Thr Asp Ala Ser Gln Val Asp Gly
                245                 250                 255
Gln Asp Asp Thr Ser Glu Asp Asp Asn Glu Ser Lys Ala Asp
                260                 265                 270
Ser Lys Ser Ala Asp Ser Glu Ser Lys Gly Gly Ala Tyr Leu Glu Met
                275                 280                 285
Glu Leu His Glu Gly Gln Asn Ser Glu Thr Leu Gly Asn Asp Glu Ala
                290                 295                 300
Arg Glu Gly Asp Ala Thr Asp Asp Met Thr Asp Met Met Thr Lys Lys
305                 310                 315                 320
Gly Lys Gly Ser Asn Asp Thr Leu Asn Arg Glu Glu Gly Asp Ala Val
                325                 330                 335
Gly Gln Ser Gln Ala Phe Gln Leu Asp Gly Val Asn Lys Asn Val Glu
                340                 345                 350
Ile Lys Trp Gln Ile Pro Glu Ile Glu Pro Gln Tyr Val Leu Glu Tyr
                355                 360                 365
Gln Glu Ser Lys Gln Asp Val Gln Tyr Glu Ile Lys Asp Leu Ile Gln
                370                 375                 380
Ile Ile Lys Lys Thr Ile Glu Arg Glu Gln Arg Asp Ala Arg Phe Asn
385                 390                 395                 400
Leu Thr Lys Gly Arg Leu Gln Lys Asp Leu Ile Asn Trp Phe Ile Asp
                405                 410                 415
Asp Gln Tyr Lys Leu Phe Tyr Lys Lys Gln Asp Leu Ser Lys Ser Phe
                420                 425                 430
Asp Ala Thr Phe Thr Leu Leu Ile Asp Ala Ser Ala Ser Met His Asp
                435                 440                 445
Lys Met Ala Glu Thr Lys Lys Gly Val Val Leu Phe His Glu Thr Leu
                450                 455                 460
Lys Ala Leu Asn Ile Lys His Glu Ile Leu Ser Phe Ser Glu Asp Ala
465                 470                 475                 480
Phe Asp Ser Asp Glu His Ala Gln Pro Asn Ile Ile Asn Glu Ile Ile
                485                 490                 495
Asn Tyr Asp Tyr Ser Thr Phe Glu Lys Asp Gly Pro Arg Ile Met Ala
                500                 505                 510
```

```
Leu Glu Pro Gln Asp Asp Asn Arg Asp Gly Val Ala Ile Arg Val Ala
        515                 520                 525

Ser Glu Arg Leu Met Arg Arg Asn Gln His Gln Arg Phe Leu Ile Val
530                 535                 540

Phe Ser Asp Gly Glu Pro Ser Ala Phe Asn Tyr Ser Gln Asp Gly Ile
545                 550                 555                 560

Ile Asp Thr Tyr Glu Ala Val Glu Met Ser Arg Lys Phe Gly Ile Glu
                565                 570                 575

Val Phe Asn Val Phe Leu Ser Gln Asp Pro Ile Thr Glu Asp Val Glu
            580                 585                 590

Gln Thr Ile His Asn Ile Tyr Gly Gln Tyr Ala Ile Phe Val Glu Gly
        595                 600                 605

Val Ala His Leu Pro Gly His Leu Ser Pro Leu Leu Lys Lys Leu Leu
    610                 615                 620

Leu Lys Ser Leu
625

<210> SEQ ID NO 30
<211> LENGTH: 154
<212> TYPE: PRT
<213> ORGANISM: Staphylococcus sp

<400> SEQUENCE: 30

Ala Glu Ile Asn Lys Gln Thr Thr Ser Gln Gly Val Thr Thr Glu Lys
1               5                  10                  15

Asn Asn Gly Ile Ala Val Leu Glu Gln Asp Val Ile Thr Pro Thr Val
            20                  25                  30

Lys Pro Gln Ala Lys Gln Asp Ile Ile Gln Ala Val Thr Thr Arg Lys
        35                  40                  45

Gln Gln Ile Lys Lys Ser Asn Ala Ser Leu Gln Asp Glu Lys Asp Val
    50                  55                  60

Ala Asn Asp Lys Ile Gly Lys Ile Glu Thr Lys Ala Ile Lys Asp Ile
65                  70                  75                  80

Asp Ala Ala Thr Thr Asn Ala Gln Val Glu Ala Ile Lys Thr Lys Ala
                85                  90                  95

Ile Asn Asp Ile Asn Gln Thr Thr Pro Ala Thr Thr Lys Ala Ala Ala
            100                 105                 110

Ala Leu Glu Glu Phe Asp Glu Val Val Gln Ala Gln Ile Asp Gln Ala
        115                 120                 125

Pro Leu Asn Pro Asp Thr Thr Asn Glu Glu Val Ala Glu Ala Ile Glu
    130                 135                 140

Arg Ile Asn Ala Ala Lys Val Ser Gly Val
145                 150

<210> SEQ ID NO 31
<211> LENGTH: 584
<212> TYPE: PRT
<213> ORGANISM: Staphylococcus sp

<400> SEQUENCE: 31

Met Lys Phe Lys Ser Leu Ile Thr Thr Leu Ala Leu Gly Val Leu
1               5                  10                  15

Ala Ser Thr Gly Ala Asn Phe Asn Asn Asn Glu Ala Ser Ala Ala Ala
            20                  25                  30

Lys Pro Leu Asp Lys Ser Ser Ser Leu His His Gly Tyr Ser Lys
        35                  40                  45
```

Val His Val Pro Tyr Ala Ile Thr Val Asn Gly Thr Ser Gln Asn Ile
 50                  55                  60

Leu Ser Ser Leu Thr Phe Asn Lys Asn Gln Asn Ile Ser Tyr Lys Asp
 65                  70                  75                  80

Leu Glu Asp Arg Val Lys Ser Val Leu Lys Ser Asp Arg Gly Ile Ser
                 85                  90                  95

Asp Ile Asp Leu Arg Leu Ser Lys Gln Ala Lys Tyr Thr Val Tyr Phe
            100                 105                 110

Lys Asn Gly Thr Lys Lys Val Ile Asp Leu Lys Ala Gly Ile Tyr Thr
            115                 120                 125

Ala Asp Leu Ile Asn Thr Ser Glu Ile Lys Ala Ile Asn Ile Asn Val
            130                 135                 140

Asp Thr Lys Lys Gln Val Glu Asp Lys Lys Asp Lys Ala Asn Tyr
145                 150                 155                 160

Gln Val Pro Tyr Thr Ile Thr Val Asn Gly Thr Ser Gln Asn Ile Leu
                165                 170                 175

Ser Asn Leu Thr Phe Asn Lys Asn Gln Asn Ile Ser Tyr Lys Asp Leu
            180                 185                 190

Glu Asp Lys Val Lys Ser Val Leu Glu Ser Asn Arg Gly Ile Thr Asp
            195                 200                 205

Val Asp Leu Arg Leu Ser Lys Gln Ala Lys Tyr Thr Val Asn Phe Lys
            210                 215                 220

Asn Gly Thr Lys Lys Val Ile Asp Leu Lys Ser Gly Ile Tyr Thr Ala
225                 230                 235                 240

Asn Leu Ile Asn Ser Ser Asp Ile Lys Ser Ile Asn Ile Asn Val Asp
                245                 250                 255

Thr Lys Lys His Ile Glu Asn Lys Ala Lys Arg Asn Tyr Gln Val Pro
            260                 265                 270

Tyr Ser Ile Asn Leu Asn Gly Thr Ser Thr Asn Ile Leu Ser Asn Leu
            275                 280                 285

Ser Phe Ser Asn Lys Pro Trp Thr Asn Tyr Lys Asn Leu Thr Ser Gln
            290                 295                 300

Ile Lys Ser Val Leu Lys His Asp Arg Gly Ile Ser Glu Gln Asp Leu
305                 310                 315                 320

Lys Tyr Ala Lys Lys Ala Tyr Tyr Thr Val Tyr Phe Lys Asn Gly Gly
                325                 330                 335

Lys Arg Ile Leu Gln Leu Asn Ser Lys Asn Tyr Thr Ala Asn Leu Val
            340                 345                 350

His Ala Lys Asp Val Lys Arg Ile Glu Ile Thr Val Lys Thr Gly Thr
            355                 360                 365

Lys Ala Lys Ala Asp Arg Tyr Val Pro Tyr Thr Ile Ala Val Asn Gly
370                 375                 380

Thr Ser Thr Pro Ile Leu Ser Asp Leu Lys Phe Thr Gly Asp Pro Arg
385                 390                 395                 400

Val Gly Tyr Lys Asp Ile Ser Lys Lys Val Lys Ser Val Leu Lys His
            405                 410                 415

Asp Arg Gly Ile Gly Glu Arg Glu Leu Lys Tyr Ala Lys Lys Ala Thr
            420                 425                 430

Tyr Thr Val His Phe Lys Asn Gly Thr Lys Val Ile Asn Ile Asn
            435                 440                 445

Ser Asn Ile Ser Gln Leu Asn Leu Leu Tyr Val Gln Asp Ile Lys Lys
450                 455                 460

```
Ile Asp Ile Asp Val Lys Thr Gly Thr Lys Ala Lys Asp Ser Tyr
465                 470                 475                 480

Val Pro Tyr Thr Ile Ala Val Asn Gly Thr Ser Thr Pro Ile Leu Ser
                485                 490                 495

Lys Leu Lys Ile Ser Asn Lys Gln Leu Ile Ser Tyr Lys Tyr Leu Asn
            500                 505                 510

Asp Lys Val Lys Ser Val Leu Lys Ser Glu Arg Gly Ile Ser Asp Leu
            515                 520                 525

Asp Leu Lys Phe Ala Lys Gln Ala Lys Tyr Thr Val Tyr Phe Lys Asn
            530                 535                 540

Gly Lys Lys Gln Val Val Asn Leu Lys Ser Asp Ile Phe Thr Pro Asn
545                 550                 555                 560

Leu Phe Ser Ala Lys Asp Ile Lys Lys Ile Asp Ile Asp Val Lys Gln
                565                 570                 575

Tyr Thr Lys Ser Lys Lys Asn Lys
            580

<210> SEQ ID NO 32
<211> LENGTH: 508
<212> TYPE: PRT
<213> ORGANISM: Staphylococcus sp

<400> SEQUENCE: 32

Met Lys Asn Lys Leu Leu Val Leu Ser Leu Gly Ala Leu Cys Val Ser
1               5                   10                  15

Gln Ile Trp Glu Ser Asn Arg Ala Ser Ala Val Val Ser Gly Glu Lys
            20                  25                  30

Asn Pro Tyr Val Ser Glu Ser Leu Lys Leu Thr Asn Asn Lys Asn Lys
            35                  40                  45

Ser Arg Thr Val Glu Glu Tyr Lys Ser Leu Asp Asp Leu Ile Trp
50                  55                  60

Ser Phe Pro Asn Leu Asp Asn Glu Arg Phe Asp Asn Pro Glu Tyr Lys
65                  70                  75                  80

Glu Ala Met Lys Lys Tyr Gln Gln Arg Phe Met Ala Glu Asp Glu Ala
                85                  90                  95

Leu Lys Lys Phe Phe Ser Glu Glu Lys Lys Ile Lys Asn Gly Asn Thr
            100                 105                 110

Asp Asn Leu Asp Tyr Leu Gly Leu Ser His Glu Arg Tyr Glu Ser Val
            115                 120                 125

Phe Asn Thr Leu Lys Lys Gln Ser Glu Glu Phe Leu Lys Glu Ile Glu
            130                 135                 140

Asp Ile Lys Lys Asp Asn Pro Glu Leu Lys Asp Phe Asn Glu Glu Glu
145                 150                 155                 160

Gln Leu Lys Cys Asp Leu Glu Leu Asn Lys Leu Glu Asn Gln Ile Leu
                165                 170                 175

Met Leu Gly Lys Thr Phe Tyr Gln Asn Tyr Arg Asp Asp Val Glu Ser
            180                 185                 190

Leu Tyr Ser Lys Leu Asp Leu Ile Met Gly Tyr Lys Asp Glu Glu Arg
            195                 200                 205

Ala Asn Lys Lys Ala Val Asn Lys Arg Met Leu Glu Asn Lys Lys Glu
            210                 215                 220

Asp Leu Glu Thr Ile Ile Asp Glu Phe Phe Ser Asp Ile Asp Lys Thr
225                 230                 235                 240

Arg Pro Asn Asn Ile Pro Val Leu Glu Asp Glu Lys Gln Glu Glu Lys
                245                 250                 255
```

Asn His Lys Asn Met Ala Gln Leu Lys Ser Asp Thr Glu Ala Ala Lys
                260                 265                 270

Ser Asp Glu Ser Lys Arg Ser Arg Ser Lys Arg Ser Leu Asn Thr
            275                 280                 285

Gln Asn His Lys Pro Ala Ser Gln Glu Val Ser Glu Gln Gln Lys Ala
        290                 295                 300

Glu Tyr Asp Lys Arg Ala Glu Glu Arg Lys Ala Arg Phe Leu Asp Asn
305                 310                 315                 320

Gln Lys Ile Lys Lys Thr Pro Val Val Ser Leu Glu Tyr Asp Phe Glu
                325                 330                 335

His Lys Gln Arg Ile Asp Asn Glu Asn Asp Lys Lys Leu Val Val Ser
            340                 345                 350

Ala Pro Thr Lys Lys Pro Thr Ser Pro Thr Thr Tyr Thr Glu Thr Thr
        355                 360                 365

Thr Gln Val Pro Met Pro Thr Val Glu Arg Gln Thr Gln Gln Ile
370                 375                 380

Ile Tyr Asn Ala Pro Lys Gln Leu Ala Gly Leu Asn Gly Glu Ser His
385                 390                 395                 400

Asp Phe Thr Thr Thr His Gln Ser Pro Thr Thr Ser Asn His Thr His
                405                 410                 415

Asn Asn Val Val Glu Phe Glu Thr Ser Ala Leu Pro Gly Arg Lys
            420                 425                 430

Ser Gly Ser Leu Val Gly Ile Ser Gln Ile Asp Ser Ser His Leu Thr
        435                 440                 445

Glu Arg Glu Lys Arg Val Ile Lys Arg Glu His Val Arg Glu Ala Gln
            450                 455                 460

Lys Leu Val Asp Asn Tyr Lys Asp Thr His Ser Tyr Lys Asp Arg Ile
465                 470                 475                 480

Asn Ala Gln Gln Lys Val Asn Thr Leu Ser Glu Gly His Gln Lys Arg
                485                 490                 495

Phe Asn Lys Gln Ile Asn Lys Val Tyr Asn Gly Lys
            500                 505

<210> SEQ ID NO 33
<211> LENGTH: 520
<212> TYPE: PRT
<213> ORGANISM: Staphylococcus sp

<400> SEQUENCE: 33

Met Leu Thr Leu Gln Ile His Thr Gly Gly Ile Asn Leu Lys Lys Lys
1               5                   10                  15

Asn Ile Tyr Ser Ile Arg Lys Leu Gly Val Gly Ile Ala Ser Val Thr
                20                  25                  30

Leu Gly Thr Leu Leu Ile Ser Gly Gly Val Thr Pro Ala Ala Asn Ala
            35                  40                  45

Ala Gln His Asp Glu Ala Gln Gln Asn Ala Phe Tyr Gln Val Leu Asn
        50                  55                  60

Met Pro Asn Leu Asn Ala Asp Gln Arg Asn Gly Phe Ile Gln Ser Leu
65                  70                  75                  80

Lys Asp Asp Pro Ser Gln Ser Ala Asn Val Leu Gly Glu Ala Gln Lys
                85                  90                  95

Leu Asn Asp Ser Gln Ala Pro Lys Ala Asp Ala Gln Gln Asn Asn Phe
            100                 105                 110

Asn Lys Asp Gln Gln Ser Ala Phe Tyr Glu Ile Leu Asn Met Pro Asn

```
            115                 120                 125
Leu Asn Glu Ala Gln Arg Asn Gly Phe Ile Gln Ser Leu Lys Asp Asp
    130                 135                 140

Pro Ser Gln Ser Thr Asn Val Leu Gly Glu Ala Lys Lys Leu Asn Glu
145                 150                 155                 160

Ser Gln Ala Pro Lys Ala Asp Asn Asn Phe Asn Lys Glu Gln Gln Asn
                165                 170                 175

Ala Phe Tyr Glu Ile Leu Asn Met Pro Asn Leu Asn Glu Glu Gln Arg
            180                 185                 190

Asn Gly Phe Ile Gln Ser Leu Lys Asp Asp Pro Ser Gln Ser Ala Asn
        195                 200                 205

Leu Leu Ser Glu Ala Lys Lys Leu Asn Glu Ser Gln Ala Pro Lys Ala
    210                 215                 220

Asp Asn Lys Phe Asn Lys Glu Gln Gln Asn Ala Phe Tyr Glu Ile Leu
225                 230                 235                 240

His Leu Pro Asn Leu Asn Glu Glu Gln Arg Asn Gly Phe Ile Gln Ser
                245                 250                 255

Leu Lys Asp Asp Pro Ser Gln Ser Ala Asn Leu Leu Ala Glu Ala Lys
            260                 265                 270

Lys Leu Asn Asp Ala Gln Ala Pro Lys Ala Asp Asn Lys Phe Asn Lys
        275                 280                 285

Glu Gln Gln Asn Ala Phe Tyr Glu Ile Leu His Leu Pro Asn Leu Thr
    290                 295                 300

Glu Glu Gln Arg Asn Gly Phe Ile Gln Ser Leu Lys Asp Asp Pro Ser
305                 310                 315                 320

Val Ser Lys Glu Ile Leu Ala Glu Ala Lys Lys Leu Asn Asp Ala Gln
                325                 330                 335

Ala Pro Lys Glu Glu Asp Asn Asn Lys Pro Gly Lys Glu Asp Gly Asn
            340                 345                 350

Lys Pro Gly Lys Glu Asp Asn Asn Lys Pro Gly Lys Glu Asp Asn Lys
        355                 360                 365

Lys Pro Gly Lys Glu Asp Asn Asn Lys Pro Gly Lys Glu Asp Asn Asn
    370                 375                 380

Lys Pro Gly Lys Glu Asp Gly Asn Lys Pro Gly Lys Glu Asp Asn Lys
385                 390                 395                 400

Lys Pro Gly Lys Glu Asp Asn Asn Lys Pro Gly Lys Glu Asp Gly Asn
                405                 410                 415

Lys Pro Gly Lys Glu Asp Gly Asn Gly Val His Val Val Lys Pro Gly
            420                 425                 430

Asp Thr Val Asn Asp Ile Ala Lys Ala Asn Gly Thr Thr Ala Asp Lys
        435                 440                 445

Ile Ala Ala Asp Asn Lys Leu Ala Asp Lys Asn Met Ile Lys Pro Gly
    450                 455                 460

Gln Glu Leu Val Val Asp Lys Lys Gln Pro Ala Asn His Ala Asp Ala
465                 470                 475                 480

Asn Lys Ala Gln Ala Leu Pro Glu Thr Gly Glu Asn Pro Phe Ile
                485                 490                 495

Gly Thr Thr Val Phe Gly Gly Leu Ser Leu Ala Leu Gly Ala Ala Leu
            500                 505                 510

Leu Ala Gly Arg Arg Arg Glu Leu
        515                 520

<210> SEQ ID NO 34
```

```
<211> LENGTH: 291
<212> TYPE: PRT
<213> ORGANISM: Staphylococcus sp

<400> SEQUENCE: 34

Ala Gln His Asp Glu Ala Lys Lys Asn Ala Phe Tyr Gln Val Leu Asn
1               5                   10                  15

Met Pro Asn Leu Asn Ala Asp Gln Arg Asn Gly Phe Ile Gln Ser Leu
            20                  25                  30

Lys Ala Ala Pro Ser Gln Ser Ala Asn Val Leu Gly Glu Ala Gln Lys
        35                  40                  45

Leu Asn Asp Ser Gln Ala Pro Lys Ala Asp Ala Gln Gln Asn Asn Phe
    50                  55                  60

Asn Lys Asp Lys Lys Ser Ala Phe Tyr Glu Ile Leu Asn Met Pro Asn
65                  70                  75                  80

Leu Asn Glu Ala Gln Arg Asn Gly Phe Ile Gln Ser Leu Lys Ala Ala
                85                  90                  95

Pro Ser Gln Ser Thr Asn Val Leu Gly Glu Ala Lys Lys Leu Asn Glu
            100                 105                 110

Ser Gln Ala Pro Lys Ala Asp Asn Asn Phe Asn Lys Glu Lys Lys Asn
        115                 120                 125

Ala Phe Tyr Glu Ile Leu Asn Met Pro Asn Leu Asn Glu Glu Gln Arg
    130                 135                 140

Asn Gly Phe Ile Gln Ser Leu Lys Ala Ala Pro Ser Gln Ser Ala Asn
145                 150                 155                 160

Leu Leu Ser Glu Ala Lys Lys Leu Asn Glu Ser Gln Ala Pro Lys Ala
                165                 170                 175

Asp Asn Lys Phe Asn Lys Glu Lys Lys Asn Ala Phe Tyr Glu Ile Leu
            180                 185                 190

His Leu Pro Asn Leu Asn Glu Glu Gln Arg Asn Gly Phe Ile Gln Ser
        195                 200                 205

Leu Lys Ala Ala Pro Ser Gln Ser Ala Asn Leu Leu Ala Glu Ala Lys
    210                 215                 220

Lys Leu Asn Asp Ala Gln Ala Pro Lys Ala Asp Asn Lys Phe Asn Lys
225                 230                 235                 240

Glu Lys Lys Asn Ala Phe Tyr Glu Ile Leu His Leu Pro Asn Leu Thr
                245                 250                 255

Glu Glu Gln Arg Asn Gly Phe Ile Gln Ser Leu Lys Ala Ala Pro Ser
            260                 265                 270

Val Ser Lys Glu Ile Leu Ala Glu Ala Lys Lys Leu Asn Asp Ala Gln
        275                 280                 285

Ala Pro Lys
    290

<210> SEQ ID NO 35
<211> LENGTH: 772
<212> TYPE: PRT
<213> ORGANISM: Staphylococcus sp

<400> SEQUENCE: 35

Met Lys Ala Leu Leu Leu Lys Thr Ser Val Trp Leu Val Leu Leu Phe
1               5                   10                  15

Ser Val Met Gly Leu Trp Gln Val Ser Asn Ala Ala Glu Gln His Thr
            20                  25                  30

Pro Met Lys Ala His Ala Val Thr Ile Asp Lys Ala Thr Thr Asp
        35                  40                  45
```

```
Lys Gln Gln Val Pro Pro Thr Lys Glu Ala Ala His His Ser Gly Lys
 50                  55                  60

Glu Ala Ala Thr Asn Val Ser Ala Ser Ala Gln Gly Thr Ala Asp Asp
 65                  70                  75                  80

Thr Asn Ser Lys Val Thr Ser Asn Ala Pro Ser Asn Lys Pro Ser Thr
                 85                  90                  95

Val Val Ser Thr Lys Val Asn Glu Thr Arg Asp Val Asp Thr Gln Gln
                100                 105                 110

Ala Ser Thr Gln Lys Pro Thr His Thr Ala Thr Phe Lys Leu Ser Asn
            115                 120                 125

Ala Lys Thr Ala Ser Leu Ser Pro Arg Met Phe Ala Ala Asn Ala Pro
        130                 135                 140

Gln Thr Thr Thr His Lys Ile Leu His Thr Asn Asp Ile His Gly Arg
145                 150                 155                 160

Leu Ala Glu Glu Lys Gly Arg Val Ile Gly Met Ala Lys Leu Lys Thr
                165                 170                 175

Val Lys Glu Gln Glu Lys Pro Asp Leu Met Leu Asp Ala Gly Asp Ala
            180                 185                 190

Phe Gln Gly Leu Pro Leu Ser Asn Gln Ser Lys Gly Glu Glu Met Ala
        195                 200                 205

Lys Ala Met Asn Ala Val Gly Tyr Asp Ala Met Ala Val Gly Asn His
210                 215                 220

Glu Phe Asp Phe Gly Tyr Asp Gln Leu Lys Lys Leu Glu Gly Met Leu
225                 230                 235                 240

Asp Phe Pro Met Leu Ser Thr Asn Val Tyr Lys Asp Gly Lys Arg Ala
                245                 250                 255

Phe Lys Pro Ser Thr Ile Val Thr Lys Asn Gly Ile Arg Tyr Gly Ile
            260                 265                 270

Ile Gly Val Thr Thr Pro Glu Thr Lys Thr Lys Thr Arg Pro Glu Gly
        275                 280                 285

Ile Lys Gly Val Glu Phe Arg Asp Pro Leu Gln Ser Val Thr Ala Glu
    290                 295                 300

Met Met Arg Ile Tyr Lys Asp Val Asp Thr Phe Val Val Ile Ser His
305                 310                 315                 320

Leu Gly Ile Asp Pro Ser Thr Gln Glu Thr Trp Arg Gly Asp Tyr Leu
                325                 330                 335

Val Lys Gln Leu Ser Gln Asn Pro Gln Leu Lys Lys Arg Ile Thr Val
            340                 345                 350

Ile Asp Gly His Ser His Thr Val Leu Gln Asn Gly Gln Ile Tyr Asn
        355                 360                 365

Asn Asp Ala Leu Ala Gln Thr Gly Thr Ala Leu Ala Asn Ile Gly Lys
    370                 375                 380

Ile Thr Phe Asn Tyr Arg Asn Gly Glu Val Ser Asn Ile Lys Pro Ser
385                 390                 395                 400

Leu Ile Asn Val Lys Asp Val Glu Asn Val Thr Pro Asn Lys Ala Leu
                405                 410                 415

Ala Glu Gln Ile Asn Gln Ala Asp Gln Thr Phe Arg Ala Gln Thr Ala
            420                 425                 430

Glu Val Ile Ile Pro Asn Asn Thr Ile Asp Phe Lys Gly Glu Arg Asp
        435                 440                 445

Asp Val Arg Thr Arg Glu Thr Asn Leu Gly Asn Ala Ile Ala Asp Ala
    450                 455                 460
```

Met Glu Ala Tyr Gly Val Lys Asn Phe Ser Lys Thr Asp Phe Ala
465                 470                 475                 480

Val Thr Asn Gly Gly Leu Arg Ala Ser Ile Ala Lys Gly Lys Val
            485                 490                 495

Thr Arg Tyr Asp Leu Ile Ser Val Leu Pro Phe Gly Asn Thr Ile Ala
            500                 505                 510

Gln Ile Asp Val Lys Gly Ser Asp Val Trp Thr Ala Phe Glu His Ser
            515                 520                 525

Leu Gly Ala Pro Thr Thr Gln Lys Asp Gly Lys Thr Val Leu Thr Ala
            530                 535                 540

Asn Gly Gly Leu Leu His Ile Ser Asp Ser Ile Arg Val Tyr Tyr Asp
545                 550                 555                 560

Ile Asn Lys Pro Ser Gly Lys Arg Ile Asn Ala Ile Gln Ile Leu Asn
            565                 570                 575

Lys Glu Thr Gly Lys Phe Glu Asn Ile Asp Leu Lys Arg Val Tyr His
            580                 585                 590

Val Thr Met Asn Asp Phe Thr Ala Ser Gly Gly Asp Gly Tyr Ser Met
            595                 600                 605

Phe Gly Gly Pro Arg Glu Glu Gly Ile Ser Leu Asp Gln Val Leu Ala
610                 615                 620

Ser Tyr Leu Lys Thr Ala Asn Leu Ala Lys Tyr Asp Thr Thr Glu Pro
625                 630                 635                 640

Gln Arg Met Leu Leu Gly Lys Pro Ala Val Ser Glu Gln Pro Ala Lys
            645                 650                 655

Gly Gln Gln Gly Ser Lys Gly Ser Lys Ser Gly Lys Asp Thr Gln Pro
            660                 665                 670

Ile Gly Asp Asp Lys Val Met Asp Pro Ala Lys Lys Pro Ala Pro Gly
            675                 680                 685

Lys Val Val Leu Leu Ala His Arg Gly Thr Val Ser Ser Gly Thr
690                 695                 700

Glu Gly Ser Gly Arg Thr Ile Glu Gly Ala Thr Val Ser Ser Lys Ser
705                 710                 715                 720

Gly Lys Gln Leu Ala Arg Met Ser Val Pro Lys Gly Ser Ala His Glu
            725                 730                 735

Lys Gln Leu Pro Lys Thr Gly Thr Asn Gln Ser Ser Ser Pro Glu Ala
            740                 745                 750

Met Phe Val Leu Leu Ala Gly Ile Gly Leu Ile Ala Thr Val Arg Arg
            755                 760                 765

Arg Lys Ala Ser
    770

<210> SEQ ID NO 36
<211> LENGTH: 190
<212> TYPE: PRT
<213> ORGANISM: Staphylococcus sp

<400> SEQUENCE: 36

Met Lys Leu Lys Ser Leu Ala Val Leu Ser Met Ser Ala Val Val Leu
1               5                   10                  15

Thr Ala Cys Gly Asn Asp Thr Pro Lys Asp Glu Thr Lys Ser Thr Glu
                20                  25                  30

Ser Asn Thr Asn Gln Asp Thr Asn Thr Thr Lys Asp Val Ile Ala Leu
            35                  40                  45

Lys Asp Val Lys Thr Ser Pro Glu Asp Ala Val Lys Lys Ala Glu Glu
50                  55                  60

```
Thr Tyr Lys Gly Gln Lys Leu Lys Gly Ile Ser Phe Glu Asn Ser Asn
 65                  70                  75                  80

Gly Glu Trp Ala Tyr Lys Val Thr Gln Gln Lys Ser Gly Glu Glu Ser
                 85                  90                  95

Glu Val Leu Val Ala Asp Lys Asn Lys Val Ile Asn Lys Lys Thr
            100                 105                 110

Glu Lys Glu Asp Thr Met Asn Glu Asn Asp Asn Phe Lys Tyr Ser Asp
            115                 120                 125

Ala Ile Asp Tyr Lys Lys Ala Ile Lys Glu Gly Gln Lys Glu Phe Asp
            130                 135                 140

Gly Asp Ile Lys Glu Trp Ser Leu Glu Lys Asp Asp Gly Lys Leu Val
145                 150                 155                 160

Tyr Asn Ile Asp Leu Lys Lys Gly Asn Lys Lys Gln Glu Val Thr Val
                165                 170                 175

Asp Ala Lys Asn Gly Lys Val Leu Lys Ser Glu Gln Asp His
            180                 185                 190

<210> SEQ ID NO 37
<211> LENGTH: 502
<212> TYPE: PRT
<213> ORGANISM: Staphylococcus sp

<400> SEQUENCE: 37

Met Arg Glu Asn Phe Lys Leu Arg Lys Met Lys Val Gly Leu Val Ser
  1               5                  10                  15

Val Ala Ile Thr Met Leu Tyr Ile Met Thr Asn Gly Gln Ala Glu Ala
                 20                  25                  30

Ser Glu Asn Gln Asn Ala Leu Ile Ser Asn Ile Asn Val Asp Asn Gln
             35                  40                  45

Glu Lys Gln Asn Asn Val Asn Gln Ala Val Gln Pro Gln Asn Asn Thr
         50                  55                  60

Asn Glu Thr Ser Lys Val Pro Ala Asn Phe Val Lys Leu Asn Asp Ile
 65                  70                  75                  80

Lys Pro Gly Asp Thr Ser Ile Gln Gly Thr Thr Leu Pro Asn Gln Phe
                 85                  90                  95

Ile Leu Leu Thr Ile Asp Lys Lys Asp Val Ser Ser Val Glu Asp Ser
            100                 105                 110

Asp Ser Ser Phe Val Met Ser Asp Lys Asp Gly Asn Phe Lys Tyr Asp
            115                 120                 125

Leu Asn Gly Arg Lys Ile Val His Asn Gln Glu Ile Glu Val Ser Ser
            130                 135                 140

Ser Asp Pro Tyr Leu Gly Asp Asp Glu Glu Asp Glu Glu Val Glu Glu
145                 150                 155                 160

Thr Ser Thr Glu Glu Val Gly Ala Glu Glu Ser Thr Glu Ala Lys
                165                 170                 175

Ala Thr Tyr Thr Thr Pro Arg Tyr Glu Lys Ala Tyr Glu Ile Pro Lys
            180                 185                 190

Glu Gln Leu Lys Glu Lys Asp Gly His His Gln Val Phe Ile Glu Pro
            195                 200                 205

Ile Thr Glu Gly Ser Gly Ile Ile Lys Gly His Thr Ser Val Lys Gly
            210                 215                 220

Lys Val Ala Leu Ser Ile Asn Asn Lys Phe Ile Asn Phe Glu Thr Asn
225                 230                 235                 240

Ala Asn Gly Gly Pro Asn Lys Glu Glu Ala Lys Ser Gly Ser Glu Gly
```

Ile Trp Met Pro Ile Asp Asp Lys Gly Tyr Phe Asn Phe Asp Phe Lys
            245                 250                 255
                260                 265                 270

Thr Lys Arg Phe Asp Asp Leu Glu Leu Lys Lys Asn Asp Glu Ile Ser
            275                 280                 285

Leu Thr Phe Ala Pro Asp Glu Asp Glu Ala Leu Lys Ser Leu Ile
            290                 295                 300

Phe Lys Thr Lys Val Thr Ser Leu Glu Asp Ile Asp Lys Ala Glu Thr
305                 310                 315                 320

Lys Tyr Asp His Thr Lys Val Glu Lys Val Lys Val Leu Lys Asp Val
            325                 330                 335

Lys Glu Asp Leu His Val Asp Glu Ile Tyr Gly Ser Leu Tyr His Thr
            340                 345                 350

Glu Lys Gly Lys Gly Ile Leu Asp Lys Glu Gly Thr Lys Val Ile Lys
            355                 360                 365

Gly Lys Thr Lys Phe Ala Asn Ala Val Val Lys Val Asp Ser Glu Leu
            370                 375                 380

Gly Glu Gly Gln Glu Phe Pro Asp Leu Gln Val Asp Glu Lys Gly Glu
385                 390                 395                 400

Phe Ser Phe Asp Val Asp His Ala Gly Phe Arg Leu Gln Asn Gly Glu
                405                 410                 415

Thr Leu Asn Phe Thr Val Val Asp Pro Ile Thr Gly Glu Leu Leu Ser
            420                 425                 430

Gly Asn Phe Val Ser Lys Asn Ile Asp Ile Tyr Glu Ser Pro Glu Glu
            435                 440                 445

Lys Ala Asp Arg Glu Phe Asp Glu Arg Met Glu Asn Thr Pro Ala Tyr
450                 455                 460

His Lys Leu His Gly Asp Lys Ile Val Gly Tyr Asp Thr Asn Gly Phe
465                 470                 475                 480

Pro Ile Thr Trp Phe Tyr Pro Leu Gly Glu Lys Lys Val Glu Arg Lys
                485                 490                 495

Ala Pro Lys Leu Glu Lys
            500

<210> SEQ ID NO 38
<211> LENGTH: 342
<212> TYPE: PRT
<213> ORGANISM: Staphylococcus sp

<400> SEQUENCE: 38

Met Lys Lys Thr Val Leu Tyr Leu Val Leu Ala Val Met Phe Leu Leu
1               5                   10                  15

Ala Ala Cys Gly Asn Asn Ser Asp Lys Glu Gln Ser Lys Ser Glu Thr
            20                  25                  30

Lys Gly Ser Lys Asp Thr Val Lys Ile Glu Asn Asn Tyr Lys Met Arg
        35                  40                  45

Gly Glu Lys Lys Asp Gly Ser Asp Ala Lys Lys Val Lys Glu Thr Val
    50                  55                  60

Glu Val Pro Lys Asn Pro Lys Asn Ala Val Val Leu Asp Tyr Gly Ala
65                  70                  75                  80

Leu Asp Val Met Lys Glu Met Gly Leu Ser Asp Lys Val Lys Ala Leu
                85                  90                  95

Pro Lys Gly Glu Gly Gly Lys Ser Leu Pro Asn Phe Leu Glu Ser Phe
            100                 105                 110

-continued

```
Lys Asp Asp Lys Tyr Thr Asn Val Gly Asn Leu Lys Glu Val Asn Phe
            115                 120                 125

Asp Lys Leu Ala Ala Thr Lys Pro Glu Val Ile Phe Ile Ser Gly Arg
        130                 135                 140

Thr Ala Asn Gln Lys Asn Leu Asp Glu Phe Lys Lys Ala Ala Pro Lys
145                 150                 155                 160

Ala Lys Ile Val Tyr Val Gly Ala Asp Glu Lys Asn Leu Ile Gly Ser
                165                 170                 175

Met Lys Gln Asn Thr Glu Asn Ile Gly Lys Ile Tyr Asp Lys Glu Asp
            180                 185                 190

Lys Ala Lys Glu Leu Asn Lys Asp Leu Asp Asn Lys Ile Ala Ser Met
        195                 200                 205

Lys Asp Lys Thr Lys Asn Phe Asn Lys Thr Val Met Tyr Leu Leu Val
    210                 215                 220

Asn Glu Gly Glu Leu Ser Thr Phe Gly Pro Lys Gly Arg Phe Gly Gly
225                 230                 235                 240

Leu Val Tyr Asp Thr Leu Gly Phe Asn Ala Val Asp Lys Lys Val Ser
                245                 250                 255

Asn Ser Asn His Gly Gln Asn Val Ser Asn Glu Tyr Val Asn Lys Glu
            260                 265                 270

Asn Pro Asp Val Ile Leu Ala Met Asp Arg Gly Gln Ala Ile Ser Gly
        275                 280                 285

Lys Ser Thr Ala Lys Gln Ala Leu Asn Asn Pro Val Leu Lys Asn Val
    290                 295                 300

Lys Ala Ile Lys Glu Asp Lys Val Tyr Asn Leu Asp Pro Lys Leu Trp
305                 310                 315                 320

Tyr Phe Ala Ala Gly Ser Thr Thr Thr Ile Lys Gln Ile Glu Glu
                325                 330                 335

Leu Asp Lys Val Val Lys
            340

<210> SEQ ID NO 39
<211> LENGTH: 241
<212> TYPE: PRT
<213> ORGANISM: Staphylococcus sp

<400> SEQUENCE: 39

Met Lys Lys Asn Ile Met Asn Lys Leu Val Leu Ser Thr Ala Leu Leu
1               5                   10                  15

Leu Leu Glu Thr Thr Ser Thr Gln Leu Pro Lys Thr Pro Ile Ser Phe
            20                  25                  30

Ser Ser Glu Ala Lys Ala Tyr Asn Ile Ser Glu Asn Glu Thr Asn Ile
        35                  40                  45

Asn Glu Leu Ile Lys Tyr Tyr Thr Gln Pro His Phe Ser Leu Ser Gly
    50                  55                  60

Lys Trp Leu Trp Gln Lys Pro Asn Gly Ser Ile His Ala Thr Leu Gln
65                  70                  75                  80

Thr Trp Val Trp Tyr Ser His Ile Gln Val Phe Gly Ser Glu Ser Trp
                85                  90                  95

Gly Asn Ile Asn Gln Leu Arg Asn Lys Tyr Val Asp Ile Phe Gly Thr
            100                 105                 110

Lys Asp Glu Asp Thr Val Glu Gly Tyr Trp Thr Tyr Asp Glu Thr Phe
        115                 120                 125

Thr Gly Gly Val Thr Pro Ala Ala Thr Ser Ser Asp Lys Pro Tyr Arg
    130                 135                 140
```

```
Leu Phe Leu Lys Tyr Ser Asp Lys Gln Gln Thr Ile Ile Gly Gly His
145                 150                 155                 160

Glu Phe Tyr Lys Gly Asn Lys Pro Val Leu Thr Leu Lys Glu Leu Asp
                165                 170                 175

Phe Arg Ile Arg Gln Thr Leu Ile Lys Asn Lys Lys Leu Tyr Asn Gly
            180                 185                 190

Glu Phe Asn Lys Gly Gln Ile Lys Ile Thr Ala Asp Gly Asn Asn Tyr
        195                 200                 205

Thr Ile Asp Leu Ser Lys Lys Leu Lys Leu Thr Asp Thr Asn Arg Tyr
    210                 215                 220

Val Lys Asn Pro Arg Asn Ala Glu Ile Glu Val Ile Leu Glu Lys Ser
225                 230                 235                 240

Asn

<210> SEQ ID NO 40
<211> LENGTH: 302
<212> TYPE: PRT
<213> ORGANISM: Staphylococcus sp

<400> SEQUENCE: 40

Met Lys Lys Leu Leu Leu Pro Leu Ile Ile Met Leu Leu Val Leu Ala
1               5                   10                  15

Ala Cys Gly Asn Gln Gly Glu Lys Asn Asn Lys Ala Glu Thr Lys Ser
                20                  25                  30

Tyr Lys Met Asp Asp Gly Lys Thr Val Asp Ile Pro Lys Asp Pro Lys
            35                  40                  45

Arg Ile Ala Val Val Ala Pro Thr Tyr Ala Gly Gly Leu Lys Lys Leu
        50                  55                  60

Gly Ala Asn Ile Val Ala Val Asn Gln Gln Val Asp Gln Ser Lys Val
65                  70                  75                  80

Leu Lys Asp Lys Phe Lys Gly Val Thr Lys Ile Gly Asp Gly Asp Val
                85                  90                  95

Glu Lys Val Ala Lys Glu Lys Pro Asp Leu Ile Ile Val Tyr Ser Thr
            100                 105                 110

Asp Lys Asp Ile Lys Lys Tyr Gln Lys Val Ala Pro Thr Val Val Val
        115                 120                 125

Asp Tyr Asn Lys His Lys Tyr Leu Glu Gln Gln Glu Met Leu Gly Lys
    130                 135                 140

Ile Val Gly Lys Glu Asp Lys Val Lys Ala Trp Lys Lys Asp Trp Glu
145                 150                 155                 160

Glu Thr Thr Ala Lys Asp Gly Lys Glu Ile Lys Lys Ala Ile Gly Gln
                165                 170                 175

Asp Ala Thr Val Ser Leu Phe Asp Glu Phe Asp Lys Lys Leu Tyr Thr
            180                 185                 190

Tyr Gly Asp Asn Trp Gly Arg Gly Gly Glu Val Leu Tyr Gln Ala Phe
        195                 200                 205

Gly Leu Lys Met Gln Pro Glu Gln Gln Lys Leu Thr Ala Lys Ala Gly
    210                 215                 220

Trp Ala Glu Val Lys Gln Glu Gly Ile Glu Lys Tyr Ala Gly Asp Tyr
225                 230                 235                 240

Ile Val Ser Thr Ser Glu Gly Lys Pro Thr Pro Gly Tyr Glu Ser Thr
                245                 250                 255

Asn Met Trp Lys Asn Leu Lys Ala Thr Lys Glu Gly His Ile Val Lys
            260                 265                 270
```

```
Val Asp Ala Gly Thr Tyr Trp Tyr Asn Asp Pro Tyr Thr Leu Asp Phe
        275                 280                 285

Met Arg Lys Asp Leu Lys Glu Lys Leu Leu Lys Ala Ala Lys
        290                 295                 300

<210> SEQ ID NO 41
<211> LENGTH: 267
<212> TYPE: PRT
<213> ORGANISM: Staphylococcus sp

<400> SEQUENCE: 41

Met Lys Lys Ile Ala Thr Ala Thr Ile Ala Thr Ala Gly Phe Ala Thr
1               5                   10                  15

Ile Ala Ile Ala Ser Gly Asn Gln Ala His Ala Ser Glu Gln Asp Asn
            20                  25                  30

Tyr Gly Tyr Asn Pro Asn Asp Pro Thr Ser Tyr Ser Tyr Thr Tyr Thr
        35                  40                  45

Ile Asp Ala Gln Gly Asn Tyr His Tyr Thr Trp Lys Gly Asn Trp His
    50                  55                  60

Pro Ser Gln Leu Asn Gln Asp Asn Gly Tyr Tyr Ser Tyr Tyr Tyr Tyr
65                  70                  75                  80

Asn Gly Tyr Asn Asn Tyr Asn Asn Tyr Asn Asn Gly Tyr Ser Tyr Asn
                85                  90                  95

Asn Tyr Ser Arg Tyr Asn Asn Tyr Ser Asn Asn Gln Ser Tyr Asn
            100                 105                 110

Tyr Asn Asn Tyr Asn Ser Tyr Asn Thr Asn Ser Tyr Arg Thr Gly Gly
        115                 120                 125

Leu Gly Ala Ser Tyr Ser Thr Ser Ser Asn Asn Val Gln Val Thr Thr
    130                 135                 140

Thr Met Ala Pro Ser Ser Asn Gly Arg Ser Ile Ser Ser Gly Tyr Thr
145                 150                 155                 160

Ser Gly Arg Asn Leu Tyr Thr Ser Gly Gln Cys Thr Tyr Tyr Val Phe
                165                 170                 175

Asp Arg Val Gly Gly Lys Ile Gly Ser Thr Trp Gly Asn Ala Ser Asn
            180                 185                 190

Trp Ala Asn Ala Ala Ala Arg Ala Gly Tyr Thr Val Asn Asn Thr Pro
        195                 200                 205

Lys Ala Gly Ala Ile Met Gln Thr Thr Gln Gly Ala Tyr Gly His Val
    210                 215                 220

Ala Tyr Val Glu Ser Val Asn Ser Asn Gly Ser Val Arg Val Ser Glu
225                 230                 235                 240

Met Asn Tyr Gly Tyr Gly Pro Gly Val Val Thr Ser Arg Thr Ile Ser
                245                 250                 255

Ala Ser Gln Ala Ala Gly Tyr Asn Phe Ile His
            260                 265

<210> SEQ ID NO 42
<211> LENGTH: 209
<212> TYPE: PRT
<213> ORGANISM: Staphylococcus sp

<400> SEQUENCE: 42

Met Lys Arg Leu Val Thr Gly Leu Leu Ala Leu Ser Leu Phe Leu Ala
1               5                   10                  15

Ala Cys Gly Gln Asp Ser Asp Gln Gln Lys Asp Gly Asn Lys Glu Lys
            20                  25                  30
```

Asp Asp Lys Ala Lys Thr Glu Gln Gln Asp Lys Lys Thr Asn Asp Ser
        35                  40                  45

Ser Lys Asp Lys Lys Asp Asn Lys Asp Asp Ser Lys Asp Val Asn Lys
 50                  55                  60

Asp Asn Lys Asp Asn Ser Ala Asn Asp Asn Gln Gln Gln Ser Asn Ser
 65                  70                  75                  80

Asn Ala Thr Asn Asn Asp Gln Asn Gln Thr Asn Asn Asn Gln Ser Ser
                85                  90                  95

Asn Asn Gln Ala Asn Asn Asn Gln Lys Ser Ser Tyr Val Ala Pro Tyr
                100                 105                 110

Tyr Gly Gln Asn Ala Ala Pro Val Ala Arg Gln Ile Tyr Pro Phe Asn
                115                 120                 125

Gly Asn Lys Asn Gln Ala Leu Gln Gln Leu Pro Asn Phe Gln Thr Ala
        130                 135                 140

Leu Asn Ala Ala Asn Asn Glu Ala Asn Lys Phe Gly Ser Asn Asn Lys
145                 150                 155                 160

Val Tyr Asn Asp Tyr Ser Ile Glu Glu His Asn Gly Asn Tyr Lys Tyr
                165                 170                 175

Val Phe Ser Phe Lys Asp Pro Asn Ala Asn Gly Lys Tyr Ser Ile Val
                180                 185                 190

Thr Val Asp Tyr Thr Gly Gln Ala Met Val Thr Asp Pro Asn Tyr Gln
                195                 200                 205

Gln

<210> SEQ ID NO 43
<211> LENGTH: 436
<212> TYPE: PRT
<213> ORGANISM: Staphylococcus sp

<400> SEQUENCE: 43

Met Lys Asn Lys Tyr Ile Ser Lys Leu Leu Val Gly Ala Ala Thr Ile
1               5                   10                  15

Thr Leu Ala Thr Met Ile Ser Asn Gly Glu Ala Lys Ala Ser Glu Asn
                20                  25                  30

Thr Gln Gln Thr Ser Thr Lys His Gln Thr Thr Gln Asn Asn Tyr Val
        35                  40                  45

Thr Asp Gln Gln Lys Ala Phe Tyr Gln Val Leu His Leu Lys Gly Ile
 50                  55                  60

Thr Glu Glu Gln Arg Asn Gln Tyr Ile Lys Thr Leu Arg Glu His Pro
 65                  70                  75                  80

Glu Arg Ala Gln Glu Val Phe Ser Glu Ser Leu Lys Asp Ser Lys Asn
                85                  90                  95

Pro Asp Arg Arg Val Ala Gln Gln Asn Ala Phe Tyr Asn Val Leu Lys
                100                 105                 110

Asn Asp Asn Leu Thr Glu Gln Glu Lys Asn Asn Tyr Ile Ala Gln Ile
                115                 120                 125

Lys Glu Asn Pro Asp Arg Ser Gln Gln Val Trp Val Glu Ser Val Gln
                130                 135                 140

Ser Ser Lys Ala Lys Glu Arg Gln Asn Ile Glu Asn Ala Asp Lys Ala
145                 150                 155                 160

Ile Lys Asp Phe Gln Asp Asn Lys Ala Pro His Asp Lys Ser Ala Ala
                165                 170                 175

Tyr Glu Ala Asn Ser Lys Leu Pro Lys Asp Leu Arg Asp Lys Asn Asn
                180                 185                 190

```
Arg Phe Val Glu Lys Val Ser Ile Glu Lys Ala Ile Val Arg His Asp
            195                 200                 205

Glu Arg Val Lys Ser Ala Asn Asp Ala Ile Ser Lys Leu Asn Glu Lys
    210                 215                 220

Asp Ser Ile Glu Asn Arg Arg Leu Ala Gln Arg Glu Val Asn Lys Ala
225                 230                 235                 240

Pro Met Asp Val Lys Glu His Leu Gln Lys Gln Leu Asp Ala Leu Val
                245                 250                 255

Ala Gln Lys Asp Ala Glu Lys Lys Val Ala Pro Lys Val Glu Ala Pro
            260                 265                 270

Gln Ile Gln Ser Pro Gln Ile Glu Lys Pro Lys Val Glu Ser Pro Lys
            275                 280                 285

Val Glu Val Pro Gln Ile Gln Ser Pro Lys Val Glu Val Pro Gln Ser
        290                 295                 300

Lys Leu Leu Gly Tyr Tyr Gln Ser Leu Lys Asp Ser Phe Asn Tyr Gly
305                 310                 315                 320

Tyr Lys Tyr Leu Thr Asp Thr Tyr Lys Ser Tyr Lys Glu Lys Tyr Asp
                325                 330                 335

Thr Ala Lys Tyr Tyr Tyr Asn Thr Tyr Tyr Lys Tyr Lys Gly Ala Ile
            340                 345                 350

Asp Gln Thr Val Leu Thr Val Leu Gly Ser Gly Ser Lys Ser Tyr Ile
            355                 360                 365

Gln Pro Leu Lys Val Asp Asp Lys Asn Gly Tyr Leu Ala Lys Ser Tyr
        370                 375                 380

Ala Gln Val Arg Asn Tyr Val Thr Glu Ser Ile Asn Thr Gly Lys Val
385                 390                 395                 400

Leu Tyr Thr Phe Tyr Gln Asn Pro Thr Leu Val Lys Thr Ala Leu Lys
                405                 410                 415

Ala Gln Glu Thr Ala Ser Ser Ile Lys Asn Thr Leu Ser Asn Leu Leu
            420                 425                 430

Ser Phe Trp Lys
            435

<210> SEQ ID NO 44
<211> LENGTH: 233
<212> TYPE: PRT
<213> ORGANISM: Staphylococcus sp

<400> SEQUENCE: 44

Met Lys Lys Thr Ile Met Ala Ser Ser Leu Ala Val Ala Leu Gly Val
1               5                   10                  15

Thr Gly Tyr Ala Ala Gly Thr Gly His Gln Ala His Ala Ala Glu Val
            20                  25                  30

Asn Val Asp Gln Ala His Leu Val Asp Leu Ala His Asn His Gln Asp
        35                  40                  45

Gln Leu Asn Ala Ala Pro Ile Lys Asp Gly Ala Tyr Asp Ile His Phe
    50                  55                  60

Val Lys Asp Gly Phe Gln Tyr Asn Phe Thr Ser Asn Gly Thr Thr Trp
65                  70                  75                  80

Ser Trp Ser Tyr Glu Ala Ala Asn Gly Gln Thr Ala Gly Phe Ser Asn
                85                  90                  95

Val Ala Gly Ala Asp Tyr Thr Thr Ser Tyr Asn Gln Gly Ser Asn Val
            100                 105                 110

Gln Ser Val Ser Tyr Asn Ala Gln Ser Ser Asn Ser Asn Val Glu Ala
```

|   |   |   | 115 |   |   |   | 120 |   |   |   | 125 |   |   |
|---|---|---|---|---|---|---|---|---|---|---|---|---|---|

Val Ser Ala Pro Thr Tyr His Asn Tyr Ser Thr Ser Thr Ser Ser
130                 135                 140

Ser Val Arg Leu Ser Asn Gly Asn Thr Ala Gly Ala Thr Gly Ser Ser
145                 150                 155                 160

Ala Ala Gln Leu Met Ala Gln Arg Thr Gly Val Ser Ala Ser Thr Trp
                165                 170                 175

Ala Ala Ile Ile Ala Arg Glu Ser Asn Gly Gln Val Asn Ala Tyr Asn
                180                 185                 190

Pro Ser Gly Ala Ser Gly Leu Phe Gln Thr Met Pro Gly Trp Gly Pro
                195                 200                 205

Thr Asn Thr Val Asp Gln Gln Ile Asn Ala Ala Val Lys Ala Tyr Lys
                210                 215                 220

Ala Gln Gly Leu Gly Ala Trp Gly Phe
225                 230

<210> SEQ ID NO 45
<211> LENGTH: 256
<212> TYPE: PRT
<213> ORGANISM: Staphylococcus sp

<400> SEQUENCE: 45

Met Met Lys Arg Leu Asn Lys Leu Val Leu Gly Ile Ile Phe Leu Phe
1               5                   10                  15

Leu Val Ile Ser Ile Thr Ala Gly Cys Gly Ile Gly Lys Glu Ala Glu
                20                  25                  30

Val Lys Lys Ser Phe Glu Lys Thr Leu Ser Met Tyr Pro Ile Lys Asn
            35                  40                  45

Leu Glu Asp Leu Tyr Asp Lys Glu Gly Tyr Arg Asp Asp Gln Phe Asp
        50                  55                  60

Lys Asn Asp Lys Gly Thr Trp Ile Ile Asn Ser Glu Met Val Ile Gln
65                  70                  75                  80

Pro Asn Asn Glu Asp Met Val Ala Lys Gly Met Val Leu Tyr Met Asn
                85                  90                  95

Arg Asn Thr Lys Thr Thr Asn Gly Tyr Tyr Tyr Val Asp Val Thr Lys
                100                 105                 110

Asp Glu Asp Glu Gly Lys Pro His Asp Asn Glu Lys Arg Tyr Pro Val
                115                 120                 125

Lys Met Val Asp Asn Lys Ile Ile Pro Thr Lys Glu Ile Lys Asp Glu
130                 135                 140

Lys Ile Lys Lys Glu Ile Glu Asn Phe Lys Phe Phe Val Gln Tyr Gly
145                 150                 155                 160

Asp Phe Lys Asn Leu Lys Asn Tyr Lys Asp Gly Asp Ile Ser Tyr Asn
                165                 170                 175

Pro Glu Val Pro Ser Tyr Ser Ala Lys Tyr Gln Leu Thr Asn Asp Asp
                180                 185                 190

Tyr Asn Val Lys Gln Leu Arg Lys Arg Tyr Asp Ile Pro Thr Ser Lys
                195                 200                 205

Ala Pro Lys Leu Leu Leu Lys Gly Ser Gly Asn Leu Lys Gly Ser Ser
                210                 215                 220

Val Gly Tyr Lys Asp Ile Glu Phe Thr Phe Val Glu Lys Lys Glu Glu
225                 230                 235                 240

Asn Ile Tyr Phe Ser Asp Ser Leu Asp Tyr Lys Lys Ser Gly Asp Val
                245                 250                 255

<210> SEQ ID NO 46
<211> LENGTH: 514
<212> TYPE: PRT
<213> ORGANISM: Staphylococcus sp

<400> SEQUENCE: 46

```
Met Lys Lys Ile Tyr Lys Ser Leu Thr Val Ser Ala Ile Val Ala Thr
1               5                   10                  15

Val Ser Leu Ser Ala Leu Pro Gln Ser Leu Ala Ile Thr His Glu Ser
            20                  25                  30

Gln Pro Thr Lys Gln Gln Arg Thr Val Leu Phe Asp Arg Ser His Gly
        35                  40                  45

Gln Thr Ala Gly Ala Ala Asp Trp Val Ser Asp Gly Ala Phe Ser Asp
    50                  55                  60

Tyr Ala Asp Ser Ile Gln Lys Gln Gly Tyr Asp Val Lys Ala Ile Asp
65                  70                  75                  80

Gly His Ser Asn Ile Thr Glu Ala Ser Leu Lys Ser Ser Lys Ile Phe
                85                  90                  95

Val Ile Pro Glu Ala Asn Ile Pro Phe Lys Glu Ser Glu Gln Ala Ala
            100                 105                 110

Ile Val Lys Tyr Val Lys Gln Gly Gly Asn Val Val Phe Ile Ser Asp
        115                 120                 125

His Tyr Asn Ala Asp Arg Asn Leu Asn Arg Ile Asp Ser Ser Glu Ala
    130                 135                 140

Met Asn Gly Tyr Arg Arg Gly Ala Tyr Glu Asp Met Ser Lys Gly Met
145                 150                 155                 160

Asn Ala Glu Glu Lys Ser Ser Thr Ala Met Gln Gly Val Lys Ser Ser
                165                 170                 175

Asp Trp Leu Ser Thr Asn Phe Gly Val Arg Phe Arg Tyr Asn Ala Leu
            180                 185                 190

Gly Asp Leu Asn Thr Ser Asn Ile Val Ser Ser Lys Glu Ser Phe Gly
        195                 200                 205

Ile Thr Glu Gly Val Lys Ser Val Ser Met His Ala Gly Ser Thr Leu
    210                 215                 220

Ala Ile Thr Asn Pro Glu Lys Ala Lys Gly Ile Val Tyr Thr Pro Glu
225                 230                 235                 240

Gln Leu Pro Ala Lys Ser Lys Trp Ser His Ala Val Asp Gln Gly Ile
                245                 250                 255

Tyr Asn Gly Gly Gly Lys Ala Glu Gly Pro Tyr Val Ala Ile Ser Lys
            260                 265                 270

Val Gly Lys Gly Lys Ala Ala Phe Ile Gly Asp Ser Ser Leu Val Glu
        275                 280                 285

Asp Ser Ser Pro Lys Tyr Val Arg Glu Asp Asn Gly Glu Lys Lys Lys
    290                 295                 300

Thr Tyr Asp Gly Phe Lys Glu Gln Asp Asn Gly Lys Leu Leu Asn Asn
305                 310                 315                 320

Ile Thr Ala Trp Met Ser Lys Asp Asn Asp Gly Lys Ser Leu Lys Ala
                325                 330                 335

Ser Ser Leu Thr Leu Asp Thr Leu Thr Lys Leu Leu Asp Phe Glu Arg
            340                 345                 350

Pro Glu Arg Ser Thr Glu Pro Glu Lys Glu Pro Trp Ser Gln Pro Pro
        355                 360                 365

Ser Gly Tyr Lys Trp Tyr Asp Pro Thr Thr Phe Lys Ala Gly Ser Tyr
    370                 375                 380
```

```
Gly Ser Glu Lys Gly Ala Asp Pro Gln Pro Asn Thr Pro Asp His
385                 390                 395                 400

Thr Pro Pro Asn Gln Asn Glu Lys Val Thr Phe Asp Ile Pro Gln Asn
            405                 410                 415

Val Ser Val Asn Glu Pro Phe Glu Met Thr Ile His Leu Lys Gly Phe
            420                 425                 430

Glu Ala Asn Gln Thr Leu Glu Asn Leu Arg Val Gly Ile Tyr Lys Glu
            435                 440                 445

Gly Gly Arg Gln Ile Gly Gln Phe Ser Ser Lys Asp Asn Asp Tyr Asn
            450                 455                 460

Pro Pro Gly Tyr Ser Thr Leu Pro Thr Val Lys Ala Asp Glu Asn Gly
465                 470                 475                 480

Asn Val Thr Ile Lys Val Asn Ala Lys Val Leu Glu Ser Met Glu Gly
                485                 490                 495

Ser Lys Ile Arg Leu Lys Leu Gly Asp Lys Thr Leu Ile Thr Thr Asp
                500                 505                 510

Phe Lys

<210> SEQ ID NO 47
<211> LENGTH: 511
<212> TYPE: PRT
<213> ORGANISM: Staphylococcus sp

<400> SEQUENCE: 47

Met Ser Asn Ile Ala Phe Tyr Val Val Ser Asp Val His Gly Tyr Ile
1               5                   10                  15

Phe Pro Thr Asp Phe Thr Ser Arg Asn Gln Tyr Gln Pro Met Gly Leu
                20                  25                  30

Leu Leu Ala Asn His Val Ile Glu Gln Asp Arg Arg Gln Tyr Asp Gln
            35                  40                  45

Ser Phe Lys Ile Asp Asn Gly Asp Phe Leu Gln Gly Ser Pro Phe Cys
    50                  55                  60

Asn Tyr Leu Ile Ala His Ser Gly Ser Ser Gln Pro Leu Val Asp Phe
65                  70                  75                  80

Tyr Asn Arg Met Ala Phe Asp Phe Gly Thr Leu Gly Asn His Glu Phe
                85                  90                  95

Asn Tyr Gly Leu Pro Tyr Leu Lys Asp Thr Leu Arg Arg Leu Asn Tyr
            100                 105                 110

Pro Val Leu Cys Ala Asn Ile Tyr Glu Asn Asp Ser Thr Leu Thr Asp
            115                 120                 125

Asn Gly Val Lys Tyr Phe Gln Val Gly Asp Gln Thr Val Gly Val Ile
    130                 135                 140

Gly Leu Thr Thr Gln Phe Ile Pro His Trp Glu Gln Pro Glu His Ile
145                 150                 155                 160

Gln Ser Leu Thr Phe His Ser Ala Phe Glu Ile Leu Gln Gln Tyr Leu
                165                 170                 175

Pro Glu Met Lys Arg His Ala Asp Ile Ile Val Val Cys Tyr His Gly
            180                 185                 190

Gly Phe Glu Lys Asp Leu Glu Ser Gly Thr Pro Thr Glu Val Leu Thr
            195                 200                 205

Gly Glu Asn Glu Gly Tyr Ala Met Leu Glu Ala Phe Ser Lys Asp Ile
    210                 215                 220

Asp Ile Phe Ile Thr Gly His Gln His Arg Gln Ile Ala Glu Arg Phe
225                 230                 235                 240
```

```
Lys Gln Thr Ala Val Ile Gln Pro Gly Thr Arg Gly Thr Thr Val Gly
                245                 250                 255

Arg Val Val Leu Ser Thr Asp Glu Tyr Glu Asn Leu Ser Val Glu Ser
            260                 265                 270

Cys Glu Leu Leu Pro Val Ile Asp Asp Ser Thr Phe Thr Ile Asp Glu
        275                 280                 285

Asp Asp Gln His Leu Arg Lys Gln Leu Glu Asp Trp Leu Asp Tyr Glu
290                 295                 300

Ile Thr Thr Leu Pro Tyr Asp Met Thr Ile Asn His Ala Phe Glu Ala
305                 310                 315                 320

Arg Val Ala Pro His Pro Phe Thr Asn Phe Met Asn Tyr Ala Leu Leu
                325                 330                 335

Glu Lys Ser Asp Ala Asp Val Ala Cys Thr Ala Leu Phe Asp Ser Ala
            340                 345                 350

Ser Gly Phe Lys Gln Val Val Thr Met Arg Asp Val Ile Asn Asn Tyr
        355                 360                 365

Pro Phe Pro Asn Thr Phe Lys Val Leu Ala Val Ser Gly Ala Lys Leu
370                 375                 380

Lys Glu Ala Ile Glu Arg Ser Ala Glu Tyr Phe Asp Val Lys Asn Asp
385                 390                 395                 400

Glu Val Ser Val Ser Ala Asp Phe Leu Glu Pro Lys Pro Gln His Phe
                405                 410                 415

Asn Tyr Asp Ile Tyr Gly Gly Val Ser Tyr Thr Ile His Val Gly Arg
            420                 425                 430

Pro Lys Gly Gln Arg Val Ser Asn Met Met Ile Gln Gly His Ala Val
        435                 440                 445

Asp Leu Lys Gln Thr Tyr Thr Ile Cys Val Asn Asn Tyr Arg Ala Val
450                 455                 460

Gly Gly Gly Gln Tyr Asp Met Tyr Ile Asp Ala Pro Val Val Lys Asp
465                 470                 475                 480

Ile Gln Val Glu Gly Ala Gln Leu Leu Ile Asp Phe Leu Ser Asn Asn
                485                 490                 495

Asn Leu Met Arg Ile Pro Gln Val Val Asp Phe Lys Val Glu Lys
            500                 505                 510

<210> SEQ ID NO 48
<211> LENGTH: 324
<212> TYPE: PRT
<213> ORGANISM: Staphylococcus sp

<400> SEQUENCE: 48

Met Lys Arg Leu Ser Ile Ile Val Ile Ile Gly Ile Phe Ile Ile Thr
1               5                   10                  15

Gly Cys Asp Trp Gln Arg Thr Ser Lys Glu Arg Ser Lys Asn Ala Gln
            20                  25                  30

Asn Gln Gln Val Ile Lys Ile Gly Tyr Leu Pro Ile Thr His Ser Ala
        35                  40                  45

Asn Leu Met Met Thr Lys Lys Leu Leu Ser Gln Tyr Asn His Pro Lys
    50                  55                  60

Tyr Lys Leu Glu Leu Val Lys Phe Asn Asn Trp Pro Asp Leu Met Asp
65                  70                  75                  80

Ala Leu Asn Ser Gly Arg Ile Asp Gly Ala Ser Thr Leu Ile Glu Leu
                85                  90                  95

Ala Met Lys Ser Lys Gln Lys Gly Ser Asn Leu Lys Ala Val Ala Leu
```

```
                100                 105                 110
Gly His His Glu Gly Asn Val Ile Met Gly Gln Lys Gly Met His Leu
            115                 120                 125
Asn Glu Phe Asn Asn Asn Gly Asp Asp Tyr His Phe Gly Ile Pro His
130                 135                 140
Arg Tyr Ser Thr His Tyr Leu Leu Glu Glu Leu Arg Lys Gln Leu
145                 150                 155                 160
Lys Ile Lys Pro Gly His Phe Ser Tyr His Glu Met Ser Pro Ala Glu
                165                 170                 175
Met Pro Ala Ala Leu Ser Glu His Arg Ile Thr Gly Tyr Ser Val Ala
            180                 185                 190
Glu Pro Phe Gly Ala Leu Gly Glu Lys Leu Gly Lys Gly Lys Thr Leu
        195                 200                 205
Lys His Gly Asp Asp Val Ile Pro Asp Ala Tyr Cys Cys Val Leu Val
    210                 215                 220
Leu Arg Gly Glu Leu Leu Asp Gln His Lys Asp Val Ala Gln Ala Phe
225                 230                 235                 240
Val Gln Asp Tyr Lys Lys Ser Gly Phe Lys Met Asn Asp Arg Lys Gln
                245                 250                 255
Ser Val Asp Ile Met Thr His His Phe Lys Gln Ser Arg Asp Val Leu
            260                 265                 270
Thr Gln Ser Ala Ala Trp Thr Ser Tyr Gly Asp Leu Thr Ile Lys Pro
        275                 280                 285
Ser Gly Tyr Gln Glu Ile Thr Thr Leu Val Lys Gln His His Leu Phe
    290                 295                 300
Asn Pro Pro Ala Tyr Asp Asp Phe Val Glu Pro Ser Leu Tyr Lys Glu
305                 310                 315                 320
Ala Ser Arg Ser

<210> SEQ ID NO 49
<211> LENGTH: 591
<212> TYPE: PRT
<213> ORGANISM: Staphylococcus sp

<400> SEQUENCE: 49

Met Lys Lys Ile Ile Ser Ile Ala Ile Ile Val Leu Ala Leu Val Leu
1               5                   10                  15
Ser Gly Cys Gly Val Pro Thr Lys Ser Glu Val Ala Gln Lys Ser Ser
                20                  25                  30
Lys Val Glu Val Lys Gly Glu Arg Pro Thr Ile His Phe Leu Gly Gln
            35                  40                  45
Ala Ser Tyr Glu Asn Asp Met Asn Ile Val Lys Asp Gln Leu Glu Asn
50                  55                  60
Ala Gly Phe Asn Val Lys Met Asn Ile Gln Pro Asp Tyr Gly Ser Tyr
65                  70                  75                  80
Arg Thr Gln Arg Gln Ala Gly Asn Tyr Asp Ile Gln Ile Asp Asp Trp
                85                  90                  95
Met Thr Val Phe Gly Asp Pro Asn Tyr Ala Met Thr Ala Leu Phe Ser
            100                 105                 110
Ser Thr Gly Ser Asn Ser Leu Leu Lys Asp Lys His Val Asp Gln Leu
        115                 120                 125
Leu Asn Lys Ala Ser Thr Gln Asn Glu Ala Asp Val Lys Gln Thr Tyr
    130                 135                 140
Lys Gln Ile Glu Asp Glu Val Val Phe Asp Lys Gly Tyr Met Ala Pro
```

-continued

```
            145                 150                 155                 160
Leu Tyr Gly Ser Lys Lys Asn Leu Val Tyr Asp Asn Lys Val Leu Asp
                165                 170                 175
Lys Asn Ser Val Gly Leu Pro Asn Ser Arg Ala Leu Ile Trp Gln Gln
                180                 185                 190
Phe Asp Tyr Asn Asn Ser Arg Glu Arg Asp Thr Arg Pro Leu Val Met
                195                 200                 205
Thr Gln Gln Asp Gly Glu Ile Pro Thr Leu Asp Pro Ile Arg Ser Ile
    210                 215                 220
Ala Pro Ser Val Tyr Ser Ile Asn Met Asn Met Tyr Thr Arg Leu Leu
225                 230                 235                 240
Leu Leu Asp Glu Asn Asp His Leu Thr Thr Lys Gly Ser Leu Ser His
                245                 250                 255
Asp Tyr Ala Val Asn Lys Asp Asn Lys Ala Phe Tyr Phe Leu Leu Arg
                260                 265                 270
Asp Asp Asp Tyr Phe Ala Lys Val Val Asn Gly Gln Ala Arg Asn Thr
            275                 280                 285
Gly Glu Arg Val Ser Ala Glu Asp Val Lys Phe Ser Leu Asp Arg Ala
    290                 295                 300
Arg Asp Lys Lys Ser Val Pro Asn Asn Asn Thr Tyr Asn Met His Lys
305                 310                 315                 320
His Ile Asn Asp Ile Lys Ile Leu Lys Asp Glu Asp Ile Asp Gln Leu
                325                 330                 335
Arg Lys Glu Lys Asp Lys Asp Lys Ser Ile Tyr Asp Lys Leu Leu
            340                 345                 350
Lys Ala Tyr Asn Val Lys Ser Leu Thr Thr Asp Gly Gln Lys Val Asn
        355                 360                 365
Asn Lys Asp Gly Ile Tyr Gln Ile Val Lys Ile Thr Thr Asp Gln Ser
    370                 375                 380
Met Pro Arg Glu Val Asn Tyr Leu Thr His Ser Ser Ala Gly Ile Leu
385                 390                 395                 400
Ser Lys Lys Phe Val Asn Gln Val Asn Gln Glu Tyr Pro Lys Gly Tyr
                405                 410                 415
Gly Asp Ser Ser Thr Ile Pro Ala Asn Ser Asp Gly Lys Asn Ala Leu
            420                 425                 430
Tyr Ala Ser Gly Ala Tyr Ile Met Thr Gln Lys Asn Ala Tyr Gln Ala
        435                 440                 445
Thr Phe Gln Arg Asn Pro Gly Phe Asn Glu Thr Glu Lys Gly Ser Tyr
    450                 455                 460
Gly Pro Ala Lys Ile Lys Asn Ile Thr Leu Lys Phe Asn Gly Asp Pro
465                 470                 475                 480
Asn Asn Ala Leu Ser Glu Leu Arg Asn His Ser Ile Asp Met Leu Ala
                485                 490                 495
Asp Val Asn Gln Lys His Phe Asp Leu Ile Lys Ser Asp Lys Asn Leu
                500                 505                 510
Ser Ile Ile Arg Lys Asn Gly Arg Lys Ser Val Phe Leu Met Leu Asn
            515                 520                 525
Ile Lys Lys Gly Ile Phe Lys Thr His Pro Asn Leu Arg Gln Ala Val
        530                 535                 540
Val Asn Ala Ile Asp Gln Asp Gln Phe Ile Lys Phe Tyr Arg Gly Asp
545                 550                 555                 560
Lys Phe Lys Ile Ala Ser Pro Ile Thr Pro Leu Val Asp Thr Gly Asn
                565                 570                 575
```

Glu Gln Arg Gln Asp Leu Glu Lys Val Glu Lys Ala Ile Asn Gln
            580                 585                 590

<210> SEQ ID NO 50
<211> LENGTH: 668
<212> TYPE: PRT
<213> ORGANISM: Staphylococcus sp

<400> SEQUENCE: 50

Met Val Ile Asn Leu Asn Asp Lys Gln Thr Lys Thr Ser Lys Glu Gly
1               5                   10                  15

Leu Ile Ser Val Ser His Pro Leu Ala Ala Lys Ile Gly Lys Asp Val
            20                  25                  30

Leu Asp Gln Gly Gly Asn Ala Met Asp Ala Val Ile Ala Ile Gln Leu
        35                  40                  45

Ala Leu Asn Val Val Glu Pro Phe Ala Ser Gly Ile Gly Gly Gly Gly
    50                  55                  60

Tyr Leu Leu Tyr Tyr Glu Gln Ser Thr Gly Ser Ile Thr Ala Phe Asp
65                  70                  75                  80

Ala Arg Glu Thr Ala Pro Glu His Val Asp Lys Gln Phe Tyr Leu Asp
                85                  90                  95

Asp Ser Gly Glu Tyr Lys Ser Phe Phe Asp Met Thr Thr His Gly Lys
            100                 105                 110

Thr Val Ala Val Pro Ala Ile Pro Lys Leu Phe Asp Tyr Ile His Lys
        115                 120                 125

Arg Tyr Ala Lys Leu Ser Leu Glu Asp Leu Ile Asn Pro Ala Ile Glu
130                 135                 140

Leu Ala Ile Glu Gly His Ala Ala Asn Trp Ala Thr Glu Lys Tyr Ser
145                 150                 155                 160

Arg Gln Gln His Ala Arg Leu Thr Lys Tyr His Glu Thr Ala Gln Val
                165                 170                 175

Phe Thr His Glu Asn Gln Tyr Trp Arg Glu Gly Asp Trp Ile Val Gln
            180                 185                 190

Pro Glu Leu Gly Lys Thr Phe Gln Ile Leu Arg Glu Gln Gly Phe Asn
        195                 200                 205

Ala Phe Tyr Lys Gly Asp Ile Ala Lys Gln Leu Val Asn Val Val Lys
    210                 215                 220

Ala Cys Gly Gly Thr Ile Thr Leu Glu Asp Leu Ala Lys Tyr Asp Ile
225                 230                 235                 240

Gln Leu Lys Ala Pro Ile Ser Ala Thr Phe Lys Asp Tyr Asp Ile Tyr
                245                 250                 255

Ser Met Gly Pro Ser Ser Gly Gly Ile Thr Val Ile Gln Ile Leu
            260                 265                 270

Lys Leu Leu Glu His Val Asp Leu Pro Ser Met Gly Pro Arg Ser Val
        275                 280                 285

Asp Tyr Leu His His Leu Ile Gln Ala Met His Leu Ala Tyr Ser Asp
    290                 295                 300

Arg Ala Gln Tyr Leu Ala Asp Asp Asn Phe His Glu Val Pro Val Gln
305                 310                 315                 320

Ser Leu Ile Asp Asp Asp Tyr Leu Lys Ala Arg Ser Thr Leu Ile Asp
                325                 330                 335

Ser Asn Lys Ala Asn Ile Asp Ile Glu His Gly Val Val Ser Asp Cys
            340                 345                 350

Ile Ser His Thr Asp Val Glu Glu Asn His Thr Glu Thr Thr His Phe

```
            355                 360                 365
Cys Val Ile Asp Lys Glu Gly Asn Ile Ala Ser Phe Thr Thr Ser Ile
370                 375                 380

Gly Met Ile Tyr Gly Ser Gly Ile Thr Ile Pro Gly Tyr Gly Val Leu
385                 390                 395                 400

Leu Asn Thr Thr Met Asp Gly Phe Asp Val Asp Gly Gly Ile Asn
                    405                 410                 415

Glu Ile Ala Pro Tyr Lys Arg Pro Leu Ser Asn Met Ala Pro Thr Ile
            420                 425                 430

Val Met Tyr His Gly Lys Pro Ile Leu Thr Val Gly Ala Pro Gly Ala
                435                 440                 445

Ile Ser Ile Ile Ala Ser Val Ala Gln Thr Leu Ile Asn Val Leu Val
450                 455                 460

Phe Gly Met Asp Ile Gln Gln Ala Ile Asp Glu Pro Arg Ile Tyr Ser
465                 470                 475                 480

Ser His Pro Asn Arg Ile Glu Trp Glu Pro Gln Phe Ser Gln Ser Thr
                    485                 490                 495

Ile Leu Ala Leu Ile Ala His Gly His Ala Met Glu His Lys Pro Asp
            500                 505                 510

Ala Tyr Ile Gly Asp Val His Gly Leu Gln Val Asp Pro Thr Thr Tyr
                515                 520                 525

Glu Ala Ser Gly Gly Ser Asp Asp Thr Arg Glu Gly Thr Val Met Gly
530                 535                 540

Gly Glu Val Leu Val Ile Arg Lys Gln Pro Leu Pro Tyr Arg Gln Met
545                 550                 555                 560

Tyr Asp Ser Asp Gly Phe Arg Leu Tyr Phe Asn Asp Val Gln Leu Pro
                    565                 570                 575

Leu Leu Ala Asp Gln Val Arg Trp Met His Asp Lys Tyr Trp Val Asp
            580                 585                 590

Glu Ser Val Val Arg Ile Ile Phe Pro Glu Val Ser Ala His Ile Glu
                595                 600                 605

Asp Leu Arg Ser Tyr Glu Asn Ala Gly Glu Asn Tyr Ile Asp Ile Ala
610                 615                 620

Trp Leu Ala Arg Lys Tyr Ala Tyr Gln Val Thr Leu Lys Asp Asp Gly
625                 630                 635                 640

Leu Tyr Leu Thr Asp Asp Thr Tyr Thr Ser Val Lys Arg Asn Thr Asn
                    645                 650                 655

Ala Tyr Tyr Arg Tyr Asp Arg Asp Ser Ile Thr Arg
            660                 665

<210> SEQ ID NO 51
<211> LENGTH: 322
<212> TYPE: PRT
<213> ORGANISM: Staphylococcus sp

<400> SEQUENCE: 51

Met Lys Ser Lys Ile Tyr Ile Leu Leu Leu Phe Leu Ile Phe Leu Ser
1               5                   10                  15

Ala Cys Ala Asn Thr Arg His Ser Glu Ser Asp Lys Asn Val Leu Thr
                20                  25                  30

Val Tyr Ser Pro Tyr Gln Ser Asn Leu Ile Arg Pro Ile Leu Asn Glu
            35                  40                  45

Phe Glu Lys Gln Glu His Val Lys Ile Glu Ile Lys His Gly Ser Thr
        50                  55                  60
```

```
Gln Val Leu Leu Ser Asn Leu His Asn Glu Asp Phe Ser Glu Arg Gly
 65                  70                  75                  80

Asp Val Phe Met Gly Gly Val Leu Ser Glu Thr Ile Asp His Pro Glu
                 85                  90                  95

Asp Phe Val Pro Tyr Gln Asp Thr Ser Val Thr Gln Gln Leu Glu Asp
            100                 105                 110

Tyr Arg Ser Asn Asn Lys Tyr Val Thr Ser Phe Leu Leu Met Pro Thr
        115                 120                 125

Val Ile Val Val Asn Ser Asp Leu Gln Gly Asp Ile Lys Ile Arg Gly
    130                 135                 140

Tyr Gln Asp Leu Leu Gln Pro Ile Leu Lys Gly Lys Ile Ala Tyr Ser
145                 150                 155                 160

Asn Pro Asn Thr Thr Thr Gly Tyr Gln His Met Arg Ala Ile Tyr
                165                 170                 175

Ser Met His His Arg Val Ser Asp Val His Gln Phe Gln Asn His Ala
                180                 185                 190

Met Gln Leu Ser Lys Thr Ser Lys Val Ile Glu Asp Val Ala Lys Gly
            195                 200                 205

Lys Tyr Tyr Ala Gly Leu Ser Tyr Glu Gln Asp Ala Arg Thr Trp Lys
        210                 215                 220

Asn Lys Gly Tyr Pro Val Ser Ile Val Tyr Pro Ile Glu Gly Thr Met
225                 230                 235                 240

Leu Asn Val Asp Gly Ile Ala Leu Val Lys Asn Ala His Pro His Pro
                245                 250                 255

Lys Arg Lys Lys Leu Val Gln Tyr Leu Thr Ser Arg Ser Val Gln Gln
            260                 265                 270

Arg Leu Val Ala Glu Phe Asp Ala Lys Ser Ile Arg Lys Asp Val Ser
        275                 280                 285

Glu Gln Ser Asp Gln Ser Ile Glu Asn Leu Lys Asn Ile Pro Leu Ile
    290                 295                 300

Pro Lys Ser Lys Leu Pro Asp Ile Pro His His Lys Phe Leu Glu Met
305                 310                 315                 320

Ile Gln

<210> SEQ ID NO 52
<211> LENGTH: 470
<212> TYPE: PRT
<213> ORGANISM: Staphylococcus sp

<400> SEQUENCE: 52

Met His Ser Ser Gly Lys Asp Leu Asn Ile Ser Leu Pro Leu Lys Thr
  1               5                  10                  15

Lys Ser Ile Ala Pro Tyr Glu Thr Asp Val Pro Val Lys Ile Gly Ala
             20                  25                  30

Ala Glu Ser Leu Phe Lys Thr Asn Asp Gln Gly Lys Ile Glu Lys Ala
         35                  40                  45

Leu Val Lys Ser Tyr His Gln Pro Asn Asp Thr Thr Leu Asp Ile Glu
 50                  55                  60

Leu Lys Asp Asn Ile Lys Phe Gln Asn Gly Gln Lys Leu Thr Ala Glu
 65                  70                  75                  80

Lys Val Lys Ser Ser Leu Glu Asn Ser Met Lys Lys Ser Asp Leu Val
             85                  90                  95

Lys Tyr Ser Leu Pro Ile Ser Ser Ile Thr Ala Lys Gly Gln Lys Leu
            100                 105                 110
```

```
Thr Ile Lys Thr Asn Ser Ala Tyr Pro Glu Leu Val Ser Glu Leu Ala
            115                 120                 125

Asn Pro Phe Met Ala Ile Tyr Asp Thr Asp Ala Lys Ser Asp Val Asn
130                 135                 140

Gln Thr Pro Val Gly Thr Gly Pro Tyr Gln Ile Lys Asp Tyr Lys Gln
145                 150                 155                 160

Ser Arg Lys Ile Ser Leu Ser Asn Phe Lys Asp Tyr Trp Gln Gly Lys
                165                 170                 175

Pro Lys Leu Asp His Ile Thr Val Thr Tyr Gln Glu Asp Gly Asn Asn
            180                 185                 190

Arg Val Arg Asn Leu Glu Ser Gln Lys Asp Asp Leu Ile Thr Asp Val
            195                 200                 205

Pro Val Asn Lys Val Gln Asp Ile Glu Asn Asn Gln Asn Leu Lys Val
            210                 215                 220

Ser Lys Glu Ser Gly Phe Arg Thr Ser Leu Leu Met Tyr Asn His Thr
225                 230                 235                 240

Asn Lys Lys Met Thr Lys Ser Val Arg Glu Ala Leu Asp His Ile Ile
                245                 250                 255

Asp Arg Gln Gly Ile Ala Asp His Ile Tyr Gln Gly Tyr Ala Lys Pro
            260                 265                 270

Ala Thr Ser Pro Phe Asn Asp Lys Ile Pro Tyr Ile Lys Glu Pro Lys
            275                 280                 285

Leu Thr Lys Gln Asn Ile Glu Gln Ala Lys Met Leu Leu Ala Lys Asp
            290                 295                 300

Gly Tyr Thr Lys Glu His Pro Leu Lys Ile Lys Leu Ile Thr Tyr Asp
305                 310                 315                 320

Gly Arg Pro Glu Leu Ser Lys Ile Ala Gln Val Leu Gln Ser Asp Ala
                325                 330                 335

Lys Lys Ala Asn Ile Glu Ile Asp Ile Lys Ser Val Asp Asp Ile Glu
            340                 345                 350

Gly Tyr Leu Lys Asp Arg Ser Ala Trp Asp Ala Thr Met Tyr Ser Phe
            355                 360                 365

Gly Thr Ile Pro Arg Gly Asp Thr Gly Tyr Phe Phe Asn Gln Ala Tyr
            370                 375                 380

Lys Lys Asp Gly Ala Ile Asn Lys Gly Asp Tyr Asn Asn Ser Asn Val
385                 390                 395                 400

Asp Asp Leu Ile Asn Gln Leu Asn His Thr Val Asp Val Lys Glu Arg
                405                 410                 415

His Asn Ile Ser Asn Asp Ile Ile Lys Leu Ser Ser Arg Asp Val Pro
            420                 425                 430

Asn Ser Tyr Ile Ala Tyr Asn Asp Gln Ile Val Ala Ala Asn Ser Lys
            435                 440                 445

Val Lys Asn Tyr Lys Val Thr Pro Glu Gly Ile Tyr Leu Ile Asp Tyr
450                 455                 460

Arg Thr Thr Ile Glu Arg
465                 470

<210> SEQ ID NO 53
<211> LENGTH: 316
<212> TYPE: PRT
<213> ORGANISM: Staphylococcus sp

<400> SEQUENCE: 53

Met Lys Lys Leu Thr Ala Ala Ile Ala Thr Met Gly Phe Ala Thr
1               5                   10                  15
```

```
Phe Thr Met Ala His Gln Ala Asp Ala Ala Glu Thr Thr Asn Thr Gln
            20                  25                  30

Gln Ala His Thr Gln Met Ser Thr Gln Ser Gln Asp Val Ser Tyr Gly
        35                  40                  45

Thr Tyr Tyr Thr Ile Asp Ser Asn Gly Asp Tyr His His Thr Pro Asp
 50                  55                  60

Gly Asn Trp Asn Gln Ala Met Phe Asp Asn Lys Glu Tyr Ser Tyr Thr
 65                  70                  75                  80

Phe Val Asp Ala Gln Gly His Thr His Tyr Phe Tyr Asn Cys Tyr Pro
                85                  90                  95

Lys Asn Ala Asn Ala Asn Gly Ser Gly Gln Thr Tyr Val Asn Pro Ala
            100                 105                 110

Thr Ala Gly Asp Asn Asn Asp Tyr Thr Ala Ser Gln Ser Gln Gln His
        115                 120                 125

Ile Asn Gln Tyr Gly Tyr Gln Ser Asn Val Gly Pro Asp Ala Ser Tyr
130                 135                 140

Tyr Ser His Ser Asn Asn Asn Gln Ala Tyr Asn Ser His Asp Gly Asn
145                 150                 155                 160

Gly Lys Val Asn Tyr Pro Asn Gly Thr Ser Asn Gln Asn Gly Gly Ser
                165                 170                 175

Ala Ser Lys Ala Thr Ala Ser Gly His Ala Lys Asp Ala Ser Trp Leu
            180                 185                 190

Thr Ser Arg Lys Gln Leu Gln Pro Tyr Gly Gln Tyr His Gly Gly Gly
        195                 200                 205

Ala His Tyr Gly Val Asp Tyr Ala Met Pro Glu Asn Ser Pro Val Tyr
210                 215                 220

Ser Leu Thr Asp Gly Thr Val Val Gln Ala Gly Trp Ser Asn Tyr Gly
225                 230                 235                 240

Gly Gly Asn Gln Val Thr Ile Lys Glu Ala Asn Ser Asn Asn Tyr Gln
                245                 250                 255

Trp Tyr Met His Asn Asn Arg Leu Thr Val Ser Ala Gly Asp Lys Val
            260                 265                 270

Lys Ala Gly Asp Gln Ile Ala Tyr Ser Gly Ser Thr Gly Asn Ser Thr
        275                 280                 285

Ala Pro His Val His Phe Gln Arg Met Ser Gly Gly Ile Gly Asn Gln
290                 295                 300

Tyr Ala Val Asp Pro Thr Ser Tyr Leu Gln Ser Arg
305                 310                 315
```

<210> SEQ ID NO 54
<211> LENGTH: 507
<212> TYPE: PRT
<213> ORGANISM: Staphylococcus sp

<400> SEQUENCE: 54

```
Met Ser Lys Lys Leu Lys Ile Ile Pro Ile Ile Val Leu Leu
 1               5                  10                  15

Leu Ile Gly Gly Ile Ala Trp Gly Val Tyr Ala Phe Phe Ala Asn Thr
            20                  25                  30

Pro Lys Asn Thr Tyr Leu Lys Ser Glu Gln Gln Thr Ala Lys Met Tyr
        35                  40                  45

Lys Asp Tyr Phe Asn Asp Arg Phe Glu Asn Glu Val Lys Phe Gln Glu
 50                  55                  60

Lys Met Lys Asp Asn Ser Phe Leu Ser Ser Leu Glu Leu Ser Ala Asp
```

```
            65                  70                  75                  80
Ala Ser Asp Glu Ile Val Lys Gly Leu Gly Ile Pro Lys Ser Val Val
                        85                  90                  95
Asn Ala Ser Lys Ile Lys Met Ser Tyr Gly His Asp Pro Lys Lys Glu
                100                 105                 110
Lys Ser Met Ile Asn Leu Glu Pro Thr Ile Ala Asp Ser Ala Leu Gly
                115                 120                 125
Lys Phe Gln Leu Ala Ala Asp Lys Asp Lys His Tyr Phe Glu Ser Pro
            130                 135                 140
Leu Phe Lys Gly Lys Tyr Ser Val Asn Asn Ser Asp Leu Leu Ser Thr
145                 150                 155                 160
Tyr Ser Lys Leu Thr Gly Glu Asp Glu Glu Thr Ala Lys Glu Asn Gly
                    165                 170                 175
Ile Thr Asn Gln Gln Leu Asn Leu Asn Thr Leu Phe Asn Asn Ala Gln
                180                 185                 190
Ala Gln Gln Ser Asp Tyr Ser Lys Ile Ala Glu Lys Tyr Ser Glu Leu
                195                 200                 205
Ile Val Asp Lys Leu Asp Asp Asn Phe Asp Lys Gly Lys Lys Glu
            210                 215                 220
Glu Ile Lys Val Asn Gly Glu Lys Tyr Lys Val Arg Pro Val Thr Leu
225                 230                 235                 240
Thr Leu Ser Arg Ala Asp Thr Lys Lys Ile Thr Leu Ala Val Leu Glu
                    245                 250                 255
Glu Ala Lys Lys Asp Lys Asp Leu Lys Lys Leu Met Glu Glu Gln Gly
                260                 265                 270
Ala Thr Lys Asp Phe Glu Lys Asp Ile Lys Ala Ile Asp Asp Val
                275                 280                 285
Lys Glu Thr Lys Lys Asp Glu Phe Ala Lys Ile Gln Ser Lys Ile Tyr
            290                 295                 300
Thr Glu Lys His Thr Ile Val Lys Arg Glu Ile Thr Ile Thr Asp Lys
305                 310                 315                 320
Glu Asn Asn Lys Thr Lys Ile Lys Gly Thr Asn Thr Leu Glu Asp Asp
                        325                 330                 335
Lys Leu Lys Leu Asp Tyr Ala Leu Asp Phe Asp Gln Asp Lys Tyr Thr
                340                 345                 350
Tyr Ala Glu Ala Lys Tyr Thr Ile Lys Gly Val Ser Ser Lys Glu Lys
            355                 360                 365
Asp Asn Lys Tyr Asn Asp Lys Tyr Glu Phe Gly Lys Lys Thr Glu Tyr
        370                 375                 380
Asp Glu Ser Lys Ile Lys Leu Asp Asn Gln Glu Lys Val Asp Gly Thr
385                 390                 395                 400
Lys Arg Gln Asp Lys Gly Lys Ile Thr Val Ala Leu Asp Lys Tyr Ser
                    405                 410                 415
Asp Glu Asn Glu Phe Thr Phe Glu Asn Asn Ile Asp Ser Asp Val Lys
                420                 425                 430
Asn Asn Thr Gln Lys Ser Thr Leu Asn Ile Gly Ile Lys Tyr Ala Glu
            435                 440                 445
Glu Pro Ile Asn Phe Ile Leu Lys Ser Ser Thr Lys Leu Lys Ala Asp
        450                 455                 460
Ile Asp Phe Asp Asp Ser Gly Ala Lys Asp Phe Asn Ser Leu Ser Ser
465                 470                 475                 480
Lys Asp Arg Glu Lys Leu Glu Lys Glu Ile Glu Lys Asn Gly Gly Lys
                    485                 490                 495
```

```
Met Phe Glu Ser Ile Leu Lys Lys Ala Ser Lys
            500                 505
```

```
<210> SEQ ID NO 55
<211> LENGTH: 297
<212> TYPE: PRT
<213> ORGANISM: Staphylococcus sp

<400> SEQUENCE: 55

Met Lys Lys Thr Ile Leu Leu Thr Met Thr Thr Leu Thr Leu Phe Ser
1               5                   10                  15

Met Ser Pro Asn Ser Ala Gln Ala Tyr Thr Asn Asp Ser Lys Thr Leu
            20                  25                  30

Glu Glu Ala Lys Lys Ala His Pro Asn Ala Gln Phe Lys Val Asn Lys
        35                  40                  45

Asp Thr Gly Ala Tyr Thr Tyr Thr Tyr Asp Lys Asn Asn Thr Pro Asn
    50                  55                  60

Asn Asn His Gln Asn Gln Ser Arg Thr Asn Asp Asn His Gln His Ala
65                  70                  75                  80

Asn Gln Arg Asp Leu Asn Asn Asn Gln Tyr His Ser Ser Leu Ser Gly
                85                  90                  95

Gln Tyr Thr His Ile Asn Asp Ala Ile Asp Ser His Thr Pro Pro Gln
            100                 105                 110

Thr Ser Pro Ser Asn Pro Leu Thr Pro Ala Ile Pro Asn Val Glu Asp
        115                 120                 125

Asn Asp Asp Glu Leu Asn Asn Ala Phe Ser Lys Asp Asn Lys Gly Leu
    130                 135                 140

Ile Thr Gly Ile Asp Leu Asp Glu Leu Tyr Asp Glu Leu Gln Ile Ala
145                 150                 155                 160

Glu Phe Asn Asp Lys Ala Lys Thr Ala Asp Gly Lys Pro Leu Ala Leu
                165                 170                 175

Gly Asn Gly Lys Ile Ile Asp Gln Pro Leu Ile Thr Ser Lys Asn Asn
            180                 185                 190

Leu Tyr Thr Ala Gly Gln Cys Thr Trp Tyr Val Phe Asp Lys Arg Ala
        195                 200                 205

Lys Asp Gly His Thr Ile Ser Thr Phe Trp Gly Asp Ala Lys Asn Trp
    210                 215                 220

Ala Gly Gln Ala Ser Ser Asn Gly Phe Lys Val Asp Arg His Pro Thr
225                 230                 235                 240

Arg Gly Ser Ile Leu Gln Thr Val Asn Gly Pro Phe Gly His Val Ala
                245                 250                 255

Tyr Val Glu Lys Val Asn Ile Asp Gly Ser Ile Leu Ile Ser Glu Met
            260                 265                 270

Asn Trp Ile Gly Glu Tyr Ile Val Ser Ser Arg Thr Ile Ser Ala Ser
        275                 280                 285

Glu Val Ser Ser Tyr Asn Tyr Ile His
    290                 295
```

```
<210> SEQ ID NO 56
<211> LENGTH: 124
<212> TYPE: PRT
<213> ORGANISM: Staphylococcus sp

<400> SEQUENCE: 56

Met Lys Arg Ile Leu Val Val Phe Leu Met Leu Ala Ile Ile Leu Ala
1               5                   10                  15
```

Gly Cys Ser Asn Lys Gly Glu Lys Tyr Gln Lys Asp Ile Asp Lys Val
                20                  25                  30

Tyr Lys Glu Gln Asn Gln Met Asn Lys Ile Ala Ser Lys Val Gln Asn
            35                  40                  45

Thr Ile Lys Thr Asp Ile Lys Gln Glu Asp Ser Asn Thr His Val Tyr
        50                  55                  60

Lys Asp Gly Lys Val Ile Val Ile Gly Ile Gln Leu Tyr Lys Asp Arg
65                  70                  75                  80

Glu Lys Met Tyr Tyr Phe Ala Tyr Gly Ile Lys Asp Gly Lys Ala Glu
                85                  90                  95

Ile Asn Arg Glu Ile Asp Pro Ile Lys Tyr Met Lys Asp His Lys Ala
            100                 105                 110

Asp Tyr Glu Asp Glu Asn Val Glu Val Glu Lys Asp
        115                 120

<210> SEQ ID NO 57
<211> LENGTH: 296
<212> TYPE: PRT
<213> ORGANISM: Staphylococcus sp

<400> SEQUENCE: 57

Met Asn Lys Ile Ser Lys Tyr Ile Ala Ile Ala Ser Leu Ser Val Ala
1               5                   10                  15

Val Thr Val Ser Ala Pro Gln Thr Thr Asn Ser Thr Ala Phe Ala Lys
                20                  25                  30

Ser Ser Ala Glu Val Gln Gln Thr Gln Gln Ala Ser Ile Pro Ala Ser
            35                  40                  45

Gln Lys Ala Asn Leu Gly Asn Gln Asn Leu Met Ala Val Ala Trp Tyr
        50                  55                  60

Gln Asn Ser Ala Glu Ala Lys Ala Leu Tyr Leu Gln Gly Tyr Asn Ser
65                  70                  75                  80

Ala Lys Thr Gln Leu Asp Lys Glu Ile Lys Asn Lys Gly Lys His
                85                  90                  95

Lys Leu Ala Ile Ala Leu Asp Leu Asp Glu Thr Val Leu Asp Asn Ser
            100                 105                 110

Pro Tyr Gln Gly Tyr Ala Ser Ile His Asn Lys Pro Phe Pro Glu Gly
        115                 120                 125

Trp His Glu Trp Val Gln Ala Ala Lys Ala Lys Pro Val Tyr Gly Ala
        130                 135                 140

Lys Glu Phe Leu Lys Tyr Ala Asp Lys Gly Val Asp Ile Tyr Tyr
145                 150                 155                 160

Ile Ser Asp Arg Asp Lys Glu Lys Asp Leu Lys Ala Thr Gln Lys Asn
                165                 170                 175

Leu Lys Gln Gln Gly Ile Pro Gln Ala Lys Lys Ser His Ile Leu Leu
            180                 185                 190

Lys Gly Lys Asp Lys Ser Lys Glu Ser Arg Arg Gln Met Val Gln
        195                 200                 205

Lys Asp His Lys Leu Val Met Leu Phe Gly Asp Asn Leu Leu Asp Phe
        210                 215                 220

Thr Asp Pro Lys Glu Ala Thr Ala Glu Ser Arg Glu Ala Leu Ile Glu
225                 230                 235                 240

Lys His Lys Asp Asp Phe Gly Lys Lys Tyr Ile Ile Phe Pro Asn Pro
                245                 250                 255

Met Tyr Gly Ser Trp Glu Ala Thr Ile Tyr Asn Asn Asn Tyr Lys Ala

```
                    260                 265                 270
Ser Asp Lys Ala Lys Asp Lys Leu Arg Lys Asn Ala Ile Lys Gln Phe
                275                 280                 285

Asp Pro Lys Thr Gly Glu Val Lys
            290                 295

<210> SEQ ID NO 58
<211> LENGTH: 690
<212> TYPE: PRT
<213> ORGANISM: Staphylococcus sp

<400> SEQUENCE: 58

Met Leu Arg Gly Gln Glu Glu Arg Lys Tyr Ser Ile Arg Lys Tyr Ser
1               5                   10                  15

Ile Gly Val Val Ser Val Leu Ala Ala Thr Met Phe Val Ser Ser
                20                  25                  30

His Glu Ala Gln Ala Ser Glu Lys Thr Ser Thr Asn Ala Ala Ala Gln
            35                  40                  45

Lys Glu Thr Leu Asn Gln Pro Gly Glu Gln Gly Asn Ala Ile Thr Ser
        50                  55                  60

His Gln Met Gln Ser Gly Lys Gln Leu Asp Asp Met His Lys Glu Asn
65                  70                  75                  80

Gly Lys Ser Gly Thr Val Thr Glu Gly Lys Asp Thr Leu Gln Ser Ser
                85                  90                  95

Lys His Gln Ser Thr Gln Asn Ser Lys Thr Ile Arg Thr Gln Asn Asp
            100                 105                 110

Asn Gln Val Lys Gln Asp Ser Glu Arg Gln Gly Ser Lys Gln Ser His
        115                 120                 125

Gln Asn Asn Ala Thr Asn Thr Glu Arg Gln Asn Asp Gln Val Gln
130                 135                 140

Asn Thr His His Ala Glu Arg Asn Gly Ser Gln Ser Thr Thr Ser Gln
145                 150                 155                 160

Ser Asn Asp Val Asp Lys Ser Gln Pro Ser Ile Pro Ala Gln Lys Val
                165                 170                 175

Ile Pro Asn His Asp Lys Ala Ala Pro Thr Ser Thr Thr Pro Pro Ser
            180                 185                 190

Asn Asp Lys Thr Ala Pro Lys Ser Thr Lys Ala Gln Asp Ala Thr Thr
        195                 200                 205

Asp Lys His Pro Asn Gln Gln Asp Thr His Gln Pro Ala His Gln Ile
    210                 215                 220

Ile Asp Ala Lys Gln Asp Asp Thr Val Arg Gln Ser Glu Gln Lys Pro
225                 230                 235                 240

Gln Val Gly Asp Leu Ser Lys His Ile Asp Gly Gln Asn Ser Pro Glu
                245                 250                 255

Lys Pro Thr Asp Lys Asn Thr Asp Asn Lys Gln Leu Ile Lys Asp Ala
            260                 265                 270

Leu Gln Ala Pro Lys Thr Arg Ser Thr Thr Asn Ala Ala Asp Ala
        275                 280                 285

Lys Lys Val Arg Pro Leu Lys Ala Asn Gln Val Gln Pro Leu Asn Lys
    290                 295                 300

Tyr Pro Val Val Phe Val His Gly Phe Leu Gly Leu Val Gly Asp Asn
305                 310                 315                 320

Ala Pro Ala Leu Tyr Pro Asn Tyr Trp Gly Gly Asn Lys Phe Lys Val
                325                 330                 335
```

Ile Glu Glu Leu Arg Lys Gln Gly Tyr Asn Val His Gln Ala Ser Val
            340                 345                 350

Ser Ala Phe Gly Ser Asn Tyr Asp Arg Ala Val Glu Leu Tyr Tyr Tyr
        355                 360                 365

Ile Lys Gly Gly Arg Val Asp Tyr Gly Ala Ala His Ala Ala Lys Tyr
    370                 375                 380

Gly His Glu Arg Tyr Gly Lys Thr Tyr Lys Gly Ile Met Pro Asn Trp
385                 390                 395                 400

Glu Pro Gly Lys Lys Val His Leu Val Gly His Ser Met Gly Gly Gln
            405                 410                 415

Thr Ile Arg Leu Met Glu Glu Phe Leu Arg Asn Gly Asn Lys Glu Glu
        420                 425                 430

Ile Ala Tyr His Lys Ala His Gly Gly Glu Ile Ser Pro Leu Phe Thr
    435                 440                 445

Gly Gly His Asn Asn Met Val Ala Ser Ile Thr Thr Leu Ala Thr Pro
450                 455                 460

His Asn Gly Ser Gln Ala Ala Asp Lys Phe Gly Asn Thr Glu Ala Val
465                 470                 475                 480

Arg Lys Ile Met Phe Ala Leu Asn Arg Phe Met Gly Asn Lys Tyr Ser
            485                 490                 495

Asn Ile Asp Leu Gly Leu Thr Gln Trp Gly Phe Lys Gln Leu Pro Asn
        500                 505                 510

Glu Ser Tyr Ile Asp Tyr Ile Lys Arg Val Ser Lys Ser Lys Ile Trp
    515                 520                 525

Thr Ser Asp Asp Asn Ala Ala Tyr Asp Leu Thr Leu Asp Gly Ser Ala
530                 535                 540

Lys Leu Asn Asn Met Thr Ser Met Asn Pro Asn Ile Thr Tyr Thr Thr
545                 550                 555                 560

Tyr Thr Gly Val Ser Ser His Thr Gly Pro Leu Gly Tyr Glu Asn Pro
            565                 570                 575

Asp Leu Gly Thr Phe Phe Leu Met Ala Thr Thr Ser Arg Ile Ile Gly
        580                 585                 590

His Asp Ala Arg Glu Glu Trp Arg Lys Asn Asp Gly Val Val Pro Val
    595                 600                 605

Ile Ser Ser Leu His Pro Ser Asn Gln Pro Phe Val Asn Val Thr Asn
610                 615                 620

Asp Glu Pro Ala Thr Arg Arg Gly Ile Trp Gln Val Lys Pro Ile Ile
625                 630                 635                 640

Gln Gly Trp Asp His Val Asp Phe Ile Gly Val Asp Phe Leu Asp Phe
            645                 650                 655

Lys Arg Lys Gly Ala Glu Leu Ala Asn Phe Tyr Thr Gly Ile Ile Asn
        660                 665                 670

Asp Leu Leu Arg Val Glu Ala Thr Glu Ser Lys Gly Thr Gln Leu Lys
    675                 680                 685

Ala Ser
    690

<210> SEQ ID NO 59
<211> LENGTH: 208
<212> TYPE: PRT
<213> ORGANISM: Staphylococcus sp

<400> SEQUENCE: 59

Met Lys Lys Arg Leu Leu Leu Ser Thr Phe Leu Ala Ser Thr Leu Ile
1               5                   10                  15

```
Leu Thr Gly Cys Ala Ser Asp Gln Ser Asp Asn Glu Asp His His Thr
            20                  25                  30

Ser Thr Gly Ile His Ala Pro Lys Ser Ala Lys Lys Leu Glu Thr Lys
            35                  40                  45

Asp Ile Phe Asn Ser Asp Lys Lys Asn Ser Asp Ile Ser Asp Ala Glu
50                  55                  60

Met Lys Gln Ala Ile Glu Lys Tyr Leu Ser Val Asn Ser Asp Ile Leu
65                  70                  75                  80

Asp Asn Lys Tyr Ile Met Gln His Lys Leu Asp Lys Gln Ile Asp Ser
                85                  90                  95

Gln Thr Lys Val Thr Glu Lys Gln Ala Glu Thr Leu Ser His Leu Ser
            100                 105                 110

Asn Leu Ala Val Lys Asn Asp Leu His Phe Lys Lys Phe Val Thr Glu
            115                 120                 125

Asn Asn Ile Pro Lys Glu Tyr Lys Lys Pro Val Glu Leu Met Met Asn
130                 135                 140

Tyr Phe Lys Ala Leu Asn Ser Thr Ile Ala Asn Val Asp Glu Asp Ile
145                 150                 155                 160

Glu Lys Leu Ser Tyr Gln Pro Gln Asn Lys Ile Asn Val Val Asp Val
                165                 170                 175

Pro Thr Lys Tyr Ala Gly Asp Val Asn Lys Lys Gln Gln Asp Lys Ile
            180                 185                 190

Lys Asp Phe Leu Lys Ser Lys Gly Ile Lys Ser Asp Val Ile Asp Lys
            195                 200                 205

<210> SEQ ID NO 60
<211> LENGTH: 261
<212> TYPE: PRT
<213> ORGANISM: Staphylococcus sp

<400> SEQUENCE: 60

Met Lys Ser Ile Lys Arg Ile Gly Leu Cys Ile Ser Leu Leu Ile Leu
1               5                   10                  15

Ile Ile Phe Val Thr Ser Cys Asp Gly Asp Asn Lys Ile Ile Gly Asp
            20                  25                  30

Ser Lys Glu Glu Gln Ile Lys Lys Ser Phe Ala Lys Thr Leu Asp Ile
            35                  40                  45

Tyr Pro Ile Lys Asn Leu Glu Asp Leu Tyr Asp Lys Glu Gly Tyr Arg
50                  55                  60

Asp Gly Glu Phe Lys Lys Asp Lys Gly Thr Trp Leu Ile Arg Ser
65                  70                  75                  80

Glu Met Lys Ile Gln Leu Lys Gly Glu Asn Leu Glu Ser Arg Gly Ala
                85                  90                  95

Val Leu Glu Ile Asn Arg Asn Thr Arg Thr Ala Lys Gly His Tyr Ile
            100                 105                 110

Val Arg Glu Val Val Glu Asp Ser Asp Gly Met Thr His Asn His Thr
            115                 120                 125

Lys Arg Tyr Pro Val Lys Met Glu Asn Asn Lys Met Ile Pro Leu Lys
130                 135                 140

Pro Ile Asp Asp Glu Lys Val Lys Lys Glu Ile Glu Glu Phe Asn Phe
145                 150                 155                 160

Phe Val Gln Tyr Gly Asn Phe Lys Glu Leu Glu Asn Tyr Lys Glu Asp
                165                 170                 175

Glu Val Ser Tyr Asn Pro Glu Val Pro Ile Tyr Ser Ala Lys Tyr Gln
```

```
                180                 185                 190
Leu Lys Asn Ser Asp Tyr Asn Val Glu Gln Leu Arg Lys Arg Tyr Asn
                195                 200                 205

Ile Pro Thr Gln Lys Ala Pro Lys Leu Leu Leu Lys Gly Ser Gly Asn
            210                 215                 220

Leu Lys Gly Ser Ser Val Gly Tyr Lys Asn Ile Glu Phe Thr Phe Ile
225                 230                 235                 240

Glu Asn Lys Glu Glu Asn Ile Tyr Phe Thr Asp Ser Ile Tyr Phe Asn
                245                 250                 255

Pro Ser Glu Asp Lys
            260

<210> SEQ ID NO 61
<211> LENGTH: 347
<212> TYPE: PRT
<213> ORGANISM: Staphylococcus sp

<400> SEQUENCE: 61

Met Asn Lys Asp Asn Lys Trp Thr Met Ile Thr Ala Leu Phe Ile Thr
1               5                   10                  15

Val Ile Ser Val Leu Leu Ala Phe His Leu Lys Gln His Tyr Asp Gln
            20                  25                  30

Ile Thr Asn Glu Asn His Ala Asn Lys Asp Lys Ile Asn Ile Lys Asn
        35                  40                  45

Lys Asn Val Arg Ile Tyr Gln Asn Leu Thr Tyr Asn Arg Val Phe Pro
50                  55                  60

Asn Ser Lys Leu Asp Ile Ile Thr Pro Val Asp Met Ser Ser Asn Ala
65                  70                  75                  80

Lys Leu Pro Val Ile Phe Trp Met His Gly Gly Gly Tyr Ile Ala Gly
                85                  90                  95

Asp Lys Gln Tyr Lys Asn Pro Leu Leu Ala Lys Ile Ala Glu Gln Gly
            100                 105                 110

Tyr Ile Val Val Asn Val Asn Tyr Ala Leu Ala Pro Gln Tyr Lys Tyr
        115                 120                 125

Pro Thr Pro Leu Ile Gln Met Asn Gln Ala Thr Gln Phe Ile Lys Glu
    130                 135                 140

Asn Lys Met Asn Leu Pro Ile Asp Phe Asn Gln Val Ile Ile Gly Gly
145                 150                 155                 160

Asp Ser Ala Gly Ala Gln Leu Ala Ser Gln Phe Thr Ala Ile Gln Thr
                165                 170                 175

Asn Asp Arg Leu Arg Glu Ala Met Lys Phe Asp Gln Ser Phe Lys Pro
            180                 185                 190

Ser Gln Ile Lys Gly Ala Ile Leu Phe Gly Gly Phe Tyr Asn Met Gln
        195                 200                 205

Thr Val Arg Glu Thr Glu Phe Pro Arg Ile Gln Leu Phe Met Lys Ser
    210                 215                 220

Tyr Thr Gly Glu Glu Asp Trp Glu Lys Ser Phe Lys Asn Ile Ser Gln
225                 230                 235                 240

Met Ser Thr Val Lys Gln Ser Thr Lys Asn Tyr Pro Pro Thr Phe Leu
                245                 250                 255

Ser Val Gly Asp Ser Asp Pro Phe Glu Ser Gln Asn Ile Glu Phe Ser
            260                 265                 270

Lys Lys Leu Gln Glu Leu Asn Val Pro Val Asp Thr Leu Phe Tyr Asp
        275                 280                 285
```

-continued

```
Gly Thr His His Leu His His Gln Tyr Gln Phe His Leu Asn Lys Pro
290                 295                 300
Glu Ser Ile Asp Asn Ile Lys Lys Val Leu Leu Phe Leu Ser Arg Asn
305                 310                 315                 320
Thr Ser Ser Ser Gly Ile Gln Thr Glu Glu Lys Pro Gln Ile Glu Asn
                325                 330                 335
Pro Ser Asn Glu Leu Pro Leu Asn Pro Leu Asn
            340                 345

<210> SEQ ID NO 62
<211> LENGTH: 265
<212> TYPE: PRT
<213> ORGANISM: Staphylococcus sp

<400> SEQUENCE: 62

Met Lys Lys Leu Ala Phe Ala Ile Thr Ala Thr Ser Gly Ala Ala Ala
1               5                   10                  15
Phe Leu Thr His His Asp Ala Gln Ala Ser Thr Gln His Thr Val Gln
                20                  25                  30
Ser Gly Glu Ser Leu Trp Ser Ile Ala Gln Lys Tyr Asn Thr Ser Val
            35                  40                  45
Glu Ser Ile Lys Gln Asn Asn Gln Leu Asp Asn Asn Leu Val Phe Pro
        50                  55                  60
Gly Gln Val Ile Ser Val Gly Gly Ser Asp Ala Gln Asn Thr Ser Asn
65                  70                  75                  80
Thr Ser Pro Gln Ala Gly Ser Ala Ser Ser His Thr Val Gln Ala Gly
                85                  90                  95
Glu Ser Leu Asn Ile Ile Ala Ser Arg Tyr Gly Val Ser Val Asp Gln
                100                 105                 110
Leu Met Ala Ala Asn Asn Leu Arg Gly Tyr Leu Ile Met Pro Asn Gln
            115                 120                 125
Thr Leu Gln Ile Pro Asn Gly Gly Ser Gly Thr Thr Pro Thr Ala
        130                 135                 140
Thr Thr Gly Ser Asn Gly Asn Ala Ser Ser Phe Asn His Gln Asn Leu
145                 150                 155                 160
Tyr Thr Ala Gly Gln Cys Thr Trp Tyr Val Phe Asp Arg Arg Ala Gln
                165                 170                 175
Ala Gly Ser Pro Ile Ser Thr Tyr Trp Ser Asp Ala Lys Tyr Trp Ala
            180                 185                 190
Gly Asn Ala Ala Asn Asp Gly Tyr Gln Val Asn Asn Thr Pro Ser Val
        195                 200                 205
Gly Ser Ile Met Gln Ser Thr Pro Gly Pro Tyr Gly His Val Ala Tyr
    210                 215                 220
Val Glu Arg Val Asn Gly Asp Gly Ser Ile Leu Ile Ser Glu Met Asn
225                 230                 235                 240
Tyr Thr Tyr Gly Pro Tyr Asn Met Asn Tyr Arg Thr Ile Pro Ala Ser
                245                 250                 255
Glu Val Ser Ser Tyr Ala Phe Ile His
            260                 265

<210> SEQ ID NO 63
<211> LENGTH: 292
<212> TYPE: PRT
<213> ORGANISM: Staphylococcus sp

<400> SEQUENCE: 63
```

```
Met Lys Lys Ile Val Ile Ile Ala Val Leu Ala Ile Leu Phe Val Val
1               5                   10                  15

Ile Ser Ala Cys Gly Asn Lys Glu Lys Glu Ala Gln His Gln Phe Thr
            20                  25                  30

Lys Gln Phe Lys Asp Val Glu Gln Lys Gln Lys Glu Leu Gln His Val
        35                  40                  45

Met Asp Asn Ile His Leu Lys Glu Ile Asp His Leu Ser Lys Thr Asp
50                  55                  60

Thr Thr Asp Lys Asn Ser Lys Glu Phe Lys Ala Leu Gln Glu Asp Val
65                  70                  75                  80

Lys Asn His Leu Ile Pro Lys Phe Glu Ala Tyr Tyr Lys Ser Ala Lys
                85                  90                  95

Asn Leu Pro Asp Asp Thr Met Lys Val Lys Leu Lys Lys Glu Tyr
            100                 105                 110

Met Thr Leu Ala Asn Glu Lys Lys Asp Ala Ile Tyr Gln Leu Lys Lys
        115                 120                 125

Phe Ile Gly Leu Cys Asn Gln Ser Ile Lys Tyr Asn Glu Asp Ile Leu
    130                 135                 140

Asp Tyr Thr Lys Gln Phe Glu Lys Asn Arg Tyr Lys Val Glu Ser Glu
145                 150                 155                 160

Ile Lys Leu Ala Asp Asn Lys Ser Glu Ala Thr Asn Leu Thr Thr Lys
                165                 170                 175

Leu Glu His Asn Asn Lys Ala Leu Arg Asp Thr Ala Lys Lys Asn Leu
            180                 185                 190

Asp Asp Ser Lys Glu Asn Glu Val Lys Gly Ala Ile Lys Asn His Ile
        195                 200                 205

Met Pro Met Ile Glu Lys Gln Ile Thr Asp Ile Asn Gln Thr Asn Ile
    210                 215                 220

Ser Asp Lys His Val Asn Asn Ala Arg Lys Asn Ala Ile Glu Met Tyr
225                 230                 235                 240

Tyr Ser Leu Gln Asn Tyr Tyr Asn Thr Arg Ile Glu Thr Ile Lys Val
                245                 250                 255

Ser Glu Lys Leu Ser Lys Val Asp Val Asp Lys Leu Pro Lys Lys Gly
            260                 265                 270

Ile Asp Ile Thr His Gly Asp Lys Ala Phe Glu Lys Lys Leu Glu Lys
        275                 280                 285

Leu Glu Glu Lys
    290

<210> SEQ ID NO 64
<211> LENGTH: 242
<212> TYPE: PRT
<213> ORGANISM: Staphylococcus sp

<400> SEQUENCE: 64

Met Lys Lys Val Met Gly Ile Leu Leu Ala Ser Thr Leu Ile Leu Gly
1               5                   10                  15

Ala Cys Gly His His Gln Asp Ser Ala Lys Lys Glu Ser Thr Ser His
            20                  25                  30

Lys Lys Lys Glu Asn Asp Asn Glu Glu Leu Asn Glu Glu Leu Lys Glu
        35                  40                  45

Phe Lys Ser Lys Lys Asn Met Asp Ile Lys Ile Lys Gly Asp Thr Ile
    50                  55                  60

Val Ser Asp Lys Phe Glu Ala Lys Ile Lys Glu Pro Phe Ile Ile Asn
65                  70                  75                  80
```

```
Glu Lys Asp Glu Lys Lys Tyr Ile Ala Phe Lys Met Glu Ile Thr
            85                  90                  95

Ala Lys Lys Asp Asp Lys Asp Leu Asn Pro Ser Ser Ile Ser His Asp
            100                 105                 110

Tyr Ile Asn Ile Thr Gln Asp Lys Asn Thr Val Asn Lys Leu Arg
            115                 120                 125

Asp Gly Tyr Leu Leu Ser Asp Lys Lys Tyr Lys Asp Trp Thr Glu His
130                 135                 140

Asn Gln Asp Gln Ile Lys Lys Gly Lys Thr Ala Gln Ala Met Phe Ile
145                 150                 155                 160

Tyr Glu Leu Arg Gly Asp Gly Asn Ile Asn Leu Asn Val His Lys Tyr
            165                 170                 175

Ser Glu Asp Lys Thr Val Asp Ser Lys Ser Phe Lys Phe Ser Lys Leu
            180                 185                 190

Lys Thr Glu Asp Phe Ser His Arg Ala Glu Thr Arg Glu Glu Val Glu
            195                 200                 205

Lys Lys Glu Lys Glu Phe Glu Glu Tyr Lys Lys Glu Gln Glu Arg
            210                 215                 220

Glu Lys Glu Lys Glu Lys Gln Lys Asp Asp His Ser Gly Leu Asp
225                 230                 235                 240

Glu Val

<210> SEQ ID NO 65
<211> LENGTH: 439
<212> TYPE: PRT
<213> ORGANISM: Staphylococcus sp

<400> SEQUENCE: 65

Met Arg Leu Thr Ile Tyr His Thr Asn Asp Ile His Ser His Leu His
1               5                   10                  15

Glu Tyr Glu Arg Leu Lys Ala Tyr Met Ala Glu His Arg Pro Arg Leu
            20                  25                  30

Asn His Pro Ser Leu Tyr Val Asp Leu Gly Asp His Val Asp Leu Ser
        35                  40                  45

Ala Pro Ile Thr Glu Ala Thr Leu Gly Lys Lys Asn Val Ala Leu Leu
50                  55                  60

Asn Glu Ala Lys Cys Asp Val Ala Thr Ile Gly Asn Asn Glu Gly Met
65                  70                  75                  80

Thr Ile Ser Tyr Glu Ala Leu Asn His Leu Tyr Asp Glu Ala Lys Phe
            85                  90                  95

Ile Val Thr Cys Ser Asn Val Ile Asp Glu Ser Gly His Leu Pro Asn
            100                 105                 110

Asn Ile Val Ser Ser Tyr Ile Lys Asp Ile Asp Gly Val Lys Ile Leu
            115                 120                 125

Phe Val Ala Ala Thr Ala Pro Phe Thr Pro Phe Tyr Arg Ala Leu Asn
130                 135                 140

Trp Ile Val Thr Asp Pro Leu Glu Ser Ile Lys Glu Glu Ile Glu Leu
145                 150                 155                 160

Gln Arg Gly Lys Phe Asp Val Leu Ile Val Leu Ser His Cys Gly Ile
            165                 170                 175

Phe Phe Asp Glu Thr Leu Cys Gln Glu Leu Pro Glu Ile Asp Val Ile
            180                 185                 190

Phe Gly Ser His Thr His His Tyr Phe Glu His Gly Glu Ile Asn Asn
            195                 200                 205
```

Gly Val Leu Met Ala Ala Gly Lys Tyr Gly Asn Tyr Leu Gly Glu
            210                 215                 220

Val Asn Leu Thr Phe Glu Ala His Lys Val His Lys Thr Ala Lys
225                 230                 235                 240

Ile Ile Pro Leu Glu Thr Leu Pro Glu Val Glu Thr Ser Phe Glu Glu
                245                 250                 255

Glu Gly Lys Thr Leu Met Ser Asn Ser Val Ile Gln His Pro Val Val
            260                 265                 270

Leu Lys Arg Ser Met Asn His Ile Thr Glu Ala Ala Tyr Leu Leu Ala
        275                 280                 285

Gln Ser Val Cys Glu Tyr Thr His Ala Gln Cys Ala Ile Ile Asn Ala
    290                 295                 300

Gly Leu Val Lys Asp Ile Val Lys Asp Glu Val Thr Glu Tyr Asp
305                 310                 315                 320

Ile His Gln Met Leu Pro His Pro Ile Asn Met Val Arg Val Arg Leu
                325                 330                 335

Phe Gly Val Lys Leu Lys Glu Ile Ile Ala Lys Ser Asn Lys Gln Glu
            340                 345                 350

Tyr Met Tyr Glu His Ala Gln Gly Leu Gly Phe Arg Gly Asn Ile Phe
        355                 360                 365

Gly Gly Tyr Ile Leu Tyr Asn Leu Gly Tyr Ile His Ser Thr Gly Arg
    370                 375                 380

Tyr Tyr Leu Asn Gly Glu Glu Ile Glu Asp Asp Lys Glu Tyr Val Leu
385                 390                 395                 400

Gly Thr Ile Asp Met Tyr Thr Phe Gly Arg Tyr Phe Pro Thr Leu Lys
                405                 410                 415

Glu Leu Pro Lys Glu Tyr Leu Met Pro Glu Phe Leu Arg Asp Ile Phe
            420                 425                 430

Lys Glu Lys Leu Leu Glu Tyr
        435

<210> SEQ ID NO 66
<211> LENGTH: 774
<212> TYPE: PRT
<213> ORGANISM: Staphylococcus sp

<400> SEQUENCE: 66

Met Glu Trp Thr Leu Val Asp Ile Gly Lys Lys His Val Ile Pro Lys
1               5                   10                  15

Ser Gln Tyr Arg Arg Lys Arg Arg Glu Phe Phe His Asn Glu Asp Arg
            20                  25                  30

Glu Glu Asn Leu Asn Gln His Gln Asp Lys Gln Asn Ile Asp Asn Thr
        35                  40                  45

Thr Ser Lys Lys Ala Asp Lys Gln Ile His Lys Asp Ser Ile Asp Lys
    50                  55                  60

His Glu Arg Phe Lys Asn Ser Leu Ser Ser His Leu Glu Gln Arg Asn
65                  70                  75                  80

Arg Asp Val Asn Glu Asn Lys Ala Glu Glu Ser Lys Ser Asn Gln Asp
                85                  90                  95

Ser Lys Ser Ala Tyr Asn Arg Asp His Tyr Leu Thr Asp Asp Val Ser
            100                 105                 110

Lys Lys Gln Asn Ser Leu Asp Ser Val Asp Gln Asp Thr Glu Lys Ser
        115                 120                 125

Lys Tyr Tyr Glu Gln Asn Ser Glu Ala Thr Leu Ser Thr Lys Ser Thr

```
                130                 135                 140
Asp Lys Val Glu Ser Thr Glu Met Arg Lys Leu Ser Ser Asp Lys Asn
145                 150                 155                 160

Lys Val Gly His Glu Gln His Val Leu Ser Lys Pro Ser Glu His
                165                 170                 175

Asp Lys Glu Thr Arg Ile Asp Ser Glu Ser Ser Arg Thr Asp Ser Asp
                180                 185                 190

Ser Ser Met Gln Thr Glu Lys Ile Lys Lys Asp Ser Ser Asp Gly Asn
                195                 200                 205

Lys Ser Ser Asn Leu Lys Ser Glu Val Ile Ser Asp Lys Ser Asn Thr
210                 215                 220

Val Pro Lys Leu Ser Glu Ser Asp Asp Glu Val Asn Asn Gln Lys Pro
225                 230                 235                 240

Leu Thr Leu Pro Glu Glu Gln Lys Leu Lys Arg Gln Gln Ser Gln Asn
                245                 250                 255

Glu Gln Thr Lys Thr Tyr Thr Tyr Gly Asp Ser Glu Gln Asn Asp Lys
                260                 265                 270

Ser Asn His Glu Asn Asp Leu Ser His His Ile Pro Ser Ile Ser Asp
                275                 280                 285

Asp Lys Asp Asn Val Met Arg Glu Asn His Ile Val Asp Asp Asn Pro
                290                 295                 300

Asp Asn Asp Ile Asn Thr Pro Ser Leu Ser Lys Thr Asp Asp Asp Arg
305                 310                 315                 320

Lys Leu Asp Glu Lys Ile His Val Glu Asp Lys His Lys Gln Asn Ala
                325                 330                 335

Asp Ser Ser Glu Thr Val Gly Tyr Gln Ser Gln Ser Thr Ala Ser His
                340                 345                 350

Arg Ser Thr Glu Lys Arg Asn Ile Ser Ile Asn Asp His Asp Lys Leu
                355                 360                 365

Asn Gly Gln Lys Thr Asn Thr Lys Thr Ser Ala Asn Asn Asn Gln Lys
                370                 375                 380

Lys Ala Thr Ser Lys Leu Asn Lys Gly Arg Ala Thr Asn Asn Asn Tyr
385                 390                 395                 400

Ser Asp Ile Leu Lys Lys Phe Trp Met Met Tyr Trp Pro Lys Leu Val
                405                 410                 415

Ile Leu Met Gly Ile Ile Leu Ile Val Ile Leu Asn Ala Ile Phe
                420                 425                 430

Asn Asn Val Asn Lys Asn Asp Arg Met Asn Asp Asn Asp Ala Asp
                435                 440                 445

Ala Gln Lys Tyr Thr Thr Thr Met Lys Asn Ala Asn Asn Thr Val Lys
450                 455                 460

Ser Val Val Thr Val Glu Asn Glu Thr Ser Lys Asp Ser Ser Leu Pro
465                 470                 475                 480

Lys Asp Lys Ala Ser Gln Asp Glu Val Gly Ser Gly Val Val Tyr Lys
                485                 490                 495

Lys Ser Gly Asp Thr Leu Tyr Ile Val Thr Asn Ala His Val Val Gly
                500                 505                 510

Asp Lys Glu Asn Gln Lys Ile Thr Phe Ser Asn Asn Lys Ser Val Val
                515                 520                 525

Gly Lys Val Leu Gly Lys Asp Lys Trp Ser Asp Leu Ala Val Val Lys
                530                 535                 540

Ala Thr Ser Ser Asp Ser Ser Val Lys Glu Ile Ala Ile Gly Asp Ser
545                 550                 555                 560
```

-continued

```
Asn Asn Leu Val Leu Gly Glu Pro Ile Leu Val Val Gly Asn Pro Leu
                565                 570                 575

Gly Val Asp Phe Lys Gly Thr Val Thr Glu Gly Ile Ile Ser Gly Leu
            580                 585                 590

Asn Arg Asn Val Pro Ile Asp Phe Asp Lys Asp Asn Lys Tyr Asp Met
        595                 600                 605

Leu Met Lys Ala Phe Gln Ile Asp Ala Ser Val Asn Pro Gly Asn Ser
    610                 615                 620

Gly Gly Ala Val Val Asn Arg Glu Gly Lys Leu Ile Gly Val Val Ala
625                 630                 635                 640

Ala Lys Ile Ser Met Pro Asn Val Glu Asn Met Ser Phe Ala Ile Pro
                645                 650                 655

Val Asn Glu Val Gln Lys Ile Val Lys Asp Leu Glu Thr Lys Gly Lys
            660                 665                 670

Ile Asp Tyr Pro Asp Val Gly Val Lys Met Lys Asn Ile Val Ser Leu
        675                 680                 685

Asn Ser Phe Glu Arg Gln Ala Val Lys Leu Pro Gly Lys Val Lys Asn
    690                 695                 700

Gly Val Val Asp Gln Val Asp Asn Gly Leu Ala Asp Gln Ser
705                 710                 715                 720

Gly Leu Lys Lys Gly Asp Val Ile Thr Glu Leu Asp Gly Lys Leu Leu
                725                 730                 735

Glu Asp Asp Leu Arg Phe Arg Gln Ile Ile Phe Ser His Lys Asp Asp
            740                 745                 750

Leu Lys Ser Ile Thr Ala Lys Ile Tyr Arg Asp Gly Lys Glu Lys Glu
        755                 760                 765

Ile Asn Ile Lys Leu Lys
    770

<210> SEQ ID NO 67
<211> LENGTH: 393
<212> TYPE: PRT
<213> ORGANISM: Staphylococcus sp

<400> SEQUENCE: 67

Met Asn Ser Ser Cys Lys Ser Arg Val Phe Asn Ile Ile Ser Ile Ile
1               5                   10                  15

Met Val Ser Met Leu Ile Leu Ser Leu Gly Ala Phe Ala Asn Asn Asn
                20                  25                  30

Lys Ala Lys Ala Asp Ser His Ser Lys Gln Leu Glu Ile Asn Val Lys
            35                  40                  45

Ser Asp Lys Val Pro Gln Lys Val Lys Asp Leu Ala Gln Gln Gln Phe
        50                  55                  60

Ala Gly Tyr Ala Lys Ala Leu Asp Lys Gln Ser Asn Ala Lys Thr Gly
65                  70                  75                  80

Lys Tyr Glu Leu Gly Glu Ala Phe Lys Ile Tyr Lys Phe Asn Gly Glu
                85                  90                  95

Glu Asp Asn Ser Tyr Tyr Tyr Pro Val Ile Lys Asp Gly Lys Ile Val
            100                 105                 110

Tyr Thr Leu Thr Leu Ser Pro Lys Asn Lys Asp Leu Asn Lys Ser
        115                 120                 125

Lys Glu Asp Met Asn Tyr Ser Val Lys Ile Ser Asn Phe Ile Ala Lys
    130                 135                 140

Asp Leu Asp Gln Ile Lys Asp Lys Asn Ser Asn Ile Thr Val Leu Thr
```

```
                145                 150                 155                 160
Asp Glu Lys Gly Phe Tyr Phe Glu Gly Asp Gly Lys Val Arg Leu Val
                    165                 170                 175

Lys Ala Thr Pro Leu Pro Gly Asn Val Lys Glu Lys Glu Ser Ala Lys
                180                 185                 190

Thr Val Ser Ala Lys Leu Lys Gln Glu Leu Lys Asn Thr Val Thr Pro
            195                 200                 205

Thr Lys Val Glu Glu Asn Glu Ala Ile Gln Asp Gln Val Gln Tyr
        210                 215                 220

Glu Asn Thr Leu Lys Asn Phe Lys Ile Arg Glu Gln Gln Phe Asp Asn
225                 230                 235                 240

Ser Trp Cys Ala Gly Phe Ser Met Ala Ala Leu Leu Asn Ala Thr Lys
                    245                 250                 255

Asn Thr Asp Thr Tyr Asn Ala His Asp Ile Met Arg Thr Leu Tyr Pro
                260                 265                 270

Glu Val Ser Glu Gln Asp Leu Pro Asn Cys Ala Thr Phe Pro Asn Gln
            275                 280                 285

Met Ile Glu Tyr Gly Lys Ser Gln Gly Arg Asp Ile His Tyr Gln Glu
        290                 295                 300

Gly Val Pro Ser Tyr Glu Gln Val Asp Gln Leu Thr Lys Asp Asn Val
305                 310                 315                 320

Gly Ile Met Ile Leu Ala Gln Ser Val Ser Gln Asn Pro Asn Asp Pro
                    325                 330                 335

His Leu Gly His Ala Leu Ala Val Val Gly Asn Ala Lys Ile Asn Asp
                340                 345                 350

Gln Glu Lys Leu Ile Tyr Trp Asn Pro Trp Asp Thr Glu Leu Ser Ile
            355                 360                 365

Gln Asp Ala Asp Ser Ser Leu Leu His Leu Ser Phe Asn Arg Asp Tyr
        370                 375                 380

Asn Trp Tyr Gly Ser Met Ile Gly Tyr
385                 390
```

<210> SEQ ID NO 68
<211> LENGTH: 336
<212> TYPE: PRT
<213> ORGANISM: Staphylococcus sp

<400> SEQUENCE: 68

```
Met Lys Gly Lys Phe Leu Lys Val Ser Ser Leu Phe Val Ala Thr Leu
1               5                   10                  15

Thr Thr Ala Thr Leu Val Ser Ser Pro Ala Ala Asn Ala Leu Ser Ser
                20                  25                  30

Lys Ala Met Asp Asn His Pro Gln Gln Thr Gln Ser Ser Lys Gln Gln
            35                  40                  45

Thr Pro Lys Ile Gln Lys Gly Gly Asn Leu Lys Pro Leu Glu Gln Arg
        50                  55                  60

Glu His Ala Asn Val Ile Leu Pro Asn Asn Asp Arg His Gln Ile Thr
65                  70                  75                  80

Asp Thr Thr Asn Gly His Tyr Ala Pro Val Thr Tyr Ile Gln Val Glu
                85                  90                  95

Ala Pro Thr Gly Thr Phe Ile Ala Ser Gly Val Val Gly Lys Asp
            100                 105                 110

Thr Leu Leu Thr Asn Lys His Val Val Asp Ala Thr His Gly Asp Pro
        115                 120                 125
```

```
His Ala Leu Lys Ala Phe Pro Ser Ala Ile Asn Gln Asp Asn Tyr Pro
    130                 135                 140

Asn Gly Gly Phe Thr Ala Glu Gln Ile Thr Lys Tyr Ser Gly Glu Gly
145                 150                 155                 160

Asp Leu Ala Ile Val Lys Phe Ser Pro Asn Glu Gln Asn Lys His Ile
                165                 170                 175

Gly Glu Val Val Lys Pro Ala Thr Met Ser Asn Asn Ala Glu Thr Gln
            180                 185                 190

Val Asn Gln Asn Ile Thr Val Thr Gly Tyr Pro Gly Asp Lys Pro Val
        195                 200                 205

Ala Thr Met Trp Glu Ser Lys Gly Lys Ile Thr Tyr Leu Lys Gly Glu
    210                 215                 220

Ala Met Gln Tyr Asp Leu Ser Thr Thr Gly Gly Asn Ser Gly Ser Pro
225                 230                 235                 240

Val Phe Asn Glu Lys Asn Glu Val Ile Gly Ile His Trp Gly Gly Val
                245                 250                 255

Pro Asn Glu Phe Asn Gly Ala Val Phe Ile Asn Glu Asn Val Arg Asn
            260                 265                 270

Phe Leu Lys Gln Asn Ile Glu Asp Ile His Phe Ala Asn Asp Asp Gln
        275                 280                 285

Pro Asn Asn Pro Asp Asn Pro Asp Asn Pro Asn Asn Pro Asp Asn Pro
    290                 295                 300

Asn Asn Pro Asp Glu Pro Asn Asn Pro Asp Asn Pro Asn Asn Pro Asp
305                 310                 315                 320

Asn Pro Asp Asn Gly Asp Asn Asn Ser Asp Asn Pro Asp Ala Ala
                325                 330                 335

<210> SEQ ID NO 69
<211> LENGTH: 397
<212> TYPE: PRT
<213> ORGANISM: Staphylococcus sp

<400> SEQUENCE: 69

Met Lys Phe Asn Lys Val Lys Leu Val Ile His Ala Cys Val Leu Leu
1               5                   10                  15

Phe Ile Ile Ile Ser Ile Ala Leu Ile Phe His Arg Leu Gln Thr Lys
                20                  25                  30

Thr His Ser Ile Asp Pro Ile His Lys Glu Thr Lys Leu Ser Asp Asn
            35                  40                  45

Glu Lys Tyr Leu Val Asp Arg Asn Lys Glu Lys Val Ala Pro Ser Lys
        50                  55                  60

Leu Lys Glu Val Tyr Asn Ser Lys Asp Pro Lys Tyr Lys Lys Ile Asp
65                  70                  75                  80

Lys Tyr Leu Gln Ser Ser Leu Phe Asn Gly Ser Val Ala Ile Tyr Glu
                85                  90                  95

Asn Gly Lys Leu Lys Met Ser Lys Gly Tyr Gly Tyr Gln Asp Phe Glu
            100                 105                 110

Lys Gly Ile Lys Asn Thr Pro Asn Thr Met Phe Leu Ile Gly Ser Ala
        115                 120                 125

Gln Lys Phe Ser Thr Gly Leu Leu Leu Lys Gln Leu Glu Glu Glu His
    130                 135                 140

Lys Ile Asn Ile Asn Asp Pro Val Ser Lys Tyr Leu Pro Trp Phe Lys
145                 150                 155                 160

Thr Ser Lys Pro Ile Pro Leu Lys Asp Leu Met Leu His Gln Ser Gly
                165                 170                 175
```

```
Leu Tyr Lys Tyr Lys Ser Ser Lys Asp Tyr Lys Asn Leu Asp Gln Ala
            180                 185                 190

Val Lys Ala Ile Gln Lys Arg Gly Ile Asp Pro Lys Lys Tyr Lys Lys
        195                 200                 205

His Met Tyr Asn Asp Gly Asn Tyr Leu Val Leu Ala Lys Val Ile Glu
    210                 215                 220

Glu Val Thr Gly Lys Ser Tyr Ala Glu Asn Tyr Tyr Thr Lys Ile Gly
225                 230                 235                 240

Asp Pro Leu Lys Leu Gln His Thr Ala Phe Tyr Asp Glu Gln Pro Phe
                245                 250                 255

Lys Lys Tyr Leu Ala Lys Gly Tyr Ala Tyr Asn Ser Thr Gly Leu Ser
            260                 265                 270

Phe Leu Arg Pro Asn Ile Leu Asp Gln Tyr Tyr Gly Ala Gly Asn Leu
        275                 280                 285

Tyr Met Thr Pro Thr Asp Met Gly Lys Leu Ile Thr Gln Ile Gln Gln
    290                 295                 300

Tyr Lys Leu Phe Ser Pro Lys Ile Thr Asn Pro Leu Leu His Glu Phe
305                 310                 315                 320

Gly Thr Lys Lys Tyr Pro Asp Glu Tyr Arg Tyr Gly Phe Tyr Ala Lys
                325                 330                 335

Pro Thr Leu Asn Arg Leu Asn Gly Gly Phe Phe Gly Gln Val Phe Thr
            340                 345                 350

Val Tyr Tyr Asn Asp Lys Tyr Val Val Leu Ala Leu Asn Val Lys
        355                 360                 365

Gly Asn Asn Glu Val Arg Ile Lys His Ile Tyr Asn Asp Ile Leu Lys
    370                 375                 380

Gln Asn Lys Pro Tyr Asn Thr Lys Gly Val Ile Val Gln
385                 390                 395

<210> SEQ ID NO 70
<211> LENGTH: 358
<212> TYPE: PRT
<213> ORGANISM: Staphylococcus sp

<400> SEQUENCE: 70

Met Arg Asn Val Lys Gln Ile Ala Thr Lys Ser Ile Ile Ala Ile Ile
1               5                   10                  15

Ser Leu Gly Ile Leu Thr Tyr Thr Thr Met Ile Gly Ser Val Leu Ala
            20                  25                  30

Asp Glu Ile Lys Tyr Pro Ser Ala Lys Phe Asn Gln Pro Glu Ala Lys
        35                  40                  45

Asp Lys Thr Glu Leu Thr Thr Ser Ile Phe Asp Glu Lys Ile Lys Glu
    50                  55                  60

Asn Lys Ala Leu Glu Leu Leu Ile Phe Asn Gln Glu Asn Lys Asn Val
65                  70                  75                  80

Thr Glu Glu Gln Gln Leu Val Asp Glu Lys Ala Gln Leu Ile Ser Asp
                85                  90                  95

Met Thr Gly Lys Ile Tyr Leu Gln Val Lys Leu Lys Gly Gln Ile Asp
            100                 105                 110

Lys Glu Gln Leu Val Phe Gln Asn Asp Lys Asn Glu Gly Phe Pro Phe
        115                 120                 125

Val Ile Lys Asp Glu Lys Asp Asp Thr Ile Val Arg Ile Leu Ile Glu
    130                 135                 140

Gln His Met Asp Lys Ile Asn Met His Val Lys Thr Leu Ala Glu Lys
```

```
                145                 150                 155                 160
Lys Asn Leu Asp Asn Lys Glu Met Val Tyr Ser Ile His Phe Lys Glu
            165                 170                 175

Lys Lys Val Gln His Asp Asp Ala Lys Glu Val Pro Ser Lys His Gln
        180                 185                 190

Asn Gln Glu Asn Asn Gln Asp Gln Leu Lys Lys Asp Ile Asp Asp Lys
    195                 200                 205

Lys Asp Ser Gln Lys Ser Asp Thr Lys Glu Arg Arg Thr Ser Leu Phe
210                 215                 220

Thr Glu Lys Gly Leu Asn Asp Ile Pro Val Gln Lys Asp Lys Val Gln
225                 230                 235                 240

Gln Asp Ser Asn Lys Lys Ile Glu Asn Glu Arg Pro Lys Ala Ser Gly
            245                 250                 255

Thr Leu Lys Val Glu Asn Ser Pro Pro Thr Ile Lys Lys Val Glu Asn
        260                 265                 270

Asn His Lys Glu Gln Pro Lys His Lys Asp Glu Lys Ser Lys Lys Glu
    275                 280                 285

Lys Lys Lys Val Val Glu Lys Glu Lys Ala Leu Pro Ala Phe Asn Arg
290                 295                 300

Asp Asp Asp Ser Lys Asn Ser Ser Gln Leu Ser Ser Asp Ile Lys Glu
305                 310                 315                 320

Leu Asp Glu Pro Asn His Lys Lys Gln Tyr Met Leu Phe Ala Ala Gly
            325                 330                 335

Ile Val Leu Ala Thr Ile Leu Leu Ile Ser Ala His Leu Tyr Ser Arg
        340                 345                 350

Lys Arg Gly Asn Gln Val
        355

<210> SEQ ID NO 71
<211> LENGTH: 282
<212> TYPE: PRT
<213> ORGANISM: Staphylococcus sp

<400> SEQUENCE: 71

Met Ile Ser Val Val Ile Leu Thr Ser Cys Gln Ser Ser Ser Ser Gln
1               5                   10                  15

Glu Ser Thr Lys Ser Gly Glu Phe Arg Ile Val Pro Thr Thr Val Ala
            20                  25                  30

Leu Thr Met Thr Leu Asp Lys Leu Asp Leu Pro Ile Val Gly Lys Pro
        35                  40                  45

Thr Ser Tyr Lys Thr Leu Pro Asn Arg Tyr Lys Asp Val Pro Glu Ile
    50                  55                  60

Gly Gln Pro Met Glu Pro Asn Val Glu Ala Val Lys Lys Leu Lys Pro
65                  70                  75                  80

Thr His Val Leu Ser Val Ser Thr Ile Lys Asp Glu Met Gln Pro Phe
            85                  90                  95

Tyr Lys Gln Leu Asn Met Lys Gly Tyr Phe Tyr Asp Phe Asp Ser Leu
        100                 105                 110

Lys Gly Met Gln Lys Ser Ile Thr Gln Leu Gly Asp Gln Phe Asn Arg
    115                 120                 125

Lys Ala Gln Ala Lys Glu Leu Asn Asp His Leu Asn Ser Val Lys Gln
130                 135                 140

Lys Ile Glu Asn Lys Ala Ala Lys Gln Lys Lys His Pro Lys Val Leu
145                 150                 155                 160
```

Ile Leu Met Gly Val Pro Gly Ser Tyr Leu Val Ala Thr Asp Lys Ser
                165                 170                 175

Tyr Ile Gly Asp Leu Val Lys Ile Ala Gly Gly Glu Asn Val Ile Lys
            180                 185                 190

Val Lys Asp Arg Gln Tyr Ile Ser Ser Asn Thr Glu Asn Leu Leu Asn
        195                 200                 205

Ile Asn Pro Asp Ile Ile Leu Arg Leu Pro His Gly Met Pro Glu Glu
    210                 215                 220

Val Lys Lys Met Phe Gln Lys Glu Phe Lys Gln Asn Asp Ile Trp Lys
225                 230                 235                 240

His Phe Lys Ala Val Lys Asn Asn His Val Tyr Asp Leu Glu Glu Val
                245                 250                 255

Pro Phe Gly Ile Thr Ala Asn Val Asp Ala Asp Lys Ala Met Thr Gln
            260                 265                 270

Leu Tyr Asp Leu Phe Tyr Lys Asp Lys Lys
        275                 280

<210> SEQ ID NO 72
<211> LENGTH: 244
<212> TYPE: PRT
<213> ORGANISM: Staphylococcus sp

<400> SEQUENCE: 72

Met Arg Met Lys Arg Phe Leu Thr Ile Val Gln Ile Leu Leu Val Val
1               5                   10                  15

Ile Ile Ile Ile Phe Gly Tyr Lys Ile Val Gln Thr Tyr Ile Glu Asp
            20                  25                  30

Lys Gln Glu Arg Ala Asn Tyr Glu Lys Leu Gln Gln Lys Phe Gln Met
        35                  40                  45

Leu Met Ser Lys His Gln Glu His Val Arg Pro Gln Phe Glu Ser Leu
    50                  55                  60

Glu Lys Ile Asn Lys Asp Ile Val Gly Trp Ile Lys Leu Ser Gly Thr
65                  70                  75                  80

Ser Leu Asn Tyr Pro Val Leu Gln Gly Lys Thr Asn His Asp Tyr Leu
                85                  90                  95

Asn Leu Asp Phe Glu Arg Glu His Arg Arg Lys Gly Ser Ile Phe Met
            100                 105                 110

Asp Phe Arg Asn Glu Leu Lys Asn Leu Asn His Asn Thr Ile Leu Tyr
        115                 120                 125

Gly His His Val Gly Asp Asn Thr Met Phe Asp Val Leu Glu Asp Tyr
    130                 135                 140

Leu Lys Gln Ser Phe Tyr Glu Lys His Lys Ile Ile Glu Phe Asp Asn
145                 150                 155                 160

Lys Tyr Gly Lys Tyr Gln Leu Gln Val Phe Ser Ala Tyr Lys Thr Thr
                165                 170                 175

Thr Lys Asp Asn Tyr Ile Arg Thr Asp Phe Glu Asn Asp Gln Asp Tyr
            180                 185                 190

Gln Gln Phe Leu Asp Glu Thr Lys Arg Lys Ser Val Ile Asn Ser Asp
        195                 200                 205

Val Asn Val Thr Val Lys Asp Arg Ile Met Thr Leu Ser Thr Cys Glu
    210                 215                 220

Asp Ala Tyr Ser Glu Thr Thr Lys Arg Ile Val Val Ala Lys Ile
225                 230                 235                 240

Ile Lys Val Ser

```
<210> SEQ ID NO 73
<211> LENGTH: 238
<212> TYPE: PRT
<213> ORGANISM: Staphylococcus sp

<400> SEQUENCE: 73

Met Ser Lys Asn Ile Thr Lys Asn Ile Ile Leu Thr Thr Thr Leu Leu
1               5                   10                  15

Leu Leu Gly Thr Val Leu Pro Gln Asn Gln Lys Pro Val Phe Ser Phe
            20                  25                  30

Tyr Ser Glu Ala Lys Ala Tyr Ser Ile Gly Gln Asp Glu Thr Asn Ile
        35                  40                  45

Asn Glu Leu Ile Lys Tyr Tyr Thr Gln Pro His Phe Ser Phe Ser Asn
    50                  55                  60

Lys Trp Leu Tyr Gln Tyr Asp Asn Gly Asn Ile Tyr Val Glu Leu Lys
65                  70                  75                  80

Arg Tyr Ser Trp Ser Ala His Ile Ser Leu Trp Gly Ala Glu Ser Trp
                85                  90                  95

Gly Asn Ile Asn Gln Leu Lys Asp Arg Tyr Val Asp Val Phe Gly Leu
            100                 105                 110

Lys Asp Lys Asp Thr Asp Gln Leu Trp Trp Ser Tyr Arg Glu Thr Phe
        115                 120                 125

Thr Gly Gly Val Thr Pro Ala Ala Lys Pro Ser Asp Lys Thr Tyr Asn
    130                 135                 140

Leu Phe Val Gln Tyr Lys Asp Lys Leu Gln Thr Ile Ile Gly Ala His
145                 150                 155                 160

Lys Ile Tyr Gln Gly Asn Lys Pro Val Leu Thr Leu Lys Glu Ile Asp
                165                 170                 175

Phe Arg Ala Arg Glu Ala Leu Ile Lys Asn Lys Ile Leu Tyr Asn Glu
            180                 185                 190

Asn Arg Asn Lys Gly Lys Leu Lys Ile Thr Gly Gly Asn Asn Tyr
        195                 200                 205

Thr Ile Asp Leu Ser Lys Arg Leu His Ser Asp Leu Ala Asn Val Tyr
    210                 215                 220

Val Lys Asn Pro Asn Lys Ile Thr Val Asp Val Leu Phe Asp
225                 230                 235

<210> SEQ ID NO 74
<211> LENGTH: 241
<212> TYPE: PRT
<213> ORGANISM: Staphylococcus sp

<400> SEQUENCE: 74

Met Asn Asn Asn Ile Thr Lys Lys Ile Ile Leu Ser Thr Thr Leu Leu
1               5                   10                  15

Leu Leu Gly Thr Ala Ser Thr Gln Phe Pro Asn Thr Pro Ile Asn Ser
            20                  25                  30

Ser Ser Glu Ala Lys Ala Tyr Tyr Ile Asn Gln Asn Glu Thr Asn Val
        35                  40                  45

Asn Glu Leu Thr Lys Tyr Tyr Ser Gln Lys Tyr Leu Thr Phe Ser Asn
    50                  55                  60

Ser Thr Leu Trp Gln Lys Asp Asn Gly Thr Ile His Ala Thr Leu Leu
65                  70                  75                  80

Gln Phe Ser Trp Tyr Ser His Ile Gln Val Tyr Gly Pro Glu Ser Trp
                85                  90                  95
```

```
Gly Asn Ile Asn Gln Leu Arg Asn Lys Ser Val Asp Ile Phe Gly Ile
                100                 105                 110

Lys Asp Gln Glu Thr Ile Asp Ser Phe Ala Leu Ser Gln Glu Thr Phe
            115                 120                 125

Thr Gly Gly Val Thr Pro Ala Ala Thr Ser Asn Asp Lys His Tyr Lys
        130                 135                 140

Leu Asn Val Thr Tyr Lys Asp Lys Ala Glu Thr Phe Thr Gly Gly Phe
145                 150                 155                 160

Pro Val Tyr Glu Gly Asn Lys Pro Val Leu Thr Leu Lys Glu Leu Asp
                165                 170                 175

Phe Arg Ile Arg Gln Thr Leu Ile Lys Ser Lys Lys Leu Tyr Asn Asn
            180                 185                 190

Ser Tyr Asn Lys Gly Gln Ile Lys Ile Thr Gly Ala Asp Asn Asn Tyr
        195                 200                 205

Thr Ile Asp Leu Ser Lys Arg Leu Pro Ser Thr Asp Ala Asn Arg Tyr
210                 215                 220

Val Lys Lys Pro Gln Asn Ala Lys Ile Glu Val Ile Leu Glu Lys Ser
225                 230                 235                 240

Asn

<210> SEQ ID NO 75
<211> LENGTH: 565
<212> TYPE: PRT
<213> ORGANISM: Staphylococcus sp

<400> SEQUENCE: 75

Met Ala Tyr Asp Gly Leu Phe Thr Lys Lys Met Val Glu Ser Leu Gln
1               5                   10                  15

Phe Leu Thr Thr Gly Arg Val His Lys Ile Asn Gln Pro Asp Asn Asp
            20                  25                  30

Thr Ile Leu Met Val Val Arg Gln Asn Arg Gln Asn His Gln Leu Leu
        35                  40                  45

Leu Ser Ile His Pro Asn Phe Ser Arg Leu Gln Leu Thr Thr Lys Lys
    50                  55                  60

Tyr Asp Asn Pro Phe Asn Pro Pro Met Phe Ala Arg Val Phe Arg Lys
65                  70                  75                  80

His Leu Glu Gly Gly Ile Ile Glu Ser Ile Lys Gln Ile Gly Asn Asp
                85                  90                  95

Arg Arg Ile Glu Ile Asp Ile Lys Ser Lys Asp Glu Ile Gly Asp Thr
            100                 105                 110

Ile Tyr Arg Thr Val Ile Leu Glu Ile Met Gly Lys His Ser Asn Leu
        115                 120                 125

Ile Leu Val Asp Glu Asn Arg Lys Ile Ile Glu Gly Phe Lys His Leu
    130                 135                 140

Thr Pro Asn Thr Asn His Tyr Arg Thr Val Met Pro Gly Phe Asn Tyr
145                 150                 155                 160

Glu Ala Pro Pro Thr Gln His Lys Ile Asn Pro Tyr Asp Ile Thr Gly
                165                 170                 175

Ala Glu Val Leu Lys Tyr Ile Asp Phe Asn Ala Gly Asn Ile Ala Lys
            180                 185                 190

Gln Leu Leu Asn Gln Phe Glu Gly Phe Ser Pro Leu Ile Thr Asn Glu
        195                 200                 205

Ile Val Ser Arg Arg Gln Phe Met Thr Ser Ser Thr Leu Pro Glu Ala
    210                 215                 220
```

```
Phe Asp Glu Val Met Ala Glu Thr Lys Leu Pro Thr Pro Ile Phe
225                 230                 235                 240

His Lys Asn His Glu Thr Gly Lys Glu Asp Phe Tyr Phe Ile Lys Leu
            245                 250                 255

Asn Gln Phe Asn Asp Asp Thr Val Thr Tyr Asp Ser Leu Asn Asp Leu
            260                 265                 270

Leu Asp Arg Phe Tyr Asp Ala Arg Gly Glu Arg Glu Arg Val Lys Gln
        275                 280                 285

Arg Ala Asn Asp Leu Val Arg Phe Val Gln Gln Leu His Lys Tyr
        290                 295                 300

Gln Asn Lys Leu Ala Lys Leu Ile Glu Glu Tyr Glu Gln Ser Lys Asn
305                 310                 315                 320

Lys Asp Thr Glu Gln Leu Tyr Gly Glu Leu Ile Thr Ala Asn Ile Tyr
                325                 330                 335

Arg Ile Lys Gln Gly Asp Lys Glu Val Thr Ala Leu Asn Tyr Tyr Thr
                340                 345                 350

Asn Glu Glu Val Val Ile Pro Leu Asn Pro Thr Lys Ser Pro Ser Ala
                355                 360                 365

Asn Ala Gln Tyr Tyr Tyr Lys Gln Tyr Asn Arg Met Lys Thr Arg Glu
        370                 375                 380

Arg Glu Leu Gln His Gln Ile Gln Leu Thr Lys Asp Asn Ile Asp Tyr
385                 390                 395                 400

Phe Ser Thr Ile Glu Gln Leu His His Ile Ser Val His Asp Ile
                405                 410                 415

Asp Glu Ile Arg Asp Glu Leu Ala Glu Gln Gly Phe Met Lys Gln Arg
                420                 425                 430

Lys Asn Gln Thr Lys Lys Lys Ala Gln Ile Gln Leu Gln His Tyr
                435                 440                 445

Val Ser Thr Asp Gly Asp Ile Tyr Val Gly Lys Asn Asn Lys Gln
        450                 455                 460

Asn Asp Tyr Leu Thr Asn Lys Lys Ala Lys Thr His Thr Trp Leu
465                 470                 475                 480

His Thr Lys Asp Ile Pro Gly Ser His Val Val Ile Phe Asn Asp Ala
                485                 490                 495

Pro Ser Asp Thr Thr Ile Lys Glu Ala Ala Met Leu Ala Gly Tyr Phe
            500                 505                 510

Ser Lys Ala Gly Asn Ser Gly Gln Ile Pro Val Asp Tyr Thr Leu Ile
        515                 520                 525

Lys Asn Val His Lys Pro Ser Gly Ala Lys Pro Gly Phe Val Thr Tyr
        530                 535                 540

Asp Asn Gln Lys Thr Leu Tyr Ala Thr Pro Asp Tyr Glu Leu Ile Gln
545                 550                 555                 560

Lys Met Lys Gln Ser
                565

<210> SEQ ID NO 76
<211> LENGTH: 317
<212> TYPE: PRT
<213> ORGANISM: Staphylococcus sp

<400> SEQUENCE: 76

Met Lys Lys Thr Leu Gly Cys Leu Leu Leu Ile Met Leu Leu Val Val
1               5                   10                  15

Ala Gly Cys Ser Phe Gly Gly Asn His Lys Leu Ser Ser Lys Lys Ser
            20                  25                  30
```

```
Glu Ser Lys Gln Glu Thr Val Lys Glu Ser Glu Glu Lys
        35                  40                  45

Asp Pro Asp Leu Glu Lys Tyr Glu Ile Glu Lys Met Lys Gly
 50                  55                  60

Ile Lys Asp Ala Pro Ser Leu Asp Lys Leu Asp Pro Leu Met Thr Glu
 65                  70                  75                  80

Lys Ser Phe Thr Asn Ser Lys Gly Ile Gln Gly Trp Lys Asp Tyr Lys
                 85                  90                  95

Glu Leu Met Gly Lys Val Glu Leu Ala Asp Tyr Arg Phe Thr Lys Asp
                100                 105                 110

Ser Lys Gly Ser Ser Ile Lys Asp Val Asp Ala Phe Phe Lys Gly Lys
            115                 120                 125

Lys Gly Ile Lys Arg Lys Val Ile Glu Thr His Asp Asp Val Lys Gln
        130                 135                 140

Val Asp Tyr Trp Tyr Val Asp Pro Asp Gly Lys Lys Ile Gly Asn Ser
145                 150                 155                 160

Asn Thr Pro Val Phe Tyr Ala Glu Ile Met Thr Lys Tyr Lys Asp Gly
                165                 170                 175

Lys Leu Val Tyr Ala Ser Val Glu Pro Gly Ser Tyr Val Ile His Lys
                180                 185                 190

Asp Asp Ala Ile Lys Tyr Asp Asp Tyr Ser Lys Leu Lys Lys Leu Ser
            195                 200                 205

Gln Leu Thr Lys Leu Asp His Pro Lys Pro Val Pro Tyr Ser Val Ala
        210                 215                 220

Gln Ile Lys Ser Phe Gly Val Pro Leu Thr Ser Val Ser Phe Met Thr
225                 230                 235                 240

His Gly Ser Lys Asp Thr Lys Asp Glu Val Leu Pro Ala Leu Ala Tyr
                245                 250                 255

Phe Thr Phe Ser Pro Lys Asn Tyr Glu Asp Lys Ser Asn Pro Asp Pro
                260                 265                 270

Lys Val Leu Asn Leu Val His Met Asp Phe Leu Asn Ala Ser Ser Asp
            275                 280                 285

Phe Gly Asn Ala His Phe Val Val Leu Ser Lys Tyr Ile Lys Glu Tyr
        290                 295                 300

Glu Ser Asn Tyr Glu Thr Ala Ser Asp Asp Ser Leu Lys
305                 310                 315

<210> SEQ ID NO 77
<211> LENGTH: 372
<212> TYPE: PRT
<213> ORGANISM: Staphylococcus sp

<400> SEQUENCE: 77

Met Asn Lys Gln Gln Ser Lys Val Arg Tyr Ser Ile Arg Lys Val Ser
 1                5                  10                  15

Ile Gly Ile Leu Ser Ile Ser Ile Gly Met Phe Leu Ala Leu Gly Met
                 20                  25                  30

Ser Asn Lys Ala Tyr Ala Asp Glu Ile Asp Lys Ser Lys Asp Phe Thr
             35                  40                  45

Arg Gly Tyr Glu Gln Asn Val Phe Ala Lys Ser Glu Leu Asn Ala Asn
         50                  55                  60

Lys Asn Thr Thr Lys Asp Lys Ile Lys Asn Glu Gly Ala Val Lys Thr
 65                  70                  75                  80

Ser Asp Thr Ser Leu Lys Leu Asp Asn Lys Ser Ala Ile Ser Asn Gly
```

```
                85                  90                  95
Asn Glu Ile Asn Gln Asp Ile Lys Ile Ser Asn Thr Pro Lys Asn Ser
            100                 105                 110
Ser Gln Gly Asn Asn Leu Val Ile Asn Asn Glu Leu Thr Lys Glu
        115                 120                 125
Ile Lys Ile Ala Asn Leu Glu Ala Gln Asn Ser Asn Gln Lys Lys Thr
    130                 135                 140
Asn Lys Val Thr Asn Asn Tyr Phe Gly Tyr Tyr Ser Phe Arg Glu Ala
145                 150                 155                 160
Pro Lys Thr Gln Ile Tyr Thr Val Lys Lys Gly Asp Thr Leu Ser Ala
                165                 170                 175
Ile Ala Leu Lys Tyr Lys Thr Thr Val Ser Asn Ile Gln Asn Thr Asn
                180                 185                 190
Asn Ile Ala Asn Pro Asn Leu Ile Phe Ile Gly Gln Lys Leu Lys Val
            195                 200                 205
Pro Met Thr Pro Leu Val Glu Pro Lys Pro Lys Thr Val Ser Ser Asn
    210                 215                 220
Asn Lys Ser Asn Ser Asn Ser Ser Thr Leu Asn Tyr Leu Lys Thr Leu
225                 230                 235                 240
Glu Asn Arg Gly Trp Asp Phe Asp Gly Ser Tyr Gly Trp Gln Cys Phe
                245                 250                 255
Asp Leu Val Asn Val Tyr Trp Asn His Leu Tyr Gly His Gly Leu Lys
                260                 265                 270
Gly Tyr Gly Ala Lys Asp Ile Pro Tyr Ala Asn Asn Phe Asn Ser Glu
            275                 280                 285
Ala Lys Ile Tyr His Asn Thr Pro Thr Phe Lys Ala Glu Pro Gly Asp
    290                 295                 300
Leu Val Val Phe Ser Gly Arg Phe Gly Gly Tyr Gly His Thr Ala
305                 310                 315                 320
Ile Val Leu Asn Gly Asp Tyr Asp Gly Lys Leu Met Lys Phe Gln Ser
                325                 330                 335
Leu Asp Gln Asn Trp Asn Asn Gly Gly Trp Arg Lys Ala Glu Val Ala
            340                 345                 350
His Lys Val Val His Asn Tyr Glu Asn Asp Met Ile Phe Ile Arg Pro
        355                 360                 365
Phe Lys Lys Ala
    370

<210> SEQ ID NO 78
<211> LENGTH: 304
<212> TYPE: PRT
<213> ORGANISM: Staphylococcus sp

<400> SEQUENCE: 78

Met Leu Lys Lys Ala Lys Phe Ile Leu Met Ala Thr Ile Leu Leu Ser
1               5                   10                  15

Gly Cys Ser Thr Thr Asn Asn Glu Ser Asn Lys Glu Thr Lys Ser Val
                20                  25                  30

Pro Glu Glu Met Asp Ala Ser Lys Tyr Val Gly Gln Gly Phe Gln Pro
            35                  40                  45

Pro Ala Glu Lys Asp Ala Ile Glu Phe Ala Lys Lys His Lys Asp Lys
        50                  55                  60

Ile Ala Lys Arg Gly Glu Gln Phe Phe Met Asp Asn Phe Gly Leu Lys
65                  70                  75                  80
```

```
Val Lys Ala Thr Asn Val Ile Gly Ser Gly Asp Gly Val Glu Val Phe
                85                  90                  95

Val His Cys Asp Asp His Asp Ile Val Phe Asn Ala Ser Ile Pro Phe
            100                 105                 110

Asp Lys Ser Ile Ile Asp Ser Asp Ser Ser Leu Arg Ser Lys Asp Lys
            115                 120                 125

Gly Asp Asp Met Ser Thr Leu Val Gly Ala Val Leu Ser Gly Phe Glu
130                 135                 140

Tyr Arg Ala Gln Lys Glu Lys Tyr Asp Lys Leu Tyr Lys Phe Phe Lys
145                 150                 155                 160

Asp Asn Glu Glu Lys Tyr Gln Tyr Thr Gly Phe Thr Lys Glu Ala Ile
                165                 170                 175

Asn Lys Thr Gln Asn Ser Gly Tyr Glu Asn Glu Tyr Phe Tyr Ile Ser
            180                 185                 190

Ala Ile Pro Tyr Asn Leu Ala Glu Tyr Arg Asp Tyr Phe Glu Pro Leu
            195                 200                 205

Leu Asn Lys Ser Asp Ser Glu Phe Ser Lys Glu Leu Ser Asn Val Lys
            210                 215                 220

Lys Gln Leu Lys Asp Lys Ser Lys Val Ser Val Thr Thr Thr Leu Phe
225                 230                 235                 240

Ser Lys Lys Asn Tyr Thr Lys Lys Ser Asn Ser Glu Asn Val Ile
                245                 250                 255

Lys Met Ala Glu Glu Ile Lys Lys Asp Lys Glu Ile Pro Asn Gly Ile
                260                 265                 270

Glu Leu Ser Ile Lys Phe Ser Asp Asn Lys Ile Asn Thr Val Lys Pro
            275                 280                 285

Asn Phe Asn Gly Glu Ser Thr Ser Glu Tyr Gly Val Phe Asp Gln Glu
            290                 295                 300

<210> SEQ ID NO 79
<211> LENGTH: 193
<212> TYPE: PRT
<213> ORGANISM: Staphylococcus sp

<400> SEQUENCE: 79

Met Lys Lys Leu Val Ser Ile Val Gly Ala Thr Leu Leu Ala Leu Gly
1               5                   10                  15

Cys Gly Ser Gln Asn Leu Ala Pro Leu Glu Glu Lys Thr Thr Asp Leu
                20                  25                  30

Arg Glu Asp Asn His Gln Leu Lys Leu Asp Ile Gln Glu Leu Asn Gln
            35                  40                  45

Gln Ile Ser Asp Ser Lys Ser Lys Ile Lys Gly Leu Glu Lys Asp Lys
50                  55                  60

Glu Asn Ser Lys Lys Thr Ala Ser Asn Asn Thr Lys Ile Lys Leu Met
65                  70                  75                  80

Asn Val Thr Ser Thr Tyr Tyr Asp Lys Val Ala Lys Ala Leu Lys Ser
                85                  90                  95

Tyr Asn Asp Ile Glu Lys Asp Val Ser Lys Asn Lys Gly Asp Lys Asn
            100                 105                 110

Val Gln Ser Lys Leu Asn Gln Ile Ser Asn Asp Ile Gln Ser Ala His
            115                 120                 125

Thr Ser Tyr Lys Asp Ala Ile Asp Gly Leu Ser Leu Ser Asp Asp Asp
            130                 135                 140

Lys Lys Thr Ser Lys Asn Ile Asp Lys Leu Asn Ser Asp Leu Asn His
145                 150                 155                 160
```

```
Ala Phe Asp Asp Ile Lys Asn Gly Tyr Gln Asn Lys Asp Lys Gln
                165                 170                 175

Leu Thr Lys Gly Gln Gln Ala Leu Ser Lys Leu Asn Leu Asn Ala Lys
            180                 185                 190

Ser

<210> SEQ ID NO 80
<211> LENGTH: 216
<212> TYPE: PRT
<213> ORGANISM: Staphylococcus sp

<400> SEQUENCE: 80

Met Lys Ile Thr Tyr Lys Tyr Arg Gly Asp Leu Pro Leu Asn Thr Glu
1               5                   10                  15

Asn Asn Lys Asn Gln Asn Gln Ser Val Lys Asn Ser Glu Arg Arg Gly
            20                  25                  30

Met Leu Lys Gly Cys Gly Gly Cys Leu Ile Ser Phe Ile Leu Leu Ile
        35                  40                  45

Ile Leu Leu Ser Ala Cys Ser Met Met Phe Ser Asn Asn Asp Asn Ser
50                  55                  60

Thr Asn Asn Gln Ser Ser Lys Thr Gln Leu Thr Gln Lys Asp Glu Asn
65                  70                  75                  80

Lys Asn Glu Asp Lys Pro Glu Glu Lys Ser Glu Thr Ala Thr Asp Glu
                85                  90                  95

Asp Leu Gln Ser Thr Glu Glu Val Pro Ala Asn Glu Asn Thr Glu Asn
            100                 105                 110

Asn Gln His Glu Ile Asp Glu Ile Thr Thr Lys Asp Gln Ser Asp Asp
        115                 120                 125

Asp Ile Asn Thr Pro Asn Val Ala Glu Asp Lys Ser Gln Asp Asp Leu
    130                 135                 140

Lys Asp Asp Leu Lys Glu Lys Gln Gln Ser Ser Asn His His Gln Ser
145                 150                 155                 160

Thr Gln Pro Lys Thr Ser Pro Ser Thr Glu Thr Asn Thr Gln Gln Ser
                165                 170                 175

Phe Ala Asn Cys Lys Gln Leu Arg Gln Val Tyr Pro Asn Gly Val Thr
            180                 185                 190

Ala Asp His Pro Ala Tyr Arg Pro His Leu Asp Arg Asp Lys Asp Lys
        195                 200                 205

Arg Ala Cys Glu Pro Asp Lys Tyr
    210                 215

<210> SEQ ID NO 81
<211> LENGTH: 208
<212> TYPE: PRT
<213> ORGANISM: Staphylococcus sp

<400> SEQUENCE: 81

Met Lys Phe Lys Ala Ile Val Ala Ile Thr Leu Ser Leu Ser Leu Leu
1               5                   10                  15

Thr Ala Cys Gly Ala Asn Gln His Lys Glu Asn Ser Ser Lys Ser Asn
            20                  25                  30

Asp Thr Asn Lys Lys Thr Gln Gln Thr Asp Asn Thr Thr Gln Ser Asn
        35                  40                  45

Thr Glu Lys Gln Met Thr Pro Gln Glu Ala Glu Asp Ile Val Arg Asn
    50                  55                  60
```

Asp Tyr Lys Ala Arg Gly Val Asn Glu Tyr Gln Thr Leu Asn Tyr Lys
65                  70                  75                  80

Thr Asn Leu Glu Arg Ser Asn Glu His Glu Tyr Tyr Val Glu His Leu
                85                  90                  95

Val Arg Asp Ala Val Gly Thr Pro Leu Lys Arg Cys Ala Ile Val Asn
            100                 105                 110

Arg His Asn Gly Thr Ile Ile Asn Ile Phe Asp Asp Met Ser Glu Lys
        115                 120                 125

Asp Lys Glu Glu Phe Glu Ala Phe Lys Lys Arg Ser Pro Lys Tyr Asn
    130                 135                 140

Pro Gly Met Asn Asn His Asp Glu Thr Asp Gly Glu Ser Glu Asp Ile
145                 150                 155                 160

Gln His His Asp Ile Asp Asn Asn Lys Ala Ile Gln Asn Asp Ile Pro
                165                 170                 175

Asp Gln Lys Val Asp Asp Lys Asn Asp Lys Asn Ala Val Asn Lys Glu
            180                 185                 190

Glu Lys His Asp Asn Gly Ala Asn Asn Ser Glu Glu Thr Lys Val Lys
        195                 200                 205

<210> SEQ ID NO 82
<211> LENGTH: 457
<212> TYPE: PRT
<213> ORGANISM: Staphylococcus sp

<400> SEQUENCE: 82

Met Lys Ile Ile Lys Arg Ala Ile Ile Ser Leu Ile Ile Leu Ser Leu
1               5                   10                  15

Leu Ile Ser Ile Thr Met Ser Asn Ala Ser Ala Ser Glu Glu Leu Tyr
                20                  25                  30

Tyr Ser Val Glu Tyr Lys Asn Thr Ala Thr Phe Asn Lys Leu Val Lys
            35                  40                  45

Lys Lys Ser Leu Asn Val Val Tyr Asn Ile Pro Glu Leu His Val Ala
        50                  55                  60

Gln Ile Lys Met Thr Lys Met His Ala Asn Ala Leu Ala Asn Tyr Lys
65                  70                  75                  80

Asn Asp Ile Lys Tyr Ile Asn Ala Thr Cys Ser Thr Cys Ile Thr Ser
                85                  90                  95

Glu Lys Thr Ile Asp Arg Thr Ser Asn Glu Ser Leu Phe Ser Arg Gln
            100                 105                 110

Trp Asp Met Asn Lys Ile Thr Asn Asn Gly Ala Ser Tyr Asp Asp Leu
        115                 120                 125

Pro Lys His Ala Asn Thr Lys Ile Ala Ile Ile Asp Thr Gly Val Met
    130                 135                 140

Lys Asn His Asp Asp Leu Lys Asn Asn Phe Ser Thr Asp Ser Lys Asn
145                 150                 155                 160

Leu Val Pro Leu Asn Gly Phe Arg Gly Thr Glu Pro Glu Thr Gly
                165                 170                 175

Asp Val His Asp Val Asn Asp Arg Lys Gly His Gly Thr Met Val Ser
            180                 185                 190

Gly Gln Thr Ser Ala Asn Gly Lys Leu Ile Gly Val Ala Pro Asn Asn
        195                 200                 205

Lys Phe Thr Met Tyr Arg Val Phe Gly Ser Lys Thr Glu Leu Leu
    210                 215                 220

Trp Val Ser Lys Ala Ile Val Gln Ala Ala Asn Asp Gly Asn Gln Val
225                 230                 235                 240

```
Ile Asn Ile Ser Val Gly Ser Tyr Ile Ile Leu Asp Lys Asn Asp His
            245                 250                 255

Gln Thr Phe Arg Lys Asp Glu Lys Val Glu Tyr Asp Ala Leu Gln Lys
            260                 265                 270

Ala Ile Asn Tyr Ala Lys Lys Lys Ser Ile Val Ala Ala Ala
            275                 280                 285

Gly Asn Asp Gly Ile Asp Val Asn Asp Lys Gln Lys Leu Lys Leu Gln
            290                 295                 300

Arg Glu Tyr Gln Gly Asn Gly Glu Val Lys Asp Val Pro Ala Ser Met
305                 310                 315                 320

Asp Asn Val Val Thr Val Gly Ser Thr Asp Gln Lys Ser Asn Leu Ser
            325                 330                 335

Glu Phe Ser Asn Phe Gly Met Asn Tyr Thr Asp Leu Ala Ala Pro Gly
            340                 345                 350

Gly Ser Phe Ala Tyr Leu Asn Gln Phe Gly Val Asp Lys Trp Met Asn
            355                 360                 365

Glu Gly Tyr Met His Lys Glu Asn Ile Leu Thr Thr Ala Asn Asn Gly
            370                 375                 380

Arg Tyr Ile Tyr Gln Ala Gly Thr Ser Leu Ala Thr Pro Lys Val Ser
385                 390                 395                 400

Gly Ala Leu Ala Leu Ile Ile Asp Lys Tyr His Leu Glu Lys His Pro
            405                 410                 415

Asp Lys Ala Ile Glu Leu Leu Tyr Gln His Gly Thr Ser Lys Asn Asn
            420                 425                 430

Lys Pro Phe Ser Arg Tyr Gly His Gly Glu Leu Asp Val Tyr Lys Ala
            435                 440                 445

Leu Asn Val Ala Asn Gln Lys Ala Ser
            450                 455

<210> SEQ ID NO 83
<211> LENGTH: 320
<212> TYPE: PRT
<213> ORGANISM: Staphylococcus sp

<400> SEQUENCE: 83

Met Lys Met Ile Asn Lys Leu Ile Val Pro Val Thr Ala Ser Ala Leu
1               5                   10                  15

Leu Leu Gly Ala Cys Gly Ala Ser Ala Thr Asp Ser Lys Glu Asn Thr
            20                  25                  30

Leu Ile Ser Ser Lys Ala Gly Asp Val Thr Val Ala Asp Thr Met Lys
        35                  40                  45

Lys Ile Gly Lys Asp Gln Ile Ala Asn Ala Ser Phe Thr Glu Met Leu
    50                  55                  60

Asn Lys Ile Leu Ala Asp Lys Tyr Lys Asn Lys Val Asn Asp Lys Lys
65                  70                  75                  80

Ile Asp Glu Gln Ile Glu Lys Met Gln Lys Tyr Gly Gly Lys Asp
            85                  90                  95

Lys Phe Glu Lys Ala Leu Gln Gln Gln Gly Leu Thr Ala Asp Lys Tyr
            100                 105                 110

Lys Glu Asn Leu Arg Thr Ala Ala Tyr His Lys Glu Leu Leu Ser Asp
            115                 120                 125

Lys Ile Lys Ile Ser Asp Ser Glu Ile Lys Glu Asp Ser Lys Lys Ala
            130                 135                 140

Ser His Ile Leu Ile Lys Val Lys Ser Lys Lys Ser Asp Lys Glu Gly
```

```
145                 150                 155                 160
Leu Asp Asp Lys Glu Ala Lys Gln Lys Ala Glu Glu Ile Gln Lys Glu
                165                 170                 175

Val Ser Lys Asp Pro Ser Lys Phe Gly Glu Ile Ala Lys Lys Glu Ser
                180                 185                 190

Met Asp Thr Gly Ser Ala Lys Lys Asp Gly Glu Leu Gly Tyr Val Leu
                195                 200                 205

Lys Gly Gln Thr Asp Lys Asp Phe Glu Lys Ala Leu Phe Lys Leu Lys
                210                 215                 220

Asp Gly Glu Val Ser Glu Val Val Lys Ser Ser Phe Gly Tyr His Leu
225                 230                 235                 240

Leu Lys Ala Asp Lys Pro Thr Asp Phe Asn Ser Glu Lys Gln Ser Leu
                245                 250                 255

Lys Glu Lys Leu Val Asp Gln Lys Val Gln Lys Asn Pro Lys Leu Leu
                260                 265                 270

Thr Asp Ala Tyr Lys Asp Leu Leu Lys Glu Tyr Asp Val Asp Phe Lys
                275                 280                 285

Asp Arg Asp Ile Lys Ser Val Val Glu Asp Lys Ile Leu Asn Pro Glu
                290                 295                 300

Lys Leu Lys Gln Gly Gly Ala Gln Gly Gly Gln Ser Gly Met Ser Gln
305                 310                 315                 320
```

<210> SEQ ID NO 84
<211> LENGTH: 388
<212> TYPE: PRT
<213> ORGANISM: Staphylococcus sp

<400> SEQUENCE: 84

```
Met Lys Arg Asn Phe Pro Lys Leu Ile Ala Leu Ser Leu Ile Phe Ser
1               5                   10                  15

Leu Ser Val Thr Pro Ile Ala Asn Ala Glu Ser Asn Ser Asn Leu Lys
                20                  25                  30

Ala Lys Asp Lys Lys His Val Gln Val Asn Val Glu Asp Lys Ser Val
                35                  40                  45

Pro Thr Asp Val Arg Asn Leu Ala Gln Lys Asp Tyr Leu Ser Tyr Val
                50                  55                  60

Thr Ser Leu Asp Lys Ile Tyr Asn Lys Glu Lys Ala Ser Tyr Thr Leu
65                  70                  75                  80

Gly Glu Pro Phe Lys Ile Tyr Lys Phe Asn Lys Lys Ser Asp Gly Asn
                85                  90                  95

Tyr Tyr Phe Pro Val Leu Asn Thr Glu Gly Asn Ile Asp Tyr Ile Val
                100                 105                 110

Thr Ile Ser Pro Lys Ile Thr Lys Tyr Ser Ser Ser Ser Ser Lys Tyr
                115                 120                 125

Thr Ile Asn Val Ser Pro Phe Leu Ser Lys Val Leu Asn Gln Tyr Lys
                130                 135                 140

Asp Gln Gln Ile Thr Ile Leu Thr Asn Ser Lys Gly Tyr Tyr Val Val
145                 150                 155                 160

Thr Gln Asn His Lys Ala Lys Leu Val Leu Lys Thr Pro Arg Leu Glu
                165                 170                 175

Asp Lys Lys Leu Lys Lys Thr Glu Ser Ile Pro Thr Gly Asn Asn Val
                180                 185                 190

Thr Gln Leu Lys Gln Lys Ala Ser Val Thr Met Pro Thr Ser Gln Phe
                195                 200                 205
```

```
Lys Ser Asn Asn Tyr Thr Tyr Asn Glu Gln Tyr Ile Asn Lys Leu Glu
    210                 215                 220

Asn Phe Lys Ile Arg Glu Thr Gln Gly Asn Asn Gly Trp Cys Ala Gly
225                 230                 235                 240

Tyr Thr Met Ser Glu Leu Leu Asn Ala Thr Tyr Asn Thr Asn Lys Tyr
                245                 250                 255

His Ala Glu Ala Val Met Arg Phe Leu His Pro Asn Leu Gln Gly Gln
            260                 265                 270

Arg Phe Gln Phe Thr Gly Leu Thr Pro Arg Glu Met Ile Tyr Phe Gly
        275                 280                 285

Gln Thr Gln Gly Arg Ser Pro Gln Leu Leu Asn Arg Met Thr Thr Tyr
    290                 295                 300

Asn Glu Val Asp Asn Leu Thr Lys Asn Asn Lys Gly Ile Ala Val Leu
305                 310                 315                 320

Gly Ser Arg Val Glu Ser Arg Asn Gly Met His Ala Gly His Ala Met
                325                 330                 335

Ala Val Val Gly Asn Ala Lys Leu Asp Asn Gly Gln Glu Val Ile Ile
            340                 345                 350

Ile Trp Asn Pro Trp Asp Asn Gly Phe Met Thr Gln Asp Ala Lys Asn
        355                 360                 365

Asn Val Ile Pro Val Ser Asn Gly Asp His Tyr Arg Trp Tyr Ser Ser
    370                 375                 380

Ile Tyr Gly Tyr
385

<210> SEQ ID NO 85
<211> LENGTH: 280
<212> TYPE: PRT
<213> ORGANISM: Staphylococcus sp

<400> SEQUENCE: 85

Met Lys Lys Phe Phe Phe Ile Gly Leu Leu Val Phe Val Val Phe Phe
1               5                   10                  15

Thr Ala Ala Thr Ile Ile Trp Phe Ser Tyr Asp Lys Asn Lys Tyr Gly
            20                  25                  30

Thr Lys Gln Tyr Asp Lys Thr Phe Lys Asp Asp Ala Phe Asp Asn Val
        35                  40                  45

Ser Ile Asn Leu Asp Ser Thr Glu Leu Arg Ile Lys Arg Gly Asn Gln
    50                  55                  60

Phe Arg Val Lys Tyr Asp Gly Asp Asn Asp Ile Leu Ile Asn Ile Val
65                  70                  75                  80

Asp Lys Thr Leu Lys Ile Ser Asp Lys Arg Ser Lys Thr Arg Gly Tyr
                85                  90                  95

Ala Ile Asp Met Asn Pro Phe His Glu Asn Lys Lys Thr Leu Thr Ile
            100                 105                 110

Glu Met Pro Asp Lys Met Ile Lys Arg Leu Asn Leu Ser Ser Gly Ala
        115                 120                 125

Gly Ser Val Arg Ile Ser Asp Val Asp Leu Glu Asn Thr Ser Ile Gln
    130                 135                 140

Ser Ile Asn Gly Glu Val Val Ile Lys Asn Ser Asn Leu Asp Ala Leu
145                 150                 155                 160

Asp Ser Lys Thr Asn Asn Ser Ser Thr Tyr Ile Ser Lys Ser Asn Ile
                165                 170                 175

Lys Asn Ser Asn Ile Lys Val Val Ile Gly Thr Leu Gln Ile Asp Lys
            180                 185                 190
```

```
Ser Gln Ile Lys Gln Ser Ile Phe Leu Asn Asp His Gly Asp Ile Glu
            195                 200                 205

Phe Lys Asn Met Pro Ser Lys Val Asp Ala Lys Ala Ser Thr Lys Gln
            210                 215                 220

Gly Asp Ile Arg Phe Lys Tyr Asp Ser Lys Pro Glu Asp Thr Ile Leu
225                 230                 235                 240

Lys Leu Asn Pro Gly Thr Gly Asp Ser Val Val Lys Asn Lys Thr Phe
                245                 250                 255

Thr Asn Gly Lys Val Gly Lys Ser Asp Asn Val Leu Glu Phe Tyr Thr
            260                 265                 270

Ile Asp Gly Asn Ile Lys Val Glu
            275                 280

<210> SEQ ID NO 86
<211> LENGTH: 303
<212> TYPE: PRT
<213> ORGANISM: Staphylococcus sp

<400> SEQUENCE: 86

Met Lys Arg Leu Ile Gly Ile Leu Leu Cys Asn Leu Phe Ile Leu Thr
1               5                   10                  15

Ala Cys Ser Ala Ser Val Asp Lys Thr Ser Asn Ser Thr Lys Thr Thr
            20                  25                  30

Asp Tyr Lys Ile Glu Asn Gly Glu Thr Leu Lys Val Pro Glu Lys Pro
            35                  40                  45

Lys Arg Val Ala Val Leu Thr Gly Phe Tyr Val Gly Asp Phe Ile Lys
50                  55                  60

Leu Gly Ile Lys Pro Ile Ala Val Ser Asp Ile Thr Lys Asp Ser Ser
65                  70                  75                  80

Ile Leu Lys Pro Tyr Leu Lys Gly Val Asp Tyr Ile Gly Glu Asn Asp
                85                  90                  95

Val Glu Arg Val Ala Lys Ala Lys Pro Asp Leu Ile Val Val Asp Ala
            100                 105                 110

Met Asp Lys Asn Ile Lys Lys Tyr Gln Lys Ile Ala Pro Thr Ile Pro
            115                 120                 125

Tyr Thr Tyr Asn Lys Tyr Asn His Lys Glu Ile Leu Lys Glu Ile Gly
            130                 135                 140

Lys Leu Thr Asn Asn Glu Asp Lys Ala Lys Lys Trp Ile Glu Glu Trp
145                 150                 155                 160

Asp Asp Lys Thr Arg Lys Asp Lys Glu Ile Gln Ser Lys Ile Gly
                165                 170                 175

Gln Ala Thr Ala Ser Val Phe Glu Pro Asp Glu Lys Gln Ile Tyr Ile
            180                 185                 190

Tyr Asn Ser Thr Trp Gly Arg Gly Leu Asp Ile Val His Asp Ala Phe
            195                 200                 205

Gly Met Pro Met Thr Lys Gln Tyr Lys Asp Lys Leu Gln Glu Asp Lys
            210                 215                 220

Lys Gly Tyr Ala Ser Ile Ser Lys Glu Asn Ile Ser Lys Tyr Ala Gly
225                 230                 235                 240

Asp Tyr Ile Phe Leu Ser Lys Pro Ser Tyr Gly Lys Phe Asp Phe Glu
                245                 250                 255

Lys Thr His Thr Trp Gln Asn Ile Glu Ala Val Lys Lys Gly His Val
            260                 265                 270

Ile Ser Tyr Lys Ala Glu Asp Tyr Trp Phe Thr Asp Pro Ile Thr Leu
```

275                 280                 285
Glu His Leu Arg Ser Lys Leu Lys Lys Glu Ile Leu Asn Lys Lys
    290                 295                 300

<210> SEQ ID NO 87
<211> LENGTH: 419
<212> TYPE: PRT
<213> ORGANISM: Staphylococcus sp

<400> SEQUENCE: 87

Met Ser Tyr His Trp Phe Lys Lys Met Leu Ser Thr Ser Ile Leu
1               5                   10                  15

Ile Leu Ser Ser Ser Leu Gly Leu Ala Thr His Thr Val Glu Ala
                20                  25                  30

Lys Asp Asn Leu Asn Gly Glu Lys Pro Thr Thr Asn Leu Asn His Asn
            35                  40                  45

Ile Thr Ser Pro Ser Val Asn Ser Glu Met Asn Asn Asn Glu Thr Gly
    50                  55                  60

Thr Pro His Glu Ser Asn Gln Thr Gly Asn Glu Gly Thr Gly Ser Asn
65                  70                  75                  80

Ser Arg Asp Ala Asn Pro Asp Ser Asn Asn Val Lys Pro Asp Ser Asn
                85                  90                  95

Asn Gln Asn Pro Ser Thr Asp Ser Lys Pro Asp Pro Asn Asn Gln Asn
            100                 105                 110

Ser Ser Pro Asn Pro Lys Pro Asp Pro Asp Asn Pro Lys Pro Lys Pro
        115                 120                 125

Asp Pro Lys Pro Asp Pro Lys Pro Lys Pro Asn Pro Asp Pro Lys
    130                 135                 140

Pro Asp Pro Asp Asn Pro Lys Pro Asn Pro Asp Pro Lys Pro Asp Pro
145                 150                 155                 160

Asp Lys Pro Lys Pro Asn Pro Asp Pro Lys Pro Asp Pro Asp Lys Pro
                165                 170                 175

Lys Pro Asn Pro Asn Pro Lys Pro Asp Pro Asn Lys Pro Asn Pro Asn
            180                 185                 190

Pro Ser Pro Asp Pro Asp Gln Pro Gly Asp Ser Asn His Ser Gly Gly
        195                 200                 205

Ser Lys Asn Gly Gly Thr Trp Asn Pro Asn Ala Ser Asp Gly Ser Asn
    210                 215                 220

Gln Gly Gln Trp Gln Pro Asn Gly Asn Gln Gly Asn Ser Gln Asn Pro
225                 230                 235                 240

Thr Gly Asn Asp Phe Val Ser Gln Arg Phe Leu Ala Leu Ala Asn Gly
                245                 250                 255

Ala Tyr Lys Tyr Asn Pro Tyr Ile Leu Asn Gln Ile Asn Lys Leu Gly
            260                 265                 270

Lys Asp Tyr Gly Glu Val Thr Asp Glu Asp Ile Tyr Asn Ile Ile Arg
        275                 280                 285

Lys Gln Asn Phe Ser Gly Asn Ala Tyr Leu Asn Gly Leu Gln Gln Gln
    290                 295                 300

Ser Asn Tyr Phe Arg Phe Gln Tyr Phe Asn Pro Leu Lys Ser Glu Arg
305                 310                 315                 320

Tyr Tyr Arg Asn Leu Asp Glu Gln Val Leu Ala Leu Ile Thr Gly Glu
                325                 330                 335

Ile Gly Ser Met Pro Asp Leu Lys Lys Pro Glu Asp Lys Pro Asp Ser
            340                 345                 350

```
Lys Gln Arg Ser Phe Glu Pro His Glu Lys Asp Asp Phe Thr Val Val
            355                 360                 365

Lys Lys Gln Glu Asp Asn Lys Lys Ser Ala Ser Thr Ala Tyr Ser Lys
    370                 375                 380

Ser Trp Leu Ala Ile Val Cys Ser Met Met Val Val Phe Ser Ile Met
385                 390                 395                 400

Leu Phe Leu Phe Val Lys Arg Asn Lys Lys Asn Lys Asn Glu Ser
                405                 410                 415

Gln Arg Arg

<210> SEQ ID NO 88
<211> LENGTH: 231
<212> TYPE: PRT
<213> ORGANISM: Staphylococcus sp

<400> SEQUENCE: 88

Met Lys Lys Thr Leu Leu Ala Ser Ser Leu Ala Val Gly Leu Gly Ile
1               5                   10                  15

Val Ala Gly Asn Ala Gly His Glu Ala His Ala Ser Glu Ala Asp Leu
            20                  25                  30

Asn Lys Ala Ser Leu Ala Gln Met Ala Gln Ser Asn Asp Gln Thr Leu
        35                  40                  45

Asn Gln Lys Pro Ile Glu Ala Gly Ala Tyr Asn Tyr Thr Phe Asp Tyr
    50                  55                  60

Glu Gly Phe Thr Tyr His Phe Glu Ser Asp Gly Thr His Phe Ala Trp
65                  70                  75                  80

Asn Tyr His Ala Thr Gly Thr Asn Gly Ala Asp Met Ser Ala Gln Ala
                85                  90                  95

Pro Ala Thr Asn Asn Val Ala Pro Ser Ala Val Gln Ala Asn Gln Val
            100                 105                 110

Gln Ser Gln Glu Val Glu Ala Pro Gln Asn Ala Gln Thr Gln Gln Pro
        115                 120                 125

Gln Ala Ser Thr Ser Asn Asn Ser Gln Val Thr Ala Thr Pro Thr Glu
    130                 135                 140

Ser Lys Ser Ser Glu Gly Ser Ser Val Asn Val Asn Ala His Leu Lys
145                 150                 155                 160

Gln Ile Ala Gln Arg Glu Ser Gly Gly Asn Ile His Ala Val Asn Pro
                165                 170                 175

Thr Ser Gly Ala Ala Gly Lys Tyr Gln Phe Leu Gln Ser Thr Trp Asp
            180                 185                 190

Ser Val Ala Pro Ala Lys Tyr Lys Gly Val Ser Pro Ala Asn Ala Pro
        195                 200                 205

Glu Ser Val Gln Asp Ala Ala Ala Val Lys Leu Tyr Asn Thr Gly Gly
    210                 215                 220

Ala Gly His Trp Val Thr Ala
225                 230

<210> SEQ ID NO 89
<211> LENGTH: 294
<212> TYPE: PRT
<213> ORGANISM: Staphylococcus sp

<400> SEQUENCE: 89

Met Gly Val Lys Ser Val Lys Lys Ile Phe Val Ile Ile Thr Thr Leu
1               5                   10                  15

Leu Ala Val Ala Ile Ile Ile Gly Ser Ile Ile Met Val Val Phe Ser
```

```
                 20                  25                  30
Gln Arg Gln Ala Gln Thr Phe Lys Ile Gln Gln Gln Phe Val Lys
             35                  40                  45

Lys Pro Ile Pro Thr Leu Phe Leu His Gly Phe Gly Gly Ser Ala Asn
 50                  55                  60

Ser Glu Lys Phe Met Val Lys Gln Ala Glu Lys Arg Gly Val Thr Lys
 65                  70                  75                  80

Asp Ile Ile Thr Ala Tyr Val Ser Lys Asp Gly Ala Val Thr Phe Lys
                 85                  90                  95

Gly Lys Leu Arg Lys Asp Ala Val Asn Pro Ile Val Lys Ile Glu Leu
            100                 105                 110

Glu Asn Asn Arg Gln Gly Tyr Leu Asp Lys Asn Ala Ala Trp Phe Lys
            115                 120                 125

Asn Val Leu Thr Lys Leu Gln Ser Glu Tyr Asn Phe Asp Lys Phe Asn
            130                 135                 140

Phe Val Gly His Ser Met Gly Asn Leu Thr Phe Ala Gln Tyr Met Met
145                 150                 155                 160

Thr Tyr Gly Asn Asp Lys Ser Leu Pro Gln Leu Asn Lys Gln Val Asn
                165                 170                 175

Ile Ala Gly Thr Phe Asn Gly Val Leu Asn Met Asn Glu Asp Val Asn
            180                 185                 190

Glu Ile Thr Val Asp Lys Asp Gly Lys Pro Ser Arg Met Asn Gln Pro
            195                 200                 205

Tyr Gln Gln Leu Arg Val Leu Lys Asp Ile Tyr Lys Gly Lys Gly Ile
            210                 215                 220

Glu Val Leu Asn Ile Tyr Gly Asp Leu Lys Asp Gly Thr His Ser Asp
225                 230                 235                 240

Gly Arg Val Ser Asn Ser Ser Lys Ser Leu Lys Tyr Leu Leu Gly
                245                 250                 255

Asn Ser Pro Lys Ser Tyr Arg Glu Ser Lys Tyr Glu Gly Glu Pro Ala
                260                 265                 270

Gln His Ser Gln Leu His Glu Asn Glu Asn Val Ala Asn Glu Leu Ile
            275                 280                 285

Asp Phe Leu Trp Lys Lys
            290

<210> SEQ ID NO 90
<211> LENGTH: 807
<212> TYPE: PRT
<213> ORGANISM: Staphylococcus sp

<400> SEQUENCE: 90

Met Thr Tyr Arg Ile Lys Lys Trp Gln Lys Leu Ser Thr Ile Thr Leu
 1               5                  10                  15

Leu Met Ala Gly Val Ile Thr Leu Asn Gly Gly Glu Phe Arg Ser Val
             20                  25                  30

Asp Lys His Gln Ile Ala Val Ala Asp Thr Asn Val Gln Thr Pro Asp
             35                  40                  45

Tyr Glu Lys Leu Arg Asn Thr Trp Leu Asp Val Asn Tyr Gly Tyr Asp
 50                  55                  60

Lys Tyr Asp Glu Asn Asn Pro Asp Met Lys Lys Lys Phe Asp Ala Thr
 65                  70                  75                  80

Glu Lys Glu Ala Thr Asn Leu Leu Lys Glu Met Lys Thr Glu Ser Gly
                 85                  90                  95
```

```
Arg Lys Tyr Leu Trp Ser Gly Ala Glu Thr Leu Glu Thr Asn Ser Ser
                100                 105                 110

His Met Thr Arg Thr Tyr Arg Asn Ile Glu Lys Ile Ala Glu Ala Met
            115                 120                 125

Arg Asn Pro Lys Thr Thr Leu Asn Thr Asp Glu Asn Lys Lys Lys Val
        130                 135                 140

Lys Asp Ala Leu Glu Trp Leu His Lys Asn Ala Tyr Gly Lys Glu Pro
145                 150                 155                 160

Asp Lys Lys Val Lys Glu Leu Ser Glu Asn Phe Thr Lys Thr Thr Gly
                165                 170                 175

Lys Asn Thr Asn Leu Asn Trp Trp Asp Tyr Glu Ile Gly Thr Pro Lys
            180                 185                 190

Ser Leu Thr Asn Thr Leu Ile Leu Leu Asn Asp Gln Phe Ser Asn Glu
        195                 200                 205

Glu Lys Lys Lys Phe Thr Ala Pro Ile Lys Thr Phe Ala Pro Asp Ser
    210                 215                 220

Asp Lys Ile Leu Ser Ser Val Gly Lys Ala Glu Leu Ala Lys Gly Gly
225                 230                 235                 240

Asn Leu Val Asp Ile Ser Lys Val Lys Leu Leu Glu Cys Ile Ile Glu
                245                 250                 255

Glu Asp Lys Asp Met Met Lys Lys Ser Ile Asp Ser Phe Asn Lys Val
            260                 265                 270

Phe Thr Tyr Val Gln Asp Ser Ala Thr Gly Lys Glu Arg Asn Gly Phe
        275                 280                 285

Tyr Lys Asp Gly Ser Tyr Ile Asp His Gln Asp Val Pro Tyr Thr Gly
    290                 295                 300

Ala Tyr Gly Val Val Leu Leu Glu Gly Ile Ser Gln Met Met Pro Met
305                 310                 315                 320

Ile Lys Glu Thr Pro Phe Asn Asp Lys Thr Gln Asn Asp Thr Thr Leu
                325                 330                 335

Lys Ser Trp Ile Asp Asp Gly Phe Met Pro Leu Ile Tyr Lys Gly Glu
            340                 345                 350

Met Met Asp Leu Ser Arg Gly Arg Ala Ile Ser Arg Glu Asn Glu Thr
        355                 360                 365

Ser His Ser Ala Ser Ala Thr Val Met Lys Ser Leu Leu Arg Leu Ser
    370                 375                 380

Asp Ala Met Asp Asp Ser Thr Lys Ala Lys Tyr Lys Lys Ile Val Lys
385                 390                 395                 400

Ser Ser Val Glu Ser Asp Ser Ser Tyr Lys Gln Asn Asp Tyr Leu Asn
                405                 410                 415

Ser Tyr Ser Asp Ile Asp Lys Met Lys Ser Leu Met Thr Asp Asn Ser
            420                 425                 430

Ile Ser Lys Asn Gly Leu Thr Gln Gln Leu Lys Ile Tyr Asn Asp Met
        435                 440                 445

Asp Arg Val Thr Tyr His Asn Lys Asp Leu Asp Phe Ala Phe Gly Leu
    450                 455                 460

Ser Met Thr Ser Lys Asn Val Ala Arg Tyr Glu Ser Ile Asn Gly Glu
465                 470                 475                 480

Asn Leu Lys Gly Trp His Thr Gly Ala Gly Met Ser Tyr Leu Tyr Asn
                485                 490                 495

Ser Asp Val Lys His Tyr His Asp Asn Phe Trp Val Thr Ala Asp Met
            500                 505                 510

Lys Arg Leu Ser Gly Thr Thr Thr Leu Asp Asn Glu Ile Leu Lys Asp
```

```
                515                 520                 525
Thr Asp Asp Lys Lys Ser Ser Lys Thr Phe Val Gly Gly Thr Lys Val
530                 535                 540

Asp Asp Gln His Ala Ser Ile Gly Met Asp Phe Glu Asn Gln Asp Lys
545                 550                 555                 560

Thr Leu Thr Ala Lys Lys Ser Tyr Phe Ile Leu Asn Asp Lys Ile Val
                565                 570                 575

Phe Leu Gly Thr Gly Ile Lys Ser Thr Asp Ser Ser Lys Asn Pro Val
                580                 585                 590

Thr Thr Ile Glu Asn Arg Lys Ala Asn Gly Tyr Thr Leu Tyr Thr Asp
                595                 600                 605

Asp Lys Gln Thr Thr Asn Ser Asp Asn Gln Glu Asn Ser Val Phe
                610                 615                 620

Leu Glu Ser Thr Asp Thr Lys Lys Asn Ile Gly Tyr His Phe Leu Asn
625                 630                 635                 640

Lys Pro Lys Ile Thr Val Lys Lys Glu Ser His Thr Gly Lys Trp Lys
                645                 650                 655

Glu Ile Asn Lys Ser Gln Lys Asp Thr Gln Lys Thr Asp Glu Tyr Tyr
                660                 665                 670

Glu Val Thr Gln Lys His Ser Asn Ser Asp Asn Lys Tyr Gly Tyr Val
                675                 680                 685

Leu Tyr Pro Gly Leu Ser Lys Asp Val Phe Lys Thr Lys Lys Asp Glu
                690                 695                 700

Val Thr Val Val Lys Gln Glu Asp Asp Phe His Val Val Lys Asp Asn
705                 710                 715                 720

Glu Ser Val Trp Ala Gly Val Asn Tyr Ser Asn Ser Thr Gln Thr Phe
                725                 730                 735

Asp Ile Asn Asn Thr Lys Val Glu Val Lys Ala Lys Gly Met Phe Ile
                740                 745                 750

Leu Lys Lys Lys Asp Asp Asn Thr Tyr Glu Cys Ser Phe Tyr Asn Pro
                755                 760                 765

Glu Ser Thr Asn Ser Ala Ser Asp Ile Glu Ser Lys Ile Ser Met Thr
                770                 775                 780

Gly Tyr Ser Ile Thr Asn Lys Asn Thr Ser Thr Ser Asn Glu Ser Gly
785                 790                 795                 800

Val His Phe Glu Leu Thr Lys
                805

<210> SEQ ID NO 91
<211> LENGTH: 166
<212> TYPE: PRT
<213> ORGANISM: Staphylococcus sp

<400> SEQUENCE: 91

Met Lys Lys Leu Val Thr Ala Thr Thr Leu Thr Ala Gly Ile Gly Thr
1               5                   10                  15

Ala Leu Val Gly Gln Ala His His Ala Asp Ala Ala Glu Asn Tyr Thr
                20                  25                  30

Asn Tyr Asn Asn Tyr Asn Tyr Asn Thr Gln Thr Thr Thr Thr
                35                  40                  45

Thr Thr Thr Thr Thr Thr Ser Ser Ile Ser His Ser Gly Asn Leu Tyr
        50                  55                  60

Thr Ala Gly Gln Cys Thr Trp Tyr Val Tyr Asp Lys Val Gly Gly Glu
65                  70                  75                  80
```

```
Ile Gly Ser Thr Trp Gly Asn Ala Asn Asn Trp Ala Ala Ala Ala Gln
                 85                  90                  95

Gly Ala Gly Phe Thr Val Asn His Thr Pro Ser Lys Gly Ala Ile Leu
            100                 105                 110

Gln Ser Ser Glu Gly Pro Phe Gly His Val Ala Tyr Val Glu Ser Val
        115                 120                 125

Asn Ser Asp Gly Ser Val Thr Ile Ser Glu Met Asn Tyr Ser Gly Gly
130                 135                 140

Pro Phe Ser Val Ser Ser Arg Thr Ile Ser Ala Ser Glu Ala Gly Asn
145                 150                 155                 160

Tyr Asn Tyr Ile His Ile
                165

<210> SEQ ID NO 92
<211> LENGTH: 516
<212> TYPE: PRT
<213> ORGANISM: Staphylococcus sp

<400> SEQUENCE: 92

Met Lys Lys Lys Leu Gly Met Leu Leu Val Pro Ala Val Thr Leu
1               5                   10                  15

Ser Leu Ala Ala Cys Gly Asn Asp Asp Gly Lys Asp Lys Asp Gly Lys
                20                  25                  30

Val Thr Ile Lys Thr Thr Val Tyr Pro Leu Gln Ser Phe Ala Glu Gln
            35                  40                  45

Ile Gly Gly Lys His Val Lys Val Ser Ser Ile Tyr Pro Ala Gly Thr
        50                  55                  60

Asp Leu His Ser Tyr Glu Pro Thr Gln Lys Asp Ile Leu Ser Ala Ser
65                  70                  75                  80

Lys Ser Asp Leu Phe Met Tyr Thr Gly Asp Asn Leu Asp Pro Val Ala
                85                  90                  95

Lys Lys Val Ala Ser Thr Ile Lys Asp Lys Asp Lys Lys Leu Ser Leu
            100                 105                 110

Glu Asp Lys Leu Asp Lys Ala Lys Leu Leu Thr Asp Gln His Glu His
        115                 120                 125

Gly Glu Glu His Glu His Gly His Asp His Glu Lys Glu Glu His
130                 135                 140

His His His Gly Gly Tyr Asp Pro His Val Trp Leu Asp Pro Lys
145                 150                 155                 160

Ile Asn Gln Thr Phe Ala Lys Glu Ile Lys Asp Glu Leu Val Lys Lys
                165                 170                 175

Asp Pro Lys His Lys Asp Asp Tyr Glu Lys Asn Tyr Lys Lys Leu Asn
            180                 185                 190

Asp Asp Leu Lys Lys Ile Asp Asn Asp Met Lys Gln Val Thr Lys Asp
        195                 200                 205

Lys Gln Gly Asn Ala Val Phe Ile Ser His Glu Ser Ile Gly Tyr Leu
210                 215                 220

Ala Asp Cys Tyr Gly Phe Val Gln Lys Gly Ile Gln Asn Met Asn Ala
225                 230                 235                 240

Glu Asp Pro Ser Gln Lys Glu Leu Thr Lys Ile Val Lys Glu Ile Arg
                245                 250                 255

Asp Ser Asn Ala Lys Tyr Ile Leu Tyr Glu Asp Asn Val Ala Asn Lys
            260                 265                 270

Val Thr Glu Thr Ile Arg Lys Glu Thr Asp Ala Lys Pro Leu Lys Phe
        275                 280                 285
```

```
Tyr Asn Met Glu Ser Leu Asn Lys Glu Gln Gln Lys Lys Asp Asn Ile
            290                 295                 300

Thr Tyr Gln Ser Leu Met Lys Ser Asn Ile Glu Asn Ile Gly Lys Ala
305                 310                 315                 320

Leu Asp Ser Gly Val Lys Val Lys Asp Lys Ala Glu Ser Lys His
                325                 330                 335

Asp Lys Ala Ile Ser Asp Gly Tyr Phe Lys Asp Glu Gln Val Lys Asp
            340                 345                 350

Arg Glu Leu Ser Asp Tyr Ala Gly Glu Trp Gln Ser Val Tyr Pro Tyr
            355                 360                 365

Leu Lys Asp Gly Thr Leu Asp Glu Val Met Glu His Lys Ala Glu Asn
            370                 375                 380

Asp Pro Lys Lys Ser Ala Lys Asp Leu Lys Ala Tyr Tyr Asp Lys Gly
385                 390                 395                 400

Tyr Lys Thr Asp Ile Thr Asn Ile Asp Ile Lys Gly Asn Glu Ile Thr
            405                 410                 415

Phe Thr Lys Asp Gly Lys Lys His Thr Gly Lys Tyr Glu Tyr Asn Gly
            420                 425                 430

Lys Lys Thr Leu Lys Tyr Pro Lys Gly Asn Arg Gly Val Arg Phe Met
            435                 440                 445

Phe Lys Leu Val Asp Gly Asn Asp Lys Asp Leu Pro Lys Phe Ile Gln
450                 455                 460

Phe Ser Asp His Asn Ile Ala Pro Lys Lys Ala Glu His Phe His Ile
465                 470                 475                 480

Phe Met Gly Asn Asp Asn Asp Ala Leu Leu Lys Glu Met Asp Asn Trp
                485                 490                 495

Pro Thr Tyr Tyr Pro Ser Lys Leu Asn Lys Asp Gln Ile Lys Glu Glu
                500                 505                 510

Met Leu Ala His
        515

<210> SEQ ID NO 93
<211> LENGTH: 309
<212> TYPE: PRT
<213> ORGANISM: Staphylococcus sp

<400> SEQUENCE: 93

Met Ile Lys Asn Lys Ile Leu Thr Ala Thr Leu Ala Val Gly Leu Ile
1               5                   10                  15

Ala Pro Leu Ala Asn Pro Phe Ile Glu Ile Ser Lys Ala Glu Asn Lys
            20                  25                  30

Ile Glu Asp Ile Gly Gln Gly Ala Glu Ile Ile Lys Arg Thr Gln Asp
        35                  40                  45

Ile Thr Ser Lys Arg Leu Ala Ile Thr Gln Asn Ile Gln Phe Asp Phe
    50                  55                  60

Val Lys Asp Lys Lys Tyr Asn Lys Asp Ala Leu Val Val Lys Met Gln
65                  70                  75                  80

Gly Phe Ile Ser Ser Arg Thr Thr Tyr Ser Asp Leu Lys Lys Tyr Pro
                85                  90                  95

Tyr Ile Lys Arg Met Ile Trp Pro Phe Gln Tyr Asn Ile Ser Leu Lys
            100                 105                 110

Thr Lys Asp Ser Asn Val Asp Leu Ile Asn Tyr Leu Pro Lys Asn Lys
            115                 120                 125

Ile Asp Ser Ala Asp Val Ser Gln Lys Leu Gly Tyr Asn Ile Gly Gly
```

```
                130               135               140
Asn Phe Gln Ser Ala Pro Ser Ile Gly Gly Ser Gly Ser Phe Asn Tyr
145                 150               155                 160

Ser Lys Thr Ile Ser Tyr Asn Gln Lys Asn Tyr Val Thr Glu Val Glu
                165               170               175

Ser Gln Asn Ser Lys Gly Val Lys Trp Gly Val Lys Ala Asn Ser Phe
            180               185               190

Val Thr Pro Asn Gly Gln Val Ser Ala Tyr Asp Gln Tyr Leu Phe Ala
        195               200               205

Gln Asp Pro Thr Gly Pro Ala Ala Arg Asp Tyr Phe Val Pro Asp Asn
210                 215               220

Gln Leu Pro Pro Leu Ile Gln Ser Gly Phe Asn Pro Ser Phe Ile Thr
225                 230               235                 240

Thr Leu Ser His Glu Arg Gly Lys Gly Asp Lys Ser Glu Phe Glu Ile
                245               250               255

Thr Tyr Gly Arg Asn Met Asp Ala Thr Tyr Ala Tyr Val Thr Arg His
            260               265               270

Arg Leu Ala Val Asp Arg Lys His Asp Ala Phe Lys Asn Arg Asn Val
        275               280               285

Thr Val Lys Tyr Glu Val Asn Trp Lys Thr His Glu Val Lys Ile Lys
290                 295               300

Ser Ile Thr Pro Lys
305

<210> SEQ ID NO 94
<211> LENGTH: 532
<212> TYPE: PRT
<213> ORGANISM: Staphylococcus sp

<400> SEQUENCE: 94

Met Arg Lys Leu Thr Lys Met Ser Ala Met Leu Leu Ala Ser Gly Leu
1               5                   10                  15

Ile Leu Thr Gly Cys Gly Gly Asn Lys Gly Leu Glu Glu Lys Lys Glu
                20                  25                  30

Asn Lys Gln Leu Thr Tyr Thr Thr Val Lys Asp Ile Gly Asp Met Asn
            35                  40                  45

Pro His Val Tyr Gly Gly Ser Met Ser Ala Glu Ser Met Ile Tyr Glu
        50                  55                  60

Pro Leu Val Arg Asn Thr Lys Asp Gly Ile Lys Pro Leu Leu Ala Lys
65                  70                  75                  80

Lys Trp Asp Val Ser Glu Asp Gly Lys Thr Tyr Thr Phe His Leu Arg
                85                  90                  95

Asp Asp Val Lys Phe His Asp Gly Thr Pro Phe Asp Ala Asp Ala Val
                100                 105                 110

Lys Lys Asn Ile Asp Ala Val Gln Glu Asn Lys Lys Leu His Ser Trp
            115                 120                 125

Leu Lys Ile Ser Thr Leu Ile Asp Asn Val Lys Val Lys Asp Lys Tyr
        130                 135                 140

Thr Val Glu Leu Asn Leu Lys Glu Ala Tyr Gln Pro Ala Leu Ala Glu
145                 150                 155                 160

Leu Ala Met Pro Arg Pro Tyr Val Phe Val Ser Pro Lys Asp Phe Lys
                165                 170                 175

Asn Gly Thr Thr Lys Asp Gly Val Lys Lys Phe Asp Gly Thr Gly Pro
            180                 185                 190
```

Phe Lys Leu Gly Glu His Lys Lys Asp Glu Ser Ala Asp Phe Asn Lys
            195                 200                 205

Asn Asp Gln Tyr Trp Gly Glu Lys Ser Lys Leu Asn Lys Val Gln Ala
        210                 215                 220

Lys Val Met Pro Ala Gly Glu Thr Ala Phe Leu Ser Met Lys Lys Gly
225                 230                 235                 240

Glu Thr Asn Phe Ala Phe Thr Asp Asp Arg Gly Thr Asp Ser Leu Asp
                245                 250                 255

Lys Asp Ser Leu Lys Gln Leu Lys Asp Thr Gly Asp Tyr Gln Val Lys
            260                 265                 270

Arg Ser Gln Pro Met Asn Thr Lys Met Leu Val Val Asn Ser Gly Lys
        275                 280                 285

Lys Asp Asn Ala Val Ser Asp Lys Thr Val Arg Gln Ala Ile Gly His
290                 295                 300

Met Val Asn Arg Asp Lys Ile Ala Lys Glu Ile Leu Asp Gly Gln Glu
305                 310                 315                 320

Lys Pro Ala Thr Gln Leu Phe Ala Lys Asn Val Thr Asp Ile Asn Phe
                325                 330                 335

Asp Met Pro Thr Arg Lys Tyr Asp Leu Lys Lys Ala Glu Ser Leu Leu
            340                 345                 350

Asp Glu Ala Gly Trp Lys Lys Gly Lys Asp Ser Asp Val Arg Gln Lys
        355                 360                 365

Asp Gly Lys Asn Leu Glu Met Ala Met Tyr Tyr Asp Lys Gly Ser Ser
370                 375                 380

Ser Gln Lys Glu Gln Ala Glu Tyr Leu Gln Ala Glu Phe Lys Lys Met
385                 390                 395                 400

Gly Ile Lys Leu Asn Ile Asn Gly Glu Thr Ser Asp Lys Ile Ala Glu
                405                 410                 415

Arg Arg Thr Ser Gly Asp Tyr Asp Leu Met Phe Asn Gln Thr Trp Gly
            420                 425                 430

Leu Leu Tyr Asp Pro Gln Ser Thr Leu Ala Ala Phe Lys Glu Lys Asn
        435                 440                 445

Gly Tyr Glu Ser Ala Thr Ser Gly Ile Glu Asn Lys Asp Lys Ile Tyr
450                 455                 460

Asn Ser Ile Asp Asp Ala Phe Lys Ile Gln Asn Gly Lys Glu Arg Ser
465                 470                 475                 480

Asp Ala Tyr Lys Asn Ile Leu Lys Gln Ile Asp Asp Glu Gly Ile Phe
                485                 490                 495

Ile Pro Ile Ser His Gly Ser Met Thr Val Val Ala Pro Lys Asp Leu
            500                 505                 510

Glu Lys Val Ser Phe Thr Gln Ser Gln Tyr Glu Leu Pro Phe Asn Glu
        515                 520                 525

Met Gln Tyr Lys
530

<210> SEQ ID NO 95
<211> LENGTH: 264
<212> TYPE: PRT
<213> ORGANISM: Staphylococcus sp

<400> SEQUENCE: 95

Met Ile His Ser Lys Lys Leu Thr Leu Gly Ile Cys Leu Val Leu Leu
1               5                   10                  15

Ile Ile Leu Ile Val Gly Tyr Val Ile Met Thr Lys Thr Asn Gly Arg
            20                  25                  30

Asn Ala Gln Ile Lys Asp Thr Phe Asn Gln Thr Leu Lys Leu Tyr Pro
            35                  40                  45

Thr Lys Asn Leu Asp Asp Phe Tyr Asp Lys Glu Gly Phe Arg Asp Gln
 50                  55                  60

Glu Phe Lys Lys Gly Asp Lys Gly Thr Trp Ile Val Asn Ser Glu Met
 65                  70                  75                  80

Val Ile Glu Pro Lys Gly Lys Asp Met Glu Thr Arg Gly Met Val Leu
                    85                  90                  95

Tyr Ile Asn Arg Asn Thr Arg Thr Thr Lys Gly Tyr Tyr Phe Ile Ser
                100                 105                 110

Glu Met Thr Asp Asp Ser Asn Gly Arg Pro Lys Asp Asp Glu Lys Arg
                115                 120                 125

Tyr Pro Val Lys Met Glu His Asn Lys Ile Ile Pro Thr Lys Pro Leu
                130                 135                 140

Pro Asn Asp Lys Leu Lys Lys Glu Ile Glu Asn Phe Lys Phe Phe Val
145                 150                 155                 160

Gln Tyr Gly Asn Phe Lys Asp Ile Asn Asp Tyr Lys Asp Gly Asp Ile
                    165                 170                 175

Ser Tyr Asn Pro Asn Val Pro Ser Tyr Ser Ala Lys Tyr Gln Leu Asn
                180                 185                 190

Asn Asp Asp Tyr Asn Val Gln Gln Leu Arg Lys Arg Tyr Asp Ile Pro
                195                 200                 205

Thr Lys Gln Ala Pro Lys Leu Leu Leu Lys Gly Asp Gly Asp Leu Lys
            210                 215                 220

Gly Ser Ser Val Gly Ser Arg Ser Leu Glu Phe Thr Phe Val Glu Asn
225                 230                 235                 240

Lys Glu Glu Asn Ile Tyr Phe Thr Asp Ser Val Gln Tyr Thr Pro Ser
                    245                 250                 255

Glu Asp Thr Arg Tyr Glu Ser Asn
                260

<210> SEQ ID NO 96
<211> LENGTH: 261
<212> TYPE: PRT
<213> ORGANISM: Staphylococcus sp

<400> SEQUENCE: 96

Met Ile His Ser Lys Lys Leu Thr Leu Gly Ile Cys Leu Val Leu Leu
 1               5                  10                  15

Ile Ile Leu Ile Gly Gly Cys Val Ile Met Thr Lys Thr Asn Gly Arg
                20                  25                  30

Asn Ala Gln Ile Lys Glu Asn Phe Asn Lys Thr Leu Ser Val Tyr Leu
            35                  40                  45

Thr Lys Asn Leu Asp Asp Phe Tyr Asp Lys Glu Gly Phe Arg Asp Gln
 50                  55                  60

Glu Phe Asp Lys Arg Asp Lys Gly Thr Trp Ile Ile Tyr Ser Glu Met
 65                  70                  75                  80

Val Ile Glu Pro Lys Gly Lys Asn Met Glu Ser Arg Gly Met Val Leu
                    85                  90                  95

Tyr Ile Asn Arg Asn Thr Arg Thr Thr Lys Gly Asn Phe Ile Val Thr
                100                 105                 110

Glu Ile Thr Glu Asp Ser Lys Gly Tyr Ser Arg Ser Lys Glu Lys Lys
                115                 120                 125

Tyr Pro Val Lys Met Glu Asn Asn Arg Ile Ile Pro Thr Lys Pro Ile

```
                130                 135                 140
Pro Asp Asp Lys Leu Lys Lys Glu Ile Glu Asn Phe Lys Phe Phe Val
145                 150                 155                 160

Gln Tyr Gly Asn Phe Lys Asp Phe Lys Asp Tyr Lys Asn Gly Asp Ile
                165                 170                 175

Ser Tyr Asn Pro Asn Val Pro Ser Tyr Ser Ala Lys Tyr Gln Leu Asn
                180                 185                 190

Asn Asp Asp Tyr Asn Val Gln Gln Leu Arg Lys Arg Tyr His Ile Pro
                195                 200                 205

Thr Lys Gln Ala Pro Glu Leu Lys Leu Lys Gly Ser Gly Asn Leu Lys
                210                 215                 220

Gly Ser Ser Val Gly Ser Lys Asp Leu Glu Phe Thr Phe Val Glu Asn
225                 230                 235                 240

Gln Glu Glu Asn Ile Tyr Phe Ser Asp Ser Val Glu Phe Thr Pro Ser
                245                 250                 255

Glu Asp Asp Lys Ser
                260

<210> SEQ ID NO 97
<211> LENGTH: 498
<212> TYPE: PRT
<213> ORGANISM: Staphylococcus sp

<400> SEQUENCE: 97

Met Ala Ala Leu Thr Leu Leu Ser Thr Leu Ser Pro Ala Ala Leu Ala
1               5                   10                  15

Ile Asp Ser Lys Asn Lys Pro Ala Asn Ser Asp Ile Lys Phe Glu Val
                20                  25                  30

Thr Gln Lys Ser Asp Ala Val Lys Ala Leu Lys Glu Leu Pro Lys Ser
            35                  40                  45

Glu Asn Val Lys Asn Ile Tyr Gln Asp Tyr Ala Val Thr Asp Val Lys
        50                  55                  60

Thr Asp Lys Lys Gly Phe Thr His Tyr Thr Leu Gln Pro Ser Val Asp
65                  70                  75                  80

Gly Val His Ala Pro Asp Lys Glu Val Lys Val His Ala Asp Lys Ser
                85                  90                  95

Gly Lys Val Val Leu Ile Asn Gly Asp Thr Asp Ala Lys Lys Val Lys
                100                 105                 110

Pro Thr Asn Lys Val Thr Leu Ser Lys Asp Asp Ala Ala Asp Lys Ala
            115                 120                 125

Phe Lys Ala Val Lys Ile Asp Lys Asn Lys Ala Lys Asn Leu Lys Asp
        130                 135                 140

Lys Val Ile Lys Glu Asn Lys Val Glu Ile Asp Gly Asp Ser Asn Lys
145                 150                 155                 160

Tyr Val Tyr Asn Val Glu Leu Ile Thr Val Thr Pro Glu Ile Ser His
                165                 170                 175

Trp Lys Val Lys Ile Asp Ala Gln Thr Gly Glu Ile Leu Glu Lys Met
                180                 185                 190

Asn Leu Val Lys Glu Ala Ala Glu Thr Gly Lys Gly Lys Gly Val Leu
            195                 200                 205

Gly Asp Thr Lys Asp Ile Asn Ile Asn Ser Ile Asp Gly Gly Phe Ser
        210                 215                 220

Leu Glu Asp Leu Thr His Gln Gly Lys Leu Ser Ala Phe Ser Phe Asn
225                 230                 235                 240
```

Asp Gln Thr Gly Gln Ala Thr Leu Ile Thr Asn Glu Asp Glu Asn Phe
            245                 250                 255

Val Lys Asp Glu Gln Arg Ala Gly Val Asp Ala Asn Tyr Tyr Ala Lys
        260                 265                 270

Gln Thr Tyr Asp Tyr Tyr Lys Asp Thr Phe Gly Arg Glu Ser Tyr Asp
            275                 280                 285

Asn Gln Gly Ser Pro Ile Val Ser Leu Thr His Val Asn Asn Tyr Gly
        290                 295                 300

Gly Gln Asp Asn Arg Asn Ala Ala Trp Ile Gly Asp Lys Met Ile
305                 310                 315                 320

Tyr Gly Asp Gly Asp Gly Arg Thr Phe Thr Ser Leu Ser Gly Ala Asn
            325                 330                 335

Asp Val Val Ala His Glu Leu Thr His Gly Val Thr Gln Glu Thr Ala
            340                 345                 350

Asn Leu Glu Tyr Lys Asp Gln Ser Gly Ala Leu Asn Glu Ser Phe Ser
            355                 360                 365

Asp Val Phe Gly Tyr Phe Val Asp Asp Glu Asp Phe Leu Met Gly Glu
            370                 375                 380

Asp Val Tyr Thr Pro Gly Lys Glu Gly Asp Ala Leu Arg Ser Met Ser
385                 390                 395                 400

Asn Pro Glu Gln Phe Gly Gln Pro Ala His Met Lys Asp Tyr Val Phe
            405                 410                 415

Thr Glu Lys Asp Asn Gly Gly Val His Thr Asn Ser Gly Ile Pro Asn
            420                 425                 430

Lys Ala Ala Tyr Asn Val Ile Gln Ala Ile Gly Lys Ser Lys Ser Glu
            435                 440                 445

Gln Ile Tyr Tyr Arg Ala Leu Thr Glu Tyr Leu Thr Ser Asn Ser Asn
        450                 455                 460

Phe Lys Asp Cys Lys Asp Ala Leu Tyr Gln Ala Ala Lys Asp Leu Tyr
465                 470                 475                 480

Asp Glu Gln Thr Ala Glu Gln Val Tyr Glu Ala Trp Asn Glu Val Gly
            485                 490                 495

Val Glu

<210> SEQ ID NO 98
<211> LENGTH: 680
<212> TYPE: PRT
<213> ORGANISM: Staphylococcus sp

<400> SEQUENCE: 98

Met Lys Ser Gln Asn Lys Tyr Ser Ile Arg Lys Phe Ser Val Gly Ala
1               5                   10                  15

Ser Ser Ile Leu Ile Ala Thr Leu Leu Phe Leu Ser Gly Gly Gln Ala
            20                  25                  30

Gln Ala Ala Glu Lys Gln Val Asn Met Gly Asn Ser Gln Glu Asp Thr
        35                  40                  45

Val Thr Ala Gln Ser Ile Gly Asp Gln Gln Thr Arg Glu Asn Ala Asn
    50                  55                  60

Tyr Gln Arg Glu Asn Gly Val Asp Glu Gln Gln His Thr Glu Asn Leu
65                  70                  75                  80

Thr Lys Asn Leu His Asn Asp Lys Thr Ile Ser Glu Glu Asn His Arg
            85                  90                  95

Lys Thr Asp Asp Leu Asn Lys Asp Gln Leu Lys Asp Asp Lys Lys Ser
            100                 105                 110

-continued

```
Ser Leu Asn Asn Lys Asn Ile Gln Arg Asp Thr Thr Lys Asn Asn Asn
        115                 120                 125

Ala Asn Pro Ser Asp Val Asn Gln Gly Leu Glu Gln Ala Ile Asn Asp
130                 135                 140

Gly Lys Gln Ser Lys Val Ala Ser Gln Gln Ser Lys Glu Ala Asp
145                 150                 155                 160

Asn Ser Gln Asp Ser Asn Ala Asn Asn Leu Pro Ser Gln Ser Arg
                165                 170                 175

Ile Lys Glu Ala Pro Ser Leu Asn Lys Leu Asp Gln Thr Ser Gln Arg
            180                 185                 190

Glu Ile Val Asn Glu Thr Glu Ile Glu Lys Val Gln Pro Gln Gln Asn
        195                 200                 205

Asn Gln Ala Asn Asp Lys Ile Thr Asn Tyr Asn Phe Asn Asn Glu Gln
    210                 215                 220

Glu Val Lys Pro Gln Lys Asp Glu Lys Thr Leu Ser Val Ser Asp Leu
225                 230                 235                 240

Lys Asn Asn Gln Lys Ser Pro Val Glu Pro Thr Lys Asp Asn Asp Lys
                245                 250                 255

Lys Asn Gly Leu Asn Leu Leu Lys Ser Ser Ala Val Ala Thr Leu Pro
            260                 265                 270

Asn Lys Gly Thr Lys Glu Leu Thr Ala Lys Ala Lys Asp Asp Gln Thr
        275                 280                 285

Asn Lys Val Ala Lys Gln Gly Gln Tyr Lys Asn Gln Asp Pro Ile Val
    290                 295                 300

Leu Val His Gly Phe Asn Gly Phe Thr Asp Asp Ile Asn Pro Ser Val
305                 310                 315                 320

Leu Ala His Tyr Trp Gly Gly Asn Lys Met Asn Ile Arg Gln Asp Leu
                325                 330                 335

Glu Glu Asn Gly Tyr Lys Ala Tyr Glu Ala Ser Ile Ser Ala Phe Gly
            340                 345                 350

Ser Asn Tyr Asp Arg Ala Val Glu Leu Tyr Tyr Ile Lys Gly Gly
        355                 360                 365

Arg Val Asp Tyr Gly Ala Ala His Ala Ala Lys Tyr Gly His Glu Arg
    370                 375                 380

Tyr Gly Lys Thr Tyr Glu Gly Ile Tyr Lys Asp Trp Lys Pro Gly Gln
385                 390                 395                 400

Lys Val His Leu Val Gly His Ser Met Gly Gly Gln Thr Ile Arg Gln
                405                 410                 415

Leu Glu Glu Leu Leu Arg Asn Gly Asn Arg Glu Glu Ile Glu Tyr Gln
            420                 425                 430

Lys Lys His Gly Gly Glu Ile Ser Pro Leu Phe Lys Gly Asn His Asp
        435                 440                 445

Asn Met Ile Ser Ser Ile Thr Thr Leu Gly Thr Pro His Asn Gly Thr
    450                 455                 460

His Ala Ser Asp Leu Ala Gly Asn Glu Ala Leu Val Arg Gln Ile Val
465                 470                 475                 480

Phe Asp Ile Gly Lys Met Phe Gly Asn Lys Asn Ser Arg Val Asp Phe
                485                 490                 495

Gly Leu Ala Gln Trp Gly Leu Lys Gln Lys Pro Asn Glu Ser Tyr Ile
            500                 505                 510

Asp Tyr Val Lys Arg Val Lys Gln Ser Asn Leu Trp Lys Ser Lys Asp
        515                 520                 525

Asn Gly Phe Tyr Asp Leu Thr Arg Glu Gly Ala Thr Asp Leu Asn Arg
```

```
                530               535               540
Lys Thr Ser Leu Asn Pro Asn Ile Val Tyr Lys Thr Tyr Thr Gly Glu
545                 550               555               560

Ala Thr His Lys Ala Leu Asn Ser Asp Arg Gln Lys Ala Asp Leu Asn
                565               570               575

Met Phe Phe Pro Phe Val Ile Thr Gly Asn Leu Ile Gly Lys Ala Thr
                580               585               590

Glu Lys Glu Trp Arg Glu Asn Asp Gly Leu Val Ser Val Ile Ser Ser
            595               600               605

Gln His Pro Phe Asn Gln Ala Tyr Thr Lys Ala Thr Asp Lys Ile Gln
        610               615               620

Lys Gly Ile Trp Gln Val Thr Pro Thr Lys His Asp Trp Asp His Val
625               630               635               640

Asp Phe Val Gly Gln Asp Ser Ser Asp Thr Val Arg Thr Arg Glu Glu
                645               650               655

Leu Gln Asp Phe Trp His His Leu Ala Asp Asp Leu Val Lys Thr Glu
                660               665               670

Lys Leu Thr Asp Thr Lys Gln Ala
        675               680

<210> SEQ ID NO 99
<211> LENGTH: 328
<212> TYPE: PRT
<213> ORGANISM: Staphylococcus sp

<400> SEQUENCE: 99

Met Lys Lys Cys Ile Lys Thr Leu Phe Leu Ser Ile Ile Leu Val Val
1               5                   10                  15

Met Ser Gly Trp Tyr His Ser Ala His Ala Ser Asp Ser Leu Ser Lys
            20                  25                  30

Ser Pro Glu Asn Trp Met Ser Lys Leu Asp Asp Gly Lys His Leu Thr
        35                  40                  45

Glu Ile Asn Ile Pro Gly Ser His Asp Ser Gly Ser Phe Thr Leu Lys
    50                  55                  60

Asp Pro Val Lys Ser Val Trp Ala Lys Thr Gln Asp Lys Asp Tyr Leu
65                  70                  75                  80

Thr Gln Met Lys Ser Gly Val Arg Phe Phe Asp Ile Arg Gly Arg Ala
                85                  90                  95

Ser Ala Asp Asn Met Ile Ser Val His His Gly Met Val Tyr Leu His
                100                 105                 110

His Glu Leu Gly Lys Phe Leu Asp Asp Ala Lys Tyr Tyr Leu Ser Ala
            115                 120                 125

Tyr Pro Asn Glu Thr Ile Val Met Ser Met Lys Asp Tyr Asp Ser
        130                 135                 140

Asp Ser Lys Val Thr Lys Thr Phe Glu Glu Ile Phe Arg Glu Tyr Tyr
145                 150                 155                 160

Tyr Asn Asn Pro Gln Tyr Gln Asn Leu Phe Tyr Thr Gly Ser Asn Ala
                165                 170                 175

Asn Pro Thr Leu Lys Glu Thr Lys Gly Lys Ile Val Leu Phe Asn Arg
            180                 185                 190

Met Gly Gly Thr Tyr Ile Lys Ser Gly Tyr Gly Ala Asp Thr Ser Gly
        195                 200                 205

Ile Gln Trp Ala Asp Asn Ala Thr Phe Glu Thr Lys Ile Asn Asn Gly
    210                 215                 220
```

```
Ser Leu Asn Leu Lys Val Gln Asp Glu Tyr Lys Asp Tyr Tyr Asp Lys
225                 230                 235                 240

Lys Val Glu Ala Val Lys Asn Leu Leu Ala Lys Ala Lys Thr Asp Ser
            245                 250                 255

Asn Lys Asp Asn Val Tyr Val Asn Phe Leu Ser Val Ala Ser Gly Gly
            260                 265                 270

Ser Ala Phe Asn Ser Thr Tyr Asn Tyr Ala Ser His Ile Asn Pro Glu
            275                 280                 285

Ile Ala Lys Thr Leu Lys Ala Asn Gly Lys Ala Arg Thr Gly Trp Leu
            290                 295                 300

Ile Val Asp Tyr Ala Gly Tyr Thr Trp Pro Gly Tyr Asp Asp Ile Val
305                 310                 315                 320

Ser Glu Ile Ile Asp Ser Asn Lys
            325

<210> SEQ ID NO 100
<211> LENGTH: 257
<212> TYPE: PRT
<213> ORGANISM: Staphylococcus sp

<400> SEQUENCE: 100

Met Lys Ala His Lys Ile Phe Trp Leu Asn Leu Ala Ala Ile Ile Ile
1               5                   10                  15

Ile Ser Ile Val Val Ser Gly Asp Met Phe Leu Ala Met Lys Trp Glu
            20                  25                  30

Gln Ile His Leu Lys Asp Gly Leu Lys Lys Val Leu Ser Thr Tyr Pro
            35                  40                  45

Ile Lys Asn Leu Glu Thr Leu Tyr Glu Ile Asp Gly His Asp Asn Pro
50                  55                  60

His Tyr Glu Asn Asn Asp Gln Asp Thr Trp Tyr Ile Glu Ser Ser Tyr
65                  70                  75                  80

Ser Val Val Gly Ser Asp Glu Leu Leu Lys Glu Asp Arg Met Leu Leu
            85                  90                  95

Lys Val Asp Lys Asn Thr His Lys Ile Thr Gly Glu Tyr Asp Thr Thr
            100                 105                 110

Thr Asn Asp Arg Lys Asn Ala Thr Asp Ser Thr Tyr Lys Ser Tyr Pro
            115                 120                 125

Val Lys Val Asn Asn Lys Ile Val Phe Thr Lys Val Lys Asp
            130                 135                 140

Pro Ala Leu Lys Gln Lys Ile Glu Asn Asn Gln Phe Leu Ile Gln Ser
145                 150                 155                 160

Gly Asp Leu Thr Ser Ile Leu Asn Ser Asn Asp Leu Lys Val Thr His
            165                 170                 175

Asp Pro Thr Thr Asp Tyr Tyr Asn Leu Ser Gly Lys Leu Ser Asn Asp
            180                 185                 190

Asn Pro Asn Val Lys Gln Leu Lys Arg Arg Tyr Asn Ile Pro Lys Asn
            195                 200                 205

Ala Ser Thr Lys Val Glu Leu Lys Gly Met Ser Asp Leu Lys Gly Asn
            210                 215                 220

Asn His Gln Asp Gln Lys Leu Tyr Phe Tyr Phe Ser Pro Gly Lys
225                 230                 235                 240

Asp Gln Ile Ile Tyr Lys Glu Ser Leu Thr Tyr Asn Lys Ile Ser Glu
            245                 250                 255

His
```

```
<210> SEQ ID NO 101
<211> LENGTH: 423
<212> TYPE: PRT
<213> ORGANISM: Staphylococcus sp

<400> SEQUENCE: 101

Met Ser Lys Ile Leu Lys Cys Ile Thr Leu Ala Val Val Met Leu Leu
1               5                   10                  15

Ile Val Thr Ala Cys Gly Pro Asn Arg Ser Lys Glu Asp Ile Asp Lys
            20                  25                  30

Ala Leu Asn Lys Asp Asn Ser Lys Asp Lys Pro Asn Gln Leu Thr Met
        35                  40                  45

Trp Val Asp Gly Asp Lys Gln Met Ala Phe Tyr Lys Lys Ile Thr Asp
    50                  55                  60

Gln Tyr Thr Lys Lys Thr Gly Ile Lys Val Lys Leu Val Asn Ile Gly
65                  70                  75                  80

Gln Asn Asp Gln Leu Glu Asn Ile Ser Leu Asp Ala Pro Ala Gly Lys
                85                  90                  95

Gly Pro Asp Ile Phe Phe Leu Ala His Asp Asn Thr Gly Ser Ala Tyr
            100                 105                 110

Leu Gln Gly Leu Ala Ala Glu Ile Lys Leu Ser Lys Asp Glu Leu Lys
        115                 120                 125

Gly Phe Asn Lys Gln Ala Leu Lys Ala Met Asn Tyr Asp Asn Lys Gln
    130                 135                 140

Leu Ala Leu Pro Ala Ile Val Glu Thr Thr Ala Leu Phe Tyr Asn Lys
145                 150                 155                 160

Lys Leu Val Lys Asn Ala Pro Gln Thr Leu Glu Glu Val Glu Ala Asn
                165                 170                 175

Ala Ala Lys Leu Thr Asp Ser Lys Lys Gln Tyr Gly Met Leu Phe
            180                 185                 190

Asp Ala Lys Asn Phe Tyr Phe Asn Tyr Pro Phe Leu Phe Gly Asn Asp
        195                 200                 205

Asp Tyr Ile Phe Lys Lys Asn Gly Ser Glu Tyr Asp Ile His Gln Leu
    210                 215                 220

Gly Leu Asn Ser Lys His Val Val Lys Asn Ala Glu Arg Leu Gln Lys
225                 230                 235                 240

Trp Tyr Asp Lys Gly Tyr Leu Pro Lys Ala Ala Thr His Asp Val Met
                245                 250                 255

Ile Gly Leu Phe Lys Glu Gly Lys Val Gly Gln Phe Val Thr Gly Pro
            260                 265                 270

Trp Asn Ile Asn Glu Tyr Gln Glu Thr Phe Gly Lys Asp Leu Gly Val
        275                 280                 285

Thr Thr Leu Pro Thr Asp Gly Lys Pro Met Lys Pro Phe Leu Gly
    290                 295                 300

Val Arg Gly Trp Tyr Leu Ser Glu Tyr Ser Lys His Lys Tyr Trp Ala
305                 310                 315                 320

Lys Asp Leu Met Leu Tyr Ile Thr Ser Lys Asp Thr Leu Gln Lys Tyr
                325                 330                 335

Thr Asp Glu Met Ser Glu Ile Thr Gly Arg Val Asp Val Lys Ser Ser
            340                 345                 350

Asn Pro Asn Leu Lys Val Phe Glu Lys Gln Ala Arg His Ala Glu Pro
        355                 360                 365

Met Pro Asn Ile Pro Glu Met Arg Gln Val Trp Glu Pro Met Gly Asn
    370                 375                 380
```

```
Ala Ser Ile Phe Ile Ser Asn Gly Lys Asn Pro Lys Gln Ala Leu Asp
385                 390                 395                 400

Glu Ala Thr Asn Asp Ile Thr Gln Asn Ile Lys Ile Leu His Pro Ser
                405                 410                 415

Gln Asn Asp Lys Lys Gly Asp
            420
```

<210> SEQ ID NO 102
<211> LENGTH: 560
<212> TYPE: PRT
<213> ORGANISM: Staphylococcus sp

<400> SEQUENCE: 102

```
Met Leu Ile Thr Ala Ala Met Val Cys Ser Phe Gly Leu Leu Lys Ser
1               5                   10                  15

Gln Ala Ala Glu Gln Gln Ser Ile Ser Asp Val Tyr Ser Val Ile Thr
                20                  25                  30

Asp Ala Lys Ser Ala Leu Ser Asn Asn Ser Ile Ser Asn Asp Asn Lys
            35                  40                  45

Gln Lys Ala Ile Glu Gln Val Val Ser Ala Val Lys Lys Leu Ser Leu
        50                  55                  60

Glu Asp Asn Ser Glu Ser Asn Ala Val Lys Ser Asp Val Arg Lys Leu
65                  70                  75                  80

Glu Asp Ala Lys Ala Asn Asp Asn Gln Lys Asp Thr Leu Ser Gln Leu
                85                  90                  95

Thr Lys Ser Leu Ile Ala Tyr Glu Glu Lys Leu Ala Ser Lys Asp Ala
            100                 105                 110

Gly Ser Lys Ile Lys Leu Leu Gln Gln Val Asp Ala Lys Asp Ala
        115                 120                 125

Ala Met Thr Lys Ala Ile Lys Asp Lys Asn Lys Ala Glu Leu Glu Ser
130                 135                 140

Leu Asn Asn Ser Leu Asn Gln Ile Trp Thr Ser Asn Glu Thr Val Ile
145                 150                 155                 160

Arg Asn Tyr Asp Ala Asn Gln Tyr Gly Gln Ile Glu Val Ala Leu Leu
                165                 170                 175

Gln Leu Arg Ile Ala Ile His Lys Ser Pro Leu Asp Thr Ala Lys Val
            180                 185                 190

Ser His Ala Trp Thr Thr Phe Lys Ser Asn Ile Asp His Val Asp Lys
        195                 200                 205

Lys Ser Asn Thr Ser Ala Asn Asp Gln Tyr His Val Ser Gln Leu Asn
210                 215                 220

Asp Ala Leu Glu Lys Ala Ile Lys Ala Ile Asp Asp Asn Gln Leu Ser
225                 230                 235                 240

Asp Ala Asp Ala Ala Leu Thr His Phe Ile Glu Thr Trp Pro Tyr Val
                245                 250                 255

Glu Gly Gln Ile Gln Thr Lys Asp Gly Ala Leu Tyr Thr Lys Ile Glu
            260                 265                 270

Asp Lys Ile Pro Tyr Tyr Gln Ser Val Leu Asp Glu His Asn Lys Ala
        275                 280                 285

His Val Lys Asp Gly Leu Val Asp Leu Asn Asn Gln Ile Lys Glu Val
290                 295                 300

Val Gly His Ser Tyr Ser Phe Val Asp Val Met Ile Ile Phe Leu Arg
305                 310                 315                 320

Glu Gly Leu Glu Val Leu Leu Ile Val Met Thr Leu Thr Thr Met Thr
```

```
                   325                 330                 335
Arg Asn Val Lys Asp Lys Gly Thr Ala Ser Val Ile Gly Gly Ala
                340                 345                 350
Ile Ala Gly Leu Val Leu Ser Ile Ile Leu Ala Ile Thr Phe Val Glu
                355                 360                 365
Thr Leu Gly Asn Ser Gly Ile Leu Arg Glu Ser Met Glu Ala Gly Leu
                370                 375                 380
Gly Ile Val Ala Val Ile Leu Met Phe Ile Val Gly Val Trp Met His
385                 390                 395                 400
Lys Arg Ser Asn Ala Lys Arg Trp Asn Asp Met Ile Lys Asn Met Tyr
                405                 410                 415
Ala Asn Ala Ile Ser Asn Gly Asn Leu Val Leu Leu Ala Thr Ile Gly
                420                 425                 430
Leu Ile Ser Val Leu Arg Glu Gly Val Glu Val Ile Ile Phe Tyr Met
                435                 440                 445
Gly Met Ile Gly Glu Leu Ala Thr Lys Asp Phe Ile Ile Gly Ile Ala
                450                 455                 460
Leu Ala Ile Val Ile Leu Ile Phe Ala Leu Leu Phe Arg Phe Ile
465                 470                 475                 480
Val Lys Leu Ile Pro Ile Phe Tyr Ile Phe Arg Val Leu Ser Ile Phe
                485                 490                 495
Ile Phe Ile Met Gly Phe Lys Met Leu Gly Val Ser Ile Gln Lys Leu
                500                 505                 510
Gln Leu Leu Gly Ala Met Pro Arg His Val Ile Glu Gly Phe Pro Thr
                515                 520                 525
Ile Asn Trp Leu Gly Phe Tyr Pro Ser Tyr Glu Pro Leu Ile Ala Gln
                530                 535                 540
Gly Ala Tyr Ile Met Val Val Ala Ile Leu Ile Phe Lys Phe Lys Lys
545                 550                 555                 560

<210> SEQ ID NO 103
<211> LENGTH: 334
<212> TYPE: PRT
<213> ORGANISM: Staphylococcus sp

<400> SEQUENCE: 103

Met Gln Lys Lys Val Leu Ala Ala Ile Ile Gly Thr Ser Ala Ile Ser
1               5                   10                  15
Ala Val Ala Ala Thr Gln Ala Asn Ala Ala Thr Thr His Thr Val Lys
                20                  25                  30
Pro Gly Glu Ser Val Trp Ala Ile Ser Asn Lys Tyr Gly Ile Ser Ile
                35                  40                  45
Ala Lys Leu Lys Ser Leu Asn Asn Leu Thr Ser Asn Leu Ile Phe Pro
                50                  55                  60
Asn Gln Val Leu Lys Val Ser Gly Ser Ser Asn Ser Thr Ser Asn Ser
65                  70                  75                  80
Ser Arg Pro Ser Thr Asn Ser Gly Gly Ser Tyr Tyr Thr Val Gln
                85                  90                  95
Ala Gly Asp Ser Leu Ser Leu Ile Ala Ser Lys Tyr Gly Thr Thr Tyr
                100                 105                 110
Gln Asn Ile Met Arg Leu Asn Gly Leu Asn Asn Phe Phe Ile Tyr Pro
                115                 120                 125
Gly Gln Lys Leu Lys Val Ser Gly Thr Ala Ser Ser Asn Ala Ala
                130                 135                 140
```

```
Ser Asn Ser Ser Arg Pro Ser Thr Asn Ser Gly Gly Ser Tyr Tyr
145                 150                 155                 160

Thr Val Gln Ala Gly Asp Ser Leu Ser Leu Ile Ala Ser Lys Tyr Gly
                165                 170                 175

Thr Thr Tyr Gln Lys Ile Met Ser Leu Asn Gly Leu Asn Asn Phe Phe
                180                 185                 190

Ile Tyr Pro Gly Gln Lys Leu Lys Val Thr Gly Asn Ala Ser Thr Asn
                195                 200                 205

Ser Gly Ser Ala Thr Thr Asn Arg Gly Tyr Asn Thr Pro Val Phe
    210                 215                 220

Ser His Gln Asn Leu Tyr Thr Trp Gly Gln Cys Thr Tyr His Val Phe
225                 230                 235                 240

Asn Arg Arg Ala Glu Ile Gly Lys Gly Ile Ser Thr Tyr Trp Trp Asn
                245                 250                 255

Ala Asn Asn Trp Asp Asn Ala Ala Ala Asp Gly Tyr Thr Ile Asp
                260                 265                 270

Asn Arg Pro Thr Val Gly Ser Ile Ala Gln Thr Asp Val Gly Tyr Tyr
                275                 280                 285

Gly His Val Met Phe Val Glu Arg Val Asn Asn Asp Gly Ser Ile Leu
    290                 295                 300

Val Ser Glu Met Asn Tyr Ser Ala Ala Pro Gly Ile Leu Thr Tyr Arg
305                 310                 315                 320

Thr Val Pro Ala Tyr Gln Val Asn Asn Tyr Arg Tyr Ile His
                325                 330

<210> SEQ ID NO 104
<211> LENGTH: 279
<212> TYPE: PRT
<213> ORGANISM: Staphylococcus sp

<400> SEQUENCE: 104

Met Lys Lys Ser Leu Thr Val Thr Val Ser Ser Val Leu Ala Phe Leu
1               5                   10                  15

Ala Leu Asn Asn Ala Ala His Ala Gln Gln His Gly Thr Gln Val Lys
                20                  25                  30

Thr Pro Val Gln His Asn Tyr Val Ser Asn Val Gln Ala Gln Thr Gln
                35                  40                  45

Ser Pro Thr Thr Tyr Thr Val Val Ala Gly Asp Ser Leu Tyr Lys Ile
    50                  55                  60

Ala Leu Glu His His Leu Thr Leu Asn Gln Leu Tyr Ser Tyr Asn Pro
65                  70                  75                  80

Gly Val Thr Pro Leu Ile Phe Pro Gly Asp Val Ile Ser Leu Val Pro
                85                  90                  95

Gln Asn Lys Val Lys Gln Thr Lys Ala Val Lys Ser Pro Val Arg Lys
                100                 105                 110

Ala Ser Gln Ala Lys Lys Val Val Lys Gln Pro Val Gln Gln Ala Ser
                115                 120                 125

Lys Lys Val Val Val Lys Gln Ala Pro Lys Gln Ala Val Thr Lys Thr
    130                 135                 140

Val Asn Val Ala Tyr Lys Pro Ala Gln Val Gln Lys Ser Val Pro Thr
145                 150                 155                 160

Val Pro Val Ala His Asn Tyr Asn Lys Ser Val Ala Asn Arg Gly Asn
                165                 170                 175

Leu Tyr Ala Tyr Gly Asn Cys Thr Tyr Tyr Ala Phe Asp Arg Arg Ala
                180                 185                 190
```

```
Gln Leu Gly Arg Ser Ile Gly Ser Leu Trp Gly Asn Ala Asn Trp
            195                 200                 205

Asn Tyr Ala Ala Lys Val Ala Gly Phe Lys Val Asp Lys Thr Pro Glu
        210                 215                 220

Val Gly Ala Ile Phe Gln Thr Ala Ala Gly Pro Tyr Gly His Val Gly
225                 230                 235                 240

Val Val Glu Ser Val Asn Pro Asn Gly Thr Ile Thr Val Ser Glu Met
                245                 250                 255

Asn Tyr Ala Gly Phe Asn Val Lys Ser Ser Arg Thr Ile Leu Asn Pro
            260                 265                 270

Gly Lys Tyr Asn Tyr Ile His
            275

<210> SEQ ID NO 105
<211> LENGTH: 346
<212> TYPE: PRT
<213> ORGANISM: Staphylococcus sp

<400> SEQUENCE: 105

Met Ile Ile Ala Ile Ile Leu Ile Phe Ile Ser Phe Phe Ser
1               5                   10                  15

Gly Ser Glu Thr Ala Leu Thr Ala Ala Asn Lys Thr Lys Phe Lys Thr
                20                  25                  30

Glu Ala Asp Lys Gly Asp Lys Lys Ala Lys Gly Ile Val Lys Leu Leu
            35                  40                  45

Glu Lys Pro Ser Glu Phe Ile Thr Thr Ile Leu Ile Gly Asn Asn Val
        50                  55                  60

Ala Asn Ile Leu Leu Pro Thr Leu Val Thr Leu Met Ala Leu Arg Trp
65                  70                  75                  80

Gly Ile Ser Val Gly Ile Ala Ser Ala Val Leu Thr Val Val Ile Ile
                85                  90                  95

Leu Ile Ser Glu Val Ile Pro Lys Ser Val Ala Ala Thr Phe Pro Asp
            100                 105                 110

Lys Ile Thr Arg Leu Val Tyr Pro Ile Ile Asn Ile Cys Val Ile Val
        115                 120                 125

Phe Arg Pro Ile Thr Leu Leu Leu Asn Lys Leu Thr Asp Ser Ile Asn
130                 135                 140

Arg Ser Leu Ser Lys Gly Gln Pro Gln Glu His Gln Phe Ser Lys Glu
145                 150                 155                 160

Glu Phe Lys Thr Met Leu Ala Ile Ala Gly His Glu Gly Ala Leu Asn
                165                 170                 175

Glu Ile Glu Thr Ser Arg Leu Glu Gly Val Ile Asn Phe Glu Asn Leu
            180                 185                 190

Lys Val Lys Asp Val Asp Thr Thr Pro Arg Ile Asn Val Thr Ala Phe
        195                 200                 205

Ala Ser Asn Ala Thr Tyr Glu Glu Val Tyr Gly Thr Val Met Asn Lys
            210                 215                 220

Pro Tyr Thr Arg Tyr Pro Val Tyr Glu Gly Asp Ile Asp Asn Ile Ile
225                 230                 235                 240

Gly Val Phe His Ser Lys Tyr Leu Leu Ala Trp Ser Asn Lys Lys Glu
                245                 250                 255

Asn Gln Ile Thr Asn Tyr Ser Ala Lys Pro Leu Phe Val Asn Glu His
            260                 265                 270

Asn Lys Ala Glu Trp Val Leu Arg Lys Met Thr Ile Ser Arg Lys His
```

```
                        275                 280                 285
Leu Ala Ile Val Leu Asp Glu Phe Gly Gly Thr Glu Ala Ile Val Ser
        290                 295                 300

His Glu Asp Leu Ile Glu Glu Leu Leu Gly Met Glu Ile Glu Asp Glu
305                 310                 315                 320

Met Asp Lys Lys Glu Lys Lys Leu Ser Gln Gln Gln Ile Gln Phe
                325                 330                 335

Gln Gln Arg Lys Asn Arg Asn Val Ser Ile
            340                 345

<210> SEQ ID NO 106
<211> LENGTH: 391
<212> TYPE: PRT
<213> ORGANISM: Staphylococcus sp

<400> SEQUENCE: 106

Met Lys Leu Lys Pro Phe Leu Pro Ile Leu Ile Ser Gly Ala Val Phe
1               5                   10                  15

Ile Val Phe Leu Leu Pro Ala Ser Trp Phe Thr Gly Leu Val Asn
            20                  25                  30

Glu Lys Thr Val Glu Asp Asn Arg Thr Ser Leu Thr Asp Gln Val Leu
        35                  40                  45

Lys Gly Thr Leu Ile Gln Asp Lys Leu Tyr Glu Ser Asn Lys Tyr Tyr
    50                  55                  60

Pro Ile Tyr Gly Ser Ser Glu Leu Gly Lys Asp Asp Pro Phe Asn Pro
65                  70                  75                  80

Ala Ile Ala Leu Asn Lys His Asn Ala Asn Lys Lys Ala Phe Leu Leu
                85                  90                  95

Gly Ala Gly Gly Ser Thr Asp Leu Ile Asn Ala Val Glu Leu Ala Ser
            100                 105                 110

Gln Tyr Asp Lys Leu Lys Gly Lys Lys Leu Thr Phe Ile Ile Ser Pro
        115                 120                 125

Gln Trp Phe Thr Asn His Gly Leu Thr Asn Gln Asn Phe Asp Ala Arg
    130                 135                 140

Met Ser Gln Thr Gln Ile Asn Gln Met Phe Gln Gln Lys Asn Met Ser
145                 150                 155                 160

Thr Glu Leu Lys Arg Arg Tyr Ala Gln Arg Leu Leu Gln Phe Pro His
                165                 170                 175

Val His Asn Lys Glu Tyr Leu Lys Ser Tyr Ala Lys Asn Pro Lys Glu
            180                 185                 190

Thr Lys Asp Ser Tyr Ile Ser Gly Phe Lys Glu Asn Gln Leu Ile Lys
        195                 200                 205

Ile Glu Ala Ile Lys Ser Leu Phe Ala Met Asp Lys Ser Pro Leu Glu
    210                 215                 220

His Val Lys Pro Ala Thr Lys Pro Asp Ala Ser Trp Asp Glu Met Lys
225                 230                 235                 240

Gln Lys Ala Val Glu Ile Gly Lys Ala Asp Thr Thr Ser Asn Lys Phe
                245                 250                 255

Gly Ile Arg Asp Gln Tyr Trp Lys Leu Ile Gln Glu Ser Lys Arg Lys
            260                 265                 270

Val Arg Arg Asp Tyr Glu Phe Asn Val Asn Ser Pro Glu Phe Gln Asp
        275                 280                 285

Leu Glu Leu Leu Val Lys Thr Met Arg Ala Ala Gly Ala Asp Val Gln
    290                 295                 300
```

```
Tyr Val Ser Ile Pro Ser Asn Gly Val Trp Tyr Asp His Ile Gly Ile
305                 310                 315                 320

Asp Lys Glu Arg Arg Gln Ala Val Tyr Lys Lys Ile His Ser Thr Val
            325                 330                 335

Val Asp Asn Gly Gly Lys Ile Tyr Asp Met Thr Asp Lys Asp Tyr Glu
            340                 345                 350

Lys Tyr Val Ile Ser Asp Ala Val His Ile Gly Trp Lys Gly Trp Val
            355                 360                 365

Tyr Met Asp Glu Gln Ile Ala Lys His Met Lys Gly Glu Pro Gln Pro
370                 375                 380

Glu Val Asp Lys Pro Lys Asn
385                 390

<210> SEQ ID NO 107
<211> LENGTH: 1256
<212> TYPE: PRT
<213> ORGANISM: Staphylococcus sp

<400> SEQUENCE: 107

Met Ala Lys Lys Phe Asn Tyr Lys Leu Pro Ser Met Val Ala Leu Thr
1               5                   10                  15

Leu Val Gly Ser Ala Val Thr Ala His Gln Val Gln Ala Ala Glu Thr
            20                  25                  30

Thr Gln Asp Gln Thr Thr Asn Lys Asn Val Leu Asp Ser Asn Lys Val
        35                  40                  45

Lys Ala Thr Thr Glu Gln Ala Lys Ala Glu Val Lys Asn Pro Thr Gln
    50                  55                  60

Asn Ile Ser Gly Thr Gln Val Tyr Gln Asp Pro Ala Ile Val Gln Pro
65                  70                  75                  80

Lys Thr Ala Asn Asn Lys Thr Gly Asn Ala Gln Val Ser Gln Lys Val
                85                  90                  95

Asp Thr Ala Gln Val Asn Gly Asp Thr Arg Ala Asn Gln Ser Ala Thr
            100                 105                 110

Thr Asn Asn Thr Gln Pro Val Ala Lys Ser Thr Ser Thr Thr Ala Pro
        115                 120                 125

Lys Thr Asn Thr Asn Val Thr Asn Ala Gly Tyr Ser Leu Val Asp Asp
    130                 135                 140

Glu Asp Asp Asn Ser Glu Asn Gln Ile Asn Pro Glu Leu Ile Lys Ser
145                 150                 155                 160

Ala Ala Lys Pro Ala Ala Leu Glu Thr Gln Tyr Lys Thr Ala Ala Pro
                165                 170                 175

Lys Ala Ala Thr Thr Ser Ala Pro Lys Ala Lys Thr Glu Ala Thr Pro
            180                 185                 190

Lys Val Thr Thr Phe Ser Ala Ser Ala Gln Pro Arg Ser Val Ala Ala
        195                 200                 205

Thr Pro Lys Thr Ser Leu Pro Lys Tyr Lys Pro Gln Val Asn Ser Ser
    210                 215                 220

Ile Asn Asp Tyr Ile Cys Lys Asn Asn Leu Lys Ala Pro Lys Ile Glu
225                 230                 235                 240

Glu Asp Tyr Thr Ser Tyr Phe Pro Lys Tyr Ala Tyr Arg Asn Gly Val
                245                 250                 255

Gly Arg Pro Glu Gly Ile Val Val His Asp Thr Ala Asn Asp Arg Ser
            260                 265                 270

Thr Ile Asn Gly Glu Ile Ser Tyr Met Lys Asn Asn Tyr Gln Asn Ala
        275                 280                 285
```

-continued

```
Phe Val His Ala Phe Val Asp Gly Asp Arg Ile Ile Glu Thr Ala Pro
    290                 295                 300
Thr Asp Tyr Leu Ser Trp Gly Val Gly Ala Val Gly Asn Pro Arg Phe
305                 310                 315                 320
Ile Asn Val Glu Ile Val His Thr His Asp Tyr Ala Ser Phe Ala Arg
                325                 330                 335
Ser Met Asn Asn Tyr Ala Asp Tyr Ala Ala Thr Gln Leu Gln Tyr Tyr
            340                 345                 350
Gly Leu Lys Pro Asp Ser Ala Glu Tyr Asp Gly Asn Gly Thr Val Trp
        355                 360                 365
Thr His Tyr Ala Val Ser Lys Tyr Leu Gly Gly Thr Asp His Ala Asp
    370                 375                 380
Pro His Gly Tyr Leu Arg Ser His Asn Tyr Ser Tyr Asp Gln Leu Tyr
385                 390                 395                 400
Asp Leu Ile Asn Glu Lys Tyr Leu Ile Lys Met Gly Lys Val Ala Pro
                405                 410                 415
Trp Gly Thr Gln Ser Thr Thr Thr Pro Thr Thr Pro Ser Lys Pro Thr
            420                 425                 430
Thr Pro Ser Lys Pro Ser Thr Gly Lys Leu Thr Val Ala Ala Asn Asn
        435                 440                 445
Gly Val Ala Gln Ile Lys Pro Thr Asn Ser Gly Leu Tyr Thr Thr Val
    450                 455                 460
Tyr Asp Lys Thr Gly Lys Ala Thr Asn Glu Val Gln Lys Thr Phe Ala
465                 470                 475                 480
Val Ser Lys Thr Ala Thr Leu Gly Asn Gln Lys Phe Tyr Leu Val Gln
                485                 490                 495
Asp Tyr Asn Ser Gly Asn Lys Phe Gly Trp Val Lys Glu Gly Asp Val
            500                 505                 510
Val Tyr Asn Thr Ala Lys Ser Pro Val Asn Val Asn Gln Ser Tyr Ser
        515                 520                 525
Ile Lys Pro Gly Thr Lys Leu Tyr Thr Val Pro Trp Gly Thr Ser Lys
    530                 535                 540
Gln Val Ala Gly Ser Val Ser Gly Ser Gly Asn Gln Thr Phe Lys Ala
545                 550                 555                 560
Ser Lys Gln Gln Gln Ile Asp Lys Ser Ile Tyr Leu Tyr Gly Ser Val
                565                 570                 575
Asn Gly Lys Ser Gly Trp Val Ser Lys Ala Tyr Leu Val Asp Thr Ala
            580                 585                 590
Lys Pro Thr Pro Thr Pro Thr Pro Lys Pro Ser Thr Pro Thr Thr Asn
        595                 600                 605
Asn Lys Leu Thr Val Ser Ser Leu Asn Gly Val Ala Gln Ile Asn Ala
    610                 615                 620
Lys Asn Asn Gly Leu Phe Thr Thr Val Tyr Asp Lys Thr Gly Lys Pro
625                 630                 635                 640
Thr Lys Glu Val Gln Lys Thr Phe Ala Val Thr Lys Glu Ala Ser Leu
                645                 650                 655
Gly Gly Asn Lys Phe Tyr Leu Val Lys Asp Tyr Asn Ser Pro Thr Leu
            660                 665                 670
Ile Gly Trp Val Lys Gln Gly Asp Val Ile Tyr Asn Asn Ala Lys Ser
        675                 680                 685
Pro Val Asn Val Met Gln Thr Tyr Thr Val Lys Pro Gly Thr Lys Leu
    690                 695                 700
```

```
Tyr Ser Val Pro Trp Gly Thr Tyr Lys Gln Glu Ala Gly Ala Val Ser
705                 710                 715                 720

Gly Thr Gly Asn Gln Thr Phe Lys Ala Thr Lys Gln Gln Ile Asp
            725                 730                 735

Lys Ser Ile Tyr Leu Phe Gly Thr Val Asn Gly Lys Ser Gly Trp Val
                740                 745                 750

Ser Lys Ala Tyr Leu Ala Val Pro Ala Ala Pro Lys Ala Val Ala
            755                 760                 765

Gln Pro Lys Thr Ala Val Lys Ala Tyr Thr Val Thr Lys Pro Gln Thr
            770                 775                 780

Thr Gln Thr Val Ser Lys Ile Ala Gln Val Lys Pro Asn Asn Thr Gly
785                 790                 795                 800

Leu Arg Ala Ser Val Tyr Glu Lys Thr Ala Lys Asn Gly Ala Lys Tyr
                805                 810                 815

Ala Asp Arg Thr Phe Tyr Val Thr Lys Glu Arg Ala His Gly Asn Glu
            820                 825                 830

Thr Tyr Val Leu Leu Asn Asn Thr Ser His Asn Ile Pro Leu Gly Trp
            835                 840                 845

Phe Asn Val Lys Asp Leu Asn Val Gln Asn Leu Gly Lys Glu Val Lys
850                 855                 860

Thr Thr Gln Lys Tyr Thr Val Asn Lys Ser Asn Asn Gly Leu Ser Met
865                 870                 875                 880

Val Pro Trp Gly Thr Lys Asn Gln Val Ile Leu Thr Gly Asn Asn Ile
                885                 890                 895

Ala Gln Gly Thr Phe Asn Ala Thr Lys Gln Val Ser Val Gly Lys Asp
            900                 905                 910

Val Tyr Leu Tyr Gly Thr Ile Asn Asn Arg Thr Gly Trp Val Asn Ala
            915                 920                 925

Lys Asp Leu Thr Ala Pro Thr Ala Val Lys Pro Thr Thr Ser Ala Ala
930                 935                 940

Lys Asp Tyr Asn Tyr Thr Tyr Val Ile Lys Asn Gly Asn Gly Tyr Tyr
945                 950                 955                 960

Tyr Val Thr Pro Asn Ser Asp Thr Ala Lys Tyr Ser Leu Lys Ala Phe
                965                 970                 975

Asn Glu Gln Pro Phe Ala Val Val Lys Glu Gln Val Ile Asn Gly Gln
            980                 985                 990

Thr Trp Tyr Tyr Gly Lys Leu Ser Asn Gly Lys Leu Ala Trp Ile Lys
            995                 1000                1005

Ser Thr Asp Leu Ala Lys Glu Leu Ile Lys Tyr Asn Gln Thr Gly
1010                1015                1020

Met Thr Leu Asn Gln Val Ala Gln Ile Gln Ala Gly Leu Gln Tyr
1025                1030                1035

Lys Pro Gln Val Gln Arg Val Pro Gly Lys Trp Thr Asp Ala Lys
1040                1045                1050

Phe Asn Asp Val Lys His Ala Met Asp Thr Lys Arg Leu Ala Gln
1055                1060                1065

Asp Pro Ala Leu Lys Tyr Gln Phe Leu Arg Leu Asp Gln Pro Gln
1070                1075                1080

Asn Ile Ser Ile Asp Lys Ile Asn Gln Phe Leu Lys Gly Lys Gly
1085                1090                1095

Val Leu Glu Asn Gln Gly Ala Ala Phe Asn Lys Ala Ala Gln Met
1100                1105                1110

Tyr Gly Ile Asn Glu Val Tyr Leu Ile Ser His Ala Leu Leu Glu
```

```
                1115                1120                1125

Thr Gly Asn Gly Thr Ser Gln Leu Ala Lys Gly Ala Asp Val Val
                1130                1135            1140

Asn Asn Lys Val Val Thr Asn Ser Asn Thr Lys Tyr His Asn Val
            1145                1150                1155

Phe Gly Leu Ala Ala Tyr Asp Asn Asp Pro Leu Arg Glu Gly Ile
        1160                1165                1170

Lys Tyr Ala Lys Gln Ala Gly Trp Asp Thr Val Ser Lys Ala Ile
    1175                1180                1185

Val Gly Gly Ala Lys Phe Ile Gly Asn Ser Tyr Val Lys Ala Gly
1190                1195                1200

Gln Asn Thr Leu Tyr Lys Met Arg Trp Asn Pro Ala His Pro Gly
    1205                1210                1215

Thr His Gln Tyr Ala Thr Asp Val Asp Trp Ala Asn Ile Asn Ala
        1220                1225                1230

Lys Ile Ile Lys Gly Tyr Tyr Asp Lys Ile Gly Glu Val Gly Lys
            1235                1240                1245

Tyr Phe Asp Ile Pro Gln Tyr Lys
        1250                1255

<210> SEQ ID NO 108
<211> LENGTH: 413
<212> TYPE: PRT
<213> ORGANISM: Staphylococcus sp

<400> SEQUENCE: 108

Met Lys Phe Ser Thr Leu Ser Glu Glu Glu Phe Thr Asn Tyr Thr Lys
1               5                   10                  15

Lys His Phe Lys His Tyr Thr Gln Ser Ile Glu Leu Tyr Asn Tyr Arg
            20                  25                  30

Asn Lys Ile Asn His Glu Ala His Ile Val Gly Val Lys Asn Asp Lys
        35                  40                  45

Asn Glu Val Leu Ala Ala Cys Leu Leu Thr Glu Ala Arg Ile Phe Lys
    50                  55                  60

Phe Tyr Lys Tyr Phe Tyr Ser His Arg Gly Pro Leu Leu Asp Tyr Phe
65                  70                  75                  80

Asp Ala Lys Leu Val Cys Tyr Phe Phe Lys Glu Leu Ser Lys Phe Ile
                85                  90                  95

Tyr Lys Asn Arg Gly Val Phe Ile Leu Val Asp Pro Tyr Leu Ile Glu
            100                 105                 110

Asn Leu Arg Asp Ala Asn Gly Arg Ile Ile Lys Asn Tyr Asn Asn Ser
        115                 120                 125

Val Ile Val Lys Met Leu Gly Lys Ile Gly Tyr Leu His Gln Gly Tyr
    130                 135                 140

Thr Thr Gly Tyr Ser Asn Lys Ser Gln Ile Arg Trp Ile Ser Val Leu
145                 150                 155                 160

Asp Leu Lys Asp Lys Asp Glu Asn Gln Leu Leu Lys Glu Met Glu Tyr
                165                 170                 175

Gln Thr Arg Arg Asn Ile Lys Lys Thr Ile Glu Ile Gly Val Lys Val
            180                 185                 190

Glu Asp Leu Ser Ile Glu Glu Thr Asn Arg Phe Tyr Lys Leu Phe Gln
        195                 200                 205

Met Ala Glu Glu Lys His Gly Phe His Phe Met Asn Glu Asp Tyr Phe
    210                 215                 220
```

```
Lys Arg Met Gln Glu Ile Tyr Lys Asp Lys Ala Met Leu Lys Ile Ala
225                 230                 235                 240

Cys Ile Asn Leu Asn Glu Tyr Gln Asp Lys Leu Lys Ile Gln Leu Leu
            245                 250                 255

Lys Ile Glu Asn Glu Met Met Thr Val Asn Arg Ala Leu Asn Glu Asn
        260                 265                 270

Pro Asn Ser Lys Lys Asn Lys Ser Lys Leu Asn Gln Leu Asn Met Gln
    275                 280                 285

Leu Ser Ser Ile Asn Asn Arg Ile Ser Lys Thr Glu Glu Leu Ile Phe
    290                 295                 300

Glu Asp Gly Pro Val Leu Asp Leu Ala Ala Ala Leu Phe Ile Cys Thr
305                 310                 315                 320

Asp Asp Glu Val Tyr Tyr Leu Ser Ser Gly Ser Asn Pro Lys Tyr Asn
                325                 330                 335

Gln Tyr Met Gly Ala Tyr His Leu Gln Trp His Met Ile Lys Tyr Ala
            340                 345                 350

Lys Ser His Asn Ile Asn Arg Tyr Asn Phe Tyr Gly Ile Thr Gly Val
        355                 360                 365

Phe Ser Asn Glu Asp Asp Phe Gly Val Gln Gln Phe Lys Lys Gly Phe
    370                 375                 380

Asn Ala His Val Glu Glu Leu Ile Gly Asp Phe Ile Lys Pro Val Arg
385                 390                 395                 400

Pro Ile Leu Tyr Lys Phe Ala Lys Leu Ile Tyr Lys Val
                405                 410

<210> SEQ ID NO 109
<211> LENGTH: 428
<212> TYPE: PRT
<213> ORGANISM: Staphylococcus sp

<400> SEQUENCE: 109

Met Lys Glu Arg Tyr Tyr Glu Leu Ile Asp Glu Arg Val Phe Glu Gln
1               5                   10                  15

Glu Leu Glu Asn Gly Leu Arg Leu Phe Ile Ile Pro Lys Pro Gly Phe
            20                  25                  30

Gln Lys Thr Phe Val Thr Tyr Thr Thr Gln Phe Gly Ser Leu Asp Asn
        35                  40                  45

Gln Phe Lys Pro Leu Gly Gln Asp Gln Phe Val Thr Val Pro Asp Gly
    50                  55                  60

Val Ala His Phe Leu Glu His Lys Leu Phe Glu Lys Glu Glu Glu Asp
65                  70                  75                  80

Leu Phe Thr Ala Phe Ala Glu Asp Asn Ala Gln Ala Asn Ala Phe Thr
                85                  90                  95

Ser Phe Asp Arg Thr Ser Tyr Leu Phe Ser Ala Thr Asp Asn Ile Glu
            100                 105                 110

Asn Asn Ile Lys Arg Leu Leu Thr Met Val Glu Thr Pro Tyr Phe Thr
        115                 120                 125

Lys Glu Thr Val Asp Lys Glu Lys Gly Ile Ile Ala Glu Glu Ile Lys
    130                 135                 140

Met Tyr Gln Glu Gln Pro Gly Tyr Lys Leu Met Phe Asn Thr Leu Arg
145                 150                 155                 160

Ala Met Tyr Gln Gln His Pro Ile Arg Val Asp Ile Ala Gly Ser Val
                165                 170                 175

Glu Ser Ile Tyr Asp Ile Thr Lys Asp Asp Leu Tyr Leu Cys Tyr Glu
            180                 185                 190
```

```
Thr Phe Tyr His Pro Ser Asn Met Val Leu Phe Val Val Gly Asp Val
            195                 200                 205

Asp Pro Glu Ala Ile Cys Arg Ile Val Lys Gln His Glu Asp Ala Arg
    210                 215                 220

Asn Lys Val Asn Gln Pro Lys Ile Glu Arg Gly Leu Val Asp Glu Pro
225                 230                 235                 240

Glu Asp Val Lys Glu Ala Phe Val Thr Glu Ser Met Lys Ile Gln Ser
                245                 250                 255

Pro Arg Leu Met Leu Gly Phe Lys Asn Lys Pro Leu Gln Glu Ala Pro
                    260                 265                 270

Gln Lys Tyr Val Gln Arg Asp Leu Glu Met Ser Leu Phe Phe Glu Leu
                275                 280                 285

Ile Phe Gly Glu Glu Thr Asp Phe Tyr Gln Asn Leu Leu Asn Glu Gly
            290                 295                 300

Leu Ile Asp Asp Thr Phe Gly Tyr Gln Phe Val Leu Glu Pro Thr Tyr
305                 310                 315                 320

Ser Phe Ser Ile Val Thr Ser Ala Thr Glu Glu Pro Asp Lys Leu Lys
                325                 330                 335

Lys Leu Leu Leu Asp Glu Leu Arg Asp Lys Lys Gly Asn Phe Gln Asp
                340                 345                 350

Ala Glu Ala Phe Glu Leu Leu Lys Lys Gln Phe Ile Gly Glu Phe Ile
            355                 360                 365

Ser Ser Leu Asn Ser Pro Glu Tyr Ile Ala Asn Gln Tyr Thr Lys Leu
        370                 375                 380

Tyr Phe Glu Gly Val Ser Val Phe Asp Met Leu Asp Ile Val Glu Asn
385                 390                 395                 400

Ile Thr Leu Asp Ser Ile Asn Glu Thr Ser Ser Leu Tyr Leu Asn Leu
                405                 410                 415

Asp Gln Gln Val Asp Ser Arg Leu Glu Ile Lys Lys
                420                 425

<210> SEQ ID NO 110
<211> LENGTH: 519
<212> TYPE: PRT
<213> ORGANISM: Staphylococcus sp

<400> SEQUENCE: 110

Met Asn Leu Leu Ser Leu Leu Leu Ile Leu Leu Gly Ile Ile Leu Gly
1               5                   10                  15

Val Val Gly Gly Tyr Val Val Ala Arg Asn Leu Leu Gln Lys Gln
                20                  25                  30

Ser Gln Ala Arg Gln Thr Ala Glu Asp Ile Val Asn Gln Ala His Lys
            35                  40                  45

Glu Ala Asp Asn Ile Lys Lys Glu Lys Leu Leu Glu Ala Lys Glu Glu
        50                  55                  60

Asn Gln Ile Leu Arg Glu Gln Thr Glu Ala Glu Leu Arg Glu Arg Arg
65                  70                  75                  80

Ser Glu Leu Gln Arg Gln Glu Thr Arg Leu Leu Gln Lys Glu Glu Asn
                85                  90                  95

Leu Glu Arg Lys Ser Asp Leu Leu Asp Lys Lys Asp Glu Ile Leu Glu
                100                 105                 110

Gln Lys Glu Ser Lys Ile Glu Glu Lys Gln Gln Val Asp Ala Lys
            115                 120                 125

Glu Ser Ser Val Gln Thr Leu Ile Met Lys His Glu Gln Glu Leu Glu
```

```
            130                 135                 140
Arg Ile Ser Gly Leu Thr Gln Glu Glu Ala Ile Asn Glu Gln Leu Gln
145                 150                 155                 160

Arg Val Glu Glu Glu Leu Ser Gln Asp Ile Ala Val Leu Val Lys Glu
                165                 170                 175

Lys Glu Lys Glu Ala Lys Glu Lys Val Asp Lys Thr Ala Lys Glu Leu
            180                 185                 190

Leu Ala Thr Ala Val Gln Arg Leu Ala Ala Asp His Thr Ser Glu Ser
        195                 200                 205

Thr Val Ser Val Val Asn Leu Pro Asn Asp Glu Met Lys Gly Arg Ile
210                 215                 220

Ile Gly Arg Glu Gly Arg Asn Ile Arg Thr Leu Glu Thr Leu Thr Gly
225                 230                 235                 240

Ile Asp Leu Ile Ile Asp Asp Thr Pro Glu Ala Val Ile Leu Ser Gly
                245                 250                 255

Phe Asp Pro Ile Arg Arg Glu Ile Ala Arg Thr Ala Leu Val Asn Leu
            260                 265                 270

Val Ser Asp Gly Arg Ile His Pro Gly Arg Ile Glu Asp Met Val Glu
        275                 280                 285

Lys Ala Arg Lys Glu Val Asp Asp Ile Ile Arg Glu Ala Gly Glu Gln
290                 295                 300

Ala Thr Phe Glu Val Asn Ala His Asn Met His Pro Asp Leu Val Lys
305                 310                 315                 320

Ile Val Gly Arg Leu Asn Tyr Arg Thr Ser Tyr Gly Gln Asn Val Leu
                325                 330                 335

Lys His Ser Ile Glu Val Ala His Leu Ala Ser Met Leu Ala Ala Glu
            340                 345                 350

Leu Gly Glu Asp Glu Thr Leu Ala Lys Arg Ala Gly Leu Leu His Asp
        355                 360                 365

Val Gly Lys Ala Ile Asp His Glu Val Glu Gly Ser His Val Glu Ile
370                 375                 380

Gly Val Glu Leu Ala Lys Lys Tyr Gly Glu Asn Glu Thr Val Ile Asn
385                 390                 395                 400

Ala Ile His Ser His His Gly Asp Val Glu Pro Thr Ser Ile Ile Ser
                405                 410                 415

Ile Leu Val Ala Ala Asp Ala Leu Ser Ala Arg Pro Gly Ala
            420                 425                 430

Arg Lys Glu Thr Leu Glu Asn Tyr Ile Arg Arg Leu Glu Arg Leu Glu
        435                 440                 445

Thr Leu Ser Glu Ser Tyr Asp Gly Val Glu Lys Ala Phe Ala Ile Gln
450                 455                 460

Ala Gly Arg Glu Ile Arg Val Ile Val Ser Pro Glu Glu Ile Asp Asp
465                 470                 475                 480

Leu Lys Ser Tyr Arg Leu Ala Arg Asp Ile Lys Asn Gln Ile Glu Asp
                485                 490                 495

Glu Leu Gln Tyr Pro Gly His Ile Lys Val Thr Val Val Arg Glu Thr
            500                 505                 510

Arg Ala Val Glu Tyr Ala Lys
        515
```

<210> SEQ ID NO 111
<211> LENGTH: 284
<212> TYPE: PRT
<213> ORGANISM: Staphylococcus sp

<400> SEQUENCE: 111

| Met | Ser | Phe | Tyr | Val | Val | Leu | Ile | Ile | Ile | Val | Ala | Leu | Ile | Gly |
| 1 | | | | 5 | | | | | 10 | | | | | 15 |

Ile Leu Val Leu Asn Gln Arg Tyr Ser Asn Ser Lys Ile Asp Thr Glu
                20                  25                  30

Val Tyr Ala Arg Lys Gln Leu Ile Lys Lys Asn Lys Ala Leu Ser Ala
            35                  40                  45

Glu Asn Ala Glu Leu Arg Ser Gln Met Leu Ser Ser Asn Asn Asp Val
        50                  55                  60

Gly His His Ala Tyr Lys Asn Ala Lys Arg Glu Leu Arg Lys Ile Leu
65                  70                  75                  80

Asp Ser Tyr Leu Glu Asn Gly Lys Leu Lys Tyr Tyr Asp Ile Ile Val
                85                  90                  95

Thr Ser Asn Leu Ala Thr Lys His Pro Phe Phe Glu Tyr Ala Arg Ser
                100                 105                 110

Phe Asp Phe Ile Ile Val Ser Asp Ile Gly Leu Ile Asn Val Asp Val
            115                 120                 125

Lys Ser Trp Gly Glu Lys Thr Phe Tyr His Phe Asp Val Pro Asp Glu
    130                 135                 140

His Asp Thr Glu Ile Ser Asn Ser Asn Ile Glu Lys Val Val Gly His
145                 150                 155                 160

Tyr Ile Ser Gln Gln Tyr His Asp Gln Phe Asn Ser Ser Arg Lys Ser
                165                 170                 175

Ile Tyr Thr Phe Thr Glu Thr Val Gln Pro Asn Arg Val Ile Tyr Asp
            180                 185                 190

Phe Tyr Asp Tyr Asp Pro Tyr Gln Leu Ala Ala Asn Ala Lys Ala
        195                 200                 205

Leu Lys Asp His Ile Glu Gln Asn Phe Asn Phe Lys Val Gln Ser Thr
    210                 215                 220

Gly Val Ile Tyr Phe Ser Asp Gly Thr Val Asn Ile Ile Gln Gly Ser
225                 230                 235                 240

Glu Glu Arg Asp Lys Tyr Val Asp Thr Val Ser Thr Lys Ser Ser Leu
                245                 250                 255

Arg Arg Ile Ile Ser Glu Ala Ile Glu Leu Ser Lys His Pro Leu Asn
            260                 265                 270

Lys Glu Gln Val Asp Gln Ile Thr Ala Ile Phe Lys
        275                 280

<210> SEQ ID NO 112
<211> LENGTH: 1274
<212> TYPE: PRT
<213> ORGANISM: Staphylococcus sp

<400> SEQUENCE: 112

Met Ser Trp Phe Asp Lys Leu Phe Gly Glu Asp Asn Asp Ser Asn Asp
1               5                   10                  15

Asp Leu Ile His Arg Lys Lys Arg Arg Gln Glu Ser Gln Asn Ile
            20                  25                  30

Asp Asn Asp His Asp Ser Leu Leu Pro Gln Asn Asn Asp Ile Tyr Ser
        35                  40                  45

Arg Pro Arg Gly Lys Phe Arg Phe Pro Met Ser Val Ala Tyr Glu Asn
    50                  55                  60

Glu Asn Val Glu Gln Ser Ala Asp Thr Ile Ser Asp Glu Lys Glu Gln
65                  70                  75                  80

```
Tyr His Arg Asp Tyr Arg Lys Gln Ser His Asp Ser Arg Ser Gln Lys
            85                  90                  95
Arg His Arg Arg Arg Asn Gln Thr Thr Glu Glu Gln Asn Tyr Ser
            100                 105                 110
Glu Gln Arg Gly Asn Ser Lys Ile Ser Gln Ser Ile Lys Tyr Lys
            115                 120                 125
Asp His Ser His Tyr His Thr Asn Lys Pro Gly Thr Tyr Val Ser Ala
            130                 135                 140
Ile Asn Gly Ile Glu Lys Glu Thr His Lys Pro Lys Thr His Asn Met
145                 150                 155                 160
Tyr Ser Asn Asn Thr Asn His Arg Ala Lys Asp Ser Thr Pro Asp Tyr
                    165                 170                 175
His Lys Glu Ser Phe Lys Thr Ser Glu Val Pro Ser Ala Ile Phe Gly
            180                 185                 190
Thr Met Lys Pro Lys Lys Leu Glu Asn Gly Arg Ile Pro Val Ser Lys
            195                 200                 205
Pro Ser Glu Lys Val Glu Ser Asp Lys Gln Lys Tyr Asp Lys Tyr Val
            210                 215                 220
Ala Lys Thr Gln Thr Ser Gln Asn Lys Gln Leu Glu Gln Glu Lys Gln
225                 230                 235                 240
Asn Asp Ser Val Val Lys Gln Gly Thr Ala Ser Lys Ser Ser Asp Glu
                    245                 250                 255
Asn Val Ser Ser Thr Thr Lys Ser Met Pro Asn Tyr Ser Lys Val Asp
                    260                 265                 270
Asn Thr Ile Lys Ile Glu Asn Ile Tyr Ala Ser Gln Ile Val Glu Glu
                    275                 280                 285
Ile Arg Arg Glu Arg Glu Arg Lys Val Leu Gln Lys Arg Arg Phe Lys
            290                 295                 300
Lys Ala Leu Gln Gln Lys Arg Glu Glu His Lys Asn Glu Glu Gln Asp
305                 310                 315                 320
Ala Ile Gln Arg Ala Ile Asp Glu Met Tyr Ala Lys Gln Ala Glu Arg
                    325                 330                 335
Tyr Val Gly Asp Ser Ser Leu Asn Asp Asp Ser Asp Leu Thr Asp Asn
            340                 345                 350
Ser Thr Asp Ala Ser Gln Leu His Thr Asn Gly Ile Glu Asn Glu Thr
            355                 360                 365
Val Ser Asn Asp Glu Asn Lys Gln Ala Ser Ile Gln Asn Glu Asp Thr
370                 375                 380
Asn Asp Thr His Val Asp Glu Ser Pro Tyr Asn Tyr Glu Glu Val Ser
385                 390                 395                 400
Leu Asn Gln Val Ser Thr Thr Lys Gln Leu Ser Asp Asp Glu Val Thr
            405                 410                 415
Val Ser Asn Val Thr Ser Gln His Gln Ser Ala Leu Gln His Asn Val
            420                 425                 430
Glu Val Asn Asp Lys Asp Glu Leu Lys Asn Gln Ser Arg Leu Ile Ala
            435                 440                 445
Asp Ser Glu Glu Asp Gly Ala Thr Asn Lys Glu Glu Tyr Ser Gly Ser
450                 455                 460
Gln Ile Asp Asp Ala Glu Phe Tyr Glu Leu Asn Asp Thr Glu Val Asp
465                 470                 475                 480
Glu Asp Thr Thr Ser Asn Ile Glu Asp Asn Thr Asn Arg Asn Ala Ser
                    485                 490                 495
```

```
Glu Met His Val Asp Ala Pro Lys Thr Gln Glu Tyr Ala Val Thr Glu
                500                 505                 510

Ser Gln Val Asn Asn Ile Asp Lys Thr Val Asp Asn Glu Ile Glu Leu
        515                 520                 525

Ala Pro Arg His Lys Lys Asp Asp Gln Thr Asn Leu Ser Val Asn Ser
    530                 535                 540

Leu Lys Thr Asn Asp Val Asn Asp Asn His Val Val Glu Asp Ser Ser
545                 550                 555                 560

Met Asn Glu Ile Glu Lys Asn Asn Ala Glu Ile Thr Glu Asn Val Gln
                565                 570                 575

Asn Glu Ala Ala Glu Ser Glu Gln Asn Val Glu Glu Lys Thr Ile Glu
            580                 585                 590

Asn Val Asn Pro Lys Lys Gln Thr Glu Lys Val Ser Thr Leu Ser Lys
            595                 600                 605

Arg Pro Phe Asn Val Val Met Thr Pro Ser Asp Lys Lys Arg Met Met
        610                 615                 620

Asp Arg Lys Lys His Ser Lys Val Asn Val Pro Glu Leu Lys Pro Val
625                 630                 635                 640

Gln Ser Lys Gln Ala Val Ser Glu Arg Met Pro Ala Ser Gln Ala Thr
                645                 650                 655

Pro Ser Ser Arg Ser Asp Ser Gln Glu Ser Asn Thr Asn Ala Tyr Lys
                660                 665                 670

Thr Asn Asn Met Thr Ser Asn Asn Val Glu Asn Asn Gln Leu Ile Gly
            675                 680                 685

His Ala Glu Thr Glu Asn Asp Tyr Gln Asn Ala Gln Gln Tyr Ser Glu
    690                 695                 700

Gln Lys Pro Ser Val Asp Ser Thr Gln Thr Glu Ile Phe Glu Glu Ser
705                 710                 715                 720

Gln Asp Asp Asn Gln Leu Glu Asn Glu Gln Val Asp Gln Ser Thr Ser
                725                 730                 735

Ser Ser Val Ser Glu Val Ser Asp Ile Thr Glu Glu Ser Glu Glu Thr
            740                 745                 750

Thr His Pro Asn Asn Thr Ser Gly Gln Gln Asp Asn Asp Asp Gln Gln
        755                 760                 765

Lys Asp Leu Gln Ser Ser Phe Ser Asn Lys Asn Glu Asp Thr Ala Asn
    770                 775                 780

Glu Asn Arg Pro Arg Thr Asn Gln Gln Asp Val Ala Thr Asn Gln Ala
785                 790                 795                 800

Val Gln Thr Ser Lys Pro Met Ile Arg Lys Gly Pro Asn Ile Lys Leu
                805                 810                 815

Pro Ser Val Ser Leu Leu Glu Glu Pro Gln Val Ile Glu Ser Asp Glu
            820                 825                 830

Asp Trp Ile Thr Asp Lys Lys Lys Glu Leu Asn Asp Ala Leu Phe Tyr
        835                 840                 845

Phe Asn Val Pro Ala Glu Val Gln Asp Val Thr Glu Gly Pro Ser Val
    850                 855                 860

Thr Arg Phe Glu Leu Ser Val Glu Lys Gly Val Lys Val Ser Arg Ile
865                 870                 875                 880

Thr Ala Leu Gln Asp Asp Ile Lys Met Ala Leu Ala Ala Lys Asp Ile
                885                 890                 895

Arg Ile Glu Ala Pro Ile Pro Gly Thr Ser Arg Val Gly Ile Glu Val
            900                 905                 910

Pro Asn Gln Asn Pro Thr Thr Val Asn Leu Arg Ser Ile Ile Glu Ser
```

```
                    915                 920                 925
Pro Ser Phe Lys Asn Ala Glu Ser Lys Leu Thr Val Ala Met Gly Tyr
            930                 935                 940

Arg Ile Asn Asn Glu Pro Leu Leu Met Asp Ile Ala Lys Thr Pro His
945                 950                 955                 960

Ala Leu Ile Ala Gly Ala Thr Gly Ser Gly Lys Ser Val Cys Ile Asn
                965                 970                 975

Ser Ile Leu Met Ser Leu Leu Tyr Lys Asn His Pro Glu Glu Leu Arg
            980                 985                 990

Leu Leu Leu Ile Asp Pro Lys Met Val Glu Leu Ala Pro Tyr Asn Gly
            995                 1000                1005

Leu Pro His Leu Val Ala Pro Val Ile Thr Asp Val Lys Ala Ala
    1010                1015                1020

Thr Gln Ser Leu Lys Trp Ala Val Glu Glu Met Glu Arg Arg Tyr
    1025                1030                1035

Lys Leu Phe Ala His Tyr His Val Arg Asn Ile Thr Ala Phe Asn
    1040                1045                1050

Lys Lys Ala Pro Tyr Asp Glu Arg Met Pro Lys Ile Val Ile Val
    1055                1060                1065

Ile Asp Glu Leu Ala Asp Leu Met Met Met Ala Pro Gln Glu Val
    1070                1075                1080

Glu Gln Ser Ile Ala Arg Ile Ala Gln Lys Ala Arg Ala Cys Gly
    1085                1090                1095

Ile His Met Leu Val Ala Thr Gln Arg Pro Ser Val Asn Val Ile
    1100                1105                1110

Thr Gly Leu Leu Lys Ala Asn Ile Pro Thr Arg Ile Ala Phe Met
    1115                1120                1125

Val Ser Ser Ser Val Asp Ser Arg Thr Ile Leu Asp Ser Gly Gly
    1130                1135                1140

Ala Glu Arg Leu Leu Gly Tyr Gly Asp Met Leu Tyr Leu Gly Ser
    1145                1150                1155

Gly Met Asn Lys Pro Ile Arg Val Gln Gly Thr Phe Val Ser Asp
    1160                1165                1170

Asp Glu Ile Asp Asp Val Val Asp Phe Ile Lys Gln Gln Arg Glu
    1175                1180                1185

Pro Asp Tyr Leu Phe Glu Glu Lys Glu Leu Leu Lys Lys Thr Gln
    1190                1195                1200

Thr Gln Ser Gln Asp Glu Leu Phe Asp Asp Val Cys Ala Phe Met
    1205                1210                1215

Val Asn Glu Gly His Ile Ser Thr Ser Leu Ile Gln Arg His Phe
    1220                1225                1230

Gln Ile Gly Tyr Asn Arg Ala Ala Arg Ile Ile Asp Gln Leu Glu
    1235                1240                1245

Gln Leu Gly Tyr Val Ser Ser Ala Asn Gly Ser Lys Pro Arg Asp
    1250                1255                1260

Val Tyr Val Thr Glu Ala Asp Leu Asn Lys Glu
    1265                1270
```

<210> SEQ ID NO 113
<211> LENGTH: 239
<212> TYPE: PRT
<213> ORGANISM: Staphylococcus sp

<400> SEQUENCE: 113

```
Met Asn Lys Asn Ile Ile Ile Lys Ser Leu Ala Ala Leu Thr Ile Leu
1               5                   10                  15

Thr Ser Ile Thr Gly Val Gly Thr Thr Met Val Glu Gly Ile Gln Gln
            20                  25                  30

Thr Ala Lys Ala Glu Asn Thr Val Lys Gln Ile Thr Asn Thr Asn Val
        35                  40                  45

Ala Pro Tyr Ser Gly Val Thr Trp Met Gly Ala Gly Thr Gly Phe Val
    50                  55                  60

Val Gly Asn His Thr Ile Ile Thr Asn Lys His Val Thr Tyr His Met
65                  70                  75                  80

Lys Val Gly Asp Glu Leu Lys Ala His Pro Asn Gly Phe Tyr Asn Asn
                85                  90                  95

Gly Gly Gly Leu Tyr Lys Val Thr Lys Ile Val Asp Tyr Pro Gly Lys
            100                 105                 110

Glu Asp Ile Ala Val Val Gln Val Glu Lys Ser Thr Gln Pro Lys
        115                 120                 125

Gly Arg Lys Phe Lys Asp Phe Thr Ser Lys Phe Asn Ile Ala Ser Glu
    130                 135                 140

Ala Lys Glu Asn Glu Pro Ile Ser Val Ile Gly Tyr Pro Asn Pro Asn
145                 150                 155                 160

Gly Asn Lys Leu Gln Met Tyr Glu Ser Thr Gly Lys Val Leu Ser Val
                165                 170                 175

Asn Gly Asn Ile Val Ser Ser Asp Ala Ile Ile Gln Pro Gly Ser Ser
            180                 185                 190

Gly Ser Pro Ile Leu Asn Ser Lys His Glu Ala Ile Gly Val Ile Tyr
    195                 200                 205

Ala Gly Asn Lys Pro Ser Gly Glu Ser Thr Arg Gly Phe Ala Val Tyr
    210                 215                 220

Phe Ser Pro Glu Ile Lys Lys Phe Ile Ala Asp Asn Leu Asp Lys
225                 230                 235

<210> SEQ ID NO 114
<211> LENGTH: 238
<212> TYPE: PRT
<213> ORGANISM: Staphylococcus sp

<400> SEQUENCE: 114

Met Asn Lys Asn Ile Ile Ile Lys Ser Leu Ala Ala Leu Thr Ile Leu
1               5                   10                  15

Thr Ser Val Thr Gly Val Gly Thr Thr Val Val Glu Gly Ile Gln Gln
            20                  25                  30

Thr Ala Lys Ala Glu His Asn Val Lys Leu Ile Lys Asn Thr Asn Val
        35                  40                  45

Ala Pro Tyr Asn Gly Val Val Ser Ile Gly Ser Gly Thr Gly Phe Ile
    50                  55                  60

Val Gly Lys Asn Thr Ile Val Thr Asn Lys His Val Ala Gly Met
65                  70                  75                  80

Glu Ile Gly Ala His Ile Ile Ala His Pro Asn Gly Glu Tyr Asn Asn
                85                  90                  95

Gly Gly Phe Tyr Lys Val Lys Ile Val Arg Tyr Ser Gly Gln Glu
            100                 105                 110

Asp Ile Ala Ile Leu His Val Glu Asp Lys Ala Val His Pro Lys Asn
        115                 120                 125

Arg Asn Phe Lys Asp Tyr Thr Gly Ile Leu Lys Ile Ala Ser Glu Ala
    130                 135                 140
```

Lys Glu Asn Glu Arg Ile Ser Ile Val Gly Tyr Pro Glu Pro Tyr Ile
145                 150                 155                 160

Asn Lys Phe Gln Met Tyr Glu Ser Thr Gly Lys Val Leu Ser Val Lys
                165                 170                 175

Gly Asn Met Ile Ile Thr Asp Ala Phe Val Glu Pro Gly Asn Ser Gly
            180                 185                 190

Ser Ala Val Phe Asn Ser Lys Tyr Glu Val Val Gly Val His Phe Gly
        195                 200                 205

Gly Asn Gly Pro Gly Asn Lys Ser Thr Lys Gly Tyr Gly Val Tyr Phe
    210                 215                 220

Ser Pro Glu Ile Lys Lys Phe Ile Ala Asp Asn Thr Asp Lys
225                 230                 235

<210> SEQ ID NO 115
<211> LENGTH: 239
<212> TYPE: PRT
<213> ORGANISM: Staphylococcus sp

<400> SEQUENCE: 115

Met Asn Lys Asn Ile Ile Lys Ser Leu Ala Ala Leu Thr Ile Leu
1               5                   10                  15

Thr Ser Ile Thr Gly Val Gly Thr Thr Val Val Asp Gly Ile Gln Gln
            20                  25                  30

Thr Ala Lys Ala Glu Asn Ser Val Lys Leu Ile Thr Asn Thr Asn Val
        35                  40                  45

Ala Pro Tyr Ser Gly Val Thr Trp Met Gly Ala Gly Thr Gly Phe Val
    50                  55                  60

Val Gly Asn His Thr Ile Ile Thr Asn Lys His Val Thr Tyr His Met
65                  70                  75                  80

Lys Val Gly Asp Glu Leu Lys Ala His Pro Asn Gly Phe Tyr Asn Asn
                85                  90                  95

Gly Gly Gly Leu Tyr Lys Val Thr Lys Ile Val Asp Tyr Pro Gly Lys
            100                 105                 110

Glu Asp Ile Ala Val Val Gln Val Glu Glu Lys Ser Thr Gln Pro Lys
        115                 120                 125

Gly Arg Lys Phe Lys Asp Phe Thr Ser Lys Phe Asn Ile Ala Ser Glu
    130                 135                 140

Ala Lys Glu Asn Glu Pro Ile Ser Val Ile Gly Tyr Pro Asn Pro Asn
145                 150                 155                 160

Gly Asn Lys Leu Gln Met Tyr Glu Ser Thr Gly Lys Val Leu Ser Val
                165                 170                 175

Asn Gly Asn Ile Val Thr Ser Asp Ala Val Val Gln Pro Gly Ser Ser
            180                 185                 190

Gly Ser Pro Ile Leu Asn Ser Lys Arg Glu Ala Ile Gly Val Met Tyr
        195                 200                 205

Ala Ser Asp Lys Pro Thr Gly Glu Ser Thr Arg Ser Phe Ala Val Tyr
    210                 215                 220

Phe Ser Pro Glu Ile Lys Lys Phe Ile Ala Asp Asn Leu Asp Lys
225                 230                 235

<210> SEQ ID NO 116
<211> LENGTH: 239
<212> TYPE: PRT
<213> ORGANISM: Staphylococcus sp

<400> SEQUENCE: 116

```
Met Asn Lys Asn Ile Val Ile Lys Ser Met Ala Ala Leu Ala Ile Leu
1               5                   10                  15

Thr Ser Val Thr Gly Ile Asn Ala Ala Val Val Glu Glu Thr Gln Gln
            20                  25                  30

Ile Ala Asn Ala Glu Lys Asn Val Thr Gln Val Lys Asp Thr Asn Ile
            35                  40                  45

Phe Pro Tyr Asn Gly Val Val Ser Phe Lys Asp Ala Thr Gly Phe Val
50                      55                  60

Ile Gly Lys Asn Thr Ile Ile Thr Asn Lys His Val Ser Lys Asp Tyr
65                  70                  75                  80

Lys Val Gly Asp Arg Ile Thr Ala His Pro Asn Gly Asp Lys Gly Asn
                85                  90                  95

Gly Gly Ile Tyr Lys Ile Lys Ser Ile Ser Asp Tyr Pro Gly Asp Glu
            100                 105                 110

Asp Ile Ser Val Met Asn Ile Glu Glu Gln Ala Val Glu Arg Gly Pro
            115                 120                 125

Lys Gly Phe Asn Phe Asn Glu Asn Val Gln Ala Phe Asn Phe Ala Lys
            130                 135                 140

Asp Ala Lys Val Asp Asp Lys Ile Lys Val Ile Gly Tyr Pro Leu Pro
145                 150                 155                 160

Ala Gln Asn Ser Phe Lys Gln Phe Glu Ser Thr Gly Thr Ile Lys Arg
                165                 170                 175

Ile Lys Asp Asn Ile Leu Asn Phe Asp Ala Tyr Ile Glu Pro Gly Asn
                180                 185                 190

Ser Gly Ser Pro Val Leu Asn Ser Asn Asn Glu Val Ile Gly Val Val
            195                 200                 205

Tyr Gly Gly Ile Gly Lys Ile Gly Ser Glu Tyr Asn Gly Ala Val Tyr
            210                 215                 220

Phe Thr Pro Gln Ile Lys Asp Phe Ile Gln Lys His Ile Glu Gln
225                 230                 235
```

<210> SEQ ID NO 117
<211> LENGTH: 240
<212> TYPE: PRT
<213> ORGANISM: Staphylococcus sp

<400> SEQUENCE: 117

```
Met Asn Lys Asn Val Val Ile Lys Ser Leu Ala Ala Leu Thr Ile Leu
1               5                   10                  15

Thr Ser Val Thr Gly Ile Gly Thr Thr Leu Val Glu Glu Val Gln Gln
            20                  25                  30

Thr Ala Lys Ala Glu Asn Asn Val Thr Lys Val Lys Asp Thr Asn Ile
            35                  40                  45

Phe Pro Tyr Thr Gly Val Val Ala Phe Lys Ser Ala Thr Gly Phe Val
50                      55                  60

Val Gly Lys Asn Thr Ile Leu Thr Asn Lys His Val Ser Lys Asn Tyr
65                  70                  75                  80

Lys Val Gly Asp Arg Ile Thr Ala His Pro Asn Ser Asp Lys Gly Asn
                85                  90                  95

Gly Gly Ile Tyr Ser Ile Lys Lys Ile Asn Tyr Pro Gly Lys Glu
            100                 105                 110

Asp Val Ser Val Ile Gln Val Glu Glu Arg Ala Ile Glu Arg Gly Pro
            115                 120                 125

Lys Gly Phe Asn Phe Asn Asp Asn Val Thr Pro Phe Lys Tyr Ala Ala
```

```
                    130                 135                 140
Gly Ala Lys Ala Gly Glu Arg Ile Lys Val Ile Gly Tyr Pro His Pro
145                 150                 155                 160

Tyr Lys Asn Lys Tyr Val Leu Tyr Glu Ser Thr Gly Pro Val Met Ser
                165                 170                 175

Val Glu Gly Ser Ser Ile Val Tyr Ser Ala His Thr Glu Ser Gly Asn
            180                 185                 190

Ser Gly Ser Pro Val Leu Asn Ser Asn Asn Glu Leu Val Gly Ile His
        195                 200                 205

Phe Ala Ser Asp Val Lys Asn Asp Asp Asn Arg Asn Ala Tyr Gly Val
    210                 215                 220

Tyr Phe Thr Pro Glu Ile Lys Lys Phe Ile Ala Glu Asn Ile Asp Lys
225                 230                 235                 240

<210> SEQ ID NO 118
<211> LENGTH: 235
<212> TYPE: PRT
<213> ORGANISM: Staphylococcus sp

<400> SEQUENCE: 118

Met Asn Lys Asn Val Met Val Lys Gly Leu Thr Ala Leu Thr Ile Leu
1               5                   10                  15

Thr Ser Leu Gly Phe Ala Glu Asn Ile Ser Asn Gln Pro His Ser Ile
            20                  25                  30

Ala Lys Ala Glu Lys Asn Val Lys Glu Ile Thr Asp Ala Thr Lys Glu
        35                  40                  45

Pro Tyr Asn Ser Val Val Ala Phe Val Gly Gly Thr Gly Val Val Val
    50                  55                  60

Gly Lys Asn Thr Ile Val Thr Asn Lys His Ile Ala Lys Ser Asn Asp
65                  70                  75                  80

Ile Phe Lys Asn Arg Val Ser Ala His His Ser Ser Lys Gly Lys Gly
                85                  90                  95

Gly Gly Asn Tyr Asp Val Lys Asp Ile Val Glu Tyr Pro Gly Lys Glu
            100                 105                 110

Asp Leu Ala Ile Val His Val His Glu Thr Ser Thr Glu Gly Leu Asn
        115                 120                 125

Phe Asn Lys Asn Val Ser Tyr Thr Lys Phe Ala Asp Gly Ala Lys Val
    130                 135                 140

Lys Asp Arg Ile Ser Val Ile Gly Tyr Pro Lys Gly Ala Gln Thr Lys
145                 150                 155                 160

Tyr Lys Met Phe Glu Ser Thr Gly Thr Ile Asn His Ile Ser Gly Thr
                165                 170                 175

Phe Met Glu Phe Asp Ala Tyr Ala Gln Pro Gly Asn Ser Gly Ser Pro
            180                 185                 190

Val Leu Asn Ser Lys His Glu Leu Ile Gly Ile Leu Tyr Ala Gly Ser
        195                 200                 205

Gly Lys Asp Glu Ser Glu Lys Asn Phe Gly Val Tyr Phe Thr Pro Gln
    210                 215                 220

Leu Lys Glu Phe Ile Gln Asn Asn Ile Glu Lys
225                 230                 235

<210> SEQ ID NO 119
<211> LENGTH: 163
<212> TYPE: PRT
<213> ORGANISM: Staphylococcus sp
```

```
<400> SEQUENCE: 119

Met Leu Lys Arg Ser Leu Leu Phe Leu Thr Val Leu Leu Leu Phe
1               5                   10                  15

Ser Phe Ser Ser Ile Thr Asn Glu Val Ser Ala Ser Ser Phe Asp
            20                  25                  30

Lys Gly Lys Tyr Lys Gly Asp Asp Ala Ser Tyr Phe Glu Pro Thr
            35                  40                  45

Gly Pro Tyr Leu Met Val Asn Val Thr Gly Val Asp Gly Lys Gly Asn
50                      55                  60

Glu Leu Leu Ser Pro His Tyr Val Glu Phe Pro Ile Lys Pro Gly Thr
65                  70                  75                  80

Thr Leu Thr Lys Glu Lys Ile Glu Tyr Tyr Val Glu Trp Ala Leu Asp
                85                  90                  95

Ala Thr Ala Tyr Lys Glu Phe Arg Val Val Glu Leu Asp Pro Ser Ala
                100                 105                 110

Lys Ile Glu Val Thr Tyr Tyr Asp Lys Asn Lys Lys Glu Glu Thr
                115                 120                 125

Lys Ser Phe Pro Ile Thr Glu Lys Gly Phe Val Val Pro Asp Leu Ser
    130                 135                 140

Glu His Ile Lys Asn Pro Gly Phe Asn Leu Ile Thr Lys Val Ile Ile
145                 150                 155                 160

Glu Lys Lys

<210> SEQ ID NO 120
<211> LENGTH: 290
<212> TYPE: PRT
<213> ORGANISM: Staphylococcus sp

<400> SEQUENCE: 120

Met Lys Lys Lys Ala Leu Leu Pro Leu Phe Leu Gly Ile Met Val Phe
1               5                   10                  15

Leu Ala Gly Cys Asp Tyr Ser Lys Pro Glu Lys Arg Ser Gly Phe Phe
            20                  25                  30

Tyr Asn Thr Phe Val Asp Pro Met Lys Asn Val Leu Asp Trp Leu Gly
            35                  40                  45

Asn Asn Leu Leu Asn Asp Asn Tyr Gly Leu Ala Ile Ile Ile Leu Val
50                      55                  60

Leu Val Ile Arg Ile Ile Leu Leu Pro Phe Met Leu Ser Asn Tyr Lys
65                  70                  75                  80

Asn Ser His Met Met Arg Gln Lys Met Lys Val Ala Lys Pro Glu Val
                85                  90                  95

Glu Lys Ile Gln Glu Lys Val Lys Arg Ala Arg Thr Gln Glu Glu Lys
                100                 105                 110

Met Ala Ala Asn Gln Glu Leu Met Gln Val Tyr Lys Lys Tyr Asp Met
                115                 120                 125

Asn Pro Ile Lys Ser Met Leu Gly Cys Leu Pro Met Leu Ile Gln Leu
    130                 135                 140

Pro Ile Ile Met Gly Leu Tyr Phe Val Leu Lys Asp Gln Leu Val Asp
145                 150                 155                 160

Gly Leu Phe Lys Tyr Pro His Phe Leu Trp Phe Asp Leu Gly Arg Pro
                165                 170                 175

Asp Ile Trp Ile Thr Ile Ile Ala Gly Val Leu Tyr Phe Ile Gln Ala
        180                 185                 190

Tyr Val Ser Ser Lys Thr Met Pro Asp Glu Gln Arg Gln Met Gly Tyr
```

```
                195                 200                 205
Met Met Met Val Ile Ser Pro Ile Met Ile Trp Ile Ser Leu Ser
    210                 215                 220

Ser Ala Ser Ala Leu Gly Leu Tyr Trp Ser Val Ser Ala Ala Phe Leu
225                 230                 235                 240

Val Val Gln Thr His Phe Ala Asn Ile Tyr Tyr Glu Lys Val Ala Lys
                245                 250                 255

Lys Glu Val Gln Pro Phe Ile Glu Ala Tyr Glu Arg Glu His Asn Gly
                260                 265                 270

Gly Ser Asn Lys Lys Gly Lys Asn Thr Gln Val Val Ser Lys Lys Lys
                275                 280                 285

Lys Lys
    290

<210> SEQ ID NO 121
<211> LENGTH: 460
<212> TYPE: PRT
<213> ORGANISM: Staphylococcus sp

<400> SEQUENCE: 121

Met Lys Ser Cys Pro Lys Cys Gly Gln Gln Ala Gln Asp Asp Val Gln
1               5                   10                  15

Ile Cys Thr Gln Cys Gly His Lys Phe Asp Ser Arg Gln Ala Leu Tyr
                20                  25                  30

Arg Lys Ser Thr Asp Glu Asp Ile Gln Thr Asn Asn Ile Lys Met Arg
            35                  40                  45

Lys Met Val Pro Trp Ala Ile Gly Phe Phe Ile Leu Ile Leu Ile Ile
    50                  55                  60

Ile Leu Phe Phe Leu Leu Arg Asn Phe Asn Ser Pro Glu Ala Gln Thr
65              70                  75                  80

Lys Ile Leu Val Asn Ala Ile Glu Asn Asn Asp Lys Gln Lys Val Ala
                85                  90                  95

Thr Leu Leu Ser Thr Lys Asp Asn Lys Val Asp Ser Glu Glu Ala Lys
            100                 105                 110

Val Tyr Ile Asn Tyr Ile Lys Asp Glu Val Gly Leu Lys Gln Phe Val
        115                 120                 125

Ser Asp Leu Lys Asn Thr Val His Lys Leu Asn Lys Ser Lys Thr Ser
130                 135                 140

Val Ala Ser Tyr Ile Gln Thr Arg Ser Gly Gln Asn Ile Leu Arg Val
145                 150                 155                 160

Ser Lys Asn Gly Thr Arg Tyr Ile Phe Phe Asp Asn Met Ser Phe Thr
                165                 170                 175

Ala Pro Thr Lys Gln Pro Ile Val Lys Pro Lys Glu Lys Thr Lys Tyr
            180                 185                 190

Glu Phe Lys Ser Gly Gly Lys Lys Met Val Ile Ala Glu Ala Asn
        195                 200                 205

Lys Val Thr Pro Ile Gly Asn Phe Ile Pro Gly Thr Tyr Arg Ile Pro
    210                 215                 220

Ala Met Lys Ser Thr Glu Asn Gly Asp Phe Ala Gly His Leu Lys Phe
225                 230                 235                 240

Asp Phe Arg Gln Ser Asn Ser Glu Thr Val Asp Val Thr Glu Asp Phe
                245                 250                 255

Glu Glu Ala Asn Ile Ser Val Thr Leu Lys Gly Asp Thr Lys Leu Asn
            260                 265                 270
```

Asp Ser Ser Lys Lys Val Thr Ile Asn Asp His Glu Met Ala Phe Ser
        275                 280                 285

Ser Ser Lys Thr Tyr Gly Pro Tyr Pro Gln Asn Lys Asp Ile Thr Ile
    290                 295                 300

Ser Ala Ser Gly Lys Ala Lys Asp Lys Thr Phe Thr Thr Gln Thr Lys
305                 310                 315                 320

Thr Leu Lys Ala Ser Asp Leu Lys Tyr Asn Thr Glu Ile Thr Leu Asn
                325                 330                 335

Phe Asp Ser Glu Asp Ile Glu Asp Tyr Val Glu Lys Lys Glu Lys Glu
            340                 345                 350

Glu Asn Ser Leu Lys Asn Lys Leu Ile Glu Phe Phe Ala Gly Tyr Ser
        355                 360                 365

Leu Ala Asn Asn Ala Ala Phe Asn Gln Ser Asp Phe Asp Phe Val Ser
    370                 375                 380

Ser Tyr Ile Lys Lys Gly Ser Ser Phe Tyr Asp Asp Val Lys Lys Arg
385                 390                 395                 400

Val Ser Lys Gly Ser Leu Met Met Ile Ser Ser Pro Gln Ile Ile Asp
                405                 410                 415

Ala Glu Lys His Gly Asp Lys Ile Thr Ala Thr Val Arg Leu Ile Asn
            420                 425                 430

Glu Asn Gly Lys Gln Val Asp Lys Glu Tyr Glu Leu Glu Gln Gly Ser
        435                 440                 445

Gln Asp Arg Leu Gln Leu Ile Lys Thr Ser Glu Lys
    450                 455                 460

<210> SEQ ID NO 122
<211> LENGTH: 322
<212> TYPE: PRT
<213> ORGANISM: Staphylococcus sp

<400> SEQUENCE: 122

Met Arg Lys Lys Trp Ser Thr Leu Ala Phe Gly Phe Leu Val Ala Ala
1               5                   10                  15

Tyr Ala His Ile Arg Ile Lys Glu Lys Arg Ser Val Lys Ser Tyr Met
            20                  25                  30

Leu Glu Gln Gly Ile Arg Leu Ser Arg Ala Lys Arg Phe Met Tyr
        35                  40                  45

Lys Glu Glu Ala Met Lys Ala Leu Glu Lys Met Ala Pro Gln Thr Ala
50                  55                  60

Gly Glu Tyr Glu Gly Thr Asn Tyr Gln Phe Lys Met Pro Val Lys Val
65                  70                  75                  80

Asp Lys His Phe Gly Ser Thr Val Tyr Thr Val Asn Asp Lys Gln Asp
                85                  90                  95

Lys His Gln Arg Val Val Leu Tyr Ala His Gly Ala Trp Phe Gln
            100                 105                 110

Asp Pro Leu Lys Ile His Phe Glu Phe Ile Asp Glu Leu Ala Glu Thr
        115                 120                 125

Leu Asn Ala Lys Val Ile Met Pro Val Tyr Pro Lys Ile Pro His Gln
    130                 135                 140

Asp Tyr Gln Ala Thr Tyr Val Leu Phe Glu Lys Leu Tyr His Asp Leu
145                 150                 155                 160

Leu Asn Gln Val Ala Asp Ser Lys Gln Ile Val Val Met Gly Asp Ser
                165                 170                 175

Ala Gly Gly Gln Ile Ala Leu Ser Phe Ala Gln Leu Leu Lys Glu Lys
            180                 185                 190

```
His Ile Val Gln Pro Gly His Ile Val Leu Ile Ser Pro Val Leu Asp
        195                 200                 205

Ala Thr Met Gln His Pro Glu Ile Pro Asp Tyr Leu Lys Lys Asp Pro
    210                 215                 220

Met Val Gly Val Asp Gly Ser Val Phe Leu Ala Glu Gln Trp Ala Gly
225                 230                 235                 240

Asp Thr Pro Leu Asp Asn Tyr Lys Val Ser Pro Ile Asn Gly Asp Leu
                245                 250                 255

Asp Gly Leu Gly Arg Ile Thr Leu Thr Val Gly Thr Lys Glu Val Leu
            260                 265                 270

Tyr Pro Asp Ala Leu Asn Leu Ser Gln Leu Leu Ser Ala Lys Gly Ile
        275                 280                 285

Glu His Asp Phe Ile Pro Gly Tyr Tyr Gln Phe His Ile Tyr Pro Val
    290                 295                 300

Phe Pro Ile Pro Glu Arg Arg Arg Phe Leu Tyr Gln Val Lys Asn Ile
305                 310                 315                 320

Ile Asn

<210> SEQ ID NO 123
<211> LENGTH: 143
<212> TYPE: PRT
<213> ORGANISM: Staphylococcus sp

<400> SEQUENCE: 123

Met Glu Tyr Lys Lys Ile Leu Ile Arg Leu Leu Ile Ala Phe Ala Val
1               5                   10                  15

Leu Phe Ser Ala Asp Phe Thr Tyr Gln Ser Val Glu Gln Thr His Gln
            20                  25                  30

Ser His Ala Ala Val Asn Tyr Tyr Ser Lys Asn Gln Cys Thr Trp Trp
        35                  40                  45

Ala Phe Lys Arg Arg Ala Gln Val Gly Lys Pro Val Ser Asn Arg Trp
    50                  55                  60

Gly Asn Ala Lys Asn Trp Tyr Tyr Asn Ala Arg Lys Ser Lys Tyr Ala
65                  70                  75                  80

Thr Gly Arg Thr Pro Arg Lys Phe Ala Val Met Gln Ser Thr Ala Gly
                85                  90                  95

Tyr Tyr Gly His Val Ala Val Val Glu Gln Val Tyr Lys Asn Gly Ser
            100                 105                 110

Ile Lys Val Ser Glu Tyr Asn Phe Tyr Arg Pro Leu Lys Tyr Asn Thr
        115                 120                 125

Arg Val Leu Ser Lys Lys Ala Ala Arg Asn Phe Asn Tyr Ile Tyr
    130                 135                 140

<210> SEQ ID NO 124
<211> LENGTH: 255
<212> TYPE: PRT
<213> ORGANISM: Staphylococcus sp

<400> SEQUENCE: 124

Met Lys Lys Ile Val Thr Ala Thr Ile Ala Thr Ala Gly Leu Ala Thr
1               5                   10                  15

Ile Ala Phe Ala Gly His Asp Ala Gln Ala Glu Gln Asn Asn Asn
            20                  25                  30

Gly Tyr Asn Ser Asn Asp Ala Gln Ser Tyr Ser Tyr Thr Tyr Thr Ile
        35                  40                  45
```

Asp Ala Gln Gly Asn Tyr His Tyr Thr Trp Thr Gly Asn Trp Asn Pro
 50                  55                  60

Ser Gln Leu Thr Gln Asn Asn Thr Tyr Tyr Asn Asn Tyr Asn Thr
 65                  70                  75                  80

Tyr Ser Tyr Asn Asn Ala Ser Tyr Asn Asn Tyr Tyr Asn His Ser Tyr
                 85                  90                  95

Gln Tyr Asn Asn Tyr Thr Asn Asn Ser Gln Thr Ala Thr Asn Asn Tyr
            100                 105                 110

Tyr Thr Gly Gly Ser Gly Ala Ser Tyr Ser Thr Thr Ser Asn Asn Val
            115                 120                 125

His Val Thr Thr Thr Ala Ala Pro Ser Ser Asn Gly Arg Ser Ile Ser
130                 135                 140

Asn Gly Tyr Ala Ser Gly Ser Asn Leu Tyr Thr Ser Gly Gln Cys Thr
145                 150                 155                 160

Tyr Tyr Val Phe Asp Arg Val Gly Gly Lys Ile Gly Ser Thr Trp Gly
                165                 170                 175

Asn Ala Ser Asn Trp Ala Asn Ala Ala Ser Ser Gly Tyr Thr Val
            180                 185                 190

Asn Asn Thr Pro Lys Val Gly Ala Ile Met Gln Thr Thr Gln Gly Tyr
            195                 200                 205

Tyr Gly His Val Ala Tyr Val Glu Gly Val Asn Ser Asn Gly Ser Val
            210                 215                 220

Arg Val Ser Glu Met Asn Tyr Gly His Gly Ala Gly Val Val Thr Ser
225                 230                 235                 240

Arg Thr Ile Ser Ala Asn Gln Ala Gly Ser Tyr Asn Phe Ile His
                245                 250                 255

<210> SEQ ID NO 125
<211> LENGTH: 131
<212> TYPE: PRT
<213> ORGANISM: Staphylococcus sp

<400> SEQUENCE: 125

Met Lys Lys Leu Ile Ile Ser Leu Met Ala Val Met Leu Phe Leu Thr
 1               5                  10                  15

Gly Cys Gly Lys Ser Gln Glu Lys Ala Thr Leu Glu Lys Asp Ile Asp
                20                  25                  30

Asn Leu Gln Lys Glu Asn Lys Glu Leu Asp Lys Lys Glu Lys Leu
            35                  40                  45

Gln Gln Glu Lys Glu Lys Leu Ala Asp Lys Gln Lys Asp Leu Glu Lys
 50                  55                  60

Glu Val Lys Asp Leu Lys Pro Ser Lys Glu Asp Asn Lys Asp Lys
 65                  70                  75                  80

Lys Asp Glu Asp Lys Asn Lys Asp Lys Asp Lys Glu Ala Ser
                85                  90                  95

Gln Asp Lys Gln Ser Lys Asp Gln Thr Lys Ser Ser Asp Lys Asp Asn
            100                 105                 110

His Lys Lys Pro Thr Ser Ala Asp Lys Asp Gln Lys Ala Asn Asp Lys
            115                 120                 125

His Gln Ser
    130

<210> SEQ ID NO 126
<211> LENGTH: 192
<212> TYPE: PRT
<213> ORGANISM: Staphylococcus sp

<400> SEQUENCE: 126

| Met | Thr | Lys | Arg | Pro | Lys | Arg | Ile | Leu | Ala | Thr | Ile | Ile | Ile | Phe | Leu |
|---|---|---|---|---|---|---|---|---|---|---|---|---|---|---|---|
| 1 | | | | 5 | | | | | 10 | | | | | 15 | |

| Ser | Leu | Leu | Phe | Thr | Ile | Ile | Tyr | Ile | Asp | Asp | Ile | Gln | Lys | Trp | Phe |
|---|---|---|---|---|---|---|---|---|---|---|---|---|---|---|---|
| | | | | 20 | | | | | 25 | | | | | 30 | |

| Asn | Gln | Tyr | Thr | Asp | Lys | Leu | Thr | Gln | Asn | His | Lys | Gly | Gln | Gly | His |
|---|---|---|---|---|---|---|---|---|---|---|---|---|---|---|---|
| | | | 35 | | | | | 40 | | | | | 45 | | |

| Ser | Lys | Trp | Glu | Asp | Phe | Phe | Arg | Gly | Ser | Arg | Ile | Thr | Glu | Thr | Phe |
|---|---|---|---|---|---|---|---|---|---|---|---|---|---|---|---|
| | 50 | | | | | 55 | | | | | 60 | | | | |

| Gly | Lys | Tyr | Gln | His | Ser | Pro | Phe | Asp | Gly | Lys | His | Tyr | Gly | Ile | Asp |
|---|---|---|---|---|---|---|---|---|---|---|---|---|---|---|---|
| 65 | | | | | 70 | | | | | 75 | | | | | 80 |

| Phe | Ala | Leu | Pro | Lys | Gly | Thr | Pro | Leu | Lys | Ala | Pro | Thr | Asn | Gly | Lys |
|---|---|---|---|---|---|---|---|---|---|---|---|---|---|---|---|
| | | | | 85 | | | | | 90 | | | | | 95 | |

| Val | Thr | Arg | Ile | Phe | Asn | Asn | Glu | Leu | Gly | Gly | Lys | Val | Leu | Gln | Ile |
|---|---|---|---|---|---|---|---|---|---|---|---|---|---|---|---|
| | | | 100 | | | | | 105 | | | | | 110 | | |

| Ala | Glu | Asp | Asn | Gly | Glu | Tyr | His | Gln | Trp | Tyr | Leu | His | Leu | Asp | Lys |
|---|---|---|---|---|---|---|---|---|---|---|---|---|---|---|---|
| | | | 115 | | | | | 120 | | | | | 125 | | |

| Tyr | Asn | Val | Lys | Val | Gly | Asp | Arg | Val | Lys | Ala | Gly | Asp | Ile | Ile | Ala |
|---|---|---|---|---|---|---|---|---|---|---|---|---|---|---|---|
| | 130 | | | | | 135 | | | | | 140 | | | | |

| Tyr | Ser | Gly | Asn | Thr | Gly | Ile | Gln | Thr | Thr | Gly | Ala | His | Leu | His | Phe |
|---|---|---|---|---|---|---|---|---|---|---|---|---|---|---|---|
| 145 | | | | | 150 | | | | | 155 | | | | | 160 |

| Gln | Arg | Met | Lys | Gly | Gly | Val | Gly | Asn | Ala | Tyr | Ala | Glu | Asp | Pro | Lys |
|---|---|---|---|---|---|---|---|---|---|---|---|---|---|---|---|
| | | | | 165 | | | | | 170 | | | | | 175 | |

| Pro | Phe | Ile | Asp | Gln | Leu | Pro | Asp | Gly | Glu | Arg | Ser | Leu | Tyr | Asp | Leu |
|---|---|---|---|---|---|---|---|---|---|---|---|---|---|---|---|
| | | | 180 | | | | | 185 | | | | | 190 | | |

<210> SEQ ID NO 127
<211> LENGTH: 505
<212> TYPE: PRT
<213> ORGANISM: Staphylococcus sp

<400> SEQUENCE: 127

| Met | Thr | Gln | Gln | Gln | Asn | Asp | Lys | Arg | Thr | Leu | Lys | Asn | Lys | His | Thr |
|---|---|---|---|---|---|---|---|---|---|---|---|---|---|---|---|
| 1 | | | | 5 | | | | | 10 | | | | | 15 | |

| Tyr | Gln | Asn | Glu | Pro | Leu | Pro | Asn | Arg | Lys | Asp | Phe | Val | Val | Ser | Phe |
|---|---|---|---|---|---|---|---|---|---|---|---|---|---|---|---|
| | | | | 20 | | | | | 25 | | | | | 30 | |

| Ile | Thr | Gly | Ala | Leu | Val | Gly | Ser | Ala | Leu | Gly | Leu | Tyr | Phe | Lys | Asn |
|---|---|---|---|---|---|---|---|---|---|---|---|---|---|---|---|
| | | | 35 | | | | | 40 | | | | | 45 | | |

| Lys | Val | Tyr | Gln | Lys | Ala | Asp | Asp | Leu | Lys | Val | Lys | Glu | Gln | Glu | Leu |
|---|---|---|---|---|---|---|---|---|---|---|---|---|---|---|---|
| | 50 | | | | | 55 | | | | | 60 | | | | |

| Ser | Gln | Lys | Phe | Glu | Glu | Arg | Lys | Thr | Gln | Leu | Glu | Glu | Thr | Val | Ala |
|---|---|---|---|---|---|---|---|---|---|---|---|---|---|---|---|
| 65 | | | | | 70 | | | | | 75 | | | | | 80 |

| Tyr | Thr | Lys | Glu | Arg | Val | Glu | Gly | Phe | Leu | Asn | Lys | Ser | Lys | Asn | Glu |
|---|---|---|---|---|---|---|---|---|---|---|---|---|---|---|---|
| | | | | 85 | | | | | 90 | | | | | 95 | |

| Gln | Ala | Ala | Leu | Lys | Ala | Gln | Gln | Ala | Ala | Ile | Lys | Glu | Glu | Ala | Ser |
|---|---|---|---|---|---|---|---|---|---|---|---|---|---|---|---|
| | | | 100 | | | | | 105 | | | | | 110 | | |

| Ala | Asn | Asn | Leu | Ser | Asp | Thr | Ser | Gln | Glu | Ala | Gln | Glu | Ile | Gln | Glu |
|---|---|---|---|---|---|---|---|---|---|---|---|---|---|---|---|
| | | | 115 | | | | | 120 | | | | | 125 | | |

| Ala | Lys | Arg | Glu | Ala | Gln | Ala | Glu | Ala | Asp | Lys | Ser | Val | Ala | Val | Ser |
|---|---|---|---|---|---|---|---|---|---|---|---|---|---|---|---|
| | 130 | | | | | 135 | | | | | 140 | | | | |

| Asn | Lys | Glu | Ser | Lys | Ala | Val | Ala | Leu | Lys | Ala | Gln | Gln | Ala | Ala | Ile |
|---|---|---|---|---|---|---|---|---|---|---|---|---|---|---|---|
| 145 | | | | | 150 | | | | | 155 | | | | | 160 |

| Lys | Glu | Glu | Ala | Ser | Ala | Asn | Asn | Leu | Ser | Asp | Thr | Ser | Gln | Glu | Ala |
|---|---|---|---|---|---|---|---|---|---|---|---|---|---|---|---|
| | | | | 165 | | | | | 170 | | | | | 175 | |

```
Gln Glu Ile Gln Glu Ala Lys Lys Glu Ala Gln Ala Glu Thr Asp Lys
            180                 185                 190

Ser Ala Ala Val Ser Asn Glu Pro Lys Ala Val Ala Leu Lys Ala
        195                 200                 205

Gln Gln Ala Ala Ile Lys Glu Glu Ala Ser Ala Asn Asn Leu Ser Asp
    210                 215                 220

Thr Ser Gln Glu Ala Gln Glu Val Gln Glu Ala Lys Lys Glu Ala Gln
225                 230                 235                 240

Ala Glu Thr Asp Lys Ser Ala Ala Val Ser Asn Glu Pro Lys Ala
            245                 250                 255

Val Ala Leu Lys Ala Gln Gln Ala Ala Ile Lys Glu Glu Ala Ser Ala
        260                 265                 270

Asn Asn Leu Ser Asp Ile Ser Gln Glu Ala Gln Glu Val Gln Glu Ala
        275                 280                 285

Lys Lys Glu Ala Gln Ala Glu Lys Asp Ser Asp Thr Leu Thr Lys Asp
    290                 295                 300

Ala Ser Ala Ala Lys Val Glu Val Ser Lys Pro Glu Ser Gln Ala Glu
305                 310                 315                 320

Arg Leu Ala Asn Ala Ala Lys Gln Lys Gln Ala Lys Leu Thr Pro Gly
            325                 330                 335

Ser Lys Glu Ser Gln Leu Thr Glu Ala Leu Phe Ala Glu Lys Pro Val
        340                 345                 350

Ala Lys Asn Asp Leu Lys Glu Ile Pro Gln Leu Val Thr Lys Lys Asn
        355                 360                 365

Asp Val Ser Glu Thr Glu Thr Val Asn Ile Asp Asn Lys Asp Thr Val
    370                 375                 380

Lys Gln Lys Glu Ala Lys Phe Glu Asn Gly Val Ile Thr Arg Lys Ala
385                 390                 395                 400

Asp Glu Lys Thr Thr Asn Asn Thr Ala Val Asp Lys Lys Ser Gly Lys
            405                 410                 415

Gln Ser Lys Lys Thr Thr Pro Ser Asn Lys Arg Asn Ala Ser Lys Ala
        420                 425                 430

Ser Thr Asn Lys Thr Ser Gly Gln Lys Gln His Asn Lys Lys Ser
        435                 440                 445

Ser Gln Gly Ala Lys Lys Gln Ser Ser Ser Lys Ser Thr Gln Lys
    450                 455                 460

Asn Asn Gln Thr Ser Asn Lys Asn Ser Lys Thr Thr Asn Ala Lys Ser
465                 470                 475                 480

Ser Asn Ala Ser Lys Thr Pro Asn Ala Lys Val Glu Lys Ala Lys Ser
            485                 490                 495

Lys Ile Glu Lys Arg Thr Phe Asn Asp
            500                 505

<210> SEQ ID NO 128
<211> LENGTH: 305
<212> TYPE: PRT
<213> ORGANISM: Staphylococcus sp

<400> SEQUENCE: 128

Met Phe Lys Arg Thr Lys Leu Ile Leu Ile Ala Thr Leu Leu Leu Ser
1               5                   10                  15

Gly Cys Ser Thr Thr Asn Asn Glu Ser Asn Lys Glu Thr Lys Ser Val
            20                  25                  30

Pro Glu Glu Met Glu Ala Ser Lys Tyr Val Gly Gln Gly Phe Gln Pro
```

```
            35                  40                  45
Pro Ala Glu Lys Asp Val Val Glu Phe Ala Lys Lys His Lys Asp Lys
         50                  55                  60
Ile Ala Lys Arg Gly Glu Gln Phe Phe Met Asp Asn Phe Gly Leu Lys
 65                  70                  75                  80
Val Lys Ala Thr Asn Val Val Gly Ser Gly Lys Gly Val Glu Val Phe
                 85                  90                  95
Val His Cys Asp Asp His Asp Ile Val Phe Asn Ala Ser Ile Pro Phe
                100                 105                 110
Asp Lys Ser Ile Ile Glu Ser Asp Ser Ser Leu Arg Ser Glu Asp Lys
            115                 120                 125
Gly Asp Asp Met Ser Thr Leu Val Gly Thr Val Leu Ser Gly Phe Glu
        130                 135                 140
Tyr Arg Thr Gln Lys Glu Lys Tyr Asp Asn Leu Tyr Lys Phe Phe Lys
145                 150                 155                 160
Asp Asn Glu Glu Lys Tyr Gln Tyr Thr Gly Phe Thr Lys Glu Ala Ile
                165                 170                 175
Asn Lys Thr Gln Asn Val Gly Tyr Lys Asn Glu Tyr Phe Tyr Ile Thr
            180                 185                 190
Tyr Ser Ser Arg Ser Leu Lys Glu Tyr Arg Lys Tyr Glu Pro Leu
        195                 200                 205
Ile His Lys Asn Asp Lys Glu Phe Lys Glu Gly Met Glu Gln Ala Arg
    210                 215                 220
Lys Glu Val Asn Tyr Ala Ala Asn Thr Asp Thr Val Thr Thr Leu Phe
225                 230                 235                 240
Ser Thr Lys Glu Asn Phe Thr Lys Asp Asn Thr Val Asp Asp Val Ile
                245                 250                 255
Glu Leu Ser Asp Lys Leu Tyr Asn Phe Lys Asn Lys Pro Glu Lys Ser
            260                 265                 270
Thr Ile Thr Ile Gln Ile Gly Lys Pro Thr Ile Asn Thr Lys Lys Ala
        275                 280                 285
Phe Tyr Asp Asp Asn Asp Pro Ile Glu Tyr Gly Val Tyr Arg Lys Asp
    290                 295                 300
Glu
305
```

<210> SEQ ID NO 129
<211> LENGTH: 226
<212> TYPE: PRT
<213> ORGANISM: Staphylococcus sp

<400> SEQUENCE: 129

```
Met Lys Phe Lys Ala Ile Ala Lys Ala Ser Leu Ala Leu Gly Met Leu
 1               5                  10                  15
Ala Thr Gly Val Ile Thr Ser Asn Val Gln Ser Val Gln Ala Lys Ala
                20                  25                  30
Glu Val Lys Gln Gln Ser Glu Ser Glu Leu Lys His Tyr Tyr Asn Lys
            35                  40                  45
Pro Ile Leu Glu Arg Lys Asn Val Thr Gly Phe Lys Tyr Thr Asp Glu
        50                  55                  60
Gly Lys His Tyr Leu Glu Val Thr Val Gly Gln Gln His Ser Arg Ile
 65                  70                  75                  80
Thr Leu Leu Gly Ser Asp Lys Asp Lys Phe Lys Asp Gly Glu Asn Ser
                85                  90                  95
```

```
Asn Ile Asp Val Phe Ile Leu Arg Glu Gly Asp Ser Arg Gln Ala Thr
            100                 105                 110

Asn Tyr Ser Ile Gly Gly Val Thr Lys Ser Asn Ser Val Gln Tyr Ile
        115                 120                 125

Asp Tyr Ile Asn Thr Pro Ile Leu Glu Ile Lys Lys Asp Asn Glu Asp
    130                 135                 140

Val Leu Lys Asp Phe Tyr Tyr Ile Ser Lys Glu Asp Ile Ser Leu Lys
145                 150                 155                 160

Glu Leu Asp Tyr Arg Leu Arg Glu Arg Ala Ile Lys Gln His Gly Leu
                165                 170                 175

Tyr Ser Asn Gly Leu Lys Gln Gly Gln Ile Thr Ile Thr Met Asn Asp
            180                 185                 190

Gly Thr Thr His Thr Ile Asp Leu Ser Gln Lys Leu Glu Lys Glu Arg
        195                 200                 205

Met Gly Glu Ser Ile Asp Gly Thr Lys Ile Asn Lys Ile Leu Val Glu
    210                 215                 220

Met Lys
225

<210> SEQ ID NO 130
<211> LENGTH: 231
<212> TYPE: PRT
<213> ORGANISM: Staphylococcus sp

<400> SEQUENCE: 130

Met Lys Met Lys Asn Ile Ala Lys Ile Ser Leu Leu Gly Ile Leu
1               5                   10                  15

Ala Thr Gly Val Asn Thr Thr Thr Glu Lys Pro Val His Ala Glu Lys
                20                  25                  30

Lys Pro Ile Val Ile Ser Glu Asn Ser Lys Lys Leu Lys Ala Tyr Tyr
            35                  40                  45

Asn Gln Pro Ser Ile Glu Tyr Lys Asn Val Thr Gly Tyr Ile Ser Phe
        50                  55                  60

Ile Gln Pro Ser Ile Lys Phe Met Asn Ile Ile Asp Gly Asn Ser Val
65                  70                  75                  80

Asn Asn Ile Ala Leu Ile Gly Lys Asp Lys Gln His Tyr His Thr Gly
                85                  90                  95

Val His Arg Asn Leu Asn Ile Phe Tyr Val Asn Glu Asp Lys Arg Phe
            100                 105                 110

Glu Gly Ala Lys Tyr Ser Ile Gly Gly Ile Thr Ser Ala Asn Asp Lys
        115                 120                 125

Ala Val Asp Leu Ile Ala Glu Ala Arg Val Ile Lys Glu Asp His Thr
    130                 135                 140

Gly Glu Tyr Asp Tyr Asp Phe Phe Pro Phe Lys Ile Asp Lys Glu Ala
145                 150                 155                 160

Met Ser Leu Lys Glu Ile Asp Phe Lys Leu Arg Lys Tyr Leu Ile Asp
                165                 170                 175

Asn Tyr Gly Leu Tyr Gly Glu Met Ser Thr Gly Lys Ile Thr Val Lys
            180                 185                 190

Lys Lys Tyr Tyr Gly Lys Tyr Thr Phe Glu Leu Asp Lys Leu Gln
        195                 200                 205

Glu Asp Arg Met Ser Asp Val Ile Asn Val Thr Asp Ile Asp Arg Ile
    210                 215                 220

Glu Ile Lys Val Leu Lys Ala
225                 230
```

```
<210> SEQ ID NO 131
<211> LENGTH: 356
<212> TYPE: PRT
<213> ORGANISM: Staphylococcus sp

<400> SEQUENCE: 131

Met Lys Met Arg Thr Ile Ala Lys Thr Ser Leu Ala Leu Gly Leu Leu
1               5                   10                  15

Thr Thr Gly Ala Ile Thr Val Thr Gln Ser Val Lys Ala Glu Lys
            20                  25                  30

Ile Gln Ser Thr Lys Val Asp Lys Val Pro Thr Leu Lys Ala Glu Arg
        35                  40                  45

Leu Ala Met Ile Asn Ile Thr Ala Gly Ala Asn Ser Ala Thr Thr Gln
50                  55                  60

Ala Ala Asn Thr Arg Gln Glu Arg Thr Pro Lys Leu Glu Lys Ala Pro
65                  70                  75                  80

Asn Thr Asn Glu Glu Lys Thr Ser Ala Ser Lys Ile Glu Lys Ile Ser
                85                  90                  95

Gln Pro Lys Gln Glu Gln Lys Thr Leu Asn Ile Ser Ala Thr Pro
            100                 105                 110

Ala Pro Lys Gln Glu Gln Ser Gln Thr Thr Thr Glu Ser Thr Thr Pro
        115                 120                 125

Lys Thr Lys Val Thr Thr Pro Pro Ser Thr Asn Thr Pro Gln Pro Met
130                 135                 140

Gln Ser Thr Lys Ser Asp Thr Pro Gln Ser Pro Thr Ile Lys Gln Ala
145                 150                 155                 160

Gln Thr Asp Met Thr Pro Lys Tyr Glu Asp Leu Arg Ala Tyr Tyr Thr
                165                 170                 175

Lys Pro Ser Phe Glu Phe Glu Lys Gln Phe Gly Phe Met Leu Lys Pro
            180                 185                 190

Trp Thr Thr Val Arg Phe Met Asn Val Ile Pro Asn Arg Phe Ile Tyr
        195                 200                 205

Lys Ile Ala Leu Val Gly Lys Asp Glu Lys Tyr Lys Asp Gly Pro
210                 215                 220

Tyr Asp Asn Ile Asp Val Phe Ile Val Leu Glu Asp Asn Lys Tyr Gln
225                 230                 235                 240

Leu Lys Lys Tyr Ser Val Gly Gly Ile Thr Lys Thr Asn Ser Lys Lys
                245                 250                 255

Val Asn His Lys Val Glu Leu Ser Ile Thr Lys Asp Asn Gln Gly
            260                 265                 270

Met Ile Ser Arg Asp Val Ser Glu Tyr Met Ile Thr Lys Glu Glu Ile
        275                 280                 285

Ser Leu Lys Glu Leu Asp Phe Lys Leu Arg Lys Gln Leu Ile Glu Lys
290                 295                 300

His Asn Leu Tyr Gly Asn Met Gly Ser Gly Thr Ile Val Ile Lys Met
305                 310                 315                 320

Lys Asn Gly Gly Lys Tyr Thr Phe Glu Leu His Lys Lys Leu Gln Glu
                325                 330                 335

His Arg Met Ala Asp Val Ile Asp Gly Thr Asn Ile Asp Asn Ile Glu
            340                 345                 350

Val Asn Ile Lys
        355
```

```
<210> SEQ ID NO 132
<211> LENGTH: 308
<212> TYPE: PRT
<213> ORGANISM: Staphylococcus sp

<400> SEQUENCE: 132

Met Lys Ile Thr Thr Ile Ala Lys Thr Ser Leu Ala Leu Gly Leu Leu
1               5                   10                  15

Thr Thr Gly Val Ile Thr Thr Thr Gln Ala Ala Asn Ala Thr Thr
            20                  25                  30

Leu Ser Ser Thr Lys Val Glu Ala Pro Gln Ser Thr Pro Pro Ser Thr
        35                  40                  45

Lys Ile Glu Ala Pro Gln Ser Lys Pro Asn Ala Thr Thr Pro Pro Ser
50                  55                  60

Thr Lys Val Glu Ala Pro Gln Gln Thr Ala Asn Ala Thr Thr Pro Pro
65                  70                  75                  80

Ser Thr Lys Val Thr Thr Pro Pro Ser Thr Asn Thr Pro Gln Pro Met
                85                  90                  95

Gln Ser Thr Lys Ser Asp Thr Pro Gln Ser Pro Thr Thr Lys Gln Val
            100                 105                 110

Pro Thr Glu Ile Asn Pro Lys Phe Lys Asp Leu Arg Ala Tyr Tyr Thr
        115                 120                 125

Lys Pro Ser Leu Glu Phe Lys Asn Glu Ile Gly Ile Ile Leu Lys Lys
130                 135                 140

Trp Thr Thr Ile Arg Phe Met Asn Val Val Pro Asp Tyr Phe Ile Tyr
145                 150                 155                 160

Lys Ile Ala Leu Val Gly Lys Asp Asp Lys Lys Tyr Gly Glu Gly Val
                165                 170                 175

His Arg Asn Val Asp Val Phe Val Val Leu Glu Glu Asn Asn Tyr Asn
            180                 185                 190

Leu Glu Lys Tyr Ser Val Gly Gly Ile Thr Lys Ser Asn Ser Lys Lys
        195                 200                 205

Val Asp His Lys Ala Gly Val Arg Ile Thr Lys Glu Asp Asn Lys Gly
210                 215                 220

Thr Ile Ser His Asp Val Ser Glu Phe Lys Ile Thr Lys Glu Gln Ile
225                 230                 235                 240

Ser Leu Lys Glu Leu Asp Phe Lys Leu Arg Lys Gln Leu Ile Glu Lys
                245                 250                 255

Asn Asn Leu Tyr Gly Asn Val Gly Ser Gly Lys Ile Val Ile Lys Met
            260                 265                 270

Lys Asn Gly Gly Lys Tyr Thr Phe Glu Leu His Lys Lys Leu Gln Glu
        275                 280                 285

Asn Arg Met Ala Asp Val Ile Asp Gly Thr Asn Ile Asp Asn Ile Glu
290                 295                 300

Val Asn Ile Lys
305

<210> SEQ ID NO 133
<211> LENGTH: 234
<212> TYPE: PRT
<213> ORGANISM: Staphylococcus sp

<400> SEQUENCE: 133

Met Lys Met Thr Ala Ile Ala Lys Ala Ser Leu Ala Leu Gly Ile Leu
1               5                   10                  15

Ala Thr Gly Thr Ile Thr Ser Leu His Gln Thr Val Asn Ala Ser Glu
```

```
                    20                  25                  30
His Lys Ala Lys Tyr Glu Asn Val Thr Lys Asp Ile Phe Asp Leu Arg
                35                  40                  45

Asp Tyr Tyr Ser Gly Ala Ser Lys Glu Leu Lys Asn Val Thr Gly Tyr
    50                  55                  60

Arg Tyr Ser Lys Gly Gly Lys His Tyr Leu Ile Phe Asp Lys Asn Arg
65                  70                  75                  80

Lys Phe Thr Arg Val Gln Ile Phe Gly Lys Asp Ile Glu Arg Phe Lys
                85                  90                  95

Ala Arg Lys Asn Pro Gly Leu Asp Ile Phe Val Val Lys Glu Ala Glu
            100                 105                 110

Asn Arg Asn Gly Thr Val Phe Ser Tyr Gly Gly Val Thr Lys Lys Asn
            115                 120                 125

Gln Asp Ala Tyr Tyr Asp Tyr Ile Asn Ala Pro Arg Phe Gln Ile Lys
        130                 135                 140

Arg Asp Glu Gly Asp Gly Ile Ala Thr Tyr Gly Arg Val His Tyr Ile
145                 150                 155                 160

Tyr Lys Glu Glu Ile Ser Leu Lys Glu Leu Asp Phe Lys Leu Arg Gln
                165                 170                 175

Tyr Leu Ile Gln Asn Phe Asp Leu Tyr Lys Lys Phe Pro Lys Asp Ser
            180                 185                 190

Lys Ile Lys Val Ile Met Lys Asp Gly Tyr Tyr Thr Phe Glu Leu
            195                 200                 205

Asn Lys Lys Leu Gln Thr Asn Arg Met Ser Asp Val Ile Asp Gly Arg
        210                 215                 220

Asn Ile Glu Lys Ile Glu Ala Asn Ile Arg
225                 230

<210> SEQ ID NO 134
<211> LENGTH: 231
<212> TYPE: PRT
<213> ORGANISM: Staphylococcus sp

<400> SEQUENCE: 134

Met Lys Leu Lys Thr Leu Ala Lys Ala Thr Leu Val Leu Gly Leu Leu
1               5                   10                  15

Ala Thr Gly Val Ile Thr Thr Glu Ser Gln Thr Val Lys Ala Ala Glu
                20                  25                  30

Ser Thr Gln Gly Gln His Asn Tyr Lys Ser Leu Lys Tyr Tyr Tyr Ser
            35                  40                  45

Lys Pro Ser Ile Glu Leu Lys Asn Leu Asp Gly Leu Tyr Arg Gln Lys
    50                  55                  60

Val Thr Asp Lys Gly Val Tyr Val Trp Lys Asp Arg Lys Asp Tyr Phe
65                  70                  75                  80

Val Gly Leu Leu Gly Lys Asp Ile Glu Lys Tyr Pro Gln Gly Glu His
                85                  90                  95

Asp Lys Gln Asp Ala Phe Leu Val Ile Glu Glu Thr Val Asn Gly
            100                 105                 110

Arg Gln Tyr Ser Ile Gly Gly Leu Ser Lys Thr Asn Ser Lys Glu Phe
        115                 120                 125

Ser Lys Glu Val Asp Val Lys Val Thr Arg Lys Ile Asp Glu Ser Ser
    130                 135                 140

Glu Lys Ser Lys Asp Ser Lys Phe Lys Ile Thr Lys Glu Glu Ile Ser
145                 150                 155                 160
```

```
Leu Lys Glu Leu Asp Phe Lys Leu Arg Lys Lys Leu Met Glu Glu Glu
                165                 170                 175
Lys Leu Tyr Gly Ala Val Asn Asn Arg Lys Gly Lys Ile Val Val Lys
            180                 185                 190
Met Glu Asp Asp Lys Phe Tyr Thr Phe Glu Leu Thr Lys Lys Leu Gln
        195                 200                 205
Pro His Arg Met Gly Asp Thr Ile Asp Gly Thr Lys Ile Lys Glu Ile
    210                 215                 220
Asn Val Glu Leu Glu Tyr Lys
225                 230

<210> SEQ ID NO 135
<211> LENGTH: 231
<212> TYPE: PRT
<213> ORGANISM: Staphylococcus sp

<400> SEQUENCE: 135

Met Lys Leu Lys Thr Leu Ala Lys Ala Thr Leu Ala Leu Gly Leu Leu
1               5                   10                  15
Thr Thr Gly Val Ile Thr Ser Glu Gly Gln Ala Val Gln Ala Lys Glu
            20                  25                  30
Lys Gln Glu Arg Val Gln His Leu Tyr Asp Ile Lys Asp Leu His Arg
        35                  40                  45
Tyr Tyr Ser Ser Glu Ser Phe Glu Phe Ser Asn Ile Ser Gly Lys Val
    50                  55                  60
Glu Asn Tyr Asn Gly Ser Asn Val Val Arg Phe Asn Gln Glu Asn Gln
65                  70                  75                  80
Asn His Gln Leu Phe Leu Leu Gly Lys Asp Lys Glu Lys Tyr Lys Glu
                85                  90                  95
Gly Ile Glu Gly Lys Asp Val Phe Val Lys Glu Leu Ile Asp Pro
            100                 105                 110
Asn Gly Arg Leu Ser Thr Val Gly Gly Val Thr Lys Lys Asn Asn Lys
        115                 120                 125
Ser Ser Glu Thr Asn Thr His Leu Phe Val Asn Lys Val Tyr Gly Gly
    130                 135                 140
Asn Leu Asp Ala Ser Ile Asp Ser Phe Ser Ile Asn Lys Glu Glu Val
145                 150                 155                 160
Ser Leu Lys Glu Leu Asp Phe Lys Ile Arg Gln His Leu Val Lys Asn
                165                 170                 175
Tyr Gly Leu Tyr Lys Gly Thr Thr Lys Tyr Gly Lys Ile Thr Ile Asn
            180                 185                 190
Leu Lys Asp Gly Glu Lys Gln Glu Ile Asp Leu Gly Asp Lys Leu Gln
        195                 200                 205
Phe Glu Arg Met Gly Asp Val Leu Asn Ser Lys Asp Ile Asn Lys Ile
    210                 215                 220
Glu Val Thr Leu Lys Gln Ile
225                 230

<210> SEQ ID NO 136
<211> LENGTH: 232
<212> TYPE: PRT
<213> ORGANISM: Staphylococcus sp

<400> SEQUENCE: 136

Met Lys Phe Thr Val Ile Ala Lys Ala Ile Phe Ile Leu Gly Ile Leu
1               5                   10                  15
```

-continued

```
Thr Thr Ser Val Met Ile Thr Glu Asn Gln Ser Val Asn Ala Lys Gly
                20                  25                  30

Lys Tyr Glu Lys Met Asn Arg Leu Tyr Asp Thr Asn Lys Leu His Gln
            35                  40                  45

Tyr Tyr Ser Gly Pro Ser Tyr Glu Leu Thr Asn Val Ser Gly Gln Ser
        50                  55                  60

Gln Gly Tyr Tyr Asp Ser Asn Val Leu Leu Phe Asn Gln Gln Asn Gln
 65                  70                  75                  80

Lys Phe Gln Val Phe Leu Leu Gly Lys Asp Glu Asn Lys Tyr Lys Glu
                85                  90                  95

Lys Thr His Gly Leu Asp Val Phe Ala Val Pro Glu Leu Val Asp Leu
            100                 105                 110

Asp Gly Arg Ile Phe Ser Val Ser Gly Val Thr Lys Lys Asn Val Lys
        115                 120                 125

Ser Ile Phe Glu Ser Leu Arg Thr Pro Asn Leu Leu Val Lys Lys Ile
    130                 135                 140

Asp Asp Lys Asp Gly Phe Ser Ile Asp Glu Phe Phe Ile Gln Lys
145                 150                 155                 160

Glu Glu Val Ser Leu Lys Glu Leu Asp Phe Lys Ile Arg Lys Leu Leu
                165                 170                 175

Ile Lys Lys Tyr Lys Leu Tyr Glu Gly Ser Ala Asp Lys Gly Arg Ile
            180                 185                 190

Val Ile Asn Met Lys Asp Glu Asn Lys Tyr Glu Ile Asp Leu Ser Asp
        195                 200                 205

Lys Leu Asp Phe Glu Arg Met Ala Asp Val Ile Asn Ser Glu Gln Ile
    210                 215                 220

Lys Asn Ile Glu Val Asn Leu Lys
225                 230

<210> SEQ ID NO 137
<211> LENGTH: 232
<212> TYPE: PRT
<213> ORGANISM: Staphylococcus sp

<400> SEQUENCE: 137

Met Lys Leu Thr Thr Ile Ala Lys Ala Thr Leu Ala Leu Gly Ile Leu
1               5                   10                  15

Thr Thr Gly Val Phe Thr Ala Glu Ser Gln Thr Gly His Ala Lys Val
                20                  25                  30

Glu Leu Asp Glu Thr Gln Arg Lys Tyr Tyr Ile Asn Met Leu His Gln
            35                  40                  45

Tyr Tyr Ser Glu Glu Ser Phe Glu Pro Thr Asn Ile Ser Val Lys Ser
        50                  55                  60

Glu Asp Tyr Tyr Gly Ser Asn Val Leu Asn Phe Lys Gln Arg Asn Lys
 65                  70                  75                  80

Ala Phe Lys Val Phe Leu Leu Gly Asp Asp Lys Asn Lys Tyr Lys Glu
                85                  90                  95

Lys Thr His Gly Leu Asp Val Phe Ala Val Pro Glu Leu Ile Asp Ile
            100                 105                 110

Lys Gly Gly Ile Tyr Ser Val Gly Gly Ile Thr Lys Lys Asn Val Arg
        115                 120                 125

Ser Val Phe Gly Phe Val Ser Asn Pro Ser Leu Gln Val Lys Lys Val
    130                 135                 140

Asp Ala Lys Asn Gly Phe Ser Ile Asn Glu Leu Phe Phe Ile Gln Lys
145                 150                 155                 160
```

```
Glu Glu Val Ser Leu Lys Glu Leu Asp Phe Lys Ile Arg Lys Leu Leu
                165                 170                 175

Ile Glu Lys Tyr Arg Leu Tyr Lys Gly Thr Ser Asp Lys Gly Arg Ile
            180                 185                 190

Val Ile Asn Met Lys Asp Glu Lys Lys His Glu Ile Asp Leu Ser Glu
        195                 200                 205

Lys Leu Ser Phe Glu Arg Met Phe Asp Val Met Asp Ser Lys Gln Ile
    210                 215                 220

Lys Asn Ile Glu Val Asn Leu Asn
225                 230

<210> SEQ ID NO 138
<211> LENGTH: 227
<212> TYPE: PRT
<213> ORGANISM: Staphylococcus sp

<400> SEQUENCE: 138

Met Lys Phe Thr Ala Leu Ala Lys Ala Thr Leu Ala Leu Gly Ile Leu
1               5                   10                  15

Thr Thr Gly Thr Leu Thr Thr Glu Val His Ser Gly His Ala Lys Gln
            20                  25                  30

Asn Gln Lys Ser Val Asn Lys His Asp Lys Glu Ala Leu Tyr Arg Tyr
        35                  40                  45

Tyr Thr Gly Lys Thr Met Glu Met Lys Asn Ile Ser Ala Leu Lys His
    50                  55                  60

Gly Lys Asn Asn Leu Arg Phe Lys Phe Arg Gly Ile Lys Ile Gln Val
65                  70                  75                  80

Leu Leu Pro Gly Asn Asp Lys Ser Lys Phe Gln Gln Arg Ser Tyr Glu
                85                  90                  95

Gly Leu Asp Val Phe Phe Val Gln Glu Lys Arg Asp Lys His Asp Ile
            100                 105                 110

Phe Tyr Thr Val Gly Gly Val Ile Gln Asn Asn Lys Thr Ser Gly Val
        115                 120                 125

Val Ser Ala Pro Ile Leu Asn Ile Ser Lys Glu Lys Gly Glu Asp Ala
    130                 135                 140

Phe Val Lys Gly Tyr Pro Tyr Tyr Ile Lys Lys Glu Lys Ile Thr Leu
145                 150                 155                 160

Lys Glu Leu Asp Tyr Lys Leu Arg Lys His Leu Ile Glu Lys Tyr Gly
                165                 170                 175

Leu Tyr Lys Thr Ile Ser Lys Asp Gly Arg Val Lys Ile Ser Leu Lys
            180                 185                 190

Asp Gly Ser Phe Tyr Asn Leu Asp Leu Arg Ser Lys Leu Lys Phe Lys
        195                 200                 205

Tyr Met Gly Glu Val Ile Glu Ser Lys Gln Ile Lys Asp Ile Glu Val
    210                 215                 220

Asn Leu Lys
225

<210> SEQ ID NO 139
<211> LENGTH: 225
<212> TYPE: PRT
<213> ORGANISM: Staphylococcus sp

<400> SEQUENCE: 139

Met Lys Leu Lys Asn Ile Ala Lys Ala Ser Leu Ala Leu Gly Ile Leu
1               5                   10                  15
```

Thr Thr Gly Met Ile Thr Thr Ala Gln Pro Val Lys Ala Ser Thr
            20                  25                  30

Leu Glu Val Arg Ser Gln Ala Thr Gln Asp Leu Ser Glu Tyr Tyr Asn
         35                  40                  45

Arg Pro Phe Phe Glu Tyr Thr Asn Gln Ser Gly Tyr Lys Glu Glu Gly
     50                  55                  60

Lys Val Thr Phe Thr Pro Asn Tyr Gln Leu Ile Asp Val Thr Leu Thr
 65                  70                  75                  80

Gly Asn Glu Lys Gln Asn Phe Gly Glu Asp Ile Ser Asn Val Asp Ile
                 85                  90                  95

Phe Val Val Arg Glu Asn Ser Asp Arg Ser Gly Asn Thr Ala Ser Ile
            100                 105                 110

Gly Gly Ile Thr Lys Thr Asn Gly Ser Asn Tyr Ile Asp Lys Val Lys
        115                 120                 125

Asp Val Asn Leu Ile Ile Thr Lys Asn Ile Asp Ser Val Thr Ser Thr
130                 135                 140

Ser Thr Ser Ser Thr Tyr Thr Ile Asn Lys Glu Glu Ile Ser Leu Lys
145                 150                 155                 160

Glu Leu Asp Phe Lys Leu Arg Lys His Leu Ile Asp Lys His Asn Leu
                165                 170                 175

Tyr Lys Thr Glu Pro Lys Asp Ser Lys Ile Arg Ile Thr Met Lys Asp
            180                 185                 190

Gly Gly Phe Tyr Thr Phe Glu Leu Asn Lys Lys Leu Gln Thr His Arg
        195                 200                 205

Met Gly Asp Val Ile Asp Gly Arg Asn Ile Glu Lys Ile Glu Val Asn
    210                 215                 220

Leu
225

<210> SEQ ID NO 140
<211> LENGTH: 116
<212> TYPE: PRT
<213> ORGANISM: Staphylococcus sp

<400> SEQUENCE: 140

Met Lys Phe Lys Lys Tyr Ile Leu Thr Gly Thr Leu Ala Leu Leu Leu
1               5                   10                  15

Ser Ser Thr Gly Ile Ala Thr Ile Glu Gly Asn Lys Ala Asp Ala Ser
            20                  25                  30

Ser Leu Asp Lys Tyr Leu Thr Glu Ser Gln Phe His Asp Lys Arg Ile
         35                  40                  45

Ala Glu Glu Leu Arg Thr Leu Leu Asn Lys Ser Asn Val Tyr Ala Leu
     50                  55                  60

Ala Ala Gly Ser Leu Asn Pro Tyr Tyr Lys Arg Thr Ile Met Met Asn
 65                  70                  75                  80

Glu Tyr Arg Ala Lys Ala Ala Leu Lys Lys Asn Asp Phe Val Ser Met
                 85                  90                  95

Ala Asp Ala Lys Val Ala Leu Glu Lys Ile Tyr Lys Glu Ile Asp Glu
            100                 105                 110

Ile Ile Asn Arg
        115

<210> SEQ ID NO 141
<211> LENGTH: 203
<212> TYPE: PRT

<213> ORGANISM: Staphylococcus sp

<400> SEQUENCE: 141

Met Phe Lys Lys Tyr Asp Ser Lys Asn Ser Ile Val Leu Lys Ser Ile
1               5                   10                  15

Leu Ser Leu Gly Ile Ile Tyr Gly Gly Thr Phe Gly Ile Tyr Pro Lys
            20                  25                  30

Ala Asp Ala Ser Thr Gln Asn Ser Ser Val Gln Asp Lys Gln Leu
        35                  40                  45

Gln Lys Val Glu Glu Val Pro Asn Asn Ser Glu Lys Ala Leu Val Lys
    50                  55                  60

Lys Leu Tyr Asp Arg Tyr Ser Lys Asp Thr Ile Asn Gly Lys Ser Asn
65                  70                  75                  80

Lys Ser Arg Asn Trp Val Tyr Ser Glu Arg Pro Leu Asn Glu Asn Gln
                85                  90                  95

Val Arg Ile His Leu Glu Gly Thr Tyr Thr Val Ala Gly Arg Val Tyr
            100                 105                 110

Thr Pro Lys Arg Asn Ile Thr Leu Asn Lys Glu Val Thr Leu Lys
        115                 120                 125

Glu Leu Asp His Ile Ile Arg Phe Ala His Ile Ser Tyr Gly Leu Tyr
    130                 135                 140

Met Gly Glu His Leu Pro Lys Gly Asn Ile Val Ile Asn Thr Lys Asp
145                 150                 155                 160

Gly Gly Lys Tyr Thr Leu Glu Ser His Lys Glu Leu Gln Lys Asp Arg
                165                 170                 175

Glu Asn Val Lys Ile Asn Thr Ala Asp Ile Lys Asn Val Thr Phe Lys
            180                 185                 190

Leu Val Lys Ser Val Asn Asp Ile Glu Gln Val
        195                 200

<210> SEQ ID NO 142
<211> LENGTH: 146
<212> TYPE: PRT
<213> ORGANISM: Staphylococcus sp

<400> SEQUENCE: 142

Met Asn Thr Lys Tyr Phe Leu Ala Ala Gly Ala Val Ile Thr Thr Leu
1               5                   10                  15

Ala Leu Gly Ala Cys Gly Asn Ser Asn Ser Gln Asp Gln Gly Asn Lys
            20                  25                  30

Thr Glu Gln Lys Thr Lys Ser Glu Asp Ser Asn Val Lys Thr Asp Lys
        35                  40                  45

Thr Lys His Leu Thr Gly Thr Phe Ser Ser Lys Asn Gly Glu Thr Val
    50                  55                  60

Glu Gly Lys Ala Glu Ile Lys Asn Gly Lys Leu Met Leu Thr Asn Tyr
65                  70                  75                  80

Lys Ser Ser Lys Gly Pro Asp Leu Tyr Val Tyr Leu Thr Lys Asn Gly
                85                  90                  95

Asp Ile Lys Asn Gly Lys Glu Ile Ala Met Val Asp Tyr Asp Lys Glu
            100                 105                 110

Lys Gln Thr Phe Asp Leu Lys Asn Val Asp Leu Ser Lys Tyr Asp Glu
        115                 120                 125

Val Thr Ile Tyr Cys Lys Lys Ala His Val Ile Phe Gly Gly Ala Lys
    130                 135                 140

Leu Lys

145

<210> SEQ ID NO 143
<211> LENGTH: 619
<212> TYPE: PRT
<213> ORGANISM: Staphylococcus sp

<400> SEQUENCE: 143

Met Pro Lys Asn Lys Ile Leu Ile Tyr Leu Leu Ser Thr Thr Leu Val
1               5                   10                  15

Leu Pro Thr Leu Val Ser Pro Thr Ala Tyr Ala Asp Thr Pro Gln Lys
            20                  25                  30

Asp Thr Thr Ala Lys Thr Thr Ser His Asp Ser Lys Lys Ser Asn Asp
        35                  40                  45

Asp Glu Thr Ser Lys Asp Thr Thr Ser Lys Asp Ile Asp Lys Ala Asp
    50                  55                  60

Lys Asn Asn Thr Ser Asn Gln Asp Asn Asn Asp Lys Lys Phe Lys Thr
65                  70                  75                  80

Ile Asp Asp Ser Thr Ser Asp Ser Asn Asn Ile Ile Asp Phe Ile Tyr
                85                  90                  95

Lys Asn Leu Pro Gln Thr Asn Ile Asn Gln Leu Leu Thr Lys Asn Lys
            100                 105                 110

Tyr Asp Asp Asn Tyr Ser Leu Thr Thr Leu Ile Gln Asn Leu Phe Asn
        115                 120                 125

Leu Asn Ser Asp Ile Ser Asp Tyr Glu Gln Pro Arg Asn Gly Glu Lys
    130                 135                 140

Ser Thr Asn Asp Ser Asn Lys Asn Ser Asp Asn Ser Ile Lys Asn Asp
145                 150                 155                 160

Thr Asp Thr Gln Ser Ser Lys Gln Asp Lys Ala Asp Asn Gln Lys Ala
                165                 170                 175

Pro Lys Ser Asn Asn Thr Lys Pro Ser Thr Ser Asn Lys Gln Pro Asn
            180                 185                 190

Ser Pro Lys Pro Thr Gln Pro Asn Gln Ser Asn Ser Gln Pro Ala Ser
        195                 200                 205

Asp Asp Lys Ala Asn Gln Lys Ser Ser Ser Lys Asp Asn Gln Ser Met
    210                 215                 220

Ser Asp Ser Ala Leu Asp Ser Ile Leu Asp Gln Tyr Ser Glu Asp Ala
225                 230                 235                 240

Lys Lys Thr Gln Lys Asp Tyr Ala Ser Gln Ser Lys Lys Asp Lys Asn
                245                 250                 255

Glu Lys Ser Asn Thr Lys Asn Pro Gln Leu Pro Thr Gln Asp Glu Leu
            260                 265                 270

Lys His Lys Ser Lys Pro Ala Gln Ser Phe Asn Asn Asp Val Asn Gln
        275                 280                 285

Lys Asp Thr Arg Ala Thr Ser Leu Phe Glu Thr Asp Pro Ser Ile Ser
    290                 295                 300

Asn Asn Asp Asp Ser Gly Gln Phe Asn Val Val Asp Ser Lys Asp Thr
305                 310                 315                 320

Arg Gln Phe Val Lys Ser Ile Ala Lys Asp Ala His Arg Ile Gly Gln
                325                 330                 335

Asp Asn Asp Ile Tyr Ala Ser Val Met Ile Ala Gln Ala Ile Leu Glu
            340                 345                 350

Ser Asp Ser Gly Arg Ser Ala Leu Ala Lys Ser Pro Asn His Asn Leu
        355                 360                 365

```
Phe Gly Ile Lys Gly Ala Phe Glu Gly Asn Ser Val Pro Phe Asn Thr
    370                 375                 380

Leu Glu Ala Asp Gly Asn Gln Leu Tyr Ser Ile Asn Ala Gly Phe Arg
385                 390                 395                 400

Lys Tyr Pro Ser Thr Lys Glu Ser Leu Lys Asp Tyr Ser Asp Leu Ile
                405                 410                 415

Lys Asn Gly Ile Asp Gly Asn Arg Thr Ile Tyr Lys Pro Thr Trp Lys
            420                 425                 430

Ser Glu Ala Asp Ser Tyr Lys Asp Ala Thr Ser His Leu Ser Lys Thr
        435                 440                 445

Tyr Ala Thr Asp Pro Asn Tyr Ala Lys Lys Leu Asn Ser Ile Ile Lys
    450                 455                 460

His Tyr Gln Leu Thr Gln Phe Asp Asp Glu Arg Met Pro Asp Leu Asp
465                 470                 475                 480

Lys Tyr Glu Arg Ser Ile Lys Asp Tyr Asp Asp Ser Asp Glu Phe
                485                 490                 495

Lys Pro Phe Arg Glu Val Ser Asp Ser Met Pro Tyr Pro His Gly Gln
                500                 505                 510

Cys Thr Trp Tyr Val Tyr Asn Arg Met Lys Gln Phe Gly Thr Ser Ile
            515                 520                 525

Ser Gly Asp Leu Gly Asp Ala His Asn Trp Asn Asn Arg Ala Gln Tyr
        530                 535                 540

Arg Asp Tyr Gln Val Ser His Thr Pro Lys Arg His Ala Ala Val Val
545                 550                 555                 560

Phe Glu Ala Gly Gln Phe Gly Ala Asp Gln His Tyr Gly His Val Ala
                565                 570                 575

Phe Val Glu Lys Val Asn Ser Asp Gly Ser Ile Val Ile Ser Glu Ser
            580                 585                 590

Asn Val Lys Gly Leu Gly Ile Ile Ser His Arg Thr Ile Asn Ala Ala
        595                 600                 605

Ala Ala Glu Glu Leu Ser Tyr Ile Thr Gly Lys
    610                 615

<210> SEQ ID NO 144
<211> LENGTH: 208
<212> TYPE: PRT
<213> ORGANISM: Staphylococcus sp

<400> SEQUENCE: 144

Met Lys Phe Gly Lys Thr Ile Ala Val Val Leu Ala Ser Ser Val Leu
1               5                   10                  15

Leu Ala Gly Cys Thr Thr Asp Lys Lys Glu Ile Lys Ala Tyr Leu Lys
            20                  25                  30

Gln Val Asp Lys Ile Lys Asp Asp Glu Pro Ile Lys Thr Val Gly
        35                  40                  45

Lys Lys Ile Ala Glu Leu Asp Glu Lys Lys Lys Leu Thr Glu Asp
    50                  55                  60

Val Asn Ser Lys Asp Thr Ala Val Arg Gly Lys Ala Val Lys Asp Leu
65                  70                  75                  80

Ile Lys Asn Ala Asp Asp Arg Leu Lys Glu Phe Glu Lys Glu Asp
            85                  90                  95

Ala Ile Lys Lys Ser Glu Gln Asp Phe Lys Lys Ala Lys Ser His Val
        100                 105                 110

Asp Asn Ile Asp Asn Asp Val Lys Arg Lys Glu Val Lys Gln Leu Asp
    115                 120                 125
```

Asp Val Leu Lys Glu Lys Tyr Lys Leu His Ser Asp Tyr Ala Lys Ala
            130                 135                 140

Tyr Lys Lys Ala Val Asn Ser Glu Lys Thr Leu Phe Lys Tyr Leu Asn
145                 150                 155                 160

Gln Asn Asp Ala Thr Gln Gln Gly Val Asn Glu Lys Ser Lys Ala Ile
                165                 170                 175

Glu Gln Asn Tyr Lys Lys Leu Lys Glu Val Ser Asp Lys Tyr Thr Lys
            180                 185                 190

Val Leu Asn Lys Val Gly Lys Glu Lys Gln Asp Val Asp Gln Phe Lys
            195                 200                 205

<210> SEQ ID NO 145
<211> LENGTH: 105
<212> TYPE: PRT
<213> ORGANISM: Staphylococcus sp

<400> SEQUENCE: 145

Met Asn Lys Leu Leu Gln Ser Leu Ser Ala Leu Gly Val Ser Ala Thr
1               5                   10                  15

Leu Val Thr Pro Asn Leu Asn Ala Asp Ala Thr Thr Asn Thr Thr Pro
            20                  25                  30

Gln Ile Lys Gly Ala Asn Asp Ile Val Ile Lys Lys Gly Gln Asp Tyr
        35                  40                  45

Asn Leu Leu Asn Gly Ile Ser Ala Phe Asp Lys Glu Asp Gly Asp Leu
    50                  55                  60

Thr Asp Lys Ile Lys Val Asp Gly Gln Ile Asp Thr Ser Lys Ser Gly
65                  70                  75                  80

Lys Tyr Gln Ile Lys Tyr His Val Thr Asp Ser Asp Gly Ala Ile Lys
                85                  90                  95

Ile Ser Thr Arg Tyr Ile Glu Val Lys
            100                 105

<210> SEQ ID NO 146
<211> LENGTH: 312
<212> TYPE: PRT
<213> ORGANISM: Staphylococcus sp

<400> SEQUENCE: 146

Met Lys Lys Leu Val Pro Leu Leu Ala Leu Leu Leu Leu Val Ala
1               5                   10                  15

Ala Cys Gly Thr Gly Lys Gln Ser Ser Asp Lys Ser Asn Gly Lys
            20                  25                  30

Leu Lys Val Val Thr Thr Asn Ser Ile Leu Tyr Asp Met Ala Lys Asn
        35                  40                  45

Val Gly Gly Asp Asn Val Asp Ile His Ser Ile Val Pro Val Gly Gln
    50                  55                  60

Asp Pro His Glu Tyr Glu Val Lys Pro Lys Asp Ile Lys Lys Leu Thr
65                  70                  75                  80

Asp Ala Asp Val Ile Leu Tyr Asn Gly Leu Asn Leu Glu Thr Gly Asn
                85                  90                  95

Gly Trp Phe Glu Lys Ala Leu Glu Gln Ala Gly Lys Ser Leu Lys Asp
            100                 105                 110

Lys Lys Val Ile Ala Val Ser Lys Asp Val Lys Pro Ile Tyr Leu Asn
        115                 120                 125

Gly Glu Glu Gly Asn Lys Asp Lys Gln Asp Pro His Ala Trp Leu Ser
    130                 135                 140

-continued

Leu Asp Asn Gly Ile Lys Tyr Val Lys Thr Ile Gln Gln Thr Phe Ile
145                 150                 155                 160

Asp Asn Asp Lys Lys His Lys Ala Asp Tyr Glu Lys Gln Gly Asn Lys
            165                 170                 175

Tyr Ile Ala Gln Leu Glu Lys Leu Asn Asn Asp Ser Lys Asp Ser Lys
        180                 185                 190

Asp Lys Phe Asn Asp Ile Pro Lys Glu Gln Arg Ala Met Ile Thr Ser
    195                 200                 205

Glu Gly Ala Phe Lys Tyr Phe Ser Lys Gln Tyr Gly Ile Thr Pro Gly
210                 215                 220

Tyr Ile Trp Glu Ile Asn Thr Glu Lys Gln Gly Thr Pro Glu Gln Met
225                 230                 235                 240

Arg Gln Ala Ile Glu Phe Val Lys Lys His Lys Leu Lys His Leu Leu
                245                 250                 255

Val Glu Thr Ser Val Asp Lys Lys Ala Met Glu Ser Leu Ser Glu Glu
            260                 265                 270

Thr Lys Lys Asp Ile Phe Gly Glu Val Tyr Thr Asp Ser Ile Gly Lys
        275                 280                 285

Glu Gly Thr Lys Gly Asp Ser Tyr Tyr Lys Met Met Lys Ser Asn Ile
    290                 295                 300

Glu Thr Val His Gly Ser Met Lys
305                 310

<210> SEQ ID NO 147
<211> LENGTH: 646
<212> TYPE: PRT
<213> ORGANISM: Staphylococcus sp

<400> SEQUENCE: 147

Met Ser Ser Gln Lys Lys Ile Ser Leu Phe Ala Phe Phe Leu Leu
1               5                   10                  15

Thr Val Ile Thr Ile Thr Leu Lys Thr Tyr Phe Ser Tyr Tyr Val Asp
            20                  25                  30

Phe Ser Leu Gly Val Lys Gly Leu Val Gln Asn Leu Ile Leu Leu Met
        35                  40                  45

Asn Pro Tyr Ser Leu Val Ala Leu Val Leu Ser Val Phe Leu Phe Phe
    50                  55                  60

Lys Gly Lys Lys Ala Phe Trp Phe Met Phe Ile Gly Gly Phe Leu Leu
65                  70                  75                  80

Thr Phe Leu Leu Tyr Ala Asn Val Val Tyr Phe Arg Phe Phe Ser Asp
                85                  90                  95

Phe Leu Thr Phe Ser Thr Leu Asn Gln Val Gly Asn Val Glu Ser Met
            100                 105                 110

Gly Gly Ala Val Ser Ala Ser Phe Lys Trp Tyr Asp Phe Val Tyr Phe
        115                 120                 125

Ile Asp Thr Leu Val Tyr Leu Phe Ile Leu Ile Phe Lys Thr Lys Trp
    130                 135                 140

Leu Asp Thr Lys Ala Phe Ser Lys Lys Phe Val Pro Val Val Met Ala
145                 150                 155                 160

Ala Ser Val Ala Leu Phe Phe Leu Asn Leu Ala Phe Ala Glu Thr Asp
                165                 170                 175

Arg Pro Glu Leu Leu Thr Arg Thr Phe Asp His Lys Tyr Leu Val Lys
            180                 185                 190

Tyr Leu Gly Pro Tyr Asn Phe Thr Val Tyr Asp Gly Val Lys Thr Ile

```
                195                 200                 205
Glu Asn Asn Gln Gln Lys Ala Leu Ala Ser Glu Asp Asp Leu Thr Lys
210                 215                 220
Val Leu Asn Tyr Thr Lys Gln Arg Gln Thr Glu Pro Asn Pro Glu Tyr
225                 230                 235                 240
Tyr Gly Val Ala Lys Lys Asn Ile Ile Lys Ile His Leu Glu Ser
            245                 250                 255
Phe Gln Thr Phe Leu Ile Asn Lys Lys Val Asn Gly Lys Glu Val Thr
            260                 265                 270
Pro Phe Leu Asn Lys Leu Ser Ser Gly Lys Glu Gln Phe Thr Tyr Phe
            275                 280                 285
Pro Asn Phe Phe His Gln Thr Gly Gln Gly Lys Thr Ser Asp Ser Glu
            290                 295                 300
Phe Thr Met Asp Asn Ser Leu Tyr Gly Leu Pro Gln Gly Ser Ala Phe
305                 310                 315                 320
Ser Leu Lys Gly Asp Asn Thr Tyr Gln Ser Leu Pro Ala Ile Leu Asp
            325                 330                 335
Gln Lys Gln Gly Tyr Lys Ser Asp Val Met His Gly Asp Tyr Lys Thr
            340                 345                 350
Phe Trp Asn Arg Asp Gln Val Tyr Lys His Phe Gly Ile Asp Lys Phe
            355                 360                 365
Tyr Asp Ala Thr Tyr Tyr Asp Met Ser Asp Lys Asn Val Val Asn Leu
370                 375                 380
Gly Leu Lys Asp Lys Ile Phe Phe Lys Asp Ser Ala Asn Tyr Gln Ala
385                 390                 395                 400
Lys Met Lys Ser Pro Phe Tyr Ser His Leu Ile Thr Leu Thr Asn His
            405                 410                 415
Tyr Pro Phe Thr Leu Asp Glu Lys Asp Ala Thr Ile Glu Lys Ser Asn
            420                 425                 430
Thr Gly Asp Ala Thr Val Asp Gly Tyr Ile Gln Thr Ala Arg Tyr Leu
            435                 440                 445
Asp Glu Ala Leu Glu Glu Tyr Ile Asn Asp Leu Lys Lys Lys Gly Leu
450                 455                 460
Tyr Asp Asn Ser Val Ile Met Ile Tyr Gly Asp His Tyr Gly Ile Ser
465                 470                 475                 480
Glu Asn His Asn Asn Ala Met Glu Lys Leu Leu Gly Glu Lys Ile Thr
            485                 490                 495
Pro Ala Lys Phe Thr Asp Leu Asn Arg Thr Gly Phe Trp Ile Lys Ile
            500                 505                 510
Pro Gly Lys Ser Gly Gly Ile Asn Asn Glu Tyr Ala Gly Gln Val Asp
            515                 520                 525
Val Met Pro Thr Ile Leu His Leu Ala Gly Ile Asp Thr Lys Asn Tyr
            530                 535                 540
Leu Met Phe Gly Thr Asp Leu Phe Ser Lys Gly His Asn Gln Val Val
545                 550                 555                 560
Pro Phe Arg Asn Gly Asp Phe Ile Thr Lys Asp Tyr Lys Tyr Val Asn
            565                 570                 575
Gly Lys Ile Tyr Ser Asn Lys Asn Glu Leu Ile Thr Thr Gln Pro
            580                 585                 590
Ala Asp Phe Glu Lys Asn Lys Lys Gln Val Glu Lys Asp Leu Glu Met
            595                 600                 605
Ser Asp Asn Val Leu Asn Gly Asp Leu Phe Arg Phe Tyr Lys Asn Pro
610                 615                 620
```

```
Asp Phe Lys Lys Val Asn Pro Ser Lys Tyr Lys Tyr Glu Thr Gly Pro
625                 630                 635                 640

Lys Ala Asn Ser Lys Lys
            645

<210> SEQ ID NO 148
<211> LENGTH: 173
<212> TYPE: PRT
<213> ORGANISM: Staphylococcus sp

<400> SEQUENCE: 148

Met Ile Asn Ile Ile Ser Ala Ile Gly Ser Ile Gly Thr Phe Ile Met
1               5                   10                  15

Ala Leu Phe Tyr Phe Val Ser Val Ser Val Gln Leu Tyr Gln Met Lys
                20                  25                  30

Ile Ser Phe Leu Pro Ala Leu Gly Phe Asn Gln Ile Leu Leu Glu Arg
            35                  40                  45

Glu Glu Asp Gln Leu Asn Ile Met Asn Ser Ala Thr Glu Glu His His
    50                  55                  60

His Lys Asp Tyr Ile Lys Leu Tyr Asn Leu Gly Gly Gly Ala Ala Lys
65                  70                  75                  80

Lys Ile Ala Ile Glu Val Leu Leu Gly Lys Asp Lys Val Ile Gln Lys
                85                  90                  95

Lys Tyr Val His Ile Leu Pro Ser Lys Glu Gly Tyr Met Leu Pro Ile
            100                 105                 110

Asn Lys Asn Val Tyr Glu Glu Leu Glu Arg Thr Ile Glu Asn Asn Gly
        115                 120                 125

His Glu Ala Asp Leu Asn Val Arg Met Thr Tyr Tyr His Asn Val Ser
    130                 135                 140

Arg Lys Gln Gln Glu Val Ile Leu Lys Gly Gln Ile Asp Arg Phe Asn
145                 150                 155                 160

Thr Tyr Asn Asn Lys Glu Ile Tyr Asp Leu Gln Phe Ile
                165                 170

<210> SEQ ID NO 149
<211> LENGTH: 156
<212> TYPE: PRT
<213> ORGANISM: Staphylococcus sp

<400> SEQUENCE: 149

Met Lys Arg Lys Val Leu Val Leu Thr Met Gly Val Ile Cys Ala Thr
1               5                   10                  15

Gln Leu Trp His Ser Asn His Ala Asn Ala Leu Val Thr Glu Ser Gly
                20                  25                  30

Ala Asn Asp Thr Lys Gln Phe Thr Glu Ile Val Ser Glu Lys Val
            35                  40                  45

Ile Thr Val Glu His Ala Gln Ile Asn Ile Phe Gln Ser Asn Ser Asn
    50                  55                  60

Ser Asn Leu Met Glu Phe Asn Ile Leu Thr Met Gly Gly Lys Ser Gly
65                  70                  75                  80

Ala Met Val Gly Tyr Ser Glu Ile Asp Ser Ser His Phe Thr Asp Arg
                85                  90                  95

Asp Lys Arg Val Ile Arg Arg Asp His Val Lys Glu Ala Gln Ser Leu
            100                 105                 110

Val Glu Asn Tyr Lys Asp Thr Gln Ser Ala Asp Ala Arg Met Lys Ala
        115                 120                 125
```

Lys Gln Lys Val Asn Thr Leu Ser Lys Pro His Gln Asn Tyr Phe Asn
            130                 135                 140

Lys Gln Ile Asp Lys Val Tyr Asn Gly Leu Gln Arg
145                 150                 155

<210> SEQ ID NO 150
<211> LENGTH: 133
<212> TYPE: PRT
<213> ORGANISM: Staphylococcus sp

<400> SEQUENCE: 150

Met Lys Lys Asn Ile Thr Lys Thr Ile Ile Ala Ser Thr Val Ile Ala
1               5                   10                  15

Ala Gly Leu Leu Thr Gln Thr Asn Asp Ala Lys Ala Phe Phe Ser Tyr
            20                  25                  30

Glu Trp Lys Gly Leu Glu Ile Ala Lys Asn Leu Ala Asp Gln Ala Lys
        35                  40                  45

Lys Asp Asp Glu Arg Ile Asp Lys Leu Met Lys Glu Ser Asp Lys Asn
50                  55                  60

Leu Thr Pro Tyr Lys Ala Glu Thr Val Asn Asp Leu Tyr Leu Ile Val
65                  70                  75                  80

Lys Lys Leu Ser Gln Gly Asp Val Lys Ala Val Val Arg Ile Lys
            85                  90                  95

Asp Gly Gly Pro Arg Asp Tyr Tyr Thr Phe Asp Leu Thr Arg Pro Leu
            100                 105                 110

Glu Glu Asn Arg Lys Asn Ile Lys Val Val Lys Asn Gly Glu Ile Asp
        115                 120                 125

Ser Ile Thr Trp Tyr
    130

<210> SEQ ID NO 151
<211> LENGTH: 274
<212> TYPE: PRT
<213> ORGANISM: Staphylococcus sp

<400> SEQUENCE: 151

Met Tyr Pro Asn Trp Gly Gln Tyr Lys Arg Ala Asp Leu Ile Gly Gln
1               5                   10                  15

Ser Ser Tyr Ile Lys Asn Asn Asp Val Val Ile Phe Asn Glu Ala Phe
            20                  25                  30

Asp Asn Gly Ala Ser Asp Lys Leu Leu Ser Asn Val Lys Lys Glu Tyr
        35                  40                  45

Pro Tyr Gln Thr Pro Val Leu Gly Arg Ser Gln Ser Gly Trp Asp Lys
50                  55                  60

Thr Glu Gly Ser Tyr Ser Ser Thr Val Ala Glu Asp Gly Gly Val Ala
65                  70                  75                  80

Ile Val Ser Lys Tyr Pro Ile Lys Glu Lys Ile Gln His Val Phe Lys
            85                  90                  95

Ser Gly Cys Gly Phe Asp Asn Asp Ser Asn Lys Gly Phe Val Tyr Thr
            100                 105                 110

Lys Ile Glu Lys Asn Gly Lys Asn Val His Val Ile Gly Thr His Thr
        115                 120                 125

Gln Ser Glu Asp Ser Arg Cys Gly Ala Gly His Asp Arg Lys Ile Arg
    130                 135                 140

Ala Glu Gln Met Lys Glu Ile Ser Asp Phe Val Lys Lys Lys Asn Ile
145                 150                 155                 160

```
Pro Lys Asp Glu Thr Val Tyr Ile Gly Gly Asp Leu Asn Val Asn Lys
                165                 170                 175

Gly Thr Pro Glu Phe Lys Asp Met Leu Lys Asn Leu Asn Val Asn Asp
            180                 185                 190

Val Leu Tyr Ala Gly His Asn Ser Thr Trp Asp Pro Gln Ser Asn Ser
        195                 200                 205

Ile Ala Lys Tyr Asn Tyr Pro Asn Gly Lys Pro Glu His Leu Asp Tyr
    210                 215                 220

Ile Phe Thr Asp Lys Asp His Lys Gln Pro Lys Gln Leu Val Asn Glu
225                 230                 235                 240

Val Val Thr Glu Lys Pro Lys Pro Trp Asp Val Tyr Ala Phe Pro Tyr
                245                 250                 255

Tyr Tyr Val Tyr Asn Asp Phe Ser Asp His Tyr Pro Ile Lys Ala Tyr
            260                 265                 270

Ser Lys

<210> SEQ ID NO 152
<211> LENGTH: 390
<212> TYPE: PRT
<213> ORGANISM: Staphylococcus sp

<400> SEQUENCE: 152

Met Leu Glu Phe Glu Gln Gly Phe Asn His Leu Ala Thr Leu Lys Val
1               5                   10                  15

Ile Gly Val Gly Gly Gly Gly Asn Asn Ala Val Asn Arg Met Ile Asp
            20                  25                  30

His Gly Met Asn Asn Val Glu Phe Ile Ala Ile Asn Thr Asp Gly Gln
        35                  40                  45

Ala Leu Asn Leu Ser Lys Ala Glu Ser Lys Ile Gln Ile Gly Glu Lys
    50                  55                  60

Leu Thr Arg Gly Leu Gly Ala Gly Ala Asn Pro Glu Ile Gly Lys Lys
65                  70                  75                  80

Ala Ala Glu Glu Ser Arg Glu Gln Ile Glu Asp Ala Ile Gln Gly Ala
                85                  90                  95

Asp Met Val Phe Val Thr Ser Gly Met Gly Gly Gly Thr Gly Thr Gly
            100                 105                 110

Ala Ala Pro Val Val Ala Lys Ile Ala Lys Glu Met Gly Ala Leu Thr
        115                 120                 125

Val Gly Val Val Thr Arg Pro Phe Ser Phe Glu Gly Arg Lys Arg Gln
    130                 135                 140

Thr Gln Ala Ala Ala Gly Val Glu Ala Met Lys Ala Ala Val Asp Thr
145                 150                 155                 160

Leu Ile Val Ile Pro Asn Asp Arg Leu Leu Asp Ile Val Asp Lys Ser
                165                 170                 175

Thr Pro Met Met Glu Ala Phe Lys Glu Ala Asp Asn Val Leu Arg Gln
            180                 185                 190

Gly Val Gln Gly Ile Ser Asp Leu Ile Ala Val Ser Gly Glu Val Asn
        195                 200                 205

Leu Asp Phe Ala Asp Val Lys Thr Ile Met Ser Asn Gln Gly Ser Ala
    210                 215                 220

Leu Met Gly Ile Gly Val Ser Ser Gly Glu Asn Arg Ala Val Glu Ala
225                 230                 235                 240

Ala Lys Lys Ala Ile Ser Ser Pro Leu Leu Glu Thr Ser Ile Val Gly
                245                 250                 255
```

```
Ala Gln Gly Val Leu Met Asn Ile Thr Gly Gly Glu Ser Leu Ser Leu
            260                 265                 270

Phe Glu Ala Gln Glu Ala Ala Asp Ile Val Gln Asp Ala Ala Asp Glu
            275                 280                 285

Asp Val Asn Met Ile Phe Gly Thr Val Ile Asn Pro Glu Leu Gln Asp
290                 295                 300

Glu Ile Val Val Thr Val Ile Ala Thr Gly Phe Asp Asp Lys Pro Thr
305                 310                 315                 320

Ser His Gly Arg Lys Ser Gly Ser Thr Gly Phe Gly Thr Ser Val Asn
                325                 330                 335

Thr Ser Ser Asn Ala Thr Ser Lys Asp Glu Ser Phe Thr Ser Asn Ser
            340                 345                 350

Ser Asn Ala Gln Ala Thr Asp Ser Val Ser Glu Arg Thr His Thr Thr
            355                 360                 365

Lys Glu Asp Asp Ile Pro Ser Phe Ile Arg Asn Arg Glu Glu Arg Arg
370                 375                 380

Ser Arg Arg Thr Arg Arg
385                 390

<210> SEQ ID NO 153
<211> LENGTH: 104
<212> TYPE: PRT
<213> ORGANISM: Staphylococcus sp

<400> SEQUENCE: 153

Met Ala Ile Val Lys Val Thr Asp Ala Asp Phe Asp Ser Lys Val Glu
1               5                   10                  15

Ser Gly Val Gln Leu Val Asp Phe Trp Ala Thr Trp Cys Gly Pro Cys
            20                  25                  30

Lys Met Ile Ala Pro Val Leu Glu Glu Leu Ala Ala Asp Tyr Glu Gly
        35                  40                  45

Lys Ala Asp Ile Leu Lys Leu Ser Val Asp Glu Asn Pro Ser Thr Ala
    50                  55                  60

Ala Lys Tyr Glu Val Met Ser Ile Pro Thr Leu Ile Val Phe Lys Asp
65                  70                  75                  80

Gly Gln Pro Val Asp Lys Val Val Gly Phe Gln Pro Lys Glu Asn Leu
                85                  90                  95

Ala Glu Val Leu Asp Lys His Leu
            100

<210> SEQ ID NO 154
<211> LENGTH: 189
<212> TYPE: PRT
<213> ORGANISM: Staphylococcus sp

<400> SEQUENCE: 154

Met Ser Leu Ile Asn Lys Glu Ile Leu Pro Phe Thr Ala Gln Ala Phe
1               5                   10                  15

Asp Pro Lys Lys Asp Gln Phe Lys Glu Val Thr Gln Glu Asp Leu Lys
            20                  25                  30

Gly Ser Trp Ser Val Val Cys Phe Tyr Pro Ala Asp Phe Ser Phe Val
        35                  40                  45

Cys Pro Thr Glu Leu Glu Asp Leu Gln Asn Gln Tyr Glu Glu Leu Gln
    50                  55                  60

Lys Leu Gly Val Asn Val Phe Ser Val Ser Thr Asp Thr His Phe Val
65                  70                  75                  80
```

```
His Lys Ala Trp His Asp His Ser Asp Ala Ile Ser Lys Ile Thr Tyr
                85              90              95

Thr Met Ile Gly Asp Pro Ser Gln Thr Ile Thr Arg Asn Phe Asp Val
            100             105             110

Leu Asp Glu Ala Thr Gly Leu Ala Gln Arg Gly Thr Phe Ile Ile Asp
            115             120             125

Pro Asp Gly Val Val Gln Ala Ser Glu Ile Asn Ala Asp Gly Ile Gly
        130             135             140

Arg Asp Ala Ser Thr Leu Ala His Lys Ile Lys Ala Ala Gln Tyr Val
145             150             155             160

Arg Lys Asn Pro Gly Glu Val Cys Pro Ala Lys Trp Glu Glu Gly Ala
                165             170             175

Lys Thr Leu Gln Pro Gly Leu Asp Leu Val Gly Lys Ile
                180             185

<210> SEQ ID NO 155
<211> LENGTH: 207
<212> TYPE: PRT
<213> ORGANISM: Staphylococcus sp

<400> SEQUENCE: 155

Met Ala Met Ile Lys Met Ser Pro Glu Glu Leu Arg Ala Lys Ser Gln
1               5               10              15

Ser Tyr Gly Gln Gly Ser Asp Gln Ile Arg Gln Ile Leu Ser Asp Leu
            20              25              30

Thr Arg Ala Gln Gly Glu Leu Ala Ala Asn Trp Glu Gly Gln Ala Phe
        35              40              45

Ser Arg Phe Glu Glu Gln Phe Gln Gln Leu Ser Pro Lys Val Glu Lys
50              55              60

Phe Ala Gln Leu Leu Glu Glu Ile Lys Gln Gln Leu Asn Ser Thr Ala
65              70              75              80

Asp Ala Val Gln Glu Gln Asp Gln Gln Leu Ser Asn Asn Phe Gly Leu
                85              90              95

Gln Ala Ser Gly Gly Gly Ser Met Gly Gly Tyr Lys Gly Leu Lys Ala
            100             105             110

Asp Gly Gly Lys Val Asp Gln Ala Lys Gln Leu Ala Ala Lys Thr Ala
        115             120             125

Lys Asp Ile Glu Ala Cys Gln Lys Gln Thr Gln Gln Leu Ala Glu Tyr
    130             135             140

Ile Glu Gly Ser Asp Trp Glu Gly Gln Phe Ala Asn Lys Val Lys Asp
145             150             155             160

Val Leu Leu Leu Met Ala Lys Phe Gln Glu Glu Leu Val Gln Pro Met
                165             170             175

Ala Asp His Gln Lys Ala Ile Asp Asn Leu Ser Gln Asn Leu Ala Lys
            180             185             190

Tyr Asp Thr Leu Ser Ile Lys Gln Gly Leu Asp Arg Val Asn Pro
        195             200             205
```